US011787825B2

(12) United States Patent
Farand et al.

(10) Patent No.: US 11,787,825 B2
(45) Date of Patent: Oct. 17, 2023

(54) THERAPEUTIC COMPOUNDS FOR HIV VIRUS INFECTION

(71) Applicant: Gilead Sciences, Inc., Foster City, CA (US)

(72) Inventors: Julie Farand, San Mateo, CA (US); Tezcan Guney, Foster City, CA (US); Darryl Kato, San Francisco, CA (US); John O. Link, San Francisco, CA (US); James B. C. Mack, San Mateo, CA (US); William J. Watkins, Saratoga, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 18/061,375

(22) Filed: Dec. 2, 2022

(65) Prior Publication Data

US 2023/0203069 A1    Jun. 29, 2023

Related U.S. Application Data

(60) Provisional application No. 63/356,889, filed on Jun. 29, 2022, provisional application No. 63/285,730, filed on Dec. 3, 2021.

(51) Int. Cl.
*C07F 9/09* (2006.01)

(52) U.S. Cl.
CPC ................... *C07F 9/095* (2013.01)

(58) Field of Classification Search
CPC ....................................... C07F 9/095
USPC .......................................... 514/126
See application file for complete search history.

(56) References Cited

U.S. PATENT DOCUMENTS

| | | |
|---|---|---|
| 3,845,770 A | 11/1974 | Theeuwes et al. |
| 4,326,525 A | 4/1982 | Swanson et al. |
| 4,816,570 A | 3/1989 | Farquhar |
| 4,902,514 A | 2/1990 | Barclay et al. |
| 4,968,788 A | 11/1990 | Farquhar |
| 4,992,445 A | 2/1991 | Lawter et al. |
| 5,001,139 A | 3/1991 | Lawler et al. |
| 5,023,252 A | 6/1991 | Hseih |
| 5,616,345 A | 4/1997 | Geoghegan et al. |
| 5,663,159 A | 9/1997 | Starrett, Jr. et al. |
| 5,792,756 A | 8/1998 | Starrett, Jr. et al. |
| 5,922,695 A | 7/1999 | Arimilli et al. |
| 5,935,946 A | 8/1999 | Munger, Jr. et al. |
| 5,977,089 A | 11/1999 | Arimilli et al. |
| 7,390,791 B2 | 6/2008 | Becker et al. |
| 7,803,788 B2 | 9/2010 | Becker et al. |
| 8,193,225 B2 | 6/2012 | Schneider et al. |
| 8,263,627 B2 | 9/2012 | Barrow et al. |
| 8,435,968 B2 | 5/2013 | Greig et al. |
| 8,748,412 B2 | 6/2014 | Liao et al. |
| 8,754,065 B2 | 6/2014 | Liu et al. |
| 8,835,488 B2 | 9/2014 | Yamashita et al. |
| 9,012,441 B2 | 4/2015 | Bondy et al. |
| 9,050,344 B2 | 6/2015 | Brizgys et al. |
| 9,216,996 B2 | 12/2015 | Jin et al. |
| 9,220,710 B2 | 12/2015 | Bondy et al. |
| 9,540,343 B2 | 1/2017 | Bondy et al. |
| 9,670,205 B2 | 6/2017 | Aktoudianakis et al. |
| 9,730,936 B2 | 8/2017 | Baszcynski et al. |
| 9,789,089 B2 | 10/2017 | Bondy et al. |
| 9,873,680 B2 | 1/2018 | Brizgys et al. |
| 9,944,619 B2 | 4/2018 | Bondy et al. |
| 9,951,043 B2 | 4/2018 | Brizgys et al. |
| 10,071,885 B2 | 9/2018 | O'Brien et al. |
| 10,071,985 B2 | 9/2018 | Graupe et al. |
| 10,294,234 B2 | 5/2019 | Bacon et al. |
| 10,370,342 B2 | 8/2019 | Chin et al. |
| 10,370,358 B2 | 8/2019 | Bondy et al. |
| 10,640,499 B2 | 5/2020 | Chin et al. |
| 10,654,827 B2 | 5/2020 | Graupe et al. |
| 10,696,657 B2 | 6/2020 | Vandehey |
| 10,836,746 B2 | 11/2020 | Brizgys et al. |
| 10,849,892 B2 | 12/2020 | Houston et al. |
| 11,034,668 B2 | 6/2021 | Bondy et al. |
| 11,078,208 B1 | 8/2021 | Bacon et al. |
| 11,084,832 B2 | 8/2021 | Chu et al. |
| 11,117,886 B2 | 9/2021 | Vandehey et al. |
| 11,266,638 B2 | 3/2022 | Houston et al. |
| 11,267,799 B2 | 3/2022 | Shi |
| 11,267,801 B2 | 3/2022 | Brizgy et al. |
| 2005/0282805 A1 | 12/2005 | Hangeland et al. |
| 2007/0083045 A1 | 4/2007 | Di Francesco et al. |
| 2008/0234251 A1 | 9/2008 | Doherty et al. |
| 2008/0306050 A1 | 12/2008 | Doherty et al. |
| 2010/0029585 A1 | 2/2010 | Dietsch et al. |
| 2010/0129306 A1 | 5/2010 | Julien et al. |
| 2010/0143301 A1 | 6/2010 | Desai et al. |
| 2010/0249176 A1 | 9/2010 | Barrow et al. |
| 2011/0092485 A1 | 4/2011 | Burgess et al. |
| 2011/0118235 A1 | 5/2011 | Burgess et al. |
| 2012/0045761 A1 | 2/2012 | Jagannath et al. |
| 2012/0082658 A1 | 4/2012 | Hershberg |
| 2012/0219615 A1 | 8/2012 | Coukos et al. |

(Continued)

FOREIGN PATENT DOCUMENTS

| | | |
|---|---|---|
| CN | 101910133 | 12/2010 |
| CN | 107207498 | 9/2017 |

(Continued)

OTHER PUBLICATIONS

[No Author Listed], "2-[9-(Difluoromethyl)-5,5-difluoro-7,8-diazatricylo[4.4.0.02,4]nona-1(6),8-dien-7-yl]acetic acid," PubChem CID 71186949, Mar. 21, 2013, 18 pages.

(Continued)

*Primary Examiner* — Kristin A Vajda
(74) *Attorney, Agent, or Firm* — Fish & Richardson P.C.

(57) ABSTRACT

The present disclosure relates generally to certain compounds, pharmaceutical compositions comprising said compounds, and methods of making and using said compounds and pharmaceutical compositions. The compounds and compositions provided herein may be used for the treatment or prevention of a Retroviridae infection, including an HIV infection.

40 Claims, No Drawings

(56) References Cited

U.S. PATENT DOCUMENTS

| | | |
|---|---|---|
| 2013/0165489 A1 | 6/2013 | Cocklin et al. |
| 2013/0251673 A1 | 9/2013 | Flores et al. |
| 2014/0045849 A1 | 2/2014 | McGowan et al. |
| 2014/0066432 A1 | 3/2014 | Burgess et al. |
| 2014/0073642 A1 | 3/2014 | Embrechts et al. |
| 2014/0088085 A1 | 3/2014 | Burgess et al. |
| 2014/0142085 A1 | 5/2014 | Bondy et al. |
| 2014/0221346 A1 | 8/2014 | Halcomb et al. |
| 2014/0221347 A1 | 8/2014 | Brizgys et al. |
| 2014/0221356 A1 | 8/2014 | Jin et al. |
| 2014/0221378 A1 | 8/2014 | Miyazaki et al. |
| 2014/0221380 A1 | 8/2014 | Miyazaki et al. |
| 2014/0221417 A1 | 8/2014 | Halcomb et al. |
| 2014/0221421 A1 | 8/2014 | Bondy et al. |
| 2014/0275167 A1 | 9/2014 | Hartman |
| 2014/0296266 A1 | 10/2014 | Hu et al. |
| 2014/0303164 A1 | 10/2014 | Brizgys et al. |
| 2014/0350031 A1 | 11/2014 | McGowan et al. |
| 2015/0104511 A1 | 4/2015 | Malhotra et al. |
| 2016/0067224 A1 | 3/2016 | Bondy et al. |
| 2016/0083368 A1 | 3/2016 | Brizgys et al. |
| 2016/0108030 A1 | 4/2016 | Brizgys et al. |
| 2016/0250215 A1 | 9/2016 | Baszcynski et al. |
| 2016/0289229 A1 | 10/2016 | Aktoudianakis et al. |
| 2016/0368881 A1 | 12/2016 | Bondy et al. |
| 2017/0137405 A1 | 5/2017 | Bondy et al. |
| 2018/0051005 A1 | 2/2018 | Graupe et al. |
| 2018/0194746 A1 | 7/2018 | Bondy et al. |
| 2018/0258097 A1 | 9/2018 | Bacon et al. |
| 2018/0273508 A1 | 9/2018 | Brizgys et al. |
| 2018/0370950 A1 | 12/2018 | Graupe et al. |
| 2019/0083478 A1 | 3/2019 | Houston et al. |
| 2019/0084963 A1 | 3/2019 | Shi |
| 2019/0300505 A1 | 10/2019 | Allan et al. |
| 2019/0345136 A1 | 11/2019 | Brizgys et al. |
| 2019/0375726 A1 | 12/2019 | Bondy et al. |
| 2020/0038389 A1 | 2/2020 | Bauer |
| 2020/0262815 A1 | 8/2020 | Graupe et al. |
| 2020/0369647 A1 | 11/2020 | Allan et al. |
| 2020/0397772 A1 | 12/2020 | Houston et al. |
| 2021/0009555 A1 | 1/2021 | Brizgys et al. |
| 2021/0188815 A1 | 6/2021 | Bekerman et al. |
| 2022/0009904 A1 | 1/2022 | Allan et al. |
| 2022/0249460 A1 | 8/2022 | Houston et al. |
| 2022/0251069 A1 | 8/2022 | Shi |
| 2022/0267302 A1 | 8/2022 | Brizgys et al. |
| 2023/0012449 A1 | 1/2023 | Bondy et al. |
| 2023/0038823 A1 | 2/2023 | Chou et al. |

FOREIGN PATENT DOCUMENTS

| | | |
|---|---|---|
| WO | WO 1991019721 | 12/1991 |
| WO | WO 2003002530 | 1/2003 |
| WO | WO 2003002553 | 1/2003 |
| WO | WO 2004050643 | 6/2004 |
| WO | WO 2004071448 | 8/2004 |
| WO | WO 2004096286 | 11/2004 |
| WO | WO 2005087725 | 9/2005 |
| WO | WO 2005123680 | 12/2005 |
| WO | WO 2006015261 | 2/2006 |
| WO | WO 2006110157 | 10/2006 |
| WO | WO 2007070826 | 8/2007 |
| WO | WO 2008013622 | 1/2008 |
| WO | WO 2008118849 | 10/2008 |
| WO | WO 2009005677 | 1/2009 |
| WO | WO 2009010804 | 1/2009 |
| WO | WO 2009062285 | 5/2009 |
| WO | WO 2009114677 | 9/2009 |
| WO | WO 2010130034 | 11/2010 |
| WO | WO 2011059887 | 5/2011 |
| WO | WO 2011143772 | 11/2011 |
| WO | WO 2012003497 | 1/2012 |
| WO | WO 2012003498 | 1/2012 |
| WO | WO 2012065062 | 5/2012 |
| WO | WO 2012145728 | 10/2012 |
| WO | WO 2013006738 | 1/2013 |
| WO | WO 2013006792 | 1/2013 |
| WO | WO 2013091096 | 6/2013 |
| WO | WO 2013159064 | 10/2013 |
| WO | WO 2014016358 | 1/2014 |
| WO | WO 2014023813 | 2/2014 |
| WO | WO 2014028931 | 2/2014 |
| WO | WO 2014056953 | 4/2014 |
| WO | WO 2014076221 | 5/2014 |
| WO | WO 2014100323 | 6/2014 |
| WO | WO 2014110297 | 7/2014 |
| WO | WO 2014110298 | 7/2014 |
| WO | WO 2014110323 | 7/2014 |
| WO | WO 2014128189 | 8/2014 |
| WO | WO 2014128213 | 8/2014 |
| WO | WO 2014134566 | 9/2014 |
| WO | WO 2015008097 | 1/2015 |
| WO | WO 2015061518 | 4/2015 |
| WO | WO 2015130966 | 9/2015 |
| WO | WO 2016033243 | 3/2016 |
| WO | WO 2016040084 | 3/2016 |
| WO | WO 2016172424 | 10/2016 |
| WO | WO 2016172425 | 10/2016 |
| WO | WO 2017007689 | 1/2017 |
| WO | WO 2018035359 | 2/2018 |
| WO | WO 2018145021 | 8/2018 |
| WO | WO 2018203235 | 11/2018 |
| WO | WO 2019035904 | 2/2019 |
| WO | WO 2019035973 | 2/2019 |
| WO | WO 2020018459 | 1/2020 |

OTHER PUBLICATIONS

[No Author Listed], "3-Methyl-3-methylsulfonylbut-1-yne," PubChem CID 14241469, Feb. 9, 2002, 16 pages.

[No Author Listed], CAS registry No. 1620056-83-8, Aug. 6, 2014, 1 page.

Bastin et al., "Salt Selection and Optimisation Procedures for Pharmaceutical New Chemical Entities," Organic Process Research & Development, Jul. 2000, 4(5): 427-435.

Benzaria et al., "Synthesis, In Vitro Antiviral Evaluation, and Stability Studies of Bis(S-Acyl-2-Thioethyl) Ester Derivatives of 9-[2-(Phosphonomethoxy)Ethyl]adenine (PMEA) as Potential PMEA Prodrugs with Improved Oral Bioavailability," J. Med. Chem., Dec. 1996, 39(25):4958-4965.

Berge et al., "Pharmaceutical Salts," J. Pharma. Sci., 1977, 66(1): 1-19.

Bhattacharya et al., Structural Basis of HIV-1 Capsid Recognition by PF74 and CPSF6, PNAS, 2014, 111(52):18625-18630.

Blair et al., "HIV Capsid is a Tractable Target for Small Molecule Therapeutic Intervention," PLoS Pathog., 2010, 6(12): e1001220, 10 pages.

Briggs et al., "Structural Organization of Authentic, Mature HIV-1 Virions and Cores," The EMBO Journal, 2003, 22(7): 1707-1715.

Brittain, "Polymorphism in pharmaceutical solids," Marcel Dekker, Inc., 1999, 235-238.

Brown et al., "Highly Enantioselective Cu-Catalyzed Conjugate Additions of Dialkylzinc Reagents to Unsaturated Furanones and Pyranones: Preparation of Air-Stable and Catalytically Active Cu-Peptide," Angew. Chem. Int. Ed. Engl., 2005, 44(33):5306-5310.

Bundgaard, "Design and Application of Prodrugs," Chapter 5 in a Textbook of Drug Design and Development, Krogsgaard-Larsen, P. et al. eds., Harwood Academic Publishers, Chur, Switzerland, 1991, pp. 113-191.

Campbell et al., "HIV-1 Capsid: The Multifaceted Key Player in HIV-1 Infection," Nat Rev Microbial., 2015, 13(8): 471-483.

Carnes et al., "Inhibitors of the HIV-1 Capsid, a Target of Opportunity," Curr. Opin. HIV AIDS, 2018, 13(4):359-365.

Chin et al., "Direct Visualization of HIV-1 Replication Intermediates Shows That Capsid and CPSF6 Modulate HIV-1 Intra-Nuclear Invasion and Integration", Cell Repotis, 2015, 13:1717-1731.

Choy et al., "Synthesis of irreversible HIV-1 protease inhibitors containing sulfonamide and sulfone as amide bond isosteres," Bioorganic & Medicinal Chemistry Letters, Oct. 1997, 7(20):2635-38.

(56) References Cited

OTHER PUBLICATIONS

Cos et al., "Structure-Activity Relationship and Classification of Flavonoids as Inhibitors of Xanthine Oxidase and Su peroxide Scavengers," J. Natl. Prod., 1998, 61:71-76.

Cossy et al., "Ring Opening of Cyclopropylketones Induced by Photochemical Election Transfer," Tetrahedron, Oct. 1995, 51 (43):11751-11764.

Curreli et al., "Virtual Screening Based Identification of Novel Small-molecule Inhibitors Targeted to the HIV-1 Capsid," Bioorganic & Medicinal Chemistry, 2011, 19:77-90.

De Lombaert et al., "N-Phosphonomethyl Dipeptides and Their Phosphonate Prodrugs, a New Generation of Neutral Endopeptidase (NEP, EC 3.4.24.11) Inhibitors," J. Med. Chem., Feb. 1994, 37(4):498-511.

Fader et al., "Optimization of a 1,5 dihydrobenzo[b][1,4]diazepine-2,4-dione Series of HIV Capsid Assembly Inhibitors 2: Structure-Activity Relationships (SAR) of the C3-Phenyl Moiety," Bioorganic & Medicinal Chemistry Letters, 2013, 23(11):3396-3400.

Farquhar et al., "Biologically Reversible Phosphate-Protective Groups," J. Pharm. Sci., Mar. 1983, 72(3):324-325.

Fields, "Methods for Removing the Fmoc Group," Methods in Molecular Biology, 1994, 35:17-27.

Fontes Ferreira da Cunha et al., "4D-QSAR Models of HOE/BAY-793 Analogues as HIV-1 Protease Inhibitors," QSAR & Combinatorial Science, 2005, 24(2): 240-253.

Forshey et al., "Formation of a Human Immunodeficiency Virus Type 1 Core of Optimal Stability Is Crucial for Viral Replication," J. Virology, 2002, 76(11) p. 5667-5677.

Foster, "Deuterium Isotope Effects in Studies of Drug Metabolism," Trends Pharmacol. Sci., 1984, 5(12):524-527.

Ganser et al., "Assembly and Analysis of Conical Models for the HIV-1 Core," Science, 1999, 283: 80-82.

Ganser-Pornillos et al., "Structure of Full-Length HIV-1 CA: A Model for the Mature Capsid Lattice," Cell, 2007, 131(1):70-9, 29 pages.

Hagmann, "The many roles for fluorine in medicinal chemistry," J. Med. Chem., 2008, 51(15):4359-4369.

Hammer et al., "Antiretroviral Treatment of Adult HIV Infection. 2008 Recommendations of the International AIDS Society: USA Panel," JAMA, Aug. 2008, 300(5):355-570.

Hanack et al., "cis—und trans bicyclo [3.1.0] hexano-(2)," Chemische Berichte, 1964, 97(6):1669-1672, XP055573746 (with English translation).

Hodgson et al. "Intramolecular Cyclopropanation of Unsaturated Terminal Epoxides," J. Am. Chem. Soc., 2004, 126(28):8664-8665.

Hodgson et al., "Intramolecular Cyclopropanation of Unsaturated Terminal Epoxides and Chlorohydrins," J. Am. Chem. Soc., 2007, 129(14):4456-4462.

Hung et al., "Large-Scale Functional Purification of Recombinant HIV-1 Capsid," PLOS One, 2013, 8(3):e58035, 11 pages.

Ishiyama et al., "Palladium(0)-Catalyzed Cross-Coupling Reaction of Alkoxydiboron with Haloarenes: A Direct Procedure for Arylboronic Esters," J. Org. Chem., 1995, 60(23):7508-7510.

Jarvis et al., "Conquering HIV's capsid", C&EN Chicago, Jul. 2017, 95(31): 23-25.

Jeong, "Synthesis of Tetrasubstituted Pyrazones and Pyrazone N-Oxides," Tetrahedron Letters, 2010, 51 (6):974-976.

Jin et al., "SAR and Molecular Mechanism Study of Novel Acylhydrazone Compounds Targeting HIV-1 CA," Bioorganic & Medicinal Chemistry, 2010, 18:2135-2140.

Jouvenet et al., "Plasma Membrane Is the Site of Productive HIV-1 Particle Assembly," PLoS Biol., 2006, 4(12):e435, 15 pages.

Kashima et al., "New Peptide Synthesis Using the Ozonolysate of 2-(1-Phthalimido)alkyl-5-Phenyloxazoles," J. Heterocyclic Chem., 1991, 28: 1241-1244.

Kelly et al., "Structure of the Antiviral Assembly Inhibitor CAP-1 Complex with the HIV-1 CA Protein," Journal of Molecular Biology, 2007, 373(2):355-66.

Khamnei et al., "Neighboring Group Catalysis in the Design of Nucleotide Prodrugs," J. Med. Chem., 1996, 39(20):4109-4115.

Kim et al., "Discovery of a New HIV-1 Inhibitor Scaffold and Synthesis of Potential Prodrugs of Indazoles," Bioorganic & Medicinal Chemistry Letters, 2013, 23(10):2888-2892.

Kocienski, "Carbonyl Protecting Groups," Chapter 5 in Protecting Groups, Thieme Publishing Group: New York, NY, May 1994, pp. 155-184.

Kocienski, "Carboxyl Protecting Groups," Chapter 4 in Protecting Groups, Thieme Publishing Group: New York, NY, May 1994, pp. 118-154.

Kocienski, "Diol Protecting Groups," Chapter 3 in Protecting Groups, Thieme Publishing Group: New York, NY, May 1994, pp. 95-117.

Kocienski, "Hydroxyl Protecting Groups," Chapter 2 in Protecting Groups, Thieme Publishing Group: New York, NY, May 1994, pp. 21-94.

Kocienski, "Protecting Groups: An Overview," Chapter 1 in Protecting Groups, Thieme Publishing Group: New York, NY, May 1994, pp. 1-20.

Lad et al., "Functional Label-Free Assays for Characterizing the in Vitro Mechanism of Action of Small Molecule Modulators of Capsid Assembly" Biochemistry, 2015, 54: 2240-2248.

Lamorte et al., "Discovery of Novel Small-Molecule HIV-1 Replication Inhibitors That Stabilize Capsid Complexes" Antimicrobial Agents and Chemotherapy, 2015, 57(10): 4622-4631.

Lazerwith et al., "New Antiretrovirals for HIV and Antivirals for HBV," in Comprehensive Medicinal Chemistry, 3rd Edition, 2017, pp. 1-36.

Lee et al., "Flexible Use of Nuclear Import Pathways by HIV-1," Cell Host & Microbe, 2010, 7:221-233.

Lemke et al., "Distinct Effects of Two HIV-1 Capsid Assembly Inhibitor Families That Bind the Same Site Within the N-Terminal Domain of the Viral CA Protein," J. Virol., Jun. 2012, 86(12):6643-6655.

Macmillan et al., "Evaluation of alternative solvent in common amide coupling reactions: replacement of dicloromethane and N,N-dimethlformamide," Green Chem, 2013, 15: 596-600.

Matreyek et al., "Nucleoporin NUP153 Phenylalanine-Glycine Motifs Engage a Common Binding Pocket within the HIV-1 Capsid Protein to Mediate Lentiviral Infectivity" PLOS Pathogens, 2013, 9(10): e1003693. 21 pages.

Mitchell et al., "Bioreversible Protection for the Phospho Group: Bioactivation of the Di(4-Acyloxybenzyl) and Mono(4-acyloxybenzyl) Phosphoesters of Methylphosphonate and Phosphonoacetate," J. Chem. Soc. Perkin Trans. 1, 1992, pp. 2345-2353.

Miyaura et al., "Palladium-Catalyzed Cross-Coupling Reactions of Oganoboron Compounds," Chem Rev, 1995, 95:2457-2483.

Molina et al., "On-Demand Preexposure Prophylaxis in Men at High Risk for HIV-1 Infection", The New England Journal of Medicine, Dec. 2015, 353:2237-2246.

Montalbetti et al., "Amide bond formation and peptide coupling," Tetrahedon, 2005, 61:10827-10852.

Morissette et al., "High-throughput crystallization: polymorphs, salts, co-crystals and solvates of pharmaceutical solids," Advanced Drug Delivery Reviews, Feb. 2004, 56(3):275-300.

Nicolaou et al., "Palladium-Catalyzed Cross-Coupling Reactions in Total Synthesis," Angew Chem Int Ed, 2005, 44:4442-4489.

Ovais et al. "Synthesis, antiproliferative and anti-inflammatory activities of some novel 6-aryl-2-(p-(methanesulfonyl)phenyl)-4,5-dihydropyridazi-3(2H)-ones," European Journal of Medicinal Chemistry, 2013, 67:352-358.

Owen et al., "Strengths, weaknesses, opportunities and challenges for long acting injectable therapies: Insights for applications in HIV therapy," Advances Drug Delivery Reviews, 2016, 103:144-156.

Palella et al., "Declining morbidity and mortality among patients with advanced human immunodeficiency virus infection," N Engl. J Med., 1998, 338:853-860.

Patel et al., "Poloxamers: a pharmaceutical excipients with therapeutic behaviors," International Journal of PharmTech Research, 2009, 1(2):299-303.

Pornillos et al., "Atomic level modeling of the HIV capsid," Nature, Jan. 2011, 469(7330):424-427.

(56) References Cited

OTHER PUBLICATIONS

Pornillos et al., "X-ray Structures of the Hexameric Building Block of the HIV Capsid" Cell, 2009, 137(7): 1282-1292.
Pornillos et al., Supplemental Data for "X-ray Structures of the Hexameric Building Block of the HIV Capsid" Cell, 2009, 137(7):1282-92.
Powers et al., "Synthesis of Methyl-, Fluoro-, and Chloro-substituted 6-Hydroxyisoindolin-1-1-Ones," Tetrahedron Letters, 2009, 50(12):1267-1269.
Price et al., "CPSF6 Defines a Conserved Capsid Interface That Modulates HIV-1 Replication," PLOS Pathogens, 2012, 8(8):e1002896, 14 pages.
Puech et al., "Intracellular Delivery of Nucleoside Monophosphates Through a Reductase-Mediated Activation Process," Antiviral Res., Oct. 1993, 22(2-3):155-174.
Pungpo et al., "Computer-aided molecular design of highly potent HIV-1 RT inhibitors: 3D QSAR and molecular docking studies of efavirenz derivatives," SAR and QSAR in Enviromnental Research, 2006, 17(4):353-370.
Registry (STN) [online], Mar. 22, 2010 [date of retrieval: Nov. 12, 2018], CAS registry No. 1213065-84-9.
Registry (STN) [online], Mar. 23, 2010 [date of retrieval: Nov. 12, 2018], CAS registry No. 1213495-28-3.
Registry (STN)[online], Nov. 15, 1991, STN Registry No. 137349-29-2, 1 page.
Rihn et al., "Extreme Genetic Fragility of the HIV-1 Capsid," PLOS One, 2013, 9(6): e1003461, 25 pages.
Shi et al., "Small-Molecule Inhibition of Human Immunodeficiency Virus Type 1 Capsid Destabilization," Journal of Virology, 2011, 85(1): 542-549.
Siddiqui et al., "The Presence of Substituents on the Aryl Moiety of the Aryl Phosphoramidate Derivative of d4T Enhances Anti-HIV Efficacy in Cell Culture: A Structure-Activity Relationship," J. Med. Chem., 1999, 42:393-399.
Silverman, "The Organic Chemistry of Drug Design and Drug Action," Elsevier, 2004, pp. 121-169.
Silvestri et al., "Novel Indolyl Aryl Sulfones Active against HIV-1 Carrying NNRTI Resistance Mutations: Synthesis and SAR Studies," Journal of Medical Chemistry, 2003, 46(12): 2482-2493.
Smith et al., "Evolutionary Dynamics of Complex Networks of HIV Drug-Resistant Strains: The Case of San Francisco," Science, 2010, 327(5966):697-701.
Sticht et al., "A peptide inhibitor of HIV-1 assembly in vitro," Nature Structural & Molecular Biology, 2005, 12(8): 671-677.
Sublocade Product Label, issued: Nov. 2017, 43 pages.
Taiwo, "Understanding Transmitted HIV Resistance Through the Experience in the USA," International Journal of Infectious Diseases, 2009, 13(5):552-559.
Talele, "The 'Cyclopropyl Fragment' is a Versatile Player that Frequently Appears in Preclinical/Clinical Drug Molecules," Journal of Medicinal Chemistry, 2016, 59(19):8712-8756.
Tanaka et al., "One-Pot Synthesis of Metalated Pyridines from Two Acetylenes, a Nitrile, and a Titanium(II) Alkoxide," J. Am. Chem. Soc., 2005, 127(21):7774-7780.
Tang et al., "Antiviral Inhibition of the HIV-1 Capsid Protein," J. Mol. Biol., 2003, 327: 1013-1020.
Thenin-Houssier et al., "HIV-1 capsid inhibitors as antiretroviral agents," Curr. HIV Res., 2016, 14(3):270-282.
Tse et al., "Discovery of Novel Potent HIV Capsid Inhibitors with Long-Acting Potential," Abstract for Oral Presentation at the Conference on Retroviruses and Opportunistic Infections (CROI), Seattle, WA, 2017, 18 pages.
Tsiang et al., "A Trimer of Dimers Is the Basic Building Block for Human Immunodeficiency Virus-1 Capsid Assembly," Biochemistry, 2012, 51: 4416-4428.
Wong et al., "SPR Assay Development to Characterize Caps id Inhibitors Binding & MOA," Poster Presented at the Developments in Protein Interaction (DiPIA), La Jolla, CA, 2014, 1 page.
Wu et al., "Selective Inhibitors of Tumor Progression Loci-2(Tpl2) Kinase with Potent Inhibition of TNF-Alpha Production in Human Whole Blood," Bioorg. Med. Chem. Lett., 2009, 19(13):3485-3488.
Xianghui et al., "In Silico Virtual Screening," Biotechnology in the Post-Genome Era, 2003, 16 pages.
Yadav et al., "Co-crystals: a novel approach to modify physicochemical properties of active pharmaceutical ingredients," Indian J. Pharm. Sci., 2009, 71(4):359-370.
Yale, "The trifluoromethyl group in medicinal chemistry," J. Med. Chem., 1958, 1(2):121-133.
Yang et al., "Design, synthesis and anti-HIV-1 evaluation of hydrazide-based peptidomimetics as selective gelatinase inhibitors," Bioorganic & Medicinal Chemistry, May 2016, 24(9):2125-2136.
Yant et al., "An Improved PF74 Analog Inhibits Multiple HIV Capsid Functions Independently of Host Cyclophilin A and CPSF6," Poster Presented at the Conference on Retroviruses and Opportunistic Infections (CROI), Boston, Massachusetts, 2014, 1 page.
Yant et al., "PF74 Inhibits Multiple HIV Capsid Functions Independently of Host Cydophilin A and CPSF6," Abstract for Poster Presented at the Conference on Retroviruses and Opportunistic Infections (CROI), Boston, Massachusetts, 2014, 1 page.
Zheng et al. "GS-6207: A Novel, Potent and Selective First-In-Class Inhibitor of HIV-1 Capsid Function Displays Nonclinical Pharmacokinetics Supporting Long-Acting Potential," Poster Presented at ID Week 2018, San Francisco, CA, 1 page.
Zhou et al. "HIV-1 Resistance to the Capsid-Targeting Inhibitor PF74 Results in Altered Dependence on Host Factors Required for Virus Nuclear Entry," Journal of Virology, 2015, 89(17): 9068-9079.
Palombo et al., "Prodrug and conjugate drug delivery strategies for improving HIV/ADS therapy," Journal of drug delivery science and technology, Jan. 2009, 19(1): 31 pages.
PCT International Search Report in International Appln. No. PCT/US2022/051734, dated Mar. 13, 2023, 3 pages.
Magiorakos et al., "Multidrug-resistant, extensively drug-resistant and pandrug-resistant bacteria: an international expert proposal for interim standard definitions for acquired resistance," Clinical Microbiology and Infection, Mar. 2012, 18(3): 268-281.

THERAPEUTIC COMPOUNDS FOR HIV VIRUS INFECTION

CROSS REFERENCE TO RELATED APPLICATIONS

This application claims the benefit of U.S. Provisional Application No. 63/285,730, filed on Dec. 3, 2021, and U.S. Provisional Application No. 63/356,889, filed on Jun. 29, 2022, the entire contents of each of which is hereby incorporated by reference in its entirety.

FIELD

This disclosure relates generally to novel compounds and pharmaceutical compositions comprising said compounds for use in the prevention or treatment of a Retroviridae viral infection, including an infection caused by the human immunodeficiency virus (HIV). This disclosure also relates to methods of making said compounds and intermediates in the preparation of said compounds.

BACKGROUND

Positive-single stranded RNA viruses comprising the Retroviridae family include those of the subfamily *Orthoretrovirinae* and genera *Alpharetrovirus, Betaretrovirus, Gammaretrovirus, Deltaretrovirus, Epsilonretrovirus, Lentivirus*, and *Spumavirus* which cause many human and animal diseases. Among the Lentivirus, HIV-1 infection in humans leads to depletion of T helper cells and immune dysfunction, producing immunodeficiency and vulnerability to opportunistic infections. Treating HIV-1 infections with highly active antiretroviral therapies (HAART) has proven to be effective at reducing viral load and significantly delaying disease progression (Hammer, S. M., et al.; *JAMA* 2008, 300: 555-570). However, these treatments could lead to the emergence of HIV strains that are resistant to current therapies (Taiwo, B., International *Journal of Infectious Diseases* 2009, 13:552-559; Smith, R. J., et al., *Science* 2010, 327: 697-701). Therefore, there is a pressing need to discover new antiretroviral agents that are active against emerging drug-resistant HIV variants.

Also of interest in the area of HIV therapies and treatments is providing regimens to patients with improved pharmacokinetic properties, including, for example, increased potency, long-acting pharmacokinetics, low solubility, low clearance, and/or other properties. While current regimens for treating HIV have progressed enough that patients no longer have to take multiple pills multiple times a day, patients today still are required to take a pill every day for the foreseeable span of their life. Thus, it would be beneficial to have HIV therapies that require patients take medication less than once a day (e.g. once every couple of days, once a week, once every other week, once a month, and so forth) or take a smaller effective dose of the medication(s) on a daily, weekly, monthly, or longer basis.

SUMMARY

In one embodiment, provided herein is a compound of Formula I,

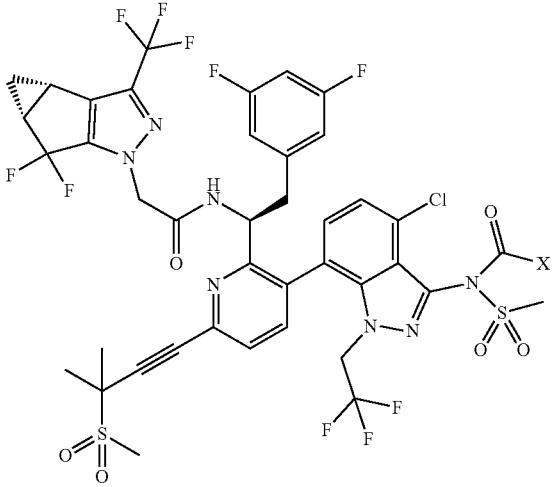

Formula I or a pharmaceutically acceptable salt thereof,
wherein
  X is —NR$^1$R$^2$, C$_{1-10}$ alkyl, or C$_{2-6}$ alkenyl,
    wherein the C$_{1-10}$ alkyl and C$_{2-6}$ alkenyl are each independently substituted with 1-3 Y groups;
  each Y independently is —B(OH)$_2$, —CN, halogen, R$^a$, R$^b$, R$^c$, phenyl, naphthalenyl, 5-6 membered monocyclic heteroaryl, or 8-10 membered fused bicyclic heteroaryl,
    wherein the phenyl, naphthalenyl, 5-6 membered monocyclic heteroaryl, and 8-10 membered fused bicyclic heteroaryl are each independently substituted with 1-5 R$^3$ groups, or
  two Y groups on the same carbon, together with the carbon to which they are attached, form a C$_{3-5}$ monocyclic cycloalkyl;
  R$^1$ is H or C$_{1-6}$ alkyl, wherein the C$_{1-6}$ alkyl is optionally substituted with 1-3 groups independently selected from —CN, halogen, R$^a$, R$^b$, and R$^c$;
  R$^2$ is phenyl or 5-6 membered monocyclic heteroaryl, wherein the phenyl and 5-6 membered monocyclic heteroaryl are each independently optionally substituted with 1-3 groups independently selected from —CN, halogen, R$^a$, R$^b$, R$^c$, and C$_{1-6}$ alkyl,
    wherein the C$_{1-6}$ alkyl is optionally substituted with 1-3 groups independently selected from —CN, halogen, R$^a$, R$^b$, and R$^c$;
  each R$^3$ independently is R$^a$, R$^b$, R$^c$, C$_{1-6}$ alkyl, or 5-6 membered monocyclic heteroaryl, wherein the C$_{1-6}$ alkyl and 5-6 membered monocyclic heteroaryl are each independently optionally substituted with 1-3 groups independently selected from —CN, halogen, R$^a$, R$^b$, and R$^c$;
  each R$^a$ independently is —P(O)(OH)$_2$ or —OP(O)(OH)$_2$;
  each R$^b$ independently is —C(O)R$^4$, —C(O)OR$^4$, —C(O)NR$^5$R$^5$, —C(O)C(O)OR$^4$, —S(O)$_2$R$^4$, —S(O)$_2$NR$^5$R$^5$, or —S(O)$_{20}$R$^4$;
  each R$^c$ independently is —OR$^4$, —OC(O)R$^4$, —OC(O)C(O)OR$^4$, —(O(C$_{1-4}$ alkyl))$_n$OR$^4$, —NR$^5$R$^5$, —N$^+$R$^5$R$^5$R$^{5a}$, —NR$^5$C(O)R$^4$, —NR$^5$C(O)NR$^5$R$^5$, —NR$^5$C(O)OR$^4$, —NR$^5$C(O)C(O)OR$^4$, or —NR$^5$S(O)$_2$R$^4$;

each $R^4$ independently is H or $C_{1-6}$ alkyl, wherein the $C_{1-6}$ alkyl is optionally substituted with 1-3 groups independently selected from —CN, halogen, $R^a$, $R^d$, and Re;

each $R^5$ independently is H, $R^d$, $C_{1-6}$ alkyl, or 5-6 membered monocyclic heteroaryl,
   wherein the $C_{1-6}$ alkyl is optionally substituted with 1-3 groups independently selected from —CN, halogen, $=NR^{5a}$, $R^a$, $R^d$, $R^c$, phenyl, naphthalenyl, and 8-10 membered fused bicyclic heteroaryl,
   wherein the 5-6 membered monocyclic heteroaryl is optionally substituted with 1-3 groups independently selected from —CN, halogen, $R^a$, $R^d$, and Re;

each $R^{5a}$ independently is H or $C_{1-3}$ alkyl;

each $R^d$ independently is —C(O)$R^6$, —C(O)O$R^6$, —C(O)N$R^7R^7$, —C(O)C(O)O$R^6$, —S(O)$_2R^6$, —S(O)$_2$N$R^7R^7$, or —S(O)$_2$O$R^6$;

each $R^c$ independently is —O$R^6$, —OC(O)$R^6$, —OC(O)C(O)O$R^6$, —N$R^7R^7$, —N$R^7$C(O)$R^7$, —N$R^7$C(O)N$R^7R^7$, —N$R^7$C(O)O$R^6$, —N$R^7$C(O)C(O)O$R^6$, or —N$R^7$S(O)$_2R^6$;

each $R^6$ independently is H or $C_{1-6}$ alkyl, wherein the $C_{1-6}$ alkyl is optionally substituted with 1-3 groups independently selected from CN, halogen, $R^a$, $R^f$, and $R^g$;

each $R^7$ independently is H, $R^f$, or $C_{1-6}$ alkyl, wherein the $C_{1-6}$ alkyl is optionally substituted with 1-3 groups independently selected from —CN, halogen, $R^a$, $R^f$, and $R^g$;

each $R^f$ independently is —C(O)$R^8$, —C(O)O$R^8$, —C(O)N$R^8R^8$, —C(O)C(O)O$R^8$, —S(O)$_2R^8$, —S(O)$_2$N$R^8R^8$, or —S(O)$_2$O$R^8$;

each $R^g$ independently is —O$R^8$, —OC(O)$R^8$, —OC(O)C(O)O$R^8$, —N$R^8R^8$, —N$R^8$C(O)$R^8$, —N$R^8$C(O)N$R^8R^8$, —N$R^8$C(O)O$R^8$, —N$R^8$C(O)C(O)O$R^8$, or —N$R^8$S(O)$_2R^8$;

each $R^8$ independently is H or $C_{1-6}$ alkyl, wherein the $C_{1-6}$ alkyl is optionally substituted with 1-3 groups independently selected from —OH, CN, halogen, —C(O)OH, and $R^a$;

n is 1, 2, 3, 4, or 5; and wherein each 5-6 membered monocyclic heteroaryl and 8-10 membered fused bicyclic heteroaryl independently have 1-4 ring heteroatoms independently selected from N, O, and S.

In one embodiment, provided herein is a pharmaceutical composition comprising a therapeutically effective amount of a compound provided herein, or a pharmaceutically acceptable salt thereof, and a pharmaceutically acceptable excipient.

In one embodiment, provided herein is a method of treating or preventing a human immunodeficiency virus (HIV) infection in a patient in need thereof comprising administering to the patient a therapeutically effective amount of a compound provided herein, or a pharmaceutically acceptable salt thereof, or a pharmaceutical composition provided herein.

In one embodiment, provided herein is a method of treating a human immunodeficiency virus (HIV) infection in a heavily treatment-experienced patient, the method comprising administering to the patient a therapeutically effective amount of a compound provided herein, or a pharmaceutically acceptable salt thereof, or a pharmaceutical composition provided herein.

In one embodiment, provided herein is a therapeutically effective amount of a compound provided herein, or a pharmaceutically acceptable salt thereof, or a pharmaceutical composition provided herein for use in therapy.

In one embodiment, provided herein is a compound provided herein, or a pharmaceutically acceptable salt thereof, or a pharmaceutical composition provided herein for use in a method of treating or preventing a human immunodeficiency virus (HIV) infection in a patient in need thereof, the method comprising administering to the patient a therapeutically effective amount of the compound, or a pharmaceutically acceptable salt thereof, or the pharmaceutical composition.

In one embodiment, provided herein is a compound provided herein, or a pharmaceutically acceptable salt thereof, or a pharmaceutical composition provided herein for use in a method of treating a human immunodeficiency virus (HIV) infection in a heavily treatment-experienced patient, the method comprising administering to the patient a therapeutically effective amount of the compound, or a pharmaceutically acceptable salt thereof, or the pharmaceutical composition.

DETAILED DESCRIPTION

I. Definitions

The description below is made with the understanding that the present disclosure is to be considered as an exemplification of the claimed subject matter, and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

As used in the present disclosure, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named. A solid line coming out of the center of a ring (including a fused, bridged or spirocyclic ring system) indicates that the point of attachment for a substituent on the ring can be at any ring atom. For example, $R^{aa}$ in the below structure can be attached to any of the five carbon ring atoms or $R^{aa}$ can replace the hydrogen attached to the nitrogen ring atom:

As another example, $R^{aa}$ in the below structure:

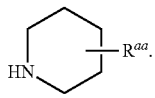

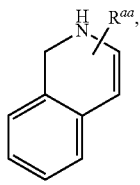

$R^{aa}$ can be attached to any of the numbered positions shown below:

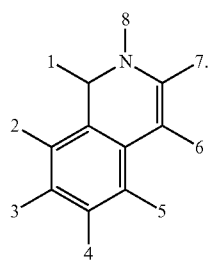

A solid line coming out of the center of a ring (including a fused, bridged, or spirocyclic ring system) indicates that the point of attachment for the ring system to the rest of the compound can be at any ring atom of the fused, bridged, or spirocyclic ring system. For example, in the below structure:

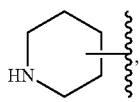

the monocyclic heterocyclyl can be attached to the rest of the compound at any of the numbered positions shown below:

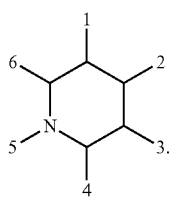

As another example, in the below fused bicyclic heterocyclic structure,

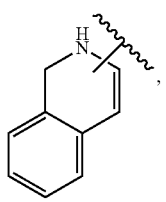

the fused bicyclic heterocyclyl can be attached to the rest of the compound at any of the eight numbered positions shown below:

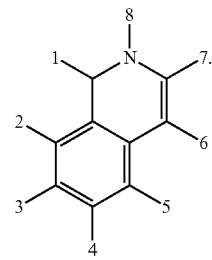

The prefix "$C_{u-v}$" indicates that the following group has from u to v carbon atoms. For example, "$C_{1-6}$ alkyl" indicates that the alkyl group has from 1 to 6 carbon atoms. Likewise, the term "x-y membered" rings, wherein x and y are numerical ranges, such as "3 to 12-membered heterocyclyl", refers to a ring containing x-y atoms (i.e., 3-12), of which up to 80% may be heteroatoms, such as N, O, S, P, and the remaining atoms are carbon.

Also, certain commonly used alternative chemical names may or may not be used. For example, a divalent group such as a divalent "alkyl" group, a divalent "aryl" group, etc., may also be referred to as an "alkylene" group or an "alkylenyl" group, or alkylyl group, an "arylene" group or an "arylenyl" group, or arylyl group, respectively.

"A compound disclosed herein" or "a compound of the present disclosure" or "a compound provided herein" or "a compound described herein" refers to the compounds of Formula I. Also included are the specific compounds of Examples 1 to 54.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, the term "about X" includes description of "X".

"Alkyl" refers to an unbranched or branched saturated hydrocarbon chain. As used herein, alkyl has 1 to 20 carbon atoms (i.e., $C_{1-20}$ alkyl), 1 to 12 carbon atoms (i.e., $C_{1-12}$ alkyl), 1 to 8 carbon atoms (i.e., $C_{1-8}$ alkyl), 1 to 6 carbon atoms (i.e., $C_{1-6}$ alkyl), 1 to 4 carbon atoms (i.e., $C_{1-4}$ alkyl), 1 to 3 carbon atoms (i.e., $C_{1-3}$ alkyl), or 1 to 2 carbon atoms (i.e., $C_{1-2}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —$(CH_2)_3CH_3$), sec-butyl (i.e. —$CH(CH_3)CH_2CH_3$), isobutyl (i.e. —$CH_2CH(CH_3)_2$) and tert-butyl (i.e. —$C(CH_3)_3$); and "propyl" includes n-propyl (i.e. —$(CH_2)_2CH_3$) and isopropyl (i.e. —$CH(CH_3)_2$).

"Alkenyl" refers to an aliphatic group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkylene" refers to a divalent and unbranched saturated hydrocarbon chain. As used herein, alkylene has 1 to 20 carbon atoms (i.e., $C_{1-20}$ alkylene), 1 to 12 carbon atoms (i.e., $C_{1-12}$ alkylene), 1 to 8 carbon atoms (i.e., $C_{1-8}$ alkylene), 1 to 6 carbon atoms (i.e., $C_{1-6}$ alkylene), 1 to 4 carbon atoms (i.e., $C_{1-4}$ alkylene), 1 to 3 carbon atoms (i.e., $C_{1-3}$ alkylene), or 1 to 2 carbon atoms (i.e., $C_{1-2}$ alkylene). Examples of alkylene groups include methylene, ethylene, propylene, butylene, pentylene, and hexylene. In some embodiments, an alkylene is optionally substituted with an alkyl group. Examples of substituted alkylene groups include —CH(CH$_3$)CH$_2$—, —CH$_2$CH(CH$_3$)—, —CH$_2$CH(CH$_2$CH$_3$)—, —CH$_2$C(CH$_3$)$_2$—, —C(CH$_3$)$_2$CH$_2$—, —CH(CH$_3$)CH(CH$_3$)—, —CH$_2$C(CH$_2$CH$_3$)(CH$_3$)—, and —CH$_2$C(CH$_2$CH$_3$)$_2$.

"Alkoxy" refers to the group "alkyl-O". Examples of alkoxy groups include methoxy, ethoxy, n-propoxy, isopropoxy, n-butoxy, tert-butoxy, sec-butoxy, n-pentoxy, n-hexoxy, and 1,2-dimethylbutoxy. "Haloalkoxy" refers to an alkoxy group as defined above, wherein one or more hydrogen atoms are replaced by a halogen.

"Acyl" refers to a group —C(=O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amido" refers to both a "C-amido" group which refers to the group —C(=O)NR$^y$R$^z$ and an "N-amido" group which refers to the group —NR$^y$C(=O)R$^z$, wherein R$^y$ and R$^z$ are independently selected from the group consisting of hydrogen, alkyl, aryl, haloalkyl, heteroaryl, cycloalkyl, or heterocyclyl; each of which may be optionally substituted.

"Amino" refers to the group —NR$^y$R$^z$ wherein R$^y$ and R$^z$ are independently selected from the group consisting of hydrogen, alkyl, haloalkyl, aryl, heteroaryl, cycloalkyl, or heterocyclyl; each of which may be optionally substituted.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Cyano" or "carbonitrile" refers to the group —CN.

"Cycloalkyl" refers to a saturated or partially saturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

"Bridged" refers to a ring fusion wherein non-adjacent atoms on a ring are joined by a divalent substituent, such as an alkylenyl group, an alkylenyl group containing one or two heteroatoms, or a single heteroatom. Quinuclidinyl and admantanyl are examples of bridged ring systems.

The term "fused" refers to a ring which is bound to an adjacent ring.

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Heteroalkylene" refers to a divalent and unbranched saturated hydrocarbon chain having one, two, or three heteroatoms selected from NH, O, or S. As used herein, a heteroalkylene has 1 to 20 carbon atoms and one, two, or three heteroatoms selected from NH, 0, and S (i.e., $C_{1-20}$ heteroalkylene); 1 to 8 carbon atoms and one, two, or three heteroatoms selected from NH, O, and S (i.e., $C_{1-8}$ heteroalkylene); 1 to 6 carbon atoms and one, two, or three heteroatoms selected from NH, O, and S S (i.e., $C_{1-6}$ heteroalkylene); 1 to 4 carbon atoms and one, two, or three heteroatoms selected from NH, O, and S (i.e., $C_{1-4}$ heteroalkylene); 1 to 3 carbon atoms and one, two, or three heteroatoms selected from NH, O, and S (i.e., $C_{1-3}$ heteroalkylene); or 1 to 2 carbon atoms and one, two, or three heteroatoms selected from NH, O, and S (i.e., $C_{1-3}$ heteroalkylene). For example, —CH$_2$O— is a $C_1$ heteroalkylene and —CH$_2$SCH$_2$— is a $C_2$ heteroalkylene. Examples of heteroalkylene groups include —CH$_2$CH$_2$OCH$_2$—, —CH$_2$SCH$_2$OCH$_2$—, —CH$_2$O—, and —CH$_2$NHCH$_2$—. In some embodiments, a heteroalkylene is optionally substituted with an alkyl group. Examples of substituted heteroalkylene groups include —CH(CH$_3$)N(CH$_3$)CH$_2$—, —CH$_2$OCH(CH$_3$)—, —CH$_2$CH(CH$_2$CH$_3$)S—, —CH$_2$NHC(CH$_3$)$_2$—, —C(CH$_3$)$_2$SCH$_2$—, —CH(CH$_3$)N(CH$_3$)CH(CH$_3$)$_0$—, —CH$_2$SC(CH$_2$CH$_3$)(CH$_3$)—, and —CH$_2$C(CH$_2$CH$_3$)$_2$NH—.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 carbon ring atoms (i.e., $C_{1-20}$ heteroaryl), 3 to 12 carbon ring atoms (i.e., $C_{3-12}$ heteroaryl), or 3 to 8 carbon ring atoms (i.e., $C_{3-8}$ heteroaryl); and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

"Heterocyclyl" or "heterocyclic ring" or "heterocycle" refers to a non-aromatic cyclic alkyl group, with one or more ring heteroatoms independently selected from nitrogen, oxygen and sulfur. As used herein, "heterocyclyl" or "heterocyclic ring" or "heterocycle" refer to rings that are saturated or partially saturated unless otherwise indicated, e.g., in some embodiments "heterocyclyl" or "heterocyclic ring" or "heterocycle" refers to rings that are partially saturated where specified. The term "heterocyclyl" or "heterocyclic ring" or "heterocycle" includes heterocycloalkenyl groups (i.e., the heterocyclyl group having at least one double bond). A heterocyclyl may be a single ring or multiple rings wherein the multiple rings may be fused, bridged, or spiro. As used herein, heterocyclyl has 2 to 20 carbon ring atoms (i.e., $C_{2-20}$ heterocyclyl), 2 to 12 carbon ring atoms (i.e., $C_{2-12}$ heterocyclyl), 2 to 10 carbon ring atoms (i.e., $C_{2-10}$ heterocyclyl), 2 to 8 carbon ring atoms (i.e., $C_{2-8}$ heterocyclyl), 3 to 12 carbon ring atoms (i.e., $C_{3-12}$ heterocyclyl), 3 to 8 carbon ring atoms (i.e., $C_{3-8}$ heterocyclyl), or 3 to 6 carbon ring atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include pyrrolidinyl, piperidinyl, piperazinyl, oxetanyl, dioxolanyl, azetidinyl, and morpholinyl. As used herein, the term "bridged-heterocyclyl" refers to a four- to ten-membered cyclic moiety connected at two non-adjacent atoms of the heterocyclyl with one or more (e.g., 1 or 2) four- to ten-membered cyclic moiety having at least one heteroatom where each heteroatom is independently selected from nitrogen, oxygen, and sulfur. As used herein, "bridged-heterocyclyl" includes bicyclic and tricyclic ring systems. Also as used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl. As used herein, the terms "heterocycle", "heterocyclyl", and "heterocyclic ring" are used interchangeably. In some embodiments, a heterocyclyl is substituted with an oxo group.

"Hydroxy" or "hydroxyl" refers to the group —OH.

"Oxo" refers to the group (═O) or (O).

"Sulfonyl" refers to the group —S(O)$_2$R$^{bb}$, where R$^{bb}$ is alkyl, haloalkyl, heterocyclyl, cycloalkyl, heteroaryl, or aryl. Examples of sulfonyl are methyl sulfonyl, ethyl sulfonyl, phenyl sulfonyl, and toluenesulfonyl.

Whenever the graphical representation of a group terminates in a singly bonded nitrogen atom, that group represents an —NH group unless otherwise indicated. Similarly, unless otherwise expressed, hydrogen atom(s) are implied and deemed present where necessary in view of the knowledge of one of skill in the art to complete valency or provide stability.

The terms "optional" or "optionally" mean that the subsequently described event or circumstance may or may not occur, and that the description includes instances where said event or circumstance occurs and instances in which it does not. Also, the term "optionally substituted" means that any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

In some embodiments, a substituted cycloalkyl, a substituted heterocyclyl, a substituted aryl, and/or a substituted heteroaryl includes a cycloalkyl, a heterocyclyl, an aryl, and/or a heteroaryl that has a substituent on the ring atom to which the cycloalkyl, heterocyclyl, aryl, and/or heteroaryl is attached to the rest of the compound. For example, in the below moiety, the cyclopropyl is substituted with a methyl group:

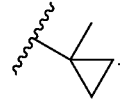

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

"Enantiomers" are a pair of stereoisomers that are non-superimposable mirror images of each other. A 1:1 mixture of a pair of enantiomers is a "racemic" mixture. A mixture of enantiomers at a ratio other than 1:1 is a "scalemic" mixture.

"Diastereoisomers" are stereoisomers that have at least two asymmetric atoms, but which are not mirror-images of each other.

A "tautomer" refers to a proton shift from one atom of a molecule to another atom of the same molecule. The present disclosure includes tautomers of any compounds provided herein.

Some of the compounds provided herein exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

A "solvate" is formed by the interaction of a solvent and a compound. Solvates of salts of the compounds provided herein are also provided. Hydrates of the compounds provided herein are also provided.

Any formula or structure provided herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I Various isotopically labeled compounds of the present disclosure, for example those into which radioactive isotopes such as $^2$H, $^3$H, $^{13}$C and $^{14}$C are incorporated, are also provided herein. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The present disclosure also includes compounds of Formula I, in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the present disclosure may have improved DMPK (drug metabolism and pharmacokinetics) properties, relating to absorption, distribution, metabolism and excretion (ADME). Substitution with heavier isotopes such as deuterium may afford certain therapeutic advantages resulting from greater metabolic stability, for example, increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure, any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure, any atom specifically designated as a deuterium (D) is meant to represent deuterium.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, mono, di or tri cycloalkyl amines, mono, di or tri arylamines or mixed amines, and the like. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Treatment" or "treating" is an approach for obtaining beneficial or desired results including clinical results. Beneficial or desired clinical results may include one or more of the following: a) inhibiting the disease or condition (i.e., decreasing one or more symptoms resulting from the disease or condition, and/or diminishing the extent of the disease or condition); b) slowing or arresting the development of one or more clinical symptoms associated with the disease or condition (i.e., stabilizing the disease or condition, preventing or delaying the worsening or progression of the disease or condition, and/or preventing or delaying the spread (i.e., metastasis) of the disease or condition); and/or c) relieving the disease, that is, causing the regression of clinical symptoms (i.e., ameliorating the disease state, providing partial or total remission of the disease or condition, enhancing effect of another medication, delaying the progression of the disease, increasing the quality of life, and/or prolonging survival).

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or pharmaceutically acceptable salts, isomer, or a mixture thereof means an amount sufficient to effect treatment when administered to a subject, to provide a therapeutic benefit such as amelioration of symptoms or slowing of disease progression. For example, a therapeutically effective amount may be an amount sufficient to improve a symptom of a Retroviridae viral infection, including but not limited to HIV infection. The therapeutically effective amount may vary depending on the subject, and the disease or condition being treated, the weight and age of the subject, the severity of the disease or condition, and the manner of administering, which can readily be determined by one of ordinary skill in the art.

II. Compounds

In one embodiment, provided herein is a compound of Formula I,

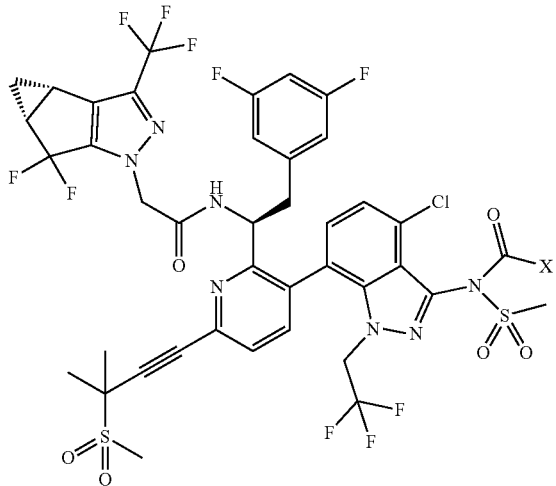

Formula I or a pharmaceutically acceptable salt thereof, wherein

X is —$NR^1R^2$, $C_{1-10}$ alkyl, or $C_{2-6}$ alkenyl,
wherein the $C_{1-10}$ alkyl and $C_{2-6}$ alkenyl are each independently substituted with 1-3 Y groups;

each Y independently is —$B(OH)_2$, —CN, halogen, $R^a$, $R^b$, $R^c$, phenyl, naphthalenyl, 5-6 membered monocyclic heteroaryl, or 8-10 membered fused bicyclic heteroaryl,
wherein the phenyl, naphthalenyl, 5-6 membered monocyclic heteroaryl, and 8-10 membered fused bicyclic heteroaryl are each independently substituted with 1-5 $R^3$ groups, or
two Y groups on the same carbon, together with the carbon to which they are attached, form a $C_{3-5}$ monocyclic cycloalkyl;

$R^1$ is H or $C_{1-6}$ alkyl, wherein the $C_{1-6}$ alkyl is optionally substituted with 1-3 groups independently selected from —CN, halogen, $R^a$, $R^b$, and Re;

$R^2$ is phenyl or 5-6 membered monocyclic heteroaryl, wherein the phenyl and 5-6 membered monocyclic heteroaryl are each independently optionally substituted with 1-3 groups independently selected from —CN, halogen, $R^a$, $R^b$, $R^c$, and $C_{1-6}$ alkyl,
wherein the $C_{1-6}$ alkyl is optionally substituted with 1-3 groups independently selected from —CN, halogen, $R^a$, $R^b$, and $R^c$;

each $R^3$ independently is $R^a$, $R^b$, $R^c$, $C_{1-6}$ alkyl, or 5-6 membered monocyclic heteroaryl, wherein the $C_{1-6}$ alkyl and 5-6 membered monocyclic heteroaryl are each independently optionally substituted with 1-3 groups independently selected from —CN, halogen, $R^a$, $R^b$, and $R^c$;

each $R^a$ independently is —$P(O)(OH)_2$ or —$OP(O)(OH)_2$;

each $R^b$ independently is —$C(O)R^4$, —$C(O)OR^4$, —$C(O)NR^5R^5$, —$C(O)C(O)OR^4$, —$S(O)_2R^4$, —$S(O)_2NR^5R^5$, or —$S(O)_{20}R^4$;

each Re independently is —$OR^4$, —$OC(O)R^4$, —$OC(O)C(O)OR^4$, —$(O(C_{1-4}\ alkyl))_nOR^4$, —$NR^5R^5$, —$N+R^5R^5R^{5a}$, —$NR^5C(O)R^4$, —$NR^5C(O)NR^5R^5$, —$NR^5C(O)OR^4$, —$NR^5C(O)C(O)OR^4$, or —$NR^5S(O)_2R^4$;

each $R^4$ independently is H or $C_{1-6}$ alkyl, wherein the $C_{1-6}$ alkyl is optionally substituted with 1-3 groups independently selected from —CN, halogen, $R^a$, $R^d$, and Re;

each $R^5$ independently is H, $R^d$, $C_{1-6}$ alkyl, or 5-6 membered monocyclic heteroaryl,
wherein the $C_{1-6}$ alkyl is optionally substituted with 1-3 groups independently selected from —CN, halogen, =$NR^{5a}$, $R^a$, $R^d$, $R^c$, phenyl, naphthalenyl, and 8-10 membered fused bicyclic heteroaryl,
wherein the 5-6 membered monocyclic heteroaryl is optionally substituted with 1-3 groups independently selected from —CN, halogen, $R^a$, $R^d$, and $R^c$;

each $R^{5a}$ independently is H or $C_{1-3}$ alkyl;

each $R^d$ independently is —$C(O)R^6$, —$C(O)OR^6$, —$C(O)NR^7R^7$, —$C(O)C(O)OR^6$, —$S(O)_2R^6$, —$S(O)_2NR^7R^7$, or —$S(O)_{20}R^6$;

each Re independently is —$OR^6$, —$OC(O)R^6$, —$OC(O)C(O)OR^6$, —$NR^7R^7$, —$NR^7C(O)R^7$, —$NR^7C(O)NR^7R^7$, —$NR^7C(O)OR^6$, —$NR^7C(O)C(O)OR^6$, or —$NR^7S(O)_2R^6$;

each $R^6$ independently is H or $C_{1-6}$ alkyl, wherein the $C_{1-6}$ alkyl is optionally substituted with 1-3 groups independently selected from CN, halogen, $R^a$, $R^f$, and $R^g$;

each $R^7$ independently is H, $R^f$, or $C_{1-6}$ alkyl, wherein the $C_{1-6}$ alkyl is optionally substituted with 1-3 groups independently selected from —CN, halogen, $R^a$, $R^f$, and $R^g$;

each $R^f$ independently is —C(O)R$^8$, —C(O)OR$^8$, —C(O)NR$^8$R$^8$, —C(O)C(O)OR$^8$, —S(O)$_2$R$^8$, —S(O)$_2$NR$^8$R$^8$, or —S(O)$_2$OR$^8$;

each $R^g$ independently is —OR$^8$, —OC(O)R$^8$, —OC(O)C(O)OR$^8$, —NR$^8$C(O)R$^8$, —NR$^8$C(O)NR$^8$R$^8$, —NR$^8$C(O)OR$^8$, —NR$^8$C(O)C(O)OR$^8$, or —NR$^8$S(O)$_2$R$^8$;

each $R^8$ independently is H or $C_{1-6}$ alkyl, wherein the $C_{1-6}$ alkyl is optionally substituted with 1-3 groups independently selected from —OH, CN, halogen, —C(O)OH, and $R^a$;

n is 1, 2, 3, 4, or 5; and wherein each 5-6 membered monocyclic heteroaryl and 8-10 membered fused bicyclic heteroaryl independently have 1-4 ring heteroatoms independently selected from N, O, and S.

In some embodiments of the compound of Formula I, or a pharmaceutically acceptable salt thereof, X is —NR$^1$R$^2$, $C_{1-10}$ alkyl, or $C_{2-6}$ alkenyl,
wherein the $C_{1-10}$ alkyl and $C_{2-6}$ alkenyl are each independently substituted with 1-3 Y groups;

each Y independently is —CN, halogen, $R^a$, $R^b$, $R^c$, $C_{3-5}$ monocyclic cycloalkyl, phenyl, or naphthalenyl,
wherein the phenyl and naphthalenyl are each independently substituted with 1-5 $R^3$ groups, or two Y groups on the same carbon, together with the carbon to which they are attached, form a $C_{3-5}$ monocyclic cycloalkyl;

$R^1$ is H or $C_{1-6}$ alkyl, wherein the $C_{1-6}$ alkyl is optionally substituted with 1-3 groups independently selected from —OH, —CN, halogen, —C(O)OH, and $R^a$;

$R^2$ is phenyl or 5-6 membered monocyclic heteroaryl, wherein the phenyl and 5-6 membered monocyclic heteroaryl are each independently optionally substituted with 1-3 groups independently selected from —CN, halogen, $R^a$, $R^b$, $R^c$, and $C_{1-6}$ alkyl;
wherein the $C_{1-6}$ alkyl is optionally substituted with 1-3 groups independently selected from —CN, halogen, $R^a$, $R^b$, and Re;

each $R^3$ independently is $R^a$, $R^b$, $R^c$, or $C_{1-6}$ alkyl, wherein the $C_{1-6}$ alkyl is optionally substituted with 1-3 groups independently selected from —CN, halogen, $R^a$, $R^b$, and $R^c$;

each $R^a$ independently is —P(O)(OH)$_2$ or —OP(O)(OH)$_2$;

each $R^b$ independently is —C(O)R$^4$, —C(O)OR$^4$, —C(O)NR$^5$R$^5$, —C(O)C(O)OR$^4$, —S(O)$_2$R$^4$, —S(O)$_2$NR$^5$R$^5$, or —S(O)$_{20}$R$^4$;

each Re independently is —OR$^4$, —OC(O)R$^4$, —OC(O)C(O)OR$^4$, —(O(C$_{1-4}$ alkyl))$_n$OR$^4$, —NR$^5$R$^5$, —N$^+$R$^5$R$^5$R$^{5a}$, —NR$^5$C(O)R$^4$, —NR$^5$C(O)NR$^5$R$^5$, —NR$^5$C(O)OR$^4$, —NR$^5$C(O)C(O)OR$^4$, or —NR$^5$S(O)$_2$R$^4$;

each $R^4$ independently is H or $C_{1-6}$ alkyl, wherein the $C_{1-6}$ alkyl is optionally substituted with 1-3 groups independently selected from —CN, halogen, $R^a$, $R^d$, and $R^c$;

each $R^5$ independently is H, $R^d$, or $C_{1-6}$ alkyl, wherein the $C_{1-6}$ alkyl is optionally substituted with 1-3 groups independently selected from —CN, halogen, =NR$^{5a}$, $R^a$, $R^d$, $R^c$, phenyl, and naphthalenyl;

each $R^{5a}$ independently is H or $C_{1-3}$ alkyl;

each $R^d$ independently is —C(O)R$^6$, —C(O)OR$^6$, —C(O)NR$^7$R$^7$, —C(O)C(O)OR$^6$, —S(O)$_2$R$^6$, —S(O)$_2$NR$^7$R$^7$, or —S(O)$_2$OR$^6$;

each $R^c$ independently is —OR$^6$, —OC(O)R$^6$, —OC(O)C(O)OR$^6$, —NR$^7$R$^7$, —NR$^7$C(O)R$^7$, —NR$^7$C(O)NR$^7$R$^7$, —NR$^7$C(O)OR$^6$, —NR$^7$C(O)C(O)OR$^6$, or —NR$^7$S(O)$_2$R$^6$;

each $R^6$ independently is H or $C_{1-6}$ alkyl, wherein the $C_{1-6}$ alkyl is optionally substituted with 1-3 groups independently selected from —OH, CN, halogen, —C(O)OH, and $R^a$;

each $R^7$ independently is H or $C_{1-6}$ alkyl, wherein the $C_{1-6}$ alkyl is optionally substituted with 1-3 groups independently selected from —OH, —CN, halogen, —C(O)OH, and $R^a$;

n is 1, 2, 3, 4, or 5; and wherein each 5-6 membered monocyclic heteroaryl and 8-10 membered fused bicyclic heteroaryl independently have 1-4 ring heteroatoms independently selected from N, O, and S.

In some embodiments of the compound of Formula I, or a pharmaceutically acceptable salt thereof, X is —NR$^1$R$^2$, $C_{1-10}$ alkyl, or $C_{2-4}$ alkenyl,
wherein the $C_{1-10}$ alkyl and $C_{2-4}$ alkenyl are each independently substituted with 1-3 Y groups;

each Y independently is —OH, —CN, halogen, $R^a$, —NR$^5$R$^5$, —N$^+$R$^5$R$^5$R$^{5a}$, —C(O)NR$^5$R$^5$, —C(O)OR$^4$, —OC(O)R$^4$, —(O(C$_{1-4}$ alkyl))$_n$OR$^4$, or phenyl,
wherein the phenyl is substituted with 1-5 $R^3$ groups, or two Y groups on the same carbon, together with the carbon to which they are attached, form a $C_{3-5}$ monocyclic cycloalkyl;

$R^1$ is H or $C_{1-4}$ alkyl, wherein the $C_{1-4}$ alkyl is optionally substituted with 1-3 groups independently selected from —OH, —CN, halogen, —C(O)OH, and $R^a$;

$R^2$ is phenyl or 5-6 membered monocyclic heteroaryl, wherein the phenyl and 5-6 membered monocyclic heteroaryl are each independently optionally substituted with 1-3 groups independently selected from —OH, —CN, halogen, —C(O)OH, and $C_{1-6}$ alkyl,
wherein the $C_{1-6}$ alkyl is optionally substituted with 1-3 groups independently selected from —OH, —CN, halogen, —C(O)OH, —NR$^5$R$^5$, and $R^a$;

each $R^3$ independently is —OH, $R^a$, $R^b$, or $C_{1-6}$ alkyl, wherein the $C_{1-6}$ alkyl is optionally substituted with 1-3 groups independently selected from —OH, —CN, halogen, —C(O)OH, $R^a$, and $R^b$;

each $R^a$ independently is —P(O)(OH)$_2$ or —OP(O)(OH)$_2$;

each $R^b$ independently is —C(O)OR$^4$ or —C(O)NR$^5$R$^5$;

each $R^4$ independently is H or $C_{1-6}$ alkyl, wherein the $C_{1-6}$ alkyl is optionally substituted with 1-3 groups independently selected from —OH, —CN, halogen, —C(O)OH, —NR$^7$R$^7$, and $R^a$;

each $R^5$ independently is H, —C(O)OR$^6$, —C(O)C(O)OR$^6$, or $C_{1-6}$ alkyl, wherein the $C_{1-6}$ alkyl is optionally substituted with 1-3 groups independently selected from —OH, —CN, halogen, —C(O)OR$^6$, =NR$^{5a}$, —NR$^7$R$^7$, $R^a$, $R^b$, and phenyl;

each $R^{5a}$ independently is H or $C_{1-3}$ alkyl;

each $R^6$ independently is H or $C_{1-6}$ alkyl, wherein the $C_{1-6}$ alkyl is optionally substituted with 1-3 groups independently selected from —OH, CN, halogen, —C(O)OH, and $R^a$;

each $R^7$ independently is H or $C_{1-3}$ alkyl, wherein the $C_{1-3}$ alkyl is optionally substituted with 1-3 groups independently selected from —OH, —CN, halogen, —C(O)OH, and n is 1, 2, 3, 4, or 5; and wherein each 5-6 membered monocyclic heteroaryl and 8-10 membered fused bicyclic heteroaryl independently have 1-4 ring heteroatoms independently selected from N, O, and S.

In some embodiments of the compound of Formula I, or a pharmaceutically acceptable salt thereof, X is —NR$^1$R$^2$, C$_{1-10}$ alkyl, or C$_{2-4}$ alkenyl,
wherein the C$_{1-10}$ alkyl and C$_{2-4}$ alkenyl are each independently substituted with 1-3 Y groups;
each Y independently is —OH, —CN, halogen, R$^a$, —NR$^5$R$^5$, —N$^+$R$^5$R$^5$R$^{5a}$, —C(O)NR$^5$R$^5$, —C(O)OR$^4$, —OC(O)R$^4$, —(O(C$_{1-4}$ alkyl))$_n$OR$^4$, C$_{3-5}$ monocyclic cycloalkyl, or phenyl,
wherein the phenyl is substituted with 1-5 R$^3$ groups, or
two Y groups on the same carbon, together with the carbon to which they are attached, form a C$_{3-5}$ monocyclic cycloalkyl;
R$^1$ is H or C$_{1-4}$ alkyl, wherein the C$_{1-4}$ alkyl is optionally substituted with 1-3 groups independently selected from —OH, —CN, halogen, —C(O)OH, and R$^a$;
R$^2$ is phenyl or 5-6 membered monocyclic heteroaryl, wherein the phenyl and 5-6 membered monocyclic heteroaryl are each independently optionally substituted with 1-3 groups independently selected from —OH, —CN, halogen, —C(O)OH, R$^a$, and C$_{1-6}$ alkyl, wherein the C$_{1-6}$ alkyl is optionally substituted with 1-3 groups independently selected from —OH, —CN, halogen, —C(O)OH, —NR$^5$R$^5$, and R$^a$;
each R$^3$ independently is —OH, —C(O)OH, R$^a$, or C$_{1-6}$ alkyl, wherein the C$_{1-6}$ alkyl is optionally substituted with 1-3 groups independently selected from —OH, —CN, halogen, —C(O)OH, and R$^a$;
each R$^a$ independently is —P(O)(OH)$_2$ or —OP(O)(OH)$_2$;
each R$^4$ independently is H or C$_{1-6}$ alkyl, wherein the C$_{1-6}$ alkyl is optionally substituted with 1-3 groups independently selected from —OH, —CN, halogen, —C(O)OH, —NR$^7$R$^7$, and R$^a$;
each R$^5$ independently is H, —C(O)OR$^6$, —C(O)C(O)OR$^6$, or C$_{1-6}$ alkyl, wherein the C$_{1-6}$ alkyl is optionally substituted with 1-3 groups independently selected from —OH, —CN, halogen, —C(O)OR$^6$, =NR$^{5a}$, —NR$^7$R$^7$, R$^a$, and phenyl;
each R$^{5a}$ independently is H or C$_{1-3}$ alkyl;
each R$^6$ independently is H or C$_{1-6}$ alkyl, wherein the C$_{1-6}$ alkyl is optionally substituted with 1-3 groups independently selected from —OH, CN, halogen, —C(O)OH, and each R$^7$ independently is H or C$_{1-3}$ alkyl, wherein the C$_{1-3}$ alkyl is optionally substituted with 1-3 groups independently selected from —OH, —CN, halogen, —C(O)OH, and
n is 1, 2, 3, 4, or 5; and
wherein each 5-6 membered monocyclic heteroaryl and 8-10 membered fused bicyclic heteroaryl independently have 1-4 ring heteroatoms independently selected from N, O, and S.

As used herein, a 5-6 membered monocyclic heteroaryl has 1~4 ring heteroatoms independently selected from N, O, and S. As used herein, a 8-10 membered fused bicyclic heteroaryl has 1~4 ring heteroatoms independently selected from N, O, and S.

In some embodiments of the compound of Formula I, or a pharmaceutically acceptable salt thereof, X is —NR$^1$R$^2$, C$_{1-10}$ alkyl, or C$_{2-6}$ alkenyl, wherein the C$_{1-10}$ alkyl and C$_{2-6}$ alkenyl are each independently substituted with 1-3 Y groups. In some embodiments of the compound of Formula I, or a pharmaceutically acceptable salt thereof, X is —NR$^1$R$^2$, C$_{1-10}$ alkyl, or C$_{2-4}$ alkenyl, wherein the C$_{1-10}$ alkyl and C$_{2-4}$ alkenyl are each independently substituted with 1-3 Y groups.

In some embodiments of the compound of Formula I, or a pharmaceutically acceptable salt thereof, X is —NR$^1$R$^2$.

In some embodiments of the compound of Formula I, or a pharmaceutically acceptable salt thereof, R$^1$ is H or C$_{1-6}$ alkyl, wherein the C$_{1-6}$ alkyl is optionally substituted with 1-3 groups independently selected from —CN, halogen, R$^a$, R$^b$, and R$^c$. In some embodiments of the compound of Formula I, or a pharmaceutically acceptable salt thereof, R$^1$ is H or C$_{1-6}$ alkyl, wherein the C$_{1-6}$ alkyl is optionally substituted with 1-3 groups independently selected from —OH, —CN, halogen, —C(O)OH, and R$^a$. In some embodiments of the compound of Formula I, or a pharmaceutically acceptable salt thereof, R$^1$ is H or C$_{1-4}$ alkyl, wherein the C$_{1-4}$ alkyl is optionally substituted with 1-3 groups independently selected from —OH, —CN, halogen, —C(O)OH, and R$^a$.

In some embodiments of the compound of Formula I, or a pharmaceutically acceptable salt thereof, R$^1$ is H.

In some embodiments of the compound of Formula I, or a pharmaceutically acceptable salt thereof, R$^1$ is C$_{1-6}$ alkyl, wherein the C$_{1-6}$ alkyl is optionally substituted with 1-3 groups independently selected from —CN, halogen, R$^a$, R$^b$, and R$^c$. In some embodiments of the compound of Formula I, or a pharmaceutically acceptable salt thereof, R$^1$ is C$_{1-6}$ alkyl, wherein the C$_{1-6}$ alkyl is optionally substituted with 1-3 groups independently selected from —OH, —CN, halogen, —C(O)OH, and R$^a$. In some embodiments of the compound of Formula I, or a pharmaceutically acceptable salt thereof, R$^1$ is C$_{1-4}$ alkyl, wherein the C$_{1-4}$ alkyl is optionally substituted with 1-3 groups independently selected from —OH, —CN, halogen, —C(O)OH, and R$^a$. In some embodiments of the compound of Formula I, or a pharmaceutically acceptable salt thereof, R$^1$ is C$_{1-3}$ alkyl, wherein the C$_{1-3}$ alkyl is optionally substituted with 1-3 groups independently selected from —C(O)OH and R$^a$. In some embodiments of the compound of Formula I, or a pharmaceutically acceptable salt thereof, R$^1$ is methyl, wherein the methyl is optionally substituted with 1-3 groups independently selected from —COOH and R$^a$.

In some embodiments of the compound of Formula I, or a pharmaceutically acceptable salt thereof, R$^1$ is C$_{1-6}$ alkyl, wherein the C$_{1-6}$ alkyl is substituted with 1-3 groups independently selected from —CN, halogen, R$^a$, R$^b$, and R$^c$. In some embodiments of the compound of Formula I, or a pharmaceutically acceptable salt thereof, R$^1$ is C$_{1-6}$ alkyl, wherein the C$_{1-6}$ alkyl is substituted with 1-3 groups independently selected from —OH, —CN, halogen, —C(O)OH, and R$^a$. In some embodiments of the compound of Formula I, or a pharmaceutically acceptable salt thereof, R$^1$ is C$_{1-4}$ alkyl, wherein the C$_{1-4}$ alkyl is substituted with 1-3 groups independently selected from —OH, —CN, halogen, —C(O)OH, and R$^a$. In some embodiments of the compound of Formula I, or a pharmaceutically acceptable salt thereof, R$^1$ is C$_{1-3}$ alkyl, wherein the C$_{1-3}$ alkyl is substituted with 1-3 groups independently selected from —C(O)OH and R$^a$. In some embodiments of the compound of Formula I, or a pharmaceutically acceptable salt thereof, R$^1$ is methyl, wherein the methyl is substituted with 1-3 groups independently selected from —COOH and R$^a$.

In some embodiments of the compound of Formula I, or a pharmaceutically acceptable salt thereof, R$^1$ is C$_{1-6}$ alkyl. In some embodiments of the compound of Formula I, or a pharmaceutically acceptable salt thereof, R$^1$ is C$_{1-4}$ alkyl. In some embodiments of the compound of Formula I, or a pharmaceutically acceptable salt thereof, $R^1$ is $C_{1-3}$ alkyl. In some embodiments of the compound of Formula I, or a pharmaceutically acceptable salt thereof, $R^1$ is methyl.

In some embodiments of the compound of Formula I, or a pharmaceutically acceptable salt thereof, $R^2$ is phenyl or 5-6 membered monocyclic heteroaryl, wherein the phenyl and 5-6 membered monocyclic heteroaryl are each independently optionally substituted with 1-3 groups independently selected from —CN, halogen, $R^a$, $R^b$, $R^c$, and $C_{1-6}$ alkyl,
wherein the $C_{1-6}$ alkyl is optionally substituted with 1-3 groups independently selected from —CN, halogen, $R^a$, $R^b$, and $R^c$.

In some embodiments of the compound of Formula I, or a pharmaceutically acceptable salt thereof, $R^2$ is phenyl or 5-6 membered monocyclic heteroaryl, wherein the phenyl and 5-6 membered monocyclic heteroaryl are each independently optionally substituted with 1-3 groups independently selected from —OH, —CN, halogen, —C(O)OH, $R^a$, and $C_{1-6}$ alkyl,
wherein the $C_{1-6}$ alkyl is optionally substituted with 1-3 groups independently selected from —OH, —CN, halogen, —C(O)OH, —NR$^5$R$^5$, and $R^a$.

In some embodiments of the compound of Formula I, or a pharmaceutically acceptable salt thereof, $R^2$ is phenyl, wherein the phenyl is optionally substituted with 1-3 groups independently selected from —CN, halogen, $R^a$, $R^b$, $R^c$, and $C_{1-6}$ alkyl, wherein the $C_{1-6}$ alkyl is optionally substituted with 1-3 groups independently selected from —CN, halogen, $R^a$, $R^b$, and $R^c$. In some embodiments of the compound of Formula I, or a pharmaceutically acceptable salt thereof, $R^2$ is phenyl, wherein the phenyl is optionally substituted with 1-3 groups independently selected from —OH, —CN, halogen, —C(O)OR$^4$, —C(O)NR$^5$R$^5$, —S(O)$_2$R$^4$, —S(O)$_2$NR$^5$R$^5$, —S(O)$_{20}$R$^4$, —NR$^5$C(O)R$^4$, —NR$^5$C(O)NR$^5$R$^5$, —NR$^5$C(O)OR$^4$, —NR$^5$S(O)$_2$R$^4$, $R^a$, and $C_{1-6}$ alkyl, wherein the $C_{1-6}$ alkyl is optionally substituted with 1-3 groups independently selected from —OH, —CN, halogen, —C(O)OR$^4$, —C(O)NR$^5$R$^5$, —NR$^5$R$^5$, —NR$^5$C(O)OR$^4$, and $R^a$. In some embodiments of the compound of Formula I, or a pharmaceutically acceptable salt thereof, $R^2$ is phenyl, wherein the phenyl is optionally substituted with 1-3 groups independently selected from —OH, —CN, halogen, —C(O)OH, $R^a$, and $C_{1-6}$ alkyl, wherein the $C_{1-6}$ alkyl is optionally substituted with 1-3 groups independently selected from —OH, —CN, halogen, —C(O)OH, —NR$^5$R$^5$, and $R^a$.

In some embodiments of the compound of Formula I, or a pharmaceutically acceptable salt thereof, $R^2$ is phenyl, wherein the phenyl is
i) substituted with $C_{1-4}$ alkyl, wherein the $C_{1-4}$ alkyl is substituted with one group selected from $R^a$ and —NR$^5$C(O)OR$^4$, and
ii) optionally substituted with 1-2 groups independently selected from —OH, —CN, halogen, —C(O)OR$^4$, —C(O)NR$^5$R$^5$, —S(O)$_2$R$^4$, —S(O)$_2$NR$^5$R$^5$, —S(O)$_{20}$R$^4$, —NR$^5$C(O)R$^4$, —NR$^5$C(O)NR$^5$R$^5$, —NR$^5$C(O)OR$^4$, —NR$^5$S(O)$_2$R$^4$, $R^a$, and $C_{1-6}$ alkyl, wherein the $C_{1-6}$ alkyl is optionally substituted with 1-3 groups independently selected from —OH, —CN, halogen, —C(O)OR$^4$, —C(O)NR$^5$R$^5$, —NR$^5$R$^5$, —NR$^5$C(O)OR$^4$, and $R^a$.

In some embodiments of the compound of Formula I, or a pharmaceutically acceptable salt thereof, $R^2$ is phenyl, wherein the phenyl is optionally substituted with 1-3 groups independently selected from —CN, halogen, $R^a$, $R^b$, and $R^c$.
In some embodiments of the compound of Formula I, or a pharmaceutically acceptable salt thereof, $R^2$ is phenyl, wherein the phenyl is optionally substituted with 1-2 groups independently selected from —C(O)OH and $R^a$.

In some embodiments of the compound of Formula I, or a pharmaceutically acceptable salt thereof, $R^2$ is phenyl, wherein the phenyl is substituted with 1-3 groups independently selected from —CN, halogen, $R^a$, $R^b$, $R^c$, and $C_{1-6}$ alkyl, wherein the $C_{1-6}$ alkyl is optionally substituted with 1-3 groups independently selected from —CN, halogen, $R^a$, $R^b$, and $R^c$. In some embodiments of the compound of Formula I, or a pharmaceutically acceptable salt thereof, $R^2$ is phenyl, wherein the phenyl is substituted with 1-3 groups independently selected from —OH, —CN, halogen, —C(O)OR$^4$, —C(O)NR$^5$R$^5$, —S(O)$_2$R$^4$, —S(O)$_2$NR$^5$R$^5$, —S(O)$_{20}$R$^4$, —NR$^5$C(O)R$^4$, —NR$^5$C(O)NR$^5$R$^5$, —NR$^5$C(O)OR$^4$, —NR$^5$S(O)$_2$R$^4$, $R^a$, and $C_{1-6}$ alkyl, wherein the $C_{1-6}$ alkyl is optionally substituted with 1-3 groups independently selected from —OH, —CN, halogen, —C(O)OR$^4$, —C(O)NR$^5$R$^5$, —NR$^5$R$^5$, —NR$^5$C(O)OR$^4$, and $R^a$. In some embodiments of the compound of Formula I, or a pharmaceutically acceptable salt thereof, $R^2$ is phenyl, wherein the phenyl is substituted with 1-3 groups independently selected from —OH, —CN, halogen, —C(O)OH, $R^a$, and $C_{1-6}$ alkyl, wherein the $C_{1-6}$ alkyl is optionally substituted with 1-3 groups independently selected from —OH, —CN, halogen, —C(O)OH, —NR$^5$R$^5$, and $R^a$.

In some embodiments of the compound of Formula I, or a pharmaceutically acceptable salt thereof, $R^2$ is phenyl, wherein the phenyl is
i) substituted with $C_{1-4}$ alkyl, wherein the $C_{1-4}$ alkyl is substituted with one group selected from $R^a$ and —NR$^5$C(O)OR$^4$, and
ii) substituted with 1-2 groups independently selected from —OH, —CN, halogen, —C(O)OR$^4$, —C(O)NR$^5$R$^5$, —S(O)$_2$R$^4$, —S(O)$_2$NR$^5$R$^5$, —S(O)$_{20}$R$^4$, —NR$^5$C(O)R$^4$, —NR$^5$C(O)NR$^5$R$^5$, —NR$^5$C(O)OR$^4$, —NR$^5$S(O)$_2$R$^4$, $R^a$, and $C_{1-6}$ alkyl, wherein the $C_{1-6}$ alkyl is optionally substituted with 1-3 groups independently selected from —OH, —CN, halogen, —C(O)OR$^4$, —C(O)NR$^5$R$^5$, —NR$^5$R$^5$, —NR$^5$C(O)OR$^4$, and $R^a$.

In some embodiments of the compound of Formula I, or a pharmaceutically acceptable salt thereof, $R^1$ is phenyl, wherein the phenyl is substituted with 1-3 groups independently selected from —CN, halogen, $R^a$, $R^b$, and $R^c$. In some embodiments of the compound of Formula I, or a pharmaceutically acceptable salt thereof, $R^1$ is phenyl, wherein the phenyl is substituted with 1-2 groups independently selected from —C(O)OH and $R^a$.

In some embodiments of the compound of Formula I, or a pharmaceutically acceptable salt thereof, $R^2$ is phenyl.

In some embodiments of the compound of Formula I, or a pharmaceutically acceptable salt thereof, $R^1$ is 5-6 membered monocyclic heteroaryl, wherein the 5-6 membered monocyclic heteroaryl is optionally substituted with 1-3 groups independently selected from —CN, halogen, $R^a$, $R^b$, $R^c$, and $C_{1-6}$ alkyl, wherein the $C_{1-6}$ alkyl is optionally substituted with 1-3 groups independently selected from —CN, halogen, $R^a$, $R^b$, and $R^c$. In some embodiments of the compound of Formula I, or a pharmaceutically acceptable salt thereof, $R^1$ is 5-6 membered monocyclic heteroaryl, wherein the 5-6 membered monocyclic heteroaryl is optionally substituted with 1-3 groups independently selected from —OH, —CN, halogen, —C(O)OH, $R^a$, and $C_{1-6}$ alkyl, wherein the $C_{1-6}$ alkyl is optionally substituted with 1-3 groups independently selected from —OH, —CN, halogen, —C(O)OH, —NR$^5$R$^5$, and $R^a$.

In some embodiments of the compound of Formula I, or a pharmaceutically acceptable salt thereof, $R^1$ is 5-6 membered monocyclic heteroaryl, wherein the 5-6 membered monocyclic heteroaryl is substituted with 1-3 groups independently selected from —CN, halogen, $R^a$, $R^b$, $R^c$, and $C_{1-6}$ alkyl, wherein the $C_{1-6}$ alkyl is optionally substituted with 1-3 groups independently selected from —CN, halogen, $R^a$, $R^b$, and $R^c$. In some embodiments of the compound of Formula I, or a pharmaceutically acceptable salt thereof, $R^1$ is 5-6 membered monocyclic heteroaryl, wherein the 5-6 membered monocyclic heteroaryl is substituted with 1-3 groups independently selected from —OH, —CN, halogen, —C(O)OH, $R^a$, and $C_{1-6}$ alkyl, wherein the $C_{1-6}$ alkyl is optionally substituted with 1-3 groups independently selected from —OH, —CN, halogen, —C(O)OH, —$NR^5R^5$, and $R^a$.

In some embodiments of the compound of Formula I, or a pharmaceutically acceptable salt thereof, $R^1$ is 5-6 membered monocyclic heteroaryl.

In some embodiments of the compound of Formula I, or a pharmaceutically acceptable salt thereof, $R^2$ is 6-membered monocyclic heteroaryl, wherein the 6-membered monocyclic heteroaryl is optionally substituted with 1-3 groups independently selected from —OH, —CN, halogen, —C(O)$OR^4$, —C(O)$NR^5R^5$, —S(O)$_2R^4$, —S(O)$_2NR^5R^5$, —S(O)$_{20}R^4$, —$NR^5$C(O)$R^4$, —$NR^5$C(O)$NR^5R^5$, —$NR^5$C(O)$OR^4$, —$NR^5$S(O)$_2R^4$, $R^a$, and $C_{1-6}$ alkyl, wherein the $C_{1-6}$ alkyl is optionally substituted with 1-3 groups independently selected from —OH, —CN, halogen, —C(O)$OR^4$, —C(O)$NR^5R^5$, —$NR^5R^5$, —$NR^5$C(O)$OR^4$, and $R^a$.

In some embodiments of the compound of Formula I, or a pharmaceutically acceptable salt thereof, $R^2$ is 6-membered monocyclic heteroaryl, wherein the 6-membered monocyclic heteroaryl is
 i) substituted with $C_{1-4}$ alkyl, wherein the $C_{1-4}$ alkyl is substituted with one group selected from $R^a$ and —$NR^5$C(O)$OR^4$, and
 ii) optionally substituted with 1-2 groups independently selected from —OH, —CN, halogen, —C(O)$OR^4$, —C(O)$NR^5R^5$, —S(O)$_2R^4$, —S(O)$_2NR^5R^5$, —S(O)$_{20}R^4$, —$NR^5$C(O)$R^4$, —$NR^5$C(O)$NR^5R^5$, —$NR^5$C(O)$OR^4$, —$NR^5$S(O)$_2R^4$, $R^a$, and $C_{1-6}$ alkyl, wherein the $C_{1-6}$ alkyl is optionally substituted with 1-3 groups independently selected from —OH, —CN, halogen, —C(O)$OR^4$, —C(O)$NR^5R^5$, —$NR^5R^5$, and $R^a$.

In some embodiments of the compound of Formula I, or a pharmaceutically acceptable salt thereof, $R^2$ is pyridinyl, wherein the pyridinyl is optionally substituted with 1-2 groups independently selected from —C(O)OH, $R^a$, and $C_{1-6}$ alkyl, wherein the $C_{1-6}$ alkyl is optionally substituted with 1-3 groups independently selected from —OH, —CN, halogen, —C(O)OH, —$NR^5R^5$, and $R^a$.

In some embodiments of the compound of Formula I, or a pharmaceutically acceptable salt thereof, $R^2$ is 6-membered monocyclic heteroaryl, wherein the 6-membered monocyclic heteroaryl is substituted with 1-3 groups independently selected from —OH, —CN, halogen, —C(O)$OR^4$, —C(O)$NR^5R^5$, —S(O)$_2R^4$, —S(O)$_2NR^5R^5$, —S(O)$_{20}R^4$, —$NR^5$C(O)$R^4$, —$NR^5$C(O)$NR^5R^5$, —$NR^5$C(O)$OR^4$, —$NR^5$S(O)$_2R^4$, $R^a$, and $C_{1-6}$ alkyl, wherein the $C_{1-6}$ alkyl is optionally substituted with 1-3 groups independently selected from —OH, —CN, halogen, —C(O)$OR^4$, —C(O)$NR^5R^5$, —$NR^5R^5$, —$NR^5$C(O)$OR^4$, and $R^a$.

In some embodiments of the compound of Formula I, or a pharmaceutically acceptable salt thereof, $R^2$ is 6-membered monocyclic heteroaryl, wherein the 6-membered monocyclic heteroaryl is
 i) substituted with $C_{1-4}$ alkyl, wherein the $C_{1-4}$ alkyl is substituted with one group selected from $R^a$ and —$NR^5$C(O)$OR^4$, and
 ii) substituted with 1-2 groups independently selected from —OH, —CN, halogen, —C(O)$OR^4$, —C(O)$NR^5R^5$, —S(O)$_2R^4$, —S(O)$_2NR^5R^5$, —S(O)$_{20}R^4$, —$NR^5$C(O)$R^4$, —$NR^5$C(O)$NR^5R^5$, —$NR^5$C(O)$OR^4$, —$NR^5$S(O)$_2R^4$, $R^a$, and $C_{1-6}$ alkyl, wherein the $C_{1-6}$ alkyl is optionally substituted with 1-3 groups independently selected from —OH, —CN, halogen, —C(O)$OR^4$, —C(O)$NR^5R^5$, —$NR^5R^5$, and $R^a$.

In some embodiments of the compound of Formula I, or a pharmaceutically acceptable salt thereof, $R^2$ is pyridinyl, wherein the pyridinyl is substituted with 1-2 groups independently selected from —C(O)OH, $R^a$, and $C_{1-6}$ alkyl, wherein the $C_{1-6}$ alkyl is optionally substituted with 1-3 groups independently selected from —OH, —CN, halogen, —C(O)OH, —$NR^5R^5$, and $R^a$. In some embodiments of the compound of Formula I, or a pharmaceutically acceptable salt thereof, $R^2$ is pyridinyl, wherein the pyridinyl is substituted with $C_{1-3}$ alkyl, wherein the $C_1$-3 alkyl is substituted with 1-3 groups independently selected from —OH, —CN, halogen, —C(O)OH, —$NR^5R^5$, and $R^a$.

In some embodiments of the compound of Formula I, or a pharmaceutically acceptable salt thereof, X is $C_{1-10}$ alkyl, wherein the $C_{1-10}$ alkyl is substituted with 1-3 Y groups. In some embodiments of the compound of Formula I, or a pharmaceutically acceptable salt thereof, X is $C_{1-10}$ alkyl, wherein the $C_{1-10}$ alkyl is substituted with two Y groups. In some embodiments of the compound of Formula I, or a pharmaceutically acceptable salt thereof, X is $C_{1-10}$ alkyl, wherein the $C_{1-10}$ alkyl is substituted with one Y group. In some embodiments of the compound of Formula I, or a pharmaceutically acceptable salt thereof, X is $C_{1-8}$ alkyl, wherein the $C_{1-8}$ alkyl is substituted with 1-3 Y groups. In some embodiments of the compound of Formula I, or a pharmaceutically acceptable salt thereof, X is $C_{1-8}$ alkyl, wherein the $C_{1-8}$ alkyl is substituted with 1-2 Y groups. In some embodiments of the compound of Formula I, or a pharmaceutically acceptable salt thereof, X is $C_{1-8}$ alkyl, wherein the $C_{1-8}$ alkyl is substituted with three Y groups. In some embodiments of the compound of Formula I, or a pharmaceutically acceptable salt thereof, X is $C_{1-8}$ alkyl, wherein the $C_{1-8}$ alkyl is substituted with two Y groups. In some embodiments of the compound of Formula I, or a pharmaceutically acceptable salt thereof, X is $C_{1-8}$ alkyl, wherein the $C_{1-8}$ alkyl is substituted with one Y group. In some embodiments of the compound of Formula I, or a pharmaceutically acceptable salt thereof, X is $C_{1-6}$ alkyl, wherein the $C_{1-6}$ alkyl is substituted with 1-3 Y groups. In some embodiments of the compound of Formula I, or a pharmaceutically acceptable salt thereof, X is $C_{1-6}$ alkyl, wherein the $C_{1-6}$ alkyl is substituted with 1-2 Y groups. In some embodiments of the compound of Formula I, or a pharmaceutically acceptable salt thereof, X is $C_{1-6}$ alkyl, wherein the $C_{1-6}$ alkyl is substituted with three Y groups. In some embodiments of the compound of Formula I, or a pharmaceutically acceptable salt thereof, X is $C_{1-6}$ alkyl, wherein the $C_{1-6}$ alkyl is substituted with two Y groups. In some embodiments of the compound of Formula I, or a pharmaceutically acceptable salt thereof, X is $C_{1-6}$ alkyl, wherein the $C_{1-6}$ alkyl is substituted with one Y group.

In some embodiments of the compound of Formula I, or a pharmaceutically acceptable salt thereof, X substituted with Y is —CH$_2$Y, —CH$_2$CH$_2$Y, —CH$_2$CH$_2$CH$_2$Y, —CH$_2$CH$_2$CH$_2$CH$_2$Y,

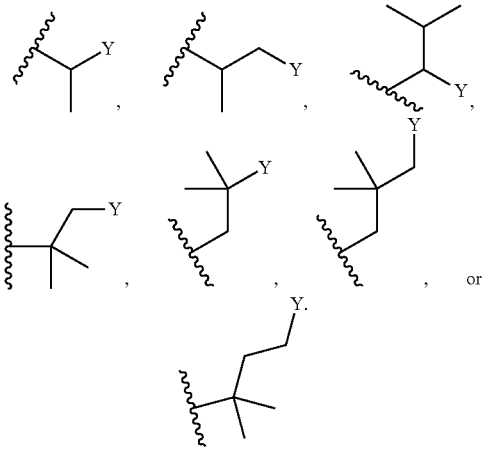

In some embodiments of the compound of Formula I, or a pharmaceutically acceptable salt thereof, X substituted with Y is

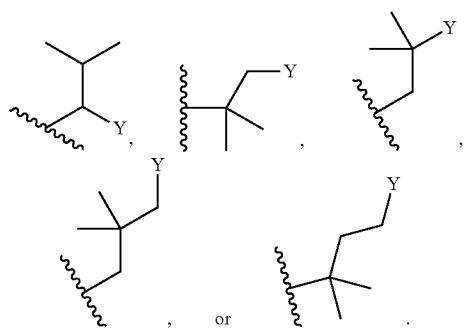

In some embodiments of the compound of Formula I, or a pharmaceutically acceptable salt thereof, X substituted with Y is

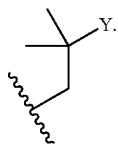

In some embodiments of the compound of Formula I, or a pharmaceutically acceptable salt thereof, X is C$_{2-6}$ alkenyl, wherein the C$_{2-6}$ alkenyl is substituted with 1-3 Y groups. In some embodiments of the compound of Formula I, or a pharmaceutically acceptable salt thereof, X is C$_{2-4}$ alkenyl, wherein the C$_{2-4}$ alkenyl is substituted with 1-3 Y groups.

In some embodiments of the compound of Formula I, or a pharmaceutically acceptable salt thereof,
each Y independently is —B(OH)$_2$, —CN, halogen, R$^a$, R$^b$, R$^c$, phenyl, naphthalenyl, 5-6 membered monocyclic heteroaryl, or 8-10 membered fused bicyclic heteroaryl,
wherein the phenyl, naphthalenyl, 5-6 membered monocyclic heteroaryl, and 8-10 membered fused bicyclic heteroaryl are each independently substituted with 1-5 R$^3$ groups, or
two Y groups on the same carbon, together with the carbon to which they are attached, form a C$_{3-5}$ monocyclic cycloalkyl.

In some embodiments of the compound of Formula I, or a pharmaceutically acceptable salt thereof,
each Y independently is —CN, halogen, R$^a$, R$^b$, R$^c$, phenyl, or naphthalenyl, wherein the phenyl and naphthalenyl are each independently substituted with 1-5 R$^3$ groups, or
two Y groups on the same carbon, together with the carbon to which they are attached, form a C$_{3-5}$ monocyclic cycloalkyl.

In some embodiments of the compound of Formula I, or a pharmaceutically acceptable salt thereof,
each Y independently is —OH, —CN, halogen, R$^a$, —NR$^5$R$^5$, —N+R$^5$R$^5$R$^{5a}$, —C(O)NR$^5$R$^5$, —C(O)OR$^4$, —OC(O)R$^4$, —(O(C$_{1-4}$ alkyl))$_n$OR$^4$, or phenyl, wherein the phenyl is substituted with 1-5 R$^3$ groups, or
two Y groups on the same carbon, together with the carbon to which they are attached, form a C$_{3-5}$ monocyclic cycloalkyl.

In some embodiments of the compound of Formula I, or a pharmaceutically acceptable salt thereof,
two Y groups on the same carbon, together with the carbon to which they are attached, form a C$_{3-5}$ monocyclic cycloalkyl, and
one Y is —B(OH)$_2$, —CN, halogen, R$^a$, R$^b$, R$^c$, phenyl, naphthalenyl, 5-6 membered monocyclic heteroaryl, or 8-10 membered fused bicyclic heteroaryl,
wherein the phenyl, naphthalenyl, 5-6 membered monocyclic heteroaryl, and 8-10 membered fused bicyclic heteroaryl are each independently substituted with 1-5 R$^3$ groups.

In some embodiments of the compound of Formula I, or a pharmaceutically acceptable salt thereof,
two Y groups on the same carbon, together with the carbon to which they are attached, form a C$_{3-5}$ monocyclic cycloalkyl, and
one Y is —CN, halogen, R$^a$, R$^b$, R$^c$, phenyl, or naphthalenyl, wherein the phenyl and naphthalenyl are each independently substituted with 1-5 R$^3$ groups.

In some embodiments of the compound of Formula I, or a pharmaceutically acceptable salt thereof,
two Y groups on the same carbon, together with the carbon to which they are attached, form a C$_{3-5}$ monocyclic cycloalkyl, and
one Y is —OH, —CN, halogen, R$^a$, —NR$^5$R$^5$, —N+R$^5$R$^5$R$^{5a}$, —C(O)NR$^5$R$^5$, —C(O)OR$^4$, —OC(O)R$^4$, —(O(C$_{1-4}$ alkyl))$_n$OR$^4$, or phenyl, wherein the phenyl is substituted with 1-5 R$^3$ groups.

In some embodiments of the compound of Formula I, or a pharmaceutically acceptable salt thereof, each Y independently is —B(OH)$_2$, —C(O)OR$^4$, —C(O)NR$^5$R$^5$, —OC(O)R$^4$, —(O(C$_{1-4}$ alkyl))$_n$OR$^4$, —NR$^5$R$^5$, —N+R$^5$R$^5$R$^{5a}$, —S(O)$_2$R$^4$, —S(O)$_2$NR$^5$R$^5$, —S(O)$_2$OR$^4$, —NR$^5$C(O)R$^4$, —NR$^5$C(O)NR$^5$R$^5$, —NR$^5$S(O)$_2$R$^4$, R$^a$, 5-6 membered monocyclic heteroaryl, or 8-10 membered fused bicyclic heteroaryl,
wherein the 5-6 membered monocyclic heteroaryl and 8-10 membered fused bicyclic heteroaryl are each independently substituted with 1-3 groups independently selected from —OH, —CN, halogen, —C(O)OR$^4$, —C(O)NR$^5$R$^5$, and R$^a$.

In some embodiments of the compound of Formula I, or a pharmaceutically acceptable salt thereof, each Y independently is $R^a$, —$NR^5R^5$, —$N+R^5R^5R^{5a}$, —C(O)OR$^4$, —OC(O)R$^4$, or —(O(C$_{1-4}$ alkyl))$_n$OR$^4$.

In some embodiments of the compound of Formula I, or a pharmaceutically acceptable salt thereof, one or more Y is —B(OH)$_2$. In some embodiments of the compound of Formula I, or a pharmaceutically acceptable salt thereof, one or more Y is —CN. In some embodiments of the compound of Formula I, or a pharmaceutically acceptable salt thereof, one or more Y is halogen. In some embodiments of the compound of Formula I, or a pharmaceutically acceptable salt thereof, one or more Y is $R^a$. In some embodiments of the compound of Formula I, or a pharmaceutically acceptable salt thereof, one or more Y is $R^b$. In some embodiments of the compound of Formula I, or a pharmaceutically acceptable salt thereof, one or more Y is $R^c$.

In some embodiments of the compound of Formula I, or a pharmaceutically acceptable salt thereof, one or more Y is —OH. In some embodiments of the compound of Formula I, or a pharmaceutically acceptable salt thereof, one or more Y is —$NR^5R^5$. In some embodiments of the compound of Formula I, or a pharmaceutically acceptable salt thereof, one or more Y is —$N^+R^5R^5R^{5a}$. In some embodiments of the compound of Formula I, or a pharmaceutically acceptable salt thereof, one or more Y is —C(O)NR$^5R^5$. In some embodiments of the compound of Formula I, or a pharmaceutically acceptable salt thereof, one or more Y is —C(O)OR$^4$. In some embodiments of the compound of Formula I, or a pharmaceutically acceptable salt thereof, one or more Y is —OC(O)R$^4$. In some embodiments of the compound of Formula I, or a pharmaceutically acceptable salt thereof, one or more Y is —(O(C$_{1-4}$ alkyl))$_n$OR$^4$. In some embodiments of the compound of Formula I, or a pharmaceutically acceptable salt thereof, one or more Y is —(O(CH$_2$CH$_2$))$_n$OR$^4$. In some embodiments of the compound of Formula I, or a pharmaceutically acceptable salt thereof, one or more Y is —S(O)$_2$R$^4$. In some embodiments of the compound of Formula I, or a pharmaceutically acceptable salt thereof, one or more Y is —S(O)$_2$NR$^5R^5$. In some embodiments of the compound of Formula I, or a pharmaceutically acceptable salt thereof, one or more Y is —S(O)$_{20}$R$^4$. In some embodiments of the compound of Formula I, or a pharmaceutically acceptable salt thereof, one or more Y is —NR$^5$C(O)R$^4$. In some embodiments of the compound of Formula I, or a pharmaceutically acceptable salt thereof, one or more Y is —NR$^5$C(O)NR$^5R^5$. In some embodiments of the compound of Formula I, or a pharmaceutically acceptable salt thereof, one or more Y is —NR$^5$S(O)$_2$R$^4$.

In some embodiments of the compound of Formula I, or a pharmaceutically acceptable salt thereof, one or more Y is phenyl, wherein the phenyl is substituted with 1-5 R$^3$ groups. In some embodiments of the compound of Formula I, or a pharmaceutically acceptable salt thereof, one or more Y is naphthalenyl, wherein the naphthalenyl is substituted with 1-5 R$^3$ groups.

In some embodiments of the compound of Formula I, or a pharmaceutically acceptable salt thereof, one or more Y is 5-6 membered monocyclic heteroaryl, wherein the 5-6 membered monocyclic heteroaryl is substituted with 1-5 R$^3$ groups. In some embodiments of the compound of Formula I, or a pharmaceutically acceptable salt thereof, one or more Y is 5-6 membered monocyclic heteroaryl, wherein the 5-6 membered monocyclic heteroaryl is substituted with 1-3 groups independently selected from —OH, —CN, halogen, —C(O)OR$^4$, —C(O)NR$^5R^5$, and $R^a$.

In some embodiments of the compound of Formula I, or a pharmaceutically acceptable salt thereof, one or more Y is 8-10 membered fused bicyclic heteroaryl, wherein the 8-10 membered fused bicyclic heteroaryl is substituted with 1-5 R$^3$ groups. In some embodiments of the compound of Formula I, or a pharmaceutically acceptable salt thereof, one or more Y is 8-10 membered fused bicyclic heteroaryl, wherein the 8-10 membered fused bicyclic heteroaryl is substituted with 1-3 groups independently selected from —OH, —CN, halogen, —C(O)OR$^4$, —C(O)NR$^5R^5$, and $R^a$.

In some embodiments of the compound of Formula I, or a pharmaceutically acceptable salt thereof, n is 1, 2, 3, 4, or 5. In some embodiments of the compound of Formula I, or a pharmaceutically acceptable salt thereof, n is 1. In some embodiments of the compound of Formula I, or a pharmaceutically acceptable salt thereof, n is 2. In some embodiments of the compound of Formula I, or a pharmaceutically acceptable salt thereof, n is 3. In some embodiments of the compound of Formula I, or a pharmaceutically acceptable salt thereof, n is 4. In some embodiments of the compound of Formula I, or a pharmaceutically acceptable salt thereof, n is 5.

In some embodiments of the compound of Formula I, or a pharmaceutically acceptable salt thereof, one Y is —C(O)OH, —NH$_2$, or —N(CH$_3$)$_2$, and one Y is —NR$^5R^5$.

In some embodiments of the compound of Formula I, or a pharmaceutically acceptable salt thereof, two Y groups on the same carbon, together with the carbon to which they are attached, form a C$_{3-5}$ monocyclic cycloalkyl.

In some embodiments of the compound of Formula I, or a pharmaceutically acceptable salt thereof, X is substituted with three Y groups, wherein two of the three Y groups are on the same carbon and wherein the two Y groups on the same carbon, together with the carbon to which they are attached, form a cyclopropyl.

In some embodiments of the compound of Formula I, or a pharmaceutically acceptable salt thereof, X substituted with three Y groups is:

In some embodiments of the compound of Formula I, or a pharmaceutically acceptable salt thereof, X is substituted with three Y groups,
wherein two Y groups are on the same carbon and wherein the two Y groups on the same carbon, together with the carbon to which they are attached, form a cyclopropyl, and
the third Y group is —NR$^5R^5$.

In some embodiments of the compound of Formula I, or a pharmaceutically acceptable salt thereof, X substituted with three Y groups is:

wherein Y is —NR$^5R^5$.

In some embodiments of the compound of Formula I, or a pharmaceutically acceptable salt thereof, one Y is phenyl, wherein the phenyl is substituted with 1-5 R$^3$ groups. In some embodiments of the compound of Formula I, or a pharmaceutically acceptable salt thereof, one Y is phenyl, wherein the phenyl is substituted with 1-3 $R^3$ groups. In some embodiments of the compound of Formula I, or a pharmaceutically acceptable salt thereof, one Y is phenyl, wherein the phenyl is substituted with three $R^3$ groups.

In some embodiments of the compound of Formula I, or a pharmaceutically acceptable salt thereof, each $R^3$ independently is $R^a$, $R^b$, $R^c$, $C_{1-6}$ alkyl, or 5-6 membered monocyclic heteroaryl, wherein the $C_{1-6}$ alkyl and 5-6 membered monocyclic heteroaryl are each independently optionally substituted with 1-3 groups independently selected from —CN, halogen, $R^a$, $R^b$, and $R^c$. In some embodiments of the compound of Formula I, or a pharmaceutically acceptable salt thereof, each $R^3$ independently is $R^a$, $R^b$, $R^c$, or $C_{1-6}$ alkyl, wherein the $C_{1-6}$ alkyl is optionally substituted with 1-3 groups independently selected from —CN, halogen, $R^a$, $R^b$, and $R^c$. In some embodiments of the compound of Formula I, or a pharmaceutically acceptable salt thereof, each $R^3$ independently is —C(O)OR$^4$, —C(O)NR$^5$R$^5$, —S(O)$_2$R$^4$, —S(O)$_2$NR$^5$R$^5$, —S(O)$_2$OR$^4$, —NR$^5$C(O)R$^4$, —NR$^5$C(O)NR$^5$R$^5$, —NR$^5$S(O)$_2$R$^4$, $R^a$, or $C_{1-6}$ alkyl, wherein the $C_{1-6}$ alkyl is optionally substituted with 1-3 groups independently selected from —OH, —CN, halogen, —C(O)OR$^4$, —C(O)NR$^5$R$^5$, and $R^a$. In some embodiments of the compound of Formula I, or a pharmaceutically acceptable salt thereof, each $R^3$ independently is —OH, —C(O)OH, $R^a$, or $C_{1-6}$ alkyl, wherein the $C_{1-6}$ alkyl is optionally substituted with 1-3 groups independently selected from —OH, —CN, halogen, —C(O)OH, and $R^a$. In some embodiments of the compound of Formula I, or a pharmaceutically acceptable salt thereof, each $R^3$ independently is —OH, —C(O)OH, —C(O)NR$^5$R$^5$, $R^a$, or $C_{1-3}$ alkyl, wherein the $C_{1-3}$ alkyl is optionally substituted with 1-3 groups independently selected from —OH, —CN, halogen, —C(O)OH, —C(O)NR$^5$R$^5$, and $R^a$. In some embodiments of the compound of Formula I, or a pharmaceutically acceptable salt thereof, each $R^3$ independently is —OH, —C(O)OH, $R^a$, or $C_{1-3}$ alkyl, wherein the $C_{1-3}$ alkyl is optionally substituted with 1-3 groups independently selected from —OH, —CN, halogen, —C(O)OH, and $R^a$. In some embodiments of the compound of Formula I, or a pharmaceutically acceptable salt thereof, each $R^3$ independently is —OH, —C(O)OH, —C(O)NR$^5$R$^5$, $R^a$, methyl, —CH$_2$P(O)(OH)$_2$, —CH$_2$C(O)OH, or —CH$_2$C(O)NR$^5$R$^5$. In some embodiments of the compound of Formula I, or a pharmaceutically acceptable salt thereof, each $R^3$ independently is —OH, —C(O)OH, $R^a$, methyl, —CH$_2$P(O)(OH)$_2$, or —CH$_2$C(O)OH.

In some embodiments of the compound of Formula I, or a pharmaceutically acceptable salt thereof, one or more $R^3$ is $R^a$. In some embodiments of the compound of Formula I, or a pharmaceutically acceptable salt thereof, one or more $R^3$ is $R^b$. In some embodiments of the compound of Formula I, or a pharmaceutically acceptable salt thereof, one or more $R^3$ is $R^c$. In some embodiments of the compound of Formula I, or a pharmaceutically acceptable salt thereof, one or more $R^3$ is —C(O)OR$^4$. In some embodiments of the compound of Formula I, or a pharmaceutically acceptable salt thereof, one or more $R^3$ is —C(O)OH. In some embodiments of the compound of Formula I, or a pharmaceutically acceptable salt thereof, one or more $R^3$ is —C(O)NR$^5$R$^5$. In some embodiments of the compound of Formula I, or a pharmaceutically acceptable salt thereof, one or more $R^3$ is —S(O)$_2$R$^4$. In some embodiments of the compound of Formula I, or a pharmaceutically acceptable salt thereof, one or more $R^3$ is —S(O)$_2$NR$^5$R$^5$. In some embodiments of the compound of Formula I, or a pharmaceutically acceptable salt thereof, one or more $R^3$ is —S(O)$_2$OR$^4$. In some embodiments of the compound of Formula I, or a pharmaceutically acceptable salt thereof, one or more $R^3$ is —NR$^5$C(O)R$^4$. In some embodiments of the compound of Formula I, or a pharmaceutically acceptable salt thereof, one or more $R^3$ is —NR$^5$C(O)NR$^5$R$^5$. In some embodiments of the compound of Formula I, or a pharmaceutically acceptable salt thereof, one or more $R^3$ is —NR$^5$S(O)$_2$R$^4$. In some embodiments of the compound of Formula I, or a pharmaceutically acceptable salt thereof, one or more $R^3$ is —OH.

In some embodiments of the compound of Formula I, or a pharmaceutically acceptable salt thereof, one or more $R^3$ is $C_{1-6}$ alkyl, wherein the $C_{1-6}$ alkyl is optionally substituted with 1-3 groups independently selected from —CN, halogen, $R^a$, $R^b$, and $R^c$. In some embodiments of the compound of Formula I, or a pharmaceutically acceptable salt thereof, one or more $R^3$ is $C_{1-6}$ alkyl, wherein the $C_{1-6}$ alkyl is optionally substituted with 1-3 groups independently selected from —OH, —CN, halogen, —C(O)OR$^4$, —C(O)NR$^5$R$^5$, and $R^a$. In some embodiments of the compound of Formula I, or a pharmaceutically acceptable salt thereof, one or more $R^3$ is $C_{1-6}$ alkyl, wherein the $C_{1-6}$ alkyl is optionally substituted with 1-3 groups independently selected from —OH, —CN, halogen, —C(O)OH, and $R^a$. In some embodiments of the compound of Formula I, or a pharmaceutically acceptable salt thereof, one or more $R^3$ is $C_{1-3}$ alkyl, wherein the $C_{1-3}$ alkyl is optionally substituted with 1-3 groups independently selected from —OH, —CN, halogen, —C(O)OH, and $R^a$.

In some embodiments of the compound of Formula I, or a pharmaceutically acceptable salt thereof, one or more $R^3$ is $C_{1-6}$ alkyl, wherein the $C_{1-6}$ alkyl is substituted with 1-3 groups independently selected from —CN, halogen, $R^a$, $R^b$, and $R^c$. In some embodiments of the compound of Formula I, or a pharmaceutically acceptable salt thereof, one or more $R^3$ is $C_{1-6}$ alkyl, wherein the $C_{1-6}$ alkyl is substituted with 1-3 groups independently selected from —OH, —CN, halogen, —C(O)OR$^4$, —C(O)NR$^5$R$^5$, and $R^a$. In some embodiments of the compound of Formula I, or a pharmaceutically acceptable salt thereof, one or more $R^3$ is $C_{1-6}$ alkyl, wherein the $C_{1-6}$ alkyl is substituted with 1-3 groups independently selected from —OH, —CN, halogen, —C(O)OH, and $R^a$. In some embodiments of the compound of Formula I, or a pharmaceutically acceptable salt thereof, one or more $R^3$ is $C_{1-3}$ alkyl, wherein the $C_{1-3}$ alkyl is substituted with 1-3 groups independently selected from —OH, —CN, halogen, —C(O)OH, and $R^a$. In some embodiments of the compound of Formula I, or a pharmaceutically acceptable salt thereof, one or more $R^3$ is —CH$_2$P(O)(OH)$_2$. In some embodiments of the compound of Formula I, or a pharmaceutically acceptable salt thereof, one or more $R^3$ is —CH$_2$C(O)OH.

In some embodiments of the compound of Formula I, or a pharmaceutically acceptable salt thereof, one or more $R^3$ is $C_{1-6}$ alkyl. In some embodiments of the compound of Formula I, or a pharmaceutically acceptable salt thereof, one or more $R^3$ is $C_{1-3}$ alkyl. In some embodiments of the compound of Formula I, or a pharmaceutically acceptable salt thereof, one or more $R^3$ is methyl.

In some embodiments of the compound of Formula I, or a pharmaceutically acceptable salt thereof, one $R^3$ is —OP(O)(OH)$_2$ and 1-2 $R^3$ is $C_{1-3}$ alkyl, wherein the $C_{1-3}$ alkyl is optionally substituted with 1-3 groups independently selected from —C(O)OH, —C(O)NR$^5$R$^5$, and $R^a$. In some embodiments of the compound of Formula I, or a pharmaceutically acceptable salt thereof, one $R^3$ is —OP(O)(OH)$_2$ and 1-2 $R^3$ is $C_{1-3}$ alkyl, wherein the $C_{1-3}$ alkyl is optionally substituted with 1-3 groups independently selected from —C(O)OH and $R^a$. In some embodiments of the compound of Formula I, or a pharmaceutically acceptable salt thereof, one $R^3$ is —OP(O)(OH)$_2$, one $R^3$ is unsubstituted $C_{1-3}$ alkyl, and one $R^3$ is $C_{1-3}$ alkyl, wherein the $C_{1-3}$ alkyl is substituted with 1-3 groups independently selected from —C(O)OH and $R^a$.

In some embodiments of the compound of Formula I, or a pharmaceutically acceptable salt thereof, one or more $R^3$ is 5-6 membered monocyclic heteroaryl, wherein the 5-6 membered monocyclic heteroaryl is optionally substituted with 1-3 groups independently selected from —CN, halogen, $R^a$, $R^b$, and $R^c$. In some embodiments of the compound of Formula I, or a pharmaceutically acceptable salt thereof, one or more $R^3$ is 5-6 membered monocyclic heteroaryl, wherein the 5-6 membered monocyclic heteroaryl is substituted with 1-3 groups independently selected from —CN, halogen, $R^a$, $R^b$, and $R^c$. In some embodiments of the compound of Formula I, or a pharmaceutically acceptable salt thereof, one or more $R^3$ is 5-6 membered monocyclic heteroaryl.

In some embodiments of the compound of Formula I, or a pharmaceutically acceptable salt thereof, one Y is phenyl, wherein the phenyl is substituted with methyl, —OP(O)(OH)$_2$, and —CH$_2$C(O)OH.

In some embodiments of the compound of Formula I, or a pharmaceutically acceptable salt thereof, X is $C_{2-6}$ alkenyl, wherein the $C_{2-6}$ alkenyl is substituted with 1-3 Y groups. In some embodiments of the compound of Formula I, or a pharmaceutically acceptable salt thereof, X is $C_{2-6}$ alkenyl, wherein the $C_{2-6}$ alkenyl is substituted with 1-2 Y groups. In some embodiments of the compound of Formula I, or a pharmaceutically acceptable salt thereof, X is $C_{2-6}$ alkenyl, wherein the $C_{2-6}$ alkenyl is substituted with two Y groups. In some embodiments of the compound of Formula I, or a pharmaceutically acceptable salt thereof, X is $C_{2-6}$ alkenyl, wherein the $C_{2-6}$ alkenyl is substituted with one Y group. In some embodiments of the compound of Formula I, or a pharmaceutically acceptable salt thereof, X is $C_{2-4}$ alkenyl, wherein the $C_{2-4}$ alkenyl is substituted with 1-3 Y groups. In some embodiments of the compound of Formula I, or a pharmaceutically acceptable salt thereof, X is $C_{2-4}$ alkenyl, wherein the $C_{2-4}$ alkenyl is substituted with 1-2 Y groups. In some embodiments of the compound of Formula I, or a pharmaceutically acceptable salt thereof, X is $C_{2-4}$ alkenyl, wherein the $C_{2-4}$ alkenyl is substituted with three Y groups. In some embodiments of the compound of Formula I, or a pharmaceutically acceptable salt thereof, X is $C_{2-4}$ alkenyl, wherein the $C_{2-4}$ alkenyl is substituted with two Y groups. In some embodiments of the compound of Formula I, or a pharmaceutically acceptable salt thereof, X is $C_{2-4}$ alkenyl, wherein the $C_{2-4}$ alkenyl is substituted with one Y group. In some embodiments of the compound of Formula I, or a pharmaceutically acceptable salt thereof, X is $C_2$ alkenyl, wherein the $C_2$ alkenyl is substituted with 1-2 Y groups. In some embodiments of the compound of Formula I, or a pharmaceutically acceptable salt thereof, X is $C_2$ alkenyl, wherein the $C_2$ alkenyl is substituted with two Y groups. In some embodiments of the compound of Formula I, or a pharmaceutically acceptable salt thereof, X is $C_2$ alkenyl, wherein the $C_2$ alkenyl is substituted with one Y group.

In some embodiments of the compound of Formula I, or a pharmaceutically acceptable salt thereof, X is $C_{2-6}$ alkenyl, wherein the $C_{2-6}$ alkenyl is substituted with 1-3 Y group and wherein one or more Y groups is —C(O)NR$^5$R$^5$. In some embodiments of the compound of Formula I, or a pharmaceutically acceptable salt thereof, X is $C_{2-6}$ alkenyl, wherein the $C_{2-6}$ alkenyl is substituted with two Y groups and wherein one or more Y groups is —C(O)NR$^5$R$^5$. In some embodiments of the compound of Formula I, or a pharmaceutically acceptable salt thereof, X is $C_{2-6}$ alkenyl, wherein the $C_{2-6}$ alkenyl is substituted with one Y group and wherein the Y group is —C(O)NR$^5$R$^5$. In some embodiments of the compound of Formula I, or a pharmaceutically acceptable salt thereof, X is $C_{2-4}$ alkenyl, wherein the $C_{2-4}$ alkenyl is substituted with 1-3 Y groups and wherein one or more Y groups is —C(O)NR$^5$R$^5$. In some embodiments of the compound of Formula I, or a pharmaceutically acceptable salt thereof, X is $C_{2-4}$ alkenyl, wherein the $C_{2-4}$ alkenyl is substituted with 1-2 Y groups and wherein one or more Y groups is —C(O)NR$^5$R$^5$. In some embodiments of the compound of Formula I, or a pharmaceutically acceptable salt thereof, X is $C_{2-4}$ alkenyl, wherein the $C_{2-4}$ alkenyl is substituted with three Y groups and wherein one or more Y groups is —C(O)NR$^5$R$^5$. In some embodiments of the compound of Formula I, or a pharmaceutically acceptable salt thereof, X is $C_{2-4}$ alkenyl, wherein the $C_{2-4}$ alkenyl is substituted with two Y groups and wherein one or more Y groups is —C(O)NR$^5$R$^5$. In some embodiments of the compound of Formula I, or a pharmaceutically acceptable salt thereof, X is $C_{2-4}$ alkenyl, wherein the $C_{2-4}$ alkenyl is substituted with one Y group and wherein the Y group is —C(O)NR$^5$R$^5$. In some embodiments of the compound of Formula I, or a pharmaceutically acceptable salt thereof, X is $C_2$ alkenyl, wherein the $C_2$ alkenyl is substituted with 1-2 Y groups and wherein one or more Y groups is —C(O)NR$^5$R$^5$. In some embodiments of the compound of Formula I, or a pharmaceutically acceptable salt thereof, X is $C_2$ alkenyl, wherein the $C_2$ alkenyl is substituted with two Y groups and wherein one or more Y groups is —C(O)NR$^5$R$^5$. In some embodiments of the compound of Formula I, or a pharmaceutically acceptable salt thereof, X is $C_2$ alkenyl, wherein the $C_2$ alkenyl is substituted with one Y group and wherein the Y group is —C(O)NR$^5$R$^5$.

In some embodiments of the compound of Formula I, or a pharmaceutically acceptable salt thereof, each $R^a$ independently is —P(O)(OH)$_2$ or —OP(O)(OH)$_2$. In some embodiments of the compound of Formula I, or a pharmaceutically acceptable salt thereof, one or more $R^a$ is —P(O)(OH)$_2$. In some embodiments of the compound of Formula I, or a pharmaceutically acceptable salt thereof, one or more $R^a$ is —OP(O)(OH)$_2$.

In some embodiments of the compound of Formula I, or a pharmaceutically acceptable salt thereof, each $R^b$ independently is —C(O)R$^4$, —C(O)OR$^4$, —C(O)NR$^5$R$^5$, —C(O)C(O)OR$^4$, —S(O)$_2$R$^4$, —S(O)$_2$NR$^5$R$^5$, or —S(O)$_{20}$R$^4$. In some embodiments of the compound of Formula I, or a pharmaceutically acceptable salt thereof, one or more $R^b$ is —C(O)R$^4$. In some embodiments of the compound of Formula I, or a pharmaceutically acceptable salt thereof, one or more $R^b$ is —C(O)OR$^4$. In some embodiments of the compound of Formula I, or a pharmaceutically acceptable salt thereof, one or more $R^b$ is —C(O)NR$^5$R$^5$. In some embodiments of the compound of Formula I, or a pharmaceutically acceptable salt thereof, one or more $R^b$ is —C(O)C(O)OR$^4$. In some embodiments of the compound of Formula I, or a pharmaceutically acceptable salt thereof, one or more $R^b$ is —S(O)$_2$R$^4$. In some embodiments of the compound of Formula I, or a pharmaceutically acceptable salt thereof, one or more $R^b$ is —S(O)$_2$NR$^5$R$^5$. In some embodiments of the compound of Formula I, or a pharmaceutically acceptable salt thereof, one or more $R^b$ is —S(O)$_2$OR$^4$.

In some embodiments of the compound of Formula I, or a pharmaceutically acceptable salt thereof, each $R^C$ independently is —OR$^4$, —OC(O)R$^4$, —OC(O)C(O)OR$^4$, —O(C$_{1-4}$ alkyl))$_n$OR$^4$, —NR$^5$R$^5$, —N$^+$R$^5$R$^5$R$^{5a}$, —NR$^5$C(O)R$^4$, —NR$^5$C(O)NR$^5$R$^5$, —NR$^5$C(O)OR$^4$, —NR$^5$C(O)C(O)OR$^4$, or —NR$^5$S(O)$_2$R$^4$. In some embodiments of the compound of Formula I, or a pharmaceutically acceptable salt thereof, one or more $R^C$ is —OR$^4$. In some embodiments of the compound of Formula I, or a pharmaceutically acceptable salt thereof, one or more $R^C$ is —OC(O)R$^4$. In some embodiments of the compound of Formula I, or a pharmaceutically acceptable salt thereof, one or more $R^C$ is —OC(O)C(O)OR$^4$. In some embodiments of the compound of Formula I, or a pharmaceutically acceptable salt thereof, one or more $R^C$ is —(O(C$_{1-4}$ alkyl))$_n$OR$^4$. In some embodiments of the compound of Formula I, or a pharmaceutically acceptable salt thereof, one or more $R^C$ is —NR$^5$R$^5$. In some embodiments of the compound of Formula I, or a pharmaceutically acceptable salt thereof, one or more $R^C$ is —N$^+$R$^5$R$^5$R$^{5a}$. In some embodiments of the compound of Formula I, or a pharmaceutically acceptable salt thereof, one or more $R^C$ is —NR$^5$C(O)R$^4$. In some embodiments of the compound of Formula I, or a pharmaceutically acceptable salt thereof, one or more $R^C$ is —NR$^5$C(O)NR$^5$R$^5$. In some embodiments of the compound of Formula I, or a pharmaceutically acceptable salt thereof, one or more $R^C$ is —NR$^5$C(O)OR$^4$. In some embodiments of the compound of Formula I, or a pharmaceutically acceptable salt thereof, one or more $R^C$ is —NR$^5$C(O)C(O)OR$^4$. In some embodiments of the compound of Formula I, or a pharmaceutically acceptable salt thereof, one or more $R^C$ is —NR$^5$S(O)$_2$R$^4$.

In some embodiments of the compound of Formula I, or a pharmaceutically acceptable salt thereof, each $R^4$ independently is H or C$_{1-6}$ alkyl, wherein the C$_{1-6}$ alkyl is optionally substituted with 1-3 groups independently selected from —CN, halogen, R$^a$, R$^d$, and Re. In some embodiments of the compound of Formula I, or a pharmaceutically acceptable salt thereof, each $R^4$ independently is H or C$_{1-6}$ alkyl, wherein the C$_{1-6}$ alkyl is optionally substituted with 1-3 groups independently selected from —OH, —CN, halogen, —C(O)OH, —NR$^7$R$^7$, and R$^a$. In some embodiments of the compound of Formula I, or a pharmaceutically acceptable salt thereof, each $R^4$ independently is H or C$_{1-6}$ alkyl, wherein the C$_{1-6}$ alkyl is optionally substituted with 1-2 groups independently selected from —C(O)OH, —NR$^5$R$^5$, and R$^a$. In some embodiments of the compound of Formula I, or a pharmaceutically acceptable salt thereof, each $R^4$ independently is C$_{1-4}$ alkyl, wherein the C$_{1-4}$ alkyl is optionally substituted with one group selected from —C(O)OH, —NR$^7$R$^7$, and W.

In some embodiments of the compound of Formula I, or a pharmaceutically acceptable salt thereof, one or more $R^4$ is H. In some embodiments of the compound of Formula I, or a pharmaceutically acceptable salt thereof, one or more $R^4$ is C$_{1-6}$ alkyl, wherein the C$_{1-6}$ alkyl is optionally substituted with 1-3 groups independently selected from —CN, halogen, R$^a$, R$^d$, and Re. In some embodiments of the compound of Formula I, or a pharmaceutically acceptable salt thereof, one or more $R^4$ is C$_{1-6}$ alkyl, wherein the C$_{1-6}$ alkyl is optionally substituted with 1-3 groups independently selected from —OH, —CN, halogen, —C(O)OH, and W. In some embodiments of the compound of Formula I, or a pharmaceutically acceptable salt thereof, one or more $R^4$ is C$_{1-6}$ alkyl, wherein the C$_{1-6}$ alkyl is optionally substituted with 1-2 groups independently selected from —C(O)OH, —NR$^7$R$^7$, and R$^a$. In some embodiments of the compound of Formula I, or a pharmaceutically acceptable salt thereof, one or more $R^4$ is C$_{1-4}$ alkyl, wherein the C$_{1-4}$ alkyl is optionally substituted with one group selected from —C(O)OH, —NR$^5$R$^5$, and R$^a$. In some embodiments of the compound of Formula I, or a pharmaceutically acceptable salt thereof, one or more $R^4$ is C$_{1-6}$ alkyl, wherein the C$_{1-6}$ alkyl is substituted with 1-3 groups independently selected from —CN, halogen, R$^a$, R$^d$, and W. In some embodiments of the compound of Formula I, or a pharmaceutically acceptable salt thereof, one or more $R^4$ is C$_{1-6}$ alkyl, wherein the C$_{1-6}$ alkyl is substituted with 1-3 groups independently selected from —OH, —CN, halogen, —C(O)OH, —NR$^5$R$^5$, and R$^a$. In some embodiments of the compound of Formula I, or a pharmaceutically acceptable salt thereof, one or more $R^4$ is C$_{1-6}$ alkyl, wherein the C$_{1-6}$ alkyl is substituted with 1-2 groups independently selected from —C(O)OH, —NR$^7$R$^7$, and R$^a$. In some embodiments of the compound of Formula I, or a pharmaceutically acceptable salt thereof, one or more $R^4$ is C$_{1-4}$ alkyl, wherein the C$_{1-4}$ alkyl is substituted with one group selected from —C(O)OH, —NR$^7$R$^7$, and W. In some embodiments of the compound of Formula I, or a pharmaceutically acceptable salt thereof, one or more $R^4$ is C$_{1-6}$ alkyl. In some embodiments of the compound of Formula I, or a pharmaceutically acceptable salt thereof, one or more $R^4$ is C$_{1-4}$ alkyl. In some embodiments of the compound of Formula I, or a pharmaceutically acceptable salt thereof, one or more $R^4$ is methyl.

In some embodiments of the compound of Formula I, or a pharmaceutically acceptable salt thereof, n is 1, 2, 3, or 4 and $R^4$ is methyl. In some embodiments of the compound of Formula I, or a pharmaceutically acceptable salt thereof, n is 4 and $R^4$ is methyl.

In some embodiments of the compound of Formula I, or a pharmaceutically acceptable salt thereof, each $R^5$ independently is H, R$^d$, C$_{1-6}$ alkyl, or 5-6 membered monocyclic heteroaryl,
  wherein the C$_{1-6}$ alkyl is optionally substituted with 1-3 groups independently selected from —CN, halogen, =NR$^{5a}$, R$^a$, R$^d$, R$^c$, phenyl, naphthalenyl, and 8-10 membered fused bicyclic heteroaryl,
  wherein the 5-6 membered monocyclic heteroaryl is optionally substituted with 1-3 groups independently selected from —CN, halogen, R$^a$, R$^d$, and Re.

In some embodiments of the compound of Formula I, or a pharmaceutically acceptable salt thereof, each $R^5$ independently is H, R$^d$, or C$_{1-6}$ alkyl, wherein the C$_{1-6}$ alkyl is optionally substituted with 1-3 groups independently selected from —CN, halogen, =NR$^{5a}$, R$^a$, R$^d$, R$^c$, phenyl, and naphthalenyl.

In some embodiments of the compound of Formula I, or a pharmaceutically acceptable salt thereof, each $R^5$ independently is H, —C(O)OR$^6$, —C(O)C(O)OR$^6$, or C$_{1-6}$ alkyl, wherein the C$_{1-6}$ alkyl is optionally substituted with 1-3 groups independently selected from —OH, —CN, halogen, —C(O)OR$^6$, =NR$^{5a}$, R$^a$, and phenyl.

In some embodiments of the compound of Formula I, or a pharmaceutically acceptable salt thereof, each $R^5$ independently is H, —C(O)OR$^6$, —C(O)C(O)OR$^6$, or C$_{1-4}$ alkyl, wherein the C$_{1-4}$ alkyl is optionally substituted with 1-2 groups independently selected from —C(O)OH, —C(O)NH$_2$, =NR$^{5a}$, —NR$^7$R$^7$, R$^a$, and phenyl.

In some embodiments of the compound of Formula I, or a pharmaceutically acceptable salt thereof, each $R^5$ independently is H, —C(O)OR$^6$, —C(O)C(O)OR$^6$, or C$_{1-4}$ alkyl, wherein the C$_{1-4}$ alkyl is optionally substituted with 1-2 groups independently selected from —C(O)OH, =NR$^{5a}$, —NR$^7$R$^7$, R$^a$, and phenyl.

In some embodiments of the compound of Formula I, or a pharmaceutically acceptable salt thereof, each $R^5$ independently is H, methyl, —CH$_2$CO$_2$H, —CH$_2$P(O)(OH)$_2$, —CH$_2$CH$_2$CO$_2$H, —C(O)OCH$_3$, —C(=NH)NH$_2$, —C(O)C(O)OH,

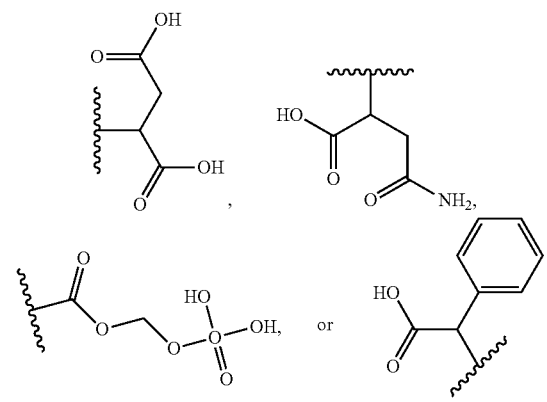

In some embodiments of the compound of Formula I, or a pharmaceutically acceptable salt thereof, each $R^5$ independently is H, methyl, —CH$_2$CO$_2$H, —CH$_2$CH$_2$CO$_2$H, —C(O)OCH$_3$, —C(=NH)NH$_2$, —C(O)C(O)OH,

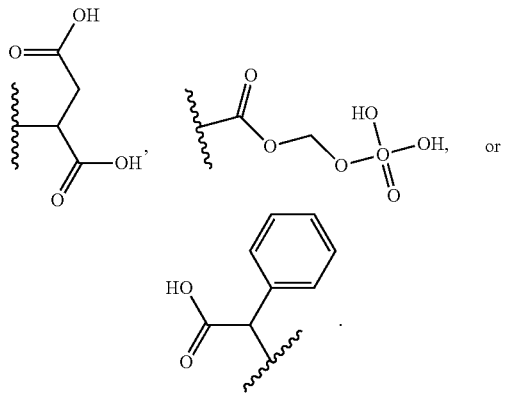

In some embodiments of the compound of Formula I, or a pharmaceutically acceptable salt thereof, one or more $R^5$ is H. In some embodiments of the compound of Formula I, or a pharmaceutically acceptable salt thereof, one or more $R^5$ is $R^d$. In some embodiments of the compound of Formula I, or a pharmaceutically acceptable salt thereof, one or more $R^5$ is —C(O)OR$^6$. In some embodiments of the compound of Formula I, or a pharmaceutically acceptable salt thereof, one or more $R^5$ is —C(O)C(O)OR$^6$.

In some embodiments of the compound of Formula I, or a pharmaceutically acceptable salt thereof, one or more $R^5$ is C$_{1-6}$ alkyl, wherein the C$_{1-6}$ alkyl is optionally substituted with 1-3 groups independently selected from —CN, halogen, =NR$^{5a}$, R$^a$, R$^d$, R$^c$, phenyl, naphthalenyl, and 8-10 membered fused bicyclic heteroaryl. In some embodiments of the compound of Formula I, or a pharmaceutically acceptable salt thereof, one or more $R^5$ is C$_{1-6}$ alkyl, wherein the C$_{1-6}$ alkyl is optionally substituted with 1-3 groups independently selected from —CN, halogen, =NR$^{5a}$, R$^a$, R$^b$, R$^c$, phenyl, and naphthalenyl. In some embodiments of the compound of Formula I, or a pharmaceutically acceptable salt thereof, one or more $R^5$ is C$_{1-6}$ alkyl, wherein the C$_{1-6}$ alkyl is optionally substituted with 1-3 groups independently selected from —OH, —CN, halogen, —C(O)OR$^6$, =NR$^{5a}$, —NR$^7$R$^7$, R$^a$, and phenyl. In some embodiments of the compound of Formula I, or a pharmaceutically acceptable salt thereof, one or more $R^5$ is C$_{1-4}$ alkyl, wherein the C$_{1-4}$ alkyl is optionally substituted with 1-2 groups independently selected from —C(O)OH, =NR$^{5a}$, —NR$^7$R$^7$, R$^a$, and phenyl.

In some embodiments of the compound of Formula I, or a pharmaceutically acceptable salt thereof, one or more $R^5$ is C$_{1-6}$ alkyl, wherein the C$_{1-6}$ alkyl is substituted with 1-3 groups independently selected from —CN, halogen, =NR$^{5a}$, R$^a$, R$^d$, R$^c$, phenyl, naphthalenyl, and 8-10 membered fused bicyclic heteroaryl. In some embodiments of the compound of Formula I, or a pharmaceutically acceptable salt thereof, one or more $R^5$ is C$_{1-6}$ alkyl, wherein the C$_{1-6}$ alkyl is substituted with 1-3 groups independently selected from —CN, halogen, =NR$^{5a}$, R$^a$, R$^d$, R$^c$, phenyl, and naphthalenyl. In some embodiments of the compound of Formula I, or a pharmaceutically acceptable salt thereof, one or more $R^5$ is C$_{1-6}$ alkyl, wherein the C$_{1-6}$ alkyl is substituted with 1-3 groups independently selected from —OH, —CN, halogen, —C(O)OR$^6$, =NR$^{5a}$, —NR$^7$R$^7$, R$^a$, and phenyl. In some embodiments of the compound of Formula I, or a pharmaceutically acceptable salt thereof, one or more $R^5$ is C$_{1-4}$ alkyl, wherein the C$_{1-4}$ alkyl is substituted with 1-2 groups independently selected from —C(O)OH, =NR$^{5a}$, —NR$^7$R$^7$, R$^a$, and phenyl.

In some embodiments of the compound of Formula I, or a pharmaceutically acceptable salt thereof, one or more $R^5$ is C$_{1-6}$ alkyl. In some embodiments of the compound of Formula I, or a pharmaceutically acceptable salt thereof, one or more $R^5$ is C$_{1-4}$ alkyl.

In some embodiments of the compound of Formula I, or a pharmaceutically acceptable salt thereof, one or more $R^5$ is 5-6 membered monocyclic heteroaryl, wherein the 5-6 membered monocyclic heteroaryl is optionally substituted with 1-3 groups independently selected from —CN, halogen, R$^a$, R$^d$, and Re. In some embodiments of the compound of Formula I, or a pharmaceutically acceptable salt thereof, one or more $R^5$ is 5-6 membered monocyclic heteroaryl, wherein the 5-6 membered monocyclic heteroaryl is substituted with 1-3 groups independently selected from —CN, halogen, R$^a$, R$^d$, and Re. In some embodiments of the compound of Formula I, or a pharmaceutically acceptable salt thereof, one or more $R^5$ is 5-6 membered monocyclic heteroaryl.

In some embodiments of the compound of Formula I, or a pharmaceutically acceptable salt thereof, one $R^5$ is

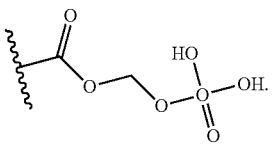

In some embodiments of the compound of Formula I, or a pharmaceutically acceptable salt thereof, one $R^5$ is

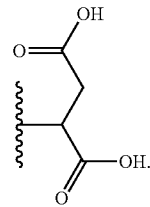

In some embodiments of the compound of Formula I, or a pharmaceutically acceptable salt thereof, one $R^5$ is

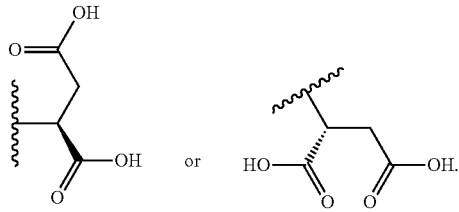 [SMILES: *[C@@H](CC(=O)O)C(=O)O ; *[C@H](CC(=O)O)C(=O)O]

In some embodiments of the compound of Formula I, or a pharmaceutically acceptable salt thereof, one $R^5$ is

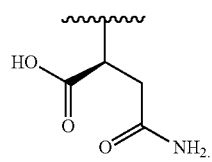

In some embodiments of the compound of Formula I, or a pharmaceutically acceptable salt thereof, each $R^{5a}$ independently is H or $C_{1-3}$ alkyl. In some embodiments of the compound of Formula I, or a pharmaceutically acceptable salt thereof, each $R^{5a}$ independently is H or methyl. In some embodiments of the compound of Formula I, or a pharmaceutically acceptable salt thereof, one or more $R^{5a}$ is H. In some embodiments of the compound of Formula I, or a pharmaceutically acceptable salt thereof, one or more $R^{5a}$ is $C_{1-3}$ alkyl. In some embodiments of the compound of Formula I, or a pharmaceutically acceptable salt thereof, one or more $R^{5a}$ is methyl.

In some embodiments of the compound of Formula I, or a pharmaceutically acceptable salt thereof, each $R^d$ independently is —C(O)$R^6$, —C(O)O$R^6$, —C(O)N$R^5R^5$, —C(O)C(O)O$R^6$, —S(O)$_2R^6$, —S(O)$_2$N$R^5R^5$, or —S(O)$_2$O$R^6$. In some embodiments of the compound of Formula I, or a pharmaceutically acceptable salt thereof, one or more $R^d$ is —C(O)$R^6$. In some embodiments of the compound of Formula I, or a pharmaceutically acceptable salt thereof, one or more $R^d$ is —C(O)O$R^6$. In some embodiments of the compound of Formula I, or a pharmaceutically acceptable salt thereof, one or more $R^d$ is —C(O)N$R^5R^5$. In some embodiments of the compound of Formula I, or a pharmaceutically acceptable salt thereof, one or more $R^d$ is —C(O)C(O)O$R^6$. In some embodiments of the compound of Formula I, or a pharmaceutically acceptable salt thereof, one or more $R^d$ is —S(O)$_2R^6$. In some embodiments of the compound of Formula I, or a pharmaceutically acceptable salt thereof, one or more $R^d$ is —S(O)$_2$N$R^7R^7$. In some embodiments of the compound of Formula I, or a pharmaceutically acceptable salt thereof, one or more $R^d$ is —S(O)$_2$O$R^6$.

In some embodiments of the compound of Formula I, or a pharmaceutically acceptable salt thereof, each Re independently is —O$R^6$, —OC(O)$R^6$, —OC(O)C(O)O$R^6$, —N$R^7R^7$, —N$R^7$C(O)$R^7$, —N$R^7$C(O)N$R^7R^7$, —N$R^7$C(O)O$R^6$, —N$R^7$C(O)C(O)O$R^6$, or —N$R^7$S(O)$_2R^6$. In some embodiments of the compound of Formula I, or a pharmaceutically acceptable salt thereof, one or more Re is —O$R^6$. In some embodiments of the compound of Formula I, or a pharmaceutically acceptable salt thereof, one or more Re is —OC(O)$R^6$. In some embodiments of the compound of Formula I, or a pharmaceutically acceptable salt thereof, one or more Re is —OC(O)C(O)O$R^6$. In some embodiments of the compound of Formula I, or a pharmaceutically acceptable salt thereof, one or more Re is —N$R^7R^7$. In some embodiments of the compound of Formula I, or a pharmaceutically acceptable salt thereof, one or more Re is —N$R^7$C(O)$R^7$. In some embodiments of the compound of Formula I, or a pharmaceutically acceptable salt thereof, one or more Re is —N$R^7$C(O)N$R^7R^7$. In some embodiments of the compound of Formula I, or a pharmaceutically acceptable salt thereof, one or more Re is —N$R^7$C(O)O$R^6$. In some embodiments of the compound of Formula I, or a pharmaceutically acceptable salt thereof, one or more Re is —N$R^7$C(O)C(O)O$R^6$. In some embodiments of the compound of Formula I, or a pharmaceutically acceptable salt thereof, one or more Re is —N$R^7$S(O)$_2R^6$.

In some embodiments of the compound of Formula I, or a pharmaceutically acceptable salt thereof, each $R^6$ independently is H or $C_{1-6}$ alkyl, wherein the $C_{1-6}$ alkyl is optionally substituted with 1-3 groups independently selected from CN, halogen, $R^a$, $R^f$, and $R^g$. In some embodiments of the compound of Formula I, or a pharmaceutically acceptable salt thereof, each $R^6$ independently is H or $C_{1-6}$ alkyl, wherein the $C_{1-6}$ alkyl is optionally substituted with 1-3 groups independently selected from —OH, CN, halogen, —C(O)OH, and $R^a$. In some embodiments of the compound of Formula I, or a pharmaceutically acceptable salt thereof, $R^6$ is H or $C_{1-3}$ alkyl, wherein the $C_{1-3}$ alkyl is optionally substituted with 1-2 $R^a$ groups.

In some embodiments of the compound of Formula I, or a pharmaceutically acceptable salt thereof, one or more $R^6$ is H. In some embodiments of the compound of Formula I, or a pharmaceutically acceptable salt thereof, one or more $R^6$ is $C_{1-6}$ alkyl, wherein the $C_{1-6}$ alkyl is optionally substituted with 1-3 groups independently selected from CN, halogen, $R^a$, $R^f$, and $R^g$. In some embodiments of the compound of Formula I, or a pharmaceutically acceptable salt thereof, one or more $R^6$ is $C_{1-6}$ alkyl, wherein the $C_{1-6}$ alkyl is optionally substituted with 1-3 groups independently selected from —OH, CN, halogen, —C(O)OH, and $R^a$. In some embodiments of the compound of Formula I, or a pharmaceutically acceptable salt thereof, one or more $R^6$ is $C_{1-3}$ alkyl, wherein the $C_{1-3}$ alkyl is optionally substituted with 1-2 $R^a$ groups.

In some embodiments of the compound of Formula I, or a pharmaceutically acceptable salt thereof, one or more $R^6$ is $C_{1-6}$ alkyl, wherein the $C_{1-6}$ alkyl is substituted with 1-3 groups independently selected from CN, halogen, $R^a$, $R^f$, and $R^g$. In some embodiments of the compound of Formula I, or a pharmaceutically acceptable salt thereof, one or more $R^6$ is $C_{1-6}$ alkyl, wherein the $C_{1-6}$ alkyl is substituted with 1-3 groups independently selected from —OH, CN, halogen, —C(O)OH, and $R^a$. In some embodiments of the compound of Formula I, or a pharmaceutically acceptable salt thereof, one or more $R^6$ is $C_{1-3}$ alkyl, wherein the $C_{1-3}$ alkyl is substituted with 1-2 $R^a$ groups. In some embodiments of the compound of Formula I, or a pharmaceutically acceptable salt thereof, one or more $R^6$ is $C_{1-6}$ alkyl. In some embodiments of the compound of Formula I, or a pharmaceutically acceptable salt thereof, one or more $R^6$ is $C_{1-3}$ alkyl.

In some embodiments of the compound of Formula I, or a pharmaceutically acceptable salt thereof, each IC independently is H, $R^f$, or $C_{1-6}$ alkyl, wherein the $C_{1-6}$ alkyl is optionally substituted with 1-3 groups independently selected from —CN, halogen, $R^a$, $R^f$, and $R^g$. In some embodiments of the compound of Formula I, or a pharmaceutically acceptable salt thereof, each $R^7$ independently is H or $C_{1-6}$ alkyl, wherein the $C_{1-6}$ alkyl is optionally substituted with 1-3 groups independently selected from —OH, —CN, halogen, —C(O)OH, and $R^a$. In some embodiments of the compound of Formula I, or a pharmaceutically acceptable salt thereof, each $R^7$ independently is H or $C_{1-3}$ alkyl, wherein the $C_{1-3}$ alkyl is optionally substituted with 1-3 groups independently selected from —OH, —CN, halogen, —C(O)OH, and $R^a$.

In some embodiments of the compound of Formula I, or a pharmaceutically acceptable salt thereof, one or more $R^7$ is H. In some embodiments of the compound of Formula I, or a pharmaceutically acceptable salt thereof, one $R^7$ is H. In some embodiments of the compound of Formula I, or a pharmaceutically acceptable salt thereof, one or more $R^7$ is $R^f$. In some embodiments of the compound of Formula I, or a pharmaceutically acceptable salt thereof, one or more $R^7$ is $C_{1-6}$ alkyl, wherein the $C_{1-6}$ alkyl is optionally substituted with 1-3 groups independently selected from —CN, halogen, $R^a$, $R^f$, and $R^g$. In some embodiments of the compound of Formula I, or a pharmaceutically acceptable salt thereof, one or more $R^7$ is $C_{1-6}$ alkyl, wherein the $C_{1-6}$ alkyl is optionally substituted with 1-3 groups independently selected from —OH, —CN, halogen, —C(O)OH, and $R^a$. In some embodiments of the compound of Formula I, or a pharmaceutically acceptable salt thereof, one or more $R^7$ is $C_{1-3}$ alkyl, wherein the $C_{1-3}$ alkyl is optionally substituted with 1-3 groups independently selected from —OH, —CN, halogen, —C(O)OH, and $R^a$. In some embodiments of the compound of Formula I, or a pharmaceutically acceptable salt thereof, one or more $R^7$ is $C_{1-6}$ alkyl, wherein the $C_{1-6}$ alkyl is substituted with 1-3 groups independently selected from —CN, halogen, $R^a$, $R^f$, and $R^g$. In some embodiments of the compound of Formula I, or a pharmaceutically acceptable salt thereof, one or more $R^1$ is $C_{1-6}$ alkyl, wherein the $C_{1-6}$ alkyl is substituted with 1-3 groups independently selected from —OH, —CN, halogen, —C(O)OH, and $R^a$. In some embodiments of the compound of Formula I, or a pharmaceutically acceptable salt thereof, one or more $R^1$ is $C_{1-3}$ alkyl, wherein the $C_{1-3}$ alkyl is substituted with 1-3 groups independently selected from —OH, —CN, halogen, —C(O)OH, and R. In some embodiments of the compound of Formula I, or a pharmaceutically acceptable salt thereof, one or more $R^7$ is $C_{1-6}$ alkyl. In some embodiments of the compound of Formula I, or a pharmaceutically acceptable salt thereof, one or more $R^1$ is $C_{1-3}$ alkyl.

In some embodiments of the compound of Formula I, or a pharmaceutically acceptable salt thereof, each $R^f$ independently is —C(O)$R^8$, —C(O)O$R^8$, —C(O)N$R^8R^8$, —C(O)C(O)O$R^8$, —S(O)$_2R^8$, —S(O)$_2$N$R^8R^8$, or —S(O)$_2$O$R^8$. In some embodiments of the compound of Formula I, or a pharmaceutically acceptable salt thereof, one or more $R^f$ is —C(O)$R^8$. In some embodiments of the compound of Formula I, or a pharmaceutically acceptable salt thereof, one or more $R^f$ is —C(O)O$R^8$. In some embodiments of the compound of Formula I, or a pharmaceutically acceptable salt thereof, one or more $R^f$ is —C(O)N$R^8R^8$. In some embodiments of the compound of Formula I, or a pharmaceutically acceptable salt thereof, one or more $R^f$ is —C(O)C(O)O$R^8$. In some embodiments of the compound of Formula I, or a pharmaceutically acceptable salt thereof, one or more $R^f$ is —S(O)$_2R^8$. In some embodiments of the compound of Formula I, or a pharmaceutically acceptable salt thereof, one or more $R^f$ is —S(O)$_2$N$R^8R^8$. In some embodiments of the compound of Formula I, or a pharmaceutically acceptable salt thereof, one or more $R^f$ is —S(O)$_2$O$R^8$.

In some embodiments of the compound of Formula I, or a pharmaceutically acceptable salt thereof, each $R^g$ independently is —O$R^8$, —OC(O)$R^8$, —OC(O)C(O)O$R^8$, —N$R^8$C(O)$R^8$, —N$R^8$C(O)N$R^8R^8$, —N$R^8$C(O)O$R^8$, —N$R^8$C(O)C(O)O$R^8$, or —N$R^8$S(O)$_2R^8$. In some embodiments of the compound of Formula I, or a pharmaceutically acceptable salt thereof, one or more $R^g$ is —O$R^8$. In some embodiments of the compound of Formula I, or a pharmaceutically acceptable salt thereof, one or more $R^g$ is —OC(O)$R^8$. In some embodiments of the compound of Formula I, or a pharmaceutically acceptable salt thereof, one or more $R^g$ is —OC(O)C(O)O$R^8$. In some embodiments of the compound of Formula I, or a pharmaceutically acceptable salt thereof, one or more $R^g$ is —N$R^8R^8$. In some embodiments of the compound of Formula I, or a pharmaceutically acceptable salt thereof, one or more $R^g$ is —N$R^8$C(O)$R^8$. In some embodiments of the compound of Formula I, or a pharmaceutically acceptable salt thereof, one or more $R^g$ is —N$R^8$C(O)N$R^8R^8$. In some embodiments of the compound of Formula I, or a pharmaceutically acceptable salt thereof, one or more $R^g$ is —N$R^8$C(O)O$R^8$. In some embodiments of the compound of Formula I, or a pharmaceutically acceptable salt thereof, one or more $R^g$ is —N$R^8$C(O)C(O)O$R^8$. In some embodiments of the compound of Formula I, or a pharmaceutically acceptable salt thereof, one or more $R^g$ is —N$R^8$S(O)$_2R^8$.

In some embodiments of the compound of Formula I, or a pharmaceutically acceptable salt thereof, each $R^8$ independently is H or $C_{1-6}$ alkyl, wherein the $C_{1-6}$ alkyl is optionally substituted with 1-3 groups independently selected from —OH, CN, halogen, —C(O)OH, and $R^a$. In some embodiments of the compound of Formula I, or a pharmaceutically acceptable salt thereof, one or more $R^8$ is H. In some embodiments of the compound of Formula I, or a pharmaceutically acceptable salt thereof, one or more $R^8$ is $C_{1-6}$ alkyl, wherein the $C_{1-6}$ alkyl is optionally substituted with 1-3 groups independently selected from —OH, CN, halogen, —C(O)OH, and $R^a$. In some embodiments of the compound of Formula I, or a pharmaceutically acceptable salt thereof, one or more $R^8$ is $C_{1-6}$ alkyl, wherein the $C_{1-6}$ alkyl is substituted with 1-3 groups independently selected from —OH, CN, halogen, —C(O)OH, and $R^a$. In some embodiments of the compound of Formula I, or a pharmaceutically acceptable salt thereof, one or more $R^8$ is $C_{1-6}$ alkyl.

In some embodiments of the compound of Formula I, provided herein is a compound selected from the group consisting of:

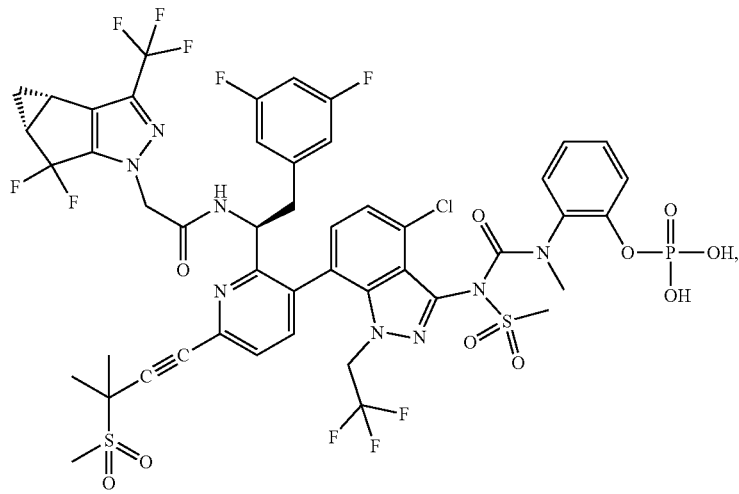

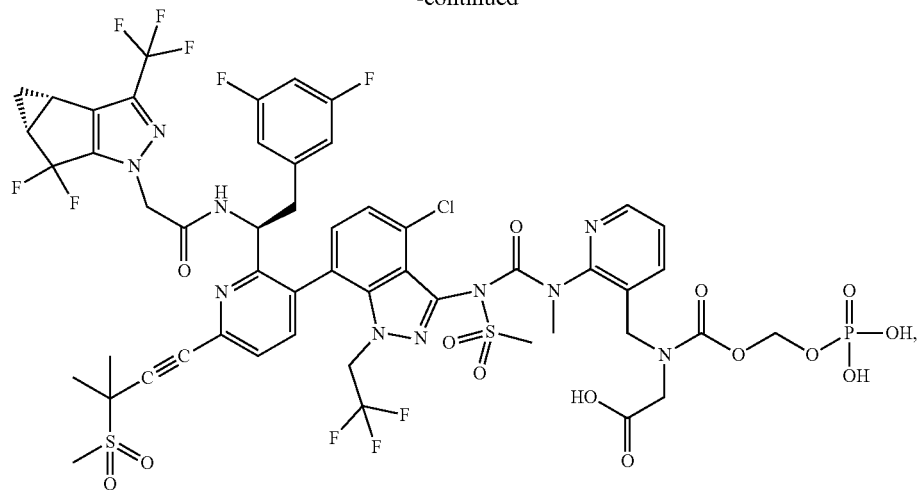
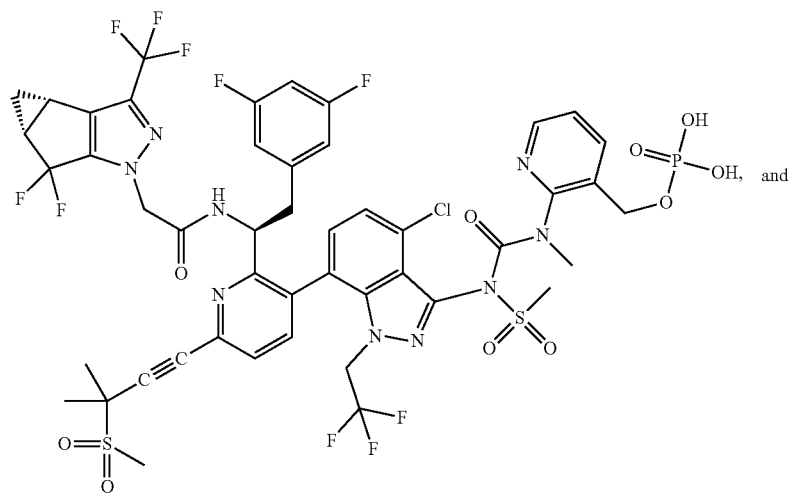
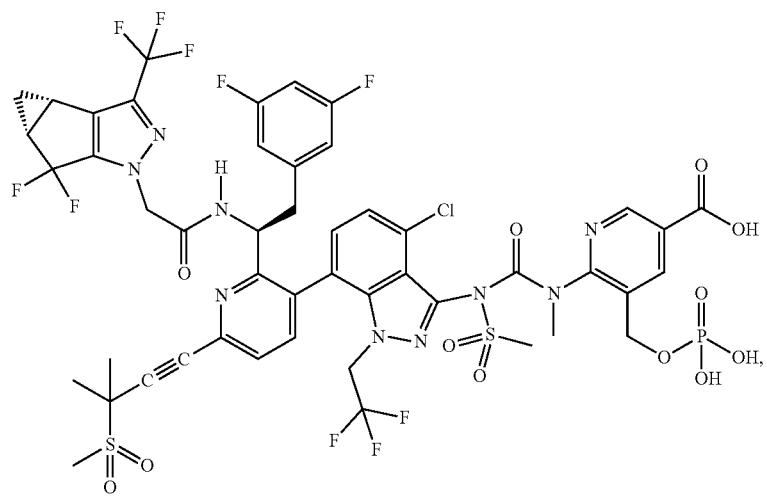 [SMILES: CN(C(=O)N(c1nn(CC(F)(F)F)c2c(-c3ccc(C#CC(C)(C)S(C)(=O)=O)nc3[C@H](Cc3cc(F)cc(F)c3)NC(=O)Cn3nc(C(F)(F)F)c4c3C(F)(F)[C@@H]3C[C@H]43)ccc(Cl)c12)S(C)(=O)=O)c1ncc(C(=O)O)cc1COP(=O)(O)O]
or a pharmaceutically acceptable salt thereof.

In some embodiments of the compound of Formula I, provided herein is a compound selected from the group consisting of:
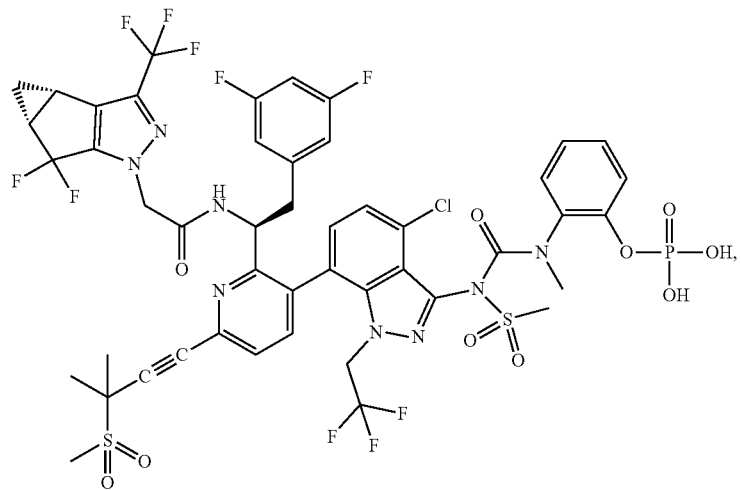
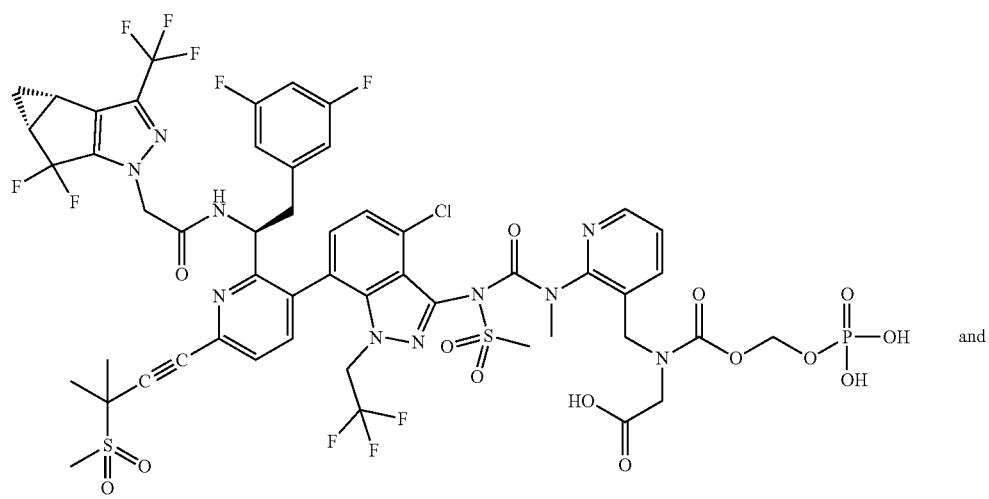
and
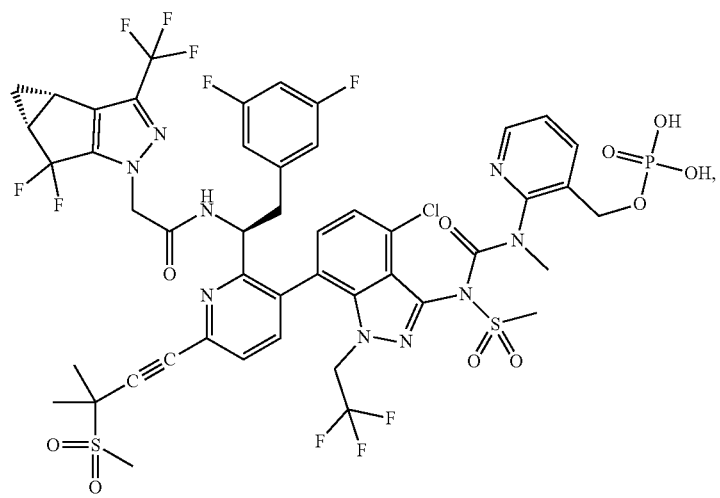
or a pharmaceutically acceptable salt thereof.

In some embodiments of the compound of Formula I, provided herein is a compound selected from the group consisting of:
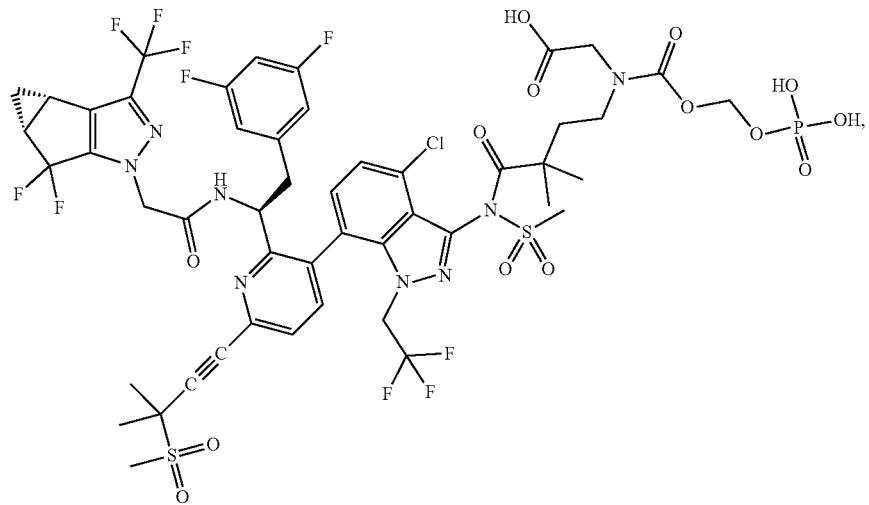
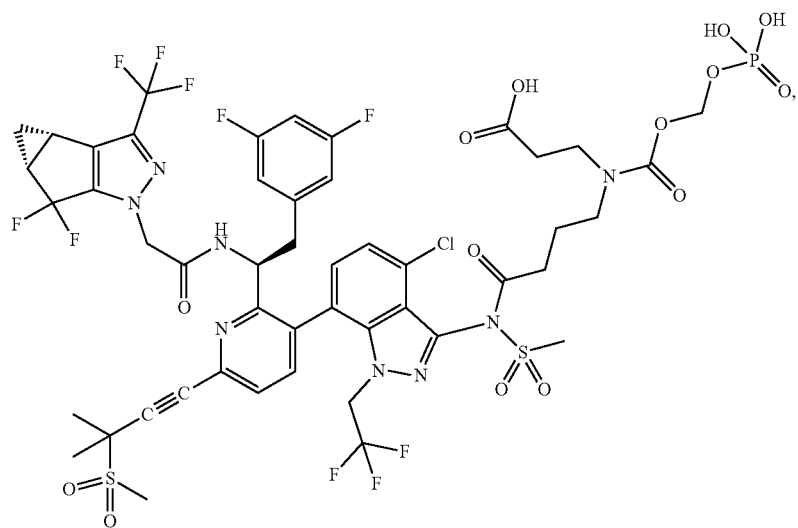
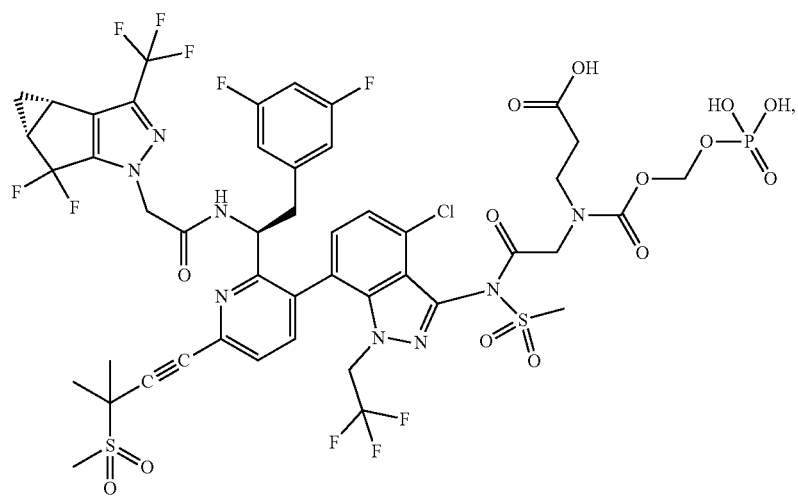

-continued
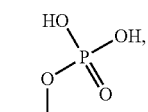
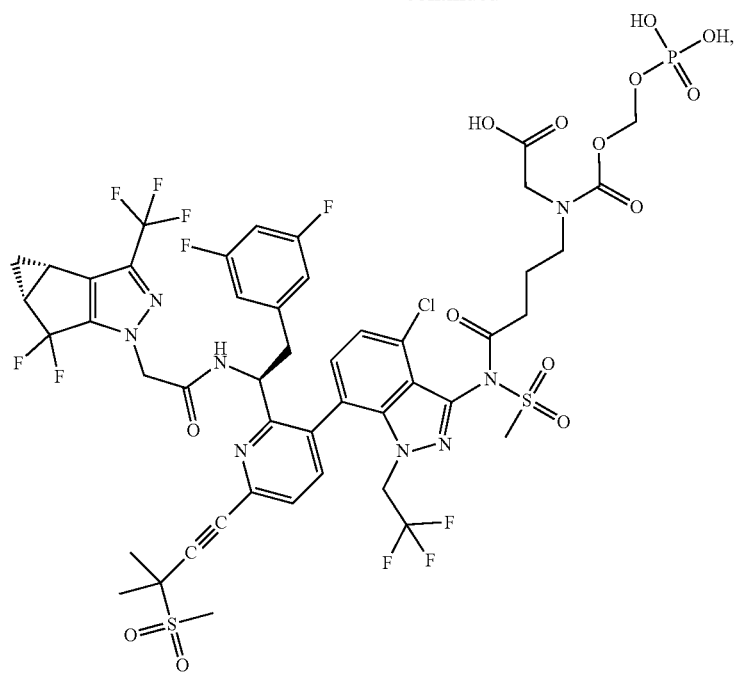
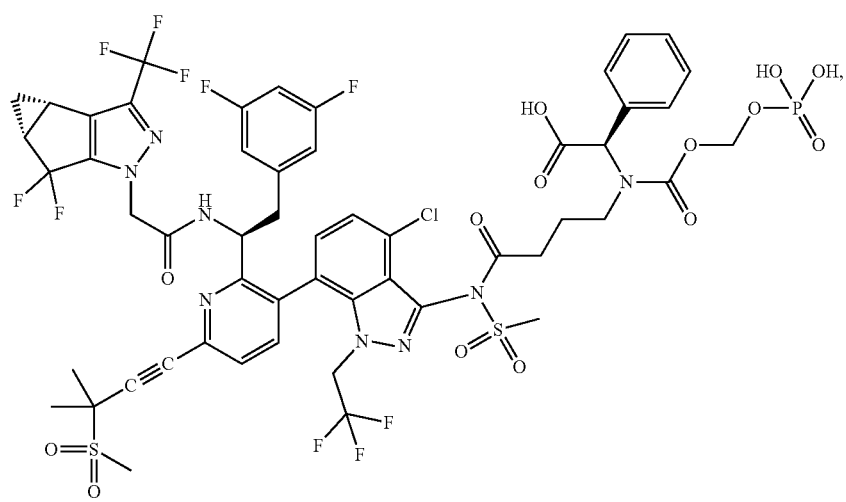

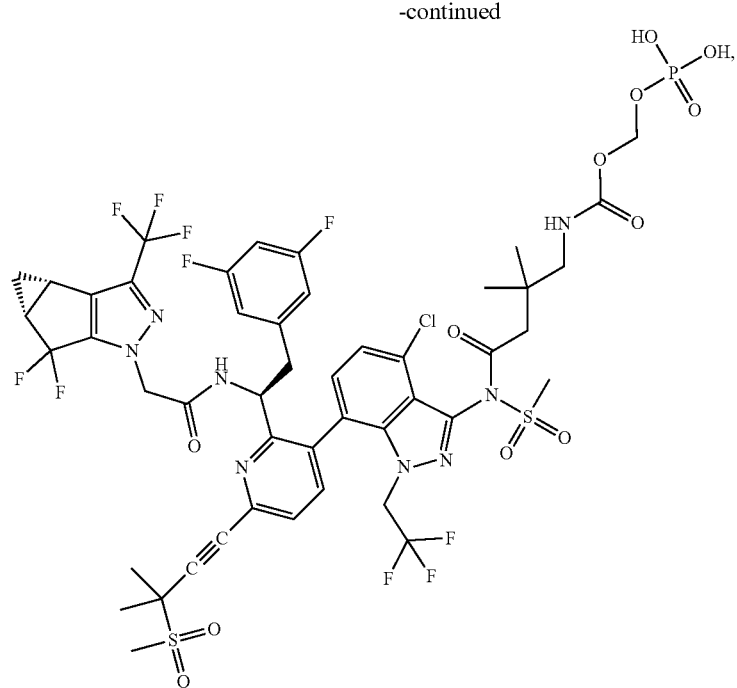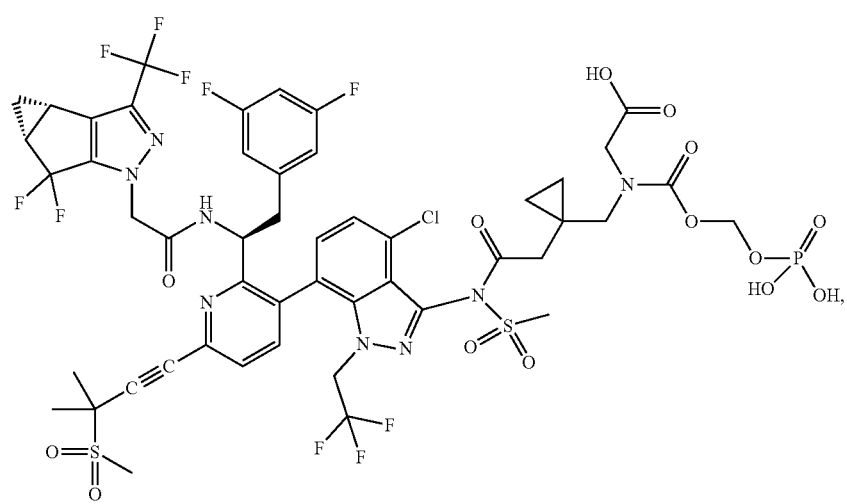

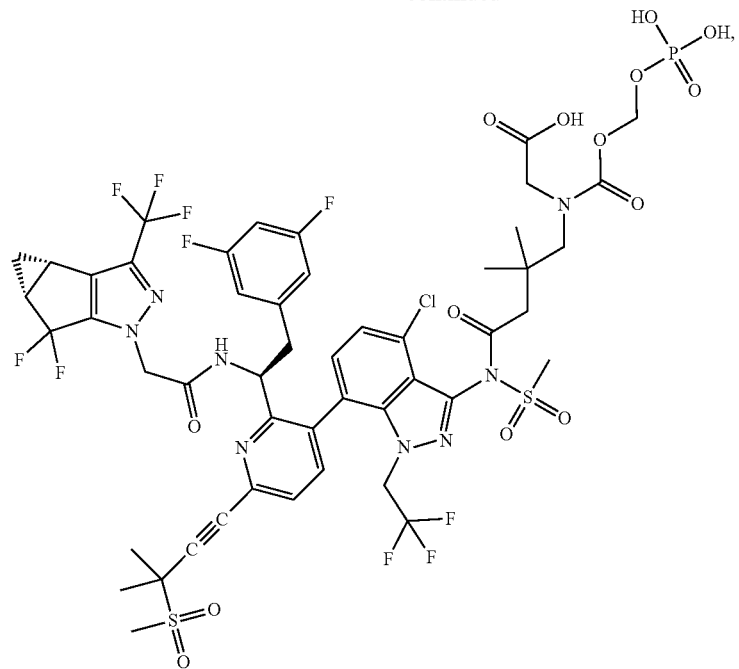
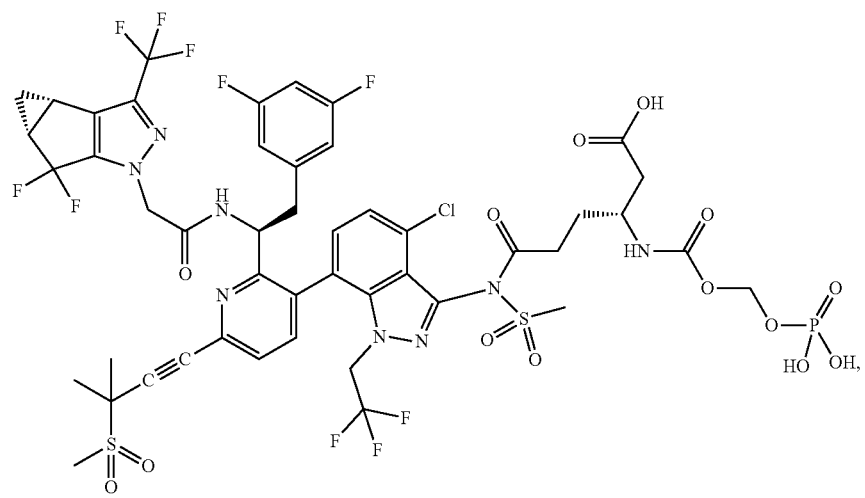
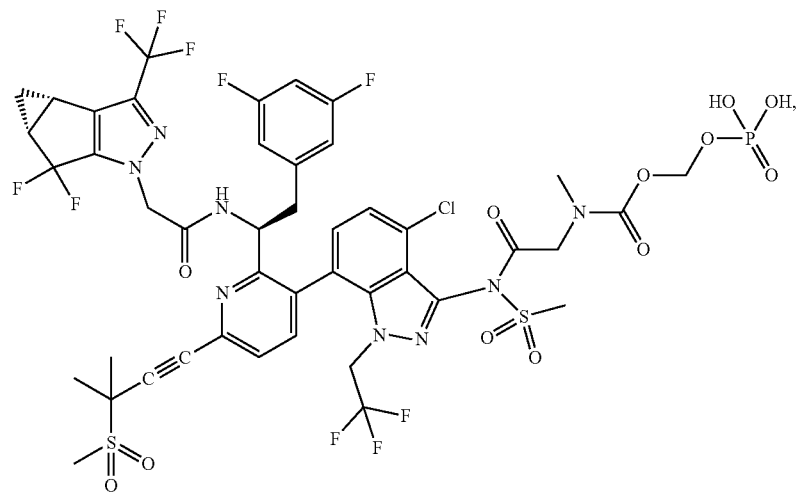

-continued
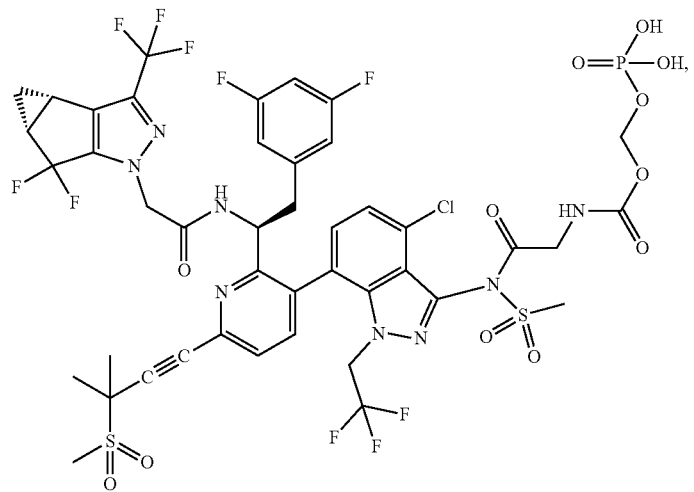
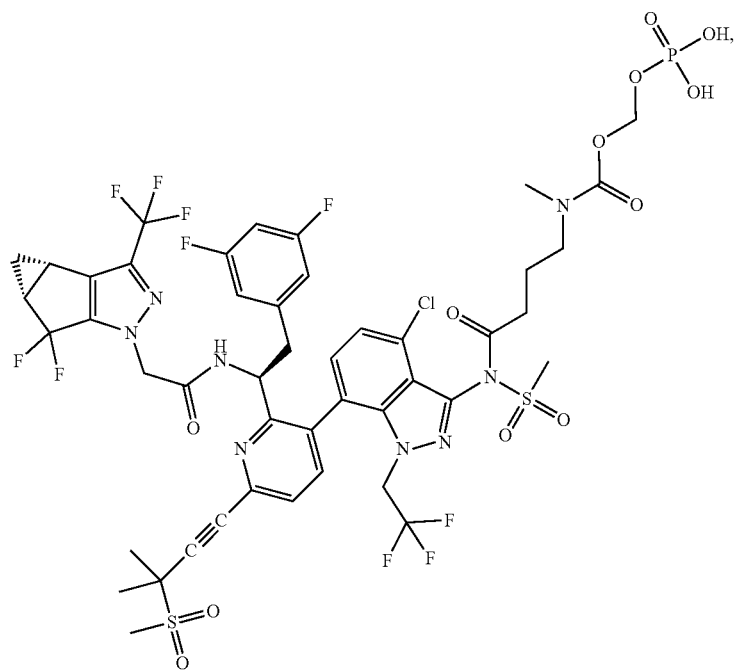
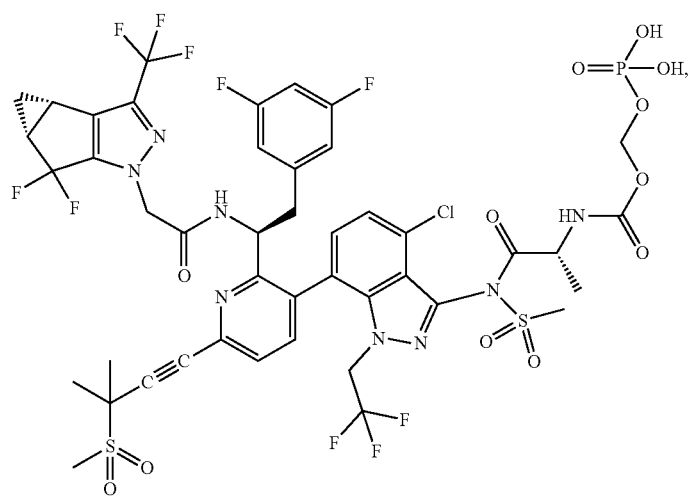

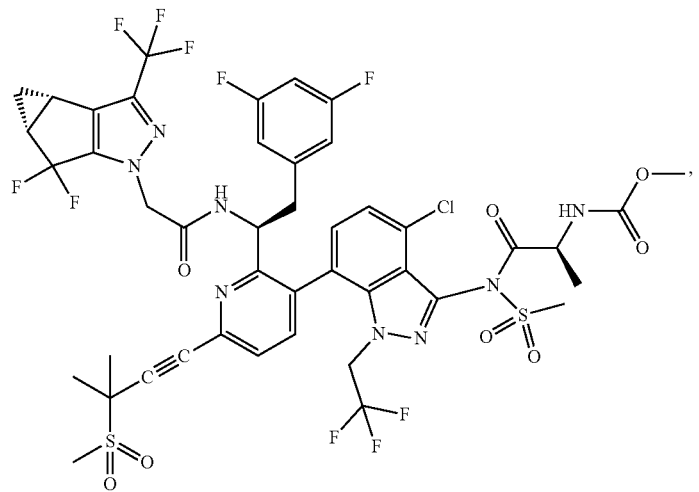
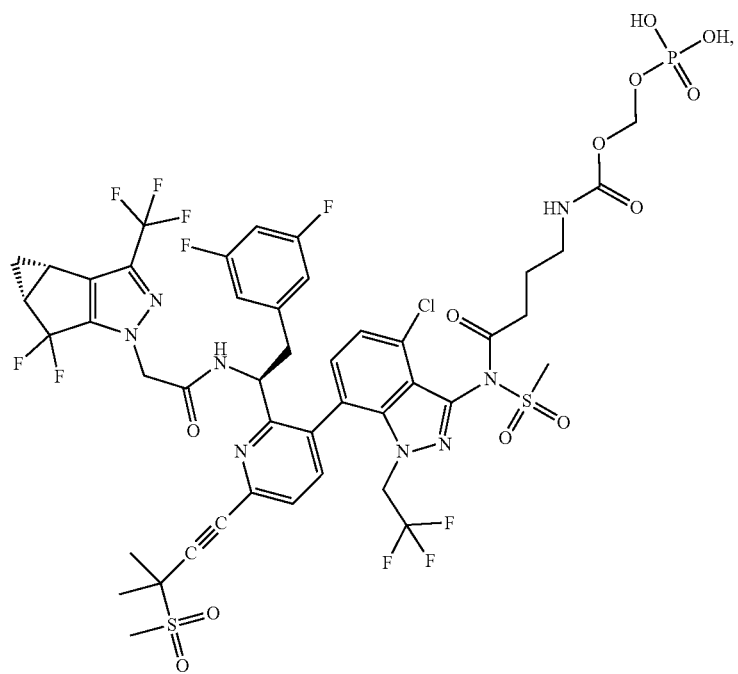
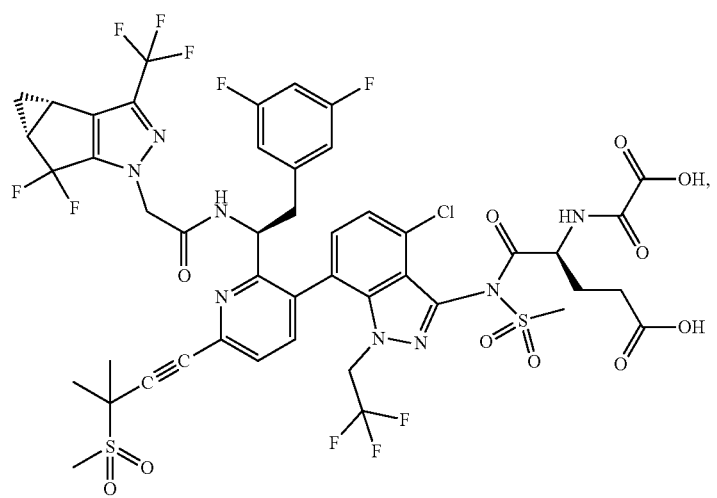

-continued
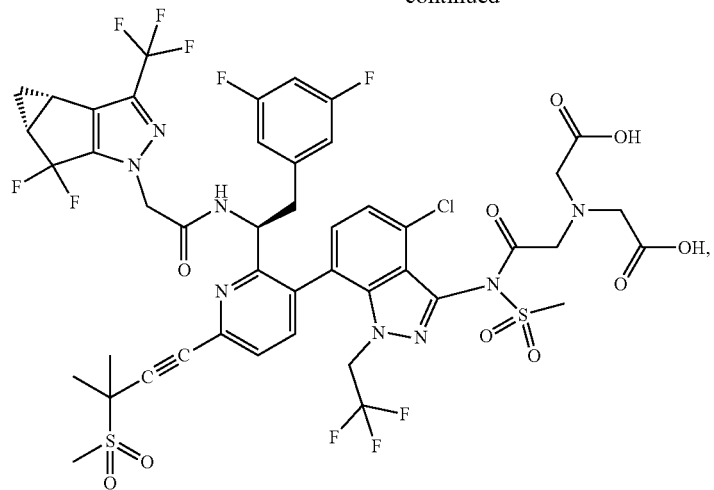
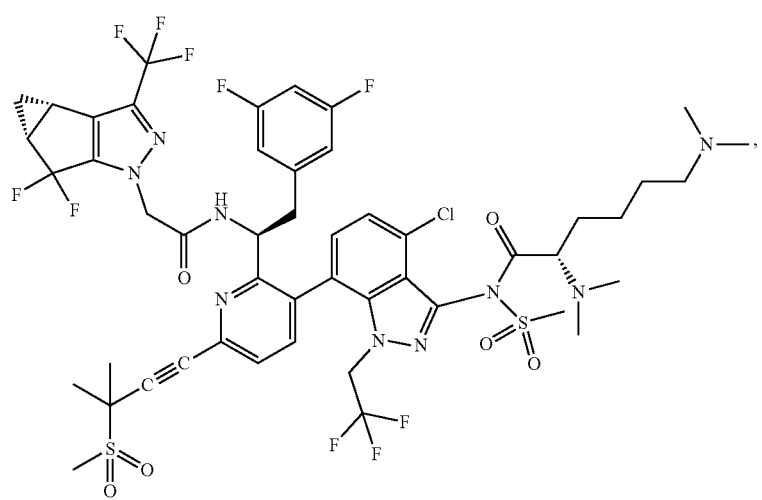
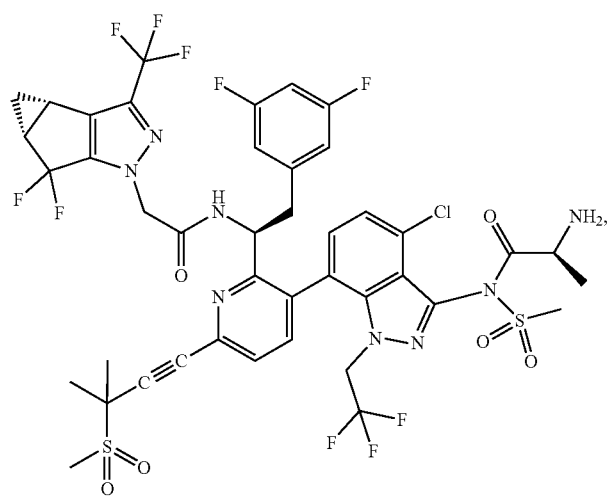

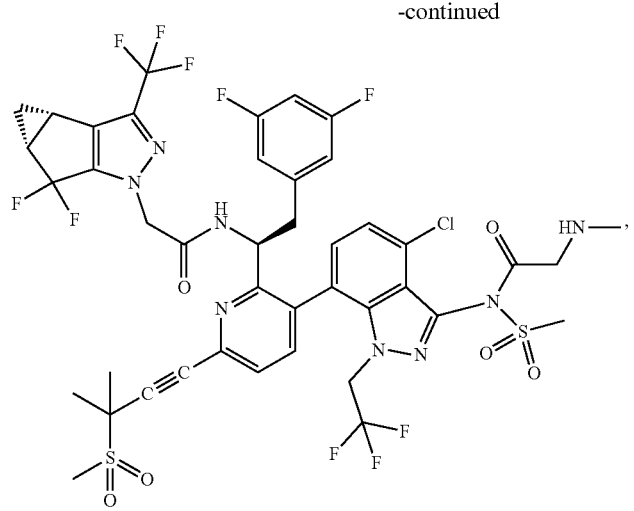
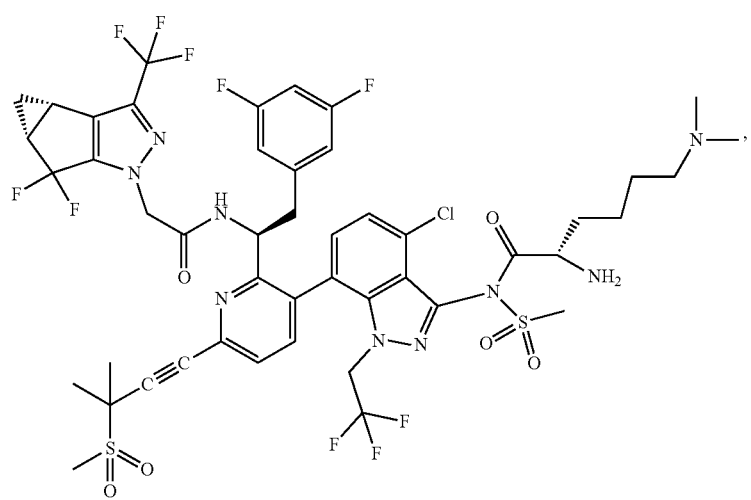
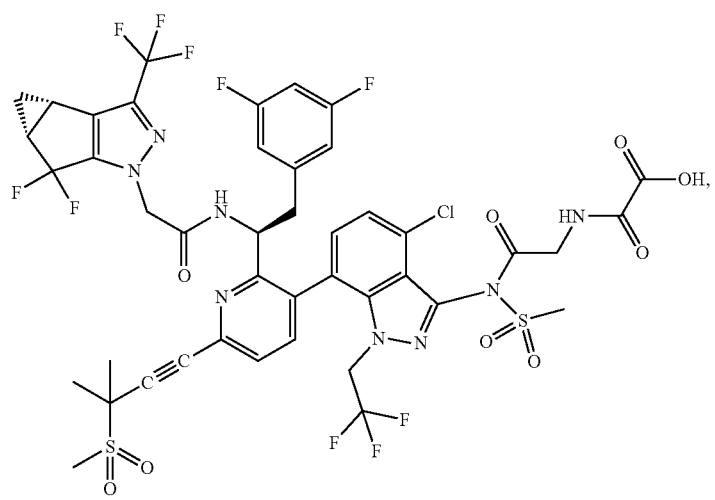

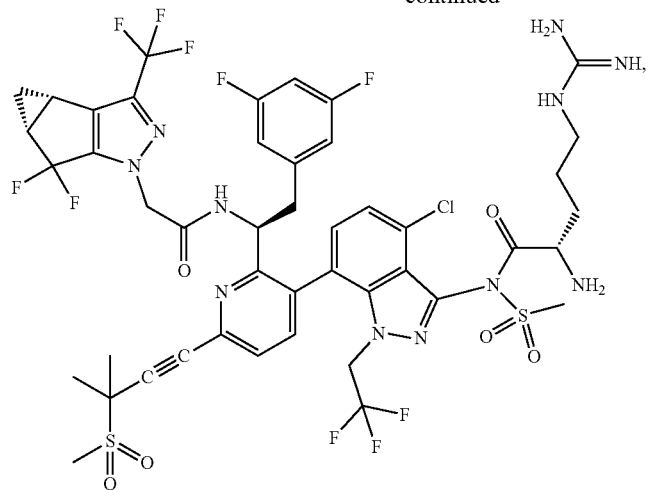
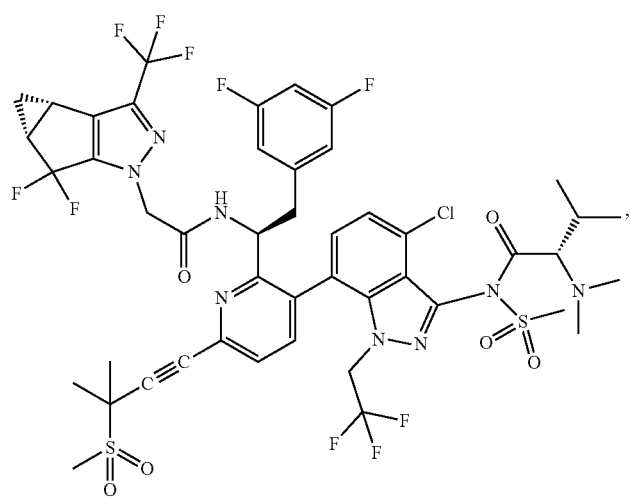
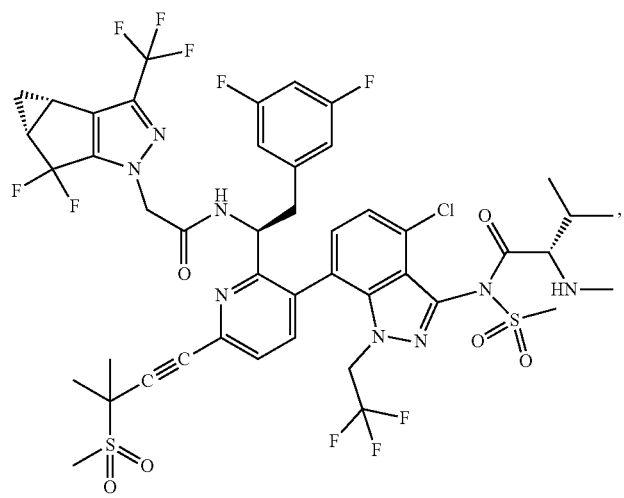 [SMILES: CN[C@H](C(=O)N(c1nn(CC(F)(F)F)c2c(-c3ccc(C#CC(C)(C)S(C)(=O)=O)nc3[C@H](Cc3cc(F)cc(F)c3)NC(=O)Cn3nc(C(F)(F)F)c4c3C(F)(F)[C@@H]3C[C@H]43)ccc(Cl)c12)S(C)(=O)=O)C(C)C]

-continued
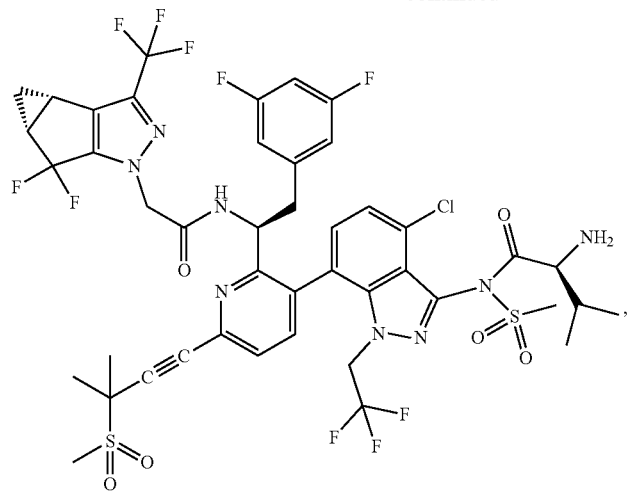
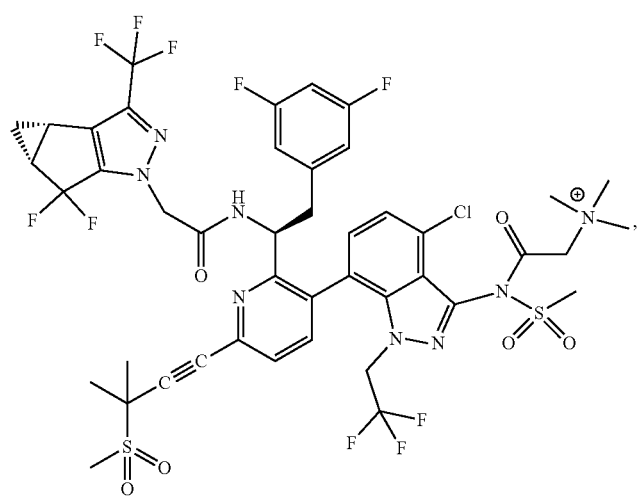
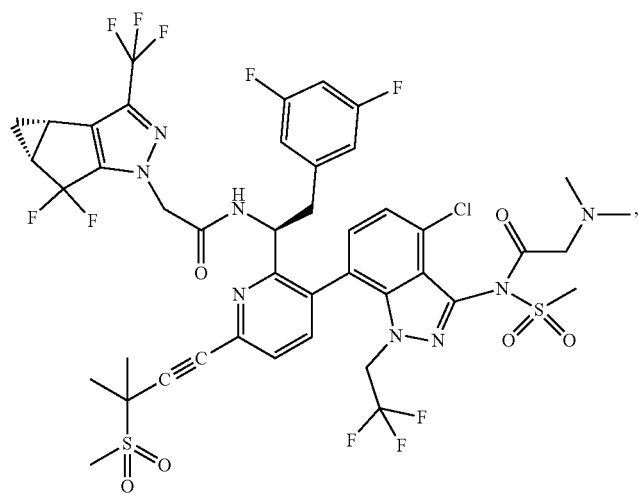

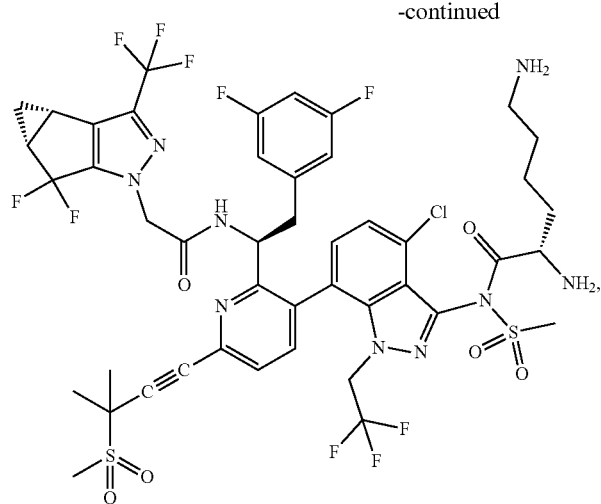
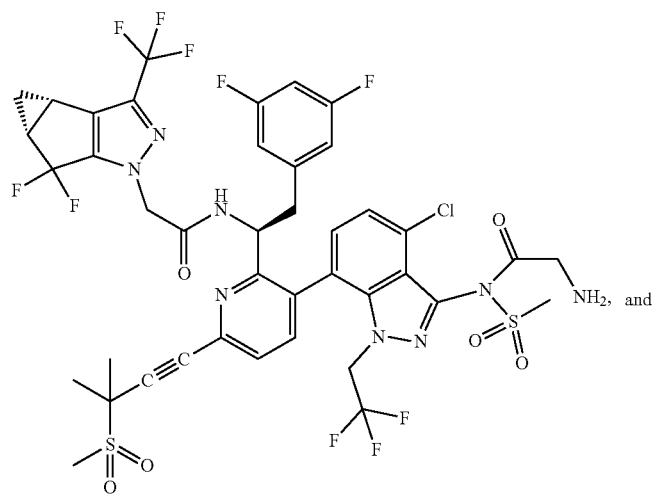
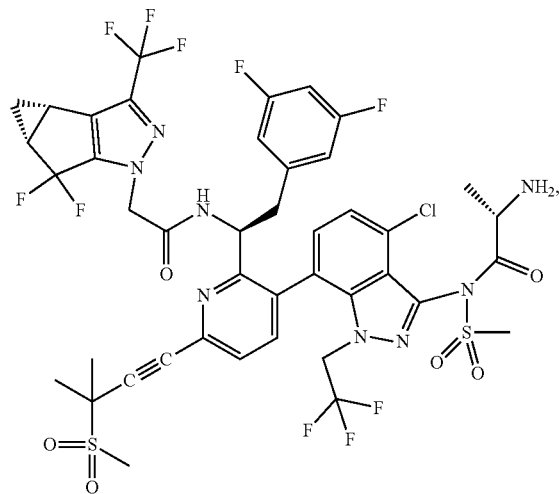
or a pharmaceutically acceptable salt thereof.

In some embodiments of the compound of Formula I, provided herein is a compound selected from the group consisting of:
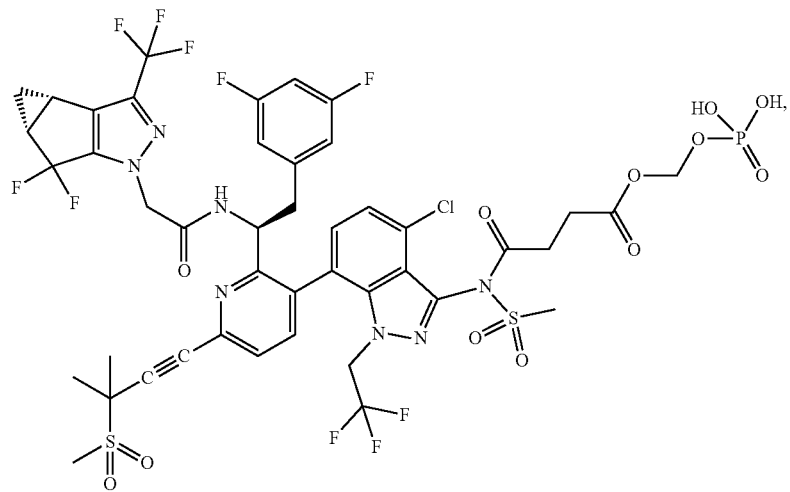
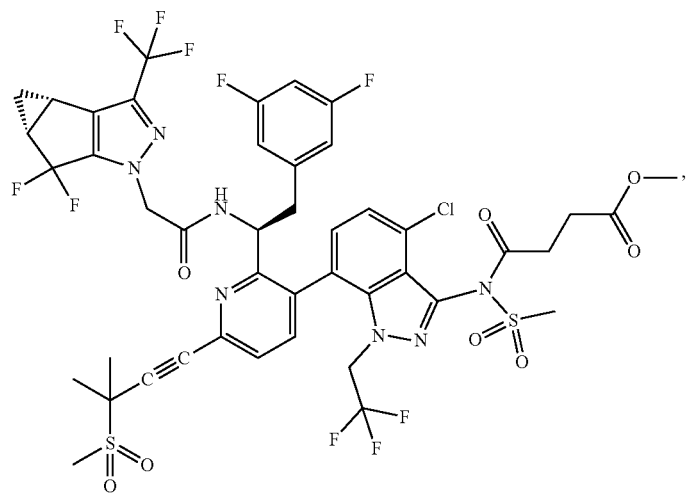
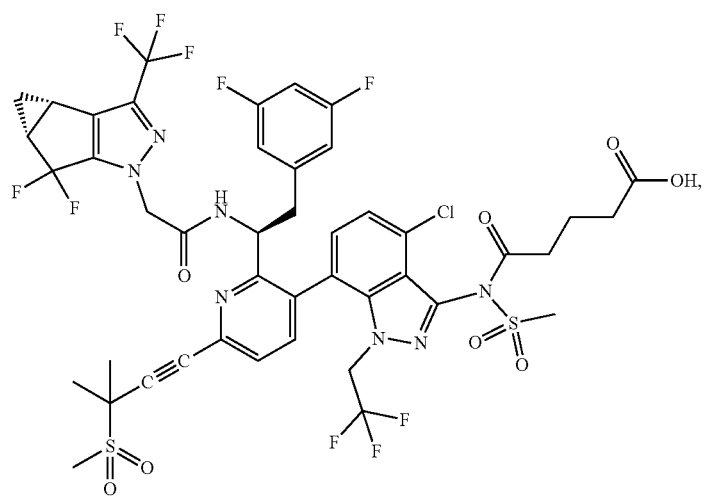

-continued
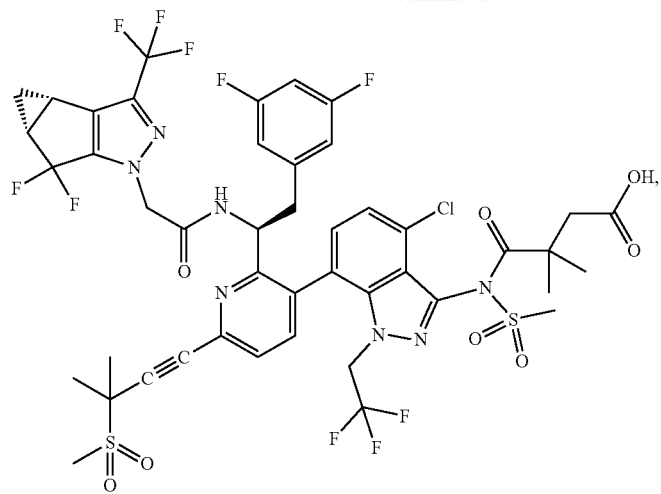
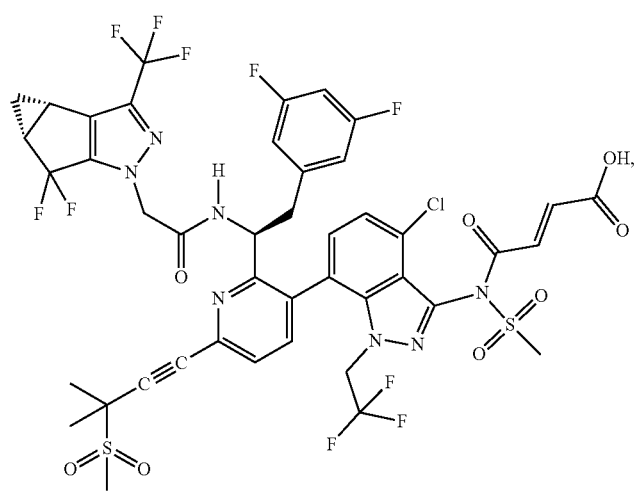
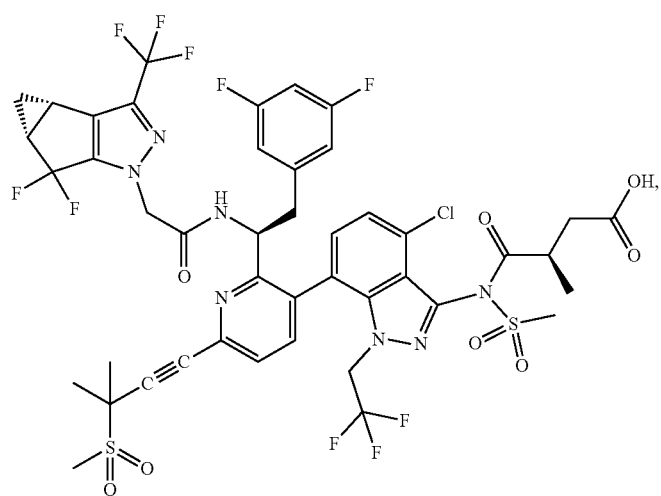

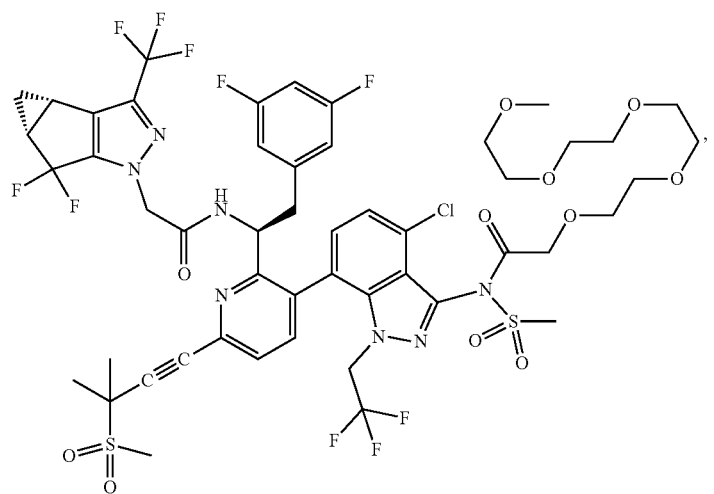
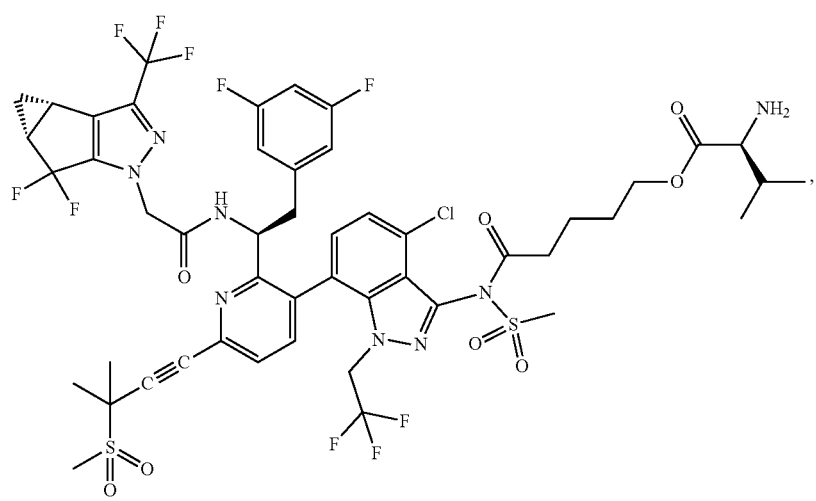
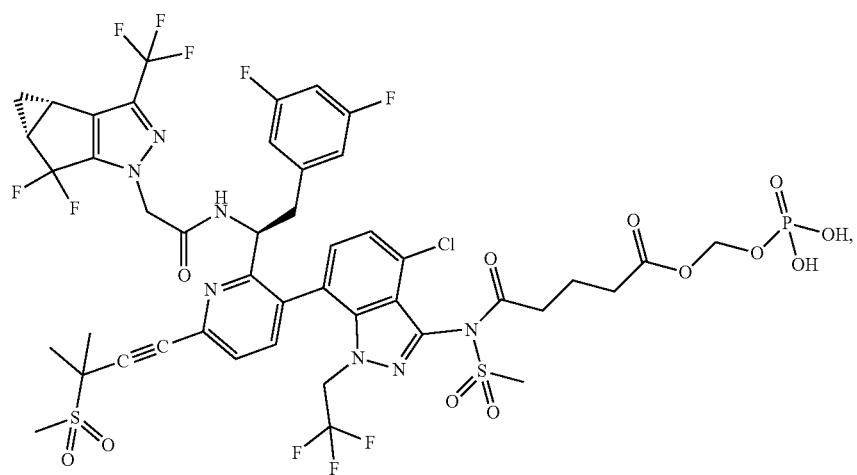

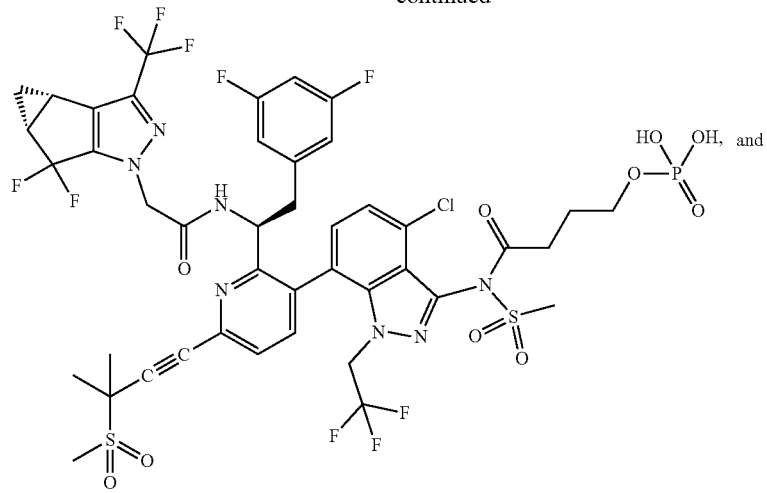
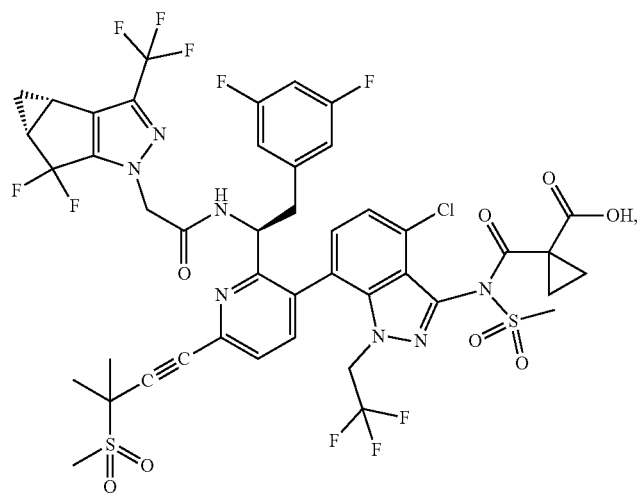
or a pharmaceutically acceptable salt thereof.
In some embodiments of the compound of Formula I, provided herein is a compound selected from the group consisting of:
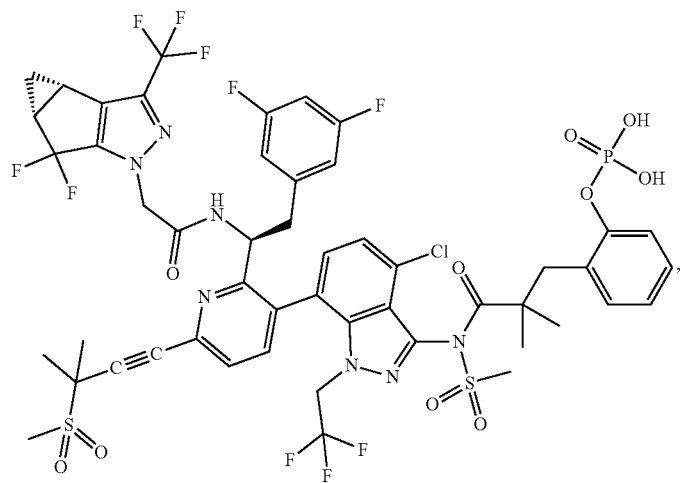

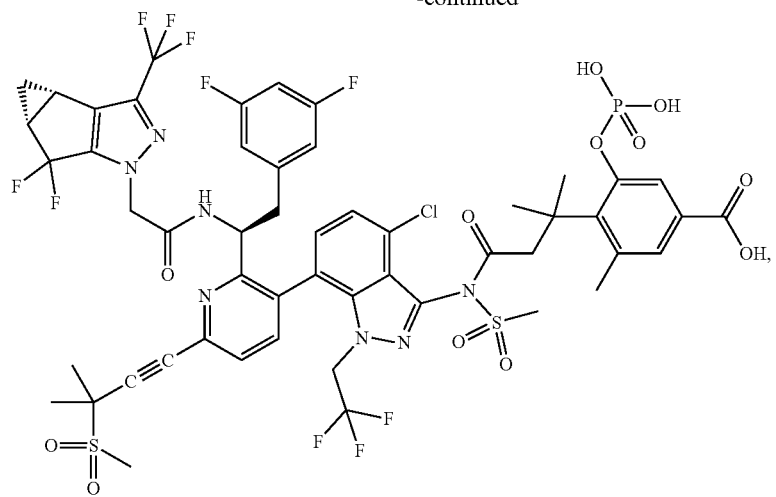
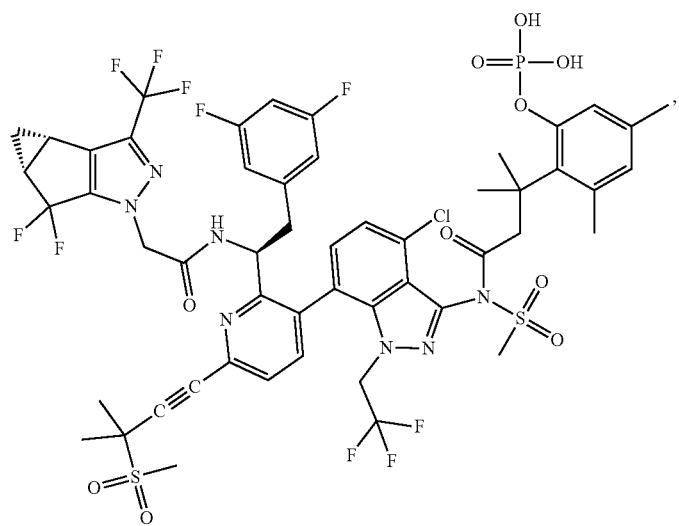
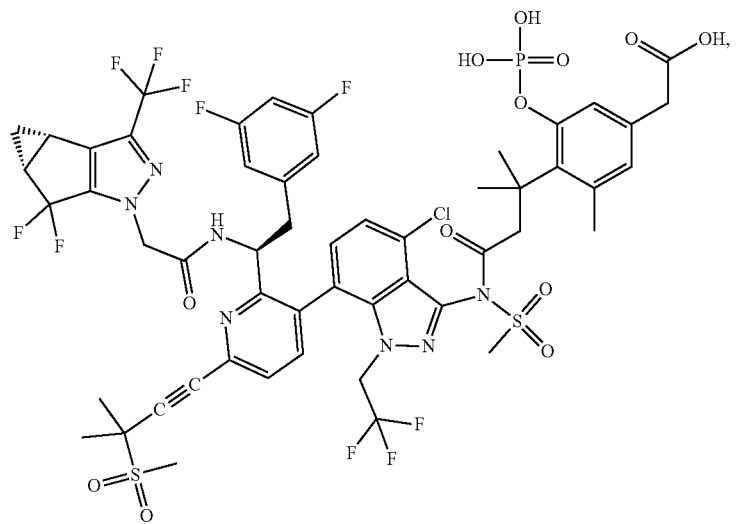

-continued
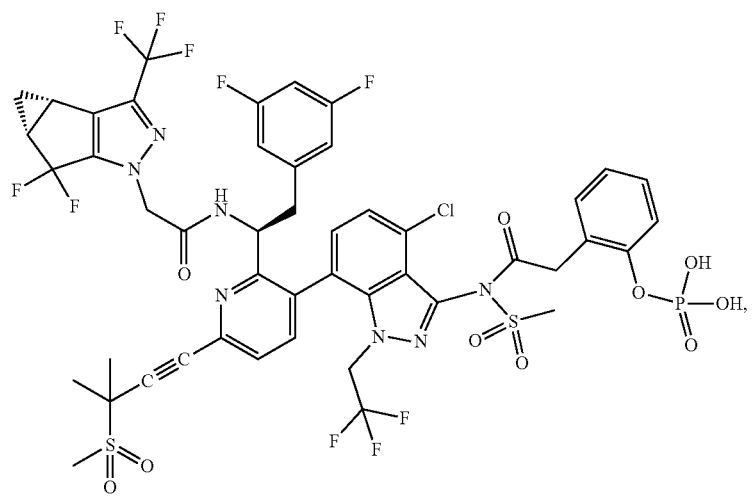
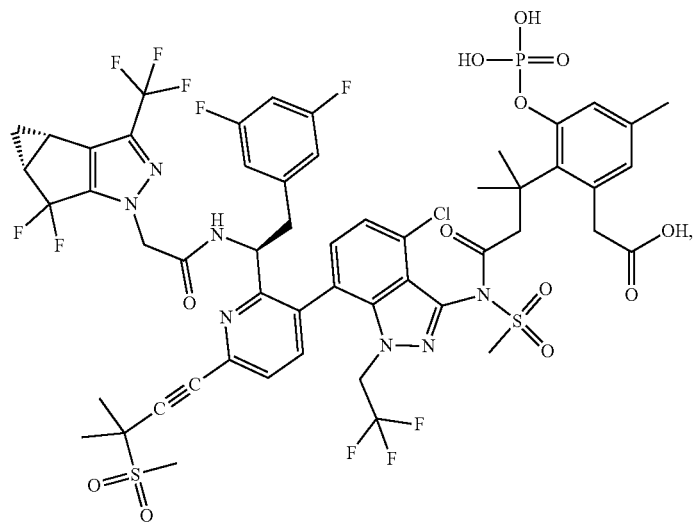
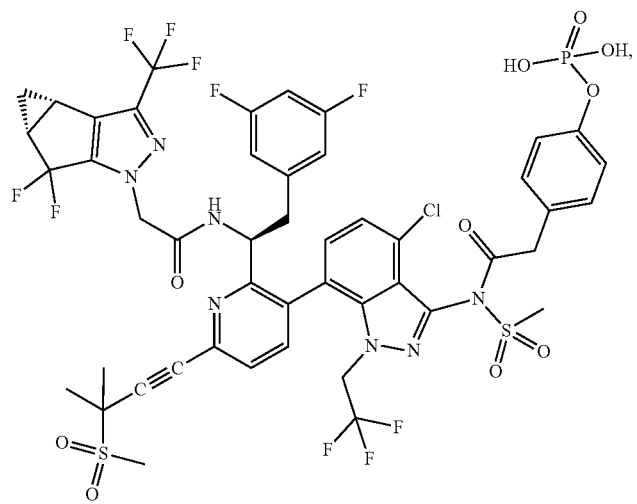

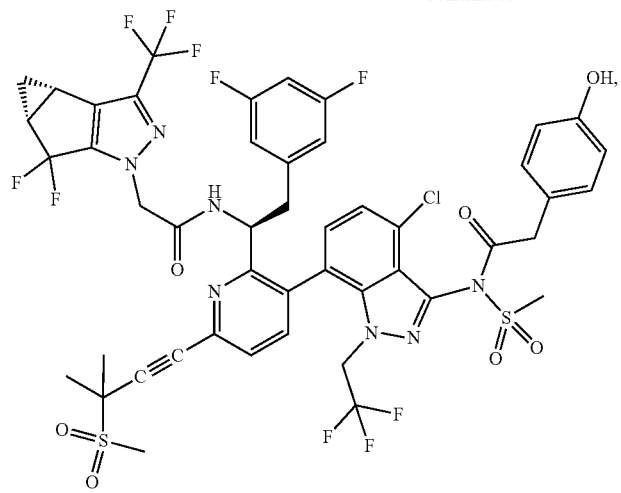
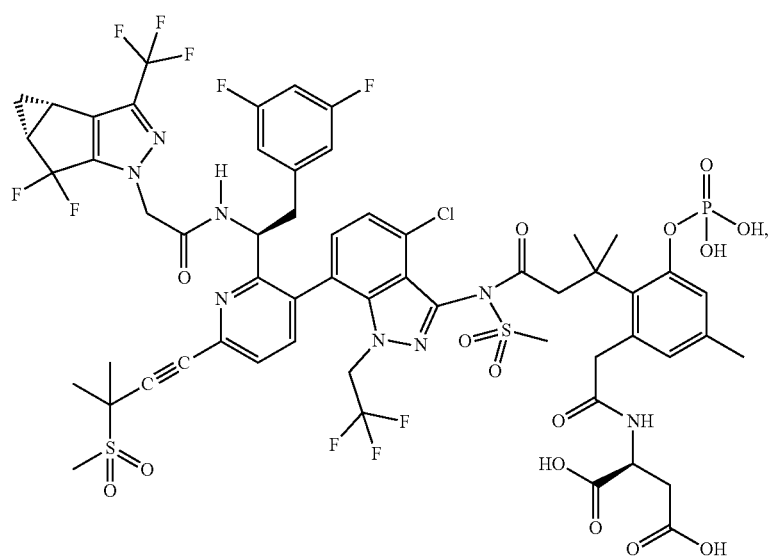
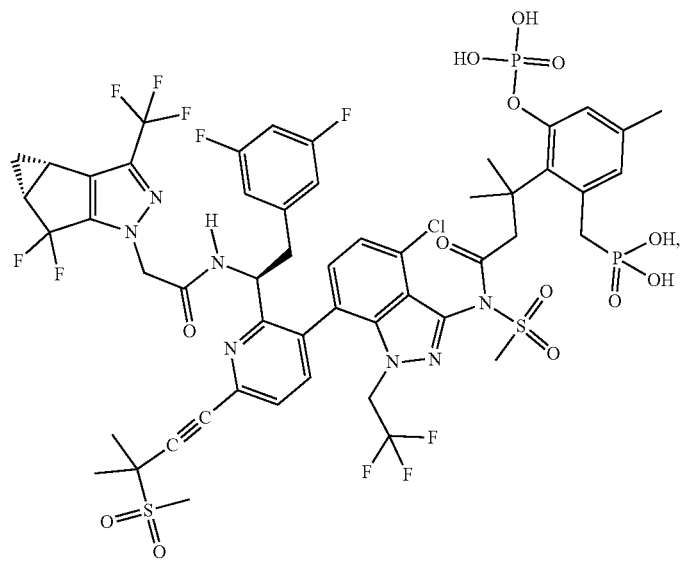

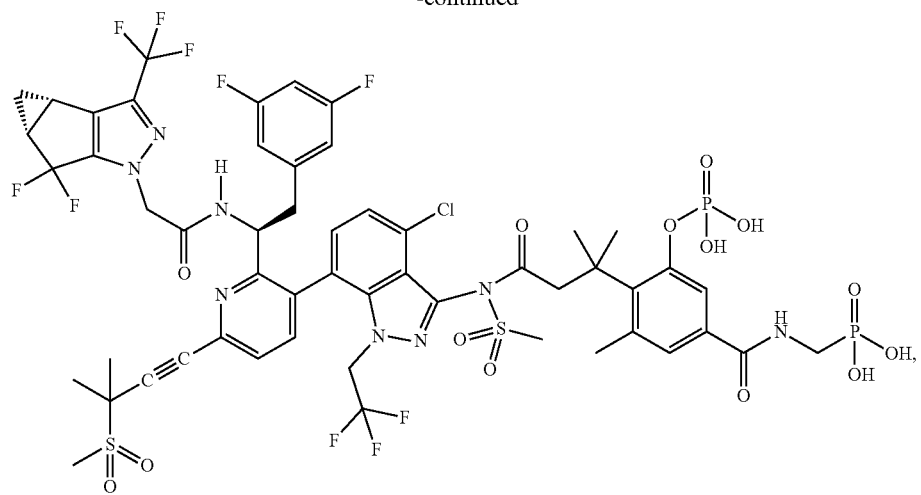
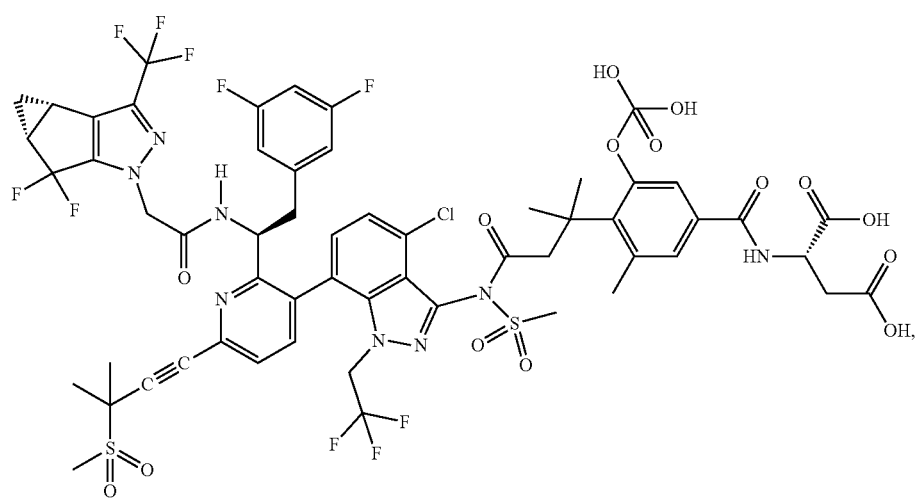
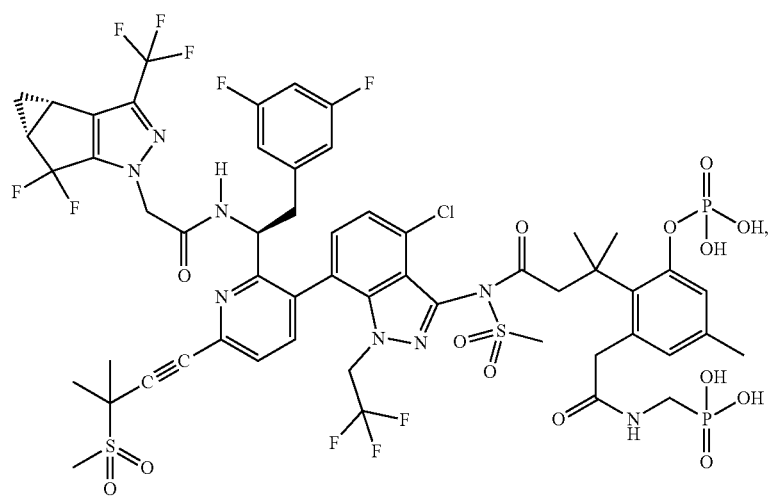

-continued
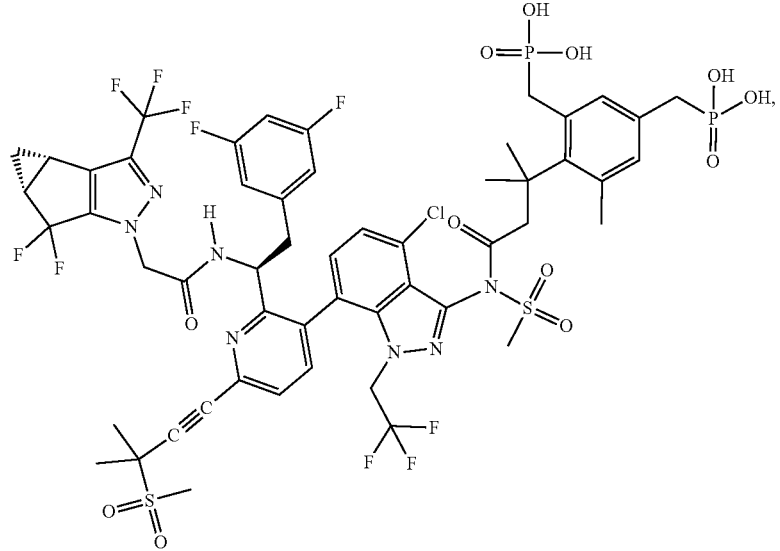
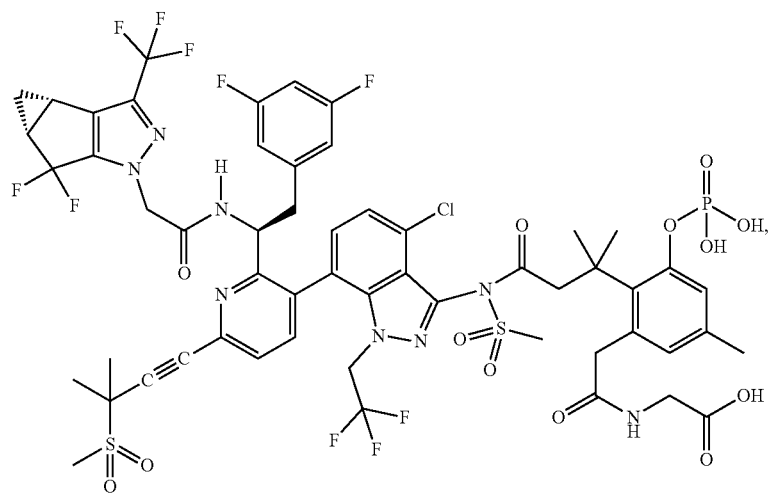
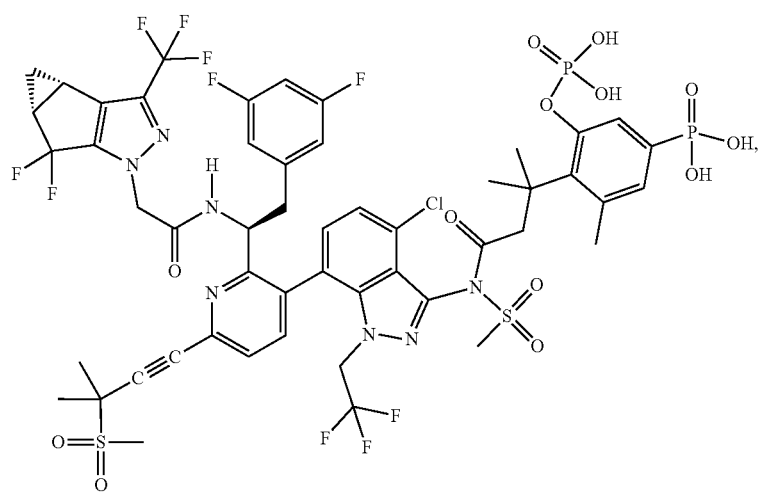

-continued
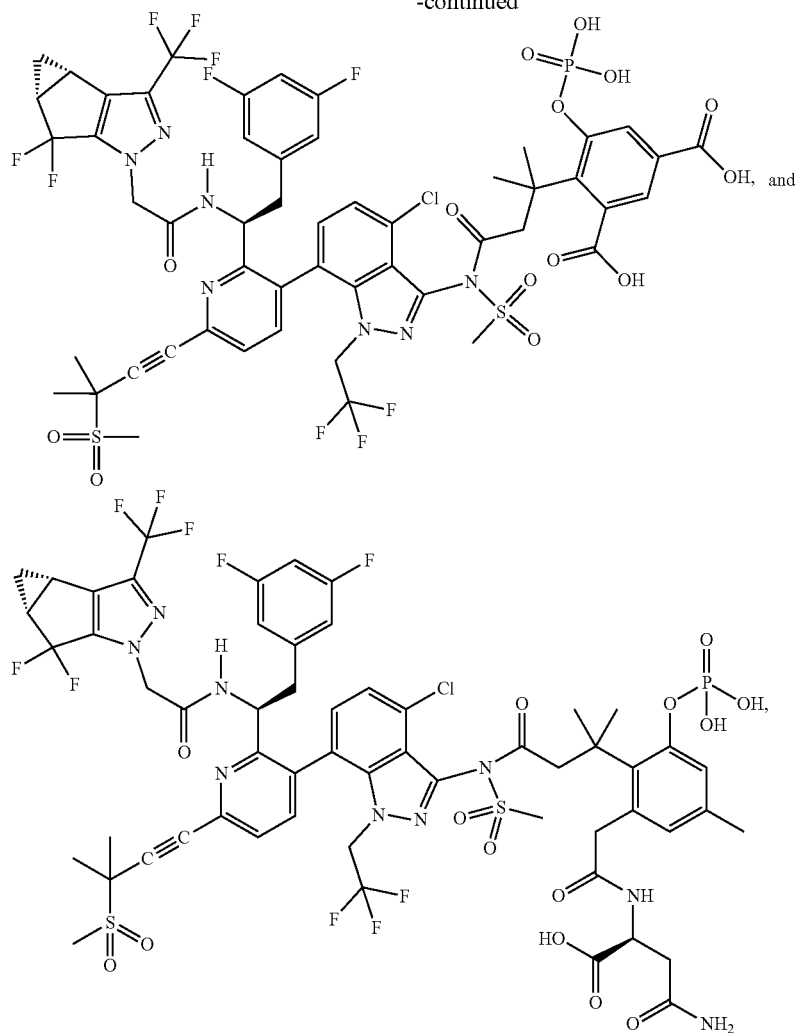
or a pharmaceutically acceptable salt thereof.
In some embodiments of the compound of Formula I, provided herein is a compound selected from the group consisting of:
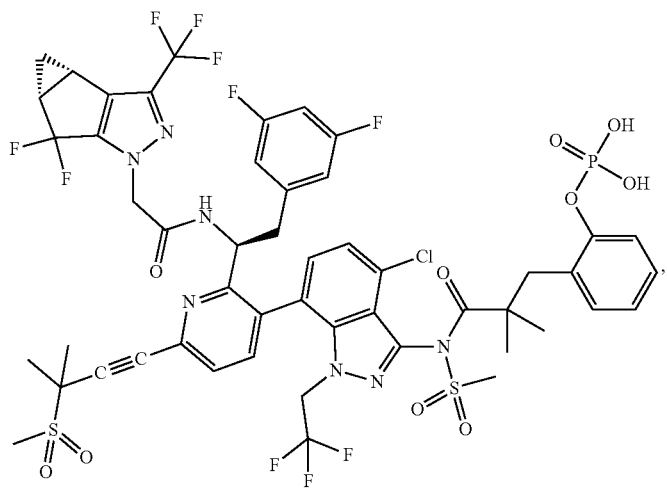

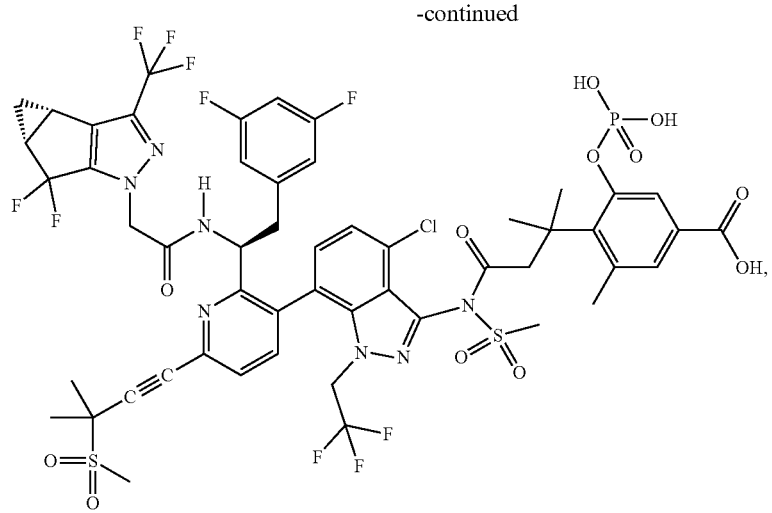
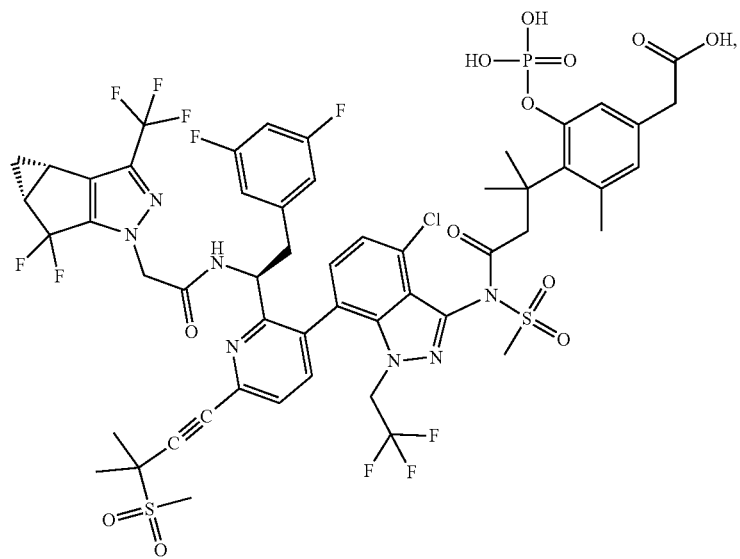
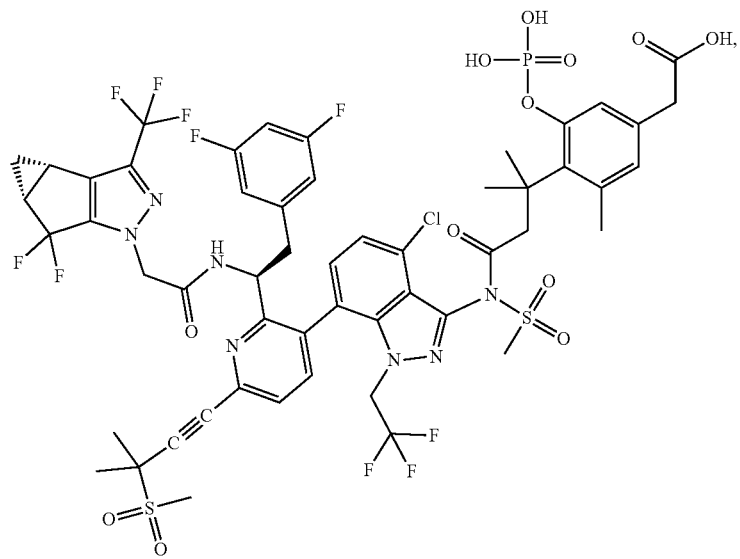

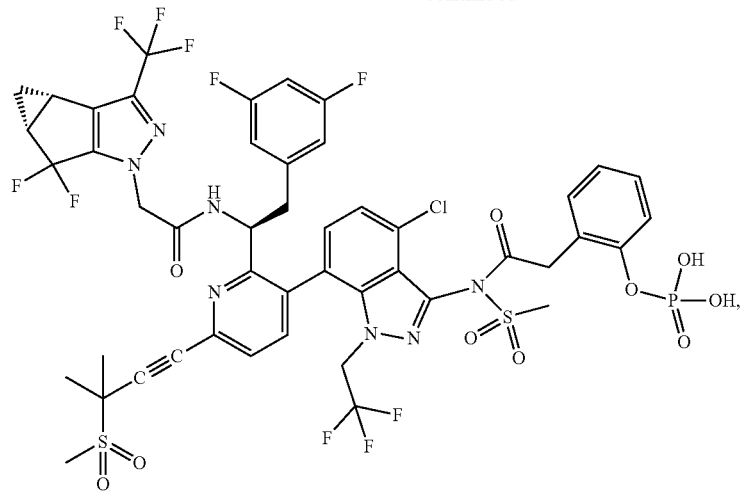
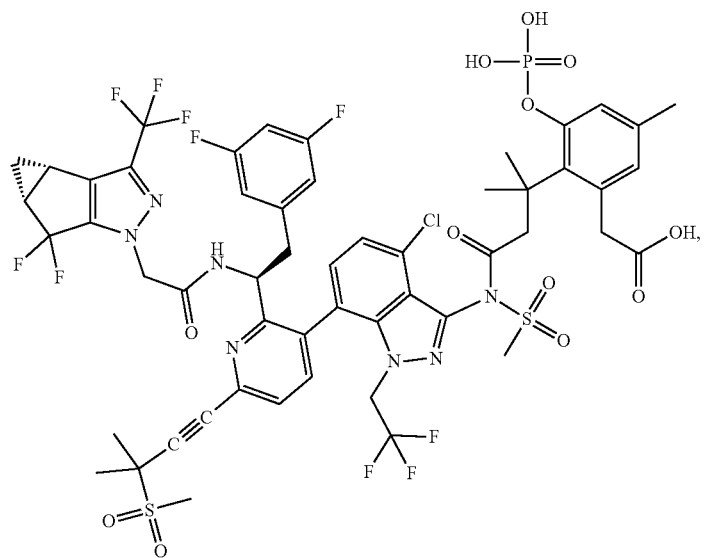
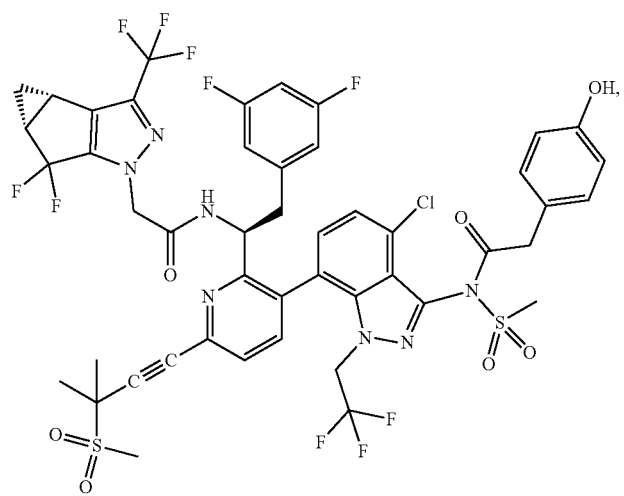

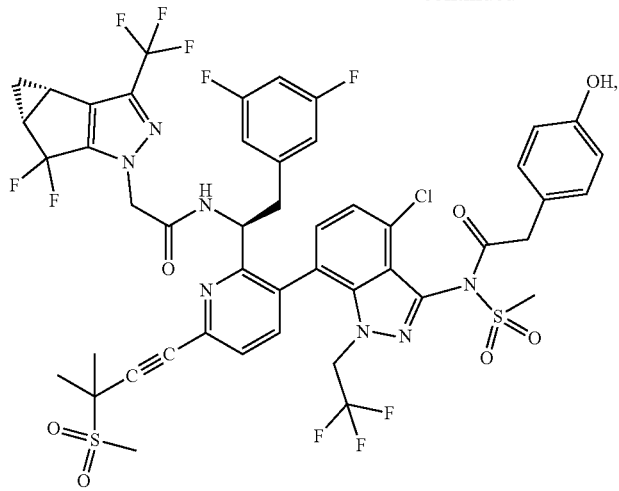
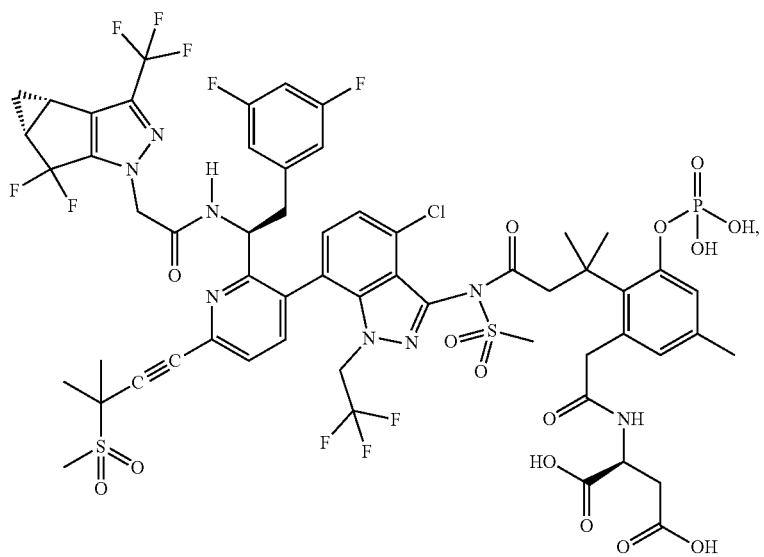
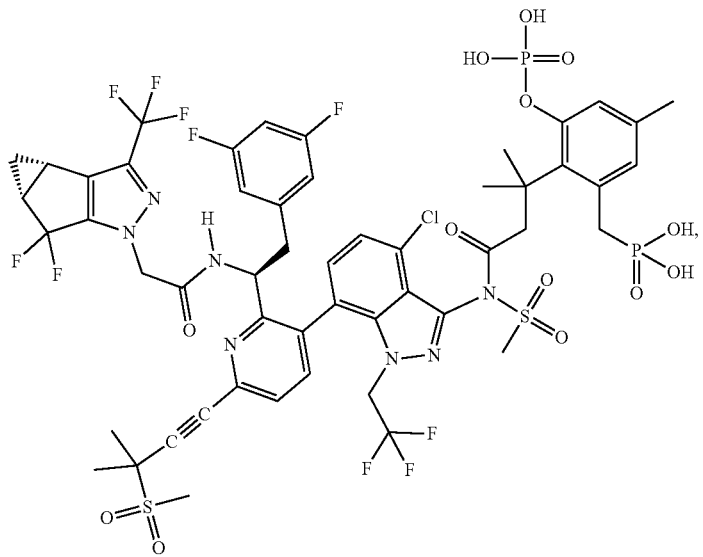

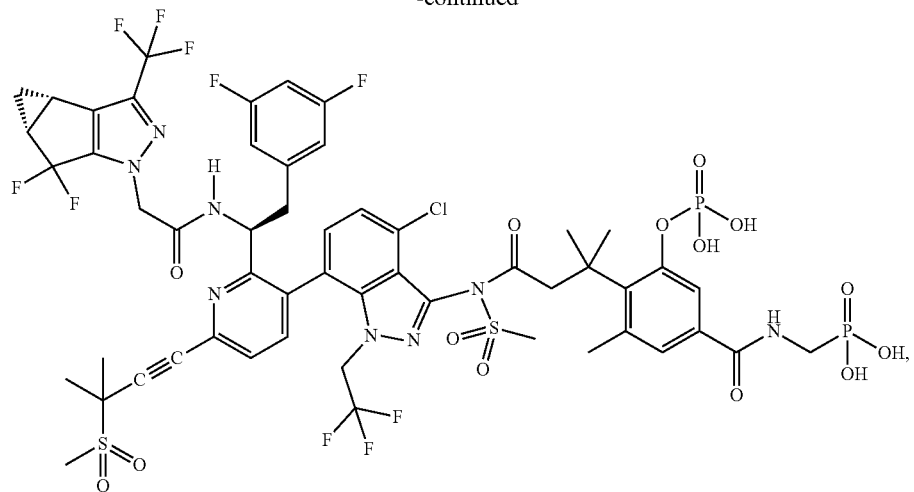
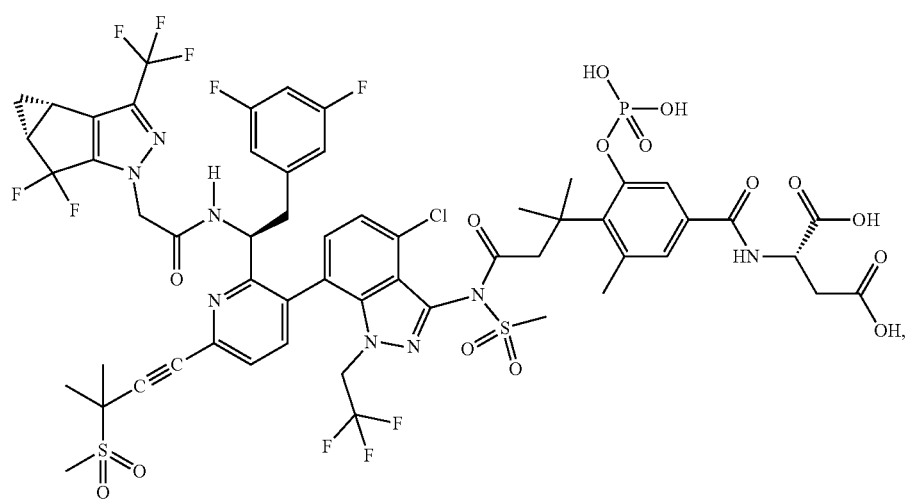
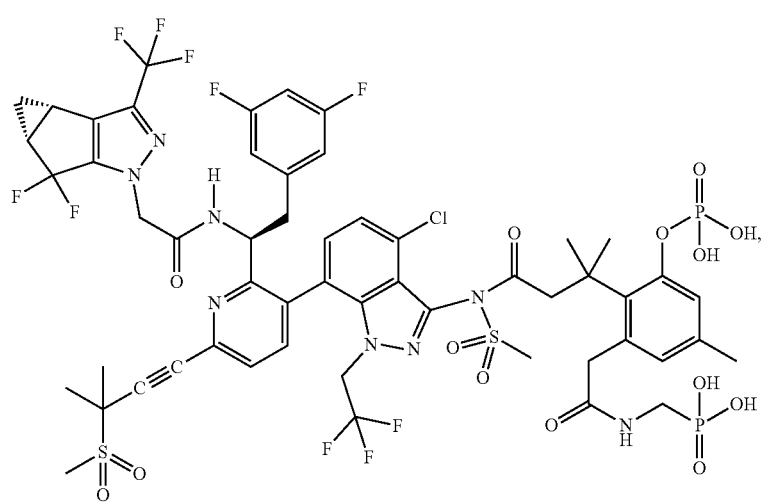

-continued
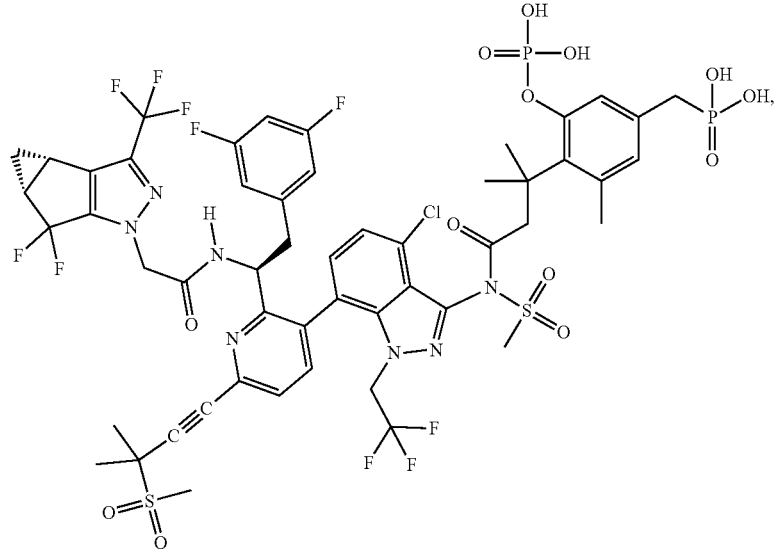
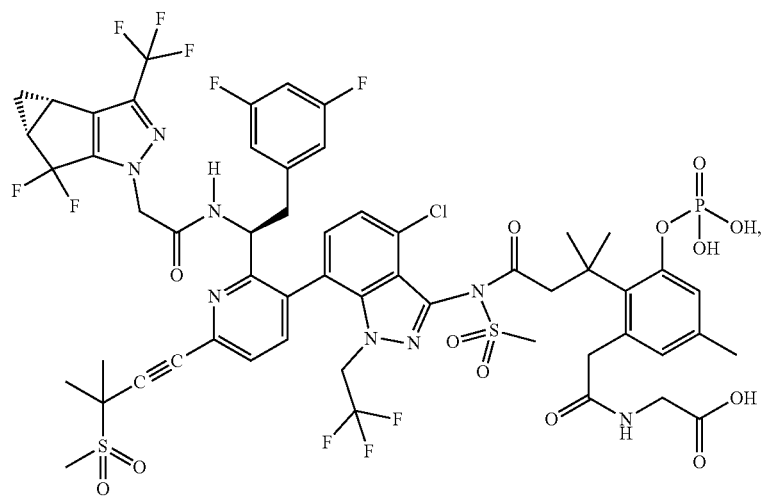
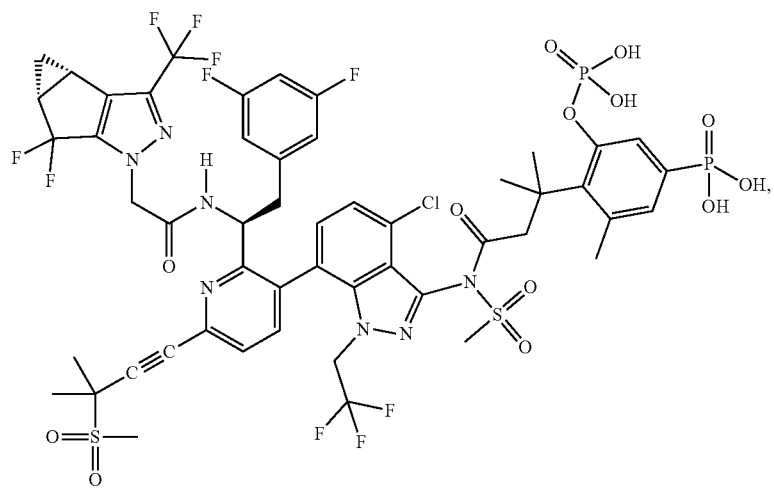

-continued
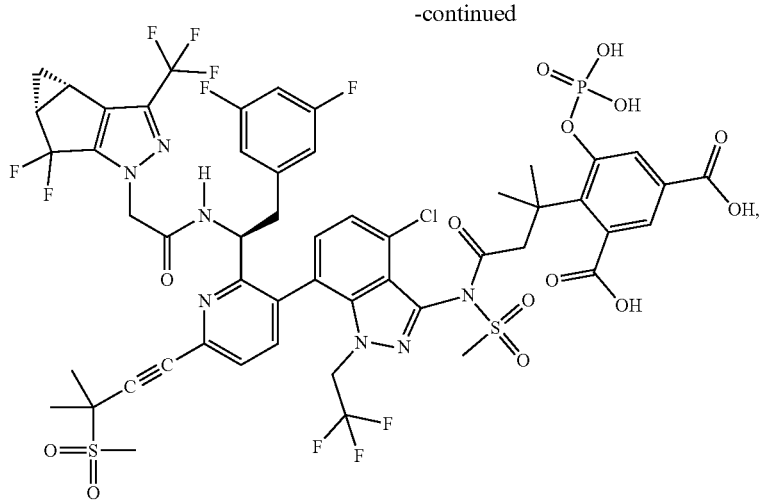
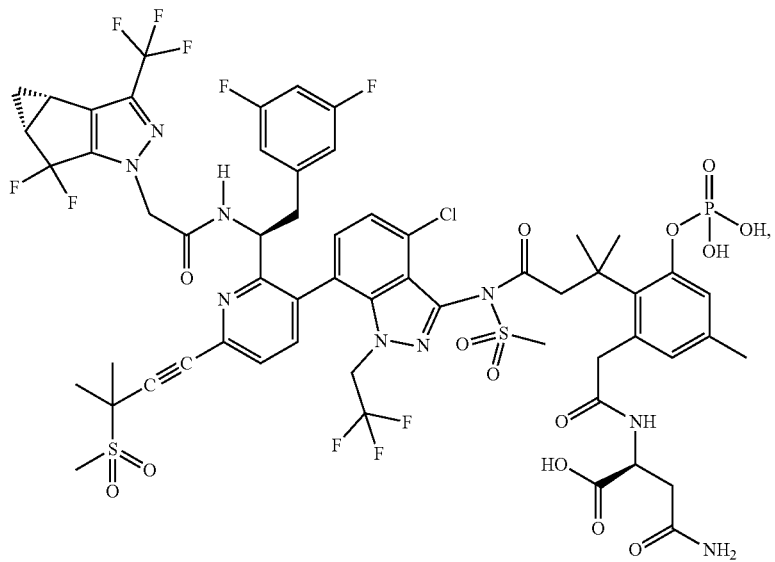
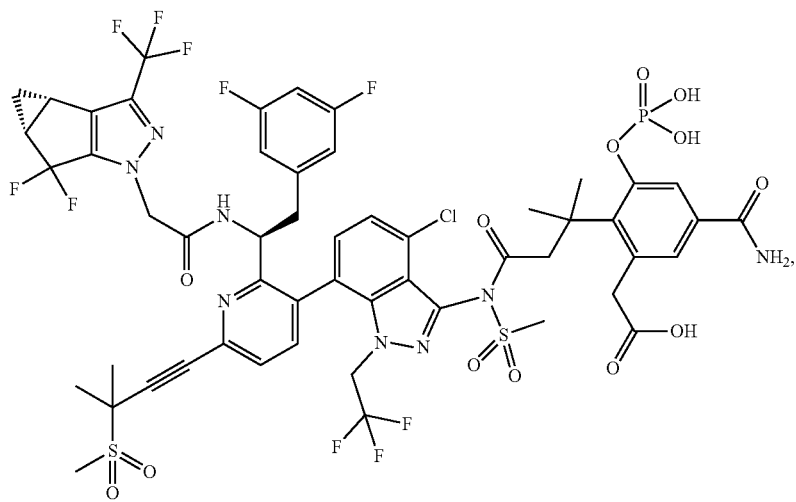

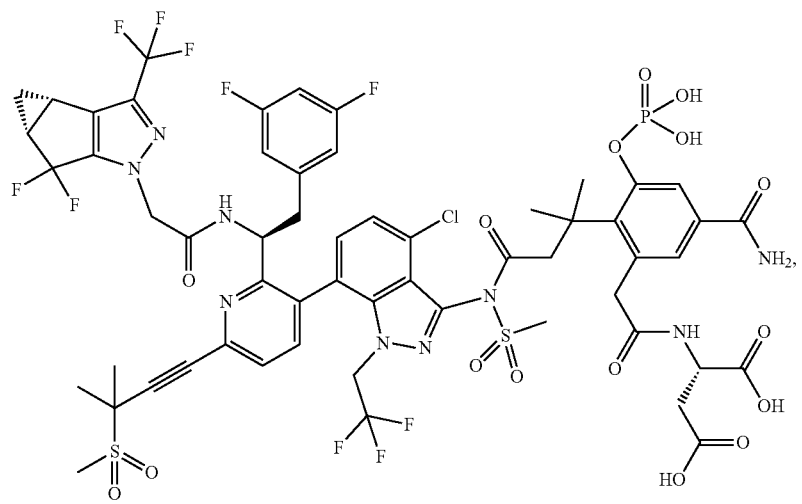
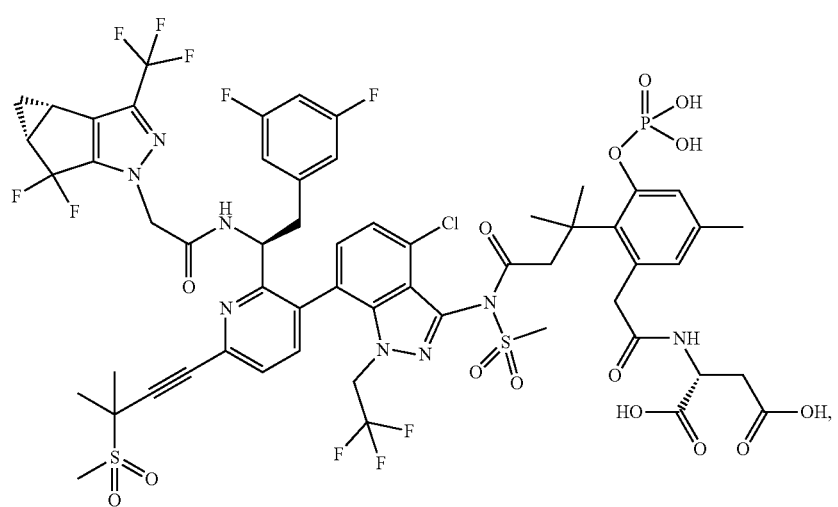
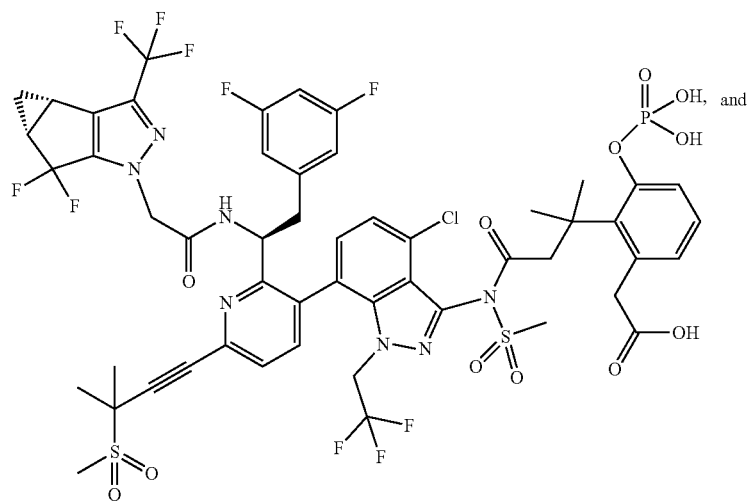

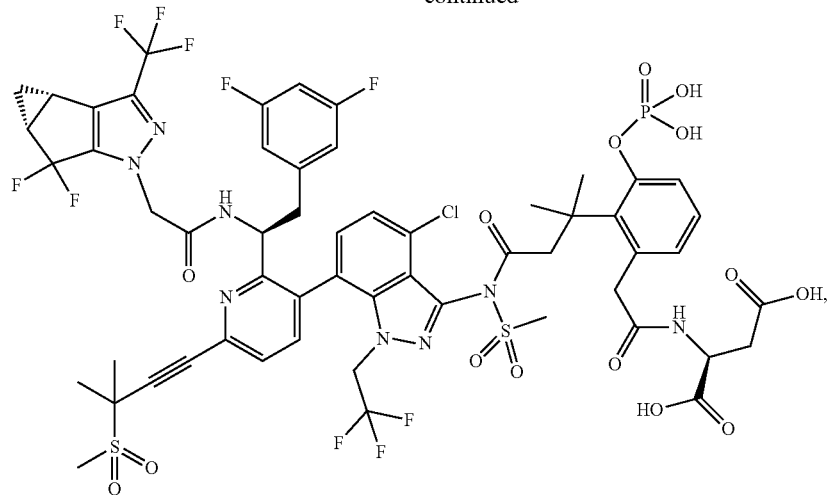
or a pharmaceutically acceptable salt thereof.
In some embodiments of the compound of Formula I, provided herein is a compound selected from the group consisting of:
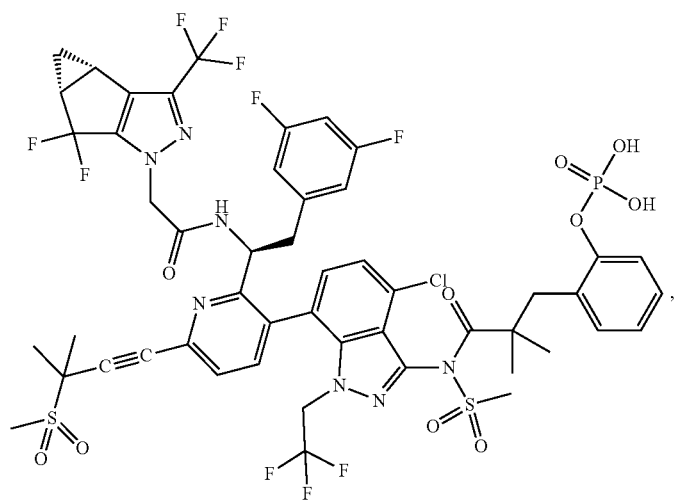
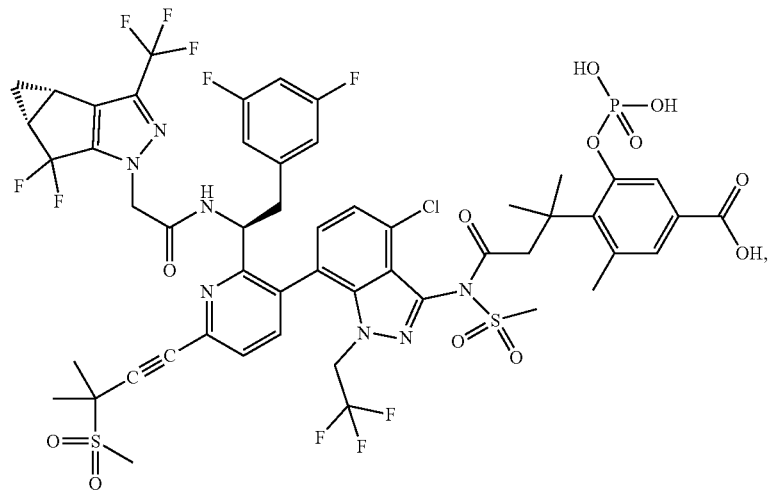

-continued
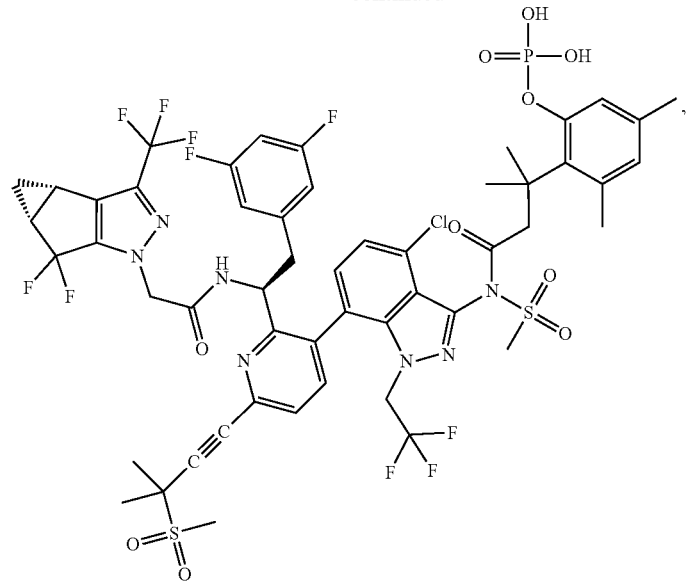
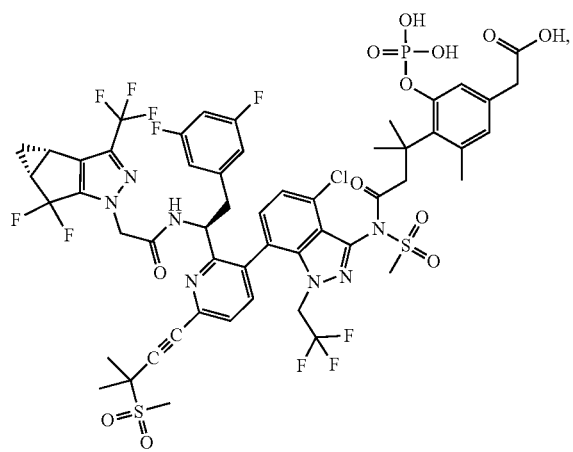
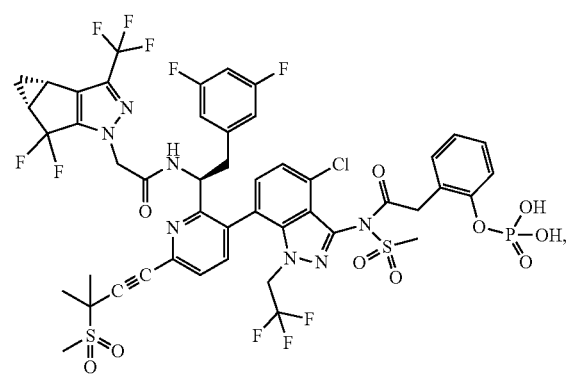

-continued
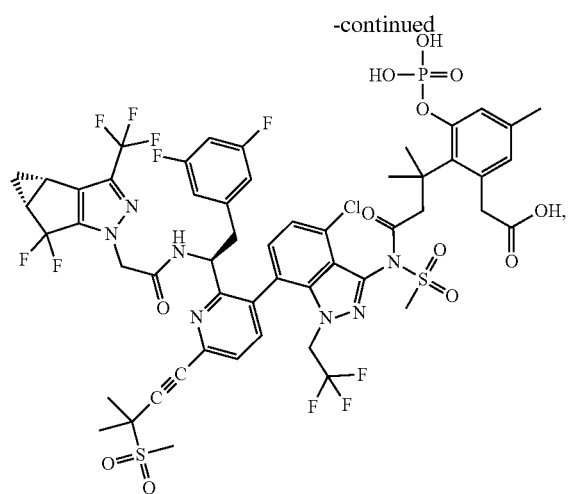
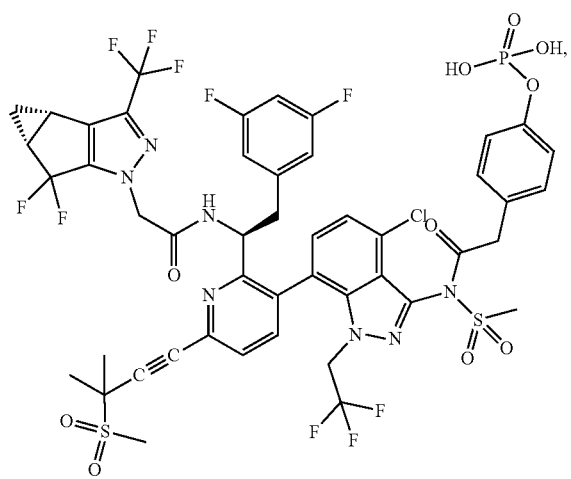
and
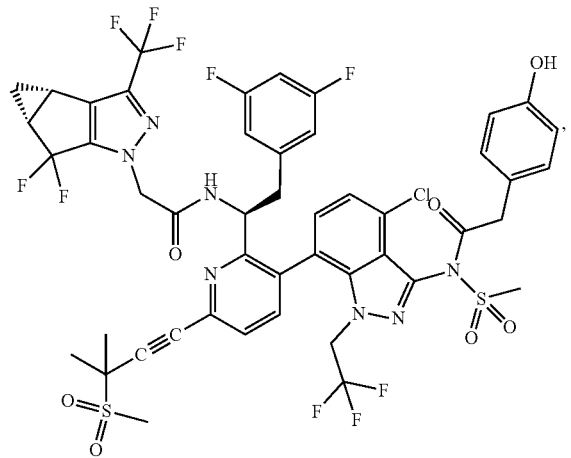
or a pharmaceutically acceptable salt thereof.

In some embodiments of the compound of Formula I, provided herein is a compound selected from the group consisting of:
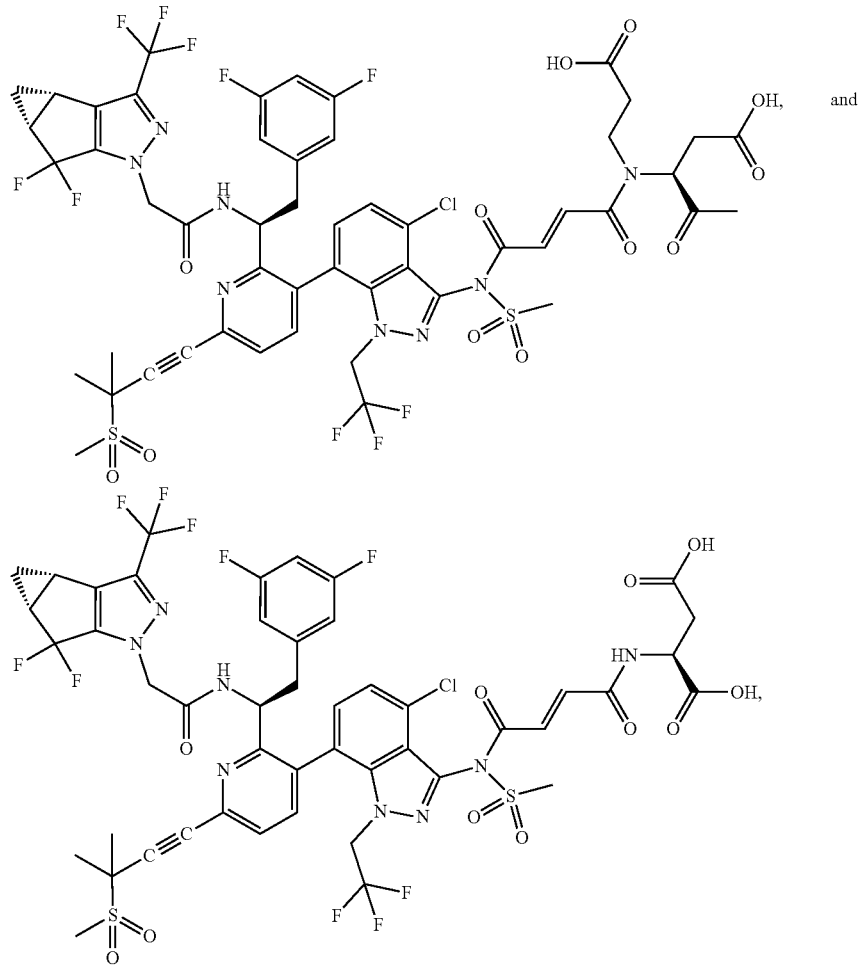
or a pharmaceutically acceptable salt thereof.
In some embodiments of the compound of Formula I, provided herein is a compound that is:
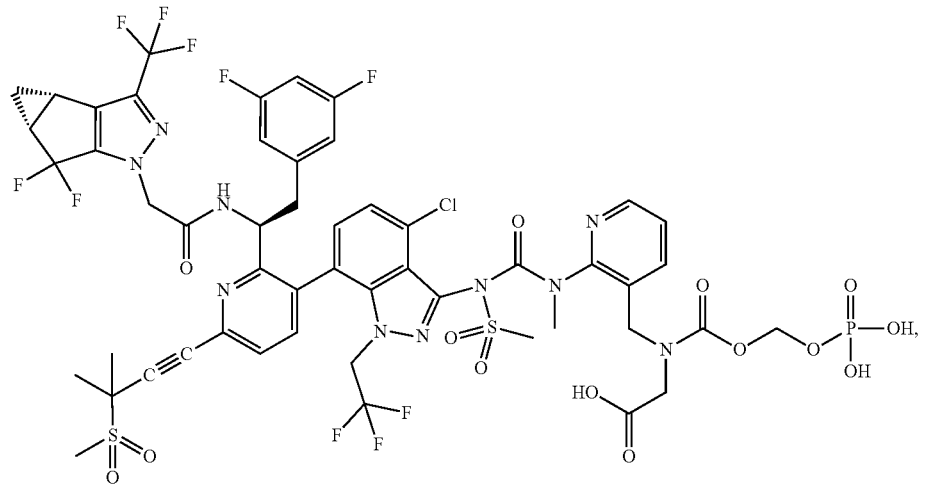 [SMILES: CN(C(=O)N(c1nn(CC(F)(F)F)c2c(-c3ccc(C#CC(C)(C)S(C)(=O)=O)nc3[C@H](Cc3cc(F)cc(F)c3)NC(=O)Cn3nc(C(F)(F)F)c4c3C(F)(F)[C@@H]3C[C@H]43)ccc(Cl)c12)S(C)(=O)=O)c1ncccc1CN(CC(=O)O)C(=O)OCOP(=O)(O)O]
or a pharmaceutically acceptable salt thereof.

In some embodiments of the compound of Formula I, provided herein is a compound that is:

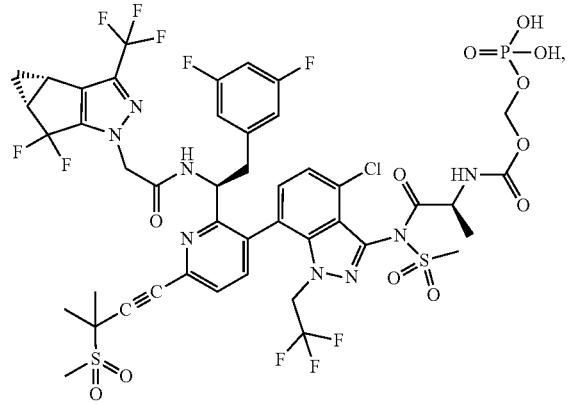 [SMILES: C[C@H](NC(=O)OCOP(=O)(O)O)C(=O)N(c1nn(CC(F)(F)F)c2c(-c3ccc(C#CC(C)(C)S(C)(=O)=O)nc3[C@H](Cc3cc(F)cc(F)c3)NC(=O)Cn3nc(C(F)(F)F)c4c3C(F)(F)[C@@H]3C[C@H]43)ccc(Cl)c12)S(C)(=O)=O]

or a pharmaceutically acceptable salt thereof.

In some embodiments of the compound of Formula I, provided herein is a compound that is:

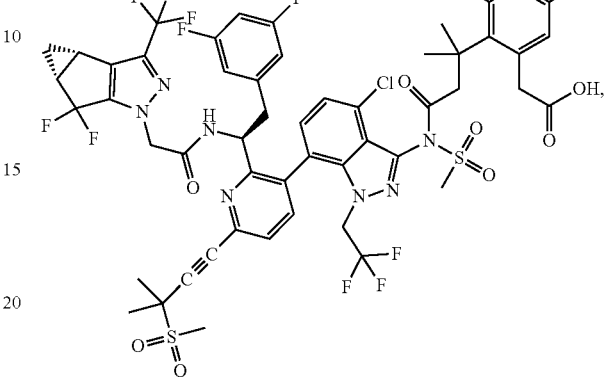

or a pharmaceutically acceptable salt thereof.

In some embodiments of the compound of Formula I, provided herein is a compound that is:

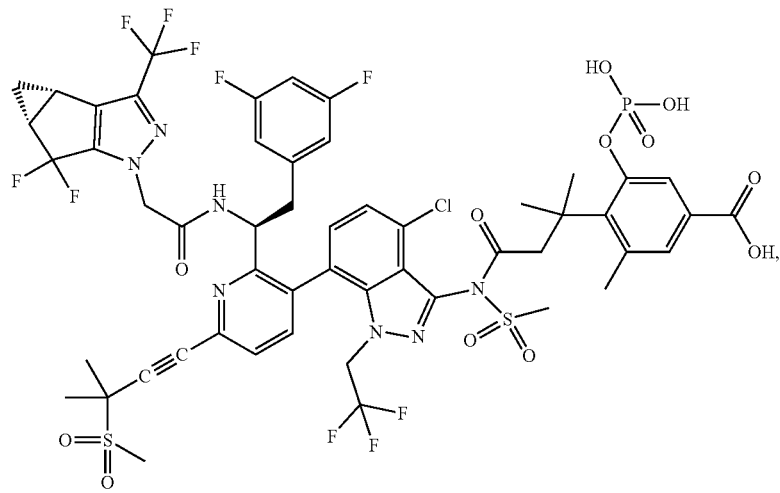 [SMILES: Cc1cc(C(=O)O)cc(OP(=O)(O)O)c1C(C)(C)CC(=O)N(c1nn(CC(F)(F)F)c2c(-c3ccc(C#CC(C)(C)S(C)(=O)=O)nc3[C@H](Cc3cc(F)cc(F)c3)NC(=O)Cn3nc(C(F)(F)F)c4c3C(F)(F)[C@@H]3C[C@H]43)ccc(Cl)c12)S(C)(=O)=O]

or a pharmaceutically acceptable salt thereof.

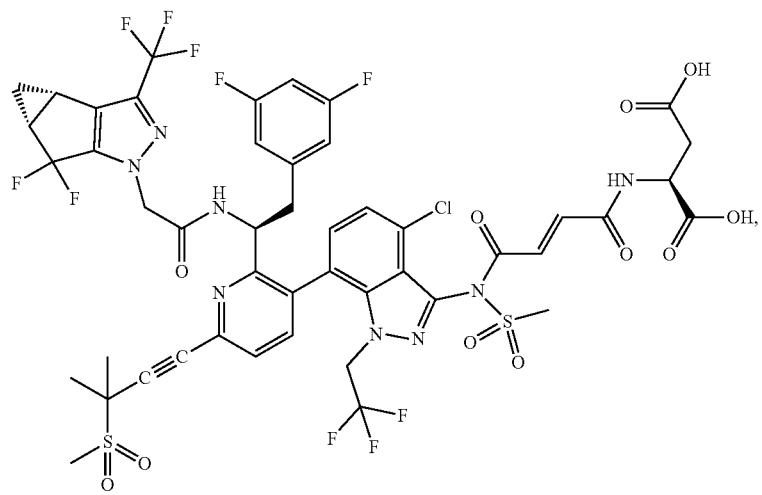 [SMILES: CC(C)(C#Cc1ccc(-c2ccc(Cl)c3c(N(C(=O)/C=C/C(=O)N[C@@H](CC(=O)O)C(=O)O)S(C)(=O)=O)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(C)(=O)=O]
or a pharmaceutically acceptable salt thereof.
In some embodiments of the compound of Formula I, provided herein is a compound that is:
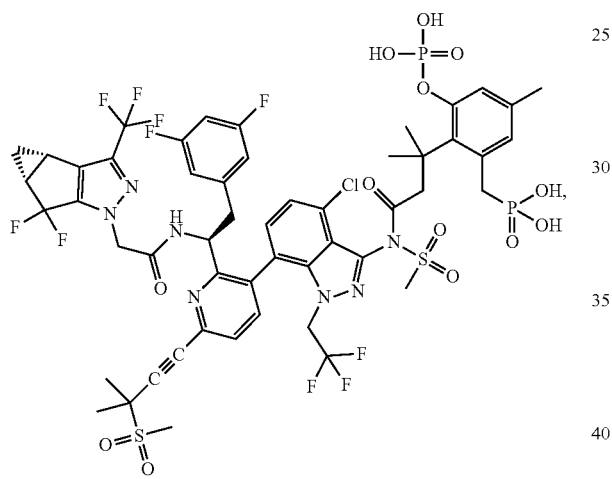
or a pharmaceutically acceptable salt thereof.
In some embodiments of the compound of Formula I, provided herein is a compound that is:
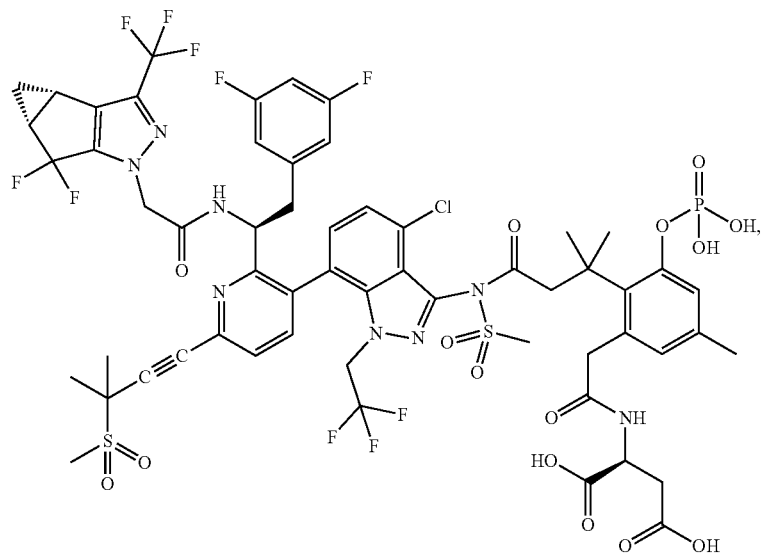 [SMILES: Cc1cc(CC(=O)N[C@@H](CC(=O)O)C(=O)O)c(C(C)(C)CC(=O)N(c2nn(CC(F)(F)F)c3c(-c4ccc(C#CC(C)(C)S(C)(=O)=O)nc4[C@H](Cc4cc(F)cc(F)c4)NC(=O)Cn4nc(C(F)(F)F)c5c4C(F)(F)[C@@H]4C[C@H]54)ccc(Cl)c23)S(C)(=O)=O)c(OP(=O)(O)O)c1]
or a pharmaceutically acceptable salt thereof.

In some embodiments of the compound of Formula I, provided herein is a compound that is:

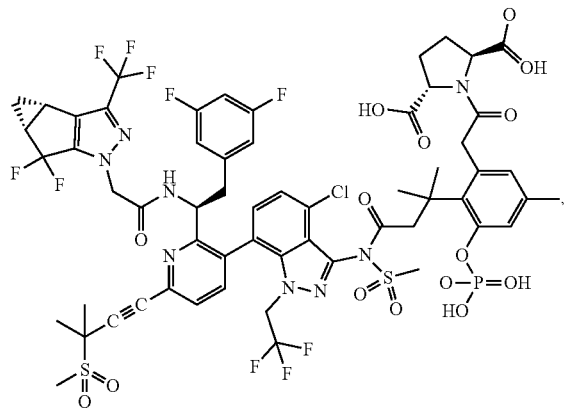 [SMILES: Cc1cc(CC(=O)N2[C@H](C(=O)O)CC[C@H]2C(=O)O)c(C(C)(C)CC(=O)N(c2nn(CC(F)(F)F)c3c(-c4ccc(C#CC(C)(C)S(C)(=O)=O)nc4[C@H](Cc4cc(F)cc(F)c4)NC(=O)Cn4nc(C(F)(F)F)c5c4C(F)(F)[C@@H]4C[C@H]54)ccc(Cl)c23)S(C)(=O)=O)c(OP(=O)(O)O)c1]

or a pharmaceutically acceptable salt thereof.

In some embodiments, the dosing of the compounds of Formula I results in the formation of lenacapavir, which is known to be active against HIV, as disclosed, for example, in U.S. Pat. No. 10,071,985. In some embodiments, the compounds of Formula I are converted to lenacapavir in the gastrointestinal tract. In some embodiments, the compounds of Formula I are more soluble than lenacapavir and thus are administered orally at a lower effective dose than the required oral effective dose for lenacapavir to achieve the same level of exposure of lenacapavir in vivo.

III. Compositions and Kits

Compounds provided herein, or pharmaceutically acceptable salts thereof, are usually administered in the form of pharmaceutical compositions. Thus, provided herein are also pharmaceutical compositions that comprise one or more of the compounds provided herein or pharmaceutically acceptable salts, isomer, or a mixture thereof and one or more pharmaceutically acceptable vehicles selected from carriers, adjuvants and excipients. The compounds provided herein, or pharmaceutically acceptable salts thereof, may be the sole active ingredient or one of the active ingredients of the pharmaceutical compositions. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

In one aspect, provided herein are pharmaceutical compositions comprising a compound provided herein (i.e., a compound of Formula I), or a pharmaceutically acceptable salt thereof, and a pharmaceutically acceptable excipient or carrier. In some embodiments, the pharmaceutical compositions comprise a therapeutically effective amount of a compound provided herein, or a pharmaceutically acceptable salt thereof, and a pharmaceutically acceptable excipient or carrier.

In some embodiments, the pharmaceutical compositions provided herein further comprise one or more (i.e., one, two, three, four; one or two; one to three; or one to four) additional therapeutic agents, or a pharmaceutically acceptable salt thereof. In some embodiments, the pharmaceutical compositions further comprise a therapeutically effective amount of the one or more (i.e., one, two, three, four; one or two; one to three; or one to four) additional therapeutic agents, or a pharmaceutically acceptable salt thereof.

In some embodiments, the one or more additional therapeutic agents include agents that are therapeutic for an HIV virus infection. In some embodiments, the one or more additional therapeutic agents is an anti-HIV agent. In some embodiments, the one or more additional therapeutic agents is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, HIV capsid inhibitors, nucleocapsid protein 7 (NCp7) inhibitors, HIV Tat or Rev inhibitors, inhibitors of Tat-TAR-P-TEFb, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T-cell receptors, TCR-T, autologous T-cell therapies, engineered B cells, NK cells), latency reversing agents, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement $C_5a$ receptor antagonists, DNA methyltransferase inhibitor, Fatty acid synthase inhibitor, HIV vif gene modulators, Vif dimerization antagonists, HIV-1 viral infectivity factor inhibitors, HIV-1 Nef modulators, TNF alpha ligand inhibitors, HIV Nef inhibitors, Hck tyrosine kinase modulators, mixed lineage kinase-3 (MLK-3) inhibitors, HIV-1 splicing inhibitors, integrin antagonists, nucleoprotein inhibitors, splicing factor modulators, COMM domain containing protein 1 modulators, HIV ribonuclease H inhibitors, IFN antagonists, retrocyclin modulators, CD3 antagonists, CDK-4 inhibitors, CDK-6 inhibitors, CDK-9 inhibitors, Cytochrome P450 3 inhibitors, CXCR4 modulators, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, HPK1 (MAP4K1) inhibitors, proprotein convertase PC9 stimulators, ATP dependent RNA helicase DDX3X inhibitors, reverse transcriptase priming complex inhibitors, G6PD and NADH-oxidase inhibitors, mTOR complex 1 inhibitors, mTOR complex 2 inhibitors, P-Glycoprotein modulators, RNA polymerase modulators, TAT protein inhibitors, Prolyl endopeptidase inhibitors, Phospholipase A2 inhibitors, pharmacokinetic enhancers, HIV gene therapy, HIV vaccines, anti-HIV peptides, and any combinations thereof.

In some embodiments, the additional therapeutic agent or agents are selected from combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and any combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and any combinations thereof.

In some embodiments, the additional therapeutic agent or agents are chosen from HIV protease inhibitors, HIV non-nucleoside or non-nucleotide inhibitors of reverse transcriptase, HIV nucleoside or nucleotide inhibitors of reverse transcriptase, HIV integrase inhibitors, HIV capsid inhibitors, gp41 inhibitors, CXCR4 inhibitors, gp120 inhibitors, CCR5 inhibitors, Nef inhibitors, latency reversing agents, HIV bNAbs, agonists of TLR7, TLR8, and TLR9, HIV vaccines, cytokines, immune checkpoint inhibitors, FLT3 ligands, T cell and NK cell recruiting bispecific antibodies, chimeric T cell receptors targeting HIV antigens, pharmacokinetic enhancers, and other drugs for treating HIV, and any combinations thereof.

In some embodiments, the additional therapeutic agent or agents are chosen from dolutegravir, cabotegravir, darunavir, bictegravir, elsulfavirine, rilpivirine, abacavir sulfate, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt thereof.

In some embodiments, the additional therapeutic agent or agents are chosen from dolutegravir, cabotegravir, darunavir, bictegravir, elsulfavirine, rilpivirine, and any combinations thereof, or a pharmaceutically acceptable salt thereof.

Examples of combination drugs include, but are not limited to, ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; tenofovir analog; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); BIKTARVY® (bictegravir+emtricitabine+tenofovir alafenamide), DOVATO® (dolutegravir+lamivudine), TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine, lopinavir+ritonavir+abacavir+lamivudine, lamivudine, cabotegravir+rilpivirine, 3-BNC117+albuvirtide, elpida (elsulfavirine, VM-1500), and VM-1500A, and dual-target HIV-1 reverse transcriptase/nucleocapsid protein 7 inhibitors.

In one embodiment, provided herein are pharmaceutical compositions comprising a therapeutically effective amount of a compound provided herein, or a pharmaceutically acceptable salt thereof, and a pharmaceutically acceptable excipient.

In some embodiments, the pharmaceutical compositions provided herein further comprise one, two, three, or four additional therapeutic agents.

In some embodiments, the pharmaceutical compositions provided herein further comprise one, two, three, or four additional therapeutic agents, wherein the additional therapeutic agents are selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, HIV capsid inhibitors, nucleocapsid protein 7 (NCp7) inhibitors, HIV Tat or Rev inhibitors, inhibitors of Tat-TAR-P-TEFb, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T-cell receptors, TCR-T, autologous T-cell therapies, engineered B cells, NK cells), latency reversing agents, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement $C_5a$ receptor antagonists, DNA methyltransferase inhibitor, Fatty acid synthase inhibitor, HIV vif gene modulators, Vif dimerization antagonists, HIV-1 viral infectivity factor inhibitors, HIV-1 Nef modulators, TNF alpha ligand inhibitors, HIV Nef inhibitors, Hck tyrosine kinase modulators, mixed lineage kinase-3 (MLK-3) inhibitors, HIV-1 splicing inhibitors, integrin antagonists, nucleoprotein inhibitors, splicing factor modulators, COMM domain containing protein 1 modulators, HIV ribonuclease H inhibitors, IFN antagonists, retrocyclin modulators, CD3 antagonists, CDK-4 inhibitors, CDK-6 inhibitors, CDK-9 inhibitors, Cytochrome P450 3 inhibitors, CXCR4 modulators, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, HPK1 (MAP4K1) inhibitors, proprotein convertase PC9 stimulators, ATP dependent RNA helicase DDX3X inhibitors, reverse transcriptase priming complex inhibitors, G6PD and NADH-oxidase inhibitors, mTOR complex 1 inhibitors, mTOR complex 2 inhibitors, P-Glycoprotein modulators, RNA polymerase modulators, TAT protein inhibitors, Prolyl endopeptidase inhibitors, Phospholipase A2 inhibitors, pharmacokinetic enhancers, HIV gene therapy, HIV vaccines, and anti-HIV peptides, or any combinations thereof.

In some embodiments, the pharmaceutical compositions provided herein further comprise one, two, three, or four additional therapeutic agents, wherein the additional therapeutic agents are selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, bispecific antibodies, "antibody-like" therapeutic proteins, or any combinations thereof.

In some embodiments, the pharmaceutical compositions provided herein further comprise one, two, three, or four additional therapeutic agents, wherein the additional therapeutic agents are selected from the group consisting of dolutegravir, cabotegravir, darunavir, bictegravir, elsulfavirine, rilpivirine, abacavir sulfate, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt thereof.

The pharmaceutical compositions may be administered in either single or multiple doses. The pharmaceutical compositions may be administered by various methods including, for example, rectal, buccal, intranasal and transdermal routes. In some embodiments, the pharmaceutical compositions may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. In some embodiments, the compounds, or pharmaceutically acceptable salts thereof, and pharmaceutical compositions disclosed herein are administered by subcutaneous injection.

The pharmaceutical compositions of the present disclosure may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

In some embodiments, the sterile injectable preparation disclosed herein may also be a sterile injectable solution or suspension prepared from a reconstituted lyophilized powder in a non-toxic parenterally acceptable diluent or solvent, such as a solution in 1,3-butane-diol. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. In certain embodiments the suspension is a microsuspension. In certain embodiments the suspension is a nanosuspension.

In some embodiments, formulations suitable for parenteral administration (e.g., intramuscular (IM) and subcutaneous (SC) administration) will include one or more excipients. Excipients should be compatible with the other ingredients of the formulation and physiologically innocuous to the recipient thereof. Examples of suitable excipients are well known to the person skilled in the art of parenteral formulation and may be found e.g., in Handbook of Pharmaceutical Excipients (eds. Rowe, Sheskey & Quinn), 6th edition 2009. Examples of solubilizing excipients in a parenteral formulation (e.g., an SC or IM formulation) include, but are not limited to, polysorbates (such as polysorbate 20 or 80) and poloxamers (such as poloxamer 338, 188, or 207).

In some embodiments, the compounds, or pharmaceutically acceptable salts thereof, and pharmaceutical compositions disclosed herein are administered with implants.

Oral administration may be another route for administration of the compounds provided herein or pharmaceutically acceptable salts thereof. Administration may be via, for example, capsule or enteric coated tablets. In making the pharmaceutical compositions that include at least one compound provided herein or pharmaceutically acceptable salts, isomer, or a mixture thereof, the active ingredient (such as a compound provided herein) is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the pharmaceutical compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose or any combinations thereof. The pharmaceutical compositions can additionally include lubricating agents such as talc, magnesium stearate, and mineral oil; wetting agents; emulsifying and suspending agents; preserving agents such as methyl and propylhydroxy-benzoates; sweetening agents; and flavoring agents; or any combinations thereof.

The pharmaceutical compositions that include at least one compound described herein or pharmaceutically acceptable salts, isomer, or a mixture thereof can be formulated so as to provide quick, sustained or delayed release of the active ingredient (such as a compound provided herein) after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds provided herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or pharmaceutically acceptable salts, isomer, or a mixture thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds provided herein or pharmaceutically acceptable salts thereof may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with materials such as shellac, cetyl alcohol, and cellulose acetate.

Pharmaceutical compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

In one embodiment, provided herein are kits that comprise a compound provided herein, (i.e., a compound of Formula I), or a pharmaceutically acceptable salt, stereoisomer, prodrug, or solvate thereof, and suitable packaging. In some embodiments, the kit further comprises instructions for use. In some embodiments, the kit comprises a compound provided herein (i.e., a compound of Formula I), or a pharmaceutically acceptable salt, stereoisomer, prodrug, or solvate thereof, and a label and/or instructions for use of the compounds in the treatment of the indications, including the diseases or conditions, described herein.

In some embodiments, the kits further comprise one or more (i.e., one, two, three, four; one or two; one to three; or one to four) additional therapeutic agents, or a pharmaceutically acceptable salt thereof.

In one embodiment, provided herein are articles of manufacture that comprise a compound described herein or pharmaceutically acceptable salts, isomer, or a mixture thereof in a suitable container. In some embodiments, the container may be a vial, jar, ampoule, preloaded syringe, or intravenous bag.

IV. Methods

The methods provided herein may be applied to cell populations in vivo or ex vivo. "In vivo" means within a living individual, as within an animal or human. In this context, the methods provided herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the present disclosure may be used for a variety of purposes, including therapeutic and experimental purposes. For example, the present disclosure may be used ex vivo to determine the optimal schedule and/or dosing of administration of a compound as disclosed herein for a given cell type, individual, and other parameters. Information gleaned from such use may be used for experimental purposes or in the clinic to set protocols for in vivo treatment. Other ex vivo uses for which the present disclosure may be suited are described below or will become apparent to those skilled in the art. The selected compounds may be further characterized to examine the safety or tolerance dosage in human or non-human subjects. Such properties may be examined using commonly known methods to those skilled in the art.

In one embodiment, the present disclosure provides a method of treating or preventing a human immunodeficiency virus (HIV) infection in a patient in need thereof comprising administering to the patient a therapeutically effective amount of a compound provided herein, or a pharmaceutically acceptable salt thereof, or a pharmaceutical composition provided herein.

In one embodiment, the present disclosure provides a method of treating a human immunodeficiency virus (HIV) infection in a heavily treatment-experienced patient, the method comprising administering to the patient a therapeutically effective amount of a compound provided herein, or a pharmaceutically acceptable salt thereof, or a pharmaceutical composition provided herein.

In some embodiments, the methods provided herein further comprise administering a therapeutically effective amount of one, two, three, or four additional therapeutic agents, or a pharmaceutically acceptable salt thereof.

In some embodiments, the one, two, three, or four additional therapeutic agents are selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, HIV capsid inhibitors, nucleocapsid protein 7 (NCp7) inhibitors, HIV Tat or Rev inhibitors, inhibitors of Tat-TAR-P-TEFb, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T-cell receptors, TCR-T, autologous T-cell therapies, engineered B cells, NK cells), latency reversing agents, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement $C_5a$ receptor antagonists, DNA methyltransferase inhibitor, Fatty acid synthase inhibitor, HIV vif gene modulators, Vif dimerization antagonists, HIV-1 viral infectivity factor inhibitors, HIV-1 Nef modulators, TNF alpha ligand inhibitors, HIV Nef inhibitors, Hck tyrosine kinase modulators, mixed lineage kinase-3 (MLK-3) inhibitors, HIV-1 splicing inhibitors, integrin antagonists, nucleoprotein inhibitors, splicing factor modulators, COMM domain containing protein 1 modulators, HIV ribonuclease H inhibitors, IFN antagonists, retrocyclin modulators, CD3 antagonists, CDK-4 inhibitors, CDK-6 inhibitors, CDK-9 inhibitors, Cytochrome P450 3 inhibitors, CXCR4 modulators, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, HPK1 (MAP4K1) inhibitors, proprotein convertase PC9 stimulators, ATP dependent RNA helicase DDX3X inhibitors, reverse transcriptase priming complex inhibitors, G6PD and NADH-oxidase inhibitors, mTOR complex 1 inhibitors, mTOR complex 2 inhibitors, P-Glycoprotein modulators, RNA polymerase modulators, TAT protein inhibitors, Prolyl endopeptidase inhibitors, Phospholipase A2 inhibitors, pharmacokinetic enhancers, HIV gene therapy, HIV vaccines, and anti-HIV peptides, or any combinations thereof.

In some embodiments, the one, two, three, or four additional therapeutic agents are selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, bispecific antibodies, and "antibody-like" therapeutic proteins, or any combinations thereof.

In some embodiments, the one, two, three, or four additional therapeutic agents are selected from the group consisting of dolutegravir, cabotegravir, darunavir, bictegravir, elsulfavirine, rilpivirine, abacavir sulfate, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt thereof.

In some embodiments of the methods provided herein, the patient is a human.

In one embodiment, the present disclosure provides a therapeutically effective amount of a compound provided herein, or a pharmaceutically acceptable salt thereof, or a pharmaceutical composition provided herein for use in therapy.

In one embodiment, the present disclosure provides a compound provided herein, or a pharmaceutically acceptable salt, or a pharmaceutical composition provided herein for use in a method of treating or preventing a human immunodeficiency virus (HIV) infection in a patient in need thereof, the method comprising administering to the patient a therapeutically effective amount of the compound, or a pharmaceutically acceptable salt thereof, or the pharmaceutical composition.

In one embodiment, the present disclosure provides a compound provided herein, or a pharmaceutically acceptable salt thereof, or a pharmaceutical composition provided herein for use in a method of treating a human immunodeficiency virus (HIV) infection in a heavily treatment-experienced patient, the method comprising administering to the patient a therapeutically effective amount of the compound, or a pharmaceutically acceptable salt thereof, or the pharmaceutical composition.

In some embodiments, the uses provided herein further comprise administering a therapeutically effective amount of one, two, three, or four additional therapeutic agents, or a pharmaceutically acceptable salt thereof.

In some embodiments of the uses provided herein, the one, two, three, or four additional therapeutic agents are selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, HIV capsid inhibitors, nucleocapsid protein 7 (NCp7) inhibitors, HIV Tat or Rev inhibitors, inhibitors of Tat-TAR-P-TEFb, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T-cell receptors, TCR-T, autologous T-cell therapies, engineered B cells, NK cells), latency reversing agents, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, Fatty acid synthase inhibitor, HIV vif gene modulators, Vif dimerization antagonists, HIV-1 viral infectivity factor inhibitors, HIV-1 Nef modulators, TNF alpha ligand inhibitors, HIV Nef inhibitors, Hck tyrosine kinase modulators, mixed lineage kinase-3 (MLK-3) inhibitors, HIV-1 splicing inhibitors, integrin antagonists, nucleoprotein inhibitors, splicing factor modulators, COMM domain containing protein 1 modulators, HIV ribonuclease H inhibitors, IFN antagonists, retrocyclin modulators, CD3 antagonists, CDK-4 inhibitors, CDK-6 inhibitors, CDK-9 inhibitors, Cytochrome P450 3 inhibitors, CXCR4 modulators, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, HPK1 (MAP4K1) inhibitors, proprotein convertase PC9 stimulators, ATP dependent RNA helicase DDX3X inhibitors, reverse transcriptase priming complex inhibitors, G6PD and NADH-oxidase inhibitors, mTOR complex 1 inhibitors, mTOR complex 2 inhibitors, P-Glycoprotein modulators, RNA polymerase modulators, TAT protein inhibitors, Prolyl endopeptidase inhibitors, Phospholipase A2 inhibitors, pharmacokinetic enhancers, HIV gene therapy, HIV vaccines, and anti-HIV peptides, or any combinations thereof.

In some embodiments of the uses provided herein, the one, two, three, or four additional therapeutic agents are selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, bispecific antibodies, and "antibody-like" therapeutic proteins, or any combinations thereof.

In some embodiments of the uses provided herein, the one, two, three, or four additional therapeutic agents are selected from the group consisting of dolutegravir, cabotegravir, darunavir, bictegravir, elsulfavirine, rilpivirine, abacavir sulfate, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt thereof.

In some embodiments of the uses provided herein, the patient is a human.

In one embodiment, provided herein is a method of phosphorylating a hydroxyl group (—OH) or an amine group (—NH$_2$) of a compound, wherein the method comprises contacting the compound with a base, HP(O)(OR$^9$)$_2$, a halogenating agent, and a solvent to form a compound of Formula IIA or IIB:

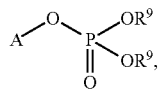

Formula IIA

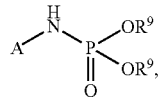

Formula IIB wherein R$^9$ is C$_{1-6}$ alkyl, phenyl, or —CH$_2$(phenyl), and wherein A is the rest of the compound to which the hydroxyl group or amine group is attached.

In some embodiments, provided herein is a method of phosphorylating a hydroxyl group (—OH)) of a compound, wherein the method comprises contacting the compound with a base, HP(O)(OR$^9$)$_2$, a halogenating agent, and a solvent to form a compound of Formula IIA:

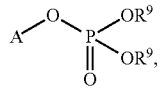

Formula IIA wherein R$^9$ is C$_{1-6}$ alkyl, phenyl, or —CH$_2$(phenyl), and wherein A is the rest of the compound to which the hydroxyl group is attached.

In some embodiments, provided herein is a method of phosphorylating an amine group (—NH$_2$) of a compound, wherein the method comprises contacting the compound with a base, HP(O)(OR$^9$)$_2$, a halogenating agent, and a solvent to form a compound of Formula IIB:

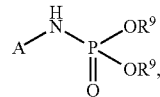

Formula IIB wherein R$^9$ is C$_{1-6}$ alkyl, phenyl, or —CH$_2$(phenyl), and wherein A is the rest of the compound to which the amine group is attached.

In some embodiments, the method further comprises contacting the compound, base, HP(O)(OR$^9$)$_2$, halogenating agent, and solvent at 0° C.

In some embodiments, A has a phenyl group and the hydroxyl group is attached to the phenyl group. In some embodiments, A has a phenyl group and the amine group is attached to the phenyl group.

In some embodiments, R$^9$ is methyl. In some embodiments, R$^9$ is ethyl. In some embodiments, R$^9$ is isopropyl. In some embodiments, R$^9$ is tert-butyl. In some embodiments, R$^9$ is —CH$_2$(phenyl).

In some embodiments, the base is sodium hydride. In some embodiments, the base is cesium carbonate.

In some embodiments, the halogenating agent is bromoform. In some embodiments, the halogenating agent is tetrabromide. In some embodiments, the halogenating agent is bromotrichloromethane. In some embodiments, the halogenating agent is carbon tetrachloride. In some embodiments, the halogenating agent is dibromodichloromethane.

In some embodiments, the solvent is a polar aprotic solvent. In some embodiments, the solvent is tetrahydrofuran. In some embodiments, the solvent is 2-methyl tetrahydrofuran. In some embodiments, the solvent is methyl tert-butyl ether. In some embodiments, the solvent is dichloromethane. In some embodiments, the solvent is N,N-dimethyl formamide.

In some embodiments, the hydroxyl group of the compound is phosphorylated by contacting the compound with:
i) sodium hydride or cesium carbonate;
ii) HP(O)(O-isopropyl)$_2$ or HP(O)(O-tert-butyl)$_2$;
iii) tetrahydrofuran or 2-methyl tetrahydrofuran; and
iv) bromoform; at 0° C.

In some embodiments, the hydroxyl group of the compound is phosphorylated by contacting the compound with:
i) Sodium Hydride or Cesium Carbonate;
ii) HP(O)(O-isopropyl)$_2$ or HP(O)(O-tert-butyl)$_2$;
iii) Tetrahydrofuran or 2-Methyl Tetrahydrofuran; and
iv) bromoform; at 0° C., wherein the compound has a phenyl group and the hydroxyl group is attached to the phenyl group.

In some embodiments, the hydroxyl group of the compound is phosphorylated by contacting the compound with:
i) Sodium Hydride;
ii) HP(O)(O-isopropyl)$_2$ or HP(O)(O-tert-butyl)$_2$;
iii) Tetrahydrofuran or 2-Methyl Tetrahydrofuran; and
iv) bromoform; at 0° C.

In some embodiments, the hydroxyl group of the compound is phosphorylated by contacting the compound with:
i) sodium hydride;
ii) HP(O)(O-isopropyl)$_2$ or HP(O)(O-tert-butyl)$_2$;
iii) tetrahydrofuran or 2-methyl tetrahydrofuran; and
iv) bromoform; at 0° C., wherein the compound has a phenyl group and the hydroxyl group is attached to the phenyl group.

In some embodiments, the hydroxyl group of the compound is phosphorylated by contacting the compound with:
i) cesium carbonate;
ii) HP(O)(O-isopropyl)$_2$ or HP(O)(O-tert-butyl)$_2$;
iii) tetrahydrofuran or 2-methyl tetrahydrofuran; and
iv) bromoform; at 0° C.

In some embodiments, the hydroxyl group of the compound is phosphorylated by contacting the compound with:
i) cesium carbonate;
ii) HP(O)(O-isopropyl)$_2$ or HP(O)(O-tert-butyl)$_2$;
iii) tetrahydrofuran or 2-methyl tetrahydrofuran; and
iv) bromoform; at 0° C., wherein the compound has a phenyl group and the hydroxyl group is attached to the phenyl group.

V. Administration

The compounds of the present disclosure or pharmaceutically acceptable salts thereof (also referred to herein as the active ingredients) can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with, for example, the condition of the recipient. An advantage of certain compounds disclosed herein, or pharmaceutically acceptable salts thereof, is that they are orally bioavailable and can be dosed orally.

A compound of the present disclosure, or a pharmaceutically acceptable salt thereof, may be administered to an individual in accordance with an effective dosing regimen for a desired period of time or duration, such as at least about one month, at least about 2 months, at least about 3 months, at least about 6 months, or at least about 12 months or longer. In some embodiments, the compound, or a pharmaceutically acceptable salt thereof, is administered on a daily or intermittent schedule for the duration of the individual's life.

The specific dose level of a compound of the present disclosure, or a pharmaceutically acceptable salt thereof, for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound provided herein, or a pharmaceutically acceptable salt thereof, per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The dosage may also be described as a total amount of a compound described herein, or a pharmaceutically acceptable salt thereof, administered per dose. The dosage or dosing frequency of a compound of the present disclosure, or a pharmaceutically acceptable salt thereof, may be adjusted over the course of the treatment, based on the judgment of the administering physician.

The compounds of the present disclosure, or pharmaceutically acceptable salts thereof, may be administered to an individual (e.g., a human) in a therapeutically effective amount. In some embodiments, the compound of Formula I, or a pharmaceutically acceptable salt thereof, is administered once daily, once weekly, once monthly, once every two months, once every three months, or once every six months. In some embodiments, the compound of Formula I, or a pharmaceutically acceptable salt thereof, is administered once daily. In some embodiments, the compound of Formula I, or a pharmaceutically acceptable salt thereof, is administered once weekly. In some embodiments, the compound of Formula I, or a pharmaceutically acceptable salt thereof, is administered once monthly. In some embodiments, the compound of Formula I, or a pharmaceutically acceptable salt thereof, is administered once every two months. In some embodiments, the compound of Formula I, or a pharmaceutically acceptable salt thereof, is administered once every three months. In some embodiments, the compound of Formula I, or a pharmaceutically acceptable salt thereof, is administered once every six months.

The compounds provided herein, or pharmaceutically acceptable salts thereof, can be administered by any useful route and means, such as by oral or parenteral (e.g., intravenous) administration. Therapeutically effective amounts of the compound, or a pharmaceutically acceptable salt thereof, may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day. In some embodiments, a therapeutically effective amount of the compounds provided herein, or pharmaceutically acceptable salts thereof, include from about 0.3 mg to about 30 mg per day, or from about 30 mg to about 300 mg per day, or from about 0.3 µg to about 30 mg per day, or from about 30 µg to about 300 µg per day.

A compound of the present disclosure, or a pharmaceutically acceptable salt thereof, may be combined with one or more additional therapeutic agents in any dosage amount of the compound of the present disclosure or a pharmaceutically acceptable salt thereof (e.g., from 1 mg to 1000 mg of compound). Therapeutically effective amounts may include from about 0.1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose, or such as from about 0.01 mg per dose to about 1000 mg per dose, or such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose, or such as from about 1 mg per dose to about 1000 mg per dose. Other therapeutically effective amounts of the compound of Formula I, or a pharmaceutically acceptable salt thereof, are about 50, 100, 125, 150, 175, 200, 225, 250, 275, or 300 mg per dose. Other therapeutically effective amounts of the compound of Formula I, or pharmaceutically acceptable salts thereof, are about 300, 325, 350, 375, 400, 425, 450, 475, 500, 525, 550, 575, 600, 625, 650, 675, 700, 725, 750, 775, 800, 825, 850, 875, 900, 925, 950, 975, or about 1000 mg per dose.

In some embodiments, a therapeutically effective amount of the compound of Formula I, or a pharmaceutically acceptable salt thereof, is about 1 mg to about 1000 mg. In some embodiments, a therapeutically effective amount of the compound of Formula I, or a pharmaceutically acceptable salt thereof, is about 1 mg to about 900 mg. In some embodiments, a therapeutically effective amount of the compound of Formula I, or a pharmaceutically acceptable salt thereof, is about 1 mg to about 800 mg. In some embodiments, a therapeutically effective amount of the compound of Formula I, or a pharmaceutically acceptable salt thereof, is about 1 mg to about 700 mg. In some embodiments, a therapeutically effective amount of the compound of Formula I, or a pharmaceutically acceptable salt thereof, is about 1 mg to about 600 mg. In some embodiments, a therapeutically effective amount of the compound of Formula I, or a pharmaceutically acceptable salt thereof, is about 1 mg to about 500 mg. In some embodiments, a therapeutically effective amount of the compound of Formula I, or a pharmaceutically acceptable salt thereof, is about 1 mg to about 400 mg. In some embodiments, a therapeutically effective amount of the compound of Formula I, or a pharmaceutically acceptable salt thereof, is about 1 mg to about 300 mg. In some embodiments, a therapeutically effective amount of the compound of Formula I, or a pharmaceutically acceptable salt thereof, is about 1 mg to about 200 mg. In some embodiments, a therapeutically effective amount of the compound of Formula I, or a pharmaceutically acceptable salt thereof, is about 1 mg to about 100 mg. In some embodiments, a therapeutically effective amount of the compound of Formula I, or a pharmaceutically acceptable salt thereof, is about 1 mg to about 75 mg. In some embodiments, a therapeutically effective amount of the compound of Formula I, or a pharmaceutically acceptable salt thereof, is about 1 mg to about 50 mg. In some embodiments, a therapeutically effective amount of the compound of Formula I, or a pharmaceutically acceptable salt thereof, is about 1 mg to about 25 mg. In some embodiments, a therapeutically effective amount of the compound of Formula I, or a pharmaceutically acceptable salt thereof, is about 1 mg to about 20 mg. In some embodiments, a therapeutically effective amount of the compound of Formula I, or a pharmaceutically acceptable salt thereof, is about 1 mg to about 15 mg. In some embodiments, a therapeutically effective amount of the compound of Formula I, or a pharmaceutically acceptable salt thereof, is about 1 mg to about 10 mg. In some embodiments, a therapeutically effective amount of the compound of Formula I, or a pharmaceutically acceptable salt thereof, is about 1 mg to about 5 mg.

In some embodiments, a therapeutically effective amount of the compound of Formula I, or a pharmaceutically acceptable salt thereof, is about 50 mg, about 75 mg, about 100 mg, about 125 mg, about 150 mg, about 175 mg, about 200 mg, about 225 mg, about 275 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, or about 1050 mg. In some embodiments, a therapeutically effective amount of the compound of Formula I, or a pharmaceutically acceptable salt thereof, is about 5 mg. In some embodiments, a therapeutically effective amount of the compound of Formula I, or a pharmaceutically acceptable salt thereof, is about 100 mg. In some embodiments, a therapeutically effective amount of the compound of Formula I, or a pharmaceutically acceptable salt thereof, is about 150 mg. In some embodiments, a therapeutically effective amount of the compound of Formula I, or a pharmaceutically acceptable salt thereof, is about 200 mg. In some embodiments, a therapeutically effective amount of the compound of Formula I, or a pharmaceutically acceptable salt thereof, is about 250 mg. In some embodiments, a therapeutically effective amount of the compound of Formula I, or a pharmaceutically acceptable salt thereof, is about 300 mg. In some embodiments, a therapeutically effective amount of the compound of Formula I, or a pharmaceutically acceptable salt thereof, is about 350 mg. In some embodiments, a therapeutically effective amount of the compound of Formula I, or a pharmaceutically acceptable salt thereof, is about 400 mg. In some embodiments, a therapeutically effective amount of the compound of Formula I, or a pharmaceutically acceptable salt thereof, is about 450 mg. In some embodiments, a therapeutically effective amount of the compound of Formula I, or a pharmaceutically acceptable salt thereof, is about 500 mg. In some embodiments, a therapeutically effective amount of the compound of Formula I, or a pharmaceutically acceptable salt thereof, is about 550 mg. In some embodiments, a therapeutically effective amount of the compound of Formula I, or a pharmaceutically acceptable salt thereof, is about 600 mg. In some embodiments, a therapeutically effective amount of the compound of Formula I, or a pharmaceutically acceptable salt thereof, is about 650 mg. In some embodiments, a therapeutically effective amount of the compound of Formula I, or a pharmaceutically acceptable salt thereof, is about 700 mg. In some embodiments, a therapeutically effective amount of the compound of Formula I, or a pharmaceutically acceptable salt thereof, is about 750 mg. In some embodiments, a therapeutically effective amount of the compound of Formula I, or a pharmaceutically acceptable salt thereof, is about 800 mg. In some embodiments, a therapeutically effective amount of the compound of Formula I, or a pharmaceutically acceptable salt thereof, is about 850 mg. In some embodiments, a therapeutically effective amount of the compound of Formula I, or a pharmaceutically acceptable salt thereof, is about 900 mg. In some embodiments, a therapeutically effective amount of the compound of Formula I, or a pharmaceutically acceptable salt thereof, is about 950 mg. In some embodiments, a therapeutically effective amount of the compound of Formula I, or a pharmaceutically acceptable salt thereof, is about 1000 mg. In some embodiments, a therapeutically effective amount of the compound of Formula I, or a pharmaceutically acceptable salt thereof, is about 1050 mg.

When administered orally, the total weekly dosage for a human subject may be between about 1 mg and 1,000 mg/week, between about 10-500 mg/week, between about 50-300 mg/week, between about 75-200 mg/week, or between about 100-150 mg/week. In some embodiments, the total weekly dosage for a human subject may be about 100, 200, 300, 400, 500, 600, 700, 800, 900, or 1000 mg/week administered in a single dose. In some embodiments, the total weekly dosage for a human subject of a compound of Formula I, or a pharmaceutically acceptable salt thereof, may be about 100 mg administered in a single dose. In some embodiments, the total weekly dosage for a human subject of a compound of Formula I, or a pharmaceutically acceptable salt thereof, may be about 150 mg administered in a single dose. In some embodiments, the total weekly dosage for a human subject of a compound of Formula I, or a pharmaceutically acceptable salt thereof, may be about 200 mg administered in a single dose. In some embodiments, the total weekly dosage for a human subject of a compound of Formula I, or a pharmaceutically acceptable salt thereof, may be about 250 mg administered in a single dose. In some embodiments, the total weekly dosage for a human subject of a compound of Formula I, or a pharmaceutically acceptable salt thereof, may be about 300 mg administered in a single dose. In some embodiments, the total weekly dosage for a human subject of a compound of Formula I, or a pharmaceutically acceptable salt thereof, may be about 350 mg administered in a single dose. In some embodiments, the total weekly dosage for a human subject of a compound of Formula I, or a pharmaceutically acceptable salt thereof, may be about 400 mg administered in a single dose. In some embodiments, the total weekly dosage for a human subject of a compound of Formula I, or a pharmaceutically acceptable salt thereof, may be about 450 mg administered in a single dose. In some embodiments, the total weekly dosage for a human subject of a compound of Formula I, or a pharmaceutically acceptable salt thereof, may be about 500 mg administered in a single dose.

When administered orally, the total monthly dosage for a human subject of a compound of Formula I, or a pharmaceutically acceptable salt thereof, may be between about 500 mg and 1,000 mg/month, between about 600-900 mg/month, or between about 700-800 mg/month. In some embodiments, the total weekly dosage for a human subject of a compound of Formula I, or a pharmaceutically acceptable salt thereof, may be about 100, 200, 300, 400, 500, 600, 700, 800, 900, or 1000 mg/week administered in a single dose. In some embodiments, the total monthly dosage for a human subject of a compound of Formula I, or a pharmaceutically acceptable salt thereof, may be about 500 mg administered in a single dose. In some embodiments, the total monthly dosage for a human subject may be about 550 mg administered in a single dose. In some embodiments, the total monthly dosage for a human subject of a compound of Formula I, or a pharmaceutically acceptable salt thereof, may be about 600 mg administered in a single dose. In some embodiments, the total monthly dosage for a human subject of a compound of Formula I, or a pharmaceutically acceptable salt thereof, may be about 650 mg administered in a single dose. In some embodiments, the total monthly dosage for a human subject of a compound of Formula I, or a pharmaceutically acceptable salt thereof, may be about 700 mg administered in a single dose. In some embodiments, the total monthly dosage for a human subject of a compound of Formula I, or a pharmaceutically acceptable salt thereof, may be about 750 mg administered in a single dose. In some embodiments, the total monthly dosage for a human subject of a compound of Formula I, or a pharmaceutically acceptable salt thereof, may be about 800 mg administered in a single dose. In some embodiments, the total monthly dosage for a human subject of a compound of Formula I, or a pharmaceutically acceptable salt thereof, may be about 850 mg administered in a single dose. In some embodiments, the total monthly dosage for a human subject of a compound of Formula I, or a pharmaceutically acceptable salt thereof, may be about 900 mg administered in a single dose. In some embodiments, the total monthly dosage for a human subject of a compound of Formula I, or a pharmaceutically acceptable salt thereof, may be about 950 mg administered in a single dose. In some embodiments, the total monthly dosage for a human subject of a compound of Formula I, or a pharmaceutically acceptable salt thereof, may be about 1000 mg administered in a single dose.

A single dose can be administered hourly, daily, weekly, or monthly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month. In some embodiments, a compound provided herein, or a pharmaceutically acceptable salt thereof, is administered once daily in a method disclosed herein. In some embodiments, a compound provided herein, or a pharmaceutically acceptable salt thereof, is administered twice daily in a method disclosed herein.

In some embodiments, a compound provided herein, or a pharmaceutically acceptable salt thereof, is administered once daily in a method disclosed herein. In some embodiments, a compound provided herein, or a pharmaceutically acceptable salt thereof, is administered once weekly in a method disclosed herein. In some embodiments, a compound provided herein, or a pharmaceutically acceptable salt thereof, is administered once monthly in a method disclosed herein. In some embodiments, a compound provided herein, or a pharmaceutically acceptable salt thereof, is administered once every two months in a method disclosed herein. In some embodiments, a compound provided herein, or a pharmaceutically acceptable salt thereof, is administered once every three months in a method disclosed herein. In some embodiments, a compound provided herein, or a pharmaceutically acceptable salt thereof, is administered once every six months in a method disclosed herein.

In some embodiments, a compound provided herein, or a pharmaceutically acceptable salt thereof, is administered orally in a single dose of about 100 mg once weekly. In some embodiments, a compound provided herein, or a pharmaceutically acceptable salt thereof, is administered orally in a single dose of about 150 mg once weekly. In some embodiments, a compound provided herein, or a pharmaceutically acceptable salt thereof, is administered orally in a single dose of about 200 mg once weekly. In some embodiments, a compound provided herein, or a pharmaceutically acceptable salt thereof, is administered orally in a single dose of about 250 mg once weekly. In some embodiments, a compound provided herein, or a pharmaceutically acceptable salt thereof, is administered orally in a single dose of about 300 mg once weekly. In some embodiments, a compound provided herein, or a pharmaceutically acceptable salt thereof, is administered orally in a single dose of about 350 mg once weekly. In some embodiments, a compound provided herein, or a pharmaceutically acceptable salt thereof, is administered orally in a single dose of about 400 mg once weekly. In some embodiments, a compound provided herein, or a pharmaceutically acceptable salt thereof, is administered orally in a single dose of about 450 mg once weekly. In some embodiments, a compound provided herein, or a pharmaceutically acceptable salt thereof, is administered orally in a single dose of about 500 mg once weekly.

In some embodiments, a compound provided herein, or a pharmaceutically acceptable salt thereof, is administered orally in a single dose of about 500 mg once monthly. In some embodiments, a compound provided herein, or a pharmaceutically acceptable salt thereof, is administered orally in a single dose of about 550 mg once monthly. In some embodiments, a compound provided herein, or a pharmaceutically acceptable salt thereof, is administered orally in a single dose of about 600 mg once monthly. In some embodiments, a compound provided herein, or a pharmaceutically acceptable salt thereof, is administered orally in a single dose of about 650 mg once monthly. In some embodiments, a compound provided herein, or a pharmaceutically acceptable salt thereof, is administered orally in a single dose of about 700 mg once monthly. In some embodiments, a compound provided herein, or a pharmaceutically acceptable salt thereof, is administered orally in a single dose of about 750 mg once monthly. In some embodiments, a compound provided herein, or a pharmaceutically acceptable salt thereof, is administered orally in a single dose of about 800 mg once monthly. In some embodiments, a compound provided herein, or a pharmaceutically acceptable salt thereof, is administered orally in a single dose of about 850 mg once monthly. In some embodiments, a compound provided herein, or a pharmaceutically acceptable salt thereof, is administered orally in a single dose of about 900 mg once monthly. In some embodiments, a compound provided herein, or a pharmaceutically acceptable salt thereof, is administered orally in a single dose of about 950 mg once monthly. In some embodiments, a compound provided herein, or a pharmaceutically acceptable salt thereof, is administered orally in a single dose of about 1000 mg once monthly.

The frequency of dosage of the compound of the present disclosure, or a pharmaceutically acceptable salt thereof, will be determined by the needs of the individual patient and can be, for example, once per day, once per week, once per month, once per every two months, once per every three months, or once per every six months. Administration of the compound, or a pharmaceutically acceptable salt thereof, continues for as long as necessary to treat the Retroviridae infection, including an HIV infection, or any other indication described herein. For example, a compound, or a pharmaceutically acceptable salt thereof, can be administered to a human suffering from a Retroviridae infection, including an HIV infection, for the duration of the human's life.

Administration can be intermittent, with a period of several or more days during which a patient receives a daily dose of the compound of the present disclosure, or a pharmaceutically acceptable salt thereof, followed by a period of several or more days during which a patient does not receive a daily dose of the compound or a pharmaceutically acceptable salt thereof. For example, a patient can receive a dose of the compound, or a pharmaceutically acceptable salt thereof, every other day, or three times per week. Again by way of example, a patient can receive a dose of the compound, or a pharmaceutically acceptable salt thereof, each day for a period of from 1 to 14 days, followed by a period of 7 to 21 days during which the patient does not receive a dose of the compound, or a pharmaceutically acceptable salt thereof, followed by a subsequent period (e.g., from 1 to 14 days) during which the patient again receives a daily dose of the compound, or a pharmaceutically acceptable salt thereof. Alternating periods of administration of the compound, or a pharmaceutically acceptable salt thereof, followed by non-administration of the compound, or a pharmaceutically acceptable salt thereof, can be repeated as clinically required to treat the patient.

The compounds of the present disclosure, or pharmaceutically acceptable salts thereof, or the pharmaceutical compositions of the present disclosure may be administered once, twice, three, or four times daily, using any suitable mode described above. Also, administration or treatment with the compounds, or pharmaceutically acceptable salts thereof, may be continued for a number of days; for example, commonly treatment would continue for at least 7 days, 14 days, or 28 days, for one cycle of treatment. Treatment cycles are well known for Retroviridae infections, including an HIV infection. In some embodiments, treatment cycles are frequently alternated with resting periods of about 1 to 28 days, commonly about 7 days or about 14 days, between cycles. The treatment cycles, in other embodiments, may also be continuous.

VI. Combination Therapy

Patients being treated by administration of the compounds provided herein, or pharmaceutically acceptable salts thereof, often exhibit diseases or conditions that benefit from treatment with other therapeutic agents, including agents that are therapeutic for Retroviridae infections, including an HIV infection. In some embodiments, the other therapeutic agent is an agent that is therapeutic for an HIV infection. Thus, one aspect of the disclosure is a method of treating an HIV infection comprising administering a compound of the present disclosure, or a pharmaceutically acceptable salt thereof, in combination with one or more compounds useful for the treatment of an HIV infection to a subject, particularly a human subject, in need thereof.

In some embodiments, a compound of the present disclosure, or a pharmaceutically acceptable salt thereof, is combined with one, two, three, four or more additional therapeutic agents. In some embodiments, a compound of the present disclosure, or a pharmaceutically acceptable salt thereof, is combined with two additional therapeutic agents. In some embodiments, a compound of the present disclosure, or a pharmaceutically acceptable salt thereof, is combined with three additional therapeutic agents. In some embodiments, a compound of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In some embodiments, when a compound of the present disclosure, or a pharmaceutically acceptable salt thereof, is combined with one or more additional therapeutic agents as described herein, the components of the composition are administered as a simultaneous or sequential regimen. When administered sequentially, the combination may be administered in two or more administrations.

In some embodiments, a compound of the present disclosure, or a pharmaceutically acceptable salt thereof, is combined with one or more additional therapeutic agents in a unitary dosage form for simultaneous administration to a patient, for example as a solid dosage form for oral administration.

In some embodiments, a compound of the present disclosure, or a pharmaceutically acceptable salt thereof, is co-administered with one or more additional therapeutic agents.

Co-administration includes administration of unit dosages of the compounds provided herein, or pharmaceutically acceptable salts thereof, before or after administration of unit dosages of one or more additional therapeutic agents. The compounds provided herein, or pharmaceutically acceptable salts thereof, may be administered within seconds, minutes, or hours of the administration of one or more additional therapeutic agents. For example, in some embodiments, a unit dose of a compound provided herein, or a pharmaceutically acceptable salt thereof, is administered first, followed within seconds or minutes by administration of a unit dose of one or more additional therapeutic agents. Alternatively, in other embodiments, a unit dose of one or more additional therapeutic agents is administered first, followed by administration of a unit dose of a compound provided herein, or a pharmaceutically acceptable salt thereof, within seconds or minutes. In some embodiments, a unit dose of a compound provided herein, or a pharmaceutically acceptable salt thereof, is administered first, followed, after a period of hours (i.e., 1-12 hours), by administration of a unit dose of one or more additional therapeutic agents. In other embodiments, a unit dose of one or more additional therapeutic agents is administered first, followed, after a period of hours (i.e., 1-12 hours), by administration of a unit dose of a compound provided herein or a pharmaceutically acceptable salt thereof.

In some embodiments, a compound of Formula I, or a pharmaceutically acceptable salt thereof, is formulated as a tablet, which may optionally contain one or more other compounds useful for treating the disease being treated. In certain embodiments, the tablet can contain another active ingredient for treating a Retroviridae infection, including an HIV infection. In some embodiments, such tablets are suitable for once daily dosing. In some embodiments, such tablets are suitable for once weekly dosing. In some embodiments, such tablets are suitable for once monthly dosing. In some embodiments, such tablets are suitable for once every two months dosing. In some embodiments, such tablets are suitable for once every three months dosing. In some embodiments, such tablets are suitable for once every six months dosing.

Also provided herein are methods of treatment in which a compound of Formula I, or a tautomer or pharmaceutically acceptable salt thereof, is given to a patient in combination with one or more additional therapeutic agents or therapy. In some embodiments, the total daily dosage of a compound of Formula I, or a tautomer, or a pharmaceutically acceptable salt thereof, may be about 1 to about 500 mg administered in a single dose for a human subject.

HIV Combination Therapy

In the above embodiments, the additional therapeutic agent or agents may be an anti-HIV agent. In some instances, the additional therapeutic agent can be HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, HIV capsid inhibitors, nucleocapsid protein 7 (NCp7) inhibitors, HIV Tat or Rev inhibitors, inhibitors of Tat-TAR-P-TEFb, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T-cell receptors, TCR-T, autologous T-cell therapies, engineered B cells, NK cells), latency reversing agents, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement $C_5a$ receptor antagonists, DNA methyltransferase inhibitor, Fatty acid synthase inhibitor, HIV vif gene modulators, Vif dimerization antagonists, HIV-1 viral infectivity factor inhibitors, HIV-1 Nef modulators, TNF alpha ligand inhibitors, HIV Nef inhibitors, Hck tyrosine kinase modulators, mixed lineage kinase-3 (MLK-3) inhibitors, HIV-1 splicing inhibitors, integrin antagonists, nucleoprotein inhibitors, splicing factor modulators, COMM domain containing protein 1 modulators, HIV ribonuclease H inhibitors, IFN antagonists, retrocyclin modulators, CD3 antagonists, CDK-4 inhibitors, CDK-6 inhibitors, CDK-9 inhibitors, Cytochrome P450 3 inhibitors, CXCR4 modulators, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, HPK1 (MAP4K1) inhibitors, proprotein convertase PC9 stimulators, ATP dependent RNA helicase DDX3X inhibitors, reverse transcriptase priming complex inhibitors, G6PD and NADH-oxidase inhibitors, mTOR complex 1 inhibitors, mTOR complex 2 inhibitors, P-Glycoprotein modulators, RNA polymerase modulators, TAT protein inhibitors, Prolyl endopeptidase inhibitors, Phospholipase A2 inhibitors, pharmacokinetic enhancers, HIV gene therapy, HIV vaccines, anti-HIV peptides, and combinations thereof.

In some embodiments, the additional therapeutic agent or agents are selected from combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In some embodiments, the additional therapeutic agent or agents are chosen from HIV protease inhibitors, HIV non-nucleoside or non-nucleotide inhibitors of reverse transcriptase, HIV nucleoside or nucleotide inhibitors of reverse transcriptase, HIV integrase inhibitors, HIV capsid inhibitors, gp41 inhibitors, CXCR4 inhibitors, gp120 inhibitors, CCR5 inhibitors, Nef inhibitors, latency reversing agents, HIV bNAbs, agonists of TLR7, TLR8, and TLR9, HIV vaccines, cytokines, immune checkpoint inhibitors, FLT3 ligands, T cell and NK cell recruiting bispecific antibodies, chimeric T cell receptors targeting HIV antigens, pharmacokinetic enhancers, and other drugs for treating HIV, and combinations thereof.

In some embodiments, the additional therapeutic agent or agents any are chosen from dolutegravir, cabotegravir, darunavir, bictegravir, elsulfavirine, rilpivirine, and lenacapavir, and combinations thereof.

HIV Combination Drugs

Examples of combination drugs include, but are not limited to, ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; tenofovir analog; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); BIKTARVY® (bictegravir+emtricitabine+tenofovir alafenamide), DOVATO® (dolutegravir+lamivudine), TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine, lopinavir+ritonavir+abacavir+lamivudine, lamivudine, cabotegravir+rilpivirine, 3-BNC117+albuvirtide, elpida (elsulfavirine, VM-1500), and VM-1500A, and dual-target HIV-1 reverse transcriptase/nucleocapsid protein 7 inhibitors.

Other HIV Drugs

Examples of other drugs for treating HIV include, but are not limited to, aspernigrin C, acemannan, alisporivir, Ban-Lec, deferiprone, Gamimune, metenkefalin, naltrexone, Prolastin, REP 9, RPI-MN, VSSP, Hlviral, SB-728-T, 1,5-dicaffeoylquinic acid, rHIV7-shl-TAR-CCR5RZ, AAV-eCD4-Ig gene therapy, MazF gene therapy, BlockAide, bevirimat derivatives, ABBV-382, ABX-464, AG-1105, APH-0812, APH0202, bryostatin-1, bryostatin analogs, BIT-225, BRII-732, BRII-778, CYT-107, CS-TATI-1, fluoro-beta-D-arabinose nucleic acid (FANA)-modified antisense oligonucleotides, FX-101, griffithsin, GSK-3739937, GSK-3739937 (long-acting), HGTV-43, HPH-116, HS-10234, hydroxychloroquine, IMB-10035, IMO-3100, IND-02, JL-18008, LADAVRU, MK-1376, MK-2048, MK-4250, MK-8507, MK-8558, NOV-205, OB-002H, ODE-Bn-TFV, PA-1050040 (PA-040), PC-707, PGN-007, QF-036, S-648414, SCY-635, SB-9200, SCB-719, TR-452, TEV-90110, TEV-90112, TEV-90111, TEV-90113, RN-18, DIACC-1010, Fasnall, Immuglo, 2-CLIPS peptide, HRF-4467, thrombospondin analogs, TBL-1004HI, VG-1177, x1-081, AVI-CO-004, rfhSP-D, [18F]-MC-225, URMC-099-C, RES-529, Verdinexor, IMC-M113V, IML-106, antiviral fc conjugate (AVC), WP-1096, WP-1097, Gammora, ISR-0048, ISR-48, ISR-49, MK-8527, cannabinoids, ENOB-HV-32, HiviCide-I, T-1144, VIR-576, nipamovir, Covimro, and ABBV-1882.

HIV Protease Inhibitors

Examples of HIV protease inhibitors include, but are not limited to, amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, ASC-09+ritonavir, AEBL-2, DG-17, GS-1156, TMB-657 (PPL-100), T-169, BL-008, MK-8122, TMB-607, GRL-02031, and TMC-310911. Additional examples of HIV protease inhibitors are described, e.g., in U.S. Pat. No. 10,294,234, and U.S. Patent Application Publication Nos. US2020030327 and US2019210978.

HIV Gag Protein Inhibitors

Examples of HIV Gag protein inhibitors include, but are not limited to, HRF-10071.

HIV Ribonuclease H Inhibitors

Examples of HIV ribonuclease H inhibitors include, but are not limited to, NSC-727447.

HIV Nef Inhibitors

Examples of HIV Nef inhibitors include, but are not limited to, FP-1.

HIV Reverse Transcriptase Inhibitors

Examples of HIV non-nucleoside or non-nucleotide inhibitors of reverse transcriptase include, but are not limited to, dapivirine, delavirdine, delavirdine mesylate, doravirine, efavirenz, etravirine, lentinan, nevirapine, rilpivirine, ACC-007, ACC-008, AIC-292, F-18, KM-023, PC-1005, M1-TFV, M2-TFV, VM-1500A-LAI, PF-3450074, elsulfavirine (sustained release oral, HIV infection), elsulfavirine (long acting injectable nanosuspension, HIV infection), and elsulfavirine (VM-1500). Additional non-limiting examples of non-nucleoside or non-nucleotide inhibitors of reverse transcriptase include the compounds disclosed in U.S. Pat. No. 10,548,898.

Examples of HIV nucleoside or nucleotide inhibitors of reverse transcriptase include, but are not limited to, adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir octadecyloxyethyl ester (AGX-1009), tenofovir disoproxil hemifumarate, VIDEX® and VIDEX EC® (didanosine, ddl), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, rovafovir etalafenamide (GS-9131), GS-9148, MK-8504, MK-8583, VM-2500, and KP-1461.

Additional examples of HIV nucleoside or nucleotide inhibitors of reverse transcriptase include, but are not limited to, those described in patent publications US2007049754, US2016250215, US2016237062, US2016251347, US2002119443, US2013065856, US2013090473, US2014221356, and WO04096286.

HIV Integrase Inhibitors

Examples of HIV integrase inhibitors include, but are not limited to, elvitegravir, elvitegravir (extended-release microcapsules), curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, PEGylated raltegravir, dolutegravir, JTK-351, bictegravir, AVX-15567, cabotegravir (long acting injectable), diketo quinolin-4-1 derivatives, integrase-LEDGF inhibitor, ledgins, M-522, M-532, MK-0536, NSC-310217, NSC-371056, NSC-48240, NSC-642710, NSC-699171, NSC-699172, NSC-699173, NSC-699174, stilbenedisulfonic acid, T169, STP-0404, VM-3500, XVIR-110, and ACC-017. Additional non-limiting examples of HIV integrase inhibitors include the compounds disclosed in U.S. Pat. No. 11,084,832.

Examples of HIV non-catalytic site, or allosteric, integrase inhibitors (NCINI) include, but are not limited to, CX-05045, CX-05168, and CX-14442.

HIV Viral Infectivity Factor Inhibitors

Examples of HIV viral infectivity factor inhibitors include, but are not limited to, 2-amino-N-(2-methoxyphenyl)-6-((4-nitrophenyl)thio)benzamide derivatives, and Irino-L.

HIV Entry Inhibitors

Examples of HIV entry (fusion) inhibitors include, but are not limited to, AAR-501, LBT-5001, cenicriviroc, CCR5 inhibitors, gp41 inhibitors, CD4 attachment inhibitors, gp120 inhibitors, gp160 inhibitors, and CXCR4 inhibitors.

Examples of CCR5 inhibitors include, but are not limited to, aplaviroc, vicriviroc, maraviroc, maraviroc (long acting injectable nanoemulsion), cenicriviroc, leronlimab (PRO-140), adaptavir (RAP-101), nifeviroc (TD-0232), anti-GP120/CD4 or CCR5 bispecific antibodies, B-07, MB-66, polypeptide $C_{25}P$, TD-0680, thioraviroc and vMIP (Haimipu).

Examples of gp41 inhibitors include, but are not limited to, albuvirtide, enfuvirtide, griffithsin (gp41/gp120/gp160 inhibitor), BMS-986197, enfuvirtide biobetter, enfuvirtide biosimilar, HIV-1 fusion inhibitors (P26-Bapc), ITV-1, ITV-2, ITV-3, ITV-4, CPT-31, Cl3hmAb, lipuvirtide, PIE-12 trimer and sifuvirtide.

Examples of CD4 attachment inhibitors include, but are not limited to, ibalizumab and CADA analogs Examples of gp120 inhibitors include, but are not limited to, anti-HIV microbicide, Radha-108 (receptol) 3B3-PE38, BMS818251, BanLec, bentonite-based nanomedicine, fostemsavir tromethamine, IQP-0831, VVX-004, and BMS-663068.

Examples of gp160 inhibitors include, but are not limited to, fangchinoline.

Examples of CXCR4 inhibitors include, but are not limited to, plerixafor, ALT-1188, N15 peptide, and vMIP (Haimipu).

HIV Maturation Inhibitors

Examples of HIV maturation inhibitors include, but are not limited to, BMS-955176, GSK-3640254 and GSK-2838232.

Latency Reversing Agents

Examples of latency reversing agents include, but are not limited to, toll-like receptor (TLR) agonists (including TLR7 agonists, e.g., GS-9620, TLR8 agonists, and TLR9 agonists), histone deacetylase (HDAC) inhibitors, proteasome inhibitors such as velcade, protein kinase C (PKC) activators, Smyd2 inhibitors, BET-bromodomain 4 (BRD4) inhibitors (such as ZL-0580, apabetalone), ionomycin, IAP antagonists (inhibitor of apoptosis proteins, such as APG-1387, LBW-242), SMAC mimetics (including TL32711, LCL161, GDC-0917, HGS1029, AT-406, Debio-1143), PMA, SAHA (suberanilohydroxamic acid, or suberoyl, anilide, and hydroxamic acid), NIZ-985, IL-15 modulating antibodies (including IL-15, IL-15 fusion proteins, and IL-15 receptor agonists), JQ1, disulfiram, amphotericin B, and ubiquitin inhibitors such as largazole analogs, APH-0812, and GSK-343. Examples of PKC activators include, but are not limited to, indolactam, prostratin, ingenol B, and DAG-lactones.

Additional examples of TLR7 agonists include, but are not limited to, those described in U.S. Patent Application Publication No. US2010143301.

Additional examples of TLR8 agonists include, but are not limited to, those described in U.S. Patent Application Publication No. US2017071944.

Histone Deacetylase (HDAC) Inhibitors

In some embodiments, the agents as described herein are combined with an inhibitor of a histone deacetylase, e.g., histone deacetylase 1, histone deacetylase 9 (HDAC9, HD7, HD7b, HD9, HDAC, HDAC7, HDAC7B, HDAC9B, HDAC9FL, HDRP, MITR; Gene ID: 9734). Examples of HDAC inhibitors include without limitation, abexinostat, ACY-241, AR-42, BEBT-908, belinostat, CKD-581, CS-055 (HBI-8000), CT-101, CUDC-907 (fimepinostat), entinostat, givinostat, mocetinostat, panobinostat, pracinostat, quisinostat (JNJ-26481585), resminostat, ricolinostat, romidepsin, SHP-141, TMB-ADC, valproic acid (VAL-001), vorinostat, tinostamustine, remetinostat, and entinostat.

Capsid Inhibitors

Examples of capsid inhibitors include, but are not limited to, capsid polymerization inhibitors or capsid disrupting compounds, HIV nucleocapsid p7 (NCp7) inhibitors such as azodicarbonamide, HIV p24 capsid protein inhibitors, lenacapavir (GS-6207), GS-CA1, AVI-621, AVI-101, AVI-201, AVI-301, and AVI-CAN1-15 series, PF-3450074, HIV-1 capsid inhibitors (HIV-1 infection, Shandong University), and compounds described in (GSK WO2019/087016).

Additional examples of capsid inhibitors include, but not limited to, those described in U.S. Patent Application Publication Nos. US2018051005 and US2016108030.

Additional examples of HIV capsid inhibitors include, but are not limited to, those described in U.S. Patent Application Publication Nos. US2014221356 and US2016016973.

Cytochrome P450 3 Inhibitors

Examples of Cytochrome P450 3 inhibitors include, but are not limited to, those described in U.S. Pat. No. 7,939,553.

RNA Polymerase Modulators

Examples of RNA polymerase modulators include, but are not limited to, those described in U.S. Pat. Nos. 10,065,958 and 8,008,264.

Immune Checkpoint Modulators

In various embodiments, the agents as described herein, are combined with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of infected cells. Activation or stimulation of stimulatory immune check points can augment the effect of immune checkpoint inhibitors in infective therapeutics. In various embodiments, the immune checkpoint proteins or receptors regulate T cell responses (e.g., reviewed in Xu et al., *J Exp Clin Cancer Res*. (2018) 37:110). In various embodiments, the immune checkpoint proteins or receptors regulate NK cell responses (e.g., reviewed in Davis et al., *Semin Immunol*. (2017) 31:64-75 and Chiossone et al., *Nat Rev Immunol*. (2018) 18(11):671-688).

Examples of immune checkpoint proteins or receptors include without limitation CD27, CD70; CD40, CD40LG; CD47, CD48 (SLAMF2), transmembrane and immunoglobulin domain containing 2 (TMIGD2, CD28H), CD84 (LY9B, SLAMFS), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell costimulator (ICOS, CD278); inducible T cell costimulator ligand (ICOSLG, B7H2); TNF receptor superfamily member 4 (TNFRSF4, OX40); TNF superfamily member 4

(TNFSF4, OX4OL); TNFRSF8 (CD30), TNFSF8 (CD3OL); TNFRSF10A (CD261, DR4, TRAILR1), TNFRSF9 (CD137), TNFSF9 (CD137L); TNFRSF1OB (CD262, DRS, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript lE (RAET1E; ULBP4); retinoic acid early transcript 1G (RAET1G; ULBP5); retinoic acid early transcript 1L (RAET1L; ULBP6); lymphocyte activating 3 (CD223); killer cell immunoglobulin like receptor, three Ig domains and long cytoplasmic tail 1 (KIR, CD158E1); killer cell lectin like receptor $C_1$ (KLRC1, NKG2A, CD159A); killer cell lectin like receptor K1 (KLRK1, NKG2D, CD314); killer cell lectin like receptor $C_2$ (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); SLAM family member 7 (SLAMF7); and Hematopoietic Progenitor Kinase 1 (HPK1, MAP4K1).

In various embodiments, the agents described herein are combined with one or more blockers or inhibitors of one or more T-cell inhibitory immune checkpoint proteins or receptors. Illustrative T-cell inhibitory immune checkpoint proteins or receptors include without limitation CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In various embodiments, the agents, as described herein, are combined with one or more agonist or activators of one or more T-cell stimulatory immune checkpoint proteins or receptors. Illustrative T-cell stimulatory immune checkpoint proteins or receptors include without limitation CD27, CD70; CD40, CD4OLG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX4OL); TNFRSF9 (CD137), TNFSF9 (CD137L); TNFRSF18 (GITR), TNF SF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu et al., *J Exp Clin Cancer Res.* (2018) 37:110.

In various embodiments, the agents as described herein, are combined with one or more blockers or inhibitors of one or more NK-cell inhibitory immune checkpoint proteins or receptors. Illustrative NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor $C_1$ (KLRC1, NKG2A, CD159A); and killer cell lectin like receptor D1 (KLRD1, CD94). In various embodiments, the agents as described herein, are combined with one or more agonist or activators of one or more NK-cell stimulatory immune checkpoint proteins or receptors. Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); SLAM family member 7 (SLAMF7). See, e.g., Davis et al., *Semin Immunol.* (2017) 31: 64-75; Fang et al., *Semin Immunol.* (2017) 31: 37-54; and Chiossone et al., *Nat Rev Immunol.* (2018) 18(11):671-688.

In some embodiments, the one or more immune checkpoint inhibitors comprises a proteinaceous (e.g., antibody or fragment thereof, or antibody mimetic) inhibitor of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4. In some embodiments, the small molecule inhibitor of CD274 or PDCD1 is selected from the group consisting of GS-4224, GS-4416, INCB086550 and MAX10181. In some embodiments, the small molecule inhibitor of CTLA4 comprises BPI-002.

Examples of inhibitors of CTLA4 that can be co-administered include without limitation ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BPI-002, as well as multi-specific inhibitors FPT- 155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of PD-L1 (CD274) or PD-1 (PDCD1) that can be co-administered include without limitation pembrolizumab, nivolumab, cemiplimab, pidilizumab, AMP-224, MEDI0680 (AMP-514), spartalizumab, atezolizumab, avelumab, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181(budigalimab), PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, GS-4224, GS-4416, INCB086550, MAX10181, as well as multispecific inhibitors FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1).

In various embodiments, the agents as described herein are combined with anti-TIGIT antibodies, such as BMS-986207, RG-6058, and AGEN-1307.

TNF Receptor Superfamily (TNFRSF) Member Agonists or Activators

In various embodiments, the agents as described herein are combined with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Examples of anti-TNFRSF4 (OX40) antibodies that can be co-administered include without limitation, MEDI6469, MEDI6383, MEDI0562 (tavolixizumab), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

Examples of anti-TNFRSF5 (CD40) antibodies that can be co-administered include without limitation RG7876, SEA-CD40, APX-005M and ABBV-428.

In some embodiments, the anti-TNFRSF7 (CD27) antibody varlilumab (CDX-1127) is co-administered.

Examples of anti-TNFRSF9 (4-1BB, CD137) antibodies that can be co-administered include without limitation urelumab, utomilumab (PF-05082566), AGEN2373 and ADG-106.

Examples of anti-TNFRSF18 (GITR) antibodies that can be co-administered include without limitation, MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Bi- and Tri-Specific Natural Killer (NK)-Cell Engagers

In various embodiments, the agents as described herein, are combined with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB). As appropriate, the anti-CD16 binding bi-specific molecules may or may not have an Fc. Illustrative bi-specific NK-cell engagers that can be co-administered target CD16 and one or more HIV-associated antigens as described herein. BiKEs and TriKEs are described, e.g., in Felices et al., *Methods Mol Biol.* (2016) 1441:333-346; Fang et al., *Semin Immunol.* (2017) 31:37-54. Examples of trispecific NK cell engagers (TRiKE) include, but are not limited to, OXS-3550, HIV-TriKE, and CD16-IL-15-B7H3 TriKE.

Indoleamine-Pyrrole-2,3-Dioxygenase (ID01) Inhibitors

In various embodiments, the agents as described herein are combined with an inhibitor of indoleamine 2,3-dioxygenase 1 (ID01; NCBI Gene ID: 3620). Examples of IDOL inhibitors include without limitation, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, shIDO-ST, EOS-200271, KHK-2455, and LY-3381916.

Toll-Like Receptor (TLR) Agonists

In various embodiments, the agents as described herein are combined with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists that can be co-administered include without limitation AL-034, DSP-0509, GS-9620 (vesatolimod), vesatolimod analog, LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7854, RG-7795, and the compounds disclosed in US20100143301 (Gilead Sciences), US20110098248

(Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). TLR7/TLR8 agonists include without limitation NKTR-262, telratolimod and BDB-001. TLR8 agonists include without limitation E-6887, IMO-4200, IMO-8400, IMO-9200, MCT-465, MEDI-9197, motolimod, resiquimod, GS-9688, VTX-1463, VTX-763, 3M-051, 3M-052, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). TLR9 agonists include without limitation AST-008, cobitolimod, CMP-001, IMO-2055, IMO-2125, S-540956, litenimod, MGN-1601, BB-001, BB-006, IMO-3100, IMO-8400, IR-103, IMO-9200, agatolimod, DIMS-9054, DV-1079, DV-1179, AZD-1419, lefitolimod (MGN-1703), CYT-003, CYT-003-QbG10, tilsotolimod and PUL-042. Examples of TLR3 agonist include rintatolimod, poly-ICLC, RIBOXXON®, Apoxxim, RIBOXXIM®, IPH-33, MCT-465, MCT-475, and ND-1.1. TLR4 agonists include, but are not limited to, G-100 and GSK-1795091.

CDK Inhibitors or Antagonists

In some embodiments, the agents described herein are combined with an inhibitor or antagonist of CDK. In some embodiments, the CDK inhibitor or antagonist is selected from the group consisting of VS2-370.

STING Agonists, RIG-I and NOD2 Modulators

In some embodiments, the agents described herein are combined with a stimulator of interferon genes (STING). In some embodiments, the STING receptor agonist or activator is selected from the group consisting of ADU-S100 (MIW-815), SB-11285, MK-1454, SR-8291, AdVCA0848, GSK-532, SYN-STING, MSA-1, SR-8291, STING agonist (latent HIV), 5,6-dimethylxanthenone-4-acetic acid (DMXAA), cyclic-GAMP (cGAMP) and cyclic-di-AMP. In some embodiments, the agents described herein are combined with a RIG-I modulator such as RGT-100, or NOD2 modulator, such as SB-9200, and IR-103.

LAG-3 and TIM-3 Inhibitors

In certain embodiments, the agents as described herein are combined with an anti-TIM-3 antibody, such as TSR-022, LY-3321367, MBG-453, INCAGN-2390.

In certain embodiments, the antibodies or antigen-binding fragments described herein are combined with an anti LAG-3 (Lymphocyte-activation) antibody, such as relatlimab (ONO-4482), LAG-525, MK-4280, REGN-3767, INCAGN2385.

Interleukin Agonists

In certain embodiments, the agents described herein are combined with an interleukin agonist, such as IL-2, IL-7, IL-15, IL-10, IL-12 agonists; examples of IL-2 agonists such as proleukin (aldesleukin, IL-2); BC-IL (Cel-Sci), pegylated IL-2 (e.g., NKTR-214); modified variants of IL-2 (e.g., THOR-707), bempegaldesleukin, AIC-284, ALKS-4230, CUI-101, Neo-2/15; examples of IL-15 agonists, such as ALT-803, NKTR-255, and hetIL-15, interleukin-15/Fc fusion protein, AM-0015, NIZ-985, SO—$C_{101}$, IL-15 Synthorin (pegylated Il-15), P-22339, and a IL-15-PD-1 fusion protein N-809; examples of IL-7 include without limitation CYT-107.

Examples of additional immune-based therapies that can be combined with an agent of this disclosure include, but are not limited to, interferon alfa, interferon alfa-2b, interferon alfa-n3, pegylated interferon alfa, interferon gamma; FLT3 agonists such as CDX-301, GS-3583, gepon, normferon, peginterferon alfa-2a, peginterferon alfa-2b, and RPI-MN.

Phosphatidylinositol 3-kinase (PI3K) Inhibitors

Examples of PI3K inhibitors include, but are not limited to, idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

alpha-4/beta-7 Antagonists

Examples of Integrin alpha-4/beta-7 antagonists include, but are not limited to, PTG-100, TRK-170, abrilumab, etrolizumab, carotegrast methyl, and vedolizumab.

HPK1 Inhibitors

Examples of HPK1 inhibitors include, but are not limited to, ZYF-0272, and ZYF-0057.

HIV Targeting Antibodies

Examples of HIV antibodies, bispecific antibodies, and "antibody-like" therapeutic proteins include, but are not limited to, DARTs®, DUOBODIES®, BITES®, XmAbs®, TandAbs®, Fab derivatives, bNAbs (broadly neutralizing HIV-1 antibodies), TMB-360, TMB-370, and those targeting HIV gp120 or gp41, antibody-Recruiting Molecules targeting HIV, anti-CD63 monoclonal antibodies, anti-GB virus C antibodies, anti-GP120/CD4, gp120 bispecific monoclonal antibody, CCR5 bispecific antibodies, anti-Nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), PGT121.414.LS, ibalizumab, ibalizumab (second generation), Immuglo, MB-66, clone 3 human monoclonal antibody targeting KLIC (HIV infection), GS-9721, BG-HIV, VRC-HIVMAB091-00-AB.

Various bNAbs may be used. Examples include, but are not limited to, those described in U.S. Pat. Nos. 8,673,307, 9,493,549, 9,783,594, 10,239,935, US2018371086, US2020223907, WO2014/063059, WO2012/158948, WO2015/117008, and PCT/US2015/41272, and WO2017/096221, including antibodies 12A12, 12A21, NIH45-46, bANC131, 8ANC134, IB2530, INC9, 8ANC195. 8ANC196, 10-259, 10-303, 10-410, 10-847, 10-996, 10-1074, 10-1121, 10-1130, 10-1146, 10-1341, 10-1369, and 10-1074GM. Additional examples include those described in Klein et al., *Nature,* 492(7427): 118-22 (2012), Horwitz et al., *Proc Natl Acad Sci USA*, 110(41): 16538-43 (2013), Scheid et al., *Science*, 333: 1633-1637 (2011), Scheid et al., *Nature*, 458:636-640 (2009), Eroshkin et al, *Nucleic Acids Res.*, 42 (Database issue):D1 133-9 (2014), Mascola et al., *Immunol Rev.*, 25-((1):225-44 (2013), such as 2F5, 4E10, M66.6, CAP206-CH12, 10E81 (all of which bind the MPER of gp41); PG9, PG16, CH01-04 (all of which bind V1V2-glycan), 2G12 (which binds to outer domain glycan); b12, HJ16, CH103-106, VRC01-03, VRC-PG04, 04b, VRC-CH30-34, 3BNC62, 3BNC89, 3BNC91, 3BNC95, 3BNC104, 3BNC176, and 8ANC131 (all of which bind to the CD4 binding site).

Additional broadly neutralizing antibodies that can be used as a second therapeutic agent in a combination therapy are described, e.g., in U.S. Pat. Nos. 8,673,307; 9,493,549; 9,783,594; and WO 2012/154312; WO2012/158948; WO 2013/086533; WO 2013/142324; WO2014/063059; WO 2014/089152, WO 2015/048462; WO 2015/103549; WO 2015/117008; WO2016/014484; WO 2016/154003; WO 2016/196975; WO 2016/149710; WO2017/096221; WO 2017/133639; WO 2017/133640, which are hereby incorporated herein by reference in their entireties for all purposes. Additional examples include, but are not limited to, those described in Sajadi et al., Cell. (2018) 173(7):1783-1795; Sajadi et al., J Infect Dis. (2016) 213(1):156-64; Klein et al., Nature, 492(7427): 118-22 (2012), Horwitz et al., Proc Natl Acad Sci USA, 110(41): 16538-43 (2013), Scheid et al., Science, 333: 1633-1637 (2011), Scheid et al., Nature, 458:636-640 (2009), Eroshkin et al., Nucleic Acids Res., 42 (Database issue):D1 133-9 (2014), Mascola et al., Immunol Rev., 25-((1):225-44 (2013), such as 2F5, 4E10, M66.6, CAP206-CH12, 10E8, 10E8v4, 10E8-5R-100cF, DH511.11P, 7b2, 10-1074, and LN01 (all of which bind the MPER of gp41).

Examples of additional antibodies include, but are not limited to, bavituximab, UB-421, BF520.1, BiIA-SG, CHO1, CH59, C2F5, C₄E10, C2F5+C₂G12+C4E10, CAP256V2LS, 3BNC117, 3BNC117-LS, 3BNC60, DH270.1, DH270.6, D1D2, 10-1074-LS, C₁₃hmAb, GS-9722 (elipovimab), DH411-2, BG18, GS-9721, GS-9723, PGT145, PGT121, PGT-121.60, PGT-121.66, PGT122, PGT-123, PGT-124, PGT-125, PGT-126, PGT-151, PGT-130, PGT-133, PGT-134, PGT-135, PGT-128, PGT-136, PGT-137, PGT-138, PGT-139, MDX010 (ipilimumab), DH511, DH511-2, N6, N6LS, N49P6, N49P7, N49P7.1, N49P9, N49P11, N60P1.1, N60P25.1, N60P2.1, N60P31.1, N60P22, NIH 45-46, PGC14, PGG14, PGT-142, PGT-143, PGT-144, PGDM1400, PGDM12, PGDM21, PCDN-33A, 2Dm2m, 4Dm2m, 6Dm2m, PGDM1400, MDX010 (ipilimumab), VRC01, VRC-01-LS, A32, 7B2, 10E8, VRC-07-523, VRC07-523LS, VRC24, VRC41.01, 10E8VLS, 3810109, 10E8v4, IMC-HIV, iMabm36, eCD4-Ig, IOMA, CAP256-VRC26.25, DRVIA7,VRC-HIVMAB080-00-AB, VRC-HIVMAB060-00-AB, P2G12, VRC07, 354BG8, 354BG18, 354BG42, 354BG33, 354BG129, 354BG188, 354BG411, 354BG426, VRC29.03, CAP256, CAP256-VRC26.08, CAP256-VRC26.09, CAP256-VRC26.25, PCT64-24E and VRC38.01, PGT-151, CAP248-2B, 35022, ACS202, VRC34 and VRC34.01, 10E8, 10E8v4, 10E8-5R-100cF, 4E10, DH511.11P, 2F5, 7b2, and LN01.

Examples of HIV bispecific and trispecific antibodies include without limitation MGD014, B12BiTe, BiIA-SG, TMB-bispecific, SAR-441236, VRC-01/PGDM-1400/10E8v4, 10E8.4/iMab, 10E8v4/PGT121-VRC01.

Examples of in vivo delivered bNAbs include without limitation AAV8-VRC07; mRNA encoding anti-HIV antibody VRC01; and engineered B-cells encoding 3BNC117 (Hartweger et al., *J. Exp. Med.* 2019, 1301).

Pharmacokinetic Enhancers

Examples of pharmacokinetic enhancers include, but are not limited to, cobicistat and ritonavir.

Additional Therapeutic Agents

Examples of additional therapeutic agents include, but are not limited to, the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

HIV Vaccines

Examples of HIV vaccines include, but are not limited to, peptide vaccines, recombinant subunit protein vaccines, live vector vaccines, DNA vaccines, HIV MAG DNA vaccine, CD4-derived peptide vaccines, vaccine combinations, adenoviral vector vaccines (an adenoviral vector such as Ad5, Ad26 or Ad35), simian adenovirus (chimpanzee, gorilla, rhesus i.e. rhAd), adeno-associated virus vector vaccines, Chimpanzee adenoviral vaccines (e.g., ChAdOX1, ChAd68, ChAd3, ChAd63, ChAd83, ChAd155, ChAd157, PanS, Pan6, Pan7, Pan9), Coxsackieviruses based vaccines, enteric virus based vaccines, Gorilla adenovirus vaccines, lentiviral vector based vaccine, arenavirus vaccines (such as LCMV, Pichinde), bi-segmented or tri-segmented arenavirus based vaccine, trimer-based HIV-1 vaccine, measles virus based vaccine, flavivirus vector based vaccines, tobacco mosaic virus vector based vaccine, Varicella-zoster virus based vaccine, Human parainfluenza virus 3 (PIV3) based vaccines, poxvirus based vaccine (modified vaccinia virus Ankara (MVA), orthopoxvirus-derived NYVAC, and avipoxvirus-derived ALVAC (canarypox virus) strains); fowlpox virus based vaccine, rhabdovirus-based vaccines, such as VSV and marabavirus; recombinant human CMV (rhCMV) based vaccine, alphavirus-based vaccines, such as semliki forest virus, venezuelan equine encephalitis virus and sindbis virus; (see Lauer, Clinical and Vaccine Immunology, 2017, DOI: 10.1128/CVI.00298-16); LNP formulated mRNA based therapeutic vaccines; LNP-formulated self-replicating RNA/self-amplifying RNA vaccines.

Examples of vaccines include: AAVLP-HIV vaccine, AE-298p, anti-CD40.Env-gp140 vaccine, Ad4-EnvC150, BG505 SOSIP.664 gp140 adjuvanted vaccine, BG505 SOSIP.GT1.1 gp140 adjuvanted vaccine, ChAdOx1.tHIVconsv1 vaccine, CMV-MVA triplex vaccine, ChAdOx1.HTI, Chimigen HIV vaccine, ConM SOSIP.v7 gp140, ALVAC HIV (vCP1521), AIDSVAX B/E (gp120), monomeric gp120 HIV-1 subtype C vaccine, MPER-656 liposome subunit vaccine, Remune, ITV-1, Contre Vir, Ad5-ENVA-48, DCVax-001 (CDX-2401), Vacc-4x, Vacc-05, VAC-3S, multiclade DNA recombinant adenovirus-5 (rAd5), rAd5 gag-pol env A/B/C vaccine, Pennvax-G, Pennvax-GP, Pennvax-G/MVA-CMDR, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multiHIV (FIT-06), ChAdV63.HIVconsv, gp140 [delta]V2.TV1+MF-59, rVSVIN HIV-1 gag vaccine, SeV-EnvF, SeV-Gag vaccine, AT-20, DNK-4, ad35-Grin/ENV, TBC-M4, HIVAX, HIVAX-2, N123-VRC-34.01 inducing epitope-based HIV vaccine, NYVAC-HIV-PT1, NYVAC-HIV-PT4, DNA-HIV-PT123, rAAV1-PG9DP, GOVX-B11, GOVX-B21, GOVX-055, TVI-HIV-1, Ad-4 (Ad4-env Clade C+Ad4-mGag), Paxvax, EN41-UGR7C, EN41-FPA2, ENOB-HV-11, ENOB-HV-12, PreVaxTat, AE-H, MYM-V101, CombiHlVvac, ADVAX, MYM-V201, MVA-CMDR, MagaVax, DNA-Ad5 gag/pol/nef/nev (HVTN505), MVATG-17401, ETV-01, CDX-1401, DNA and Sev vectors vaccine expressing SCaVII, rcAD26.MOS1.HIV-Env, Ad26.Mod.HIV vaccine, Ad26.Mod.HIV+MVA mosaic vaccine+gp140, AGS-004, AVX-101, AVX-201, PEP-6409, SAV-001, ThV-01, TL-01, TUTI-16, VGX-3300, VIR-1111, IHV-001, and virus-like particle vaccines such as pseudovirion vaccine, CombiVlCHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines (such as DermaVir), gag-based DNA vaccine, GI-2010, gp41 HIV-1 vaccine, HIV vaccine (PIKA adjuvant), i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, rgp160 HIV vaccine, RNActive HIV vaccine, SCB-703, Tat Oyi vaccine, TBC-M4, UBI HIV gp120, Vacc-4x+romidepsin, variant gp120 polypeptide vaccine, rAd5 gag-pol env A/B/C vaccine, DNA.HTI and MVA.HTI, VRC-HIVDNA016-00-VP+VRC-HIVADV014-00-VP, INO-6145, JNJ-9220, gp145 C.6980; eOD-GT8 60mer based vaccine, PD-201401, env (A, B, C, A/E)/gag (C) DNA Vaccine, gp120 (A,B,C,A/E) protein vaccine, PDPHV-201401, Ad4-EnvCN54, EnvSeq-1 Envs HIV-1 vaccine (GLA-SE adjuvanted), HIV p24gag prime-boost plasmid DNA vaccine, HIV-1 iglb12 neutralizing VRC-01 antibody-stimulating anti-CD4 vaccine, arenavirus vector-based vaccines (Vaxwave, TheraT), MVA-BN HIV-1 vaccine regimen, mRNA based prophylactic vaccines, VPI-211, multimeric HIV gp120 vaccine (Fred Hutchinson cancer center), TBL-1203HI, CH505 TF chTrimer, CD40.HIVRI.Env vaccine, Drep-HIV-PT-1, mRNA-1644, and mRNA-1574.

Birth Control (Contraceptive) Combination Therapy

In certain embodiments, the agents described herein are combined with a birth control or contraceptive regimen. Therapeutic agents used for birth control (contraceptive) that can be combined with an agent of this disclosure include without limitation cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

In a particular embodiment, a compound disclosed herein, or a pharmaceutically acceptable salt thereof, is combined with one, two, three, or four additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+ FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); BIKTARVY (bictegravir+emtricitabine+tenofovir alafenamide), adefovir; adefovir dipivoxil; cobicistat; emtricitabine; tenofovir; tenofovir alafenamide and elvitegravir; tenofovir alafenamide+elvitegravir (rectal formulation, HIV infection); tenofovir disoproxil;

tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; PEGylated raltegravir; raltegravir and lamivudine; lamivudine+lopinavir+ritonavir+abacavir; maraviroc; tenofovir+emtricitabine+maraviroc, enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In some embodiments, an agent disclosed herein, or a pharmaceutical composition thereof, is combined with an HIV nucleoside or nucleotide inhibitor of reverse transcriptase and an HIV non-nucleoside inhibitor of reverse transcriptase. In another specific embodiment, an agent disclosed herein, or a pharmaceutical composition thereof, is combined with an HIV nucleoside or nucleotide inhibitor of reverse transcriptase, and an HIV protease inhibiting compound. In an additional embodiment, an agent disclosed herein, or a pharmaceutical composition thereof, is combined with an HIV nucleoside or nucleotide inhibitor of reverse transcriptase, an HIV non-nucleoside inhibitor of reverse transcriptase, and a pharmacokinetic enhancer. In certain embodiments, an agent disclosed herein, or a pharmaceutical composition thereof, is combined with at least one HIV nucleoside inhibitor of reverse transcriptase, an integrase inhibitor, and a pharmacokinetic enhancer. In another embodiment, an agent disclosed herein, or a pharmaceutical composition thereof, is combined with two HIV nucleoside or nucleotide inhibitors of reverse transcriptase.

In another embodiment, an agent disclosed herein, or a pharmaceutical composition thereof, is combined with a first additional therapeutic agent chosen from dolutegravir, cabotegravir, darunavir, bictegravir, elsulfavirine, rilpivirine, and lenacapavir and a second additional therapeutic agent chosen from emtricitabine and lamivudine.

In some embodiments, an agent disclosed herein, or a pharmaceutical composition thereof, is combined with a first additional therapeutic agent (a contraceptive) selected from the group consisting of cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

Gene Therapy and Cell Therapy

In certain embodiments, the agents described herein are combined with a gene or cell therapy regimen. Gene therapy and cell therapy include without limitation the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection. Examples of cell therapy include without limitation LB-1903, ENOB-HV-01, ENOB-HV-21, ENOB-HV-31, GOVX-BO1, HSPCs overexpressing ALDH1 (LV-800, HIV infection), AGT103-T, and SupT1 cell based therapy. Examples of dendritic cell therapy include without limitation AGS-004. CCR5 gene editing agents include without limitation SB-728T, SB-728-HSPC. CCR5 gene inhibitors include without limitation Cal-1, and lentivirus vector CCR5 shRNA/TRIM5alpha/TAR decoy-transduced autologous CD34-positive hematopoietic progenitor cells (HIV infection/HIV-related lymphoma). In some embodiments, $C_{34}$-CCR5/$C_{34}$-CXCR4 expressing CD4-positive T-cells are co-administered with one or more multi-specific antigen binding molecules. In some embodiments, the agents described herein are co-administered with AGT-103-transduced autologous T-cell therapy or AAV-eCD4-Ig gene therapy.

Gene Editors

In certain embodiments, the agents described herein are combined with a gene editor, e.g., an HIV targeted gene editor. In various embodiments, the genome editing system can be selected from the group consisting of: a CRISPR/Cas9 complex, a zinc finger nuclease complex, a TALEN complex, a homing endonucleases complex, and a meganuclease complex. An illustrative HIV targeting CRISPR/Cas9 system includes without limitation EBT-101.

CAR-T Cell Therapy

In some embodiments, the agents described herein can be co-administered with a population of immune effector cells engineered to express a chimeric antigen receptor (CAR), wherein the CAR comprises an HIV antigen binding domain. The HIV antigen include an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T-cell or an NK cell. In some embodiments, the T-cell is a CD4+T-cell, a CD8+T-cell, or a combination thereof. Cells can be autologous or allogeneic. Examples of HIV CAR-T include A-1801, A-1902, convertible CAR-T, VC-CAR-T, CMV-N6-CART, anti-HIV duoCAR-T, anti-CD4 CART-cell therapy, CD4 CAR+C34-CXCR4+CCR5 ZFN T-cells, dual anti-CD4 CART-T cell therapy (CD4 CAR+C34-CXCR4 T-cells), anti-CD4 MicAbody antibody+anti-MicAbody CAR T-cell therapy (iNKG2D CAR, HIV infection), GP-120 CAR-T therapy, autologous hematopoietic stem cells genetically engineered to express a CD4 CAR and the C46 peptide.

TCR T-cell Therapy

In certain embodiments, the agents described herein are combined with a population of TCR-T-cells. TCR-T-cells are engineered to target HIV derived peptides present on the surface of virus-infected cells, for example, ImmTAV.

B-cell Therapy

In certain embodiments, the antibodies or antigen-binding fragments described herein are combined with a population of B cells genetically modified to express broadly neutralizing antibodies, such as 3BNC117 (Hartweger et al., *J. Exp. Med.* 2019, 1301, Moffett et al., Sci. *Immunol.* 4, eaax0644 (2019) 17 May 2019.

A compound as disclosed herein (e.g., any compound of Formula I) may be combined with one, two, three, or four additional therapeutic agents in any dosage amount of the compound of Formula I (e.g., from 1 mg to 500 mg of compound).

In one embodiment, kits comprising a compound disclosed herein, or a pharmaceutically acceptable salt thereof, in combination with one or more (e.g., one, two, three, one or two, or one to three) additional therapeutic agents are provided.

In one embodiment, the additional therapeutic agent or agents of the kit is an anti-HIV agent, selected from HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T cell receptors, TCR-T, autologous T cell therapies), compounds that target the HIV capsid, latency reversing agents, HIV bNAbs, immune-based therapies, phosphatidylinositol 3-kinase (PI3K) inhibitors, HIV antibodies, broadly neutralizing HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement $C_5a$ receptor antagonists, DNA methyltransferase inhibitor, HIV vif gene modulators, Vif dimerization antagonists, HIV viral infectivity factor inhibitors, TAT protein inhibitors, HIV Nef modulators, Hck tyrosine kinase modulators, mixed lineage kinase-3 (MLK-3) inhibitors, HIV splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent or agents of the kit are selected from combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In a specific embodiment, the kit includes a compound disclosed herein, or a pharmaceutically acceptable salt thereof, and an HIV nucleoside or nucleotide inhibitor of reverse transcriptase. In a specific embodiment, the kit includes a compound disclosed herein, or a pharmaceutically acceptable salt thereof, and an HIV nucleoside or nucleotide inhibitor of reverse transcriptase and an HIV non-nucleoside inhibitor of reverse transcriptase. In another specific embodiment, the kit includes a compound disclosed herein, or a pharmaceutically acceptable salt thereof, and an HIV nucleoside or nucleotide inhibitor of reverse transcriptase, and an HIV protease inhibiting compound. In an additional embodiment, the kit includes a compound disclosed herein, or a pharmaceutically acceptable salt thereof, an HIV nucleoside or nucleotide inhibitor of reverse transcriptase, an HIV non-nucleoside inhibitor of reverse transcriptase, and a pharmacokinetic enhancer. In certain embodiments, the kit includes a compound disclosed herein, or a pharmaceutically acceptable salt thereof, at least one HIV nucleoside inhibitor of reverse transcriptase, an integrase inhibitor, and a pharmacokinetic enhancer. In another embodiment, the kit includes a compound disclosed herein, or a pharmaceutically acceptable salt thereof, and two HIV nucleoside or nucleotide inhibitors of reverse transcriptase. In a specific embodiment, the kit includes a compound disclosed herein, or a pharmaceutically acceptable salt thereof, an HIV nucleoside or nucleotide inhibitor of reverse transcriptase and an HIV capsid inhibitor. In a specific embodiment, the kit includes a compound disclosed herein, or a pharmaceutically acceptable salt thereof, an HIV nucleoside inhibitor of reverse transcriptase and an HIV capsid inhibitor. In a specific embodiment, the kit includes a compound disclosed herein, or a pharmaceutically acceptable salt thereof, and an HIV capsid inhibitor. In a specific embodiment, the kit includes a compound disclosed herein, or a pharmaceutically acceptable salt thereof, and one, two, three or four HIV bNAbs. In a specific embodiment, the kit includes a compound disclosed herein, or a pharmaceutically acceptable salt thereof, one, two, three or four HIV bNAbs and an HIV capsid inhibitor. In a specific embodiment, the kit includes a compound disclosed herein, or a pharmaceutically acceptable salt thereof, one, two, three or four HIV bNAbs, an HIV capsid inhibitor, and an HIV nucleoside inhibitor of reverse transcriptase.

HIV Long acting Therapy

Examples of drugs that are being developed as long acting regimens include, but are not limited to, cabotegravir, rilpivirine, any integrase LA, VM-1500 LAI, maraviroc (LAI), tenofovir implant, doravirine, raltegravir, and long acting dolutegravir.

VII. Compound Preparation

Some embodiments of the present disclosure are directed to processes and intermediates useful for preparing the compounds provided herein or pharmaceutically acceptable salts thereof.

Compounds described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography.

During any of the processes for preparation of the compounds provided herein, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4$^{th}$ ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used. Isolation of final compounds can be performed by various methods known to those skilled in the art but is optimally reverse phase HPLC followed by lyophilization from various organic solvents. Repeated lyophilization can optionally be performed to reduce the amount of residual acidic modifiers resulting from the purification process. In some embodiments, the final compounds provided herein were isolated as mono- or bis-trifluoroacetic acid salts.

The methods of the present disclosure generally provide a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or diastereomerically pure.

Representative syntheses of compounds of the present disclosure are described in the schemes below, and the particular examples that follow.

| List of Abbreviations and Acronyms | |
|---|---|
| Abbreviation/Acronym | Meaning |
| 1,2-EDT | 1,2-ethanedithiol |
| Ac | Acetate |
| ACN or MeCN | Acetonitrile |
| AcOH | Acetic acid |
| aq. | Aqueous |
| Ar | Argon |
| atm | atmospheric pressure |
| Bn | Benzyl |
| BnBr | Benzyl bromide |
| BnOH | Benzyl alcohol |
| Boc | Tert-butyloxycarbonyl |
| Boc$_2$O | Di-tert-butyl dicarbonate |
| br s | broad singlet |
| bu | butyl |
| Bu$_4$N | Tetrabutylammonium |
| C | Celsius |
| CH$_2$N$_4$ | 1-H-tetrazole |
| COMU | (1-Cyano-2-ethoxy-2-oxoethylidenaminooxy)dimethylamino-morpholino-carbenium hexafluorophosphate |
| d | doublet |
| DBDMH | 1,3-dibromo-5,5-dimethylhydantoin |
| DCE | 1,2-dichloroethane |
| DCM | Dichloromethane |
| dd | doublet of doublets |
| ddd | doublet of doublet of doublets |
| ddt | doublet of doublet of triplets |
| DIEA or DIPEA | N,N-diisopropylethylamine |
| DMAc | N,N-dimethylacetamide |
| DMAP | 4-dimethylaminopyridine |
| DME | 1,2-dimethoxyethane |
| DMF | N,N-Dimethylformamide |
| DMSO | Dimethylsulfoxide |
| dppe | 1,2-bis(diphenylphosphino)ethane |
| dq | doublet of quartets |
| dt | doublet of triplets |
| dtt | doublet of triplet of triplets |
| EDC | N-(3-Dimethylaminopropyl)-N'-ethylcarbodiimide hydrochloride |
| EDTA | ethylenediamine tetraacetic acid |
| equiv | equivalent |
| ESI | Electrospray ionization |
| Et | Ethyl |
| Et$_3$N | Triethylamine |

-continued

List of Abbreviations and Acronyms

| Abbreviation/Acronym | Meaning |
| --- | --- |
| EtOAc | Ethyl acetate |
| g | gram |
| (g) | gaseous |
| Gly | glycine |
| h or hr(s) | Hour(s) |
| H | hydrogen |
| HATU | 1-[Bis(dimethylamino)methylene]-1H-1,2,3-triazolo[4,5-b]pyridiunium 3-oxide hexafluorophosphate |
| HBpin | pinacolborane or 4,4,5,5-tetratmethyl-1,3,2-dioxaborolane |
| HPLC | High pressure liquid chromatography |
| Hz | hertz |
| i-Pr or $^i$Pr or iPr | Isopropyl |
| [Ir(cod)Cl]$_2$ | 1,5-cyclooctadiene-iridium(I) chloride dimer |
| LCMS | Liquid chromatography mass spectrometry |
| Lys | lysine |
| m | multiplet |
| M | molarity |
| Me | Methyl |
| MEK | Methyl ethyl ketone |
| MeOH | Methanol |
| MeSO$_3$H/MsOH | Methanesulfonic acid |
| MeTHF or 2-MeTHF | 2-methyltetrahydrofuran |
| MHz | megahertz |
| min or mins | minute |
| μg | microgram |
| μl or μL | microliter |
| μM | micromolar |
| ml or mL | milliliter |
| mmol | millimole |
| Moc | methoxycarbonyl |
| MS | Mass spectrometry |
| MsCl | Methanesulfonyl chloride |
| m/z | Mass to charge ratio |
| N | normal |
| n-bu | normal butyl |
| NaOAc | Sodium acetate |
| nM | nanomolar |
| NMR | Nuclear magnetic resonance spectroscopy |
| NMM | 4-methylmorpholine |
| NMI | 1-methylimidazole |
| OMs | Methanesulfonate |
| OTs | para-toluenesulfonate |
| PBS | phosphate buffered saline |
| Pd/C | palladium on carbon |
| Pd(dba)$_2$ | bis(dibenzylideneacetone)palladium(0) |
| Pd$_2$(dba)$_3$] | tris(dibenzylideneacetone)dipalladium(0) |
| Pd(dppf)Cl$_2$ | [1,1'-bis(diphenylphosphino)ferrocene]dichloropalladium(II) |
| Pd(OAc)$_2$ | palladium(II) acetate |
| pH | potential of hydrogen |
| PhG | α-Phenylglycine |
| PhMe | Toluene |
| PPm | parts per million |
| q | quartet |
| Qphos | pentaphenyl(di-tert-butylphosphino)ferrocene |
| Ra-Ni | Raney nickel |
| RBF | Round-bottom flask |
| RP | Reverse phase |
| rpm | rotations per minute |
| RT or rt | Room temperature |
| s | singlet |
| sat. or satd. or sat'd | Saturated |
| t | triplet |
| T3P | Propylphosphonic anhydride |
| t-Bu or $^t$Bu or Bu | Tert-butyl |
| TBAI | Tetrabutylammonium iodide |
| TBSCl | Tert-butyldimethylsilyl chloride |
| t-BuBrettPhos | 2-(di-tert-butylphosphino)-2',4',6'-triisopropyl-3,6-dimethoxy-1,1'-biphenyl |
| TCFH | N'-tetramethylformamidinium hexafluorophosphate |
| TEA | Triethylamine |

-continued

List of Abbreviations and Acronyms

| Abbreviation/Acronym | Meaning |
| --- | --- |
| TEMPO | 2,2,6,6-tetramethylpiperidine 1-oxyl |
| Tf$_2$O | Triflic anhydride (also known as trifluoromethanesulfonic anhydride) |
| TFA | Trifluoroacetic acid |
| THF | Tetrahydrofuran |
| TLC | thin layer chromatography |
| TMSBr | trimethylbromosilane |
| tt | triplet of triplets |
| v/v | volume per volume |
| wt | weight |
| w/w | weight by weight |
| XPhos | 2-dicycloexylphosphino-2',4',6'-triisopropylbiphenyl |

General Synthetic Schemes

General Reaction Schemes 1-6 are provided as further embodiments of the present disclosure and illustrate general methods which were used to prepare certain compounds of the present disclosure and which can be used to prepare additional compounds of the present disclosure. Each of the variables (e.g. R', $R^2$, $R^3$, $R^4$) of the compounds disclosed in General Reaction Schemes 1-6 are as defined herein.

The compounds of the present disclosure may be prepared using the methods disclosed herein and routine modifications thereof, which will be apparent to a skilled artisan given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers. In general, compounds described herein are typically stable and isolatable at room temperature and pressure.

Typical embodiments of compounds disclosed herein may be synthesized using the general reaction schemes described below. It will be apparent to a skilled artisan given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments disclosed in the present disclosure, inspection of the structure of the compound to be synthesized will provide the identity of each substituent group. The identity of the final product will generally render apparent the identity of the necessary starting materials by a simple process of inspection, given the examples herein.

The terms "solvent", "inert organic solvent", or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, and the like). Unless specified to the contrary, the solvents used in the reactions of the present disclosure are inert organic solvents, and the reactions are carried out under an inert gas, preferably nitrogen or argon.

General Synthetic Scheme 1.
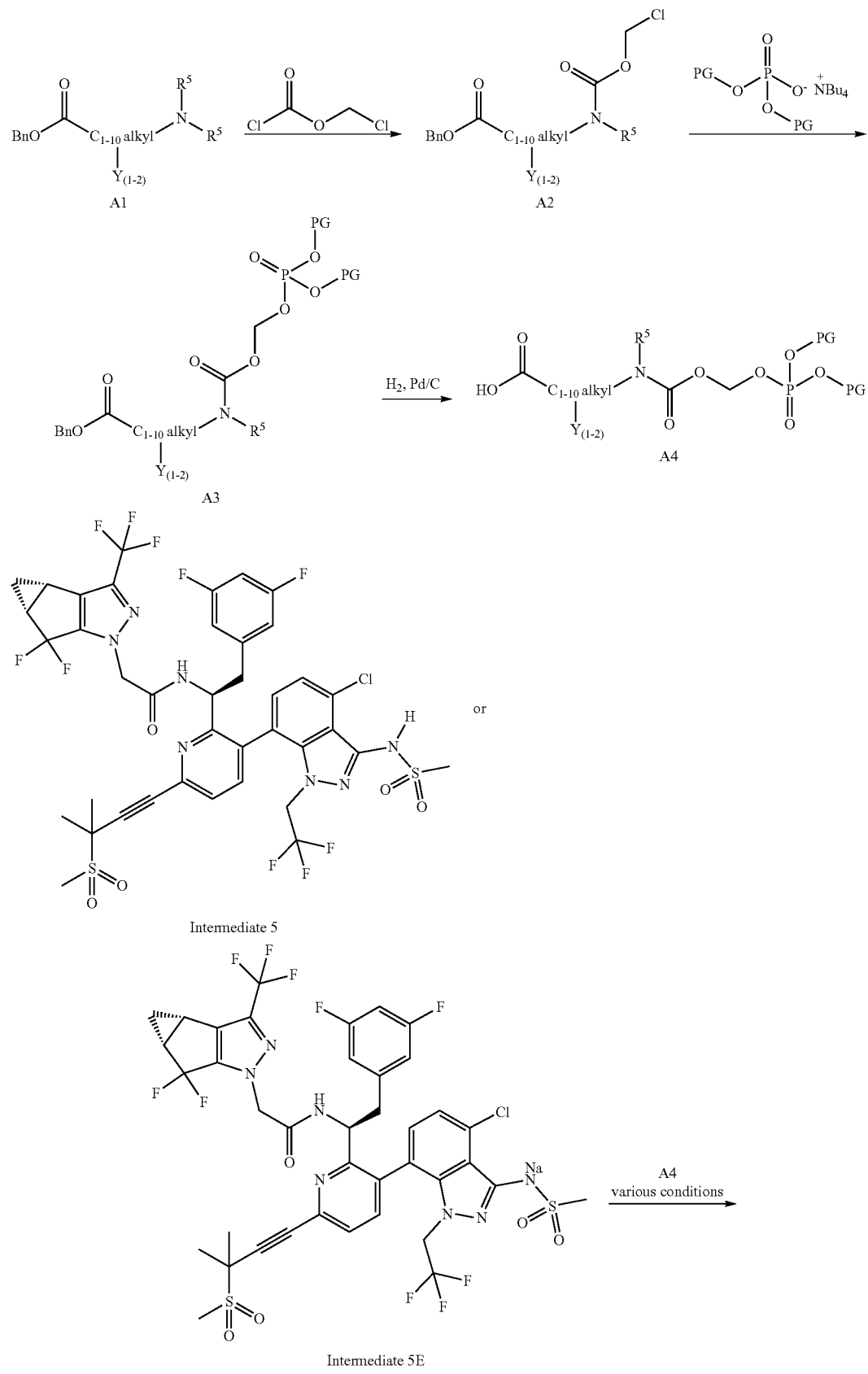

-continued

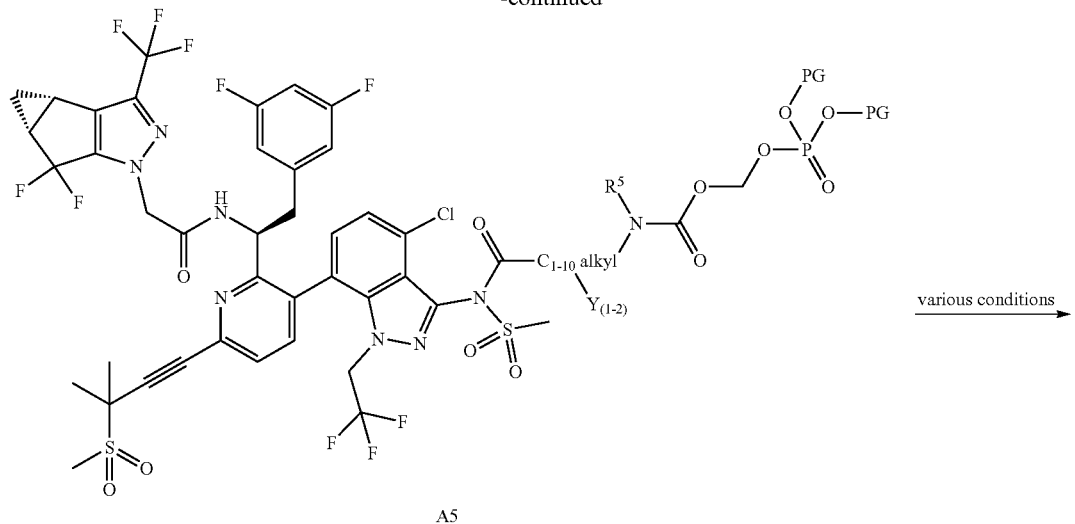

A5

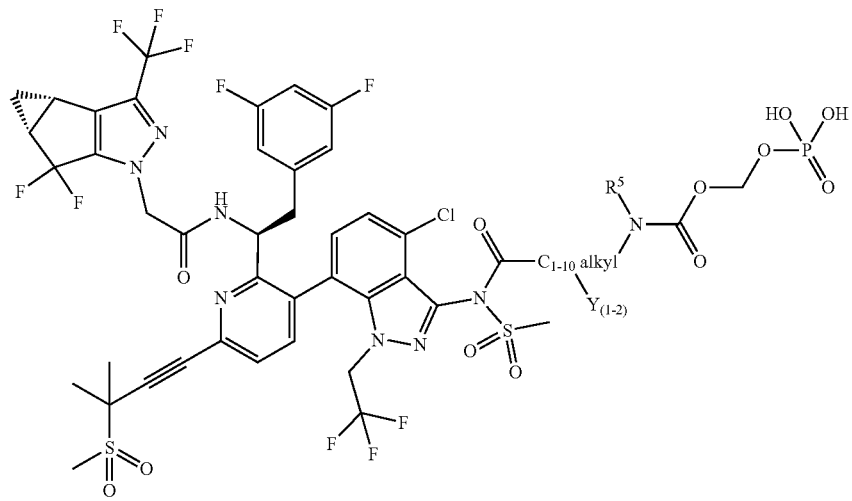

A6

Compounds of formula A6 can be prepared according to General Synthetic Scheme 1, wherein $R^5$ and Y are as defined herein and PG is a protecting group known in the art. In accordance with General Synthetic Scheme 1, a compound of formula A1 can be reacted with chloromethyl chloroformate in the presence of base in an appropriate solvent to generate a compound of Formula A2. A compound of formula A2 can be reacted with a di-tert-butyl phosphate equivalent, including but not limited to tetrabutylammonium di-tert-butyl phosphate or potassium di-tert-butyl phosphate, to generate a compound of formula A3. A compound of formula A3 can be converted to a compound of formula A4 under various reducing conditions such as using palladium on carbon under an atmosphere of hydrogen gas. A compound of formula A4 can be coupled through various conditions to Intermediate 5E or Intermediate 5 to generate a compound of formula A5. Non-limiting exemplary coupling conditions include coupling reagents such as HATU, COMU, TCFH, or EDC under appropriate solvent and temperature conditions in the presence of a base. A compound of formula A5 can be deprotected to produce a compound of Formula A6 under appropriate conditions, including but not limited to phosphoric acid, trifluoroacetic acid, hydrochloric acid, boron tribromide, or trimethylsilyl iodide in various solvents.

A compound of formula A1 can be obtained commercially or readily synthesized by those skilled in the art according to known methods. Methods for preparation include but are not limited to preparation of a benzyl ester under appropriate conditions, introduction of —NR⁵R⁵ using methods known in the art, including but not limited to alkylation or reductive amination. Where one of the R⁵ groups is —H, the amino group can be functionalized with additional R⁵ groups using methods known in the art, including but not limited to reaction with chloroformates, reductive amination with an aldehyde, or alkylation with an appropriate electrophile.

General Synthetic Scheme 2.

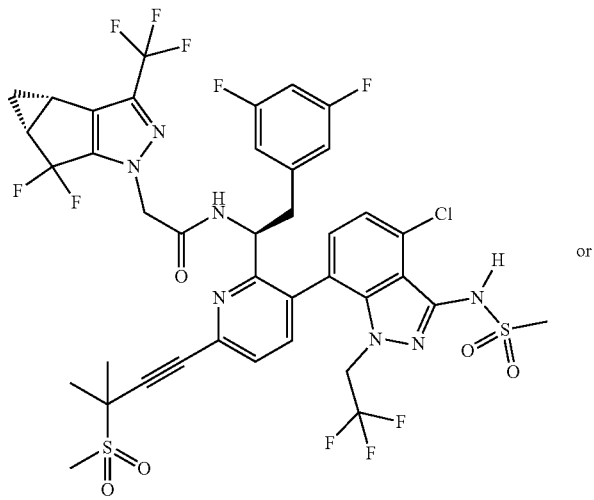

Intermediate 5

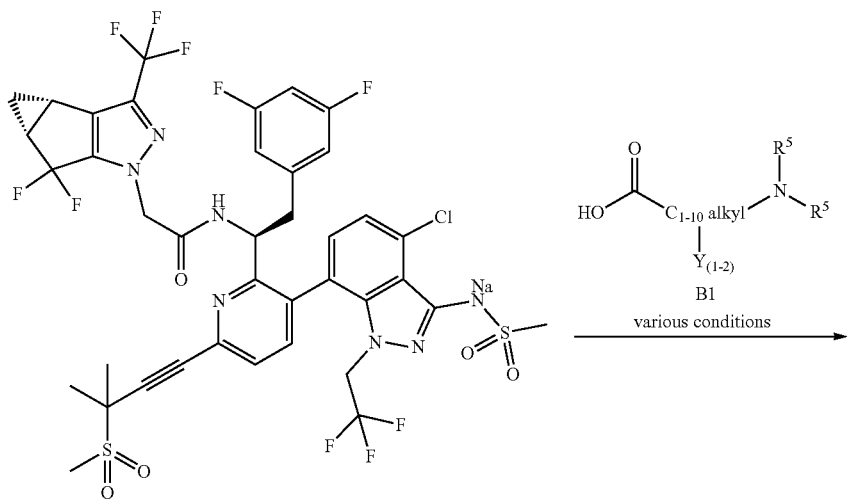

Intermediate 5E

-continued

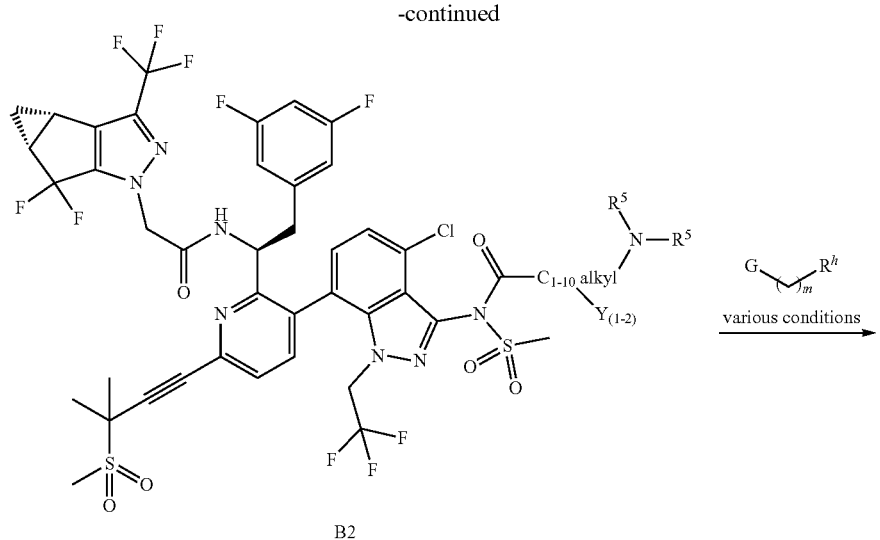

B2

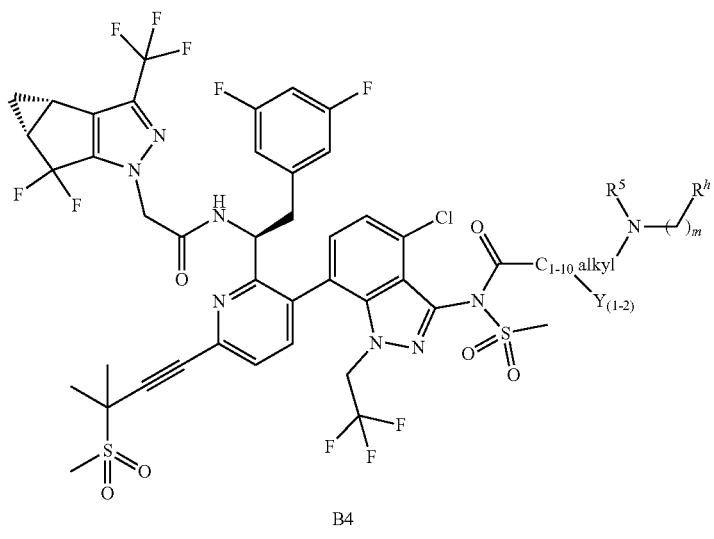

B4

Compounds of formula B2 and B4 can be prepared according to General Synthetic Scheme 2, wherein $R^5$ and Y are as defined herein; m is 0, 1, 2, 3, 4, 5, or 6; $R^h$ is $R^a$, $R^b$, or $R^c$ as defined herein; and G is a general leaving group including but not limited to —$C_1$, —Br, —I, —F, or -OTs. In accordance with General Synthetic Scheme 2, a compound of formula B1 can be reacted with Intermediate 5 or Intermediate 5E to generate compounds of formula B2. A compound of formula B2 can be converted to a compound of formula B4 by employing various conditions known in the art for alkylation or acylation using a compound of formula B3, with optional deprotection in cases where a protected functional group has been introduced. Compounds of formula B1 and B3 can be obtained commercially, or readily synthesized from known materials and reagents in one or more steps by those skilled in the art.

General Synthetic Scheme 3.
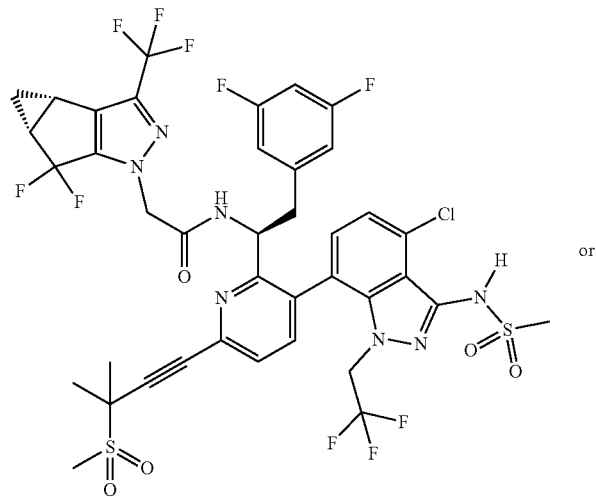
Intermediate 5
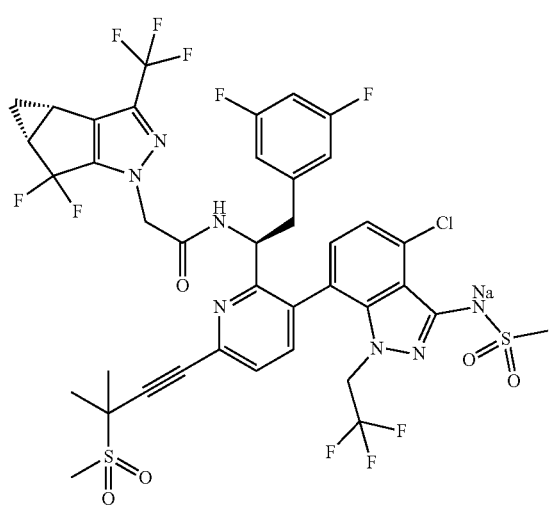
Intermediate 5E
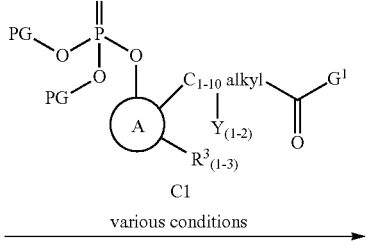
C1
various conditions →
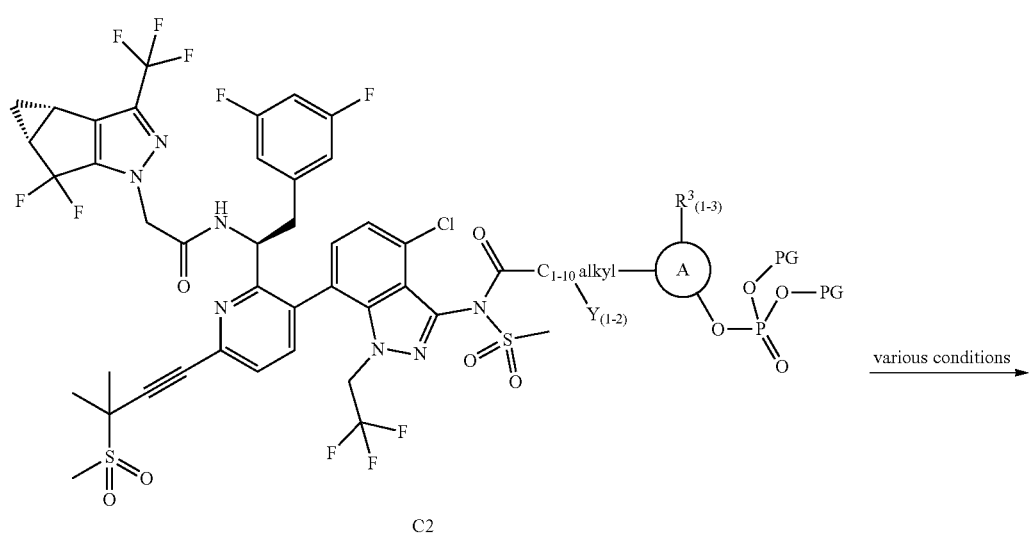
C2
various conditions →

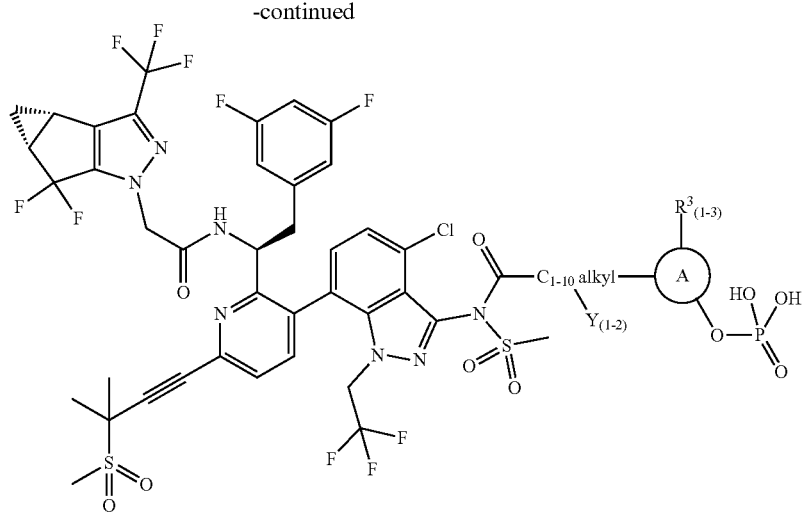

C3

Compounds of formulas C₂ and C₃ can be prepared according to General Synthetic Scheme 3, wherein $R^1$ and Y are as defined herein; cyclic group A is phenyl, naphthalenyl, 5-6 membered monocyclic heteroaryl, or 8-10 membered fused bicyclic heteroaryl, each of which are optionally substituted with 1-3 $R^3$ groups as defined herein; G' is a general leaving group that includes but is not limited to —Cl, —Br, —F, or —OH; and PG is a protecting group known in the art. In accordance with General Synthetic Scheme 3, a compound of formula C₁ can be reacted with Intermediate 5 or Intermediate 5E to generate compounds of Formula C₂. Non-limiting exemplary coupling conditions include the use of coupling reagents such as HATU, COMU, TCFH, or EDC under appropriate solvent and temperature conditions in the presence of a base. A compound of formula C2 can be converted to a compound of formula C3 by employing appropriate conditions for deprotection known to those of skill in the art. Compounds of formula C1 can be obtained commercially, or readily synthesized from known materials and reagents in one or more steps by those skilled in the art.

General Synthetic Scheme 4.

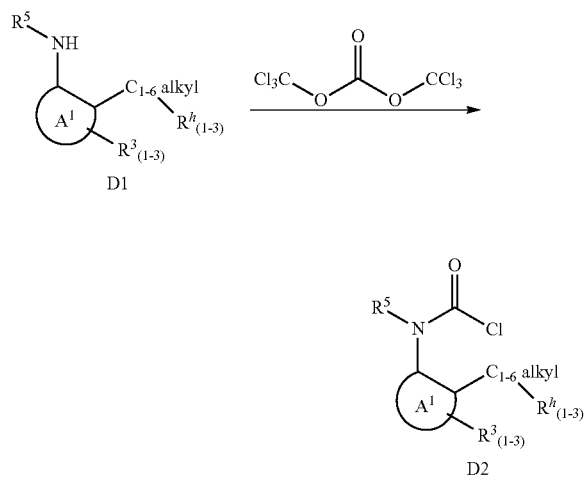

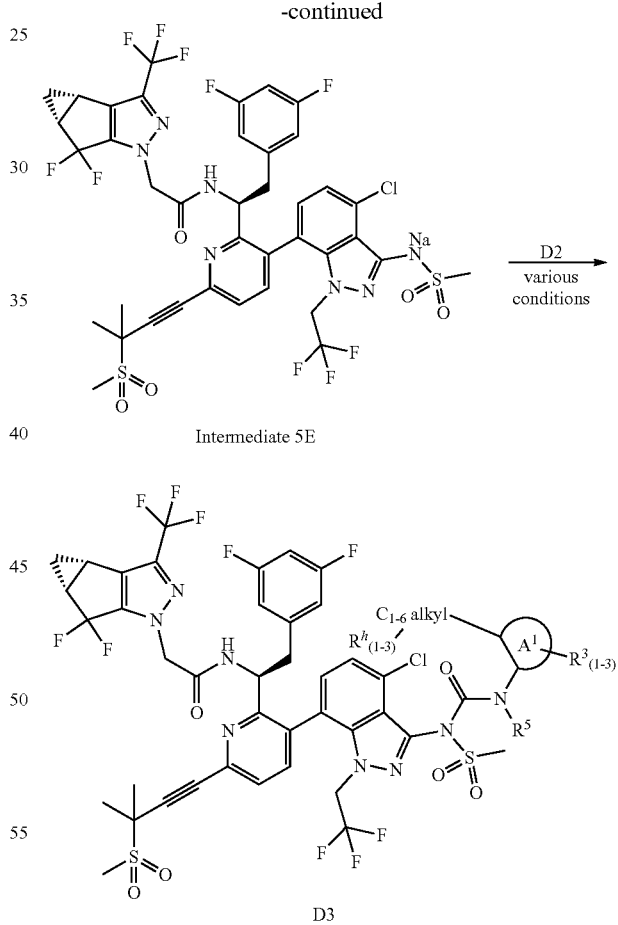

Compounds of formula D3 can be prepared according to General Synthetic Scheme 4, wherein R¹, $R^3$, and $R^5$ are as defined herein; $R^h$ is $R^a$, $R^b$, or $R^c$ as defined herein; and cyclic group $A^1$ is phenyl, naphthalenyl, 5-6 membered monocyclic heteroaryl, or 8-10 membered fused bicyclic heteroaryl, each of which are optionally substituted with 1-3$R^3$ groups as defined herein. In accordance with General Synthetic Scheme 4, a compound of formula D1 can be reacted with a carbonyl group transfer reagent, including but not limited to triphosgene, to generate a compound of formula D2. A compound of formula D2 can be converted to a compound of Formula D3 by reacting under various conditions with Intermediate 5E, and following optional deprotection of any intermediate obtained. Non-limiting exemplary coupling conditions include incubation of a compound of formula D2 and Intermediate 5E under appropriate solvent and temperature conditions in the presence of a base. Compounds of formula D1 can be obtained commercially, or readily synthesized from known materials and reagents in one or more steps by those skilled in the art.

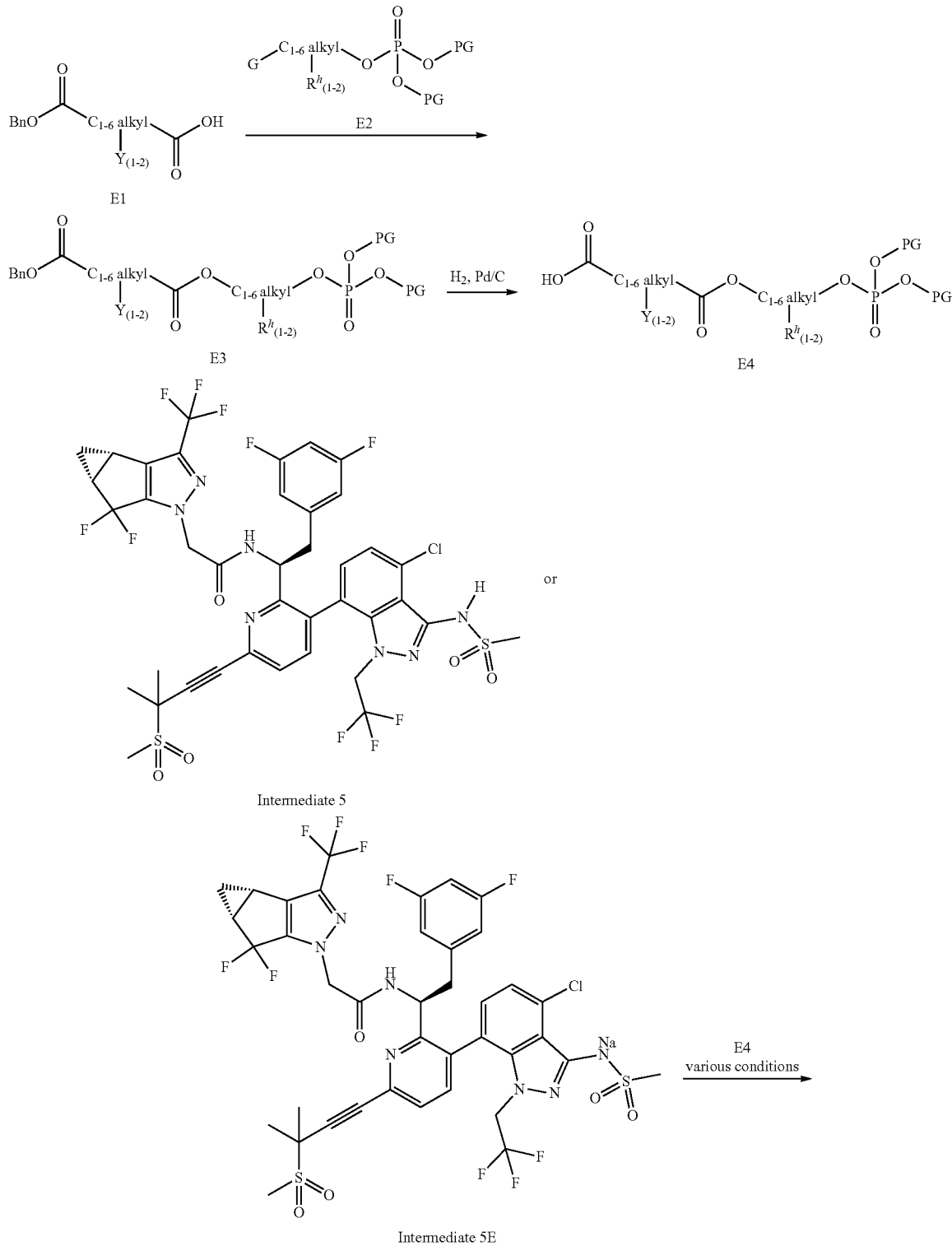

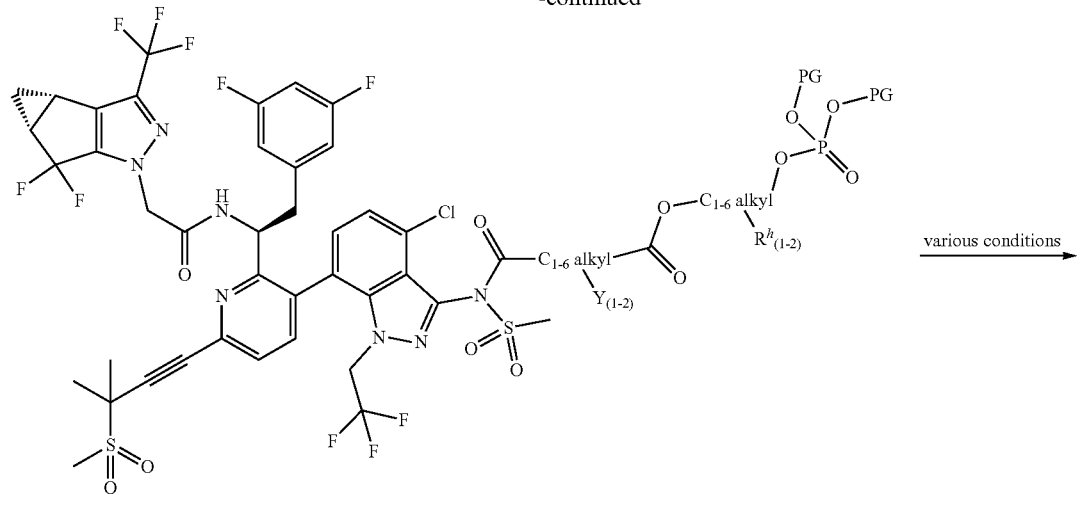

E5

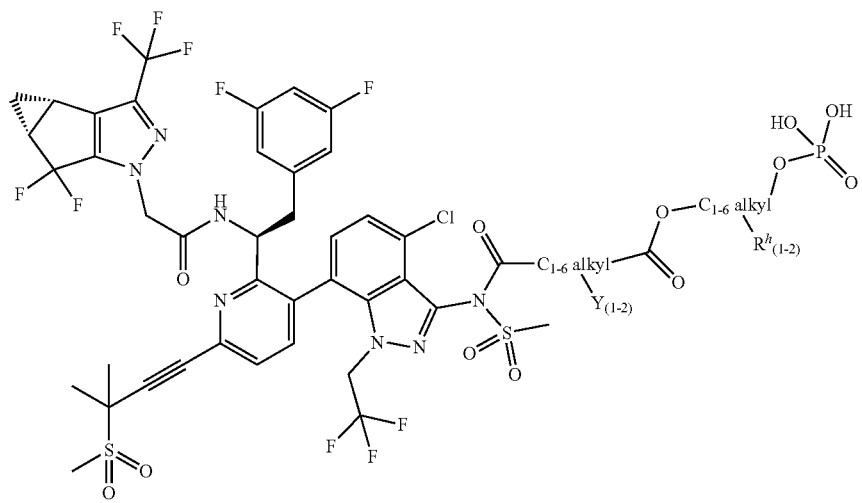

E6

Compounds of formula E6 can be prepared according to General Synthetic Scheme 5, wherein Y is as defined herein; $R^h$ is $R^a$, $R^b$, or $R^C$ as defined herein; and G is a general leaving group including but not limited to —Cl, —Br, —I, —F, or -OTs. In accordance with General Synthetic Scheme 5, a compound of formula E1 can be reacted with a compound of formula E2 in the presence of base to generate a compound of formula E3. A compound of Formula E4 can be prepared from hydrogenation of a compound of formula E3. A compound of formula E4 can be reacted with Intermediate 5 or Intermediate 5E, in the presence of base and an appropriate coupling reagent to generate a compound of formula E5, which can then be deprotected under acidic conditions to yield a compound of formula E6. Non-limiting exemplary coupling conditions include the use of coupling reagents such as HATU, COMU, TCFH, or EDC under appropriate solvent and temperature conditions in the presence of a base. Compounds of formula E1 and E2 can be obtained commercially, or readily synthesized from known materials and reagents in one or more steps by those skilled in the art.

General Synthetic Scheme 6.

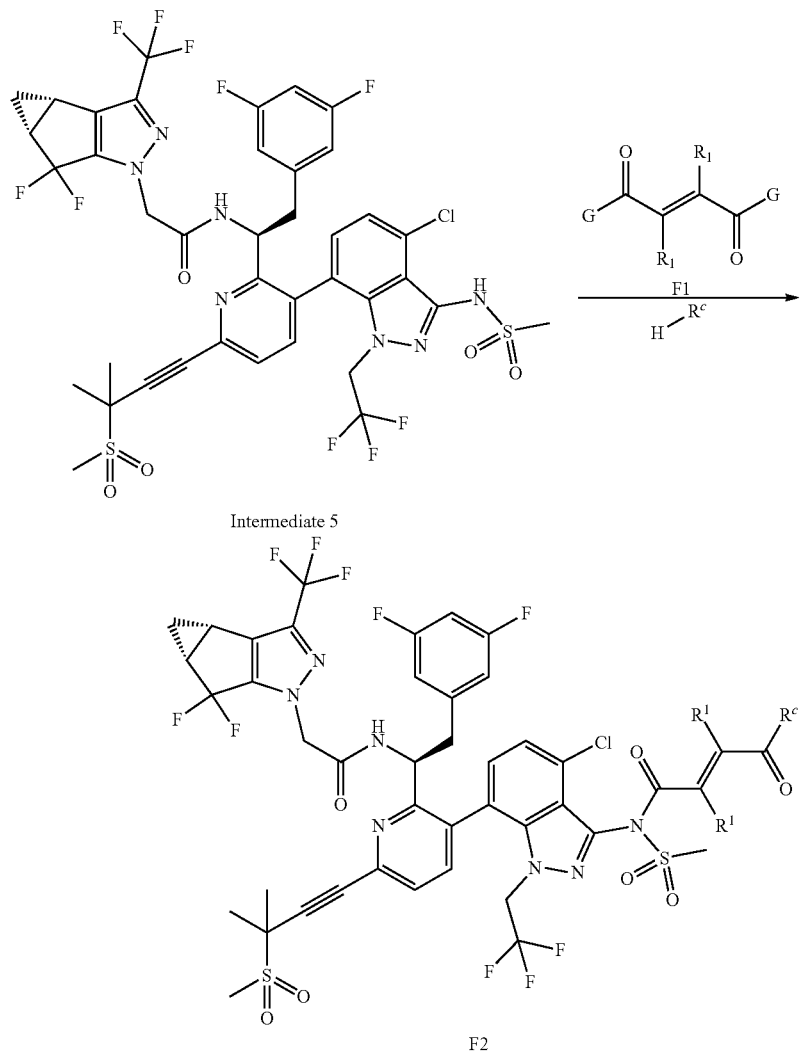

Compounds of formula F2 can be prepared according to General Synthetic Scheme 6, wherein R' and $R^C$ are as defined herein. G denotes a general leaving group including but not limited to —Cl, —Br, —I, —F, or -OTs. In accordance with General Synthetic Scheme 5, Intermediate 5 can be reacted with a compound of formula F1 in the presence of base and nucleophilic $R^C$ group to generate a compound of formula F2, which can optionally be deprotected under appropriate conditions in cases where $R^C$ contains protected functionality. Compounds of formula F1 can be obtained commercially, or readily synthesized from known materials and reagents in one or more steps by those skilled in the art.

VIII. EXAMPLES

Exemplary chemical entities of the present disclosure are provided in the specific examples that follow. Those skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

In the following description of the Examples, specific embodiments are described. These embodiments are described in sufficient detail to enable those skilled in the art to practice certain embodiments of the present disclosure. Other embodiments may be utilized and logical and other changes may be made without departing from the scope of the disclosure. The following description is, therefore, not intended to limit the scope of the present disclosure.

Intermediates:

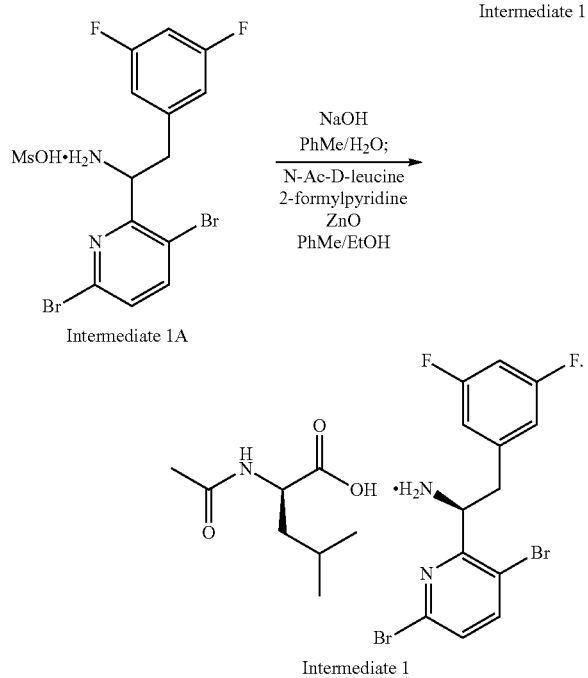

Intermediate 1

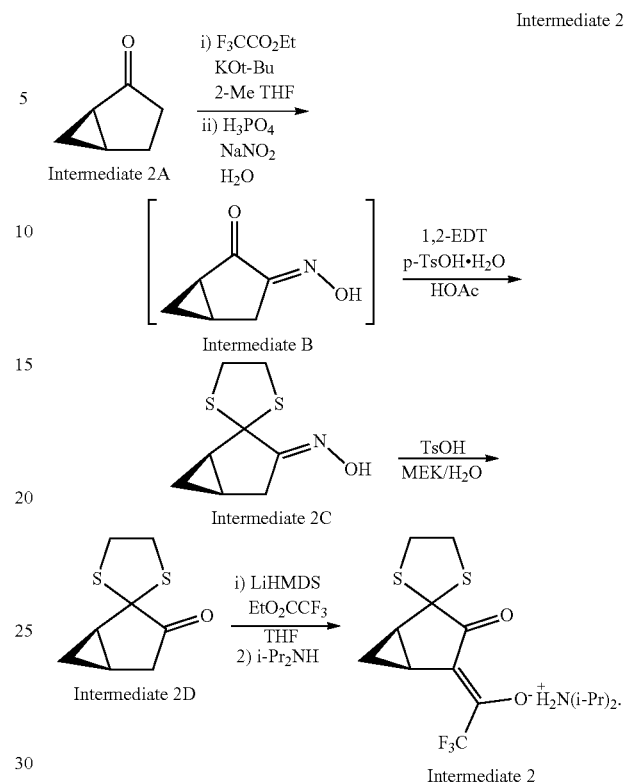

Intermediate 2

Synthesis of (S)-1-(3,6-dibromopyridin-2-yl)-2-(3,5-difluorophenyl)ethan-1-amine acetyl-D-leucinate (Intermediate 1): A mixture of Intermediate 1A (30.8 mmol, 1.00 equiv), 2-methyltetrahydrofuran (75 mL), water (45 g), and NaOH (37.9 mmol, 1.23 equiv) were agitated for 2 h. The aqueous phase was discarded and the organic phase was washed twice with water (45 mL). The organic phase was solvent exchanged into toluene, distilling to a final volume of 3 ml/g before diluting with toluene (224 mL). To the solution was added N-acetyl-D-leucine (43.3 mmol), zinc oxide (6.25 mmol), and 2-pyridinecarboxaldehyde (1.6 mmol). The mixture was agitated at 35° C. for 157 h prior to cooling to 20° C. The mixture was treated with a solution of NaOH (45 mmol) in water (75 mL) and then filtered through celite (7.5 g), rinsing forward toluene (30 mL). The aqueous phase was discarded and the organic phase was washed three times with water (75 mL). To the organic phase were added EtOH (15 mL), water (7.5 mL), toluene (76 mL), and N-acetyl-D-leucine (27.7 mmol). The mixture was cooled to 0° C. and filtered. The filter cake was washed with toluene (76 mL) and dried under vacuum to yield title compound Intermediate 1. $^1$H NMR (400 MHz, DMSO-$d_6$) δ 8.03 (d, J=8.0 Hz, 1H), 7.95 (d, J=8.3 Hz, 1H), 7.49 (d, J=8.3 Hz, 1H), 7.03 (tt, J=9.5, 2.4 Hz, 1H), 6.87 (dtd, J=8.4, 6.2, 2.2 Hz, 2H), 5.49 (s, 3H), 4.42 (dd, J=7.9, 5.9 Hz, 1H), 4.18 (q, J=7.8 Hz, 1H), 2.93 (dd, J=13.3, 5.9 Hz, 1H), 2.85 (dd, J=13.2, 8.0 Hz, 1H), 1.83 (s, 3H), 1.71-1.54 (m, 1H), 1.47 (dd, J=8.4, 6.2 Hz, 2H), 0.88 (d, J=6.6 Hz, 3H), 0.83 (d, J=6.5 Hz, 3H) ppm. $^{13}$C NMR (101 MHz, DMSO-$d_6$) δ 174.72, 169.03, 162.07 (dd, J=245.5, 13.3 Hz), 161.79, 143.51, 142.82 (t, J=9.4 Hz), 139.72, 128.39, 119.30, 113.36-111.39 (m), 101.73 (t, J=25.7 Hz), 55.19, 50.69, 41.74 (d, J=2.3 Hz), 40.51, 24.36, 22.91, 22.44, 21.46 ppm.

Synthesis of (1R,5R,E)-3-(hydroxyimino)bicyclo[3.1.0]hexan-2-one (Intermediate 2B): To a mixture of ketone Intermediate 2A (111 mmol) and ethyl trifluoroacetate (121 mmol) in 2-methyltetrahydrofuran (50 mL) at 5° C. was added 2 M potassium t-butoxide in 2-methyltetrahydrofuran (62.4 mL, 1.2 equiv). After 1 h, the solution was warmed to 20° C. and agitated for 3 h. The mixture was cooled to 5° C. and a solution of 86% phosphoric acid (133 mmol) in water (50 mL) was added. The mixture was warmed to 20° C. and sodium nitrite (122 mmol) was added. After 16 h, water (100 mL) was added and the aqueous phase was separated. The aqueous phase was back-extracted with 3 portions of 2-methyltetrahydrofuran (80 mL, 80 mL, and 50 mL). The combined organic phases were distilled to 3 mL/g and then exchanged into acetic acid, distilling to a total volume of 5 mL/g to afford a solution of the title compound Intermediate 2B. $^1$H NMR (400 MHz, DMSO-$d_6$) δ 12.26 (s, 1H), 2.73 (d, J=18.5 Hz, 1H), 2.63 (ddd, J=18.6, 5.3, 2.0 Hz, 1H), 2.17-2.01 (m, 2H), 1.34 (dddd, J=9.2, 7.1, 4.9, 2.0 Hz, 1H), 0.77 (td, J=4.6, 3.4 Hz, 1H) ppm.

Synthesis of (1R,5R,E)-spiro[bicyclo[3.1.0]hexane-2,2'-[1,3]dithiolan]-3-one oxime (Intermediate 2C): To a solution of Intermediate 2B (102 mmol) in acetic acid (55 mL total volume) at 20° C. was added 1,2-ethanedithiol (117 mmol) and p-toluenesulfonic acid (42 mmol). After 20 h, water (60 mL) was added and the mixture was cooled to 5° C. After 3 h, the reaction was filtered and then the filter cake was washed with 2 portions of a mixture of 2-propanol (24 mL) and water (6 mL) and dried under vacuum to afford title compound Intermediate 2C. $^1$H NMR (400 MHz, DMSO-$d_6$) δ 10.93 (s, 1H), 3.63-3.51 (m, 2H), 3.51-3.42 (m, 1H), 3.39-3.31 (m, 1H), 2.83 (d, J=17.4 Hz, 1H), 2.59-2.52 (m, 1H), 1.87 (ddd, J=8.0, 6.2, 3.7 Hz, 1H), 1.65 (dddd, J=7.7, 6.2, 5.2, 3.9 Hz, 1H), 0.93 (tdd, J=7.6, 5.5, 1.7 Hz, 1H), 0.02 (dt, J=5.5, 3.8 Hz, 1H) ppm.

Synthesis of (1R,5R)-Spiro[bicyclo[3.1.0]hexane-2,2'-[1,3]dithiolan]-3-one (Intermediate 2D): Para-toluenesulfonic acid (0.90 g) was charged to a vessel containing a suspension of Intermediate 2C (2.5 mmol) in methyl ethyl ketone (2.5 mL) and water (2.5 mL). The mixture was agitated at about 85° C. until the reaction was complete. The product was isolated from the reaction mixture by cooling to about 20° C., adding water (2.50 mL), and cooling to about 0° C. The slurry was filtered and the filter cake was washed with water, then deliquored thoroughly to afford title compound Intermediate 2D. $^1$H NMR (400 MHz, DMSO-d$_6$) δ 3.55-3.37 (m, 3H), 3.28-3.13 (m, 1H), 3.03 (ddd, J=18.5, 5.6, 2.2 Hz, 1H), 2.20 (d, J=18.5 Hz, 1H), 1.84 (ddd, J=8.0, 7.0, 3.8 Hz, 1H), 1.66 (tdd, J=7.2, 5.6, 4.1 Hz, 1H), 1.03 (tdd, J=7.9, 5.9, 2.1 Hz, 1H), 0.06 (dt, J=6.0, 4.0 Hz, 1H).

Synthesis of Diisopropylammonium (Z)-2,2,2-trifluoro-1-01R,5S)-3-oxospiro[bicyclo[3.1.0]hexane-2,2'-[1,3]dithiolan]-4-ylidene)ethan-1-olate (Intermediate 2): Intermediate 2D (756 mg) was charged to a vessel and dissolved in 2-methyltetrahydrofuran (7.6 mL). To this mixture was charged ethyl trifluoroacetate (0.57 g) and the reaction was cooled to about 0° C. Lithium hexamethyldisilazide (1.0 M solution in THF, 4.5 g) was charged over about 60 minutes and the reaction was agitated until complete. A solution of sulfuric acid (2.0 g) in water (5.6 mL) was charged, then the reaction was warmed to about 20° C. and agitated for about 20 minutes. Layers were separated and the aqueous layer was extracted twice with 2-methyltetrahydrofuran (5.3 mL). The combined organic layers were concentrated and 1V,N-diisopropyl amine (0.5 g) was charged. The product was crystallized by the addition of heptane (11 ml). The reaction was filtered and the filter cake was washed with heptane, then deliquored thoroughly, and dried to afford title compound Intermediate 2. $^1$H NMR (400 MHz, Acetonitrile-d$_3$) δ 7.84 (m, 2H), 3.58 (d, J=8.7 Hz, 2H), 3.47-3.27 (m, 4H), 2.20 (s, 1H), 1.81 1.68 (m, 1H), 1.24 (dd, J=6.5, 0.6 Hz, 12H), 0.99 (q, J=6.5 Hz, 1H), 0.13 (s, 1H).

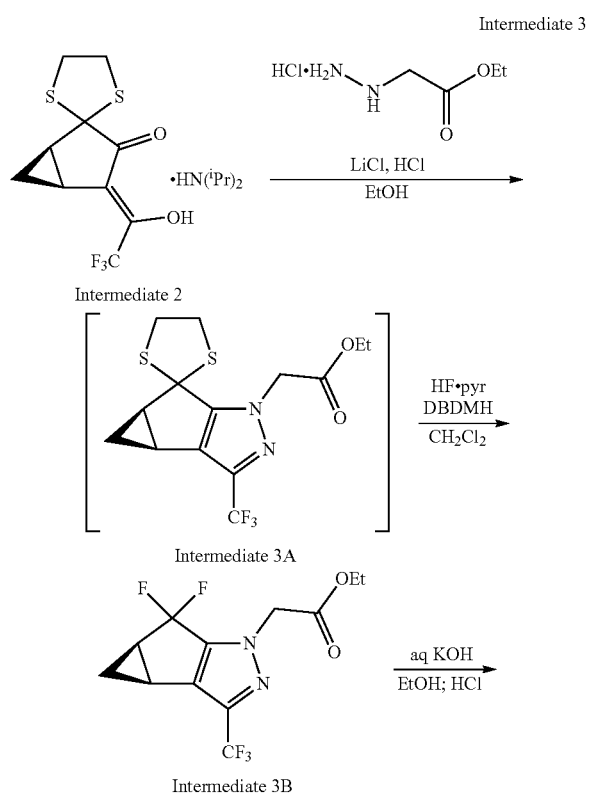

Intermediate 3

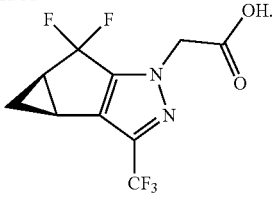

Intermediate 3

Synthesis of Ethyl 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetate (Intermediate 3B): Acetyl chloride (940 mmol) was added to EtOH (324 g) to produce a solution of anhydrous HCl in EtOH. To the solution were charged 2-ethyl hydrazinoacetate HCl (293 mmol), LiCl (850 mmol), Intermediate 2 (235 mmol), and EtOH (36 g). The mixture was stirred for 44 h and then concentrated to a volume of 2 mL/g prior to diluting with dichloromethane (1170 g). The mixture was washed with water (450 g) followed by solutions of sodium bicarbonate (428 mmol) in water (451 g) and NaCl (50.7 g) in water (452 g). The organic phase was treated with silica gel (45.1 g), filtered, and azeotropically distilled to a volume of 2 mL/g prior to dilution with dichloromethane (451 g). The crude Intermediate 3A was used in the following step.

To a mixture of dibromodimethylhydantoin (93.5 mmol) and dichloromethane (170 mL) at –13° C. was charged 70% w/w hydrogen fluoride pyridine (2652 mmol). To the resulting mixture was charged crude Intermediate 3A (27.4 mmol) in dichloromethane (50 mL). After 2.5 h, water (105 mL), a solution of sodium metabisulfite (109 mmol) in water (159 g), and a solution of 45% KOH (128 g) were added to the mixture in succession. The mixture was warmed to 20° C. and the aqueous phase was separated and discarded. The organic phase was washed with a solution of 35% HCl (113 mmol) in water (103 g) and a solution of NaCl (5.2 g) in water (105 g). The organic solution was exchanged to EtOH, distilling to a final volume of 8.2 mL/g. To the solution was added activated carbon (3.0 g) and stirred for 30 min. The mixture was filtered, rinsing forward additional EtOH (42 mL). The solution was distilled to a volume of 5.5 mL/g and water (50 mL) was added. The reaction was filtered and the filter cake was washed with a mixture of EtOH (20 mL) and water (20 L) and dried under vacuum to afford title compound Intermediate 3B. $^1$H NMR (400 MHz, DMSO-d$_6$) δ 5.31-5.04 (m, 2H), 4.17 (q, J=7.1 Hz, 2H), 2.78-2.57 (m, 2H), 1.47 (dddd, J=8.5, 7.1, 5.5, 1.4 Hz, 1H), 1.19 (t, J=7.1 Hz, 3H), 1.04 (tdt, J=5.3, 4.0, 1.8 Hz, 1H). $^{13}$C NMR (101 MHz, DMSO-d$_6$) δ 166.79, 143.15 (t, J=29.4 Hz), 134.65 (q, J=39.0 Hz), 132.99, 121.05 (q, J=268.4 Hz), 120.52 (t, J=243.3 Hz), 62.09, 52.49, 27.95 (dd, J=34.7, 29.0 Hz), 23.82 (d, J=2.6 Hz), 14.25, 12.14 (t, J=3.1 Hz). $^{19}$F NMR (376 MHz, DMSO-d$_6$) δ-60.47, −79.68 (dd, J=253.5, 13.2 Hz), −103.09 (dd, J=253.3, 9.8 Hz) ppm.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (Intermediate 3): To a mixture of Intermediate 3B (64.6 mmol) in EtOH (9.3 g) and water (80.3 g) was added 45% KOH (130 mmol) and the mixture was warmed to 50° C. After 17 h, the solution was added to a mixture of 35% HCl (170 mmol) in water (102 g). The reaction was filtered and the filter cake was washed with water (120 g) and dried under vacuum to afford title compound Intermediate 3. $^1$H NMR (400 MHz, DMSO-d$_6$) δ 13.50 (s, 1H), 5.14-4.81 (m, 2H), 2.82-2.56 (m, 2H), 1.46 (dddd, J=8.5, 7.1, 5.5, 1.4 Hz, 1H), 1.08-1.00 (m, 1H). $^{13}$C NMR (101 MHz, DMSO-d$_6$) δ 168.16, 143.05 (t, J=29.4 Hz), 134.40 (q, J=38.9 Hz), 132.80, 121.11 (q, J=268.4 Hz), 120.55 (t, J=243.3 Hz), 52.54, 27.97 (dd, J=34.7, 29.0 Hz), 23.81 (d, J=2.5 Hz), 12.13 (t, J=3.1 Hz). $^{19}$F NMR (376 MHz, DMSO-d$_6$) δ -60.39 (d, J=1.4 Hz), -79.83 (dd, J=253.2, 13.1 Hz), -102.97 (dd, J=253.2, 9.8 Hz).

Synthesis of 4-chloro-7-(4,4,5,5-tetramethyl-1,3,2-dioxaborolan-2-yl)-1-(2,2,2-trifluoroethyl)-1H-indazol-3-amine (Intermediate 4): A mixture of bis(triphenylphosphine)palladium(II) dichloride (0.46 mmol), bis(pinacolato)diboron (33 mmol), Intermediate 4A (30.5 mmol), potassium propionate (89.3 mmol), toluene (44 g), and DMF (29 g) were degassed and then warmed to 107° C. After 7 h, the mixture was cooled to 60° C., treated with a solution of N-acetylcysteine (6.1 mmol) in water (20 g), and agitated for 18 h. The mixture was cooled to 20° C., diluted with EtOAc (50 g), and filtered through celite, rinsing forward additional EtOAc (40 g). The aqueous phase was discarded and the organic phase was washed 3 times with a solution of LiCl (6.0 g) in water (60 g). The organic phase was treated with activated carbon, rinsing forward additional EtOAc (80 g). The solution was exchanged into 2-propanol, distilling to a final volume of 4 mL/g. The mixture was diluted with n-heptane (41 g), warmed to 82° C., and then cooled to 15° C. The mixture was filtered and the filter cake was, washed with 2-propanol (32 g) and dried under vacuum to afford title compound Intermediate 4. $^1$H NMR (400 MHz, DMSO-d$_6$) δ 7.70 (dd, J=7.6, 1.0 Hz, 1H), 7.07 (dd, J=7.6, 1.0 Hz, 1H), 5.58 (s, 2H), 5.46 (q, J=9.1 Hz, 2H), 1.32 (s, 12h).

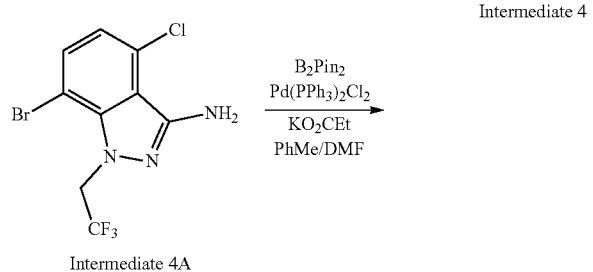

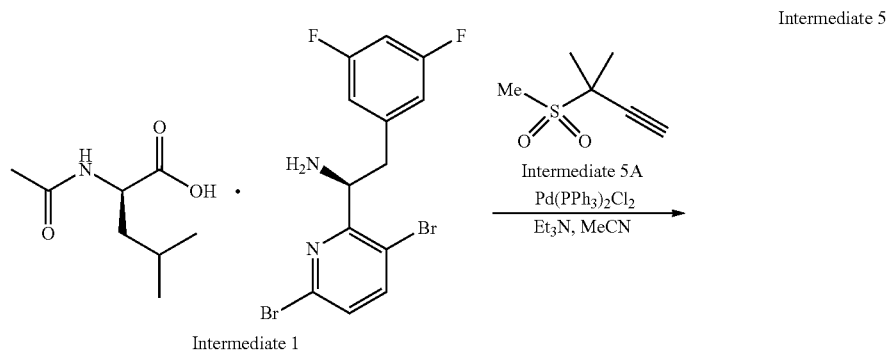

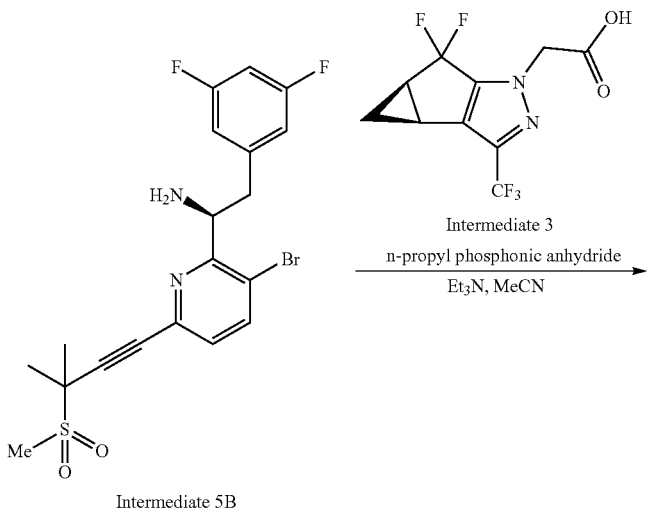

-continued
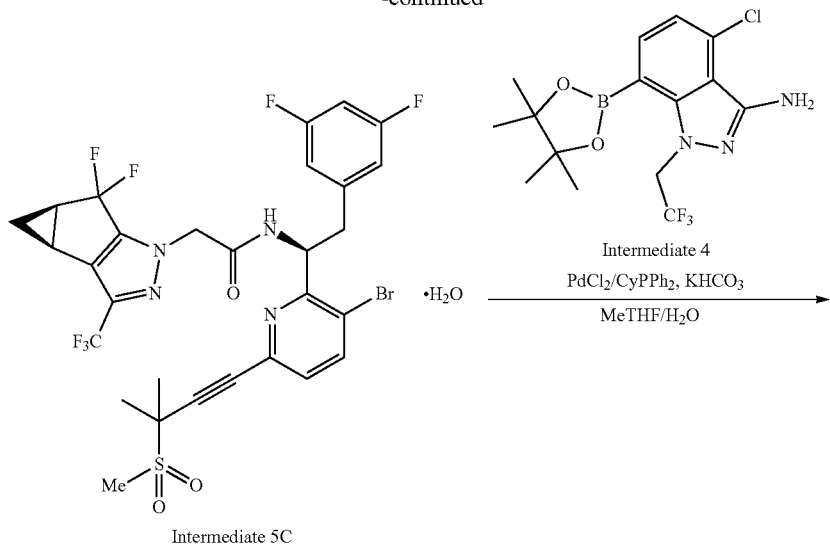
Intermediate 5C
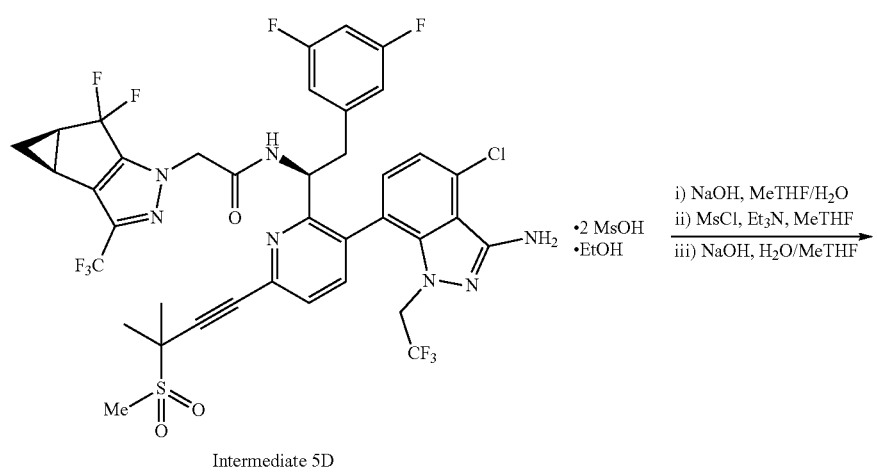
Intermediate 5D
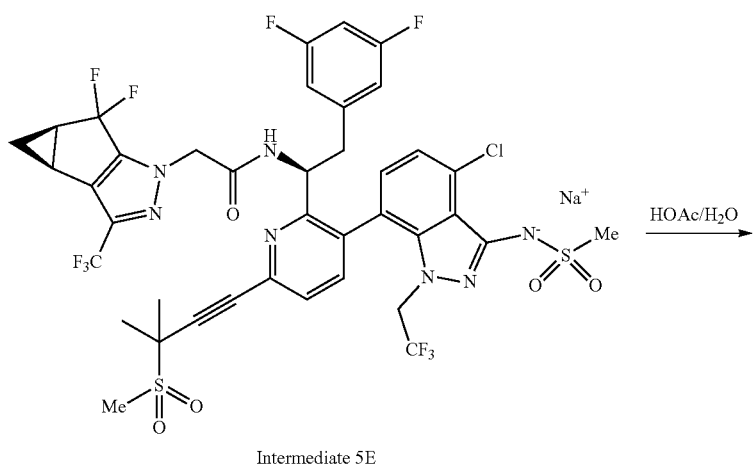
Intermediate 5E -continued

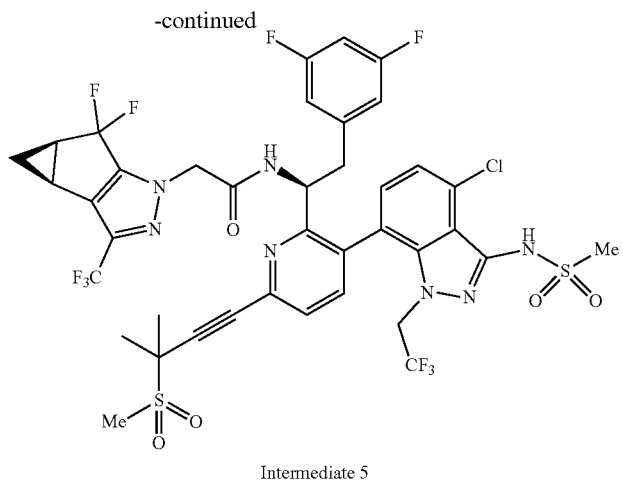

Intermediate 5

Synthesis of (S)-1-(3-bromo-6-(3-methyl-3-(methylsulfonyl)but-1-yn-1-yl)pyridin-2-yl)-2-(3,5-difluorophenyl)ethan-1-amine (Intermediate 5B): A mixture of Intermediate 1 (35.33 mmol, 1.00 equiv), Intermediate 5A (39.7 mmol, 1.12 equiv), bis(triphenylphosphine)palladium(II) dichloride (0.54 mmol, 0.015 equiv), and triethylamine (178.7 mmol, 5.06 equiv) in MeCN (64 g) was heated at 70° C. for 6 h. Water (10.1 g) was added and the mixture was cooled to 50° C. N-Acetyl-L-cysteine (0.60 g) was added and the mixture was cooled to RT. Water (150 g) was added and the reaction was filtered. The filter cake was washed with a mixture of MeCN (20 g) and water (52 g) and dried under vacuum to yield title compound Intermediate 5B. $^1$H NMR (400 MHz, DMSO-$d_6$) δ 8.05 (d, J=8.2 Hz, 1H), 7.42 (d, J=8.2 Hz, 1H), 7.01 (tt, J=9.5, 2.4 Hz, 1H), 6.97-6.84 (m, 2H), 4.41 (dd, J=8.5, 5.2 Hz, 1H), 3.20 (s, 3H), 2.93 (dd, J=13.3, 5.2 Hz, 1H), 2.79 (dd, J=13.3, 8.5 Hz, 1H), 1.99 (s, 2H), 1.68 (s, 6H). $^{13}$C NMR (101 MHz, DMSO-$d_6$) δ 162.25, 162.00 (dd, J=245.2, 13.4 Hz), 143.88 (t, J=9.4 Hz), 141.09, 139.72, 127.51, 120.08, 112.58-112.12 (m), 101.45 (t, J=25.7 Hz), 87.94, 84.25, 57.24, 55.90, 42.57, 34.99, 22.19.

Synthesis of N—((S)-1-(3-bromo-6-(3-methyl-3-(methylsulfonyl)but-1-yn yDpyridin-2-yl)-2-(3,5-difluoropheny D-ethy D-2-((3bS,4aR)-5,5-difluoro-3-(trifluoromethy D-3b,4,4a,5-tetrahydro-1H-cyclopropa[3,4]cyclopenta[1,2-c]pyrazol-1-yl)acetamide (Intermediate 5C): To a mixture of Intermediate 5B (43.8 mmol, 1.00 equiv), Intermediate 3 (48.1 mmol, 1.10 equiv), triethylamine (65.3 mmol, 1.49 equiv) in MeCN (100 g) was added a 50% (w/w) T3P/DMF solution (132 mmol, 1.5 equiv) and the mixture was stirred for 3 h. DMF (20.1 g) and water (50.1 g) were added followed by seed crystals of title compound Intermediate 5C (0.06 g). Water (90.0 g) was added and the reaction was filtered. The filter cake was washed with a mixture of MeCN (70.0 g) and water (90.1 g) and dried under vacuum to yield title compound Intermediate 5C. $^1$H NMR (400 MHz, DMSO-$d_6$) δ9.19 (d, J=8.3 Hz, 1H), 8.12 (d, J=8.3 Hz, 1H), 7.50 (d, J=8.3 Hz, 1H), 7.07 (tt, J=9.4, 2.4 Hz, 1H), 6.96-6.87 (m, 2H), 5.52 (td, J=8.8, 5.3 Hz, 1H), 4.93-4.73 (m, 2H), 3.22 (s, 3H), 3.11-2.90 (m, 2H), 2.66-2.52 (m, 2H), 1.69 (s, 6H), 1.45-1.36 (m, 1H), 1.02-0.93 (m, 1H). $^{13}$C NMR (100 MHz, DMSO-$d_6$): δ 164.42, 163.62, 163.49, 161.17, 161.04, 158.19, 142.92, 142.20, 142.10, 142.01, 141.63, 140.23, 134.11, 133.73, 132.14, 128.66, 122.23, 120.49, 119.56, 112.49, 112.25, 104.75, 102.25, 88.62, 84.20, 57.44, 53.85, 53.03, 35.21, 23.41, 22.46, 22.40, 11.79.

Synthesis of N—((S)-1-(3-(3-amino-4-chloro-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-03bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (Intermediate 5D): A mixture of Intermediate 5C (88.0 mmol, 1.00 equiv), Intermediate 4 (105 mmol, 1.19 equiv), potassium bicarbonate (266 mmol, 3.03 equiv), palladium(II) chloride (1.3 mmol, 0.015 equiv), and cyclohexyldiphenylphosphine (2.7 mmol, 0.030 equiv) in 2-methyltetrahydrofuran (449 g) and water (130 g) was heated at 70° C. for 15 h and then cooled to 40° C. N-Acetyl-L-cysteine (19.5 g), water (202 g), NaOH (6.5 g), and EtOH (48.7 g) were added and the mixture was stirred for 1 h. The aqueous phase was removed and the organic phase was washed with a mixture of N-acetyl-L-cysteine (19.5 g), water (429 g), NaOH (6.5 g), and EtOH (48.8 g) followed by a solution of water (293 g) and sodium dihydrogen phosphate (32.5 g). A portion of the organic phase (97.5 g) was azeotropically distilled with additional 2-methyltetrahydrofuran, followed by solvent exchange into EtOH and distillation to a volume of about 4 ml/g. Methanesulfonic acid (39.1 mmol) and seed crystals of title compound Intermediate 5D (0.06 g) were added followed by di-n-butyl ether (86.3 g). The reaction was filtered and the filter cake was washed with twice with a mixture of di-n-butyl ether (24 g) and ethanol (5.0 g) and dried under vacuum to yield title compound Intermediate 5D. $^1$H NMR (400 MHz, DMSO-$d_6$) δ 9.19 (d, J=8.3 Hz, 2H), 7.84-7.69 (m, 4H), 7.11 (d, J=7.7 Hz, 2H), 7.07-6.95 (m, 3H), 6.82 (d, J=7.7 Hz, 2H), 6.54-6.40 (m, 4H), 4.90 (d, J=16.4 Hz, 2H), 4.76-4.60 (m, 4H), 4.15 (dq, J=16.6, 8.4 Hz, 2H), 3.75 (dt, J=16.3, 8.7 Hz, 2H), 3.25 (s, 7H), 2.99-2.86 (m, 4H), 2.63 2.50 (m, 3H), 2.41 (s, 14H), 1.73 (d, J=2.1 Hz, 13H), 0.93 (dd, J=6.1, 3.9 Hz, 2H).

Synthesis of N—((S)-1-(3-(3-amino-4-chloro-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (Intermediate 5E): A mixture of Intermediate 5D (17.8 mmol, 1.00 equiv) in 2-methyltetrahydrofuran (181 g) was washed with a solution of sodium carbonate (38 mmol, 2.1 equiv) in water (200 g). The aqueous phase was discarded and the organic phase was washed twice with a solution of sodium carbonate 38 mmol, 2.1 equiv) and sodium chloride (4.0 g) in water (200 g). The organic phase was azeotropically distilled with additional 2-methyltetrahydrofuran, followed by distillation to a volume of about 3 ml/g. Additional 2-methyltetrahydrofuran (240 g) was added, the temperature was adjusted to 10° C., and triethylamine (112 mmol, 6.3 equiv) and methanesulfonyl chloride (52 mmol, 2.9 equiv) were added. After 1.5 h, the mixture was washed with water (100 g). The organic phase was treated with a solution of sodium hydroxide (61 mmol, 3.4 equiv) in water (60 g) and warmed to 35° C. The aqueous phase was discarded and the organic phase was washed with water (60 g) and then azeotropically distilled with additional 2-methyltetrahydrofuran, followed by solvent exchange into EtOH and distillation to a volume of about 3 ml/g. Additional EtOH (32 g) was charged followed by n-heptane (69 g). The reaction was filtered and the filter cake was washed with a mixture of n-heptane (34 g) and ethanol (40 g) and dried under vacuum to yield title compound Intermediate 5E. $^1$H NMR (400 MHz, DMSO-d$_6$) δ 9.09 (d, J=8.0 Hz, 1H), 8.93* (d, J=8.5 Hz), 7.80-7.72* (m), 7.71 (s, 2H), 6.99 (tt, J=9.5, 2.4 Hz, 1H), 6.94 (d, J=7.6 Hz, 1H), 6.90* (d, J=6.3 Hz), 6.69 (d, J=7.6 Hz, 1H), 6.57-6.51* (m), 6.48-6.40 (m, 2H), 4.90 (d, J=16.5 Hz, 1H), 4.77 (d, J=16.4 Hz, 1H), 4.70 (td, J=8.3, 5.2 Hz, 1H), 4.63* (d, J=16.5 Hz), 4.22 (dq, J=16.7, 8.4 Hz, 1H), 3.90-3.75 (m, 1H), 3.26 (s, 3H), 2.92 (td, J=13.8, 8.5 Hz, 2H), 2.83* (s), 2.80 (s, 3H), 2.64-2.51 (m, 2H), 1.74 (d, J=2.2 Hz, 6H), 1.44-1.34 (m, 1H), 0.94 (dq, J=6.0, 3.7 Hz, 1H); $^{13}$C NMR (100 MHz, dmso) δ 164.39, 163.43, 163.39, 163.25, 160.94, 160.91, 160.81, 158.93, 158.22, 152.64, 151.94, 142.92, 142.72, 142.63, 142.43, 142.34, 142.19, 142.10, 142.00, 141.43, 141.14, 139.55, 139.36, 133.95, 133.56, 133.17, 132.12, 131.93, 131.68, 129.66, 129.56, 128.17, 127.91, 126.86, 126.76, 125.02, 122.35, 122.21, 122.08, 122.05, 119.93, 119.88, 119.38, 118.88, 118.18, 117.54, 117.21, 117.04, 112.18, 112.02, 111.95, 111.84, 111.78, 102.28, 102.03, 101.81, 88.14, 88.00, 84.69, 84.65, 57.33, 53.22, 52.96, 52.76, 52.44, 40.15, 39.94, 39.73, 39.52, 39.31, 39.10, 38.97, 38.89, 38.65, 35.10, 35.08, 27.86, 27.56, 27.52, 27.23, 23.19, 22.42, 22.41, 22.30, 22.28, 11.63. * Signals arising from minor atropisomer. $^{13}$C NMR data is reported for the mixture of atropisomers.

Synthesis of N—((S)-1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (Intermediate 5): Intermediate 5E (1.0 g) and glacial acetic acid (2.1 g) were combined at about 20° C. and were agitated until dissolved. The resultant solution was transferred to a reactor containing water (15 g) over about 1 hour. The resultant slurry was further agitated for about one hour, and was filtered. The filter cake was washed with water (2×5 g), deliquored, and dried at about 60° C. under vacuum to provide title compound Intermediate 5, which is also known as lenacapavir. $^1$H NMR (400 MHz, δ6-DMSO; 5:1 mixture of atropisomers) δ 10.11* (s), 10.00 (s, 1H), 9.25 (d, J=8.0 Hz, 1H), 8.92* (d, J=8.4 Hz), 7.90* (d, J=7.6 Hz), 7.81 (d, J=8.0 Hz, 1H), 7.76 (d, J=8.0 Hz, 1H), 7.32 (d, J=7.6 Hz, 1H), 7.23* (d, J=8.0 Hz), 7.19* (d, J=8.0 Hz), 7.02 (tt, J=9.4, 2.4 Hz, 1H), 6.94* (m), 6.86 (d, J=7.6 Hz, 1H), 6.54* (m), 6.48 (m, 2H), 4.92 (d, J=16.4 Hz, 1H), 4.77* (d, J=16.4 Hz), 4.71 (d, J=16.4 Hz, 1H), 4.68* (m), 4.51 (dq, J=16.4, 8.3 Hz, 1H), 4.19* (dq, J=16.4, 8.2 Hz), 3.96 (dq, J=16.8, 8.4 Hz, 1H), 3.27 (s, 3H), 3.24* (s), 3.17 (s, 3H), 3.11* (dd, J=13.0, 3.4 Hz), 3.02 (dd, J=13.6, 5.6 Hz, 1H), 2.95 (dd, J=13.8, 8.6 Hz, 1H), 2.92* (m), 2.60 (m, 1H), 2.55 (m, 1H), 1.74 (s, 6H), 1.40 (m, 1H), 0.96 (m, 1H); $^{13}$C NMR (100 MHz, δ6-DMSO; 5:1 mixture of atropisomers) δ 164.5, 163.4*, 162.1 (dd, J=246.0, 13.4 Hz), 162.0* (dd, J=246.1, 13.4 Hz), 158.8, 158.1*, 142.7 (t, J=29.3 Hz), 142.3, 142.1* (m), 141.9 (t, J=9.5 Hz), 141.7*, 140.2*, 140.0*, 139.8*, 139.5, 139.3, 139.2, 133.8 (q, J=38.7 Hz), 132.0 (m), 131.7*, 131.1, 130.3*, 130.0, 126.8, 126.4, 126.2*, 123.0* (m), 122.9 (q, J=281.7 Hz), 122.7*, 122.1, 120.7 (q, J=268.3 Hz), 119.9 (t, J=243.4 Hz), 119.0, 118.7*, 117.5*, 117.4, 112.0 (m), 102.1 (t, J=25.6 Hz), 101.9* (m), 88.5*, 88.4, 84.5, 57.3, 52.8, 52.7, 52.4*, 50.2 (q, J=33.3 Hz), 50.0 (m), 41.4*, 41.2, 39.8, 38.7, 35.1, 27.5 (dd, J=35.1, 29.0 Hz), 23.2, 22.4, 22.3, 22.2*, 11.6. * Signals arising from the minor atropisomer.

FINAL EXAMPLES

Example 1

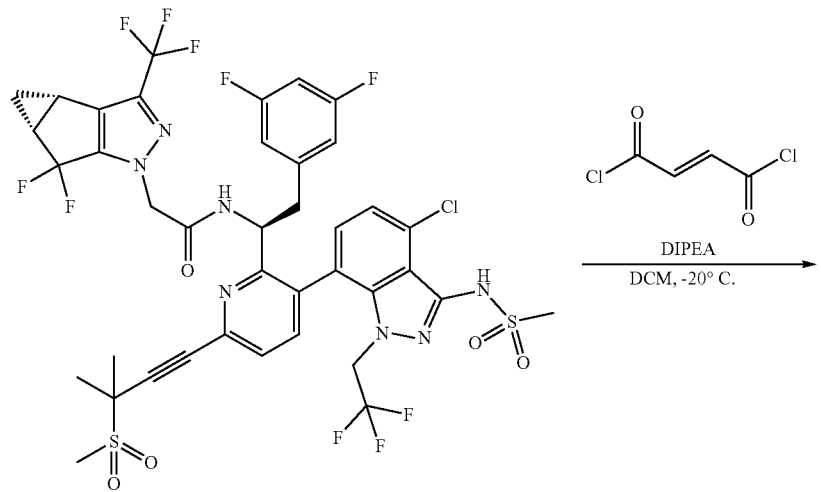

Intermediate 5

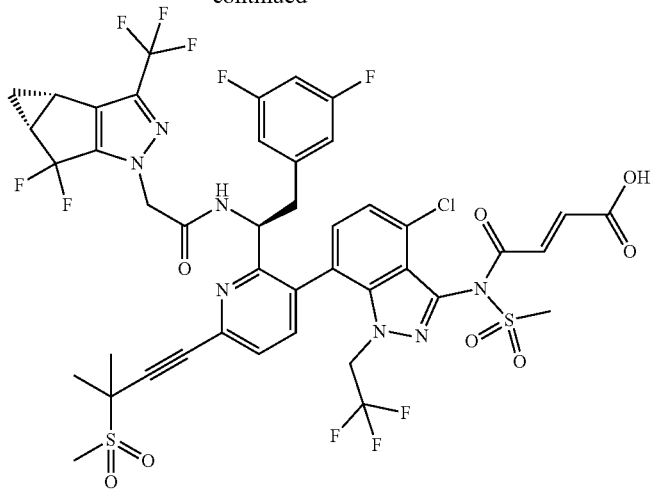

Synthesis of (E)-4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-4-oxobut-2-enoic acid (1): To a solution of fumaryl chloride (0.41 mmol, 1 equiv) in 3 mL of DCM at −20° C. was added a solution of Intermediate 5 (0.413 mmol) and DIPEA (12.9 mmol, 5 equiv). When full conversion was observed, the reaction was quenched with 1 mL of 1:1 MeCN:H$_2$O, then transferred to a separatory funnel using 20 mL of DCM and 50 mL of H$_2$O. The organic fraction was collected, dried over Na$_2$SO$_4$, concentrated under reduced pressure and purified by reverse phase HPLC. Fractions containing the product were pooled and lyophilized to give title compound 1 as a mixture of atropisomers. $^1$H NMR (400 MHz, DMSO-d$_6$) δ 8.87-8.80 (m), 8.74-8.64 (m), 7.97 (s), 7.92-7.65 (m), 7.41-7.28 (m), 7.26-7.19 (m), 6.92-6.79 (m), 6.82 6.68 (m), 6.68-6.54 (m), 6.56-6.46 (m), 6.41-6.35 (m), 6.31-6.23 (m), 6.27 (s), 4.81-4.66 (m), 4.61 (s), 4.14-3.94 (m), 3.61-3.53 (m), 3.50 (s), 3.26-3.20 (m), 3.13-3.03 (m), 3.06-2.86 (m), 2.88-2.83 (m), 2.48 (s), 1.84-1.78 (m), 1.46-1.35 (m) ppm. $^{19}$F NMR (375 MHz, DMSO-d$_6$) δ-63.54--63.69 (m), −71.75--71.93 (m), −72.41--72.58 (m), −78.26, −82.25-82.39 (m), −82.93--83.07 (m), −104.66--104.76 (m), −105.19--105.29 (m), −105.34--105.43 (m), −105.88--105.97 (m), −111.91, −112.06--112.30 (m) ppm. MS (m/z) 1066.67 [M+H]$^+$.

Example 2

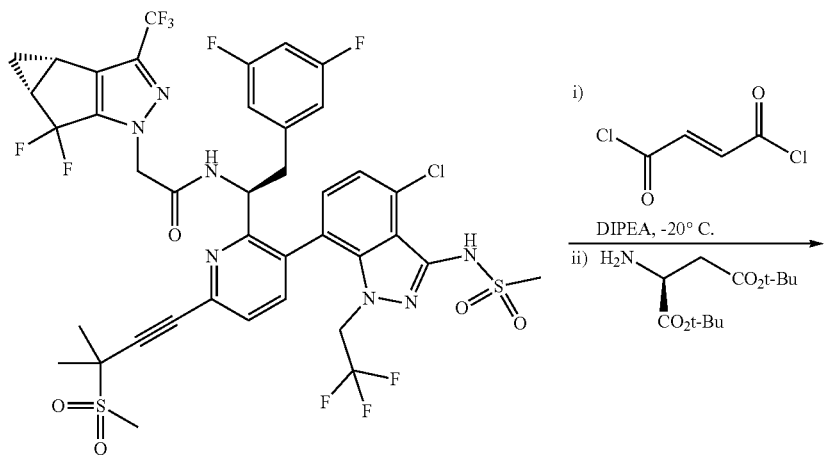

Intermediate 5

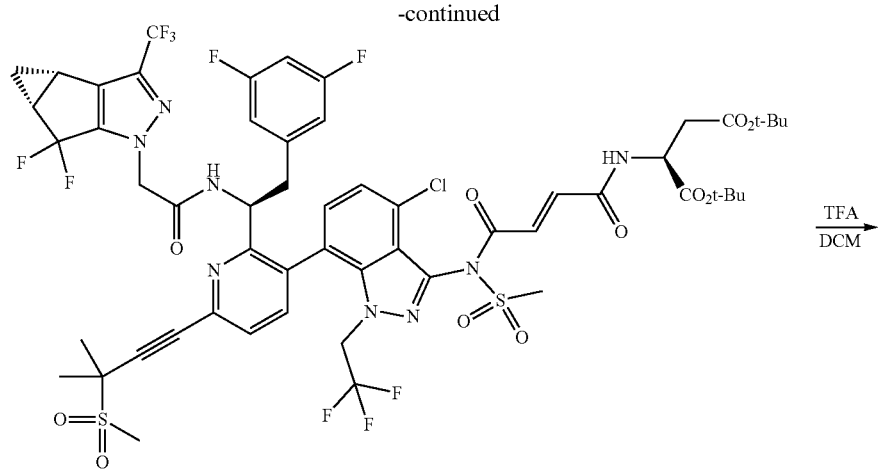

2A

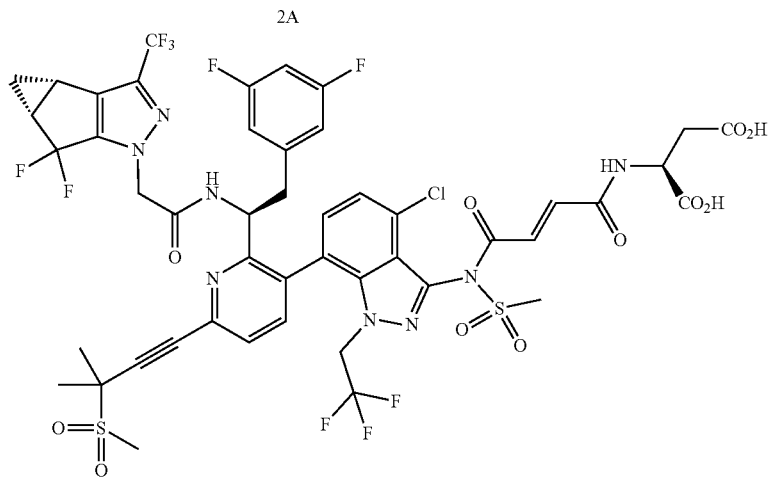

2

Synthesis of di-tert-butyl ((E)-4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-4-oxobut-2-enoyl)-L-aspartate (2A): To a solution of fumaryl chloride (2.07 mmol, 2 equiv) in 6 mL of DCM was added a 2 mL of a DCM solution containing DIPEA (5.16 mmol, 2 equiv) and Intermediate 5 (1.03 mmol, 1 equiv) at −20° C. over 5 minutes and stirred for a further 10 minutes. To the reaction was then added 5 mL of a DCM solution containing DIPEA (7.74 mmol, 3 equiv) and di-tert-butyl L-aspartate hydrochloride (3.1 mmol, 3 equiv.) as a single portion after which the reaction was gradually warmed to rt over 1 hour. Upon completion of this time, the reaction contents were transferred to a separatory funnel using DCM (100 mL) and the organic layer was successively washed with sat. NaHCO$_3$ (20 mL) and 1M HCl (20 mL). The organic fraction was collected, dried over Na$_2$SO$_4$, concentrated under reduced pressure, and purified by reverse phase HPLC. Fractions containing the product were pooled and lyophilized to give title compound 2A as a mixture of atropisomers. MS (m/z) 1294.61 [M+H]$^+$.

Synthesis of ((E)-4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol yl)acetamido)-2-(3,5-difluorophenyl)ethyl)-6-(3-methyl-3-(methylsulfonyl)but-1-yn yl)pyridin-3-yl)-1-(2,2,2-trifluoroethyl)-1H-indazol-3-yl)methylsulfonamido)-4-oxobut enoyl)-L-aspartic acid (2): To a solution of 2A (0.387 mmol) in 20 mL of DCM was added TFA (1 mL) at rt. When full conversion was observed, the reaction was concentrated under reduced pressure and purified by reverse phase HPLC. Fractions containing the product were pooled and lyophilized to give title compound 2 as a mixture of atropisomers. $^1$H NMR (400 MHz, DMSO-d$_6$) δ 9.20 (t), 9.03 (dd), 7.91-7.86 (m), 7.86-7.71 (m), 7.51 (d), 7.33-7.21 (m), 7.09-6.95 (m), 6.60-6.39 (m), 4.88 (d), 4.82-4.66 (m), 4.66-4.48 (m), 4.16 (m), 3.65 (s), 3.62 (s), 3.13-2.88 (m), 2.75-2.54 (m), 1.75 (d), 1.44-1.34 (m), 1.05-0.90 (m) ppm. $^{19}$F NMR (375 MHz, DMSO-d$_6$) δ-60.86 (d), −69.33--69.92 (m), −75.66, −79.64--81.09 (m), −102.75--103.38 (m), −103.43--104.06 (m), −110.40--110.97 (m) ppm. MS (m/z): 1181.11 [M+H]$^+$.

Example 3
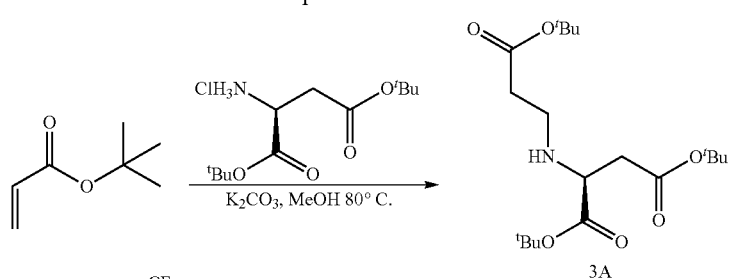
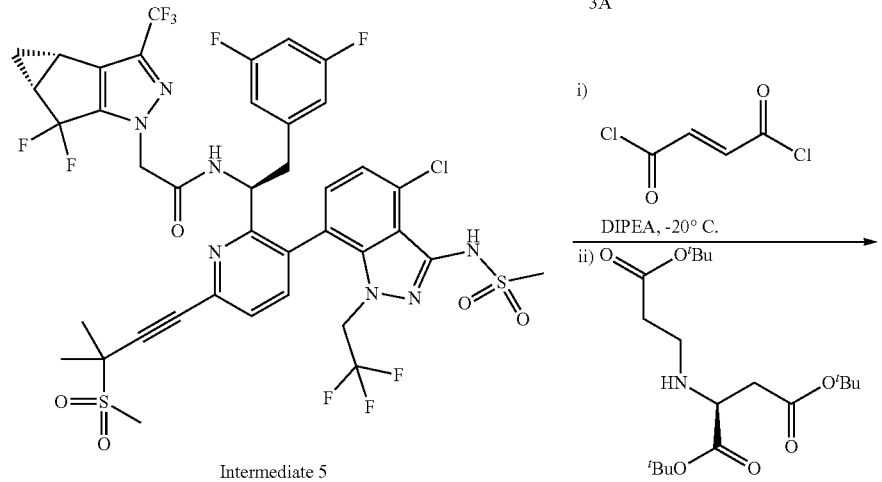
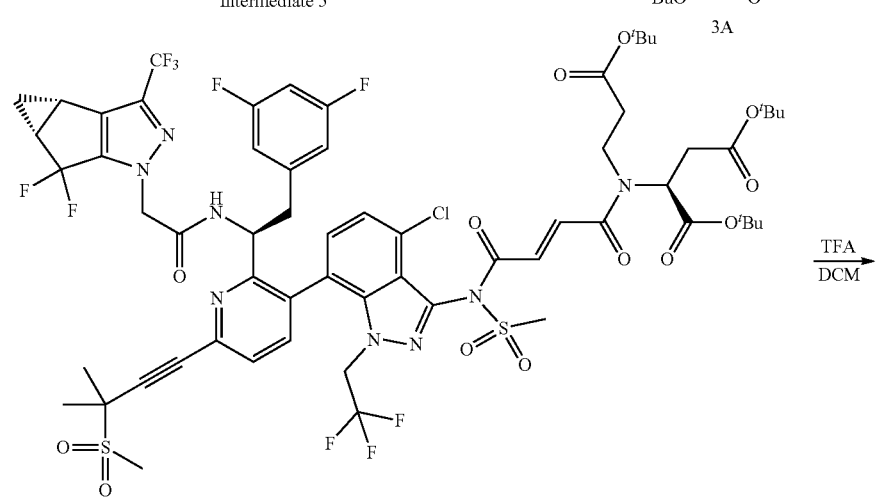
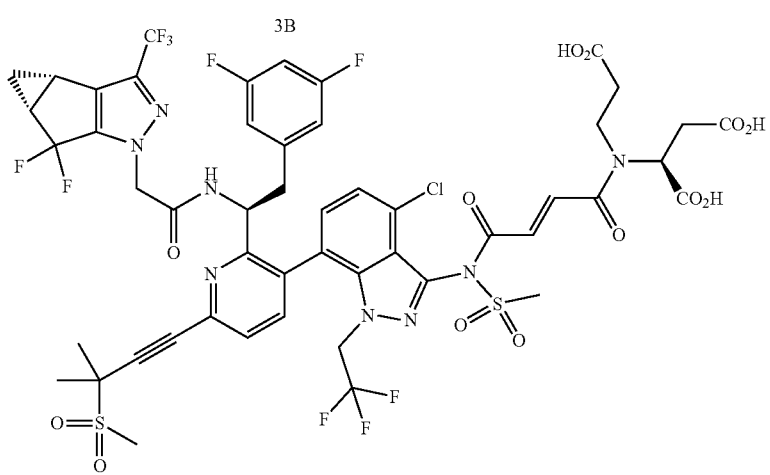

Synthesis of ditert-butyl (2S)-2-[(3-tert-butoxy-3-oxo-propyl)amino]butanedioate (3A): To a flask was added [(1S)-3-tert-butoxy-1-tert-butoxycarbonyl-3-oxo-propyl]ammonium chloride (28 mmol), tert-butyl acrylate (284 mmol), potassium carbonate (28 mmol), and MeOH (57 mL). The reaction was sealed, heated to 80° C., and stirred for 16 hours. Upon completion, the reaction was concentrated and dissolved in EtOAc (150 mL). The reaction was transferred to a separatory funnel and extracted with water (50 mL). The organic fraction was collected, dried over Na$_2$SO$_4$, concentrated, and purified with silica chromatography. Fractions containing the product were pooled and concentrated to yield title compound 3A. MS (m/z): 374.30 [M+H]$^+$.

Synthesis of di-tert-butyl N-(3-(tert-butoxy)-3-oxopropyl)-N—((E)-4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-4-oxobut-2-enoyl)-L-aspartate (3B): To a −20° C. solution of fumaryl chloride (6.2 mmol) and DCM (15 mL) was added a solution of 3A (3.1 mmol) and N,N-diisopropylethylamine (6.2 mmol) in DCM (15 mL). The reaction was sealed, cooled to −20° C., and stirred for 10 minutes. Then a solution of ditert-butyl (2S)-2-[(3-tert-butoxy-3-oxo-propyl)amino]butanedioate (9.3 mmol) and N,N-diisopropylethylamine (9.3 mmol) in DCM (15 mL) was added to the reaction. The reaction was sealed, cooled to −20° C., and stirred for 10 minutes. Upon completion, the reaction was diluted with DCM (250 mL). The reaction was transferred to a separatory funnel and extracted with water (100 mL) and 1M HCl (100 mL). The organic fraction was collected, dried over Na$_2$SO$_4$, and concentrated to yield title compound 3B as a mixture of atropisomers. MS (m/z): 1421.50 [M+H]$^+$.

Synthesis of N-(2-carboxyethyl)-N—((E)-4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-4-oxobut-2-enoyl)-L-aspartic acid (3): To a flask was added 3B (3.1 mmol) and 6:4 TFA/DCM (40 mL). The reaction was sealed and stirred for 1 hour. Upon completion, the reaction mixture was concentrated, diluted in DMF, filtered, and purified by reverse phase HPLC. Fractions containing the product were pooled and lyophilized to yield title compound 3 as a mixture of atropisomers. $^1$H NMR (400 MHz, CD3CN) δ 7.75 (dd), 7.65 (d), 7.55 (dd), 7.45 (d), 7.41-7.19 (m), 6.77 (td), 6.70 (d), 6.56-6.37 (m), 6.32 (t), 5.11-4.04 (m), 3.81-3.70 (m), 3.70-3.51 (m), 3.17 (s), 3.13-2.83 (m), 2.67-2.56 (m), 2.56-2.44 (m), 2.09 (s), 1.78 (s), 1.39 (p), 1.13-1.08 (m), 1.07-1.01 (m). $^{19}$F NMR (377 MHz, CD3CN) δ-62.55-62.78 (m), −69.98--72.46 (m), −77.35, −80.63--82.29 (m), −104.78 (ddd), −112.00 (d). MS (m/z): 1253.20 [M+H]$^+$.

Example 4

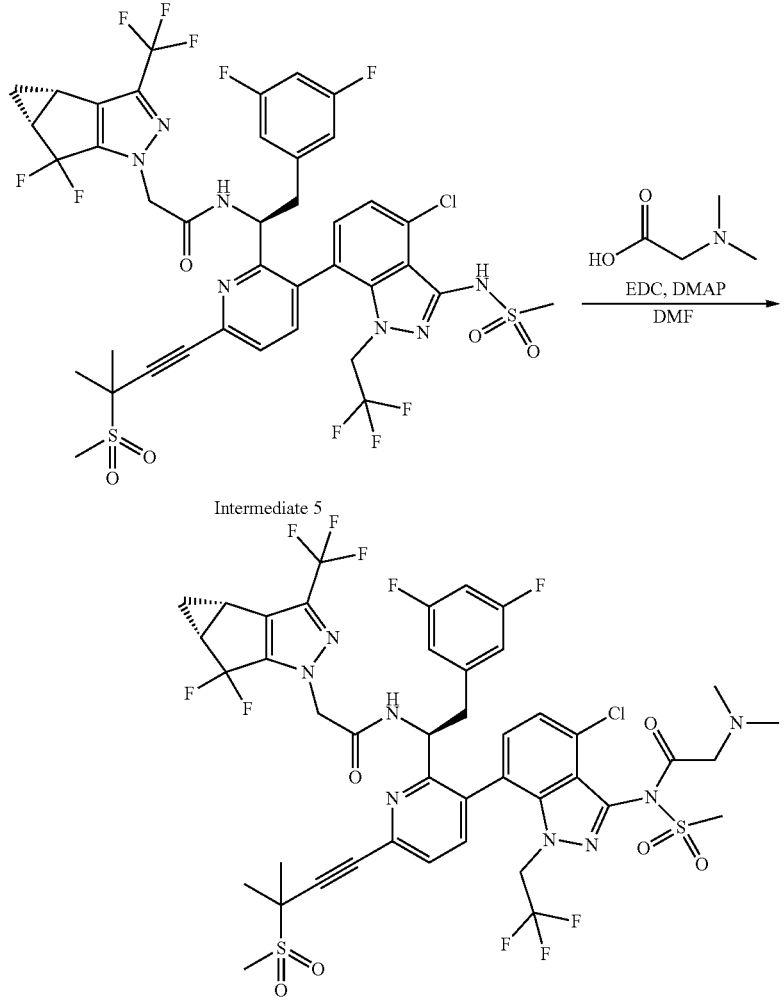

Synthesis of N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-2-(dimethylamino)-N-(methylsulfonyl)acetamide (4): To a solution of Intermediate 5 (0.124 mmol) and dimethylglycine (0.372 mmol) in DMF (1.5 ml) was added 1-(3-dimethylaminopropyl)-3-ethylcarbodiimide hydrochloride (0.372 mmol) and 4-(Dimethylamino)pyridine (0.372 mmol). The reaction was stirred at 60° C. Upon completion, the reaction was cooled to rt and poured into sat'd $NH_4Cl$ aqueous solution. The crude product was collected by vacuum filtration and purified by reverse phase HPLC. Fractions containing the product were pooled and lyophilized to give title compound 4 as a mixture of atropisomers. $^1$H NMR (400 MHz, Methanol-$d_4$) δ 9.11 (d, J=9.4 Hz), 8.13-7.87 (m), 7.84-7.61 (m), 7.51-7.10 (m), 6.97-6.51 (m), 6.41-6.13 (m,), 5.06-4.90 (m), 4.85-4.64 (m), 4.63-4.29 (m), 4.11-3.91 (m), 3.89-3.73 (m), 3.71-3.45 (m), 3.23 (s), 3.17-2.84 (m), 2.72 (s), 2.65-2.33 (m), 1.82 (d, J=2.4 Hz), 1.46 (q, J=7.1 Hz), 1.22-0.96 (m) ppm. MS (m/z) 1054.74 [M+H]$^+$.

Example 5

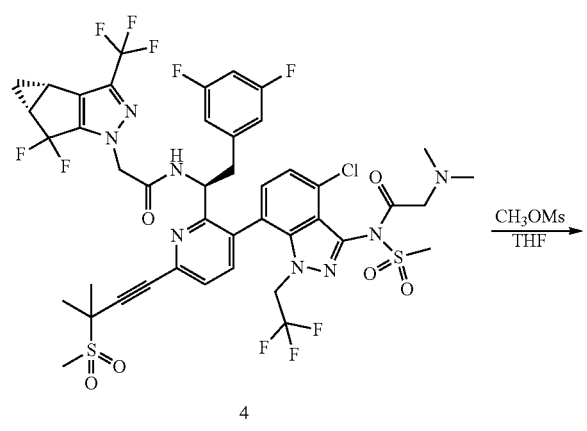

4

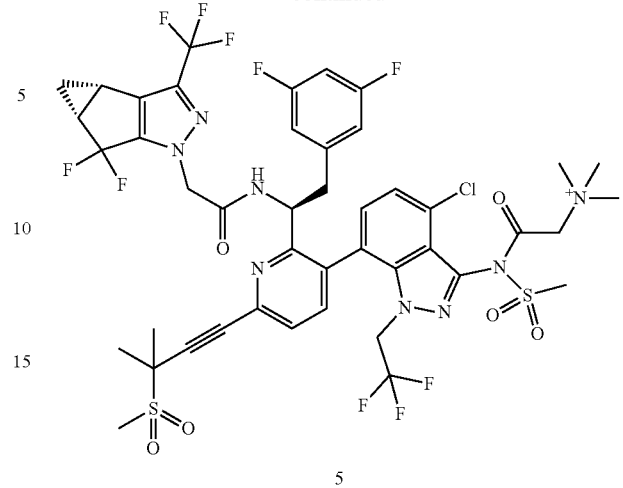

5

Synthesis of 2-(N-(4-chloro-7-(2-((S)-1-(2-((3bS,4aR)-5,5-difluoro (trifluoromethyl)-3b,4,4a,5-tetrahydro-1H-cyclopropa[3,4] cyclopenta[1,2-c]pyrazol yl)acetamido)-2-(3,5-difluorophenyl)ethyl)-6-(3-methyl-3-(methylsulfonyl)but-1-yn yl)pyridin-3-yl)-1-(2,2,2-trifluoroethyl)-1H-indazol-3-yl)methylsulfonamido)-N,N,N-trimethyl-2-oxoethan-1-aminium (5): To a solution of 4 (0.057 mmol) in THF (2 mL) was added methyl methanesulfonate (0.114 mmol) at rt. After two hours, more methyl methanesulfonate (0.114 mmol) was added and the reaction was heated to 65° C. for overnight. Upon completion, the reaction was concentrated under reduced pressure and the product was precipitated from diethyl ether to afford title compound 5 after collection by filtration. $^1$H NMR (400 MHz, Methanol-$d_4$) δ 9.09 (d, J=9.3 Hz), 8.08-7.60 (m), 7.56-7.18 (m), 6.94-6.59 (m), 6.29 (d, J=7.3 Hz), 5.19-4.87 (m), 4.72 (dd, J=15.6, 7.8 Hz), 4.60-4.21 (m), 4.22-3.78 (m), 3.67 (d, J=4.8 Hz), 3.58 (d, J=2.9 Hz), 3.49-3.34 (m), 3.22 (d, J=3.6 Hz), 3.15 (s, 9H), 3.12 (s), 3.09-2.71 (m), 2.69 (s), 2.66-2.33 (m), 1.81 (d, J=4.7 Hz), 1.57-1.35 (m), 1.15-0.91 (m) ppm. MS (m/z) 1067.30 [M+H]$^+$.

Example 6

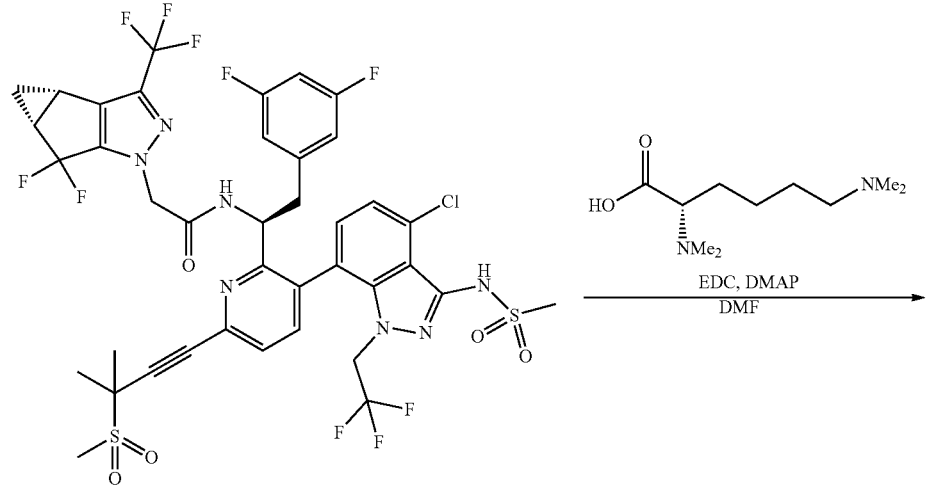

Intermediate 5

-continued

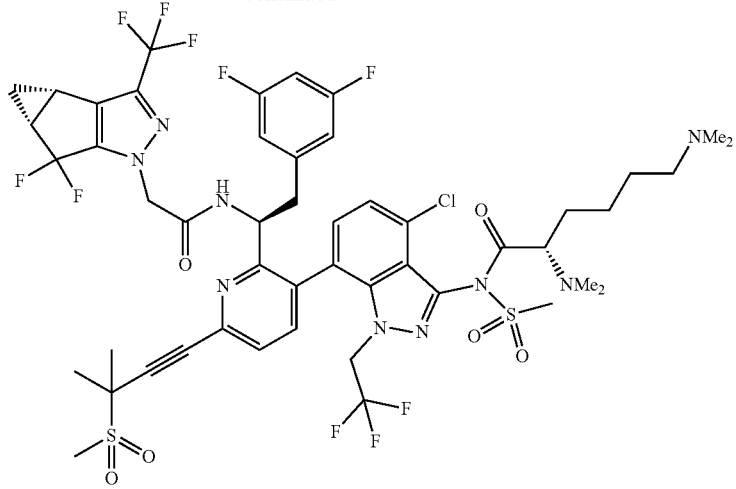

6

Synthesis of (S)—N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-2,6-bis(dimethylamino)-N-(methylsulfonyl)hexanamide (6): To a solution of Intermediate 5 (0.103 mmol), $N^2,N^2,N^6,N^6$-tetramethyl-L-lysine (0.310 mmol, 3 equiv), and DMAP (0.310 mmol, 3 equiv) in DMF (2 mL) was added EDC (0.310 mmol, 3 equiv). When the reaction had reached completion, the mixture was filtered then purified by reverse phase HPLC. Fractions containing the product were pooled and lyophilized to give title compound 6 as a mixture of atropisomers. $^1$H NMR (400 MHz, DMSO-d$_6$) δ 10.14 (s, 1H), 9.69 (s, 1H), 9.36-9.29 (m, 1H), 8.21 (s, 1H), 7.96 (s, 1H), 7.90-7.78 (m, 2H), 7.54-7.47 (m, 1H), 7.27 (s), 7.24-7.17 (m, 1H), 7.04-6.93 (m, 1H), 6.68-6.61 (m), 6.54-6.46 (m, 2H), 4.98-4.89 (m, 1H), 4.78-4.65 (m, 1H), 4.52-4.43 (m, 1H), 3.27 (s, 3H), 3.09-3.02 (m, 3H), 3.02-2.95 (m, 2H), 2.90 (s, 3H), 2.76 (d, J=20.0 Hz, 9H), 2.61 (s, 1H), 1.75 (s, 6H), 1.47-1.39 (m, 1H), 1.10 (s, 1H), 1.02-0.91 (m, 4H) ppm. $^{19}$F NMR (375 MHz, DMSO-d$_6$) δ-60.72--60.92 (m), −60.95, −69.09--69.24 (m), −69.56, −74.37, −75.63--75.84 (m), −79.81--79.98 (m), −80.49--80.65 (m), −103.73--103.93 (m), −110.99 ppm. MS (m/z) 1152.10 [M+H]$^+$.

Example 7

Synthesis of methyl ((S)-1-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-1-oxopropan-2-yl)carbamate (7): An atropisomeric mixture of the title compound was prepared according to the method presented for the synthesis of compound 6 of Example 6 utilizing Moc-L-alanine in the place of $N^2,N^2,N^6,N^6$-tetramethyl-L-lysine. $^1$H NMR (400 MHz, DMSO-d$_6$) δ 9.31-9.17 (m), 7.92-7.85 (m), 7.86-7.76 (m), 7.47-7.39 (m), 7.36-7.28 (m), 7.15-7.09 (m), 7.08-6.98 (m), 6.86-6.73 (m), 6.58-6.51 (m), 6.46-6.33 (m), 5.13-4.97 (m), 4.95-4.82 (m), 4.76-4.57 (m), 4.05-3.90 (m), 3.62-3.56 (m), 3.54 (s), 3.55-3.49 (m), 3.48 (s), 3.38-3.31 (m), 3.29 (s), 3.30-3.25 (m), 3.11-2.99 (m), 2.99-2.87 (m), 2.66-2.54 (m), 1.76 (s), 1.77-1.72 (m), 1.47-1.37 (m), 1.13-0.98 (m), 0.99-0.88 (m) ppm. $^{19}$F NMR (375 MHz, DMSO-d$_6$) δ-60.63--61.37 (m), −69.09--70.30 (m), −75.35, −79.66--80.01 (m), −80.26-80.68 (m), −102.79, −103.47, −110.56--111.21 (m) ppm. MS (m/z) 1098.82 [M+H]$^+$.

Example 8

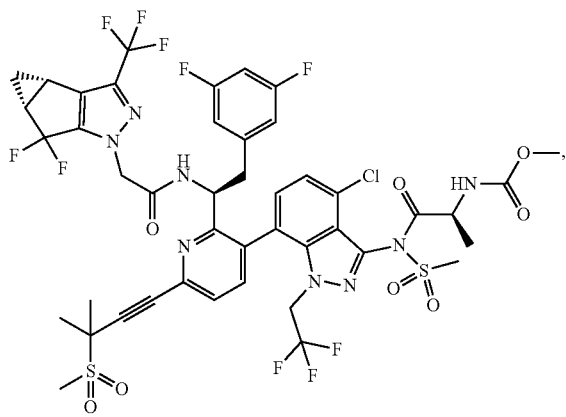

7

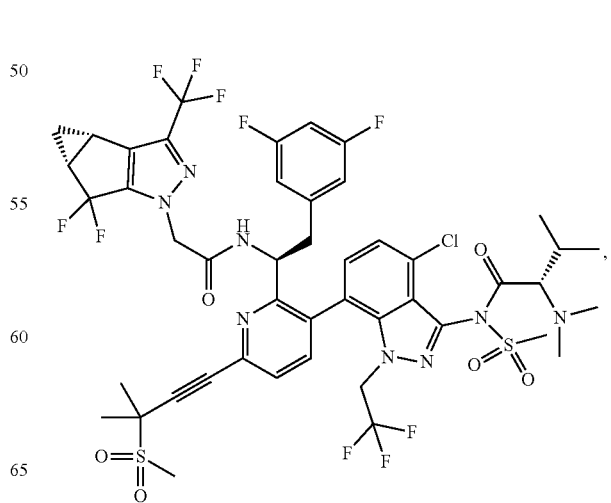

8

Synthesis of N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-2-(dimethylamino)-3-methyl-N-(methylsulfonyl)butanamide (8): An atropisomeric mixture of the title compound was prepared according to the method presented for the synthesis of compound 6 of Example 6 utilizing N,N-dimethyl-L-serine in the place of $N^2,N^2,N^6,N^6$-tetramethyl-L-lysine. $^1$H NMR (400 MHz, Methanol-d$_4$) δ 9.32 (d), 7.94 (dd), 7.88-7.77 (m), 7.56-7.43 (m), 6.91-6.81 (m), 6.39 6.25 (m), 4.77-4.61 (m), 4.01 (dq), 3.82-3.72 (m), 3.67-3.61 (m), 3.37 (s), 3.26 (s), 3.08 (dd), 3.02-2.88 (m), 2.69 (s), 2.62-2.48 (m), 2.18 (h), 2.05 (s), 1.87-1.79 (m), 1.55-1.38 (m), 1.19 (dq), 1.16-1.03 (m) ppm. $^{19}$F NMR (375 MHz, Methanol-d$_4$) δ-63.40--63.73 (m), −70.96 (t), −71.92, −72.42 (t), −77.85, −81.70 (d), −82.25--82.72 (m), −105.07 (d), −105.76 (d), −111.76--112.26 (m) ppm. MS (m/z): 1096.146 [M+H]$^+$.

utilizing 2,5,8,11,14-pentaoxahexadecan-16-oic acid in the place of $N^2,N^2,N^6,N^6$-tetramethyl-L-lysine. $^1$H NMR (400 MHz, Methanol-d$_4$) δ 8.98-8.84 (m), 7.89-7.70 (m), 7.74-7.65 (m), 7.42-7.15 (m), 6.84-6.67 (m), 6.62-6.44 (m), 6.37-6.24 (m), 4.92-4.52 (m), 4.18-4.03 (m), 4.02-3.72 (m), 3.66-3.46 (m), 3.50-3.37 (m), 3.41-3.31 (m), 3.26-3.20 (m), 3.19-3.01 (m), 3.02-2.87 (m), 2.61-2.44 (m), 1.85-1.79 (m), 1.48-1.37 (m), 1.32-1.26 (m), 1.11-0.99 (m) ppm. MS (m/z): 1217.55 [M+H]$^+$.

Example 10

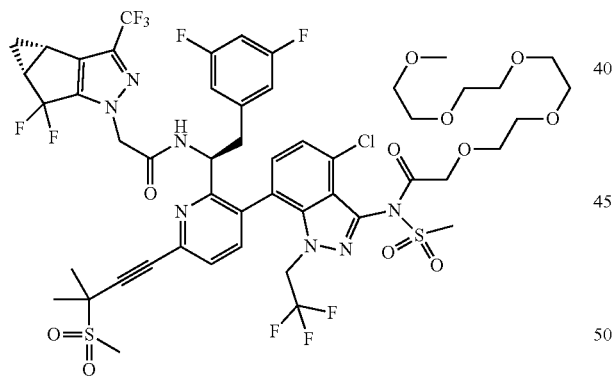

10

Example 9

9

Synthesis of methyl 4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-4-oxobutanoate (10): An atropisomeric mixture of the title compound was prepared according to the method presented for the synthesis of compound 6 of Example 6 utilizing succinic acid mono-methyl ester in the place of $N^2,N^2,N^6,N^6$-tetramethyl-L-lysine. $^1$H NMR (400 MHz, DMSO-d$_6$) δ 9.17 (dd), 7.93 (d), 7.82 (d), 7.49 (t), 7.07-6.96 (m), 6.90 (d), 6.45 (ddd), 4.96 (d), 4.91-4.74 (m), 4.70-4.50 (m), 3.98 (dt), 3.28 (s), 3.07-2.84 (m), 2.44-2.32 (m), 2.24 (dd), 1.75 (d), 1.41 (q), 0.98 (s). ppm. $^{19}$F NMR (375 MHz, DMSO-d$_6$) δ-60.94 (d), −69.55 (t), −69.92 (t), −74.87, −79.83 (dd), −80.50 (dd), −103.25 (dd), −103.92 (dd), −110.74 (dt) ppm. MS (m/z) 1082.50 [M+H]$^+$.

Synthesis of N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn yl)pyridin-3-yl)-1-(2,2,2-trifluoroethyl)-1H-indazol-3-yl)-N-(methylsulfonyl)-2,5,8,11,14-pentaoxahexadecan-16-amide (9): An atropisomeric mixture of the title compound was prepared according to the method presented for the synthesis of compound 6 of Example 6

Example 11

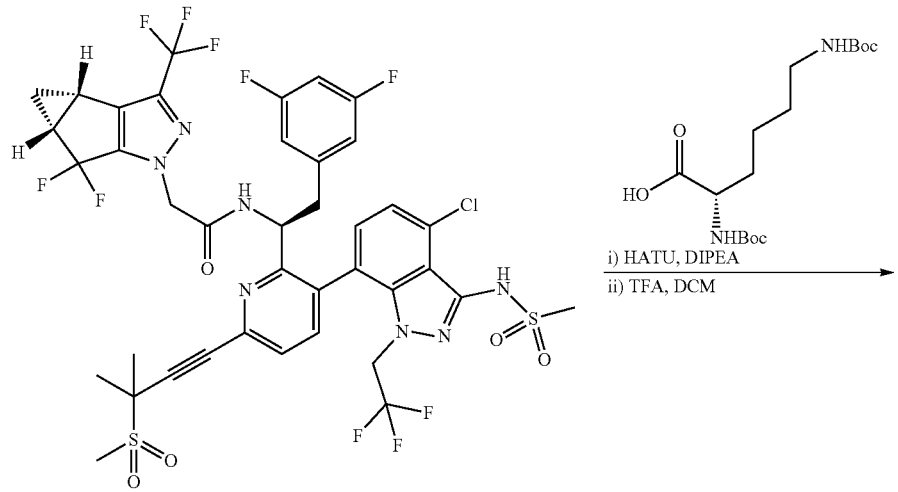

Intermediate 5

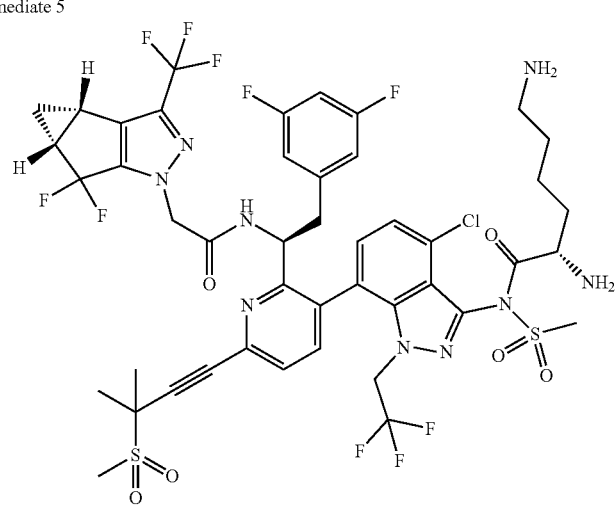

11

Synthesis of (S)-2,6-diamino-N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-N-(methylsulfonyl)hexanamide (11): To a solution of Intermediate 5 (0.0516 mmol) and Boc-L-Lys-(Boc)-OH (0.103 mmol) in 1 mL of DMF was added HATU (0.155 mmol) and DIPEA (0.258 mmol). The reaction was stirred at rt overnight then diluted with DCM (1 mL) and added TFA (1 mL). Upon completion, the reaction was filtered and purified by reverse phase HPLC. Fractions containing the product were pooled and lyophilized to give title compound 11 as a mixture of atropisomers. $^1$H NMR (400 MHz, Methanol-$d_4$) δ 7.96-7.65 (m), 7.56-7.13 (m), 6.93-6.70 (m), 6.66 (m), 6.49 (d), 6.29 (dd), 5.00-4.53 m), 4.49-3.82 (m), 3.68 (d), 3.57 (s), 3.47 (s), 3.22 (q), 3.17-2.64 (m), 2.63-2.38 (m), 2.07-1.88 (m), 1.81 (d), 1.72-1.57m), 1.58-1.36 (m), 1.33-0.93 (m) ppm. MS (m/z) 1096.15 [M+H]$^+$.

Example 12

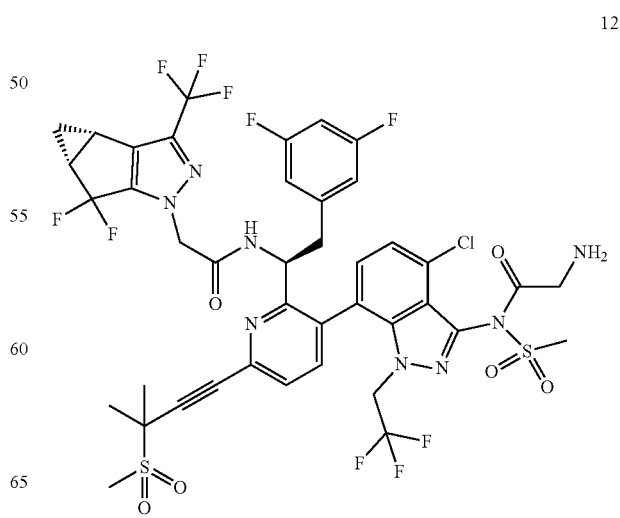

12

Synthesis of 2-amino-N-(4-chloro-7-(2-((S)-1-(2-((3bS,4aR)-5,5-difluoro (trifluoromethyl)-3b,4,4a,5-tetrahydro-1H-cyclopropa[3,4]cyclopenta[1,2-c]pyrazol yl)acetamido)-2-(3,5-difluorophenyl)ethyl)-6-(3-methyl-3-(methylsulfonyl)but-1-yn yl)pyridin-3-yl)-1-(2,2,2-trifluoroethyl)-1H-indazol-3-yl)-N-(methylsulfonyl) acetamide (12): An atropisomeric mixture of the title compound was prepared according to the method presented for the synthesis of compound 11 of Example 11 utilizing using Boc-Gly-OH in the place of Boc-L-Lys-(Boc)-OH. $^1$H NMR (400 MHz, Methanol-$d_4$) δ 9.08 (d), 8.91 (d), 7.82 (d), 7.71 (dd), 7.54-7.06 (m), 6.85-6.75 (m), 6.69 (d), 6.58 (d), 6.38-6.08 (m), 4.83-4.48 (m), 4.07 (dt), 4.00-3.69 (m), 3.68-3.46 (m), 3.22 (s), 3.09 (ddd), 2.92 (dt), 2.67-2.35 (m), 1.81 (d), 1.61-1.30 (m), 1.05 (s) ppm. MS (m/z) 1025.04 [M+H]$^+$.

Example 13

Synthesis of 2-((2-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-oxoethyl)amino)-2-oxoacetic acid (13): To a solution of 12 (0.006 mmol) in DCM (0.5 mL) was added DIPEA (0.088 mmol) followed by tert-butyl-2-chloro-2-oxoacetate (0.053 mmol) and the resulting mixture was stirred for 10 mins. Trifluoroacetic acid (0.653 mmol) was then added with a further 10 mins stirring at which time the reaction was diluted with 1:1 H$_2$O:MeCN (1 mL). The reaction contents were then transferred to a separatory funnel with DCM (15 mL) and washed once with 1M HCl (20 mL). The organic fraction was collected, dried over Na$_2$SO$_4$, concentrated under reduced pressure, and purified by reverse phase HPLC. Fractions containing the product were pooled and lyophilized to give title compound 13 as a mixture of atropisomers. $^1$H NMR (400 MHz, Methanol-$d_4$) δ 9.11 (d), 7.81 (d), 7.73 (d), 7.25 (d), 6.84-6.74 (m), 6.46 (d), 6.29 (d), 3.88 (td), 3.79 (d), 3.68-3.51 (m), 3.45 (s), 3.32-3.16 (m),

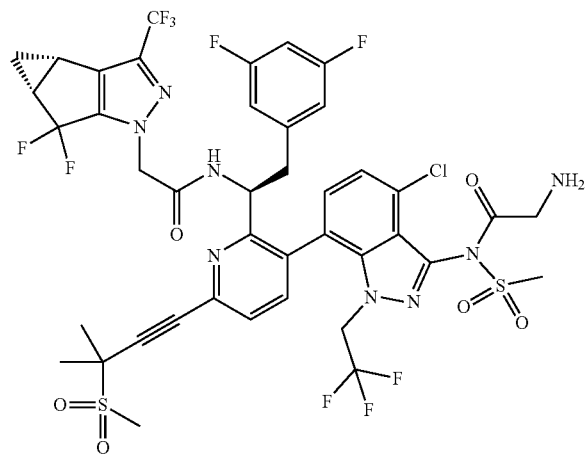

12

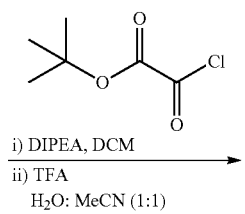

i) DIPEA, DCM
ii) TFA
H$_2$O: MeCN (1:1)

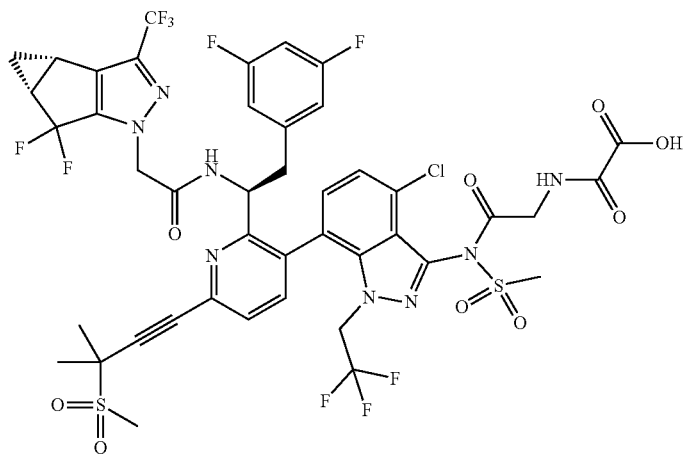

13

3.05-2.95 (m), 1.84 (d), 1.47 (q), 1.20 (t), 1.07 (d) ppm. $^{19}$F NMR (375 MHz, Methanol-$d_4$) δ -63.56, -63.62 (d), -63.65, -72.24, -72.62 (t), -77.65, -82.36, -83.07, -105.76 (d), -106.45 (d), -112.44 (t) ppm. MS (m/z) 1097.401 [M+H]$^+$.

Example 14

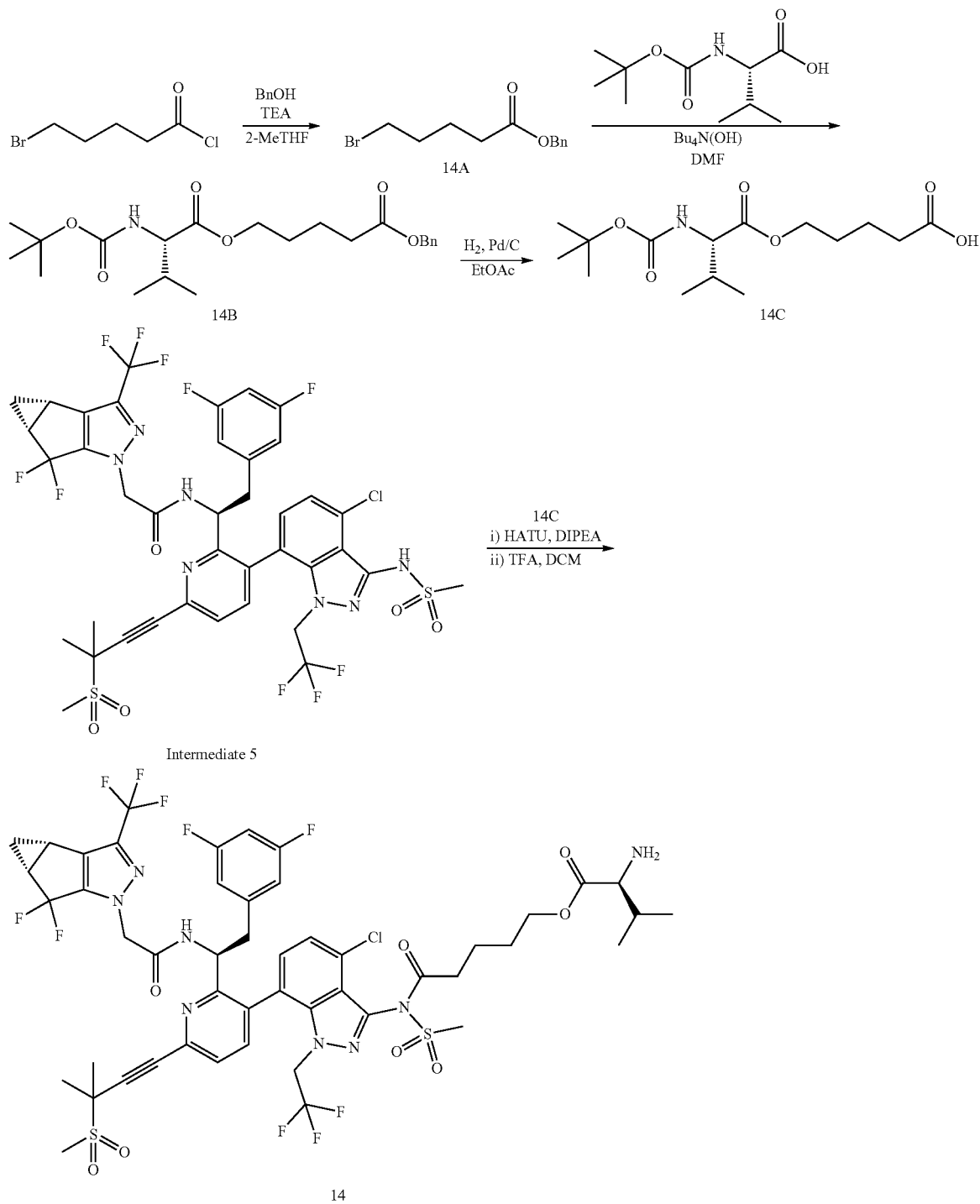

Synthesis of benzyl 5-bromopentanoate (14A): A mixture of benzyl alcohol (2.59 mL, 25.1 mmol), triethylamine (25.1 mmol) and 2-methyl THF (3 mL) was cooled to 0° C. 5-Bromopentanoyl chloride (25.1 mmol) was added dropwise over 5 minutes. Stirring was continued at 0° C. for 30 min and then at ambient temperature overnight. The mixture was diluted with ethyl acetate (50 mL), washed with water and brine, and evaporated under reduced pressure, then purified by silica gel chromatography. Fractions containing the product were pooled and concentrated to give title compound 14A.

Synthesis of benzyl 5-(((tert-butoxycarbonyl)-L-valyl)oxy)pentanoate (14B): Boc-L-valine (5.98 mmol) was dissolved in 1,4-dioxane (5 mL). Tetrabutylammonium hydroxide (40% solution in water, 5.98 mmol) was added. The mixture was evaporated under vacuum and azeotroped four times with toluene. The residue was dissolved in DMF (15 mL) and 14A (4.79 mmol) was added. The mixture was stirred at ambient temperature for two days, then diluted with ethyl acetate (100 mL), washed with water and brine, placed under reduced pressure, then purified by silica gel chromatography (eluting with 0-50% ethyl acetate/hexane). Fractions containing the product were pooled and concentrated to give title compound 14B.

Synthesis of 5-(((tert-butoxycarbonyl)-L-valyl)oxy)pentanoic acid (14C): 14B (3.94 mmol) was dissolved in 20 mL ethyl acetate and 20 mL ethanol. Palladium on carbon (0.2 g) was added and the mixture was stirred under an atmosphere of hydrogen for 20 minutes. After purging with nitrogen, the mixture was filtered through a pad of Celite®. The reaction was evaporated under reduced pressure to yield title compound 14C, which was used without purification. $^1$H NMR (400 MHz, CDCl$_3$) δ 5.05 (d, J=9.2 Hz, 1H), 4.23-4.11 (m, 3H), 2.43-2.35 (m, 2H), 2.17-2.04 (m, 1H), 1.76-1.66 (m, 4H), 1.43 (s, 9H), 0.92 (d, 6.9 Hz, 3H), 0.88 (d, 6.9 Hz, 3H) ppm.

Synthesis of ((1s,3R)-3-amino-N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-N-(methylsulfonyl) cyclobutane-1-carboxamide) (14): An atropisomeric mixture of the title compound was prepared according to the two-step method presented for the synthesis of compound 11 of Example 11 utilizing using compound 14C in the place of Boc-L-Lys-(Boc)-OH. $^1$H NMR (400 MHz, DMSO-d$_6$) δ 9.07 (d), 8.29-8.21 (m), 7.99-7.72 (m), 7.48-7.22 (m), 7.03-6.85 (m), 6.60-6.31 (m), 5.00-4.51 (m), 4.16-3.85 (m), 3.51 (s), 2.99-2.84 (m), 2.59-2.49 (m), 2.24-1.84 (m), 1.63-1.24 (m), 0.98-0.87 (m) ppm. MS (m/z): 1167.31 [M+H]$^+$.

Example 15

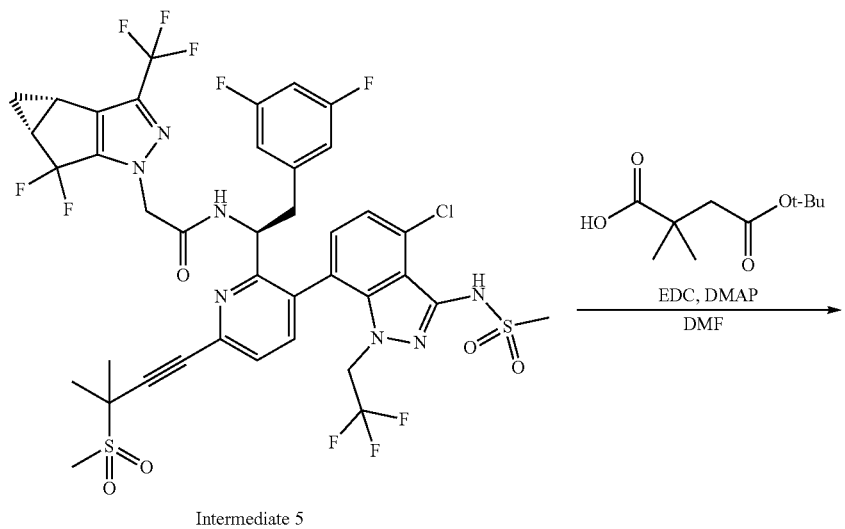

Intermediate 5

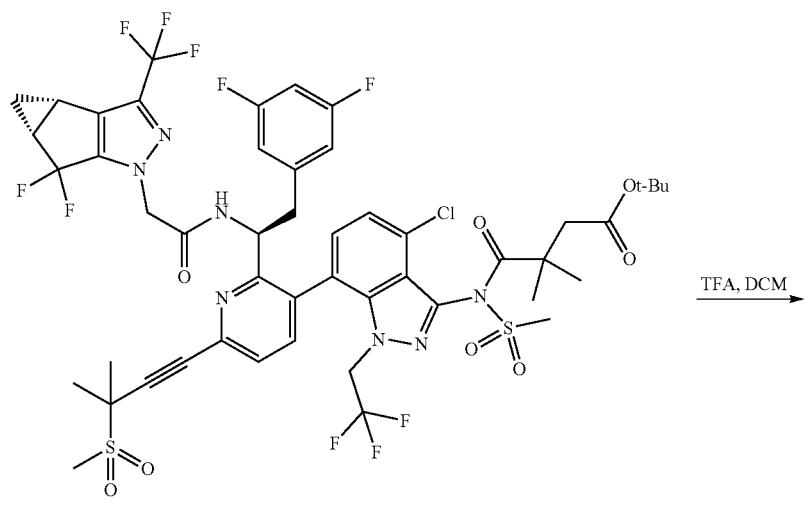

15A

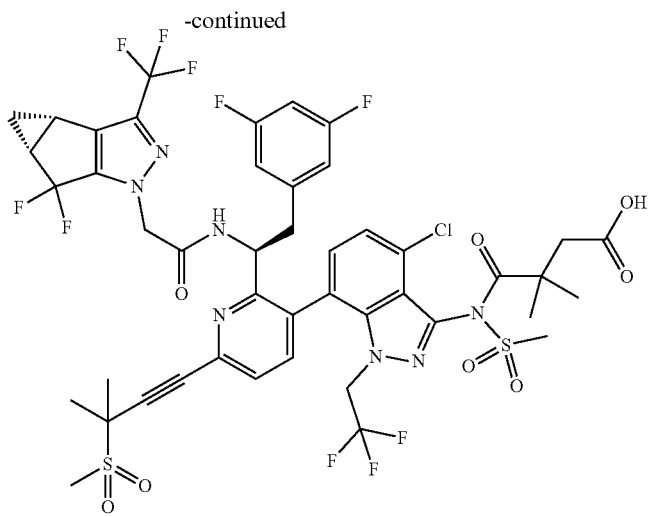

15

Synthesis tert-butyl 4-(N-(4-chloro-7-(2-((S)-1-(2-((3bS,4aR)-5,5-difluoro (trifluoromethyl)-3b,4,4a,5-tetrahydro-1H-cyclopropa[3,4]cyclopenta[1,2-c]pyrazol yl)acetamido)-2-(3,5-difluorophenyl)ethyl)-6-(3-methyl-3-(methylsulfonyl)but-1-yn yl)pyridin-3-yl)-1-(2,2,2-trifluoroethyl)-1H-indazol-3-yl)methylsulfonamido)-3,3-dimethyl-4-oxobutanoate (15A): To a solution of Intermediate 5 (0.103 mmol), 3-tert-butoxy-2,2-dimethyl-4-oxobutanoic acid (0.310 mmol, 3 equiv), and DMAP (0.310 mmol, 3 equiv) in DMF (2 mL) was added EDC (0.310 mmol, 3 equiv). When the reaction had reached completion, the mixture was filtered then purified by reverse phase HPLC. Fractions containing the product were pooled and lyophilized to give title compound 15A as a mixture of atropisomers. MS (m/z) 1095.4 [M−tBu]⁺.

Synthesis of 4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-3,3-dimethyl-4-oxobutanoic acid (15): To a solution of 15A (0.052 mmol) in DCM (2 mL) was added trifluoroacetic acid (0.1 mL) with stirring. When full conversion was observed, the reaction was concentrated under reduced pressure and purified by reverse phase HPLC. Fractions containing the product were pooled and lyophilized to give title compound 15 as a mixture of atropisomers. $^1$H NMR (400 MHz, DMSO-d$_6$) δ 10.01 (s), 9.22 (dd), 9.08 (d), 7.98 (d), 7.94-7.78 (m), 7.77 (d), 7.50 (dd), 7.36-7.16 (m), 7.09-6.91 (m), 6.87 (d), 6.58-6.46 (m), 6.47 (d), 6.35-6.27 (m), 5.07-4.83 (m), 4.82-4.44 (m), 3.98 (dq), 3.62-3.50 (m), 3.31-3.21 (m), 3.17 (s), 3.07 2.80 (m), 2.58 (dt), 2.13 (s), 1.78-1.72 (m), 1.41 (q), 1.33 (s), 1.16 (s), 1.15-1.04 (m), 1.02 0.93 (m), 0.74 (d) ppm. $^{19}$F NMR (375 MHz, DMSO-d$_6$) δ-60.77-−61.01 (m), −69.41 (t, J=8.5 Hz), −69.55-−69.91 (m), −70.12 (t, J=8.5 Hz), −74.94, −79.82 (d, J=12.7 Hz), −80.24 (d, J=12.8 Hz), −80.48 (t, J=14.6 Hz), −80.91 (d, J=13.1 Hz), −102.48 (d, J=10.9 Hz), −102.61, −103.11 (dd, J=32.6, 10.3 Hz), −103.76 (t, J=9.9 Hz), −110.51-−110.64 (m), −110.72-−111.01 (m) ppm. MS (m/z) 1097.30 [M+H]⁺.

Example 16

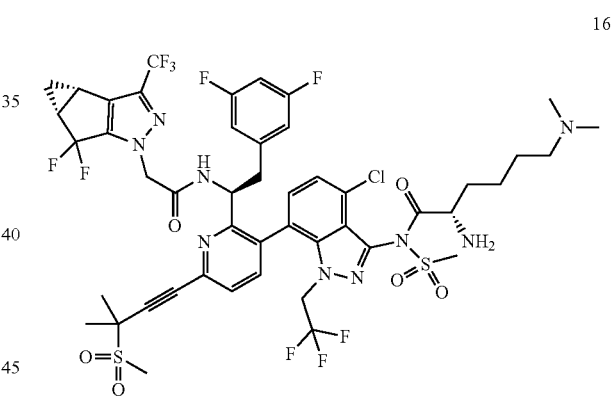

16

Synthesis of ((S)-2-amino-N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol yl)acetamido)-2-(3,5-difluorophenyl)ethyl)-6-(3-methyl-3-(methylsulfonyl)but-1-yn yl)pyridin-3-yl)-1-(2,2,2-trifluoroethyl)-1H-indazol-3-yl)-6-(dimethylamino)-N-(methylsulfonyl)hexanamide) (16): An atropisomeric mixture of the title compound was prepared according to the two-step method presented for the synthesis of compound 15 of Example 15 utilizing (2S)-2-(tert-butoxycarbonylamino)-6-(dimethylamino)hexanoic acid in the place of 3-tert-butoxy-2,2-dimethyl-4-oxobutanoic acid. $^1$H NMR (400 MHz, Methanol-d$_4$) δ 9.14-8.95 (m), 7.95-7.76 (m), 7.75 (dt), 7.54-7.35 (m), 6.88-6.63 (m), 6.35 (d), 6.28 (d), 4.18 (dt), 3.72 (s), 3.65-3.53 (m), 3.26 (d), 3.25 (s), 3.20-2.94 (m), 2.89 (d), 2.67 (s), 2.55 (d), 1.84 (s), 1.46 (dt), 1.17-1.03 (m) ppm. MS (m/z): 1124.55 [M+H]⁺.

Example 17

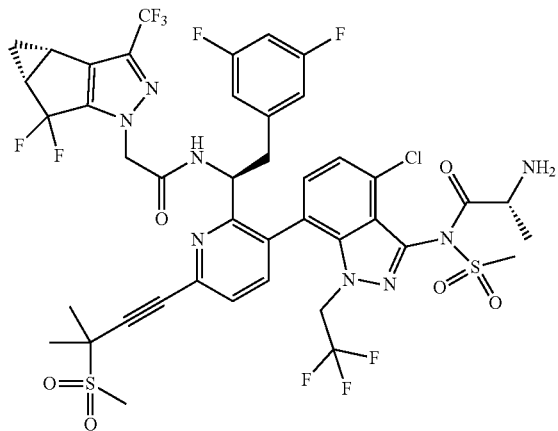

17

Synthesis of ((S)-2-amino-N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-N-(methylsulfonyl)propenamide) (17): An atropisomeric mixture of the title compound was prepared according to the two-step method presented for the synthesis of compound 15 of Example 15 utilizing (2R)-2-(tert-butoxycarbonylamino)propanoic acid in the place of 3-tert-butoxy-2,2-dimethyl-4-oxobutanoic acid. $^1$H NMR (400 MHz, Methanol-$d_4$) δ 9.10 (d), 8.98 (d), 7.97-7.67 (m), 7.39 (d), 6.82 (tt), 6.73 (d), 6.30 (h), 4.76 (d), 4.60-4.46 (m), 4.23 ( ), 4.05 (ddt), 3.88 (d), 3.75 (d), 3.63 (d), 3.54 (s), 3.26 (s), 3.17-3.04 (m), 3.04-2.86 (m), 2.75 (d), 2.54 (d), 1.85 (d), 1.84 (s), 1.84 (s), 1.47 (dt), 1.08 (s), 1.17-1.04 (m) ppm. MS (m/z): 1040.54 [M+H]$^+$.

Example 18

18

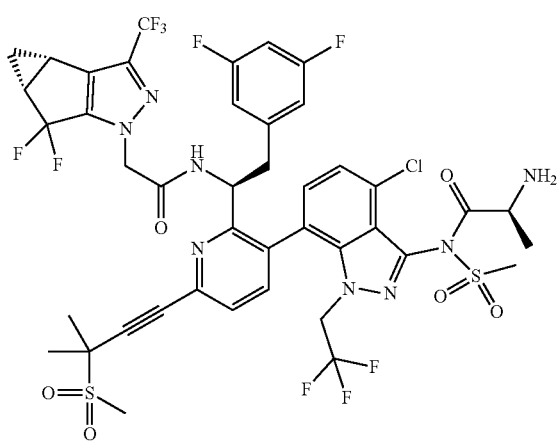

Synthesis of (S)-2-amino-N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-N-(methylsulfonyl)propenamide (18): An atropisomeric mixture of the title compound was prepared according to the two-step method presented for the synthesis of compound 15 of Example 15 utilizing N-(tert-butoxycarbonyl)-L-alanine in the place of 3-tert-butoxy-2,2-dimethyl-4-oxobutanoic acid. $^1$H NMR (400 MHz, DMSO-$d_6$) δ 9.32-9.21 (m), 8.43 (s), 7.91-7.75 (m), 7.59-7.53 (m), 7.50-7.42 (m), 7.12-6.98 (m), 6.84-6.77 (m), 6.51-6.43 (m), 5.06-4.97 (m), 4.93-4.84 (m), 4.83-4.70 (m), 4.72-4.58 (m), 4.46 (s), 4.12-3.97 (m), 3.85 (s), 3.28 (s), 3.30-3.25 (m), 3.16-3.06 (m), 3.02-2.92 (m), 2.64-2.58 (m), 1.76 (s), 1.77-1.72 (m), 1.49-1.35 (m), 1.20 1.07 (m), 1.01-0.94 (m) ppm. $^{19}$F NMR (375 MHz, DMSO-$d_6$) δ-60.62--61.12 (m), -69.34-69.98 (m), -74.09--74.45 (m), -79.53--79.97 (m), -80.21--80.65 (m), -102.83, -103.50, -110.56 ppm. MS (m/z) 1039.51 [M+H]$^+$.

Example 19

19

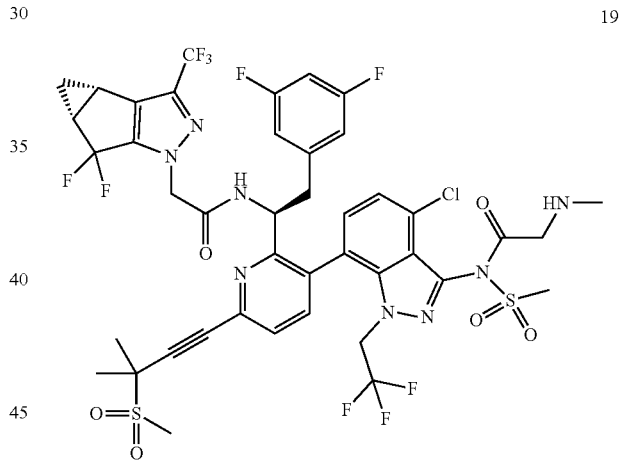

Synthesis of (N-(4-chloro-7-(2-((S)-1-(2-((3bS,4aR)-5,5-difluoro (trifluoromethyl)-3b,4,4a,5-tetrahydro-1H-cyclopropa[3,4]cyclopenta[1,2-c]pyrazol yl)acetamido)-2-(3,5-difluorophenyl)ethyl)-6-(3-methyl-3-(methylsulfonyl)but-1-yn yl)pyridin-3-yl)-1-(2,2,2-trifluoroethyl)-1H-indazol-3-yl)-2-(methylamino)-N-(methylsulfonyl)acetamide) (19): An atropisomeric mixture of the title compound was prepared according to the two-step method presented for the synthesis of compound 15 of Example 15 utilizing 2-[tert-butoxycarbonyl(methyl)amino]acetic acid in the place of 3-tert-butoxy-2,2-dimethyl-4-oxobutanoic acid. $^1$H NMR (400 MHz, Methanol-$d_4$) δ 9.10 (d), 8.98 (dd), 7.97-7.67 (m), 7.39 (dd), 6.82 (tt), 6.73 (dd), 6.30 (h), 4.76 (d), 4.60-4.46 ( ), 4.23 (s), 4.05 (ddt), 3.88 ( ), 3.75 (d), 3.63 (d), 3.54 (s), 3.26 (s), 3.17-3.04 (m), 3.04-2.86 (m), 2.75 (d), 2.54 (d), 1.85 (d), 1.84 (s), 1.84 (s), 1.47 (dt), 1.08 (s), 1.17-1.04 (m) ppm. MS (m/z): 1039.23 [M+H]$^+$.

Example 20

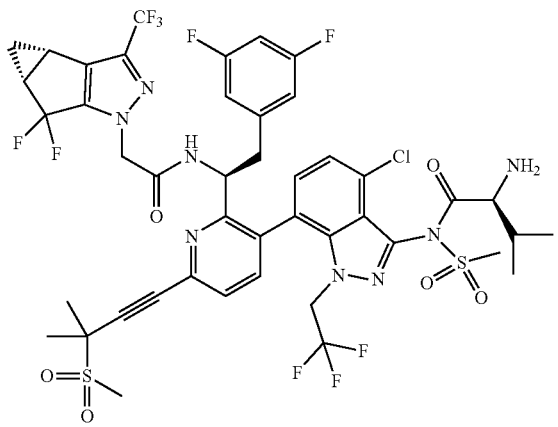

20

Synthesis of (S)-2-amino-N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-3-methyl-N-(methylsulfonyl)butanamide (20): An atropisomeric mixture of the title compound was prepared according to the two-step method presented for the synthesis of compound 15 of Example 15 utilizing N-(tert-butoxycarbonyl)-L-valine in the place of 3-tert-butoxy-2,2-dimethyl-4-oxobutanoic acid. $^1$H NMR (400 MHz, Methanol-$d_4$) δ 9.12 (d), 7.87-7.78 (m), 7.74 (dd), 7.42 (dd), 6.87-6.65 (m), 6.36-6.29 (m), 4.76 (d), 4.11 (tt), 3.85 (d), 3.65 (s), 3.52 (s), 3.25 (d), 3.18-3.11 (m), 3.01 (ddd), 2.90 (dd), 2.55 (ddd), 2.34-2.24 (m), 2.12 (d), 1.84 (d), 1.45 (dq), 1.04 (t), 0.90 (d), 0.78 (d), 0.63 (d) ppm. $^{19}$F NMR (375 MHz, Methanol-$d_4$) δ−63.47--63.69 (m), −71.61 (t), −72.24 (t), −72.48 (t), −77.86, −77.72--77.98 (m), −82.40 (t), −83.08 (t), −105.23 (t), −105.92 (d), −111.96--112.30 (m) ppm. MS (m/z) 1067.628 [M+H]$^+$.

Example 21

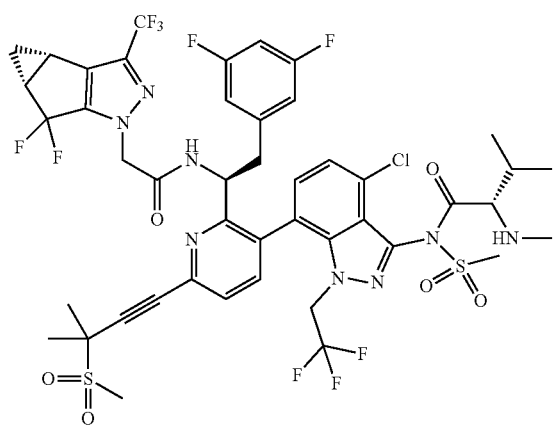

21

Synthesis of N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-3-methyl-2-(methylamino)-N-(methylsulfonyl)butanamide (21): An atropisomeric mixture of the title compound was prepared according to the two-step method presented for the synthesis of compound 15 of Example 15 utilizing N-(tert-butoxycarbonyl)-N-methyl-L-valine in the place of 3-tert-butoxy-2,2-dimethyl-4-oxobutanoic acid. $^1$H NMR (400 MHz, Methanol-$d_4$) δ 7.81 (td), 7.78-7.68 (m), 7.49-7.36 (m), 6.81 (dtt), 6.43-6.35 (m), 5.50 (s), 4.12 (q), 3.69 (s), 3.46 (s), 3.25 (t), 2.75 (d), 2.60-2.46 (m), 2.04 (d), 1.84 (d), 1.50-1.38 (m), 1.26 (t), 1.05 (dd), 0.98-0.88 (m), 0.74 (d) ppm. $^{19}$F NMR (375 MHz, Methanol-$d_4$) δ−63.39--63.66 (m), −71.38 (t), −71.80--72.19 (m), −72.31 (t), −77.58--78.41 (m), −78.00, −82.07--82.68 (m), −82.99 (dd), −104.88--105.48(m), −105.71--106.16 (m), −111.85--112.41 (m) ppm. MS (m/z) 1081.465 [M+H]$^+$.

Example 22

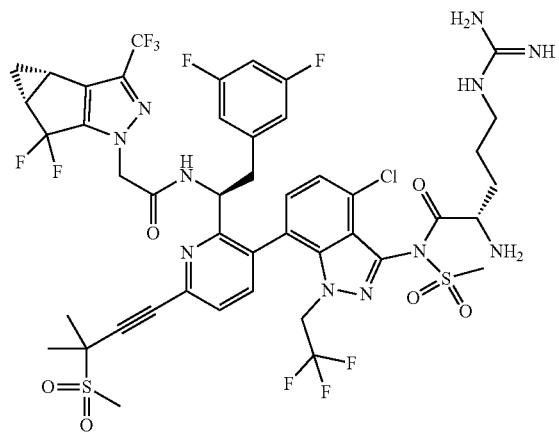

22

Synthesis of 2-amino-N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol yl)acetamido)-2-(3,5-difluorophenyl)ethyl)-6-(3-methyl-3-(methylsulfonyl)but-1-yn yl)pyridin-3-yl)-1-(2,2,2-trifluoroethyl)-1H-indazol-3-yl)-5-guanidino-N-(methylsulfonyl)pentanamide (22): An atropisomeric mixture of the title compound was prepared according to the two-step method presented for the synthesis of compound 15 of Example 15 utilizing (S,E)-5-(2,3-Bis(tert-butoxycarbonyl)guanidino)-2-((tert-butoxycarbonyl)amino)pentanoic acid in the place of 3-tert-butoxy-2,2-dimethyl-4-oxobutanoic acid. $^1$H NMR (400 MHz, Methanol-$d_4$) δ 9.23 (d), 7.84 (d), 7.73 (dd), 7.46 (d), 7.40 (dt), 6.87 (d), 6.80 (t), 6.71-6.61 (m), 6.26 (d), 6.19 (d), 4.16 (dt), 3.66 (s), 3.63-3.56 (m), 3.49 (s), 3.22 (d), 3.16-2.84 (m), 2.50 (d), 1.81 (s), 1.79-1.48 (m), 1.44 (dt), 1.04 (s) ppm. MS (m/z): 1124.357 [M+H]$^+$.

Example 23

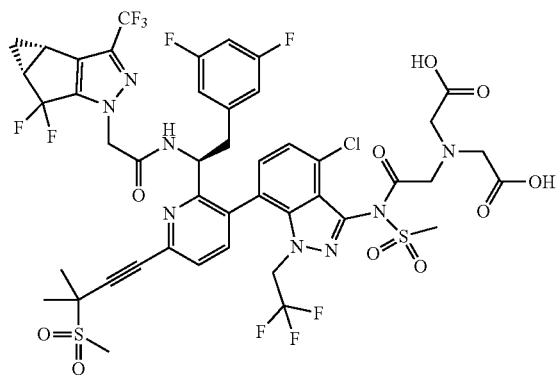

Synthesis of 2,2'-((2-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-3-(methylsulfonyl)ureido)propane-1,3-diyl)bis(oxy))bis(2-oxoacetic acid) (23): An atropisomeric mixture of the title compound was prepared according to the two-step method presented for the synthesis of compound 15 of Example 15 utilizing 2-(Bis(2-(tert-butoxy)-2-oxoethyl)amino)acetic acid in the place of 3-tert-butoxy-2,2-dimethyl-4-oxobutanoic acid. $^1$H NMR (400 MHz, DMSO-$d_6$) δ 9.20 (dd), 7.96 (s), 7.89-7.72 (m), 7.33 (t), 7.02 (dd), 6.61 (d), 6.44 (ddd), 4.92 (dd), 4.79-4.65 (m), 4.65-4.50 (m), 3.61-3.51 (m), 3.46 (s), 3.34 (d), 3.27 (d), 2.99 (ddt), 2.90 (s), 2.74 (s), 1.78-1.71 (m), 1.40 (p), 1.00 (d) ppm. $^{19}$F NMR (375 MHz, DMSO-$d_6$) δ-60.86 (t), −69.34-−69.76 (m), −70.05 (t), −75.26, −79.70 (dd), −80.37 (dd), −102.80 (d), −103.21 (d), −103.47 (d), −103.89 (d), −110.58 (q), −110.78 (dt) ppm. MS (m/z) 1141.974 [M+H]$^+$.

Example 24

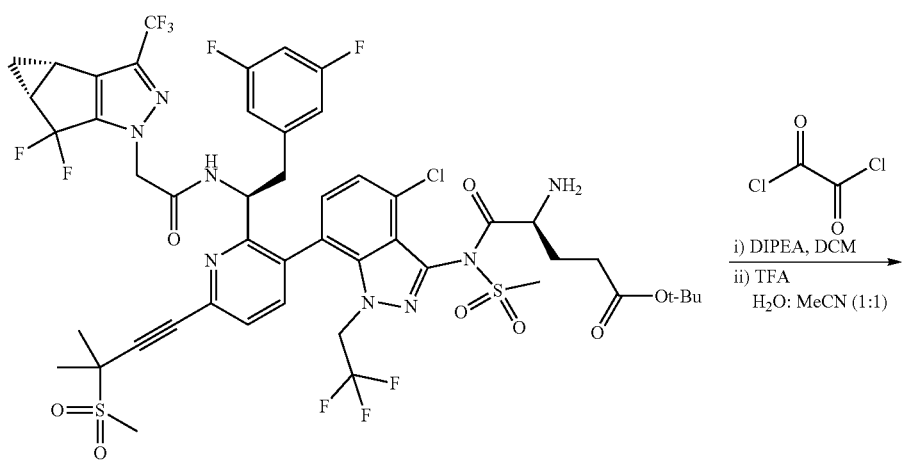

24A

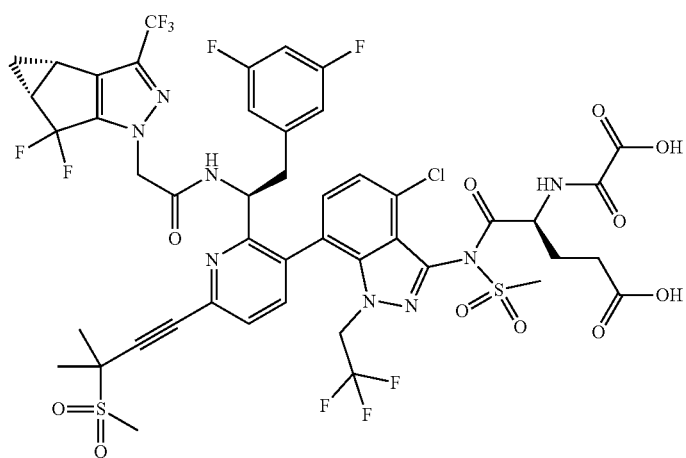

24

Synthesis of tert-butyl (S)-4-amino-5-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-5-oxopentanoate (24A): An atropisomeric mixture of the title compound was prepared according to the two-step method presented for the synthesis of compound 15 of Example 15 utilizing (S)-5-(tert-butoxy)-2-((tert-butoxycarbonyl)amino)-5-oxopentanoic acid in the place of 3-tert-butoxy-2,2-dimethyl-4-oxobutanoic acid. MS (m/z) 1153.41 [M+H]+.

Synthesis of (S)-4-(carboxyformamido)-5-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-5-oxopentanoic acid (24): To a solution of 24A (0.087 mmol) in DCM (4 mL) at −78° C. was added oxalyl chloride (0.173 mmol) followed by DIPEA (0.173 mmol, 2 equiv) and the resulting mixture was stirred for 10 mins. Trifluoroacetic acid (0.653 mmol) was then added with a further 10 mins stirring at which time the reaction was diluted with 1:1 H2O:MeCN (1 mL). The reaction contents were then transferred to a separatory funnel with DCM (15 mL) and washed once with 1M HCl (20 mL). The organic fraction was collected, dried over Na2SO4, concentrated under reduced pressure, and purified by reverse phase HPLC. Fractions containing the product were pooled and lyophilized to give title compound 24 as a mixture of atropisomers. $^1$H NMR (400 MHz, Methanol-$d_4$) δ 10.01 (s), 9.28-9.16 (m), 9.19-9.11 (m), 9.07-8.89 (m), 7.99-7.71 (m), 7.51-7.37 (m), 7.38-7.15 (m), 7.09-6.91 (m), 6.90-6.83 (m), 6.67-6.49 (m), 6.54-6.42 (m), 5.05-4.79 (m), 4.83-4.58 (m), 4.63-4.54 (m), 4.58-4.45 (m), 4.28-4.18 (m), 3.61 (s), 3.55 (s), 3.30-3.21 (m), 3.17 (s), 3.04-2.93 (m), 2.60 (s), 2.32-2.26 (m), 2.29-2.05 (m), 2.01-1.87 (m), 1.79-1.72 (m), 1.46-1.35 (m), 1.24 (s), 1.06-0.99 (m), 0.96 (s) ppm. $^{19}$F NMR (375 MHz, Methanol-$d_4$) δ −60.73−−60.96 (m), −69.00−−69.11 (m), −69.13−−69.24 (m), −69.35−−69.51 (m), −69.62−−69.73 (m), −69.87−−69.96 (m), −70.00−−70.12 (m), −74.72, −79.71−−79.87 (m), −80.05, −80.38-80.55 (m), −80.73, −103.02−−103.11 (m), −103.25, −103.69−−103.79 (m), −103.87−−103.97 (m), −110.58−−110.69 (m), −110.69−−110.81 (m), −110.88−−111.00 (m) ppm. MS (m/z) 1168.96 [M+H]+.

Example 25

25

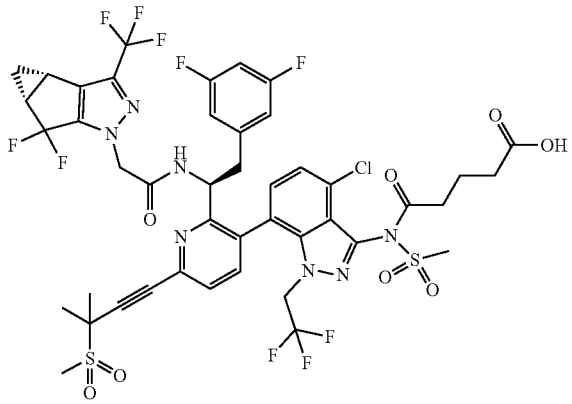

Synthesis of 5-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-5-oxopentanoic acid (25): An atropisomeric mixture of title compound was prepared according to the two-step method presented for the synthesis of compound 15 of Example 15 utilizing 5-(tert-butoxy)-5-oxopentanoic acid in the place of 3-tert-butoxy-2,2-dimethyl-4-oxobutanoic acid. $^1$H NMR (400 MHz, CD$_3$OD) δ 7.86-7.79 (m), 7.80-7.67 (m), 7.37-7.28 (m), 7.30-7.17 (m), 6.84-6.74 (m), 6.59-6.46 (m), 6.35-6.28 (m), 4.80 (s), 4.76-4.67 (m), 4.65-4.57 (m), 4.02-3.91 (m), 3.49 (s), 3.28-3.23 (m), 3.15-3.05 (m), 3.01-2.91 (m), 2.57-2.48 (m), 2.44 2.36 (m), 2.36-2.27 (m), 2.25-2.07 (m), 2.00-1.81 (m), 1.44 (s), 1.31 (s), 1.11-1.02 (m) ppm. $^{19}$F NMR (375 MHz, DMSO-$d_6$) δ-63.56, −63.65, −72.24−−72.31 (m), −72.49−−72.59 (m), −77.49, −82.42, −83.10, −112.23, −112.31−−112.39 (m) ppm. MS (m/z) 1082.18 [M+H]+.

Example 26

26

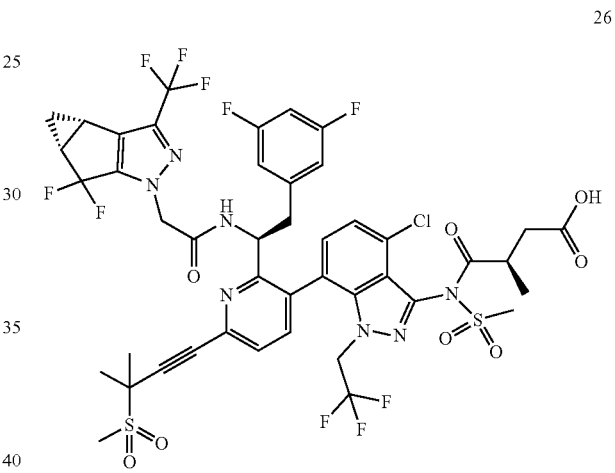

Synthesis of (R)-4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-3-methyl-4-oxobutanoic acid (26): An atropisomeric mixture of title compound was prepared according to the two-step method presented for the synthesis of compound 15 of Example 15 utilizing (R)-4-(tert-butoxy)-2-methyl-4-oxobutanoic acid in the place of 3-tert-butoxy-2,2-dimethyl-4-oxobutanoic acid. $^1$H NMR (400 MHz, DMSO-$d_6$) δ 10.01 (s), 9.36-9.16 (m), 7.93-7.73 (m), 7.41-7.30 (m), 7.29-7.16 (m), 7.10-7.00 (m), 6.93-6.85 (m), 6.64-6.38 (m), 5.00-4.83 (m), 4.83-4.43 (m), 4.17 (dd, J=14.7, 6.7 Hz), 4.07-3.87 (m), 3.32-3.19 (m), 3.17 (s), 3.13 2.87 (m), 2.75-2.66 (m), 2.66-2.54 (m), 1.79-1.70 (m), 1.46-1.35 (m), 1.30-1.21 (m), 1.04-0.93 (m), 0.91-0.81 (m) ppm. $^{19}$F NMR (375 MHz, DMSO-$d_6$) δ−60.78−−60.96 (m), −61.03, −69.27−−69.46 (m), −69.68 (t, J=8.5 Hz), −69.75−−69.94 (m), −75.04, −79.72−−79.87 (m), −79.95−−80.13 (m), −80.39−−80.54 (m), −80.62−−80.80 (m), −102.84−−102.92 (m), −103.02−−103.11 (m), −103.19−103.28 (m), −103.51−−103.60 (m), −103.70−−103.78 (m), −103.87−−103.95 (m), −110.51−−110.61 (m), −110.62−−110.80 (m), −110.89−−110.96 (m), −111.14−−111.22 (m) ppm. MS (m/z) 1082.11 [M+H]+.

Example 27

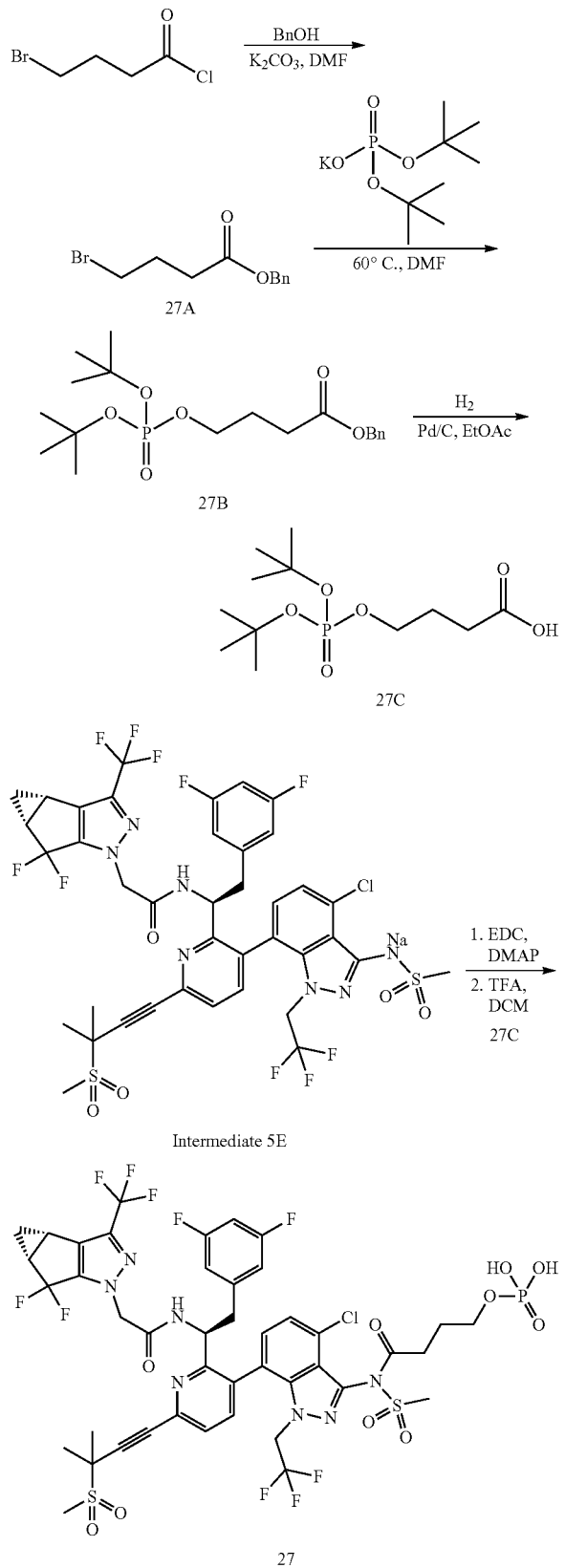

Synthesis of benzyl 4-bromobutanoate (27A): To a solution of 4-bromobutanoyl chloride (27.8 mmol) in 60 mL of DCM was added benzyl alcohol (28.7 mmol, 1.05 equiv) and K2CO₃ (30.2 mmol 1.1 equiv). The reaction mixture was allowed to stir overnight at rt. When completion was determined by TLC, the reaction mixture was transferred to a separatory funnel using DCM (100 mL) and washed sequentially with water and brine (100 mL each). The organic fraction was collected, dried over Na₂SO₄ and concentrated under reduced pressure to yield title compound 27A which was used without further purification. MS (m/z): 257.12 [M+H]⁺.

Synthesis of benzyl 4-((di-tert-butoxyphosphoryl)oxy)butanoate (27B): To a solution of 27A (18.3 mmol) in DMF (30 mL) was added potassium di-tert-butyl phosphate (55.1 mmol, 3.05 equiv). The reaction mixture was allowed to stir at 60° C. overnight. When completion was determined by TLC, the reaction mixture was transferred to a separatory funnel using EtOAc (400 mL) and washed sequentially water and brine (3×200 mL each). The organic fraction was collected, dried over Na₂SO₄, and purified via silica gel chromatography. Fractions containing the product were pooled and concentrated under reduced pressure to give title compound 27B. ¹H NMR (400 MHz, DMSO-d₆) δ 7.36-7.33 (m, 5H), 5.12 (s, 2H), 3.99 (q, J=6.8 Hz 2 H), 2.51 (t, J=7.2 Hz, 2H), 2.00 (t, J=7.2 Hz, 2H), 1.47 (s, 18H) ppm.

Synthesis of 4-((di-tert-butoxyphosphoryl)oxy)butanoic acid (27C): A solution of 27B (9.59 mmol) in 30 mL of EtOH was sparged for 5m with Ar. To the solution was then carefully added Pd/C (10% Pd on activated carbon, 0.372 mmol, 0.03 equiv). The reaction was then sparged with H₂ for 5m, then stirred under 1 atm H2 for 2h until full conversion was seen by TLC. Upon completion, the reaction was diluted with 20 mL of EtOAc and sparged with Ar for 5m before filtration over celite. The filter cake was washed carefully with 3×50 mL of EtOAc, and the organic filtrate concentrated under reduced pressure to yield title compound 27C which was used without further purification. ¹H NMR (400 MHz, CDCl₃) δ 6.46 (br s, 1H), 4.11-3.99 (m, 2H), 2.51 (t, J=7.2 Hz, 2H), 2.00 (t, J=6.4 Hz, 2H), 1.46 (s, 18H) ppm. MS (m/z): 296.90 [M+H]⁺. 4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-4-oxobutyl dihydrogen phosphate (27): An atropisomeric mixture of the title compound was prepared according to the two-step method presented for the synthesis of compound 15 of Example 15 utilizing 4-((di-tert-butoxyphosphoryl)oxy) butanoic acid in the place of 3-tert-butoxy-2,2-dimethyl-4-oxobutanoic acid and Intermediate 5E in the place of Intermediate 5. ¹H NMR (400 MHz, DMSO-d₆) δ 9.16 (dd), 7.83 (ddd), 7.47 (dd), 7.07-6.96 (m), 6.80 (d), 6.53-6.45 (m), 6.46-6.37 (m), 5.00 (d), 4.93-4.72 (m), 4.69 (d), 4.61 (dd), 4.20 (dt), 3.97 (dq), 3.79-3.59 (m), 3.28 (d), 3.09-3.00 (m), 3.04-2.87 (m), 2.30 (t), 2.14-2.05 (m), 1.88-1.72 (m), 1.59 (dt), 1.41 (q), 0.99 (s) ppm. ¹⁹F NMR (375 MHz, DMSO-d₆) δ −60.92 (d), −69.41−69.74 (m), −69.98 (t), −75.15, −79.78 (d), −80.10 (d), −80.46 (d), −80.78 (d), −102.87 (d), −103.22 (d), −103.55 (d), −103.90 (d), −110.61 (d), −110.69−110.86 (m), −110.99 ppm. MS (m/z) 1135.255 [M+H]⁺.

Example 28
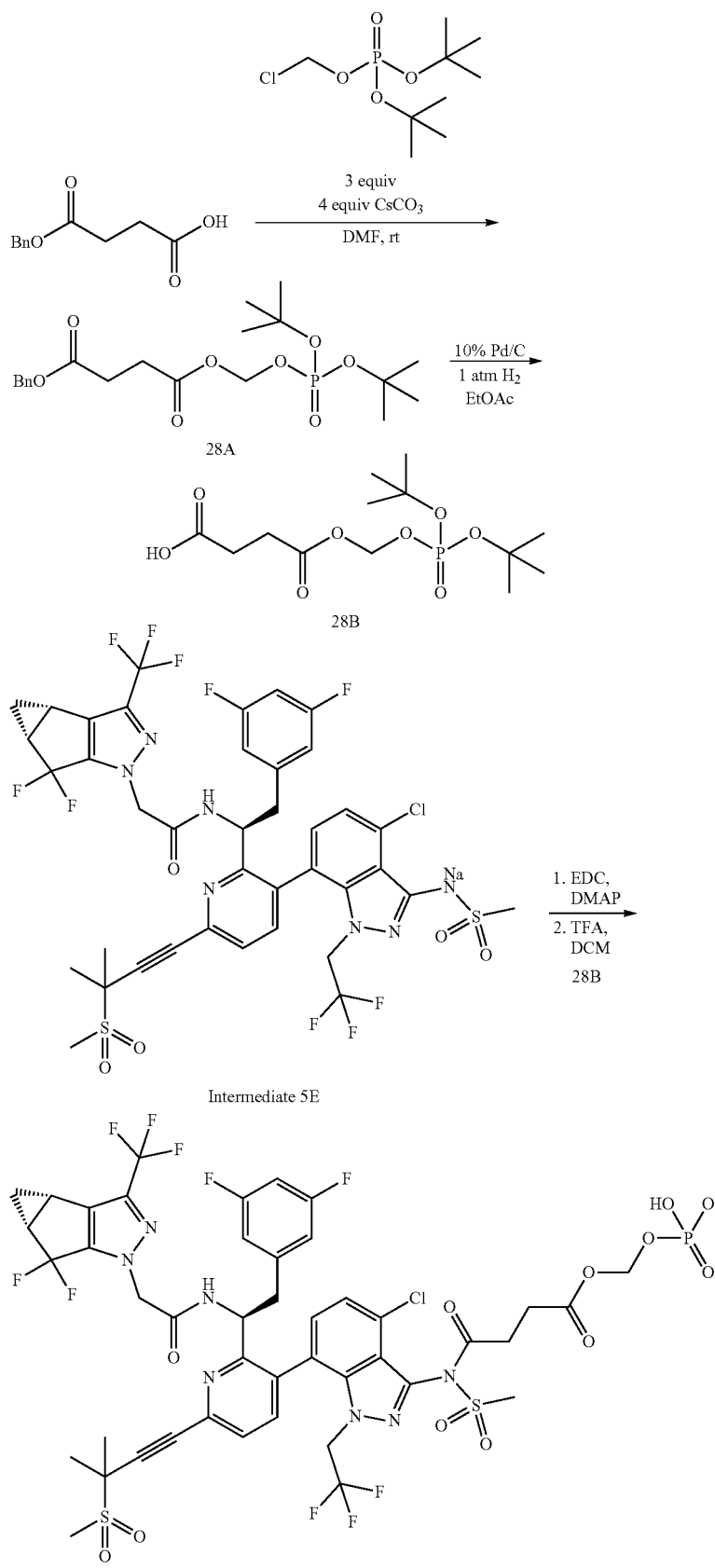

Synthesis of benzyl ((((di-tert-butoxyphosphoryl)oxy)methyl) succinate (28A): To a solution of succinic acid monobenzyl ester (1 equiv, 1.92 mmol) in 2 mL of dry DMF were added sequentially cesium carbonate (4 equiv, 7.78 mmol) and di-tert-butyl chloromethyl phosphate (3 equiv, 5.76 mmol). The reaction vessel was sealed and was allowed to stir for 20 h at rt. Upon completion of this time, the reaction contents were transferred to a separatory funnel using 50 mL of dichloromethane and 10 mL of H$_2$O. The organic layer was washed with 1M aqueous HCl (3×50 mL), dried over Na$_2$SO$_4$, concentrated under reduced pressure, and purified by silica gel chromatography. Fractions containing the product were pooled and concentrated under reduced pressure to yield title compound 28A. $^1$H NMR (400 MHz, CDCl$_3$) δ 7.42-7.32 (m, 5H), 5.61 (d, J=12.9 Hz, 2H), 5.16 (s, 2H), 2.74 (d, J=1.9 Hz, 4H), 1.51 (s, 18H) ppm.

Synthesis of 4-((((di-tert-butoxyphosphoryl)oxy)methoxy)-4-oxobutanoic acid (28B): To a solution of benzyl ((((di-tert-butoxyphosphoryl)oxy)methyl) succinate (0.279 mmol, 1 equiv) in 2 mL of EtOAc was sparged for 5m with Ar. To the solution was then carefully added Pd/C (10% Pd on activated carbon, 0.028 mmol, 0.1 equiv). The reaction was then sparged with H$_2$ for 5m, then stirred under 1 atm H2 for 2h until full conversion of 2 was observed by TLC (30% EtOAc/hexanes). Upon completion, the reaction was diluted with 10 mL of EtOAc and sparged with Ar for 5m before filtration over Celite®. The filter cake was washed carefully with 3×10 mL of EtOAc, and the organic filtrate was concentrated under reduced pressure to yield title compound 28B which was used without further purification. $^1$H NMR (400 MHz, CDCl$_3$) δ 7.42-7.32 (m, 5H), 5.61 (d, J=12.9 Hz, 2H), 5.16 (s, 2H), 2.74 (d, J=1.9 Hz, 4H), 1.51 (s, 18H) ppm.

Synthesis of (phosphonooxy)methyl 4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-4-oxobutanoate (28): An atropisomeric mixture of the title compound was prepared according to the two-step method presented for the synthesis of compound 15 of Example 15 utilizing 28B in the place of 3-tert-butoxy-2,2-dimethyl-4-oxobutanoic acid and Intermediate 5E in the place of Intermediate 5. $^1$H NMR (400 MHz, DMSO-d$_6$) δ 9.17 (dd), 8.01-7.88 (m), 7.88-7.73 (m), 7.49 (t), 7.07-6.98 (m), 6.88 (d), 6.45 (ddd), 5.51-5.40 (m), 4.97 (d), 4.91-4.67 (m), 4.62 (dd), 3.27 (d), 3.06-2.90 (m), 2.35-2.16 (m), 1.75 (d), 1.40 (d), 0.97 (s). $^{19}$F NMR (375 MHz, DMSO-d$_6$) δ−60.74-−60.88 (m), −60.99, −69.43-−69.57 (m), −69.66 (t), −69.91 (t), −74.71, −79.77 (d), −79.88 (d), −80.45 (d), −80.55 (d), −103.22, −103.30 (d), −103.89 (d), −103.97 (d), −110.58 (t), −110.82 (t), −111.19 ppm. MS (m/z) 1178.13 [M+H]$^+$.

Example 29

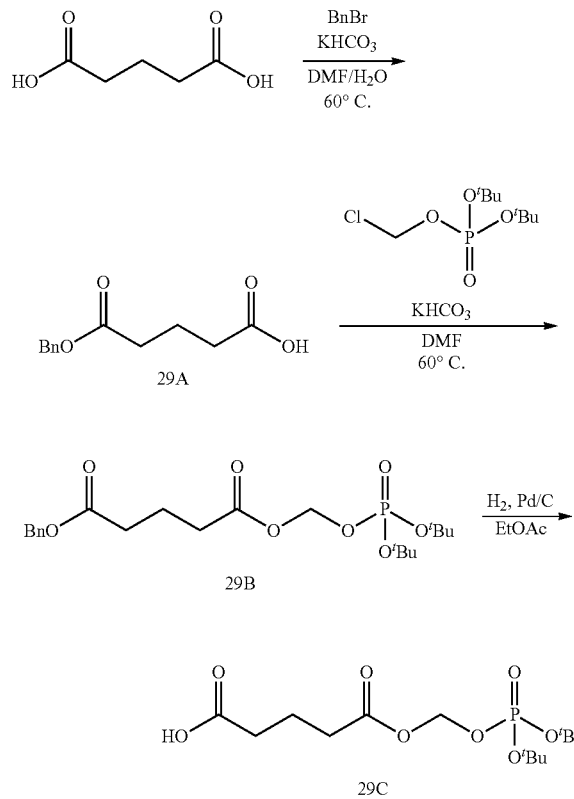

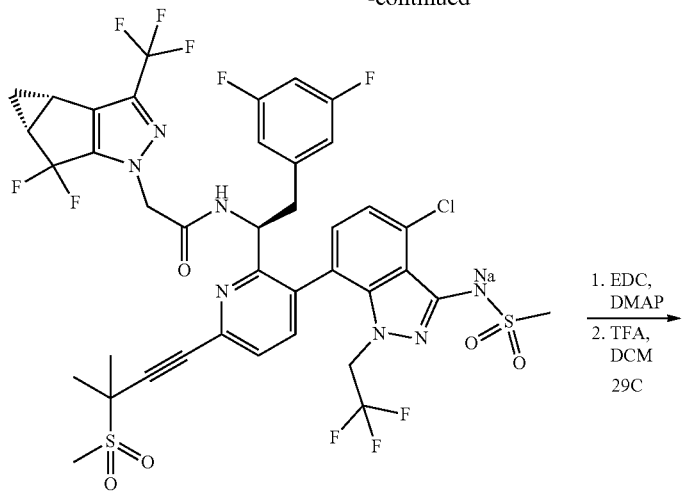

Intermediate 5E

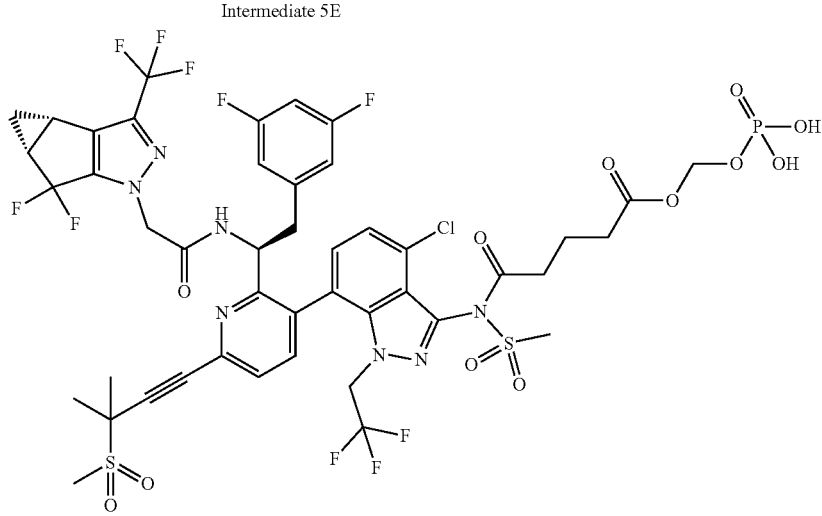

29

Synthesis of 5-benzyloxy-5-oxo-pentanoic acid (29A): To a flask was added glutaric acid (22.7 mmol), potassium bicarbonate (17.0 mmol), benzyl bromide (17 mmol), and 1:9 H$_2$O/DMF (23 mL). The reaction was sealed, heated to 60° C., and stirred for 16 hours. Upon completion, the reaction was diluted with 0.1M HCl (230 mL). The reaction was transferred to a separatory funnel and extracted 3× with EtOAc (100 mL). The organic fraction was collected, washed with 5% LiCl (110 mL), dried over Na$_2$SO$_4$, concentrated, and purified with silica chromatography. Fractions containing the product were pooled and concentrated to yield title compound 29A. MS (m/z) 223.20 [M+H]$^+$.

Synthesis of benzyl ((((di-tert-butoxyphosphoryl)oxy)methyl) glutarate (29B): To a flask was added 29A (2.7 mmol), potassium bicarbonate (4.0 mmol), ditert-butyl chloromethyl phosphate (5.4 mmol), and DMF (3.2 mL). The reaction was sealed, heated to 40° C., and stirred for 16 hours. Upon completion, the reaction was diluted with EtOAc (50 mL). The reaction was transferred to a separatory funnel and washed with 0.1M HCl (50 mL) followed by 5% LiCl (50 mL). The organic fraction was collected, dried over Na$_2$SO$_4$, concentrated, and purified with silica chromatography. Fractions containing the product were pooled and concentrated to yield title compound 29B. MS (m/z) 467.20 [M+Na]$^+$.

Synthesis of 5-((((di-tert-butoxyphosphoryl)oxy)methoxy)-5-oxopentanoic acid (29C): To a flask was added 29B (2.14 mmol), palladium on carbon (0.21 mmol), and EtOAc (7.1 mL). The reaction was sealed, purged with argon for 15 minutes, purged with H$_2$, and stirred under H$_2$ for 2 hours. Upon completion, the reaction was purged with argon for 15 minutes, diluted with Celite 545 (230 mg) and EtOAc (7.1 mL), and filtered. The reaction was concentrated to yield title compound 29C. MS (m/z): 377.20 [M+Na]$^+$.

Synthesis of (phosphonooxy)methyl 5-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-5-oxopentanoate (29): An atropisomeric mixture of the title compound was prepared according to the two-step method presented for the synthesis of compound 15 of Example 15 utilizing 29C in the place of 3-tert-butoxy-2,2-dimethyl-4-oxobutanoic acid and Intermediate 5E in the place of Intermediate 5. $^1$H NMR (400 MHz, CD$_3$CN) δ 8.96 (s), 7.83 (dd), 7.71 (d), 7.60 (d), 7.50 (d), 7.30 (dd), 6.80-6.67 (m), 6.56 (d), 6.34 (dd), 6.28-6.21 (m), 5.55-5.44 (m), 4.85-4.60 (m), 4.20-3.92 (m), 3.47 (d), 3.16 (d), 3.06-2.84 (m), 2.54-2.40 (m), 2.34-2.00 (m), 1.77 (d, 1.37 (q), 1.06-0.95 (m). $^{19}$F NMR (377 MHz, DMSO) δ-60.95 (d), −68.74--70.93 (m), −75.53, −79.23--81.77 (m), −103.33 (ddd), −110.17--111.09 (m). MS (m/z): 1192.20 [M+H]$^+$.

Example 30
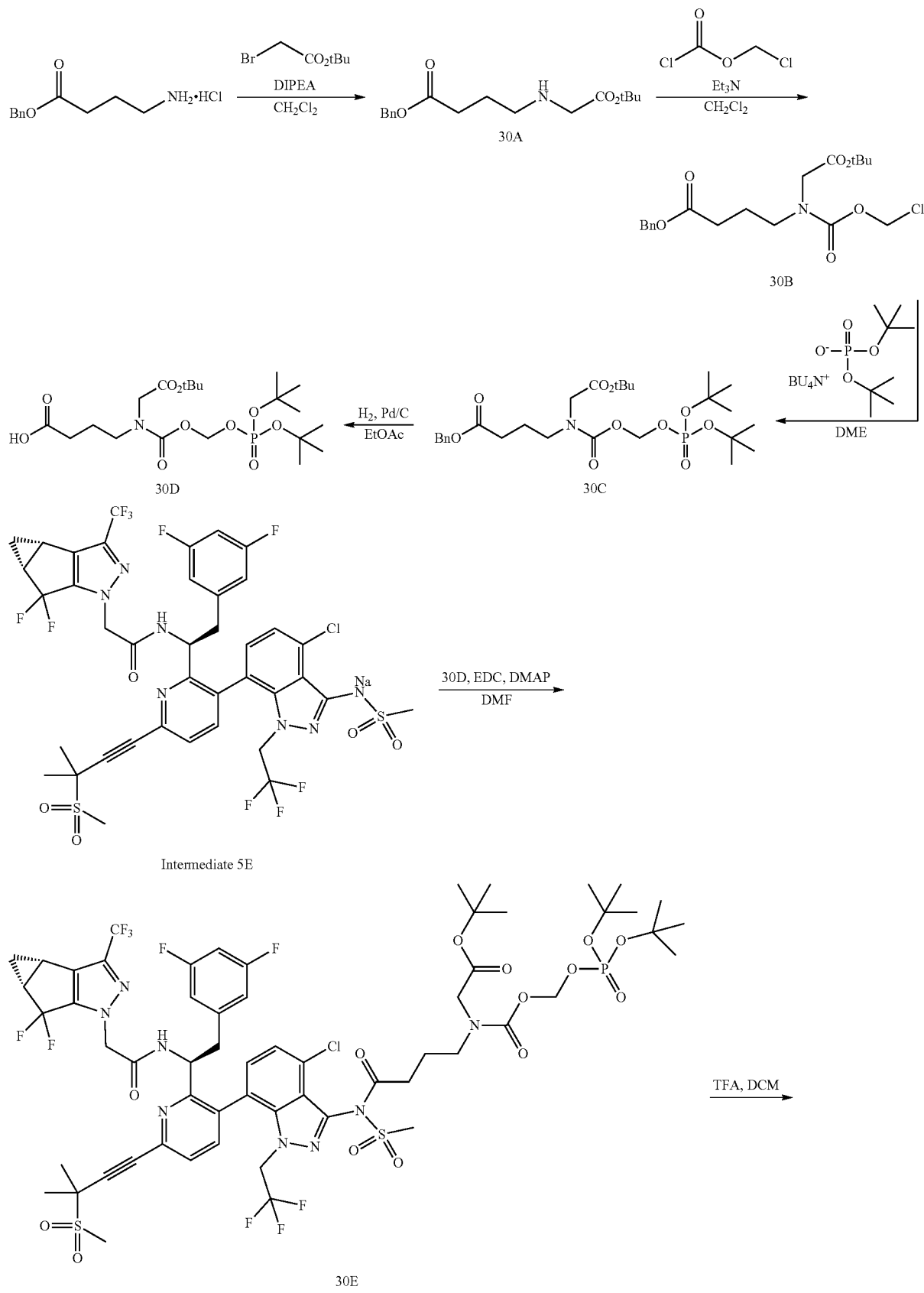

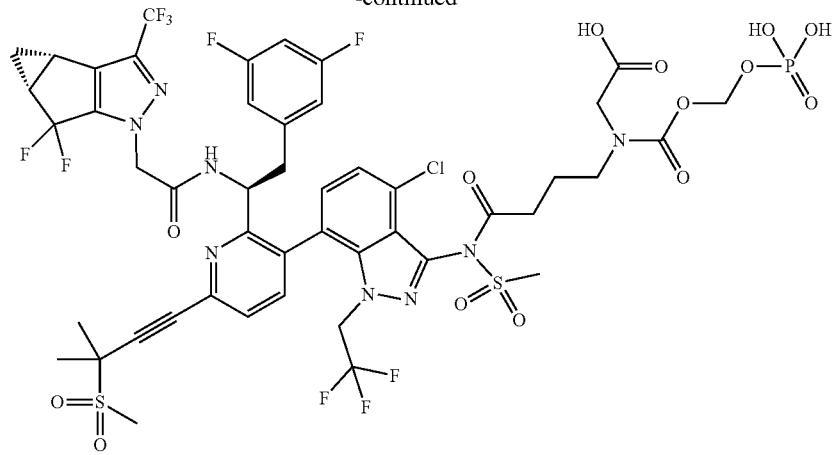

30

Synthesis of benzyl 4-((2-(tert-butoxy)-2-oxoethyl) amino)butanoate (30A): To a stirred suspension of benzyl 4-aminobutanoate hydrochloride (113.2 mmol) in CH$_2$Cl$_2$ (560 mL) was added DIPEA (249 mmol), then the reaction mixture was cooled to 0° C. t-Butyl bromoacetate (56.6 mmol) in CH$_2$Cl$_2$ (25 mL) was added dropwise via syringe pump (1 mL/min). The resulting reaction mixture was stirred at 0° C. for 1 h then warmed to room temp. After stirring for an additional 1.5 h, the mixture was washed with 0.5 M aq. HCl solution (~300 mL), water (~200 mL), and brine. The combined organic layers were dried over anhydrous Na$_2$SO$_4$, filtered, and concentrated. The crude mixture was purified by column chromatography (0% to 10% MeOH in CH$_2$Cl$_2$) to afford title compound 30A. $^1$H NMR (400 MHz, Chloroform-d) δ 9.45 (s, 1H), 7.40-7.29 (m, 5H), 5.13 (s, 2H), 3.77 (t, J=5.4 Hz, 2H), 3.28-3.19 (m, 2H), 2.61 (t, J=6.6 Hz, 2H), 2.24 (p, J=6.9 Hz, 2H), 1.50 (s, 9H) ppm. MS (m/z) 308.4 [M+H]$^+$.

Synthesis of benzyl 4-((2-(tert-butoxy) oxoethyl)((chloromethoxy)carbonyl)amino)butanoate (30B): To a stirred solution of 30A (23.4 mmol) in CH$_2$Cl$_2$ (234 mL) at 0° C. was added triethylamine (59 mmol). Chloromethyl chloroformate (35 mmol) was then added and the reaction mixture was stirred at 0° C. and monitored by TLC and LCMS. After completion, the reaction mixture was washed with sat. aq. solutions of NH$_4$C$_1$ and brine. The combined organic layers were dried over anhydrous Na2SO$_4$, filtered, and concentrated to afford title compound 30B, which was used without purification. MS (m/z) 401.5 [M+H]$^+$.

Synthesis of benzyl 4-((2-(tert-butoxy)-2-oxoethyl)(((((di-tert-butoxyphosphoryl)oxy)methoxy)carbonyl)amino)butanoate (30C): 30B (21 mmol) was dissolved in dimethoxyethane (87 mL) then di-t-butyl phosphate tetrabutylammonium salt (35 mmol) was added and the mixture was heated to 80° C. for 1 h. The mixture was cooled to room temperature and concentrated. The crude material was dissolved in EtOAc and washed with water (3×), brine, dried over Na$_2$SO$_4$, filtered, and concentrated. The crude mixture was purified by column chromatography (30% to 100% EtOAc in hexanes) to afford title compound 30C. $^1$H NMR (400 MHz, Chloroform-d) δ 7.40-7.28 (m, 5H), 5.59 (t, J=12.5 Hz, 2H), 5.11 (s, 2H), 3.88 (d, J=2.4 Hz, 2H), 3.41-3.35 (m, 2H), 2.41 (q, J=7.6 Hz, 2H), 1.89 (m, 2H), 1.46 (d, J=10.0 Hz, 27H). MS (m/z) 574.6 [M+H]$^+$.

Synthesis of 4-((2-(t-butoxy)-2-oxoethyl)((((di-t-butoxyphosphoryl)oxy)methoxy) carbonyl)amino)butanoic acid 30D: 30C (22 mmol) was dissolved in EtOAc then palladium on carbon (4.3 mmol) was added. After stirring for 1 h under hydrogen gas (1 atm), product formation was observed. The crude product was isolated after filtration over a pad of Celite®. The product was purified by column chromatography (0% to 10% MeOH in CH$_2$Cl$_2$) to afford title compound 30D. MS (m/z) 484.8 [M+H]$^+$.

Synthesis of tert-butyl N-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl) acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido) oxobutyl)-N-((((di-tert-butoxyphosphoryl)oxy)methoxy) carbonyl)glycinate (30E): To a solution of Intermediate 5E (0.404 mmol), 30D (1.21 mmol, 3 equiv), and DMAP (0.808 mmol, 2 equiv) in DMF (4 mL) was added EDC (0.310 mmol, 3 equiv). When the reaction had reached completion, the mixture was partitioned between EtOAc and water. The organic fraction was washed with 1N HCl and brine, then collected, dried over Na$_2$SO$_4$ and concentrated to afford an atropisomeric mixture of title compound 30E which was used without purification. MS (m/z) 1455.40 [M+Na]$^+$.

Synthesis of N-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-4-oxobutyl)-N-(((phosphonooxy)methoxy)carbonyl)glycine (30): To a solution of 30E (0.54 mmol) in DCM (4 mL) was added trifluoroacetic acid (17 mmol, 31 equiv) with stirring. When full conversion was observed, the reaction was concentrated under reduced pressure and purified by reverse phase HPLC. Fractions containing the product were pooled and lyophilized to give title compound 30 as a mixture of atropisomers. $^1$H NMR (400 MHz, DMSO-d$_6$) δ 9.24-9.09 (m), 7.99-7.86 (m), 7.85-7.71 (m), 7.57-7.39 (m), 7.09-6.94 (m), 6.77 (dd), 6.55-6.34 (m), 5.54-5.26 (m), 5.02 (d), 4.96-4.57 (m), 4.04-3.78 (m), 3.65-3.47 (m), 3.28 (d), 3.20-2.86 (m), 2.28-2.14 (m), 2.04-1.94 (m), 1.75 (d), 1.59-1.47 (m), 1.44-1.33 (m), 0.98 (s) ppm. $^{19}$F NMR (376 MHz, DMSO-d$_6$) δ-60.60--61.12 (m), -69.53--69.64 (m), -69.83--70.08 (m), -79.20--81.57 (m), -101.61--104.49 (m), -109.63--111.23 (m) ppm. MS (m/z) 1266.895 [M+H]$^+$.

Example 31
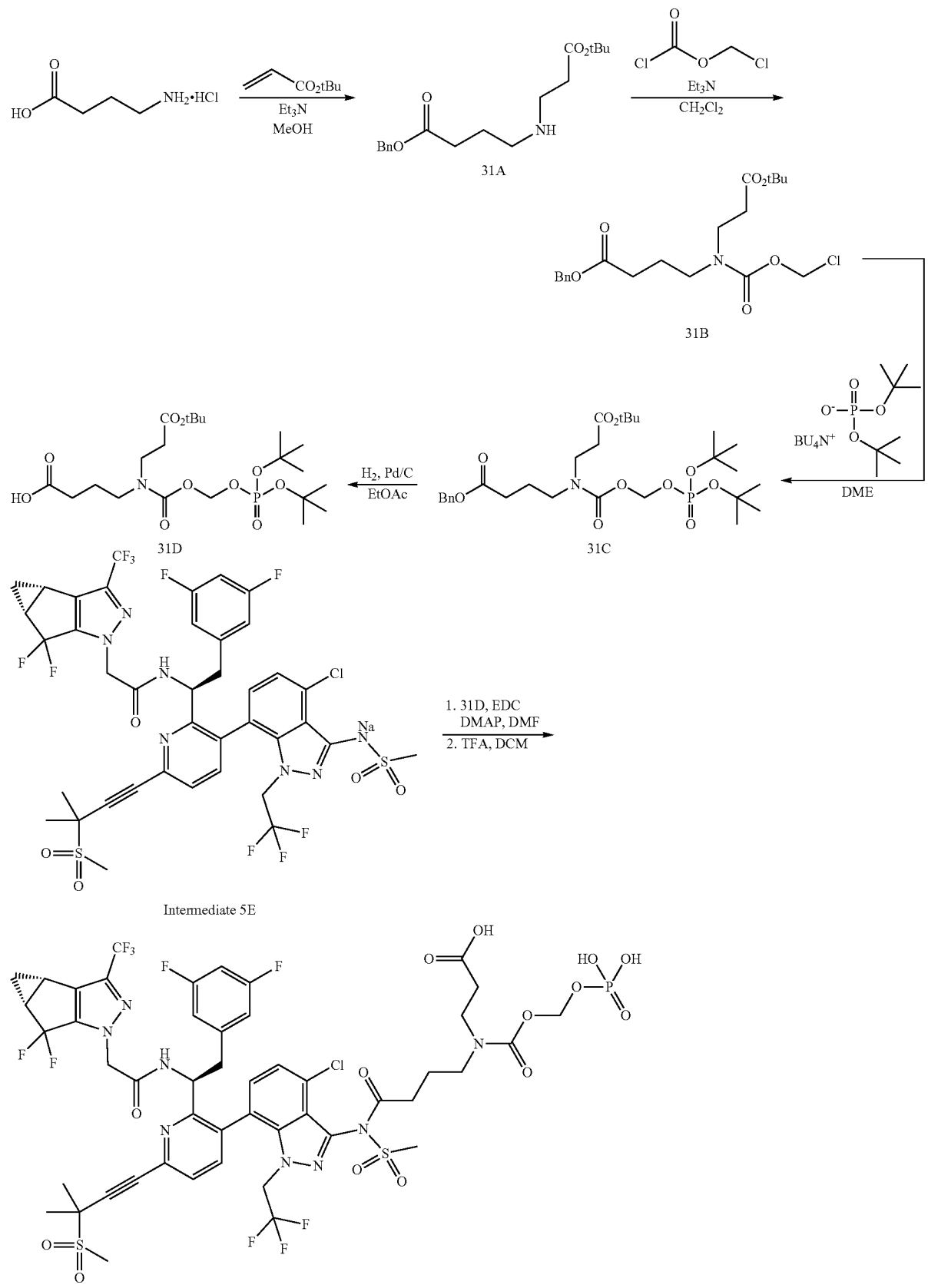

Synthesis of benzyl 4-((3-(tert-butoxy)-3-oxopropyl)amino)butanoate (31A): To a solution of benzyl 4-aminobutanoate hydrochloride (30 mmol) in methanol (15 mL) was added t-butyl acrylate (20 mmol) followed by triethylamine (30 mmol). The resulting mixture was stirred at room temperature for 3 h while monitoring by LCMS. After completion, the reaction mixture was diluted with EtOAc, and washed with sat. aq. solutions of $NH_4C_1$ and brine. The combined organic layers were dried over anhydrous $Na_2SO_4$, filtered, and concentrated. The crude mixture was purified by column chromatography (0% to 10% MeOH in $CH_2Cl_2$) to afford title compound 31A. $^1$H NMR (400 MHz, Chloroform-d) δ 9.66 (s, 1H), 7.41-7.31 (m, 5H), 5.13 (s, 2H), 3.25-3.17 (m, 2H), 3.13-3.05 (m, 2H), 2.95 (t, J=7.2 Hz, 2H), 2.57 (t, J=6.9 Hz, 2H), 2.25-2.18 (m, 2H), 1.47 (s, 9H). MS (m/z): 322.5 $[M+H]^+$.

Synthesis of benzyl 4-((3-(tert-butoxy)-3-oxopropyl)((chloromethoxy)carbonyl)amino)butanoate (31B): To a stirred solution of 31A (4.0 mmol) in $CH_2Cl_2$ (20 mL) at 0° C. was added triethylamine (10 mmol). Chloromethyl chloroformate (6.0 mmol) was then added and the reaction mixture was stirred at 0° C. and monitored by TLC and LCMS. After completion, the reaction mixture was washed with sat. aq. solutions of $NH_4C_1$ and brine. The combined organic layers were dried over anhydrous $Na_2SO_4$, filtered, and concentrated to afford title compound 31B, which was used without purification. MS (m/z): 437.0 $[M+Na]^+$.

Synthesis of benzyl 4-((3-(tert-butoxy)-3-oxopropyl)(((di-tert-butoxyphosphoryl)oxy)methoxy)carbonyl)amino)butanoate (31C): 31B (4.0 mmol) was dissolved in dimethoxyethane (17 mL) then di-t-butyl phosphate tetrabutylammonium salt (6.8 mmol) was added and the mixture was heated to 80° C. for 1 h. The mixture was cooled to room temperature and concentrated. The crude material was dissolved in EtOAc and washed with water (3×), brine, dried over $Na_2SO_4$, filtered, and concentrated to afford title compound 31C, which was used without purification. MS (m/z): 610.7 $[M+Na]^+$.

Synthesis of 4-((3-(tert-butoxy)-3-oxopropyl)((((di-tert-butoxyphosphoryl)oxy)methoxy)carbonyl)amino)butanoic acid (31D): 31C (4.0 mmol) was dissolved in EtOAc (20 mL) then palladium on carbon (0.21 mmol) was added. After stirring for 1 h under hydrogen gas (1 atm), product formation was observed. The crude product was isolated after filtration over a pad of Celite® and concentrated. The crude mixture was purified by column chromatography (0% to 10% MeOH in $CH_2Cl_2$) to afford the 1.0 g of title compound 31D. $^1$H NMR (400 MHz, Chloroform-d) δ 5.67-5.57 (m, 2H), 3.56-3.50 (m, 2H), 3.44-3.30 (m, 2H), 2.58-2.49 (m, 2H), 2.45-2.37 (m, 2H), 1.99-1.87 (m, 2H), 1.51 (d, J=3.3 Hz, 18H), 1.46 (s, 9H). MS (m/z): 498.5 $[M+H]^+$.

Synthesis of 3-((4-(N-(4-chloro-7-(2-(((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-4-oxobutyl)(((phosphonooxy)methoxy)carbonyl)amino)propanoic acid (31): An atropisomeric mixture of the title compound was prepared according to the method presented for the synthesis of compound 30 of Example 30 utilizing 31D in the place of 30D. $^1$H NMR (400 MHz, DMSO-$d_6$) δ 9.36-8.99 (m), 7.99-7.67 (m), 7.47 (dd), 7.42-7.22 (m), 7.17-6.94 (m), 6.91-6.77 (m), 6.70-6.24 (m), 5.54-5.23 (m), 5.09-4.53 (m), 4.30-4.13 (m), 4.11-3.93 (m), 3.62-3.49 (m), 3.28 (d), 3.16-2.92 (m), 2.21-1.89 (m), 1.75 (d), 1.59-1.47 (m), 1.41 (q), 0.98 (s). $^{19}$F NMR (375 MHz, DMSO-$d_6$) δ-60.93 (d), −68.70--71.51 (m), −80.26 (ddd), −101.74-−104.76 (m), −109.37-−112.19 (m). MS (m/z): 1280.208 $[M+H]^+$.

Example 32

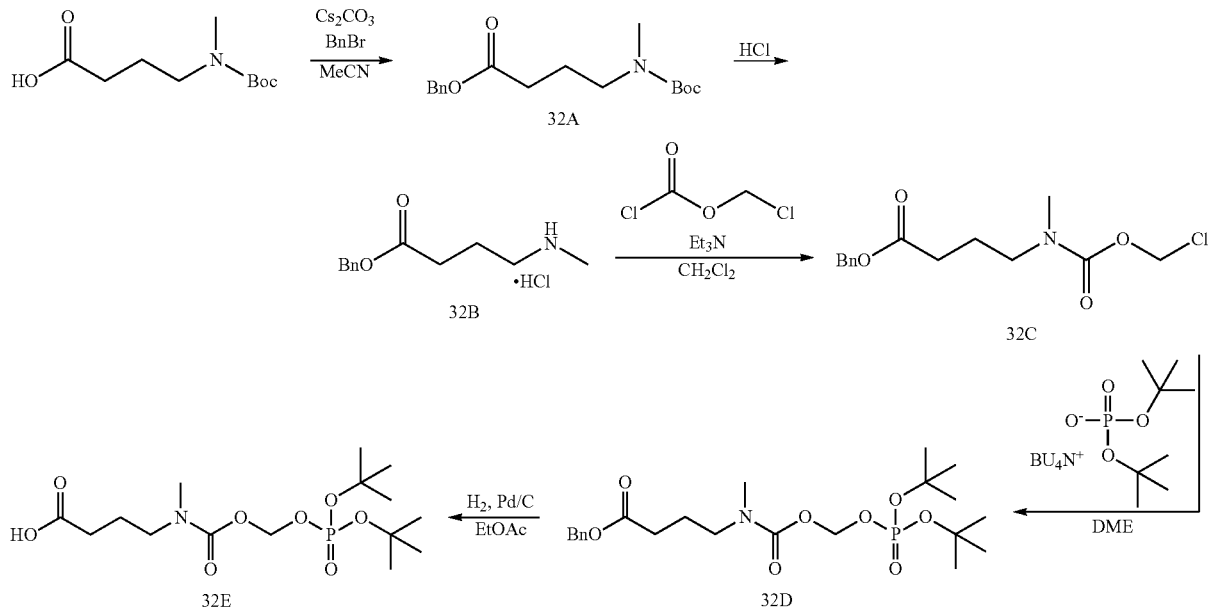

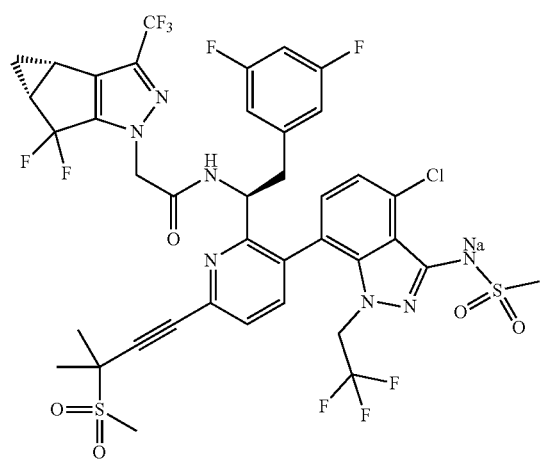

Intermediate 5E 1. 32E, EDC DMAP, DMF
2. TFA, DCM

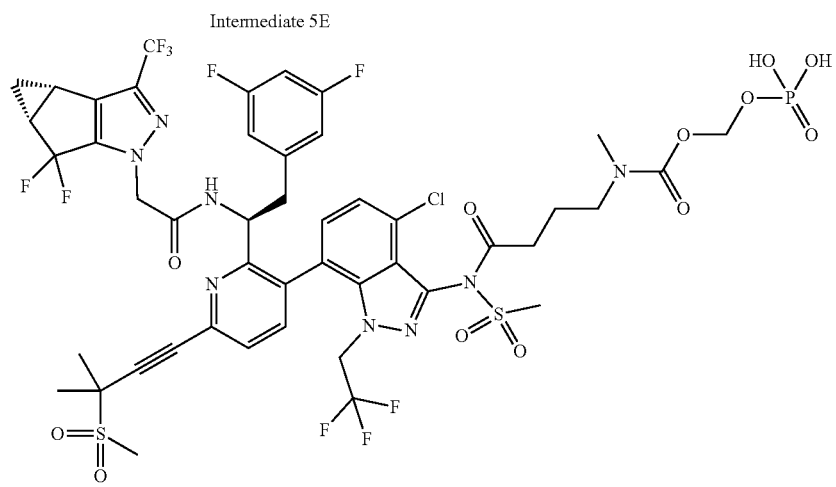

32

Synthesis of benzyl 4-((tert-butoxycarbonyl)(methyl)amino)butanoate (32A): To a solution of 4-[t-butoxycarbonyl(methyl)amino]butanoic acid (23 mmol) in MeCN (76 mL) was added cesium carbonate (46 mmol) and benzyl bromide (35 mmol) at room temperature. The resulting mixture was stirred for 16 h at room temperature and monitored by TLC and LCMS. Upon completion, the reaction mixture was filtered through a pad of Celite® and concentrated. The crude mixture was purified by column chromatography (0% to 30% EtOAc in hexanes) to afford title compound 32A. MS (m/z): 308.4 [M+H]$^+$.

Synthesis of benzyl 4-(methylamino)butanoate hydrochloride (32B): 32A (23 mmol) was treated with HCl (15 mL, 4N in dioxane) at room temperature and the reaction was monitored by TLC and LCMS. Upon completion, the mixture was concentrated to afford title compound 32B, which was used without further purification. MS (m/z): 208.3 [M+H]$^+$.

Synthesis of benzyl 4-(((chloromethoxy)carbonyl)(methyl)amino)butanoate (32C): To a stirred solution of 32B (8.2 mmol) in CH$_2$Cl$_2$ (82 mL) at 0° C. was added triethylamine (21 mmol). Chloromethyl chloroformate (11 mmol) was then added and the reaction mixture was stirred at 0° C. and monitored by TLC and LCMS. After completion, the reaction mixture was washed with sat. aq. solutions of NH$_4$C$_1$ and brine. The combined organic layers were dried over anhydrous Na$_2$SO$_4$, filtered, and concentrated to afford title compound 32C, which was used without purification. MS (m/z): 322.8 [M+Na]$^+$.

Synthesis of benzyl 4-(((((di-tert-butoxyphosphoryl)oxy)methoxy)carbonyl)(methyl)amino)butanoate (32D): 32C (8.2 mmol) was dissolved in dimethoxyethane (41 mL) then di-t-butyl phosphate tetrabutylammonium salt (14 mmol) was added and the mixture was heated to 80° C. for 1 h. The mixture was cooled to room temperature and concentrated. The crude material was dissolved in EtOAc and washed with water (3×), brine, dried over Na$_2$SO$_4$, filtered, and concentrated. The crude mixture was purified by column chromatography (10% to 100% EtOAc in hexanes) to afford title compound 32D. $^1$H NMR (400 MHz, Chloroform-d) δ 7.42-7.31 (m, 5H), 5.64-5.58 (m, 2H), 5.14 (s, 2H), 3.38-3.31 (m, 2H), 2.94 (s, 3H), 2.40 (q, J=7.4 Hz, 2H), 1.91 (p, J=7.4 Hz, 2H), 1.50 (s, 18H). MS (m/z): 496.5 [M+Na]$^+$.

Synthesis of 4-(((((di-tert-butoxyphosphoryl)oxy)methoxy)carbonyl)(methyl)amino)butanoic acid (32E): 32D (2.1 mmol) was dissolved in EtOAc (8 mL) then palladium on carbon (0.21 mmol) was added. After stirring for 1 h under hydrogen gas (1 atm), product formation was observed. The crude product was isolated after filtration over a pad of Celite®. The mother liquor was concentrated under reduced pressure to afford title compound 32E, which was immediately used in the subsequent step without purification. $^1$H NMR (400 MHz, Chloroform-d) δ 5.62 (dd, J=14.3, 2.4 Hz, 2H), 3.44-3.34 (m, 2H), 2.95 (d, J=3.9 Hz, 3H), 2.46-2.37 (m, 2H), 1.98-1.87 (m, 2H), 1.51 (s, 18H). MS (m/z): 406.4 [M+Na]+.

Synthesis of (phosphonooxy)methyl (4-(N-(4-chloro-7-(2-((S)-1-(2-((3bS,4aR)-5,5-difluoro-3-(trifluoromethyl)-3b,4,4a,5-tetrahydro-1H-cyclopropa[3,4] cyclopenta [1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-4-oxobutyl)(methyl)carbamate (32): An atropisomeric mixture of the title compound was prepared according to the method presented for the synthesis of compound 30 of Example 30 utilizing 32E in the place of 30D. 1H NMR (400 MHz, DMSO) δ 9.25-8.97 (m), 7.94 (d), 7.80 (dd), 7.56-7.43 (m), 7.40-7.24 (m), 7.10-6.86 (m), 6.68-6.27 (m), 5.48-5.24 (m), 5.02 (d), 4.95-4.54 (m), 4.26-3.87 (m), 3.65-3.46 (m), 3.27 (d), 3.21-2.91 (m), 2.87-2.69 (m), 1.97-1.87 (m), 1.75 (d), 1.68-1.56 (m), 1.55-1.35 (m), 0.98 (s). 19F NMR (377 MHz, DMSO) δ~59.18--62.34 (m), -68.87--70.91 (m), -79.67--81.32 (m), -101.88--104.50(m), -109.59--111.57 (m). MS (m/z): 1222.060 [M+H]+.

Example 33

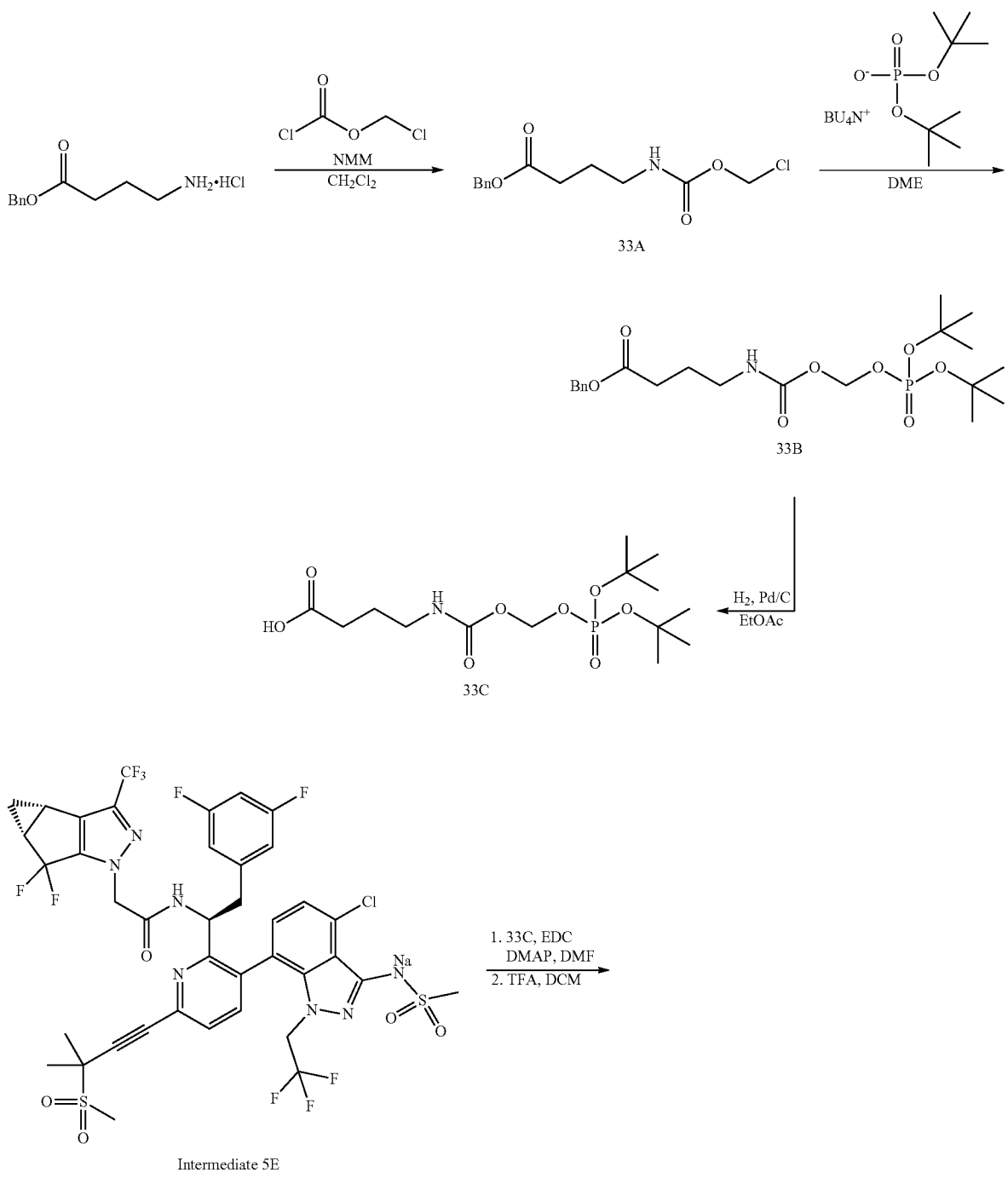

Intermediate 5E

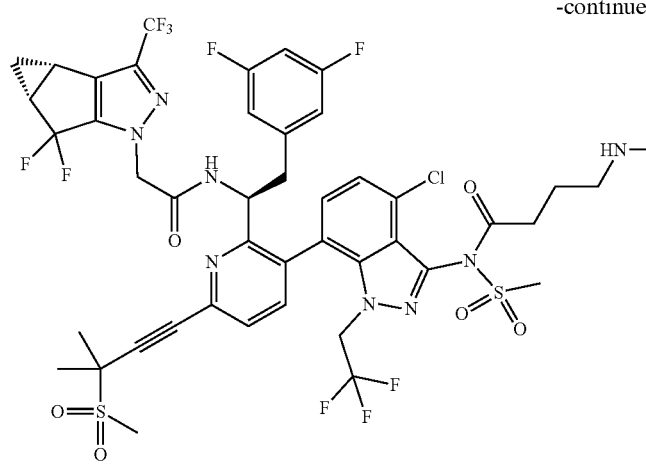

33

Synthesis of benzyl 4-(((chloromethoxy)carbonyl)amino)butanoate (33A): To a stirred solution of benzyl 4-aminobutanoate hydrochloride (51.7 mmol) in CH$_2$Cl$_2$ (70 mL) at 0° C. was added N-methylmorpholine (129 mmol). Chloromethyl chloroformate (51.7 mmol) was then added and the reaction mixture was stirred at 0° C. and monitored by TLC and LCMS. After completion, the reaction mixture was washed with sat. aq. solutions of NH$_4$C$_1$ and brine. The combined organic layers were dried over anhydrous Na$_2$SO$_4$, filtered, and concentrated. The crude mixture was purified by column chromatography (10% to 50% EtOAc in hexanes) to afford title compound 33A. MS (m/z) 286.1 [M+H]$^+$.

Synthesis of benzyl 4-(((((di-tert-butoxyphosphoryl)oxy)methoxy)carbonyl)amino)butanoate (33B): 33A (10.5 mmol) was dissolved in dimethoxyethane (165 mL) then di-t-butyl phosphate tetrabutylammonium salt (15.7 mmol) was added and the mixture was heated to 80° C. for 1 h. The mixture was cooled to room temperature and concentrated. The crude material was dissolved in EtOAc and washed with water (3×), brine, dried over Na$_2$SO$_4$, filtered, and concentrated. The crude mixture was purified by column chromatography (10% to 100% EtOAc in hexanes) to afford title compound 33B. MS (m/z) 482.0 [M+Na].

Synthesis of 4-(((((di-tert-butoxyphosphoryl)oxy)methoxy)carbonyl)amino)butanoic acid (33C): 33B (7.6 mmol) was dissolved in EtOAc (21 mL) then palladium on carbon (0.76 mmol) was added. After stirring for 1 h under hydrogen gas (1 atm), product formation was observed. The crude product was isolated after filtration over a pad of Celite®. The product was purified by column chromatography (0% to 10% MeOH in CH$_2$Cl$_2$) to afford title compound 33C. $^1$H NMR (MeOD-d$_4$ 400 MHz): δ 5.53 (d, J=12.8 Hz, 2H), 3.17 (t, J=6.8 Hz, 2H), 2.33 (t, J=8.4 Hz, 2H), 1.81-1.77 (m, 2H), 1.49 (s, 18H).

Synthesis of (phosphonooxy)methyl (4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-4-oxobutyl)carbamate (33): An atropisomeric mixture of the title compound was prepared according to the method presented for the synthesis of compound 30 of Example 30 utilizing 33C in the place of 30D. $^1$H NMR (400 MHz, DMSO-d$_6$) δ 9.27-9.02 (m), 8.00-7.70 (m), 7.57-7.23 (m), 7.15-6.97 (m), 6.83 (d), 6.62-6.27 (m), 5.52-5.23 (m), 5.00 (d), 4.93-4.51 (m), 4.26-3.91 (m), 3.55 (d), 3.28 (d), 3.10-2.85 (m), 2.86-2.70 (m), 2.35-1.95 (m), 1.84-1.70 (m), 1.67-1.36 (m), 1.15-0.89 (m). $^{19}$F NMR (375 MHz, DMSO-d$_6$) δ −60.61−−61.28 (m), −69.16−−70.30 (m), −79.08−−81.65 (m), −102.35−−104.89 (m), −109.87−−111.43 (m). MS (m/z) 1230.122 [M+Na]$^+$.

Example 34

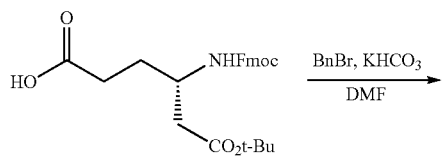

-continued
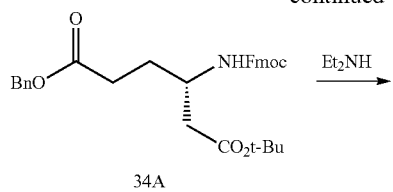
34A
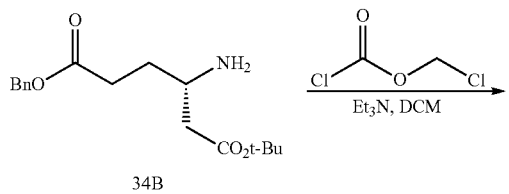
34B
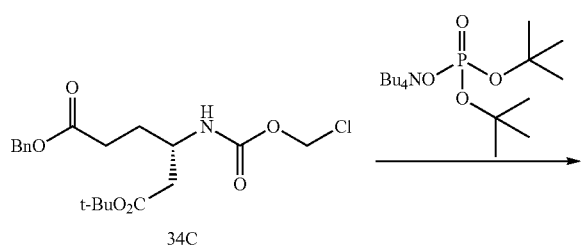
34C
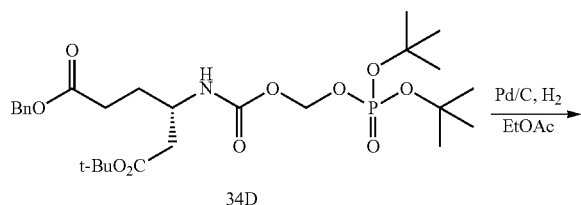
34D
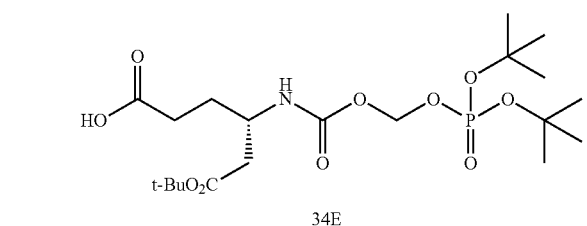
34E
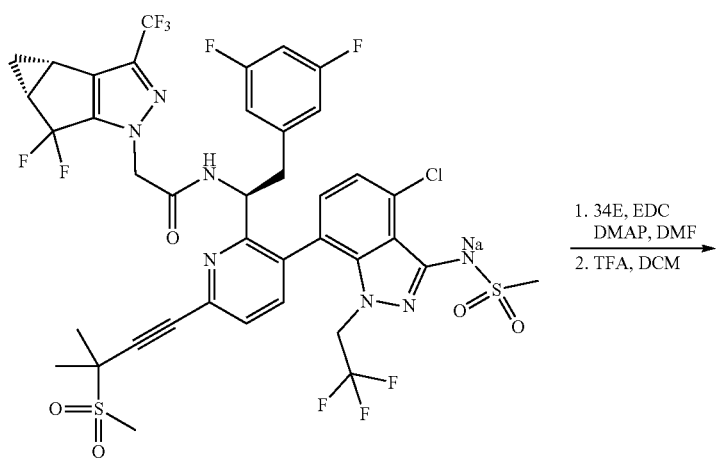
Intermediate 5E

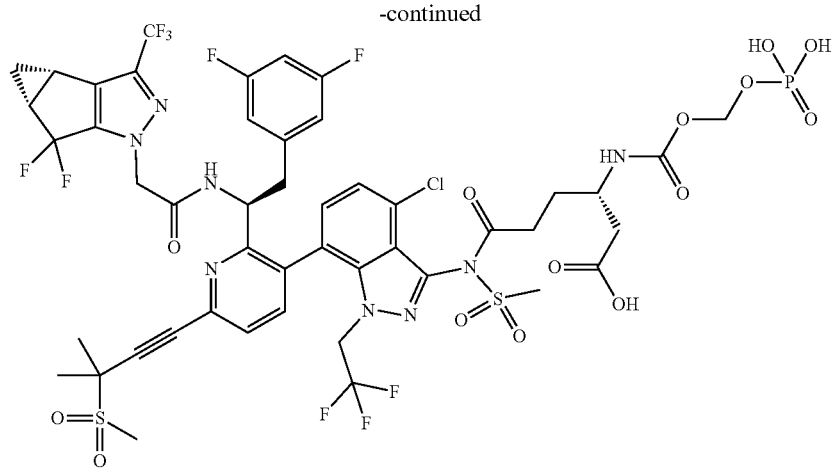

34

Synthesis of 6-benzyl 1-(tert-butyl) (S)-3-((((9H-fluoren-9-yl)methoxy)carbonyl)amino)hexanedioate (34A): To a solution of (S)-4-((((9H-fluoren-9-yl)methoxy)carbonyl)amino)-6-(tert-butoxy)-6-oxohexanoic acid (2.28 mmol) in 5 mL of DMF were added sequentially K2CO3 (3.41 mmol, 1.5 equiv) and BnBr (6.83 mmol, 3 equiv) and the resulting mixture allowed to stir at rt. Upon completion, the reaction contents were transferred to a separatory funnel using DCM (100 mL) and 5% LiCl solution (100 mL). The organic layer was extracted with further 5% LiCl solution (2×100 mL) and then collected, dried over Na$_2$SO$_4$, concentrated under reduced pressure and purified by silica gel chromatography to yield title compound 34A. MS (m/z) 552.21 [M+Na]$^+$.

Synthesis of 6-benzyl 1-(tert-butyl) (S)-3-aminohexanedioate (34B): To a solution of 34A (2.4 mmol) in 15 mL of DCM at 0° C. was added diethylamine (24 mmol, 10 equiv) with continued stirring. When the reaction was complete, the solvent was removed under reduced pressure and the residue transferred to a separatory funnel using DCM (200 mL) and 1M aqueous Na$_2$CO$_3$ (100 mL). The organic fraction was collected, dried over Na$_2$SO$_4$, and used directly in the next reaction without concentration. MS (m/z): 308.20 [M+H]$^+$.

Synthesis of 6-benzyl 1-(tert-butyl) (S) (((chloromethoxy)carbonyl)amino)hexanedioate (34C): The title compound was prepared according to the method presented for the synthesis of compound 30B of Example 30 utilizing 34B in the place of 30A. MS (m/z) 422.11 [M+Na]$^+$.

Synthesis of 6-benzyl 1-(tert-butyl) (S)-3-(((((di-tert-butoxyphosphoryl)oxy)methoxy)carbonyl)amino)hexanedioate (34D): The title compound was prepared according to the method presented for the synthesis of compound 30C of Example 30 utilizing 34C in the place of 30B. MS (m/z) 596.30 [M+H]$^+$.

Synthesis of (S)-6-(tert-butoxy)-4-(((((di-tert-butoxyphosphoryl)oxy)methoxy)carbonyl)amino)-6-oxohexanoic acid (34E): The title compound was prepared according to the method presented for the synthesis of compound 30D of Example 30 utilizing 34D in the place of 30C. MS (m/z) 485.19 [M+H]$^+$.

Synthesis of (R)-6-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-6-oxo-3-(((((phosphonooxy)methoxy)carbonyl)amino)hexanoic acid (34): An atropisomeric mixture of the title compound was prepared according to the method presented for the synthesis of compound 30 of Example 30 utilizing 34E in the place of 30D. $^1$H NMR (400 MHz, DMSO-d$_6$) δ 9.22-9.12 (m), 7.91-7.82 (m), 7.85-7.72 (m), 7.53-7.45 (m), 7.46-7.30 (m), 7.34-7.19 (m), 7.07-6.96 (m), 6.71-6.64 (m), 6.53-6.44 (m), 6.41-6.32 (m), 5.46-5.27 (m), 5.28-5.15 (m), 5.03-4.93 (m), 4.93-4.55 (m), 4.28-4.13 (m), 4.06-3.91 (m), 3.76-3.64 (m), 3.55 (s), 3.28 (d, J=4.3 Hz), 3.09-2.85 (m), 2.67-2.51 (m), 2.35-2.08 (m), 1.82-1.68 (m), 1.67-1.53 (m), 1.47-1.34 (m), 1.21-1.05 (m), 1.04-0.93 (m). $^{19}$F NMR (375 MHz, DMSO-d$_6$) δ −60.66--−61.06 (m), −69.42--−69.88 (m), −69.94--−70.23 (m), −75.24--−75.61 (m), −75.42, −79.66--−79.96 (m), −80.33--−80.64 (m), −102.60--−102.87 (m), −103.12--−103.54 (m), −103.77--−104.03 (m), −110.47--−110.97 (m) ppm. MS (m/z) 1265.20 [M+H]$^+$.

Example 35

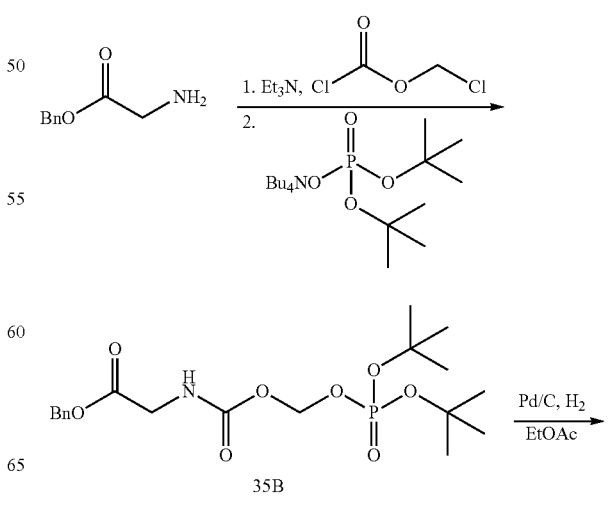

35B

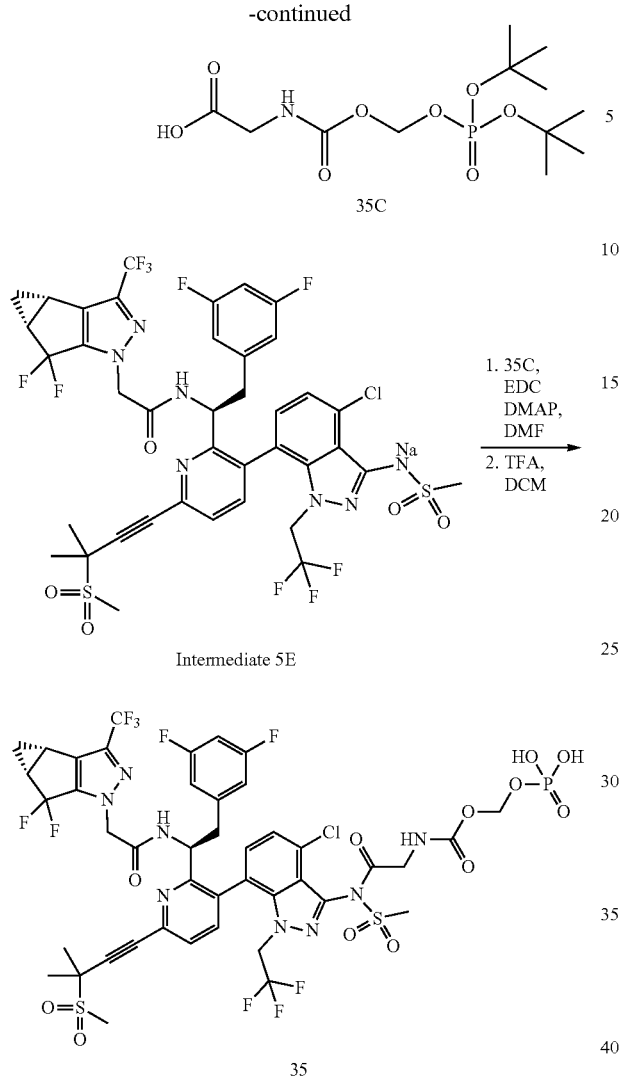

Intermediate 5E

35

Synthesis of benzyl ((chloromethoxy)carbonyl)glycinate (35A): The title compound was prepared according to the method presented for the synthesis of compound 30B of Example 30 utilizing glycine benzyl ester hydrochloride in the place of 30A. MS (m/z) 280.79 [M+Na]$^+$.

Synthesis of benzyl (((((di-tert-butoxyphosphoryl)oxy)methoxy)carbonyl)glycinate (35B): The title compound was prepared according to the method presented for the synthesis of compound 30C of Example 30 utilizing 35A in the place of 30B. MS (m/z) 468.30 [M+Na]$^+$.

Synthesis of (((((di-tert-butoxyphosphoryl)oxy)methoxy)carbonyl)glycine (35C): The title compound was prepared according to the method presented for the synthesis of compound 30D of Example 30 utilizing 35B in the place of 30C. MS (m/z) 341.10 [M+H]$^+$.

Synthesis of (phosphonooxy)methyl (2-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-oxoethyl)carbamate (35): An atropisomeric mixture of the title compound was prepared according to the method presented for the synthesis of compound 30 of Example 30 utilizing 35C in the place of 30D. $^1$H NMR (400 MHz, DMSO-d$_6$) δ 9.26-9.18 (m), 7.92-7.79 (m), 7.83-7.73 (m), 7.69-7.61 (m), 7.54-7.38 (m), 7.09-7.00 (m), 7.04-6.85 (m), 6.83-6.76 (m), 6.58-6.45 (m), 5.49-5.34 (m), 4.95-4.80 (m), 4.80-4.59 (m), 4.27-4.14 (m), 4.10-3.95 (m), 3.72-3.51 (m), 3.51-3.40 (m), 3.30-3.25 (m), 3.14-2.93 (m), 2.61-2.53 (m), 1.79-1.72 (m), 1.44-1.34 (m), 1.00-0.92 (m) ppm. $^{19}$F NMR (375 MHz, DMSO-d$_6$) −60.72–−60.97 (m), −69.39–−69.57 (m), −69.66–−69.86 (m), −75.17–−75.39 (m), −75.28, −79.72–−79.84 (m), −80.02–−80.15 (m), −80.39–−80.52 (m), −80.70–−80.82 (m), −103.05, −103.23, −103.66–−103.95 (m), −110.53–−110.64 (m), −110.62 ppm. MS (m/z) 1179.90 [M+H]$^+$.

Example 36

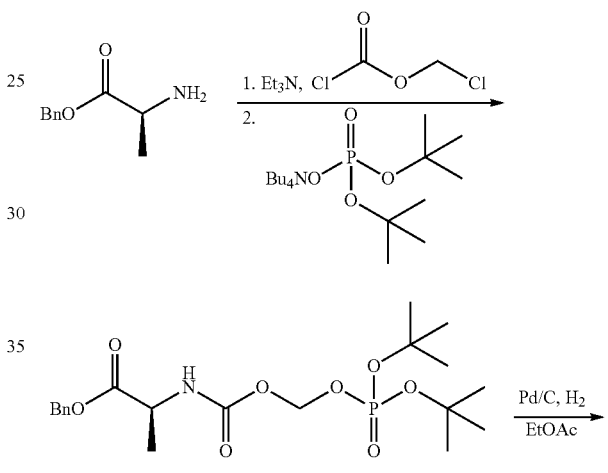

36B

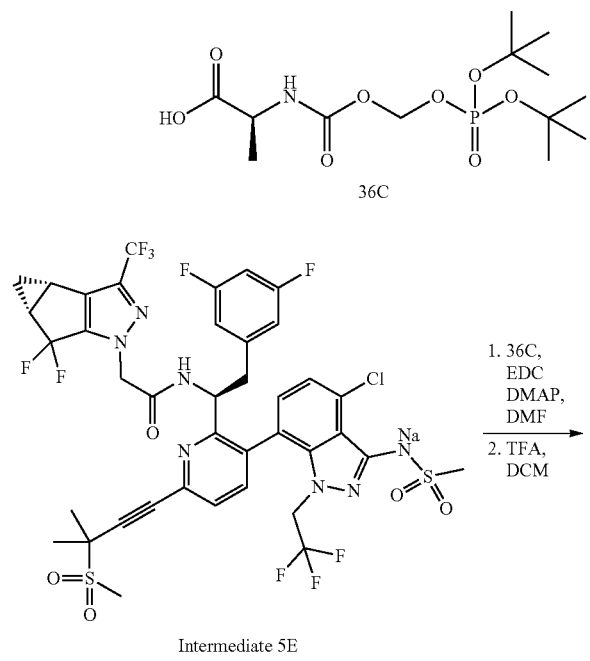

Intermediate 5E

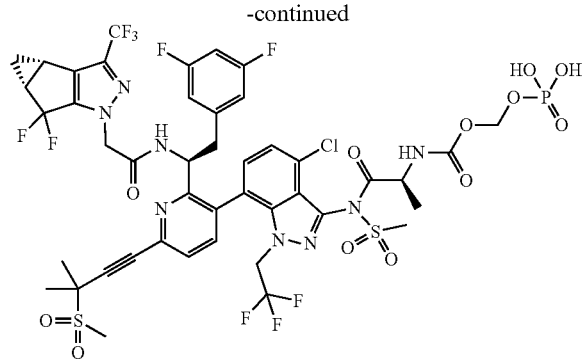

36

Synthesis of benzyl ((chloromethoxy)carbonyl)-L-alaninate (36A): The title compound was prepared according to the method presented for the synthesis of compound 30B of Example 30 utilizing L-alanine benzyl ester hydrochloride in the place of 30A. MS (m/z) 294.11 [M+Na]$^+$.

Synthesis of benzyl ((((di-tert-butoxyphosphoryl)oxy)methoxy)carbonyl)-L-alaninate (36B): The title compound was prepared according to the method presented for the synthesis of compound 30C of Example 30 utilizing 36A in the place of 30B. $^1$H NMR (400 MHz, CDCl$_3$) δ 7.42-7.35 (m, 5H), 5.60 (ddd, J=30.4, 12.8, 5.3 Hz, 2H), 5.32 (s, 2H), 5.21 (d, J=1.6 Hz, 2H), 1.51 (s, 18H) ppm. MS (m/z) 467.97 [M+Na]$^+$.

Synthesis of ((((di-tert-butoxyphosphoryl)oxy)methoxy)carbonyl)-L-alanine (36C): The title compound was prepared according to the method presented for the synthesis of compound 30D of Example 30 utilizing 36B in the place of 30C. MS (m/z) 364.90 [M+Na]$^+$.

Synthesis of (phosphonooxy)methyl ((S)-1-(N-(4-chloro-7-(2-((S)-1-(2-((3bS,4aR)-5,5-difluoro-3-(trifluoromethyl)-3b,4,4a,5-tetrahydro cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol yl)methylsulfonamido)-1-oxopropan-2-yl)carbamate (36): An atropisomeric mixture of the title compound was prepared according to the method presented for the synthesis of compound 30 of Example 30 utilizing 36C in the place of 30D. $^1$H NMR (400 MHz, DMSO-d$_6$) δ 9.30-9.23 (m), 9.20-9.13 (m), 8.05-7.94 (m), 7.90-7.75 (m), 7.78-7.68 (m), 7.55-7.48 (m), 7.40-7.30 (m), 7.11-6.98 (m), 6.60-6.46 (m), 6.44-6.36 (m), 5.49-5.36 (m), 5.38-5.26 (m), 5.07-4.98 (m), 4.89-4.59 (m), 4.07-3.91 (m), 3.84 (s), 3.62 (s), 3.58 (s), 3.53 (s), 3.14-3.02 (m), 3.03-2.87 (m), 2.74 (s), 1.76 (s), 1.77-1.72 (m), 1.48-1.37 (m), 1.24 (s), 1.16-0.93 (m) ppm. $^{19}$F NMR (375 MHz, DMSO-d$_6$) δ -60.75--61.09 (m), -69.30--69.41 (m), -69.51--69.62 (m), -69.90--70.05 (m), -74.72, -79.74--79.84 (m), -80.42--80.52 (m), -102.51--102.61 (m), -103.19--103.29 (m), -110.47--110.59 (m), -110.60--110.69 (m), -110.84 ppm. MS (m/z) 1193.96 [M+H]$^+$.

Example 37

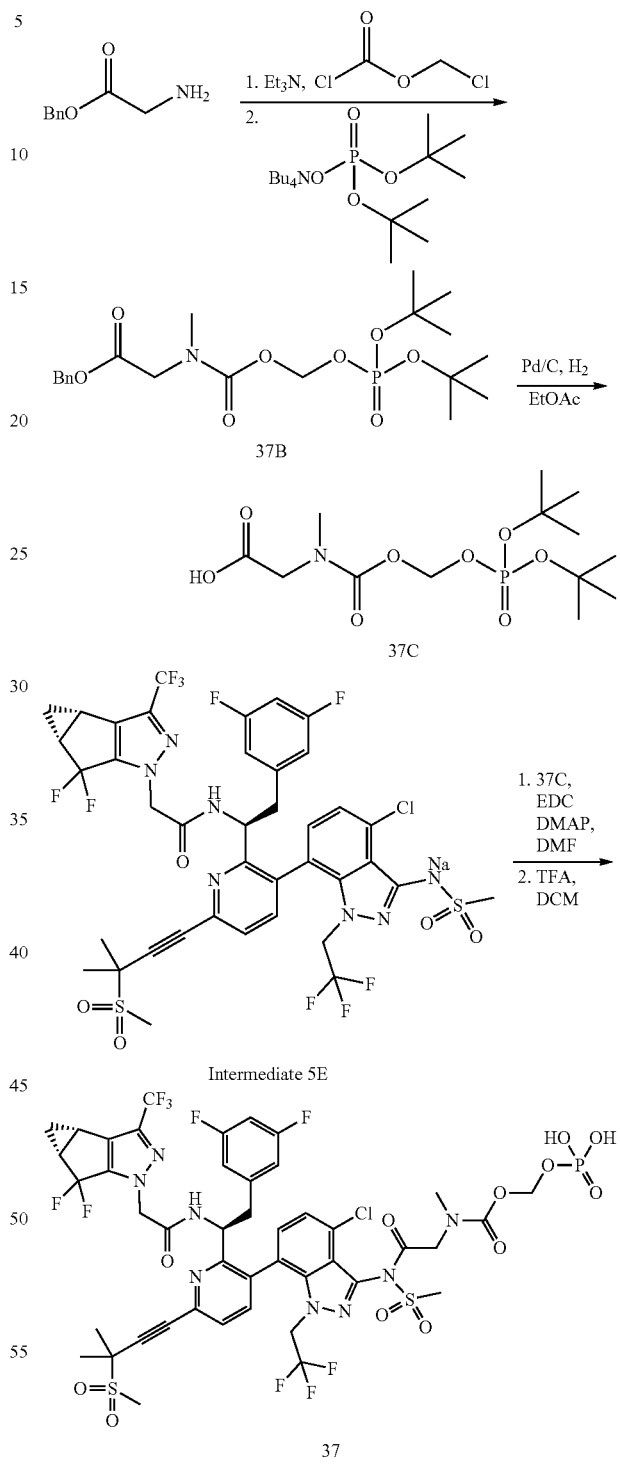

Synthesis of benzyl N-((chloromethoxy)carbonyl)-N-methylglycinate (37A): The title compound was prepared according to the method presented for the synthesis of compound 30B of Example 30 utilizing sarcosine benzyl ester hydrochloride in the place of 30A. MS (m/z) 271.80 [M+H]$^+$.

Synthesis of benzyl N-((((di-tert-butoxyphosphoryl)oxy)methoxy)carbonyl)-N-methylglycinate (37B): The title compound was prepared according to the method presented for the synthesis of compound 30C of Example 30 utilizing 37A in the place of 30B. $^1$H NMR (400 MHz, CDCl$_3$) δ 7.44-7.34 (m, 5H), 5.70-5.55 (m, 2H), 4.12 (d, J=6.8 Hz, 2H), 3.04 (d, J=5.6 Hz, 3H), 1.50 (d, J=8.3 Hz, 19H) ppm. MS (m/z) 468.10 [M+Na]$^+$.

Synthesis of N-((((di-tert-butoxyphosphoryl)oxy)methoxy)carbonyl)-N-methylglycine (37C): The title compound was prepared according to the method presented for the synthesis of compound 30D of Example 30 utilizing 37B in the place of 30C. MS (m/z) 355.67 [M+H]$^+$.

Synthesis of (phosphonooxy)methyl (2-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-oxoethyl)(methyl)carbamate (37): An atropisomeric mixture of the title compound was prepared according to the method presented for the synthesis of compound 30 of Example 30 utilizing 37C in the place of 30D. $^1$H NMR (400 MHz, DMSO-d$_6$) δ 9.24-9.13 (m), 8.01-7.89 (m), 7.85-7.75 (m), 7.55-7.43 (m), 7.08-6.97 (m), 6.95-6.86 (m), 6.85-6.78 (m), 6.62-6.47 (m), 6.43-6.34 (m), 5.51-5.33 (m), 5.05-4.95 (m), 4.95-4.80 (m), 4.80-4.55(m), 4.30-4.16(m), 4.11-3.77(m), 3.76-3.57(m), 3.30-3.25(m), 3.10-2.83 (m), 2.71 (s), 2.68-2.56 (m), 2.59-2.51 (m), 1.78-1.72 (m), 1.45-1.35 (m), 1.02-0.93 (m) ppm. $^{19}$F NMR (375 MHz, DMSO-d$_6$) δ-60.65--61.16 (m), -69.26--70.20 (m), -75.48, -75.34--75.81 (m), -79.58--81.00 (m), -102.82--103.39 (m), -103.49--104.07 (m), -110.41-111.00 (m), -111.20 ppm. MS (m/z) 1192.87 [M+H]$^+$.

Example 38

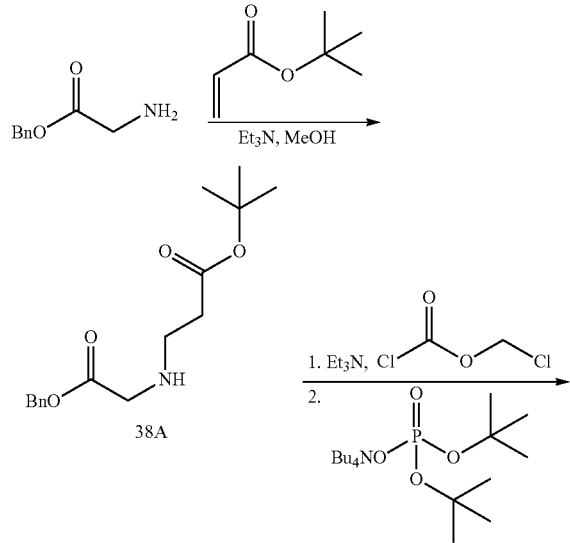

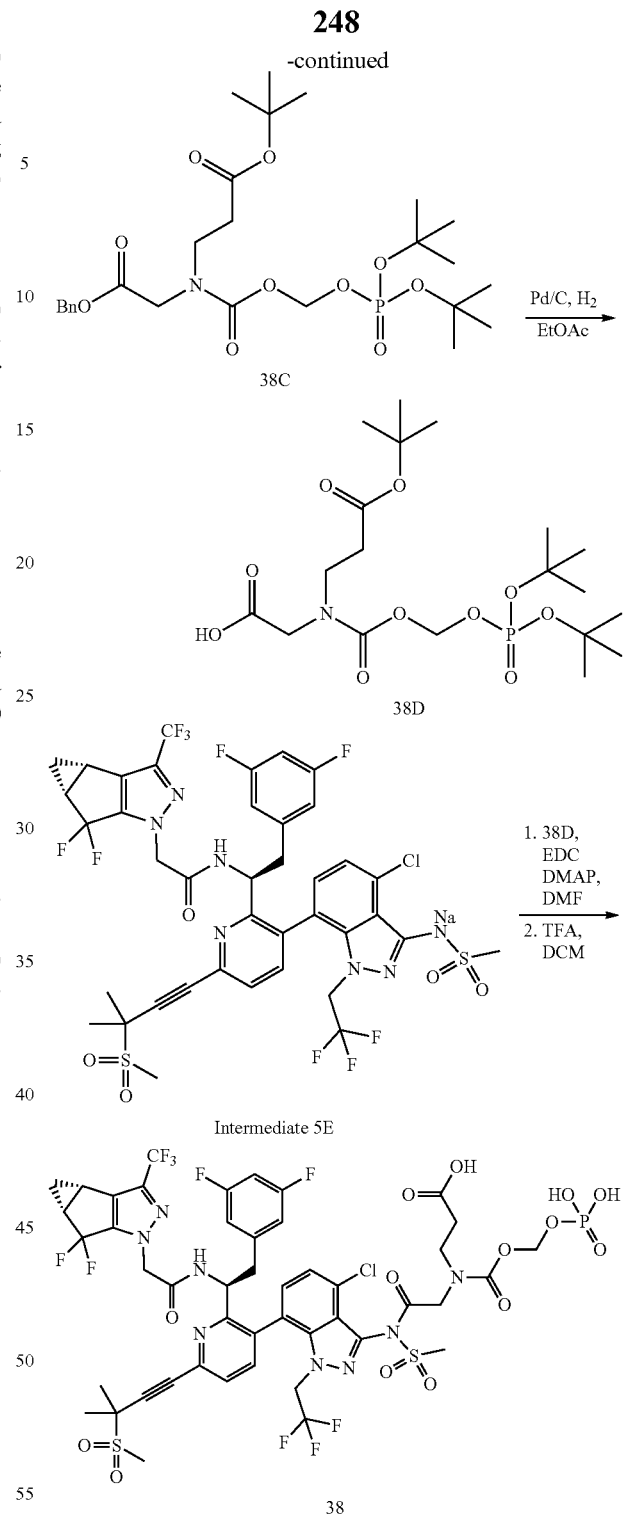

Synthesis of tert-butyl 3-((2-(benzyloxy)-2-oxoethyl)amino)propanoate (38A): The title compound was prepared according to the method presented for the synthesis of compound 3A of Example 3 utilizing glycine benzyl ester hydrochloride in the place of [(1S)-3-tert-butoxy-1-tert-butoxycarbonyl-3-oxo-propyl]ammonium chloride. $^1$H NMR (400 MHz, CDCl$_3$) 7.40-7.35 (m, 5H), 5.20 (s, 2H), 3.76 (s, 1H), 3.52 (s, 2H), 2.91 (t, J=6.5 Hz, 2H), 2.49 (td, J=6.6, 5.0 Hz, 3H), 1.47 (s, 9H) ppm. MS (m/z) 293.92 [M+H]$^+$.

Synthesis of tert-butyl 3-((2-(benzyloxy)-2-oxoethyl)((chloromethoxy)carbonyl)amino)propanoate (38B): The title compound was prepared according to the method presented for the synthesis of compound 30B of Example 30 utilizing 38A in the place of 30A. $^1$H NMR (400 MHz, CDCl$_3$) δ 7.44-7.33 (m, 5H), 5.83 (s, 1H), 5.70 (s, 1H), 5.19 (s, 2H), 4.21 (s, 1H), 4.16 (d, J=2.1 Hz, 1H), 3.76 (s, 1H), 3.62 (dt, J=11.7, 6.5 Hz, 3H), 2.60 (dtd, J=16.2, 6.5, 2.8 Hz, 3H), 1.46 (dd, J=4.4, 3.4 Hz, 9H) ppm. MS (m/z) 408.20 [M+Na]$^+$.

Synthesis of tert-butyl 3-((2-(benzyloxy)-2-oxoethyl)(((((di-tert-butoxyphosphoryl)oxy)methoxy)carbonyl)amino)propanoate (38C): The title compound was prepared according to the method presented for the synthesis of compound 30C of Example 30 utilizing 38B in the place of 30B. MS (m/z) 582.48 [M+Na]$^+$.

Synthesis of N-(3-(tert-butoxy)-3-oxopropyl)-N-((((di-tert-butoxyphosphoryl)oxy)methoxy)carbonyl)glycine (38D): The title compound was prepared according to the method presented for the synthesis of compound 30D of Example 30 utilizing 37C in the place of 30C. MS (m/z) 492.11 [M+Na]$^+$.

Synthesis of tert-butyl 3-((2-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-oxoethyl)(((phosphonooxy)methoxy)carbonyl)amino)propanoate (38): An atropisomeric mixture of the title compound was prepared according to the method presented for the synthesis of compound 30 of Example 30 utilizing 38D in the place of 30D. $^1$H NMR (400 MHz, DMSO-d$_6$) δ 9.25-9.15 (m), 7.92-7.79 (m), 7.83-7.73 (m), 7.54-7.40 (m), 7.07-6.91 (m), 6.89-6.83 (m), 6.56-6.39 (m), 5.53-5.32 (m), 4.96-4.80 (m), 4.80-4.56 (m), 4.29-4.14 (m), 4.15-3.81 (m), 3.67-3.59 (m), 3.48-3.33 (m), 3.30-3.18 (m), 3.10-2.87 (m), 2.66-2.52 (m), 2.51-2.40 (m), 1.77-1.72 (m), 1.44-1.34 (m), 1.02-0.93 (m) ppm. $^{19}$F NMR (375 MHz, DMSO-d$_6$) δ −60.72−−60.96 (m), −69.36−−69.60 (m), −69.78−−70.03 (m), −75.47, −75.39-75.61 (m), −79.77 (d, J=12548.4 Hz), −79.86−−79.98 (m), −80.37−−80.66 (m), −103.07−−103.27 (m), −103.75−−103.95 (m), −110.55−−110.71 (m), −110.76 (m), −110.80−−110.92 (m) ppm. MS (m/z) 1251.78 [M+H]$^+$.

Example 39

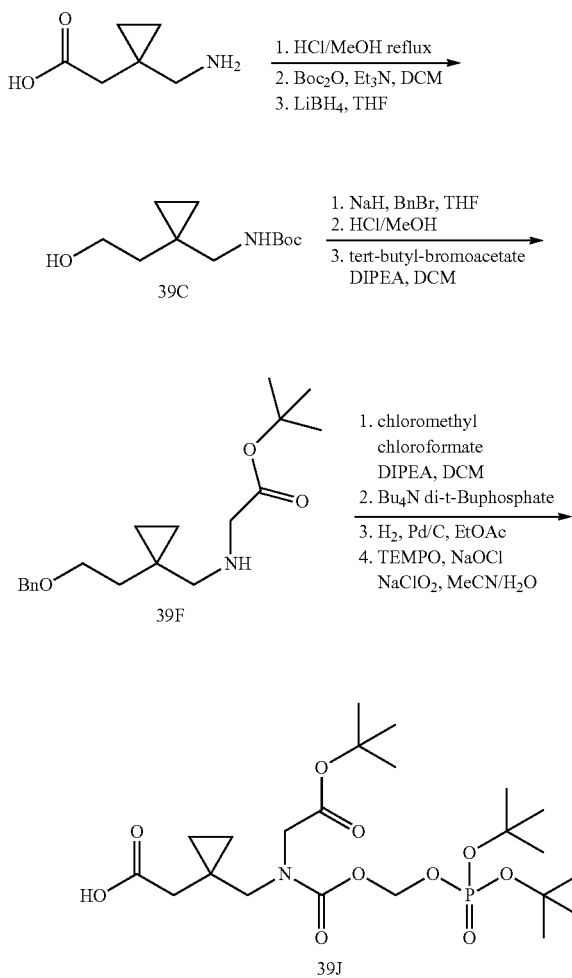

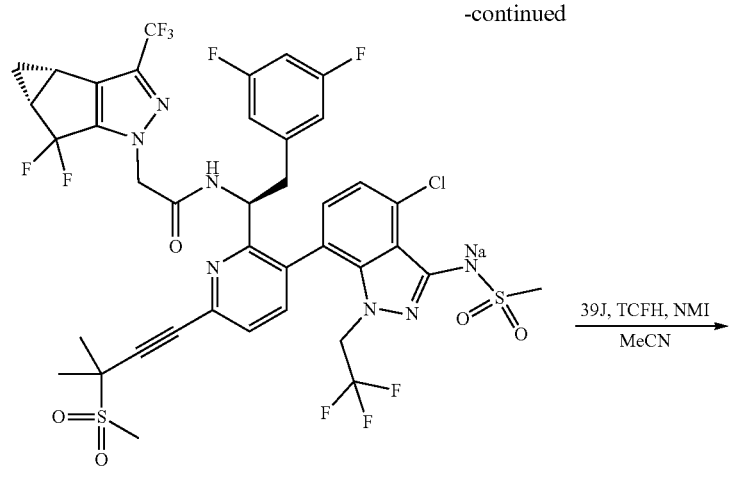

Compound 5E

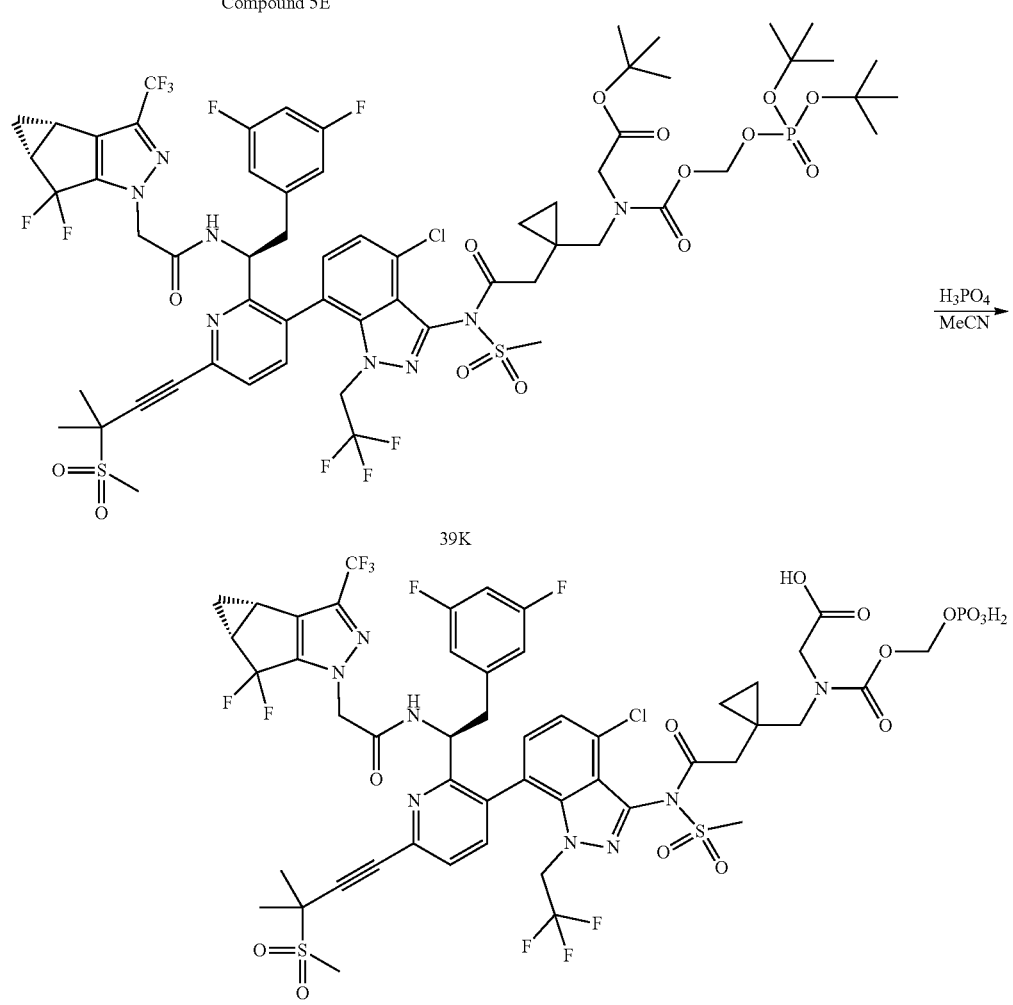

Synthesis of methyl 2-(1-(aminomethyl)cyclopropyl)acetate (39A): A solution of 2-(1-(aminomethyl)cyclopropyl) acetic acid (35.4 mmol) in HCl in MeOH (1M, 50 mL) was brought to reflux. When full conversion was observed, the reaction was concentrated under reduced pressure then reconstituted in MeCN, frozen in a dry ice bath, and lyophilized to give title compound 39A which was used without further purification. $^1$H NMR (400 MHz, Methanol-d$_4$) δ 3.72 (s, 3H), 3.02 (d, J=2.9 Hz, 2H), 2.53 (d, J=9.5 Hz, 2H), 0.81-0.72 (m, 2H), 0.68-0.63 (m, 2H) ppm.

Synthesis of methyl 2-(1-(((tert-butoxycarbonyl)amino) methyl)cyclopropyl)acetate (39B): To a solution of methyl 2-(1-(aminomethyl)cyclopropyl)acetate (39A, 25.8 mmol) in 32 mL of DCM was added di-tert-butyl dicarbonate (32.3 mmol, 1.25 equiv) followed by dropwise addition of triethylamine (36.1 mmol, 1.4 equiv) at 0° C. When the reaction was complete, the contents were transferred to a separatory funnel using DCM (100 mL) and 0.1 M HCl solution (100 mL). The organic layer was washed, then collected, dried over $Na_2SO_4$, and concentrated under reduced pressure to yield title compound 39B which was used without further purification. MS (m/z) 244.14 [M+H]$^+$.

Synthesis of tert-butyl ((1-(2-hydroxyethyl)cyclopropyl)methyl)carbamate (39C): To a solution of methyl 2-(1-(((tert-butoxycarbonyl)amino)methyl)cyclopropyl)acetate (39B, 4.11 mmol) in 20 mL of THF was carefully added $LiBH_4$ solution (2M solution in THF, 6.17 mmol). The resulting mixture was then heated to 40° C. When the reaction was complete, residual reagent was quenched with the slow addition of water followed by 1 M HCl solution, after which the contents were transferred to a separatory funnel using DCM (100 mL) and water (100 mL). The organic fraction was washed, then collected, dried over $Na_2SO_4$, concentrated under reduced pressure, and purified using silica gel chromatography. Fractions containing the product were pooled and concentrated under reduced pressure to give title compound 39C. $^1$H NMR (400 MHz, DMSO-$d_6$) δ 4.31 (t, J=5.0 Hz, 1H), 3.54-3.43 (m, 2H), 2.86 (d, J=6.1 Hz, 2H), 1.38 (s, 11H), 0.37-0.27 (m, 2H), 0.27-0.20 (m, 2H) ppm.

Synthesis of tert-butyl ((1-(2-(benzyloxy)ethyl)cyclopropyl)methyl)carbamate (39D): To a solution of 39C (17.8 mmol) in 50 mL of THF at 0° C. was added portionwise NaH (60% dispersion in mineral oil, 20.5 mmol, 1.15 equiv) and the resulting mixture was stirred for 10 minutes before slowly warming to room temperature. Benzyl bromide (44.6 mmol, 2.5 equiv) was then added and the reaction was allowed to stir overnight. Upon completion of the reaction the solvent was removed under reduced pressure and the residue was purified by silica gel chromatography. Fractions containing the product were pooled and concentrated under reduced pressure to give title compound 39D. $^1$H NMR (400 MHz, CDCl$_3$) δ 7.40-7.29 (m, 5H), 4.54 (s, 2H), 3.61 (t, J=6.4 Hz, 2H), 3.04 (d, J=5.7 Hz, 2H), 1.65 (t, J=6.4 Hz, 2H), 1.46 (s, 9H), 0.48-0.36 (m, 4H) ppm.

Synthesis of (1-(2-(benzyloxy)ethyl)cyclopropyl)methanamine (39E): To a solution of tert-butyl ((1-(2-(benzyloxy)ethyl)cyclopropyl)methyl)carbamate (39D, 2.93 mmol) in 20 mL of DCM was added HCl in MeOH (3M solution, 11.7 mmol, 4 equiv). When full conversion was observed, the reaction was concentrated under reduced pressure to give title compound 39E, which was used without purification. $^1$H NMR (400 MHz, DMSO-$d_6$) δ 7.84 (s, 2H), 7.49-7.21 (m, 5H), 4.49 (s, 2H), 3.54 (t, J=6.3 Hz, 2H), 2.73 (s, 2H), 1.66 (t, J=6.4 Hz, 2H), 0.69-0.33 (m, 4H) ppm.

Synthesis of tert-butyl ((1-(2-(benzyloxy)ethyl)cyclopropyl)methyl)glycinate (39F): To a solution of (1-(2-(benzyloxy)ethyl)cyclopropyl)methanamine (39E, 3.95 mmol, 2 equiv) in 10 mL of DCM was added DIPEA (4.34 mmol, 2.2 equiv) and the reaction was cooled to 0° C. A solution of tert-butyl bromoacetate in DCM (1.97 mmol) was then added dropwise over 10 minutes with continued stirring at 0° C. for 1 h. When the reaction was complete, the contents were transferred to a separatory funnel using DCM (10 mL) and water (10 mL). The organic fraction was washed, collected, dried over $Na_2SO_4$, concentrated under reduced pressure and purified by silica gel chromatography. Fractions containing the product were pooled and concentrated under reduced pressure to give title compound 39F. $^1$H NMR (400 MHz, DMSO-$d_6$) δ 7.39-7.23 (m, 5H), 4.44 (s, 2H), 3.53 (t, J=6.9 Hz, 2H), 3.17 (s, 2H), 2.35 (s, 2H), 1.60 (t, J=6.9 Hz, 2H), 1.41 (s, 9H), 0.34-0.22 (m, 4H) ppm. MS (m/z) 320.28 [M+H]$^+$.

Synthesis of tert-butyl N-((1-(2-(benzyloxy)ethyl)cyclopropyl)methyl)-N-((chloromethoxy)carbonyl)glycinate (39G): To a solution of 39F (4.02 mmol) in 100 mL of DCM at 0° C. was added triethylamine (8.05 mmol, 2 equiv) followed by dropwise addition of chloromethyl chloroformate (6.03 mmol, 1.5 equiv). When the reaction was complete, the contents were transferred to a separatory funnel using DCM (50 mL) and saturated ammonium chloride solution (100 mL). The organic fraction was washed, collected, dried over $Na_2SO_4$, concentrated under reduced pressure to yield title compound 39G, which was used without purification. $^1$H NMR (400 MHz, DMSO-$d_6$) δ 7.46-7.15 (m, 5H), 5.86 (d, J=5.3 Hz, 2H), 4.44 (d, J=4.0 Hz, 2H), 3.97 (d, J=2.5 Hz, 2H), 3.59-3.47 (m, 2H), 3.32 (s, 1H), 3.23 (d, J=3.6 Hz, 2H), 1.56 (t, J=6.8 Hz, 2H), 1.41 (d, J=3.2 Hz, 8H), 0.45-0.32 (m, 4H) ppm.

Synthesis of tert-butyl N-((1-(2-(benzyloxy)ethyl)cyclopropyl)methyl)-N-((((di-tert-butoxyphosphoryl)oxy)methoxy)carbonyl)glycinate (3911): To a solution of tert-butyl N-((1-(2-(benzyloxy)ethyl)cyclopropyl)methyl)-N-((chloromethoxy)carbonyl)glycinate (39G, 0.255 mmol) in 1 mL of 1,2-dimethoxyethane was added tetrabutylammonium di-tert-butyl phosphate (0.357 mmol, 1.4 equiv). When the reaction was complete, the contents were transferred to a separatory funnel using DCM (10 mL) and water (2×10 mL) and brine (1×10 mL). The organic fraction was washed, collected, dried over $Na_2SO_4$, concentrated under reduced pressure and purified by silica gel chromatography. Fractions containing the product were pooled and concentrated under reduced pressure to give title compound 3911. $^1$H NMR (400 MHz, DMSO-$d_6$) δ 7.45-7.19 (m, 5H), 5.46 (d, J=12.4 Hz, 2H), 4.44 (d, J=4.2 Hz, 2H), 4.09-3.92 (m, 3H), 3.57-3.46 (m, 2H), 3.24 (d, J=8.9 Hz, 2H), 2.00 (s, 1H), 1.56 (q, J=6.6 Hz, 2H), 1.41 (s, 27H), 1.18 (t, J=7.1 Hz, 1H), 0.41-0.32 (m, 4H) ppm. MS (m/z) 608.39 [M+Na]$^+$.

Synthesis of tert-butyl N-((((di-tert-butoxyphosphoryl)oxy)methoxy)carbonyl)-N-41-(2-hydroxyethyl)cyclopropyl)methyl)glycinate (39I): The title compound was prepared according to the method presented for the synthesis of compound 30D of Example 30 utilizing tert-butyl N-((1-(2-(benzyloxy)ethyl)cyclopropyl)methyl)-N-((((di-tert-butoxyphosphoryl)oxy)methoxy)carbonyl)glycinate (39G) in the place of 30C. $^1$H NMR (400 MHz, DMSO-$d_6$) δ 5.56-5.38 (m, 2H), 4.08-3.91 (m, 3H), 3.49 (t, J=6.8 Hz, 2H), 3.23 (d, J=7.6 Hz, 2H), 1.99 (s, 1H), 1.42 (d, J=3.0 Hz, 27H), 1.18 (t, J=7.1 Hz, 1H), 0.41-0.26 (m, 4H) ppm. MS (m/z) 518.30 [M+H]$^+$.

Synthesis of 2-(1-(((2-(tert-butoxy)-2-oxoethyl)(((di-tert-butoxyphosphoryl)oxy)methoxy)carbonyl)amino)methyl)cyclopropyl)acetic acid (39J): To a solution of tert-butyl N-((((di-tert-butoxyphosphoryl)oxy)methoxy)carbonyl)-N-((1-(2-hydroxyethyl)cyclopropyl)methyl)glycinate (39I, 3.07 mmol) in ACN/water (1:1, 24 mL) was added TEMPO (0.153 mmol, 0.05 equiv), potassium dihydrogen phosphate (1.53 mmol, 0.5 equiv) and dipotassium hydrogen phosphate (1.53 mmol, 0.5 equiv). The solution was cooled to 0° C. Sodium chlorite (4.6 mmol, 1.5 equiv) was added, followed by sodium hypochlorite (8.25% NaOCl, 3.63 mL). The ice bath was removed and the reaction was stirred for 3.5 hours. The reaction was diluted with water, extracted with EtOAc (3×), the combined organic layers were washed with brine, dried over MgSO$_4$, filtered and concentrated under reduced pressure to yield title compound 39J, which was used without purification. $^1$H NMR (400 MHz, DMSO-$d_6$) δ 5.54-5.37 (m, 2H), 4.05-3.88 (m, 3H), 3.31 (t, J=3.0 Hz, 2H), 2.23 (d, J=5.5 Hz, 2H), 2.07 (s, 3H), 1.41 (d, J=1.8 Hz, 27H), 0.52-0.35 (m, 4H) ppm. MS (m/z) 532.30 [M+H]$^+$.

Synthesis of tert-butyl N-((1-(2-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-oxoethyl)cyclopropyl)methyl)-N-((((di-tert-butoxyphosphoryl)oxy)methoxy)carbonyl)glycinate (39K): To a suspension of Intermediate 5E (3.39 mmol, 1.2 equiv), 1-methylimidazole (25.93 mmol, 2.1 equiv), and 39J (2.83 mmol) in MeCN (12 mL) was added TCFH (2.97 mmol, 1.05 equiv) and the resulting mixture was stirred at rt. Upon completion of the reaction the solvent was removed under reduced pressure and the resulting residue purified by reverse phase HPLC. Fractions containing the product were pooled and lyophilized to give title compound 39K as a mixture of atropisomers. $^1$H NMR (400 MHz, DMSO-$d_6$) δ 7.93-7.86 (m), 7.84-7.70 (m), 7.51-7.38 (m), 7.06-6.96 (m), 6.89-6.81 (m), 6.43-6.34 (m), 5.60-5.35 (m), 5.05-4.96 (m), 4.74-4.65 (m), 4.65-4.54 (m), 4.09-4.02 (m), 4.05-3.98 (m), 4.01-3.83 (m), 3.83 (s), 3.63-3.50 (m), 3.32-3.21 (m), 3.08-2.97 (m), 2.98-2.82 (m), 2.40-2.30 (m), 2.00 (s), 1.78-1.64 (m), 1.45-1.37 (m), 1.28 (s), 1.30-1.09 (m), 1.00 (s), 0.39-0.30 (m), 0.25 (s) ppm. $^{19}$F NMR (375 MHz, DMSO-$d_6$) δ-60.75--61.01 (m), -69.56--69.76 (m), -69.76--69.91 (m), -69.92--70.12 (m), -80.03--80.16 (m), -80.42--80.5((m), -80.67--80.83 (m), -110.49--110.78 (m) ppm. MS (m/z) 1481.4 [M+Na]$^+$.

Synthesis of N-41-(2-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-oxoethyl)cyclopropyl)methyl)-N-(((phosphonooxy)methoxy)carbonyl)glycine (39): To a solution of 39K (0.034 mmol) in 0.1 mL of MeCN was added 85% aqueous phosphoric acid (0.343 mmol, 10 equiv) and the resulting suspension stirred overnight. When full conversion was observed, the reaction was concentrated under reduced pressure and purified by reverse phase HPLC. Fractions containing the product were pooled and lyophilized to give title compound 39 as a mixture of atropisomers. $^1$H NMR (400 MHz, DMSO-$d_6$) δ 1H NMR (400 MHz, DMSO-$d_6$) δ 9.21-9.04 (m), 7.98-7.87 (m), 7.86-7.72 (m), 7.51-7.39 (m), 7.06-6.90 (m), 6.87-6.80 (m), 6.53-6.46 (m), 6.39-6.30 (m), 5.57-5.32 (m), 5.06-4.80 (m), 4.80-4.69 (m), 4.70-4.59 (m), 4.63-4.45 (m), 4.21 (s), 4.08-3.84 (m), 3.85-3.75 (m), 3.71 3.62 (m), 3.62-3.47 (m), 3.35-3.24 (m), 3.07-2.84 (m), 2.63-2.56 (m), 2.30-2.16 (m), 1.82-1.67 (m), 1.47-1.36 (m), 1.41 (s), 1.00 (s), 0.50 (s), 0.37 (s) ppm. $^{19}$F NMR (375 MHz, DMSO-$d_6$) δ-60.71--60.99 (m), -69.49--69.75 (m), -69.99--70.20 (m), -75.32, -75.37 (d), -79.70--79.85 (m), -80.03--80.25 (m), -80.37--80.52 (m), -80.70--80.92 (m), -102.46, -103.01--103.19 (m), -103.26, -110.55--110.78 (m), -110.75, -110.94 ppm. MS (m/z) 1291.20 [M+H]$^+$.

Example 40

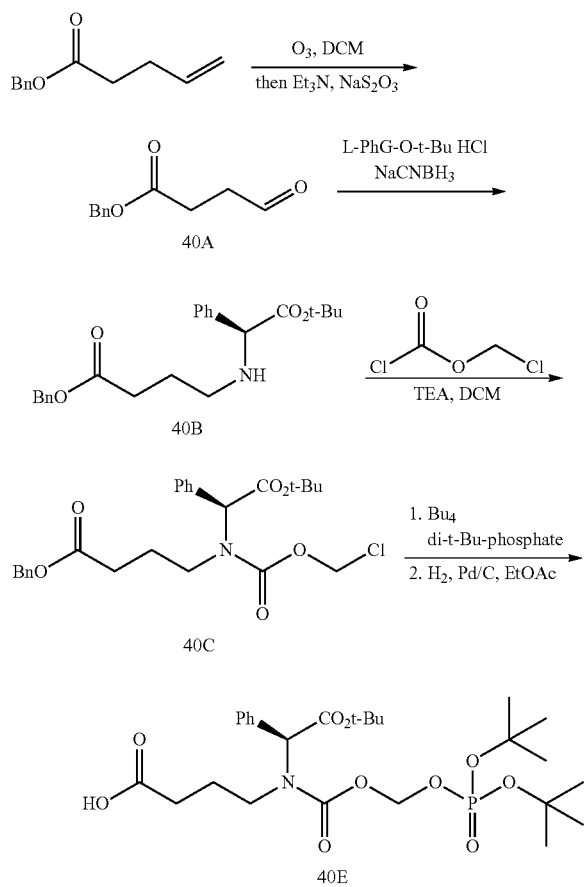

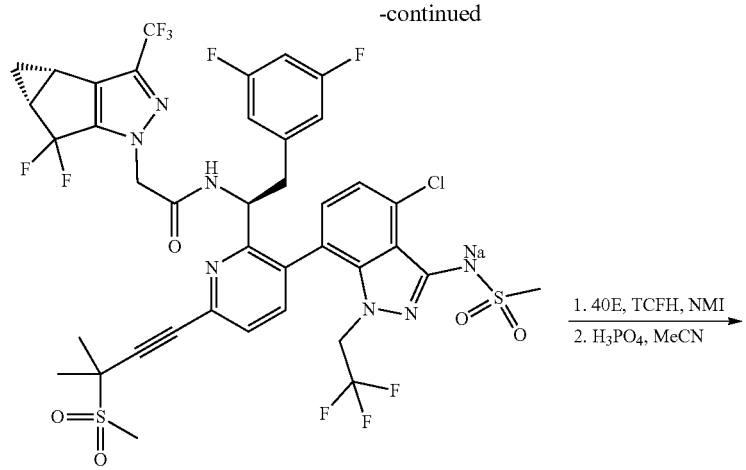

Compound 5E

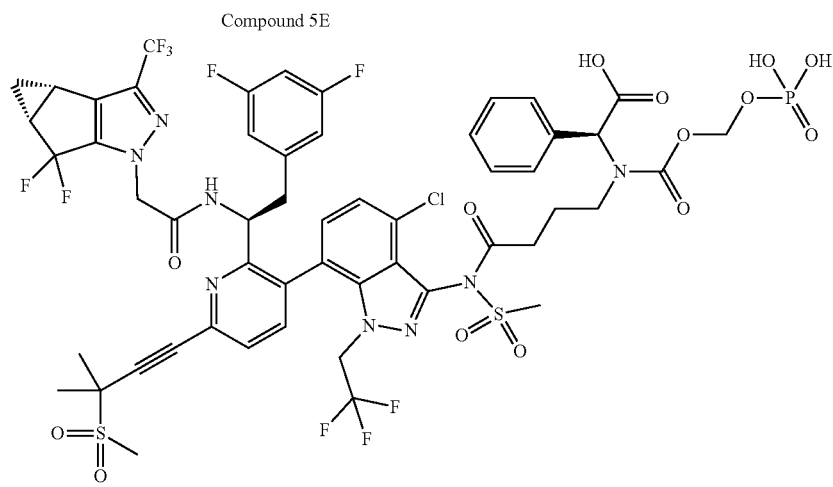

40

Synthesis of benzyl 4-oxobutanoate (40A): To a solution of benzyl pent-4-enoate (2.63 mmol) in a 1:1 mixture of DCM/MeOH (10 mL) was carefully bubbled $O_3$ gas) at −78° C. When full conversion was observed, the reaction was sparged with Ar gas for 5 mins, after which $Et_3N$ (5.26 mmol, 2 equiv) was carefully added. To the resulting mixture was then added 20 mL of concentrated $Na_2S_2O_3$ and the reaction was stirred a further 1 h. Upon completion of this time, the contents were transferred to a separatory funnel using DCM (100 mL) and $H_2O$ (100 mL). The aqueous layer was extracted with DCM (2×50 mL) and the organic fractions were collected, dried over $Na_2SO_4$, concentrated under reduced pressure to yield title compound 40A which was taken forward without further purification. MS (m/z) 191.161 [M+H]$^+$.

Synthesis of benzyl (S)-4-((2-(tert-butoxy)-2-oxo-1-phenylethyl)amino)butanoate (40B): To a solution of 40A (2.63 mmol) in 44 mL of MeOH were added sequentially L-Phenylglycine tert-butyl ester hydrochloride (5.25 mmol, 2 equiv) and sodium cyanoborohydride (5.78 mmol, 2.2 equiv). When full conversion was observed, the reaction was concentrated under reduced pressure and transferred to a separatory funnel using DCM (25 mL) and saturated aqueous $NaHCO_3$(25 mL). The aqueous layer was extracted with further DCM (2×10 mL) and the organic fractions combined, dried over $Na_2SO_4$, concentrated under reduced pressure and purified by silica gel chromatography. Fractions containing the product were pooled and concentrated under reduced pressure to give title compound 40B. $^1$H NMR (400 MHz, $CDCl_3$) δ 7.43-7.32 (m, 10H), 5.11 (s, 2H), 2.70 (dt, J=11.5, 6.7 Hz, 1H), 2.57 (dt, J=11.6, 7.1 Hz, 1H), 2.46 (t, J=7.3 Hz, 3H), 1.90 (p, J=7.1 Hz, 2H), 1.41 (s, 9H) ppm. MS (m/z): 384.30 [M+H]$^+$.

Synthesis of benzyl (S)-4-((2-(tert-butoxy)-2-oxo-1-phenylethyl)((chloromethoxy)carbonyl)amino)butanoate (40C): The title compound was prepared according to the method presented for the synthesis of compound 30B of Example 30 utilizing benzyl 40B in the place of 30A. $^1$H NMR (400 MHz, $CDCl_3$) δ 7.45-7.29 (m, 10H), 5.85 (dd, J=15.6, 5.0 Hz, 1H), 5.74-5.64 (m, 1H), 5.07 (s, 2H), 3.41-3.27 (m, 1H), 3.23-3.08 (m, 1H), 2.94-2.80 (m, 1H), 2.23-2.11 (m, 2H), 1.77-1.63 (m, 1H), 1.52 (s, 9H) ppm. MS (m/z): 498.20 [M+Na]$^+$.

Synthesis of benzyl (S)-4-((2-(tert-butoxy)-2-oxo-1-phenylethyl)((((di-tert-butoxyphosphoryl)oxy)methoxy)carbonyl)amino)butanoate (40D): The title compound was prepared according to the method presented for the synthesis of compound 30C of Example 30 utilizing benzyl 40C in the place of 30B. MS (m/z): 672.40 [M+Na]$^+$.

Synthesis of (S)-4-((2-(tert-butoxy)-2-oxo-1-phenylethyl)((((di-tert-butoxyphosphoryl)oxy)methoxy)carbonyl)amino)butanoic acid (40E): The title compound was prepared according to the method presented for the synthesis of compound 30D of Example 30 utilizing benzyl (S)-4-((2-

(tert-butoxy)-2-oxo-1-phenylethyl)((((di-tert-butoxyphosphoryl)oxy)methoxy)carbonyl)amino)butanoate (40D) in the place of 30C. MS (m/z) 582.30 [M+Na]⁺.

Synthesis of (S)-2-((4-(N-(4-chloro-7-(2-((S)-1-(2-O3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-4-oxobutyl)(((phosphonooxy)methoxy)carbonyl)amino)-2-phenylacetic acid (40): An atropisomeric mixture of the title compound was prepared according to the method presented for the synthesis of compound 39 of Example 39 utilizing 40E in the place of 39J. ¹H NMR (400 MHz, DMSO-d₆) δ 9.22-9.08 (m), 7.90-7.73 (m), 7.53-7.40 (m), 7.30-7.21 (m), 7.08-6.97 (m), 6.90-6.77 (m), 6.51-6.39 (m), 5.74 (s), 5.64-5.44 (m), 5.39 (s), 5.02-4.93 (m), 4.90-4.68 (m), 4.71-4.59 (m), 4.20 (s), 3.60-3.43 (m), 3.15-3.05 (m), 3.06-2.87 (m), 1.98 (s), 1.94-1.85 (m), 1.78-1.72 (m), 1.68 (s), 1.40 (s), 1.30 (s), 0.97 (s) ppm. ¹⁹F NMR (375 MHz, DMSO-d₆) δ −60.70−−61.07 (m), −69.52−−69.70 (m), −69.81−−69.98 (m), −74.69, −79.79 (m), −80.38−−80.54 (m), −102.73, −103.25, −103.41, −103.92, −110.56−−110.72 (m) ppm. MS (m/z) 1341.3 [M+H]⁺.

Example 41

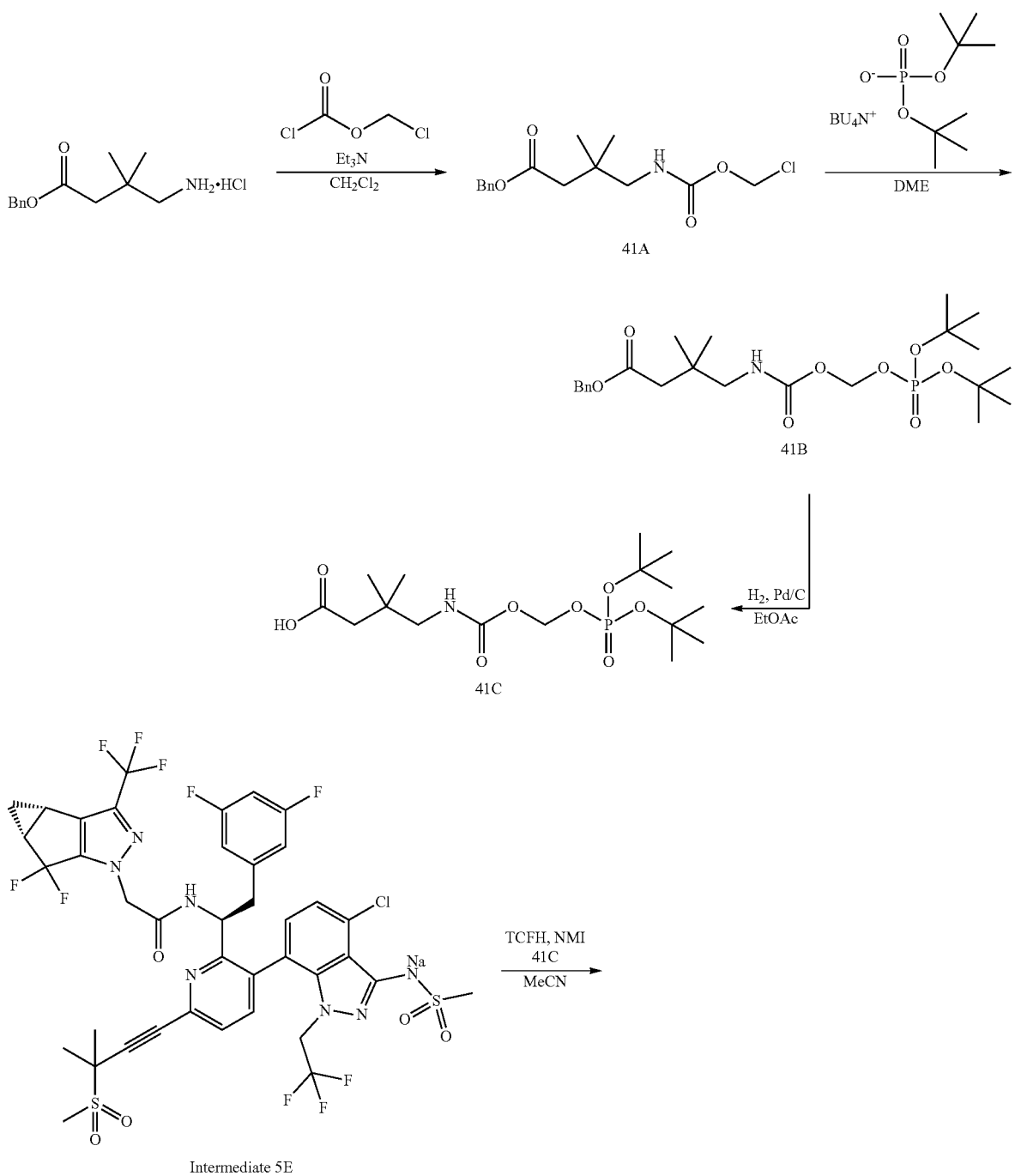

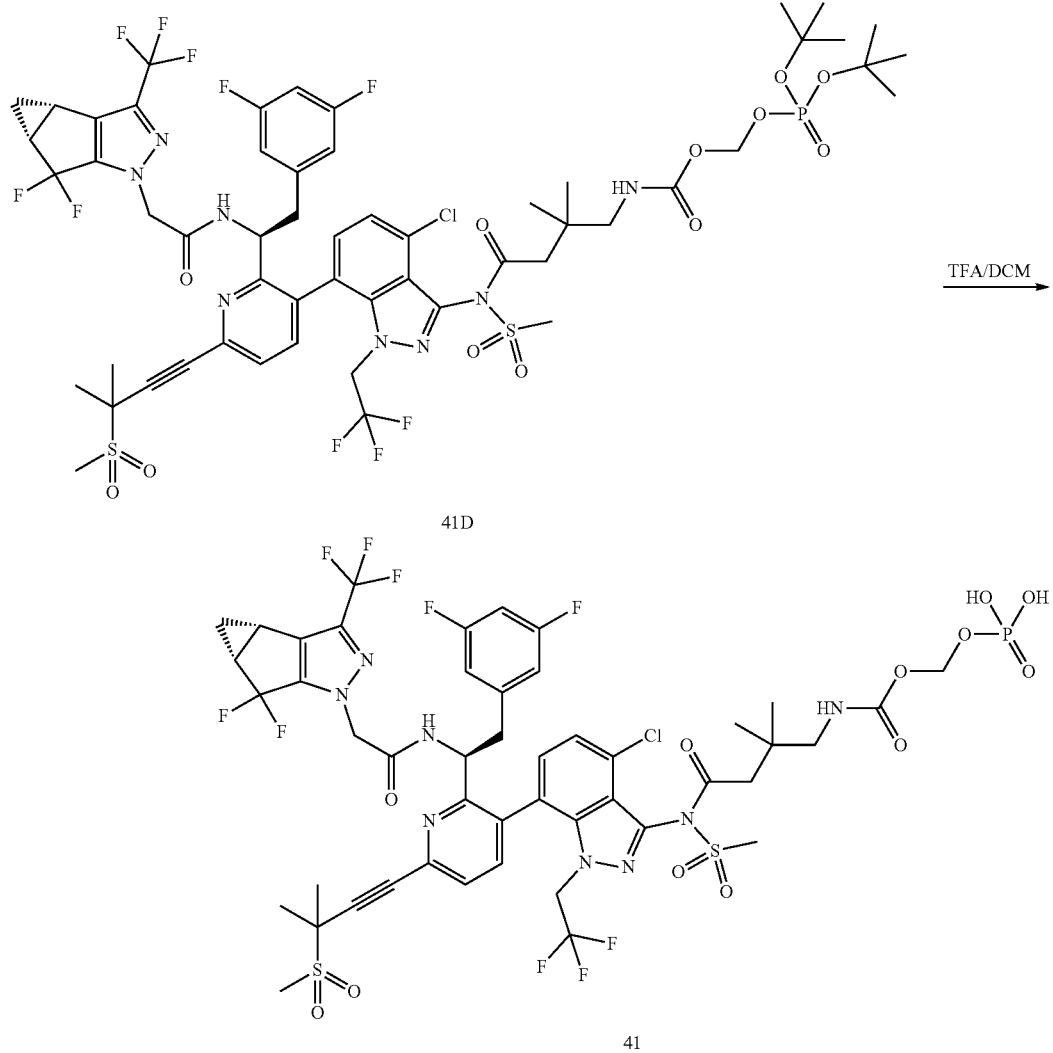

Synthesis of benzyl 4-(((chloromethoxy)carbonyl)amino)-3,3-dimethylbutanoate (41A): To a stirred solution of benzyl 4-amino-3,3-dimethylbutanoate hydrochloride (7.4 mmol) in CH$_2$Cl$_2$ (74 mL) at 0° C. was added triethylamine (24.0 mmol). Chloromethyl chloroformate (11 mmol) was then added and the reaction mixture was stirred at 0° C. and monitored by TLC and LCMS. After completion, the reaction mixture was washed with sat. aq. solutions of NH$_4$C$_1$ and brine. The combined organic layers were dried over anhydrous Na$_2$SO$_4$, filtered, concentrated under reduced pressure, and purified by silica gel chromatography (eluting 0-25% EtOAc in hexanes). Fractions containing the product were pooled and concentrated under reduced pressure to give title compound 41A. MS (m/z) 336.2 [M+Na]$^+$.

Synthesis of benzyl 4-(((((di-tert-butoxyphosphoryl)oxy)methoxy)carbonyl)amino)-3,3-dimethylbutanoate (41B): The title compound was prepared according to the method presented for the synthesis of compound 30C of Example 30 utilizing 41A in the place of 30B. MS (m/z) 510.3 [M+Na]$^+$.

Synthesis of 4-(((((di-t-butoxyphosphoryl)oxy)methoxy)carbonyl)amino)-3,3-dimethylbutanoic acid (41C): The title compound was prepared according to the method presented for the synthesis of compound 30D of Example 30 utilizing 41B in the place of 30C. MS (m/z) 420.2 [M+Na]$^+$.

Synthesis of ((di-tert-butoxyphosphoryl)oxy)methyl (4-(N-(4-chloro-7-(2-45)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2,2-dimethyl-4-oxobutyl) carbamate (41D): To a suspension of Intermediate 5E (3.76 mmol, 1.3 equiv), 1-methylimidazole (10.1 mmol, 3.5 equiv), and 41C (2.83 mmol) in MeCN (12 mL) was added TCFH (3.47 mmol, 1.20 equiv) and the resulting mixture was stirred at rt. Upon completion of the reaction the solvent was removed under reduced pressure and the resulting residue purified by silica gel chromatography. Fractions containing the product were pooled and concentrated under reduced pressure to give title compound 41D as a mixture of atropisomers. MS (m/z) 1369.39 [M+Na]$^+$.

Synthesis of (phosphonooxy)methyl (4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2, 2-dimethyl-4-oxobutyl)carbamate (41): To a solution of 41D (2.2 mmol) in DCM (20 mL) was added TFA (5.1 mL). When the reaction had reached completion, the solvent was removed under reduced pressure and the residue purified by reverse phase HPLC. Product-containing fractions were pooled and lyophilized to yield title compound 41 as a mixture of atropisomers. $^1$H NMR (400 MHz, DMSO-$d_6$) δ 9.17 (dd), 7.92 (d), 7.86-7.73 (m), 7.53-7.39 (m), 7.12 (t), 7.08-6.93 (m), 6.87 (d), 6.53-6.45 (m), 6.39-6.32 (m), 5.45-5.26 (m), 5.01 (d), 4.91-4.82 (m), 4.84-4.72 (m), 4.71-4.57 (m), 4.26-4.14 (m), 4.05-3.92 (m), 3.55 (d), 3.28 (d), 3.02-2.87 (m), 2.08-1.80 (m), 1.76 (s), 1.47-1.35 (m), 0.99 (s), 0.88 (d), 0.68 (s), 0.60 (s) ppm. $^{19}$F NMR (376 MHz, DMSO-$d_6$) δ−60.90 (d), −69.94 (d), −78.30-81.85 (m), −100.97−−106.03 (m), −110.77 (d) ppm. MS (m/z): 1236.300 [M+H]$^+$.

Example 42

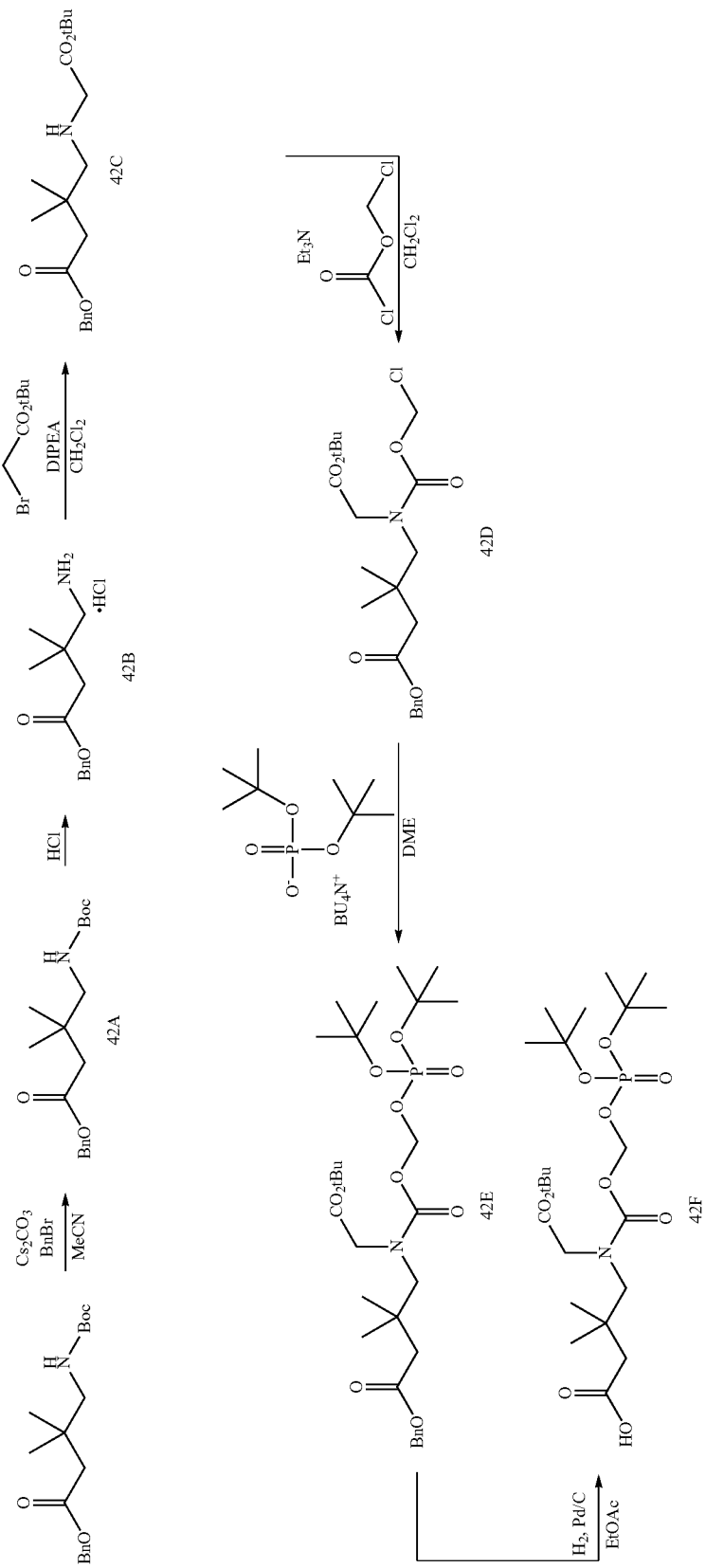

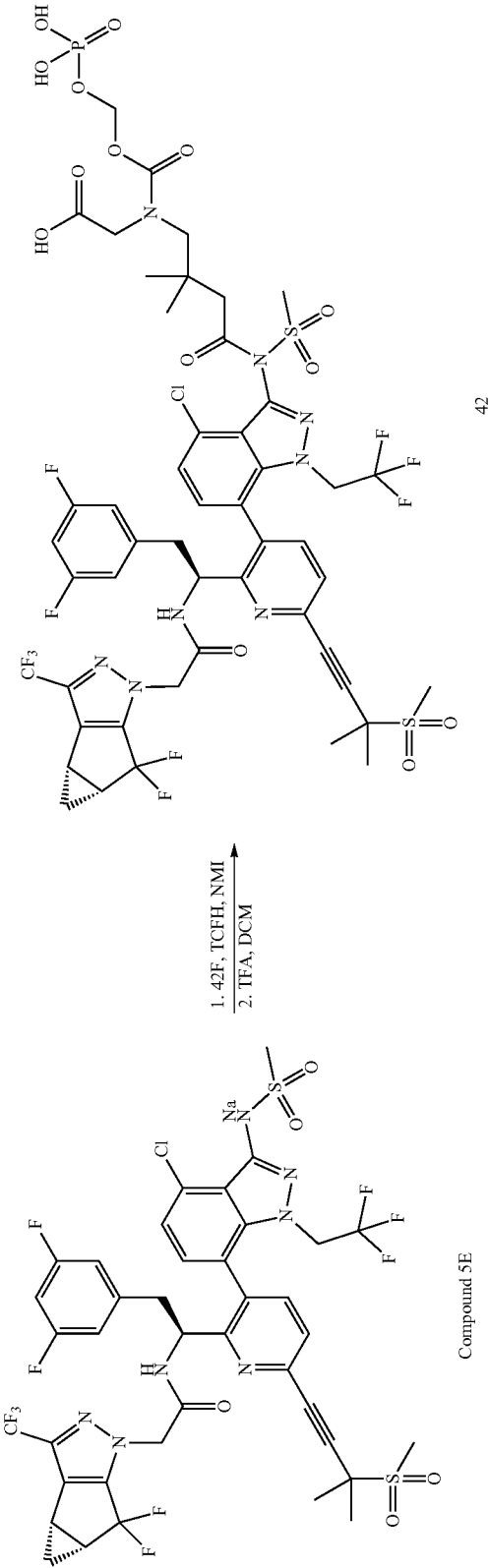

Synthesis of benzyl 4-((tert-butoxycarbonyl)amino)-3,3-dimethylbutanoate (42A): 4-(t-butoxycarbonylamino)-3,3-dimethyl-butanoic acid (8.6 mmol) was dissolved in MeCN (72 mL). Cesium carbonate (10 mmol) and BnBr (10 mmol) were added sequentially and the resulting mixture was stirred at room temperature for 15 h and monitored by TLC and LCMS. Upon completion, the mixture was filtered through a pad of Celite®. The filtered reaction was concentrated under reduced pressure and purified via silica gel chromatography to afford title compound 42A. $^1$H NMR (400 MHz, Chloroform-d) δ 7.42-7.31 (m, 5H), 5.13 (s, 2H), 3.04 (d, J=6.7 Hz, 2H), 2.29 (s, 2H), 1.46 (s, 9H), 1.00 (s, 6H) ppm. MS (m/z): 322.5 [M+H]$^+$.

Synthesis of benzyl 4-amino-3,3-dimethylbutanoate hydrochloride (42B): 42A (7.8 mmol) was treated with hydrochloric acid (31 mL, 4N in dioxane). After stirring for 4 h, the reaction mixture was concentrated to afford title compound 42B, which was used without purification. $^1$H NMR (400 MHz, Chloroform-d) δ 8.47 (s, 2H), 7.38-7.28 (m, 5H), 5.11 (s, 2H), 3.02 (s, 2H), 2.49 (s, 2H), 1.15 (s, 6H). MS (m/z): 222.4 [M+H]$^+$.

Synthesis of benzyl 4-((2-(tert-butoxy)-2-oxoethyl)amino)-3,3-dimethylbutanoate (42C): To a stirred suspension of 42B (7.8 mmol) in CH$_2$Cl$_2$ (90 mL) was added DIPEA (23 mmol) and the reaction mixture was cooled to 0° C. t-Butyl bromoacetate (3.9 mmol) in CH$_2$Cl$_2$ (10 mL) was added dropwise via syringe pump (1 mL/min). The resulting reaction mixture was stirred at 0° C. for 1 h then warmed to room temp. After stirring for an additional 24 h, the mixture was washed with 0.5 M aq. HCl solution (~75 mL), water (~50 mL), and brine. The combined organic layers were dried over anhydrous Na$_2$SO$_4$, filtered, and concentrated. The residue was purified by column chromatography (0% to 10% MeOH in CH$_2$Cl$_2$) to afford title compound 42C. $^1$H NMR (400 MHz, Chloroform-d) δ 7.38-7.34 (m, 5H), 5.10 (s, 2H), 3.32 (s, 2H), 2.52 (s, 2H), 2.38 (s, 2H), 1.47 (s, 9H), 1.03 (s, 6H). MS (m/z): 336.3 [M+H]$^+$.

Synthesis of benzyl 4-((2-(tert-butoxy)-2-oxoethyl)((chloromethoxy)carbonyl)amino)-3,3-dimethylbutanoate (42D): To a stirred solution of 42C (2.7 mmol) in CH$_2$Cl$_2$ (18 mL) at 0° C. was added triethylamine (5.9 mmol). Chloromethyl chloroformate (2.7 mmol) was then added and the reaction mixture was stirred at 0° C. and monitored by TLC and LCMS. After completion, the reaction mixture was washed with sat. aq. solutions of NH$_4$C$_1$ and brine. The combined organic layers were dried over anhydrous Na$_2$SO$_4$, filtered, and concentrated to afford of title compound 42D, which was used without purification. MS (m/z) 450.2 [M+Na]$^+$.

Synthesis of benzyl 4-((2-(tert-butoxy)-2-oxoethyl)(((((di-tert-butoxyphosphoryl)oxy)methoxy)carbonyl)amino)-3,3-dimethylbutanoate (42E): 42D (1.3 mmol) was dissolved in dimethoxyethane (4.6 mL) then di-t-butyl phosphate tetrabutylammonium salt (1.9 mmol) was added and the mixture was heated to 80° C. for 1 h. The mixture was cooled to room temperature and concentrated. The crude material was dissolved in EtOAc and washed with water (3×), brine, dried over Na$_2$SO$_4$, filtered, and concentrated to yield title compound 42E which was used without further purification.

Synthesis of 4-02-(t-butoxy)-2-oxoethyl)(((((di-t-butoxyphosphoryl)oxy)methoxy) carbonyl)amino)-3,3-dimethylbutanoic acid (42F): 42E (1.3 mmol) was dissolved in EtOAc (30 mL) and palladium on carbon (0.27 mmol) was added. After stirring for 1 h under hydrogen gas (1 atm), product formation was observed. The crude product was isolated after filtration over a pad of Celite®. Upon concentration, the crude was purified by column chromatography (0% to 10% MeOH in CH$_2$Cl$_2$) to afford title compound 42F. MS (m/z) 534.3 [M+Na]$^+$.

Synthesis of N-(4-(N-(4-chloro-7-(2-((S)-1-(2-((3bS,4aR)-5,5-difluoro (trifluoromethyl)-3b,4,4a,5-tetrahydro-1H-cyclopropa[3,4]cyclopenta[1,2-c]pyrazol yl)acetamido)-2-(3,5-difluorophenyl)ethyl)-6-(3-methyl-3-(methylsulfonyl)but-1-yn yl)pyridin-3-yl)-1-(2,2,2-trifluoroethyl)-1H-indazol-3-yl)methylsulfonamido)-2,2-dimethyl-4-oxobutyl)-N-(((phosphonooxy)methoxy)carbonyl)glycine (42): The title compound was prepared according to the method presented for the synthesis of 41 of Example 41 utilizing 42F in the place of 41C. $^1$H NMR (400 MHz, DMSO-d$_6$) δ 9.28-9.10 (m), 8.00-7.68 (m), 7.59-7.37 (m), 7.13-6.95 (m), 6.79 (dd), 6.55-6.46 (m), 6.46-6.24 (m), 5.50-5.33 (m), 5.25 (dd), 5.03 (dd), 4.96-4.76 (m), 4.74-4.47 (m), 4.04-3.64 (m), 3.55 (d), 3.28 (d), 3.23-3.08 (m), 3.07-2.85 (m), 2.20-1.99 (m), 1.90 (d), 1.46-1.34 (m), 1.09-0.94 (m), 0.91 (s), 0.78 (d), 0.62 (d) ppm. $^{19}$F NMR (375 MHz, DMSO-d$_6$) δ−59.74−−62.28 (m), −69.07−−70.40 (m), −79.59−−81.05 (m), −101.60−−104.56 (m), −110.72 (d) ppm. MS (m/z): 1294.30 [M+H]$^+$.

Example 43

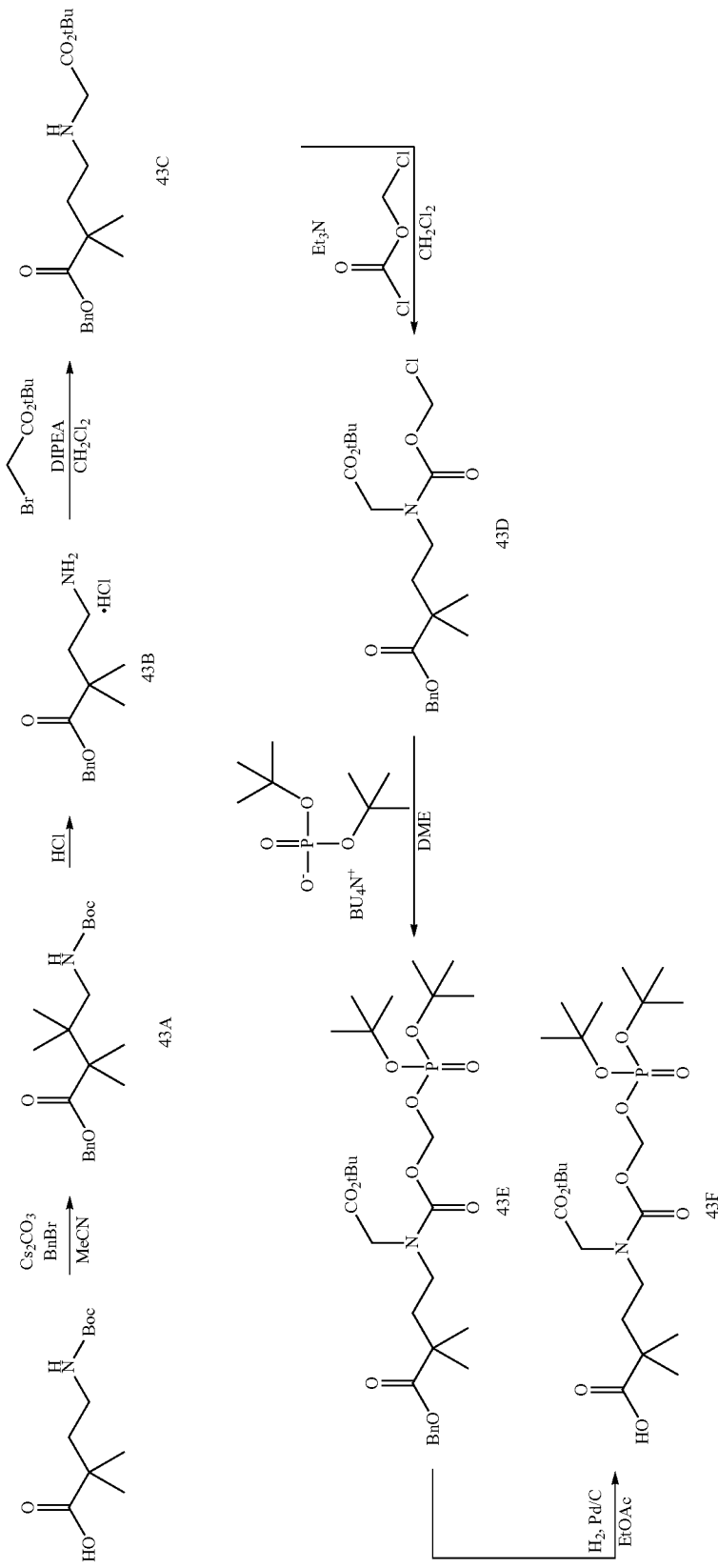

-continued
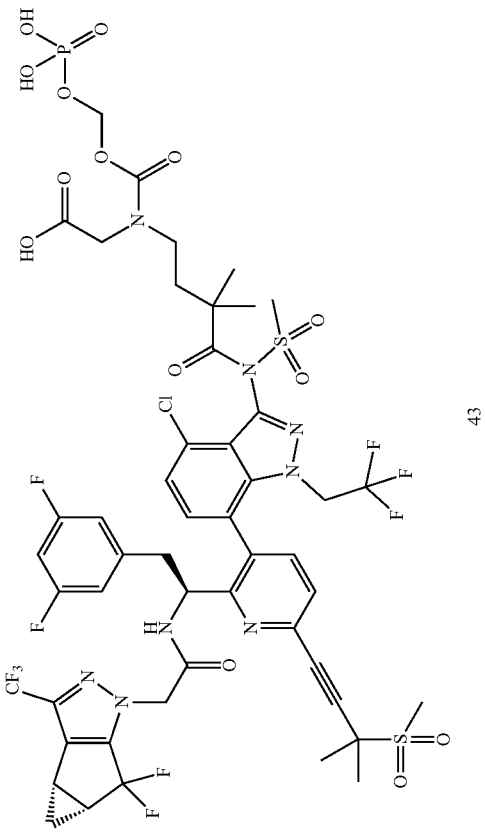
43
1. 43F, TCFH, NMI
2. TFA, DCM
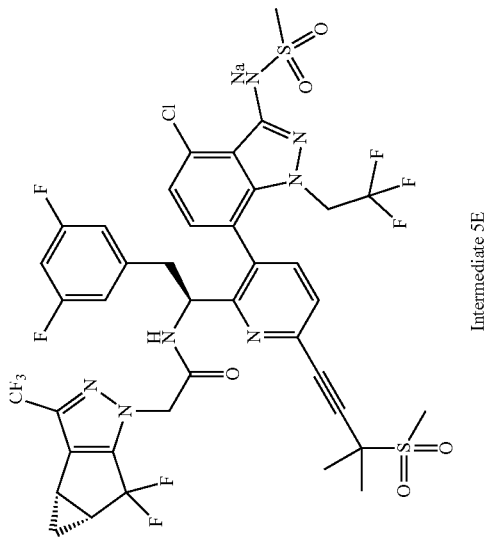
Intermediate 5E Synthesis of benzyl 4-((tert-butoxycarbonyl)amino)-2,2-dimethylbutanoate (43A): 4-(t-butoxycarbonylamino)-2,2-dimethyl-butanoic acid (22 mmol) was dissolved in MeCN (72 mL). Cesium carbonate (26 mmol) and BnBr (26 mmol) were added sequentially and the resulting mixture was stirred at room temperature for 15 h and monitored by TLC and LCMS. Upon completion, the mixture was filtered through a pad of Celite®. The filtered reaction was concentrated and purified by column chromatography to afford title compound 43A. $^1$H NMR (400 MHz, Chloroform-d) δ 7.42-7.31 (m, 5H), 5.13 (s, 2H), 3.14 (s, 2H), 1.83-1.76 (m, 2H), 1.45 (s, 10H), 1.25 (s, 6H) ppm.

Synthesis of benzyl 4-amino-2,2-dimethylbutanoate hydrochloride (43B): 43A (20 mmol) was dissolved in dioxane (20 mL) and treated with hydrochloric acid (20 mL, 4N in dioxane). After stirring for 4 h, the reaction mixture was concentrated to afford title compound 43B, which was used without further purification. MS (m/z) 222.3 [M+H]$^+$.

Synthesis of benzyl 4-((2-(tert-butoxy)-2-oxoethyl)amino)-2,2-dimethylbutanoate (43C): To a stirred suspension of 43B (20 mmol) in CH$_2$Cl$_2$ (200 mL) was added DIPEA (11 mL, 60 mmol) and the reaction mixture was cooled to 0° C. t-Butyl bromoacetate (10 mmol) in CH$_2$Cl$_2$ (10 mL) was added dropwise via syringe pump (1 mL/min). The resulting reaction mixture was stirred at 0° C. for 1 h, then warmed to room temperature. After stirring for an additional 24 h, the mixture was then washed with 0.5 M aq. HCl solution (~150 mL), water (~100 mL), and then brine. The combined organic layers were dried over anhydrous Na$_2$SO$_4$, filtered, and concentrated. The crude mixture was purified by column chromatography (0% to 10% MeOH in CH$_2$Cl$_2$) to afford title compound 43C. $^1$H NMR (400 MHz, Chloroform-d) δ 7.42-7.31 (m, 5H), 5.15 (s, 2H), 3.67 (s, 2H), 3.14 (s, 2H), 2.20-2.12 (m, 2H), 1.52 (s, 9H), 1.28 (s, 6H). MS (m/z) 336.5 [M+H]$^+$.

Synthesis of benzyl 4-((2-(tert-butoxy)-2-oxoethyl)((chloromethoxy)carbonyl)amino)-2,2-dimethylbutanoate (43D): To a stirred solution of the 43C (9.5 mmol) in CH$_2$Cl$_2$ (95 mL) at 0° C. was added triethylamine (3.3 mL, 24 mmol). Chloromethyl chloroformate (1.3 mL, 14 mmol) was then added and the reaction mixture was stirred at 0° C. and monitored by TLC and LCMS. After completion, the reaction mixture was washed with sat. aq. solutions of NH$_4$Cl and brine. The combined organic layers were dried over anhydrous Na$_2$SO$_4$, filtered, and concentrated to afford title compound 43D, which was used without purification. MS (m/z) 450.9 [M+Na]$^+$.

Synthesis of benzyl 4-((2-(tert-butoxy)-2-oxoethyl)(((((di-tert-butoxyphosphoryl)oxy)methoxy)carbonyl)amino)-2,2-dimethylbutanoate (43E): 43D (5.8 mmol) was dissolved in dimethoxyethane (20 mL) then di-t-butyl phosphate tetrabutylammonium salt (8.2 mmol) was added and the mixture was heated to 80° C. for 1 h.

The mixture was cooled to room temperature and concentrated. The crude material was dissolved in EtOAc and washed with water (3×), brine, dried over Na$_2$SO$_4$, filtered, and concentrated to yield title compound 43E, which was used without further purification. MS (m/z) 602.7 [M+H]$^+$.

Synthesis of 4-((2-(tert-butoxy)-2-oxoethyl)((((di-tert-butoxyphosphoryl)oxy)methoxy)carbonyl)amino)-2,2-dimethylbutanoic acid (43F): 43E (4.8 mmol) was dissolved in EtOAc (30 mL) then palladium on carbon (1.2 mmol) was added. After stirring for 1 h under hydrogen gas (1 atm), product formation was observed. The crude product was isolated after filtration over a pad of Celite®. Upon concentration, the crude was purified by column chromatography (0% to 10% MeOH in CH$_2$Cl$_2$) to afford the title compound 43F. $^1$H NMR (400 MHz, Chloroform-d) δ 5.60 (dd, J=30.6, 15.2 Hz, 2H), 3.88 (d, J=31.2 Hz, 2H), 3.48 (t, J=6.5 Hz, 1H), 3.37-3.31 (m, 1H), 1.92-1.86 (m, 2H), 1.54-1.50 (m, 18H), 1.47 (d, J=7.6 Hz, 9H), 1.24 (d, J=17.5 Hz, 6H). MS (m/z) 534.5 [M+Na]$^+$.

Synthesis of N-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-3,3-dimethyl-4-oxobutyl)-N-(((phosphonooxy)methoxy)carbonyl)glycine (43): The title compound was prepared according to the method presented for the synthesis of compound 41 of Example 41 utilizing 43F in the place of 41D. $^1$H NMR (400 MHz, DMSO) δ 9.34-9.14 (m), 7.98-7.91 (m), 7.91-7.66 (m), 7.61-7.39 (m), 7.10-6.93 (m), 6.86 (dd), 6.48-6.20 (m), 5.59-5.27 (m), 4.96 (ddd), 4.87-4.40 (m), 4.17-3.64 (m), 3.47 (d), 3.34 (d), 3.28 (s), 1.75 (s), 1.54-1.35 (m), 1.02-0.92 (m), 0.84-0.70 (m), 0.66 (s), 0.55 (s). $^{19}$F NMR (376 MHz, DMSO) δ−60.97 (d), −69.48--70.36 (m), −79.25--81.30 (m), −102.61--103.97 (m), −110.18--111.26 (m). MS (m/z): 1253.032 [M+H]$^+$.

Example 44

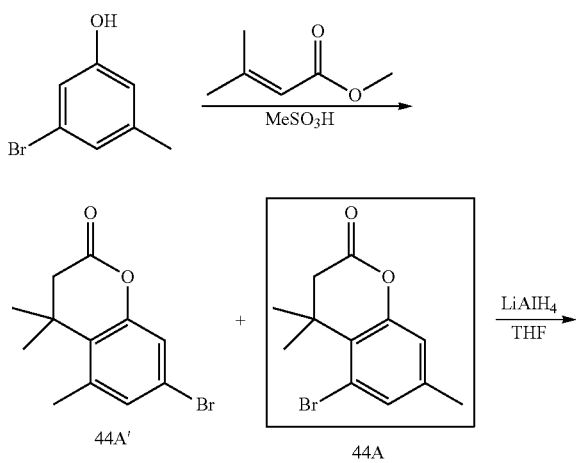

-continued
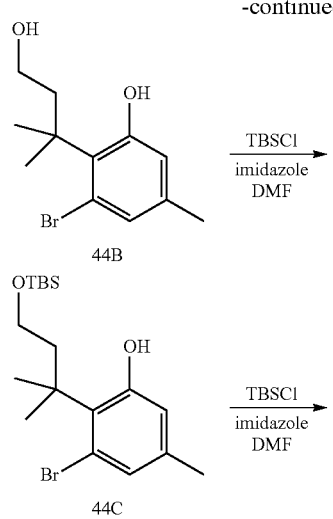
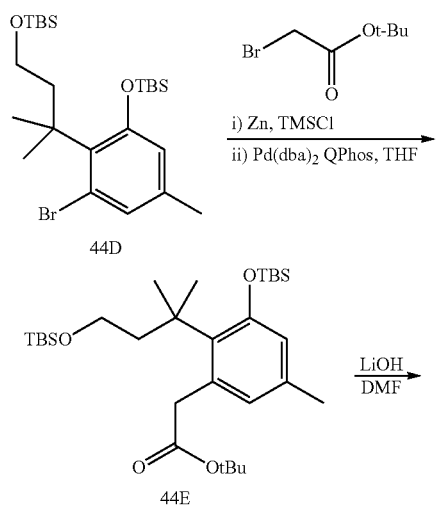
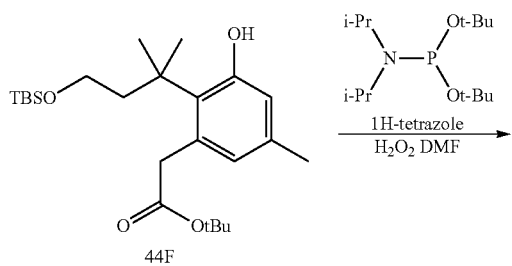
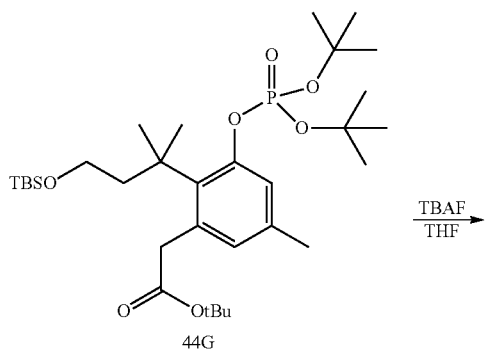

-continued
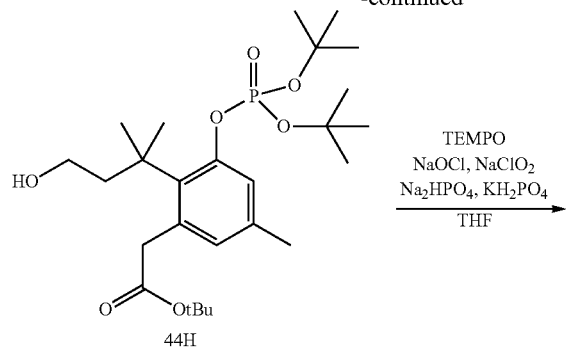
44H
TEMPO
NaOCl, NaClO₂
Na₂HPO₄, KH₂PO₄
———————→
THF
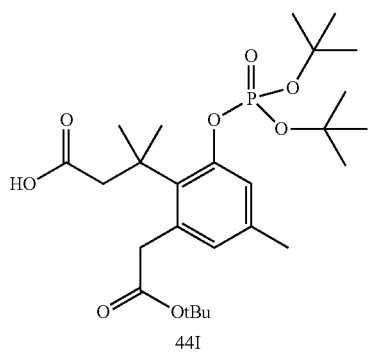
44I
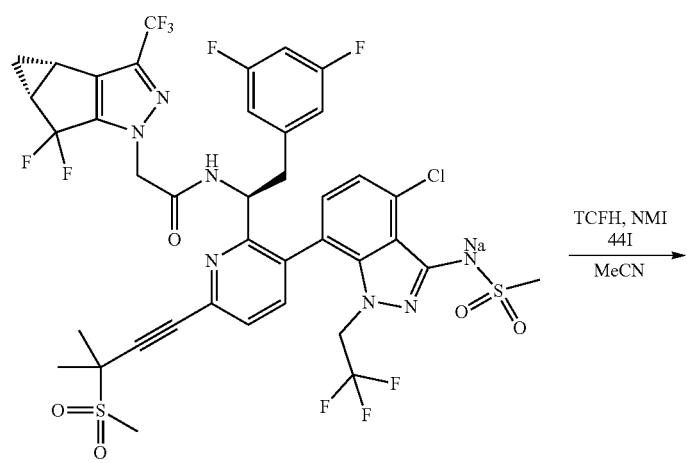
Intermediate 5E
TCFH, NMI
44I
————→
MeCN
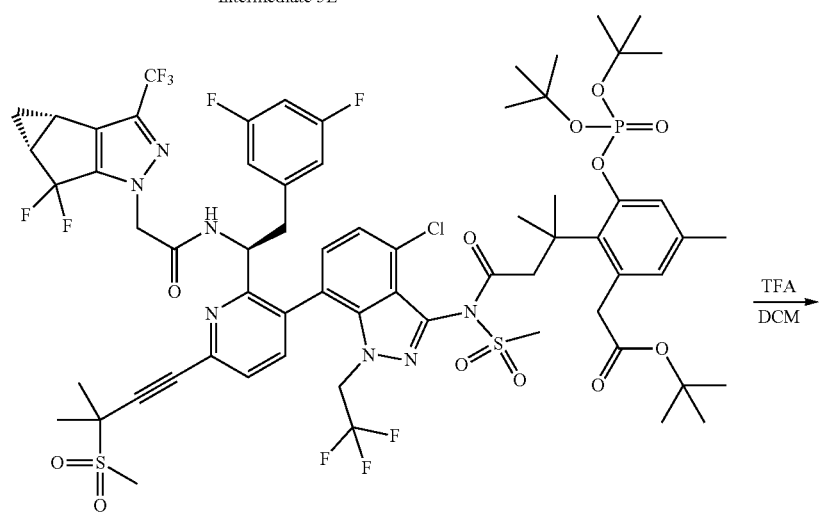
44J
TFA
———→
DCM

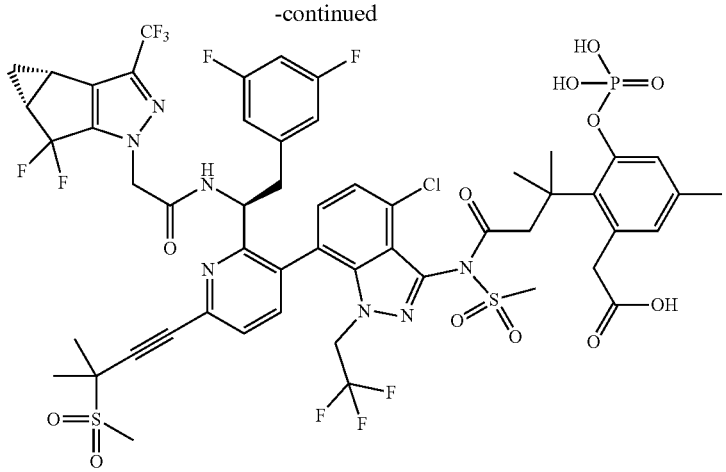

44

Synthesis of 5-Bromo-4,4,7-trimethylchroman-2-one (44A): A flask was charged with 3-bromo-5-methylphenol (26.7 mmol) and methanesulfonic acid (53.5 mmol) under nitrogen. Methyl 3-methylbut-2-enoate (29.4 mmol) was added, the flask was fitted with a reflux condenser and the reaction was heated at 90° C. for 30 minutes, 120° C. for 30 minutes and 150° C. for 3 hours. The reaction was cooled to RT, placed into an ice-water bath and diluted with water (150 mL). The aqueous layer was extracted with EtOAc (2×200 mL), washed with sat. NaHCO$_3$(2×100 mL), washed with brine, dried over MgSO$_4$, filtered and concentrated under reduced pressure. The residue was purified by silica gel chromatography to afford title compound 44A. MS (m/z) 269.02/270.95 [M+H]$^+$.

Synthesis of 3-Bromo-2-(4-hydroxy-2-methylbutan-2-yl)-5-methylphenol (44B): A flask was charged with a solution of LAH (2.0M in THF, 8.17 mmol) and THF (10 mL). The solution was cooled to 0° C. A solution of 44A (7.43 mmol) in THF (20 mL) was added dropwise. The ice bath was removed and the reaction was stirred at RT for 2.5 hours. The reaction was cooled to 5° C. Water (310 µL) was added slowly, followed by 15% NaOH$_{(aq)}$ (310 µL), then water again (930 µL). The mixture was warmed to RT and stirred overnight. The mixture was diluted with EtOAc, MgSO$_4$ was added and the mixture was filtered. The filter cake was rinsed with EtOAc. The crude product was purified by silica gel chromatography to afford title compound 44B. MS (m/z) 271.15/273.03 [M-H]$^+$.

Synthesis of 3-Bromo-2-(4-((tert-butyldimethylsilyl)oxy)-2-methylbutan-2-yl)-5-methylphenol (44C): A flask was charged with 44B (6.55 mmol), DMF (15.0 mL) and imidazole (16.4 mmol) under nitrogen. The solution was cooled to 0° C., TBSCl (8.51 mmol) was added in one portion, the ice bath was removed and the reaction was stirred at RT for 2 hours and then cooled to 0° C. The reaction was diluted with water (75 mL), extracted with EtOAc (3×), washed with 5% LiCl$_{(aq)}$, dried over MgSO$_4$, filtered and concentrated. The crude product was purified by silica gel chromatography to afford title compound 44C. MS (m/z) 385.31/386.9 [M−H]$^+$.

Synthesis of (3-Bromo-2-(4-((tert-butyldimethylsilyl)oxy)-2-methylbutan-2-yl)-5-methylphenoxy)(tert-butyl)dimethylsilane (44D): A flask was charged with 44C (2.55 mmol), DMF (12.0 mL) and imidazole (6.37 mmol) under nitrogen. TBSCl (3.31 mmol) was added in one portion and the flask was fitted with a reflux condenser. The reaction was heated at 65° C. for 8 hours. The reaction was concentrated, diluted with water, extracted with EtOAc (3×), washed with 5% LiCl$_{(aq)}$, dried over MgSO$_4$, filtered and concentrated. The mixture was purified by silica gel chromatography to afford title compound 44D. $^1$H NMR (400 MHz, Chloroform-d) δ 7.04 (d, J=1.6 Hz, 1H), 6.53 (d, J=1.8 Hz, 1H), 3.52-3.43 (m, 2H), 2.29-2.20 (m, 2H), 2.17 (s, 3H), 1.60 (s, 6H), 1.00 (s, 9H), 0.83 (s, 9H), 0.29 (s, 6H), 0.03 (s, 6H) ppm.

Synthesis of tert-butyl 2-(3-((tert-butyldimethylsilyl)oxy)-2-(4-((tert-butyldimethylsilyl)oxy)-2-methylbutan-2-yl)-5-methylphenyl)acetate (44E): A flask was charged with zinc dust (<10 µm, 9.00 mmol) and THF (3.6 mL) under nitrogen. The flask was fitted with an internal temperature probe. Chlorotrimethylsilane (0.60 mmol) was added and the mixture was stirred for 15 minutes (a 1-2° C. exotherm was recorded). A solution of tert-butyl 2-bromoacetate (6.00 mmol) in THF (2.66 mL) was added cautiously. The mixture was stirred until it cooled back to RT and then stirring was stopped. The supernatant was titrated using I2 in a 0.5M solution of LiCl in THF. The concentration of the 2-tert-butoxy-2-oxoethylzinc bromide organozinc reagent was determined to be 0.63M. A separate flask was charged with 44D (1.35 mmol), Pd(dba)$_2$ (0.068 mmol) and QPhos (0.068 mmol). The flask was purged with nitrogen. THF (4.7 mL) was added, followed by 2-tert-butoxy-2-oxoethylzinc bromide (1.62 mmol). The flask was fitted with a reflux condenser and the reaction was heated at 55° C. for 15-30 minutes. The reaction was cooled to RT, quenched with sat. NH$_4$Cl $_{(aq)}$, extracted with EtOAc (3×), washed with brine, dried over MgSO$_4$, filtered and concentrated. The crude product was purified by silica gel chromatography to afford title compound 44E. MS (m/z) 559.13 [M+Na]$^+$.

Synthesis of tert-butyl 2-(2-(4-((tert-butyldimethylsilyl)oxy)-2-methylbutan-2-yl)-3-hydroxy-5-methylphenyl)acetate (44F): To a solution of 44E (5.14 mmol) in DMF (4.0 mL) was added LiOH (5.14 mmol) under nitrogen. The mixture was stirred at RT for 18 hours. The reaction was diluted with water, extracted with EtOAc (3×), the combined organic layers were sequentially washed with 5% aqueous LiCl and brine, then dried over MgSO$_4$, filtered and concentrated under reduced pressure. The residue was purified by silica gel chromatography to afford title compound 44F. MS (m/z) 421.16 [M−H]$^+$.

Synthesis of tert-butyl 2-(2-(4-((tert-butyldimethylsilyl)oxy)-2-methylbutan-2-yl)-3-((di-tert-butoxyphosphoryl)oxy)-5-methylphenyl)acetate (44G): To a solution of 44F (0.821 mmol) in DMF (3.0 mL) was added di-tert-butyl N,N-diisopropylphosphoramidite (2.46 mmol) followed by 1H-tetrazole (2.87 mmol). The solution was heated at 50° C. for 5 hours. The reaction was cooled to 0° C., 30% $H_2O_2$ $_{(aq)}$(3.28 mmol) was added, and the reaction was stirred for 1 hour then allowed to warm to RT. The reaction was diluted with water and extracted with 25% EtOAc/hexanes (3×). The combined organic layers were washed with 5% LiCl $_{(aq)}$, then sat. aqueous $Na_2S_2O_3$, dried over $MgSO_4$, filtered and concentrated. The residue was purified by silica gel chromatography to yield title compound 44G. MS (m/z) 637.05 $[M+Na]^+$.

Synthesis of tert-butyl 2-(3-((di-tert-butoxyphosphoryl)oxy)-2-(4-hydroxy methylbutan-2-yl)-5-methylphenyl)acetate (44H): A solution of 44G (0.569 mmol) in THF (5.0 mL) was cooled to 0° C. TBAF (1.0 M in THF, 1.14 mmol) was added and the reaction was stirred for 18 hours, gradually warming up to RT. The reaction was concentrated and diluted with EtOAc. The organic layer was washed with water (2×) and brine, dried over $MgSO_4$, then filtered and concentrated under reduced pressure. The residue was purified by silica gel chromatography to yield title compound 44H. MS (m/z) 522.95 $[M+Na]^+$.

Synthesis of 3-(2-(2-(Tert-butoxy)-2-oxoethyl)-6-((di-tert-butoxyphosphoryl)oxy)-4-methylphenyl)-3-methylbutanoic acid (44I): To a solution of 44H (0.356 mmol) in ACN/water (1:1, 3.0 mL) was added TEMPO (0.018 mmol), potassium dihydrogen phosphate (0.178 mmol) and disodium hydrogen phosphate (0.178 mmol). The solution was cooled to 0° C. Sodium chlorite (0.533 mmol) was added, followed by sodium hypochlorite (8.25% NaOCl, 266 The ice bath was removed and the reaction was stirred for 3.5 hours. The reaction was diluted with water, extracted with EtOAc (3×), the combined organic layers were washed with brine, dried over $MgSO_4$, filtered and concentrated under reduced pressure to yield title compound 44I which was used without further purification. MS (m/z) 536.85 $[M+Na]^+$.

Synthesis of tert-butyl 2-(2-(4-(N-(4-chloro-7-(2-((1S)-1-(2-((3bS,4aR)-5,5-difluoro-3-(trifluoromethyl)-3b,4,4a,5-tetrahydro-1H-cyclopropa[3,4]cyclopenta[1,2-c]pyrrol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-((di-tert-butoxyphosphoryl)oxy)-5-methylphenyl)acetate (44J): To a solution of crude 44I (0.361 mmol) in ACN (3.6 mL) was added N-methylimidazole (1.27 mmol), Intermediate 5E (0.361 mmol) and TCFH (0.361 mmol). The reaction was stirred at RT for 18 hours. The reaction was quenched with sat. aqueous $NH_4C_1$ and extracted with EtOAc (3×). The combined organic layers were washed with brine, dried over $MgSO_4$, filtered and concentrated under reduced pressure. The crude material was purified by reverse phase HPLC. Fractions containing title compound were pooled and concentrated to afford an atropisomeric mixture of title compound 44J. MS (m/z) 1486.07 $[M+Na]^+$.

Synthesis of 2-(2-(4-(N-(4-chloro-7-(2-01S)-1-(2-((3bS,4aR)-5,5-difluoro-3-(trifluoromethyl)-3b,4,4a,5-tetrahydro-1H-cyclopropa[3,4]cyclopenta[1,2-c]pyrrol-1-yl)acetamido)-2-(3,5-difluorophenyl)ethyl)-6-(3-methyl-3-(methylsulfonyl)but-1-yn yl)pyridin-3-yl)-1-(2,2,2-trifluoroethyl)-1H-indazol-3-yl)methylsulfonamido)-2-methyl oxobutan-2-yl)-5-methyl-3-(phosphonooxy)phenyl) acetic acid (44): 44J (0.128 mmol) was dissolved in DCM/TFA (3:1, 4.0 mL). The reaction was stirred at RT until reaction completion (2-4 hours) and concentrated. The crude product was purified by RP chromatography (60-100% ACN/water with 0.1% TFA). Fractions containing the product were pooled and lyophilized to afford an atropisomeric mixture of title compound 44. $^1$H NMR (400 MHz, DMSO-$d_6$) δ 12.01 (bs), 9.17 (t), 9.00 (d), 8.87 (d), 8.00-7.91 (m), 7.90-7.71 (m), 7.47-7.40 (m), 7.39-7.32 (m), 7.31-7.25 (m), 7.14 (bs), 7.07-6.97 (m), 6.96-6.84 (m), 6.70-6.58 (m), 6.57-6.52 (m), 6.52-6.42 (m), 6.41-6.36 (m), 4.97-4.58 (m), 4.58-4.41 (m), 4.40-4.30 (m), 4.30-4.15 (m), 4.14-3.93 (m), 3.88 (d), 3.84 (d), 3.80-3.67 (m), 3.66-3.54 (m), 3.52 (d), 3.47 (d), 3.27 (d), 3.24-3.16 (m), 3.16-2.85 (m), 2.81-2.65 (m), 2.63-2.47 (m), 2.17 (s), 1.74 (bs), 1.50-1.11 (m), 1.06-0.94 (m). $^{19}$F NMR (377 MHz, DMSO-$d_6$) δ−60.81 (d), −60.86, −60.92, −69.38 (t), −69.47−69.67 (m), −69.83 (t), −79.81 (d), −80.10−80.30 (m), −80.48 (d), −80.77−80.96 (m), −101.82−102.26 (bs), −102.53−102.97 (m), −103.11 (d), −103.25 (d), −103.41−103.51 (m), −103.79 (d), −103.93 (d), −110.52 (t), −110.62 (t), −110.76 (t), −110.90 (t) ppm. MS (m/z) 1295.75 $[M+H]^+$.

Example 45

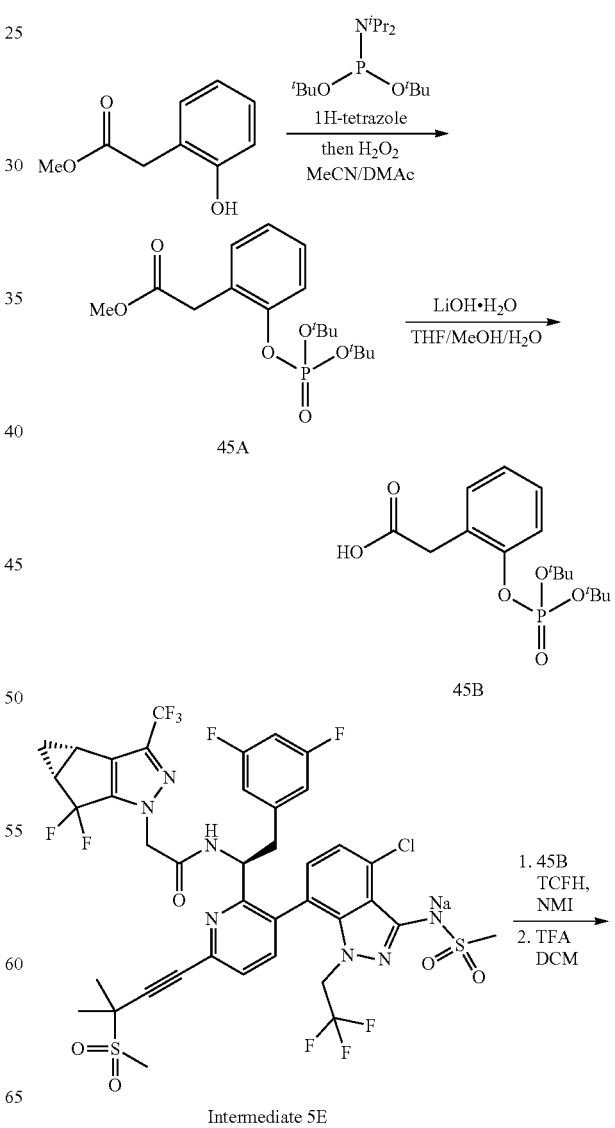

285
-continued

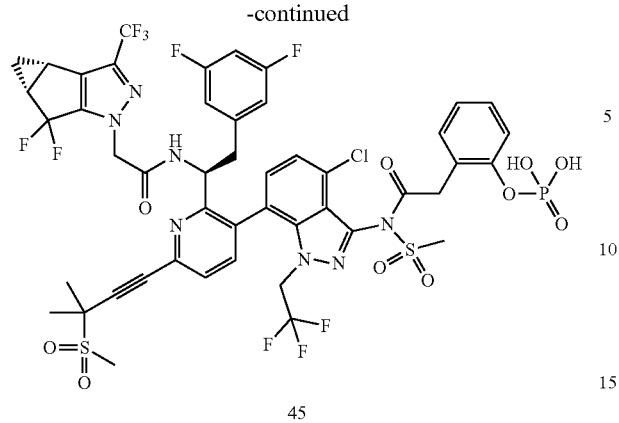

45

Synthesis of methyl 2-(2-((di-tert-butoxyphosphoryl)oxy) phenyl)acetate (45A): To a solution of methyl 2-(2-hydroxyphenyl)acetate (6.9 mmol), 0.45M 1H-tetrazole in MeCN (17.3 mmol), and N,N-dimethylacetamide (14 mL) was added di-tert-butyl N,N-diisopropylphosphoramidite (13.8 mmol). The reaction was sealed and stirred for 16 hours. Then 50% $H_2O_2$ (34.6 mmol) was added to the reaction. The reaction was sealed and stirred for 1 hour. Upon completion, the reaction was diluted with water (100 mL) and quenched with sat. $Na_2SO_3$ (14 mL). The reaction was transferred to a separatory funnel and extracted 3× with 1:1 EtOAc/Hexanes (90 mL). The organic fraction was collected, washed with 0.1M HCl (120 mL), 5% LiCl (120 mL), sat. NaCl (60 mL), dried over $Na_2SO_4$, concentrated, and purified with silica chromatography. Fractions containing the product were pooled and concentrated to yield title compound 45A. MS (m/z): 381.20 [M+Na]$^+$.

Synthesis of 2-(2-((di-tert-butoxyphosphoryl)oxy)phenyl)acetic acid (45B): To a flask was added 45A (5.6 mmol), lithium hydroxide monohydrate (14.0 mmol), and 2:2:1 THF/MeOH/$H_2O$ (50 mL). The reaction was sealed and stirred for 3 hours. Upon completion, the reaction was diluted with water (100 mL) and acidified with 1M HCl (13 mL). The reaction was transferred to a separatory funnel and extracted 3× with EtOAc (100 mL). The organic fraction was collected, dried over $Na_2SO_4$, concentrated, and purified with silica chromatography. Fractions containing the product were pooled and concentrated to yield title compound 45B. MS (m/z): 367.20 [M+Na]$^+$.

Synthesis of 2-(2-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-oxoethyl)phenyl dihydrogen phosphate (45): An atropisomeric mixture of the title compound was prepared according to the method presented for the synthesis of compound 41 of Example 41 utilizing 45B in the place of 41C. $^1$H NMR (400 MHz, MeOD) δ 7.98 (s), 7.78 (dd), 7.69 (d), 7.36 (d), 7.32-7.13 (m), 6.97 (d), 6.86-6.69 (m), 6.53 (dd), 6.35 (dd), 4.87-4.62 (m), 4.18 (h), 4.05 (h), 3.74-3.62 (m), 3.51 (s), 3.24 (s), 2.99 (s), 2.86 (s), 2.53-2.44 (m), 1.82 (s), 1.46-1.35 (m), 1.10-1.07 (m), 1.05-0.97 (m). $^{19}$F NMR (377 MHz, MeOD) δ −63.55 (d), −72.07 (dt), −78.08-−78.53 (m), −82.67 (dd), −105.48 (ddd), −112.08 (dt). MS (m/z) 1182.20 [M+H]$^+$.

286
Example 46

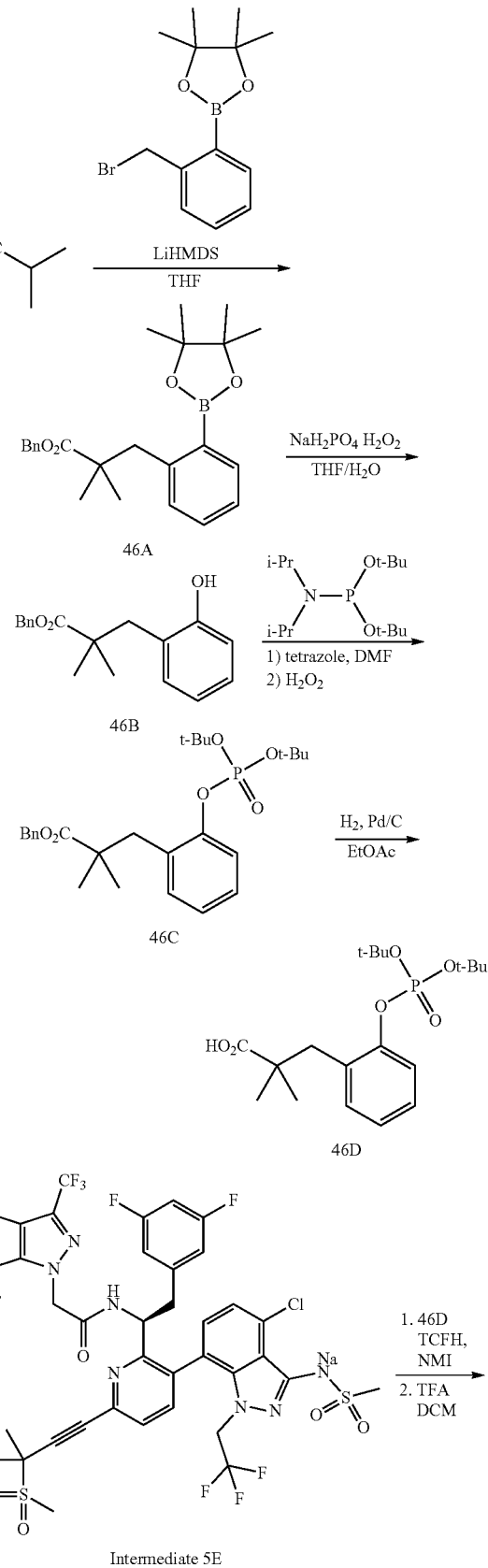

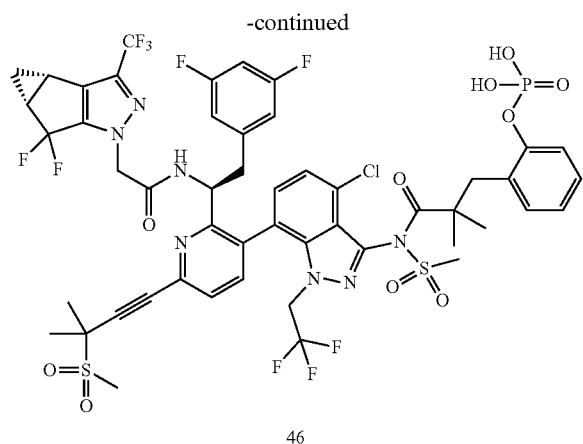

46

Synthesis of benzyl 2,2-dimethyl-3-(2-(4,4,5,5-tetramethyl-1,3,2-dioxaborolan-2-yl)phenyl)propanoate (46A): To a solution of benzyl 2-methylpropanoate (13 mmol) in THF (50 mL) was added a solution of LiHMDS (13 mmol, 1.0 M in THF) at −78° C. and the resulting mixture was stirred for 1 h. A solution of 2-[2-(bromomethyl)phenyl]-4,4,5,5-tetramethyl-1,3,2-dioxaborolane (6.7 mmol) in THF (6.0 mL) was then added. The reaction mixture was stirred for an additional 1 h at −78° C. and gradually warmed to room temperature over 16 h. After completion, the reaction mixture was diluted with EtOAc and washed with sat. aq. solutions of $NH_4C_1$ and brine. The combined organic layers were dried over anhydrous $Na_2SO_4$, filtered, concentrated and purified by silica gel chromatography (eluting 0-100% EtOAc in hexanes). Fractions containing the product were pooled and concentrated under reduced pressure to give title compound 46A. MS (m/z): 417.3 $[M+Na]^+$.

Synthesis of benzyl 3-(2-hydroxyphenyl)-2,2-dimethylpropanoate (46B): 46A was dissolved in a THF/$H_2O$ mixture (25 mL, 3:1) and treated with sodium dihydrogen phosphate (14 mmol) and aq. $H_2O_2$ solution (3 mL, 50 wt. %). After stirring for 16 h, the reaction mixture was treated with sat. aq. sodium thiosulfate solution and extracted with EtOAc. The combined organic layers were dried over anhydrous $Na_2SO_4$, filtered, concentrated and purified by silica gel chromatography (eluting 0-100% EtOAc in hexanes). Fractions containing the product were pooled and concentrated under reduced pressure to give title compound 46B. MS (m/z): 285.2 $[M+H]^+$.

Synthesis of benzyl 3-(2-((di-tert-butoxyphosphoryl)oxy)phenyl)-2,2-dimethylpropanoate (46C): To a stirred solution of 46B (3.5 mmol) in DMF (34 mL) was added di-t-butyl-N,N-diisopropylphosphoramidite (11 mmol) and 1-H-tetrazole (14 mmol) sequentially. The reaction mixture was stirred at room temperature and monitored by TLC and LCMS. After 2 h, the reaction mixture was cooled to 0° C. and treated with aq. $H_2O_2$ solution (2.5 mL, 30 wt. %). The reaction was gradually warmed to room temperature and stirred. After completion, the reaction mixture was diluted with EtOAc and washed with sat. aq. sodium thiosulfate solution. The combined organic layers were dried over anhydrous $Na_2SO_4$, filtered, and concentrated. The crude mixture was purified by column chromatography (0% to 60% EtOAc in hexanes) to afford title compound 46C. MS (m/z): 499.3 $[M+Na]^+$.

Synthesis of 3-(2-((di-tert-butoxyphosphoryl)oxy)phenyl)-2,2-dimethylpropanoic acid (46D): 46C (2.3 mmol) was dissolved in EtOAc (12 mL) then palladium on carbon (0.46 mmol) was added. After stirring for 1 h under hydrogen gas (1 atm), product formation was observed. Title compound 46D was isolated after filtration over a pad of Celite® and was directly used in the subsequent reaction without purification. MS m/z=409.2 $[M+Na]^+$.

Synthesis of 2-(3-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2,2-dimethyl-3-oxopropyl)phenyl dihydrogen phosphate (46): An atropisomeric mixture of the title compound was prepared according to the method presented for the synthesis of compound 41 of Example 41 utilizing 46D in the place of 41C. $^1$H NMR (400 MHz, DMSO-$d_6$) δ 9.27-9.14 (m), 7.93-7.73 (m), 7.39 (d), 7.32-6.80 (m), 6.44-6.36 (m), 6.34-6.26 (m), 4.96 (t), 4.74 (d), 4.69-4.55 (m), 4.12-3.94 (m), 3.40 (d), 3.27 (d), 2.96-2.83 (m), 2.36-2.26 (m), 1.75 (s), 1.43-1.36 (m), 1.35-1.28 (m), 1.21 (s), 1.07 (s), 1.01 (s, 3H), 0.92-0.85 (m), 0.80 (s), 0.62 (s). $^{19}$F NMR (377 MHz, DMSO-$d_6$) δ−60.98 (d), −69.74 (d), −70.16 (t), −79.73-−81.25 (m) ppm. MS (m/z) 1246.20 $[M+Na]^+$.

Example 47

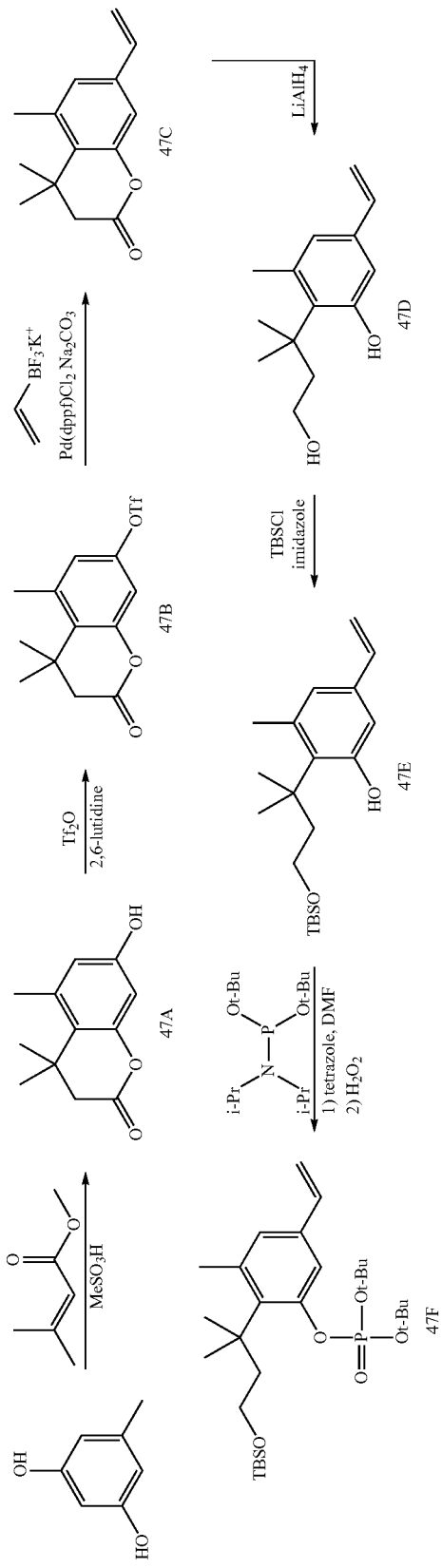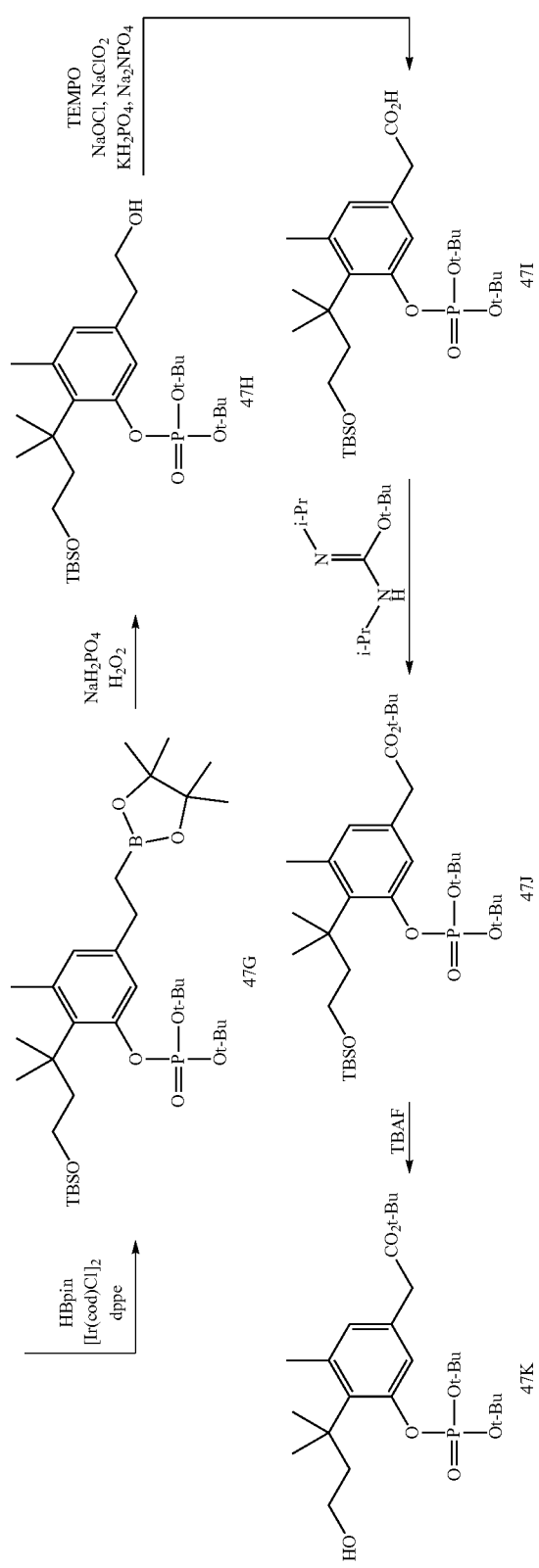

-continued
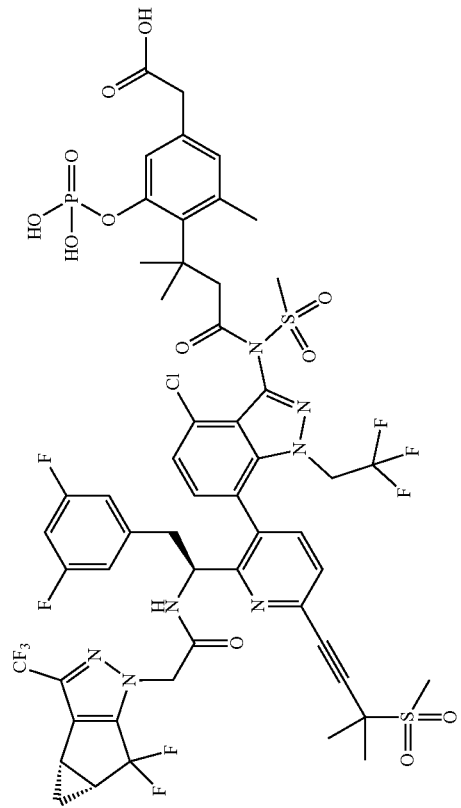
47
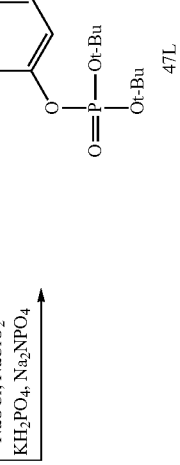
47L
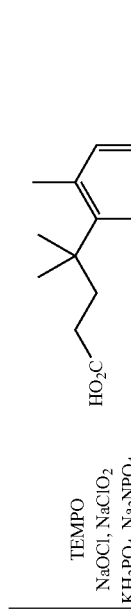
TEMPO
NaOCl, NaClO$_2$
KH$_2$PO$_4$, Na$_2$NPO$_4$
1. 47L
TCFH, NMI
2. TFA, DCM
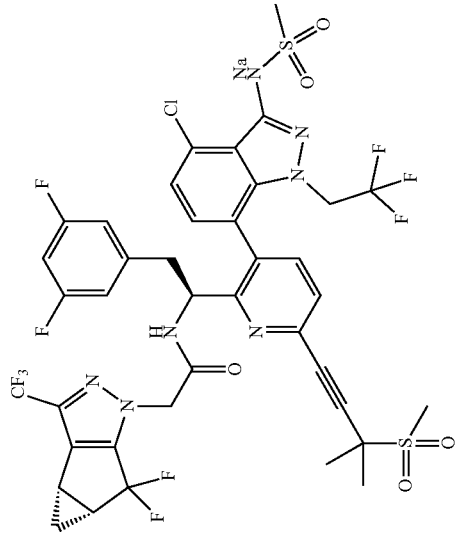
Intermediate 5E Synthesis of 7-hydroxy-4,4,5-trimethylchroman-2-one (47A): To a stirred solution of 3,5-dihydroxytoluene (483 mmol) in methanesulfonic acid (62.8 mL) was added methyl 3-methylbut-2-enoate (532 mmol). The mixture was stirred at 80° C. for 3 h and monitored by LCMS. After completion, the reaction mixture was diluted with water and extracted with EtOAc. The combined organic layers were dried over anhydrous $Na_2SO_4$, filtered, and concentrated. The crude mixture was purified by column chromatography (0% to 30% EtOAc in hexanes) to afford title compound 47A. MS (m/z) 207.1 $[M+H]^+$.

Synthesis of 4,4,5-trimethyl-2-oxochroman-7-yl trifluoromethanesulfonate (47B): To a stirred solution 47A (249 mmol) in dichloromethane (20 mL) at 0° C. was added 2,6-lutidine (274 mmol) followed by triflic anhydride (262 mmol, 1.05 equiv) and the reaction mixture was stirred for 2 h and monitored by LCMS. After completion, the reaction mixture was diluted with dichloromethane, washed with 1M HCl and brine. The combined organic layers were dried over anhydrous $Na_2SO_4$, filtered, and concentrated. The crude mixture was purified by column chromatography (0% to 10% EtOAc in hexanes) to afford title compound 47B. MS (m/z) 339.1 $[M+H]^+$.

Synthesis of 4,4,5-trimethyl-7-vinylchroman-2-one (47C): To a stirred solution of 47B (161 mmol) in dioxane (130 mL) and water (15 mL) was added potassium vinyltrifluoroborate (193 mmol), sodium carbonate (483 mmol) and $Pd(dppf)Cl_2$ (16.1 mmol). The mixture was degassed and backfilled with argon (3×) and heated to 100° C. for 2 h and monitored by LCMS. After completion, the reaction mixture was diluted with EtOAc and washed with sat. aq. solutions of $NH_4C_1$ and brine. The combined organic layers were dried over anhydrous $Na_2SO_4$, filtered, and concentrated. The crude mixture was purified by column chromatography (0% to 10% EtOAc in hexanes) to afford title compound 47C. MS (m/z) 217.2 $[M+H]^+$.

Synthesis of 2-(4-hydroxy-2-methylbutan-2-yl)-3-methyl-5-vinylphenol (47D): 47C (83.2 mmol) was dissolved in THF (121 mL), cooled to 0° C. and treated with $LiAlH_4$ (53 mL, 2 M in THF). The reaction mixture was then gradually warmed to room temperature over 16 h. After completion, the reaction mixture was quenched with ice water, filtered through a pad of Celite®, and extracted with EtOAc. The combined organic layers were dried over anhydrous $Na_2SO_4$, filtered, and concentrated to yield title compound 47D which was used without purification.

Synthesis of 2-(4-((tert-butyldimethylsilyl)oxy)-2-methylbutan-2-yl)-3-methyl-5-vinylphenol (47E): To a solution of 47D (20.1 mmol) in DMF (30 mL) was added imidazole (50.2 mmol) and TBSCl (26 mmol) sequentially. The reaction mixture was stirred for 2 h and monitored by LCMS. After completion, the reaction mixture was diluted with diethyl ether and washed with water. The combined organic layers were dried over anhydrous $Na_2SO_4$, filtered, and concentrated. The crude mixture was purified by column chromatography (0% to 10% EtOAc in hexanes) to afford title compound 47E. MS (m/z) 358.1 $[M+Na]^+$.

Synthesis of di-tert-butyl (2-(4-((tert-butyldimethylsilyl)oxy)-2-methylbutan-2-yl)-3-methyl-5-vinylphenyl) phosphate (47F): To a solution of 47E (18.7 mmol) in DMF (200 mL) was added di-t-butyl-N,N-diisopropylphosphoramidite (56.0 mmol) and 1-H-tetrazole (7.1 mmol) sequentially. The reaction mixture was stirred at room temperature while monitored by TLC and LCMS. After 6 h, the reaction mixture was cooled to 0° C. and treated with aq. $H_2O_2$ solution (24 mL, 50 wt. %). The reaction was gradually warmed to room temperature and stirred. After completion, the reaction mixture was diluted with EtOAc and washed with sat. aq. sodium thiosulfate solution. The combined organic layers were dried over anhydrous $Na_2SO_4$, filtered, and concentrated. The crude mixture was purified by column chromatography to afford title compound 47F. MS (m/z) 549.2 $[M+Na]^+$.

Synthesis of di-tert-butyl (2-(4-((tert-butyldimethylsilyl)oxy)-2-methylbutan-2-yl)-3-methyl-5-(2-(4,4,5,5-tetramethyl-1,3,2-dioxaborolan-2-yl)ethyl)phenyl) phosphate (47G): A solution of 47F (2.4 mmol) in dichloromethane (25 mL) was degassed and backfilled with argon (3×). Bis(1,5-cyclooctadiene)diiridium(I) dichloride (0.24 mmol) and bis(diphenylphosphino)ethane (0.48 mmol) were added and the resulting mixture was degassed and backfilled with argon (3×). After stirring for 20 minutes, the mixture was cooled to 0° C. and the previously degassed solution of pinacolborane (3.8 mmol) in dichloromethane (3.0 mL) was added over 1 h via syringe pump. The reaction mixture was gradually warmed to room temperature over 16 h. After completion, the reaction mixture was diluted with dichloromethane and washed with sat. aq. solutions of $NH_4C_1$ and brine. The combined organic layers were dried over anhydrous $Na_2SO_4$, filtered, and concentrated to yield title compound 47G which was used without further purification. MS (m/z) 677.5 $[M+Na]^+$.

Synthesis of di-tert-butyl (2-(4-((tert-butyldimethylsilyl)oxy)-2-methylbutan-2-yl)-5-(2-hydroxyethyl)-3-methylphenyl) phosphate (47H): 47G (2.4 mmol) was dissolved in a $THF/H_2O$ mixture (24 mL, 3:1) and treated with sodium dihydrogen phosphate (5.3 mmol) and aq. $H_2O_2$ solution (1.15 mL, 50 wt. %). After stirring for 4 h, the reaction mixture was treated with sat. aq. sodium thiosulfate solution and extracted with EtOAc. The combined organic layers were dried over anhydrous $Na_2SO_4$, filtered, and concentrated to yield title compound 47H which was used without further purification. MS (m/z) 567.4 $[M+Na]^+$.

Synthesis of 2-(4-(4-((tert-butyldimethylsilyl)oxy)-2-methylbutan-2-yl) ((di-tert-butoxyphosphoryl)oxy)-5-methylphenyl)acetic acid (47I): To a stirred solution of 47H (2.4 mmol) in MeCN (12 mL) and water (12 mL) was added TEMPO (0.12 mmol), $KH_2PO_4$ (1.2 mmol), and $Na_2HPO_4$ (1.2 mmol) then the mixture was cooled to 0° C. NaClO (2.9 mmol, 8 wt. %) and $NaClO_2$ (3.6 mmol) were then added and the reaction was gradually warmed to room temperature and. After completion, the reaction mixture was diluted with EtOAc and washed with sat. aq. sodium thiosulfate solution. The combined organic layers were dried over anhydrous $Na_2SO_4$, filtered, and concentrated to yield title compound 47I which was used without further purification. MS (m/z) 581.4 $[M+Na]^+$.

Synthesis of tert-butyl 2-(4-(4-((tert-butyldimethylsilyl)oxy)-2-methylbutan-2-yl)-3-((di-tert-butoxyphosphoryl)oxy)-5-methylphenyl)acetate (47J): 47I (2.4 mmol) in 3 mL of dichloromethane was slowly added 2-tert-butyl-1,3-diisopropylurea (12.0 mmol) and the resulting mixture was stirred at room temperature for 15 h. After completion, the reaction mixture was diluted with dichloromethane and filtered. The resulting solution was concentrated and purified by column chromatography (0% to 20% EtOAc in hexanes) to afford title compound 47J. MS (m/z) 637.3 $[M+Na]^+$.

Synthesis of tert-butyl 2-(3-((di-tert-butoxyphosphoryl)oxy)-4-(4-hydroxy-2-methylbutan-2-yl)-5-methylphenyl) acetate (47K): To a stirred solution of 47J (1.4 mmol) in THF (7 mL) at 0° C. was added TBAF (0.3 mL, 1 M in THF) and the reaction mixture was stirred at room temperature for 12 h. After completion, the reaction mixture was diluted with EtOAc and washed with sat. aq. solutions of $NH_4C_1$ and brine. The combined organic layers were dried over anhydrous Na$_2$SO$_4$, filtered, and concentrated to yield title compound 47K which was used without further purification. MS (m/z) 523.4 [M+Na]$^+$.

Synthesis of 4-(4-(2-(tert-butoxy)-2-oxoethyl)-2-((di-tert-butoxyphosphoryl)oxy)-6-methylphenyl)-4-methylpentanoic acid (47L): To a stirred solution of 47K (1.4 mmol) in MeCN (12 mL) and water (12 mL) was added TEMPO (0.07 mmol), KH$_2$PO$_4$ (0.7 mmol), and Na$_2$HPO$_4$ (0.7 mmol) then the mixture was cooled to 0° C. NaClO (1.7 mmol, 8 wt. %) and NaClO$_2$ (2.1 mmol) were then added and the reaction was gradually warmed to room temperature and stirred. After completion, the reaction mixture was diluted with EtOAc and washed with sat. aq. sodium thiosulfate solution. The combined organic layers were dried over anhydrous Na$_2$SO$_4$, filtered, and concentrated to yield title compound 47L which was used without further purification. MS (m/z): 537.3 [M+Na]$^+$.

Synthesis of 2-(4-(4-(N-(4-chloro-7-(2-((S)-1-(2-((3bS,4aR)-5,5-difluoro (trifluoromethyl)-3b,4,4a,5-tetrahydro-1H-cyclopropa[3,4]cyclopenta[1,2-c]pyrazol yl)acetamido)-2-(3,5-difluorophenyl)ethyl)-6-(3-methyl-3-(methylsulfonyl)but-1-yn yl)pyridin-3-yl)-1-(2,2,2-trifluoroethyl)-1H-indazol-3-yl)methylsulfonamido)-2-methyl oxobutan-2-yl)-3-methyl-5-(phosphonooxy)phenyl) acetic acid (47): An atropisomeric mixture of the title compound was prepared according to the method presented for the synthesis of compound 41 of Example 41 utilizing 47L in the place of 41C. $^1$H NMR (400 MHz, DMSO-d$_6$) δ 9.18 (d), 7.90 (dd), 7.76 (d), 7.46 (dd), 7.17 (s), 7.07-6.95 (m), 6.87 (d), 6.69 (dd), 6.53-6.46 (m), 6.44-6.33 (m), 5.16-4.54 (m), 4.27-3.97 (m), 3.48 (d), 3.40 (s), 3.28 (d), 3.04-2.91 (m), 2.24 (s), 1.75 (dd), 1.54-1.33 (m), 1.21 (d), 0.99 (s). $^{19}$F NMR (376 MHz, DMSO-d$_6$) δ−60.91 (d), −69.31−−70.45 (m), −71.64, −79.20−−82.23 (m), −102.94 (dd), −110.66 (d). MS (m/z): 1297.300 [M+H]$^+$.

Example 48

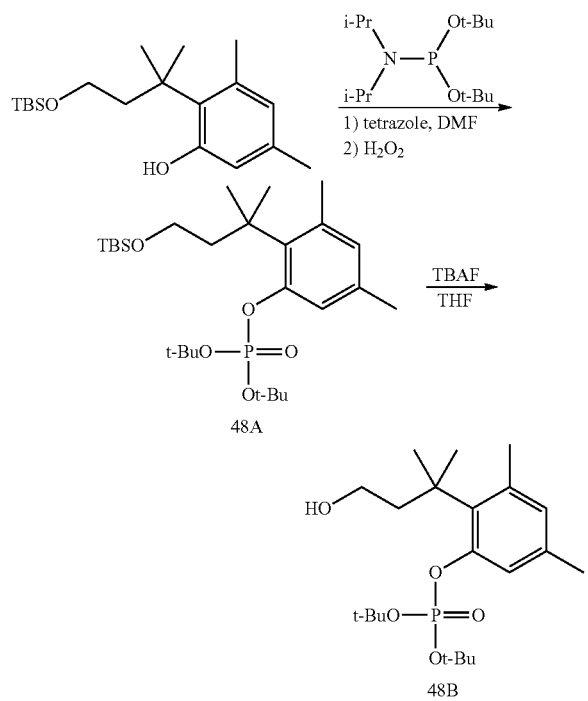

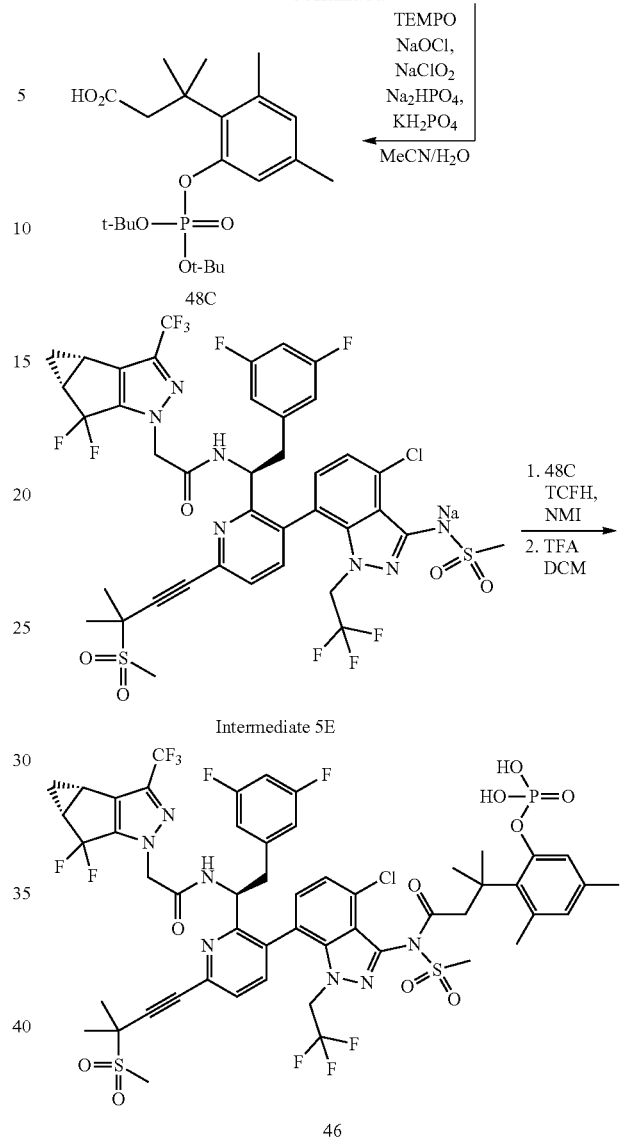

Synthesis of di-tert-butyl (2-(4-((tert-butyldimethylsilyl)oxy)-2-methylbutan-2-yl)-3,5-dimethylphenyl) phosphate (48A): To a stirred solution of 1-H-tetrazole (372 mmol) in MeCN (843 mL) and THF (123 mL) was added 2-(4-tert-Butyldimethylsilyl)oxy) methylbutan-2-yl)-3,5-dimethylphenol (62.0 mmol) and the mixture was cooled to 0° C. Di-t-butyl-N,N-diisopropylphosphoramidite (372 mmol) was then added and the reaction mixture was stirred at room temperature while monitored by TLC and LCMS. After 12 h, the reaction mixture was cooled to 0° C. and treated with aq. H$_2$O$_2$ solution (60 mL, 30 wt. %). The reaction was gradually warmed to room temperature and stirred. After completion, the reaction mixture was diluted with EtOAc and washed with sat. aq. sodium thiosulfate solution. The combined organic layers were dried over anhydrous Na$_2$SO$_4$, filtered, and concentrated. The crude mixture was purified by column chromatography to afford title compound 48A. MS (m/z) 537.5 [M+Na]$^+$.

48A can also be prepared according to the following method: To a solution of 2-(4-((tert-Butyldimethylsilyl)oxy)-2-methylbutan-2-yl)-3,5-dimethylphenol (0.155 mmol) in 0.3 mL of THF at 0° C. were added sequentially di-tert-butyl phosphite (0.207 mmol) and bromoform (0.211 mmol) and finally Cs$_2$CO$_3$ (0.225 mmol). The resulting suspension was gradually warmed to rt, with continued stirring. After completion, the reaction mixture was quenched with water and extracted with ethyl acetate. The organic fractions were combined, dried over Na$_2$SO$_4$, concentrated under reduced pressure, and purified by column chromatography (eluting with 0 to 60% EtOAc in hexanes) to afford title compound 48A. MS (m/z) 537.5 [M+Na]$^+$.

Synthesis of di-tert-butyl (2-(4-hydroxy-2-methylbutan-2-yl)-3,5-dimethylphenyl) phosphate (48B): To a stirred solution of 48A (9.7 mmol) in THF (50 mL) at 0° C. was added TBAF (20 mL, 1 M in THF) and the reaction mixture was stirred at room temperature for 12 h. After completion, the reaction mixture was diluted with EtOAc, washed with sat. aq. solutions of NH$_4$C$_1$ and brine. The combined organic layers were dried over anhydrous Na$_2$SO$_4$, filtered, and concentrated to yield title compound 48B, which was directly used in the subsequent reaction without purification.

Synthesis of 3-(2-((di-tert-butoxyphosphoryl)oxy)-4,6-dimethylphenyl)-3-methylbutanoic acid (48C): To a stirred solution of 48B (7.11 mmol) in MeCN (32 mL) and water (32 mL) was added TEMPO (0.36 mmol), KH$_2$PO$_4$ (3.5 mmol), and Na$_2$HPO$_4$ (3.5 mmol) then the mixture was cooled to 0° C. NaClO (8.6 mmol, 10 wt. %) and NaClO$_2$ (10.6 mmol) were then added and the reaction was gradually warmed to room temperature and stirred. After completion, the reaction mixture was diluted with EtOAc and washed with sat. aq. sodium thiosulfate solution. The combined organic layers were dried over anhydrous Na$_2$SO$_4$, filtered, and concentrated. The crude mixture was purified by column chromatography to afford title compound 48C. MS (m/z) 415.1 [M+H]$^+$.

Synthesis of 2-(4-(N-(4-chloro-7-(2-((S)-1-(2-03bS,4aR)-5,5-difluoro (trifluoromethyl)-3b,4,4a,5-tetrahydro-1H-cyclopropa[3,4]cyclopenta[1,2-c]pyrazol yl)acetamido)-2-(3,5-difluorophenyl)ethyl)-6-(3-methyl-3-(methylsulfonyl) but-1-yn yl)pyridin-3-yl)-1-(2,2,2-trifluoroethyl)-1H-indazol-3-yl)methylsulfonamido)-2-methyl oxobutan-2-yl)-3,5-dimethylphenyl dihydrogen phosphate (48): An atropisomeric mixture of the title compound was prepared according to the method presented for the synthesis of compound 41 of Example 41 utilizing 48C in the place of 41C. $^1$H NMR (400 MHz, DMSO-d$_6$) δ 9.27-9.10 (m), 7.96-7.65 (m), 7.55-7.40 (m), 7.10-6.93 (m), 6.88 (d), 6.70-6.26 (m), 5.08-4.52 (m), 4.12 (ddd), 3.60-3.43 (m), 3.28 (d), 3.10-2.83 (m), 2.75-2.60 (m), 2.47-2.34 (m), 2.18 (d), 1.75 (dd), 1.47 (s), 1.46-1.32 (m), 1.22 (d), 1.00 (s). $^{19}$F NMR (376 MHz, DMSO-d$_6$) δ−60.52--61.19 (m), −69.46--69.68 (m), −70.01 (t), −79.32--81.66 (m), −101.21--105.14 (m), −109.50--112.08 (m). MS (m/z) 1253.032 [M+H]$^+$.

Example 49

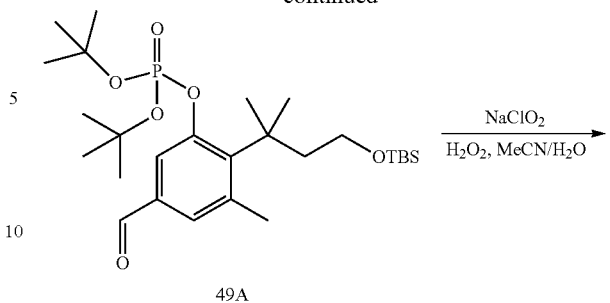

49A

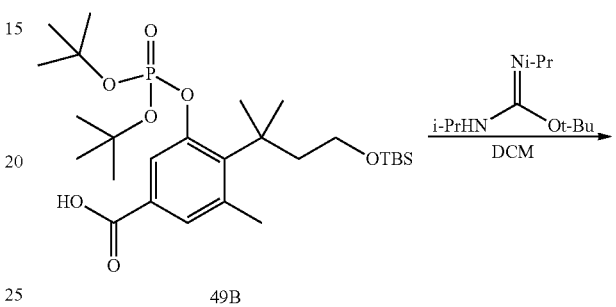

49B

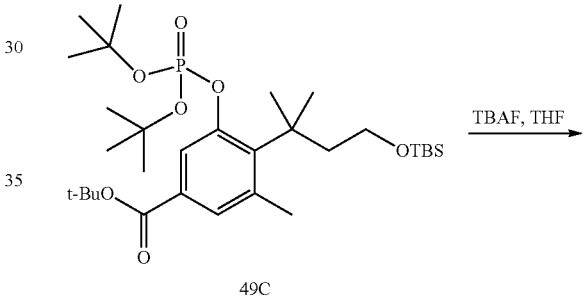

49C

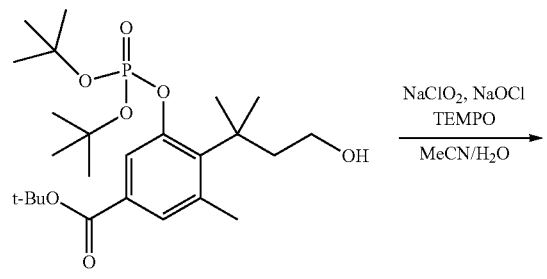

49D

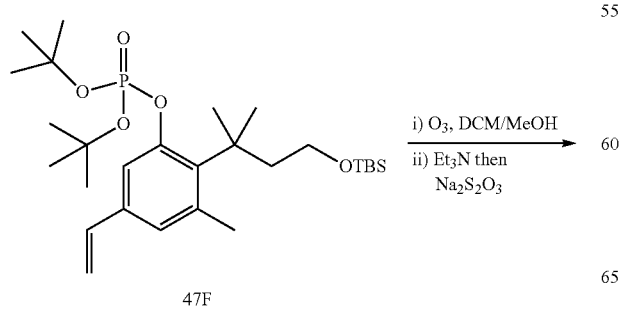

47F

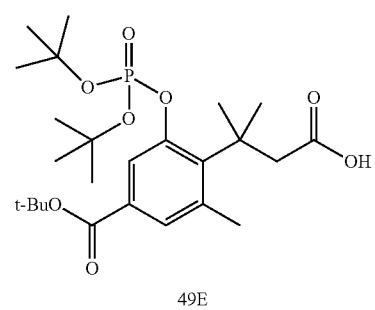

49E

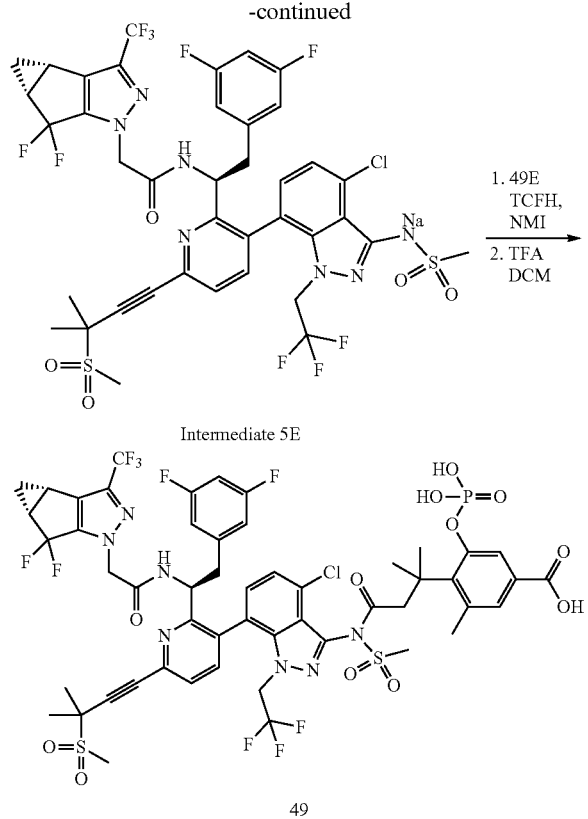

Intermediate 5E

49

Synthesis of di-tert-butyl (2-(4-((tert-butyldimethylsilyl)oxy)-2-methylbutan-2-yl)-5-formyl-3-methylphenyl) phosphate (49A): To a solution of di-tert-butyl (2-(4-((tert-butyldimethylsilyl)oxy)-2-methylbutan-2-yl)-3-methyl-5-vinylphenyl) phosphate (26.8 mmol) in 120 mL of a 1:1 mixture of DCM/MeOH was carefully bubbled $O_3$ gas) at −78° C. When full conversion was observed, the reaction was sparged with Ar gas for 5 mins, after which $Et_3N$ (10 mL) was carefully added. To the resulting mixture was then added 200 mL of saturated $Na_2S_2O_3$ and the reaction was stirred a further 1 h. Upon completion of this time, the contents were transferred to a separatory funnel using DCM (200 mL) and $H_2O$ (200 mL). The aqueous layer was extracted with DCM (2×100 mL) and the organic fractions were collected, dried over $Na_2SO_4$, concentrated under reduced pressure to yield title compound 49A, which was used without further purification. MS (m/z) 551.30 $[M+Na]^+$.

Synthesis of 4-(4-((tert-butyldimethylsilyl)oxy)-2-methylbutan-2-yl)-3-((di-tert-butoxyphosphoryl)oxy)-5-methylbenzoic acid (49B): To a solution of 49A (17.9 mmol), $KH_2PO_4$ (7.15 mmol, 0.4 equiv), hydrogen peroxide (30% aqueous solution, 26.8 mmol, 1.5 equiv) in 75 mL of 1:1 MeCN/$H_2O$ was added a solution of sodium chlorite (35.7 mmol, 2 equiv) at 0° C. and the resulting mixture stirred for 30 mins at this temperature before slowly warming to room temperature. Upon full conversion, the reaction was quenched with saturated sodium sulfite solution and the contents were transferred to a separatory funnel using DCM (200 mL) and $H_2O$ (200 mL) where the pH was carefully adjusted to 2 with 1M HCl solution. The aqueous layer was extracted with DCM (2×100 mL) and the organic fractions were collected, dried over $Na_2SO_4$, concentrated under reduced pressure to yield title compound 49B which was used without further purification. MS (m/z) 567.3 $[M+Na]^+$.

Synthesis of tert-butyl 4-(4-((tert-butyldimethylsilyl)oxy)-2-methylbutan-2-yl)-3-((di-tert-(butoxyphosphoryl) oxy)-5-methylbenzoate (49C): To a solution of 49B (23.3 mmol) in 50 mL of DCM was added 2-tert-butyl-1,3-diisopropylurea (117 mmol, 5 equiv) at rt and the resulting solution left to stir overnight. Upon completion, the reaction was diluted with DCM (100 mL), filtered, and the filter cake washed with further DCM (3×50 mL). The mother liquor was then concentrated under reduced pressure, and the residue purified by silica gel chromatography. Fractions containing the product were pooled and lyophilized to give title compound 49C. $^1$H NMR (400 MHz, $CDCl_3$) δ 7.96-7.90 (m, 1H), 7.50 (d, J=1.9 Hz, 1H), 3.48 (t, J=7.2 Hz, 2H), 3.38 (dq, J=18.7, 6.8 Hz, 1H), 2.59 (s, 3H), 2.14 (t, J=7.1 Hz, 2H), 1.57 (s, 16H), 1.51 (s, 18H), 1.46 (s, 8H), 1.21 (d, J=6.7 Hz, 5H), 0.83 (s, 10H), −0.05 (s, 7H) ppm. MS (m/z) 601.4 $[M+H]^+$.

Synthesis tert-butyl 3-((di-tert-butoxyphosphoryl)oxy)-4-(4-hydroxy methylbutan-2-yl)-5-methylbenzoate (49D): To a solution of 49C (14.7 mmol) in 50 mL of THF was added TBAF solution (1.0M in THF, 20 mmol, 1.5 equiv). When full conversion was observed, the reaction was concentrated under reduced pressure and transferred to a separatory funnel using DCM (200 mL) and water (200 mL). The organic layer was washed with brine (4×200 mL), dried over $Na_2SO_4$, concentrated under reduced pressure and the residue purified by silica gel chromatography. Fractions containing the product were pooled and concentrated under reduced pressure to give title compound 49D. MS (m/z) 486.21 $[M+H]^+$.

Synthesis of 3-(4-(tert-butoxycarbonyl)-2-((di-tert-butoxyphosphoryl)oxy)-6-methylphenyl)-3-methylbutanoic acid (49E): To a solution of 49D (9.68 mmol), TEMPO (0.484 mmol, 0.05 equiv), $KHPO_4$ (4.84 mmol, 0.5 equiv), and K2HPO4 (4.84 mmol, 0.5 equiv) in 100 mL of $H_2O$/MeCN (1:1) at 0° C. were added sequentially sodium hypochlorite (8.25% aqueous solution, 11.8 mmol, 1.22 equiv) and sodium chlorite (14.5 mmol, 1.5 equiv). The solution was stirred for 1 h at 0° C. and then warmed to rt. When full conversion was observed, the reaction was quenched with saturated sodium sulfite solution and the contents were transferred to a separatory funnel using DCM (150 mL) and $H_2O$ (150 mL) where the pH was carefully adjusted to 2 with 1M HCl solution. The aqueous layer was extracted with DCM (2×100 mL) and the organic fractions were collected, dried over $Na_2SO_4$, concentrated under reduced pressure. The title compound was obtained by recrystallization from EtOAc/Hexanes to yield title compound 49E. MS (m/z) 523.29 $[M+Na]^+$.

Synthesis of 4-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-methyl-5-(phosphonooxy) benzoic acid (49): An atropisomeric mixture of the title compound was prepared according to the method presented for the synthesis of compound 41 of Example 41 utilizing 49E in the place of 41C. $^1$H NMR (400 MHz, DMSO-$d_6$) δ 9.18 (d), 8.02-7.73 (m), 7.50-7.26 (m), 7.06-6.95 (m), 6.99-6.86 (m), 6.48 (dd), 6.42-6.34 (m), 5.72 (s), 5.01 (d), 4.91-4.76 (m), 4.80-4.57 (m), 4.21 (dq), 4.03 (dq), 3.56-3.44 (m), 3.12 (t), 3.07-2.86 (m), 2.76-2.64 (m), 2.61-2.42 (m), 2.33 (s), 1.75 (dd), 1.50 (s), 1.45 1.33 (m), 1.28 (s), 1.18 (s), 1.03-0.95 (m) ppm. $^{19}$F NMR (375 MHz, DMSO-$d_6$) δ−60.48−−61.19 (m), −69.57 (h), −70.05 (t), −75.49, −75.08−−76.16 (m), −80.03−−80.64 (m), −80.71−−81.24 (m), −102.15, −102.70 (d), −110.65 (d) ppm. MS (m/z) 1282.30 $[M+H]^+$.

Example 50
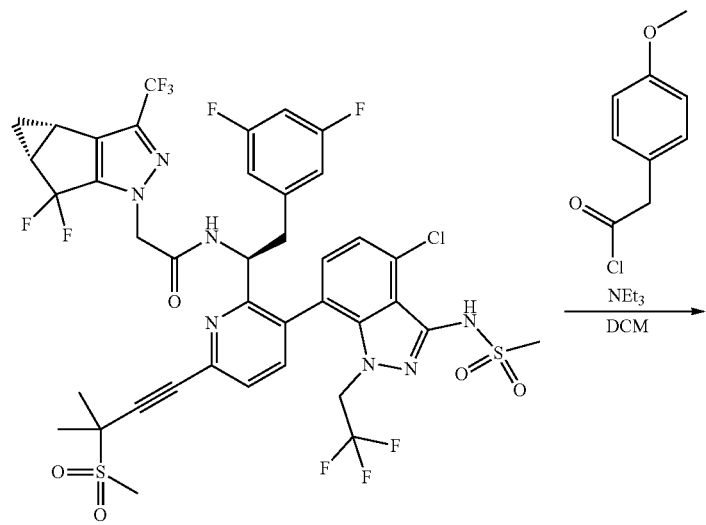
Intermediate 5
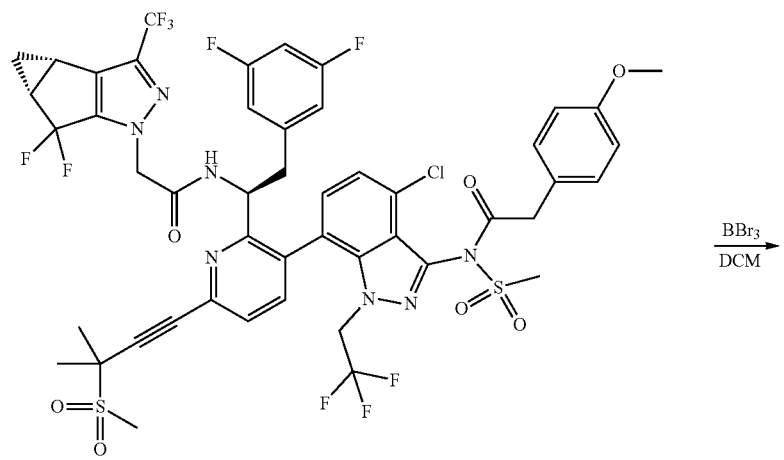
50A
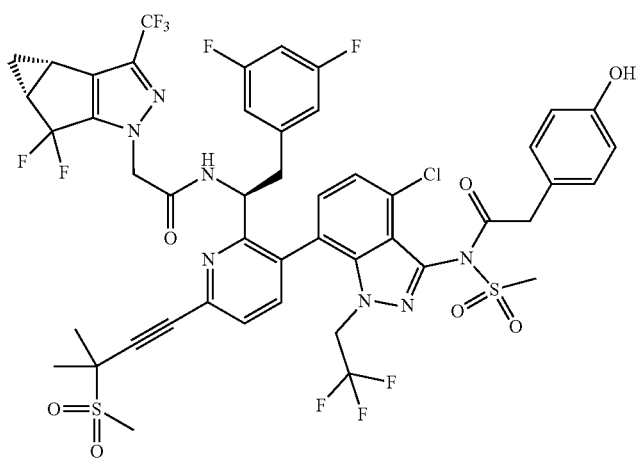
50

Synthesis of N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-2-(4-methoxyphenyl)-N-(methylsulfonyl)acetamide (50A): To a solution of Intermediate 5 (0.103 mmol) in DCM was added triethylamine (0.258 mmol) followed by 2-(4-methoxyphenyl)acetyl chloride (0.134 mmol). The reaction mixture was stirred at room temperature for 10 minutes, then concentrated in vacuo and purified by silica gel column chromatography (eluent: hexanes/ethyl acetate) to provide an atropisomeric mixture of title compound 50A.

Synthesis of N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-2-(4-hydroxyphenyl)-N-(methylsulfonyl)acetamide (50): A flask containing a solution of 50A (0.103 mmol) in DCM (1.0 mL) was flushed with argon, then boron tribromide (1M in DCM, 0.36 mmol) was added dropwise. The reaction mixture was stirred at room temperature for 4 hours, then diluted with DCM and quenched with water. The organic layer was isolated, dried over sodium sulfate, isolate by vacuum filtration, concentrated in vacuo, and purified by reverse phase HPLC (eluent: water/acetonitrile containing 0.1% v/v TFA) to provide title compound 50 as a mixture of atropisomers. $^1$H NMR (400 MHz, Methanol-$d_4$) δ 8.86 (d), 8.79 (d), 7.81-7.74 (m), 7.73-7.66 (m), 7.65-7.55 (m), 7.29-7.17 (m), 7.17-7.07 (m), 6.68 (s), 6.66 (s), 6.64-6.59 (m), 6.56-6.48 (m), 6.46-6.42 (m), 6.32 (s), 6.30 (s), 6.24-6.16 (m), 4.67-4.49 (m), 3.96-3.81 (m), 3.46-3.41 (m), 3.40-3.37 (m), 3.35 (s), 3.16-3.13 (m), 3.10-3.05 (m), 3.03 (dt), 2.95-2.85 (m), 2.45-2.31 (m), 1.73 (s), 1.73 (s), 1.72 (s), 1.71 (s), 1.37-1.24 (m), 0.98 (s), 0.95-0.87 (m). MS (m/z) 1102.5 [M+H]$^+$.

Example 51

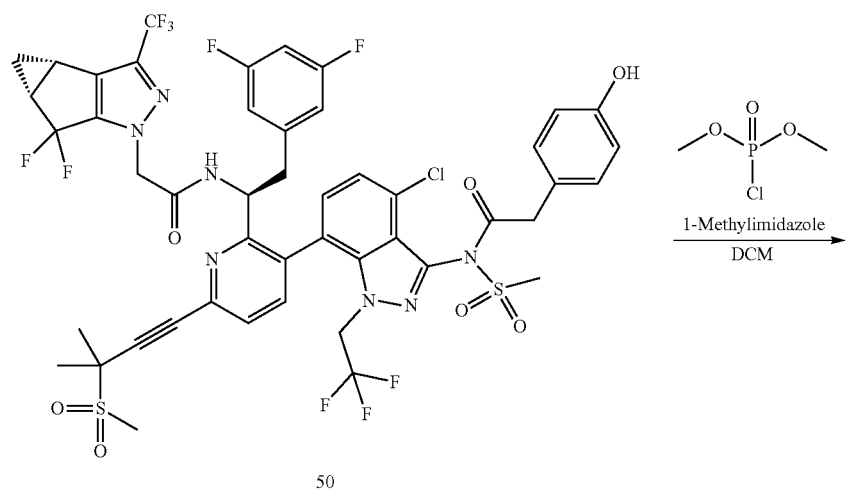

50

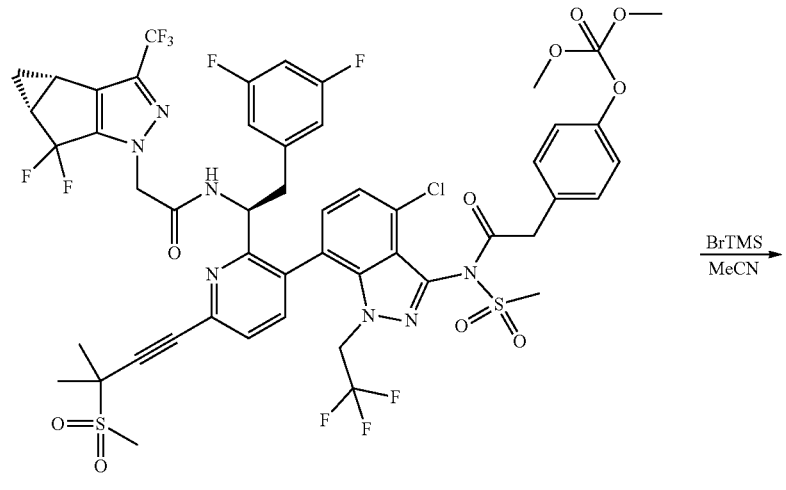

51A

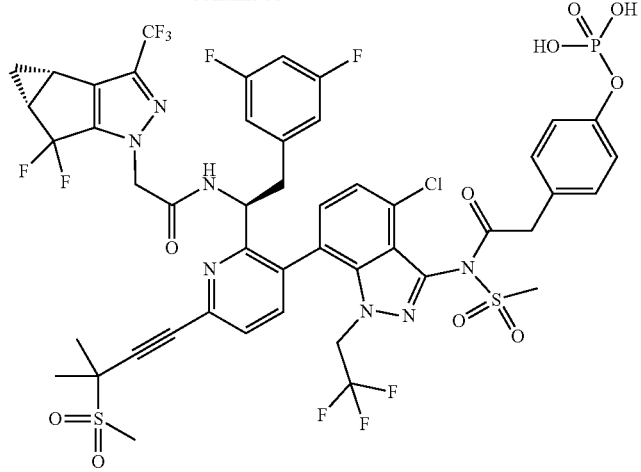

51

Synthesis of 4-(2-(N-(4-chloro-7-(2-((S)-1-(2-(((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-oxoethyl)phenyl dimethyl phosphate (51A): To a solution of 50 (0.018 mmol) in DCM (0.5 mL) was added dimethyl chlorophosphate (0.022 mmol) followed by 1-methylimidazole (0.031 mmol). The reaction was stirred at room temperature for 30 minutes, then concentrated and partitioned between water and EtOAc. The organic layer was isolated, dried over sodium sulfate, isolated by vacuum filtration, concentrated in vacuo, to obtain an atropisomeric mixture of title compound 51A, which was used without purification.

Synthesis of 4-(2-(N-(4-chloro-7-(2-((S)-1-(2-(((3bS,4aR)-5,5-difluoro (trifluoromethyl)-3b,4,4a,5-tetrahydro-1H-cyclopropa[3,4]cyclopenta[1,2-c]pyrazol yl)acetamido)-2-(3,5-difluorophenyl)ethyl)-6-(3-methyl-3-(methylsulfonyl)but-1-yn yl)pyridin-3-yl)-1-(2,2,2-trifluoroethyl)-1H-indazol-3-yl)methylsulfonamido)oxoethyl)phenyl dihydrogen phosphate (51): To a solution of 51A (0.066 mmol) in MeCN (8.0 mL) was added bromotrimethylsilane (0.99 mmol). The reaction mixture was stirred at room temperature for 3 hours, then concentrated in vacuo and purified by reverse phase HPLC (eluent: water/acetonitrile containing 0.1% v/v TFA) to provide title compound 51 as a mixture of atropisomers. $^1$H NMR (400 MHz, Methanol-$d_4$) δ 8.97 (d), 7.92-7.85 (m), 7.83 (s), 7.81 (s), 7.75 (s), 7.74 (s), 7.72 (s), 7.44-7.33 (m), 7.30-7.23 (m), 7.13-7.03 (m), 7.03-6.91 (m), 6.78-6.63 (m), 6.59-6.54 (m), 6.55-6.47 (m), 6.39-6.26 (m), 4.71 (s), 4.67 (s), 4.62-4.53 (m), 4.05-3.92 (m), 3.55-3.52 (m), 3.47 (s), 3.46 (s), 3.37 (d), 3.24 (s), 3.24 (d), 3.23 (s), 3.19 3.12 (m), 3.00-3.00 (m), 2.98 (d), 2.95 (d), 2.55-2.38 (m), 1.83 (s), 1.83 (s), 1.82 (s), 1.81 (s), 1.46-1.34 (m), 1.12-1.06 (m), 1.03-0.91 (m). MS (m/z) 1182.7 [M+H]$^+$.

Example 52

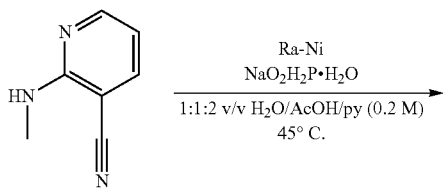

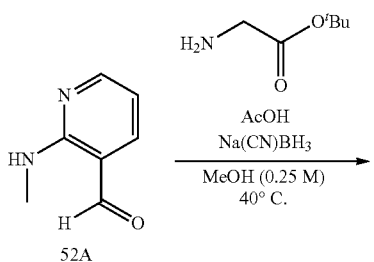

52A

-continued
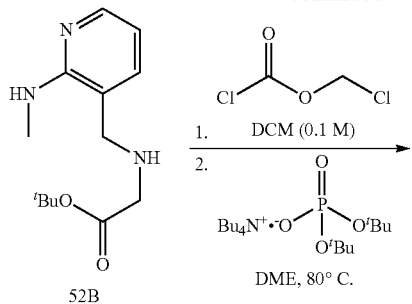
52B
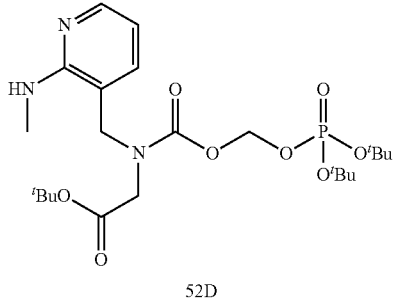
52D
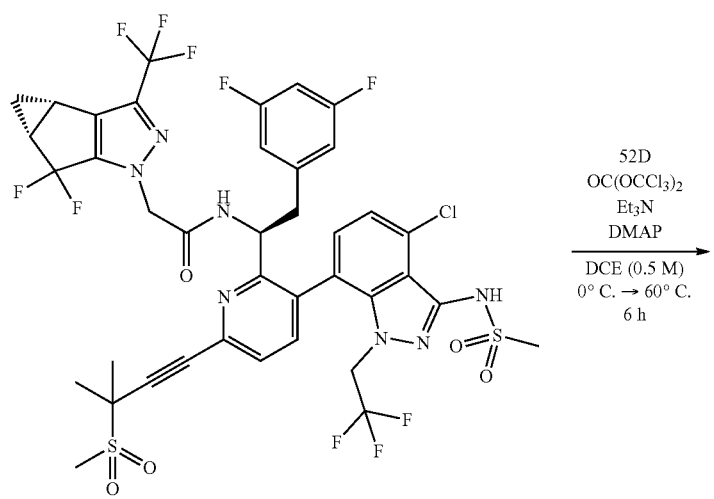
Intermediate 5
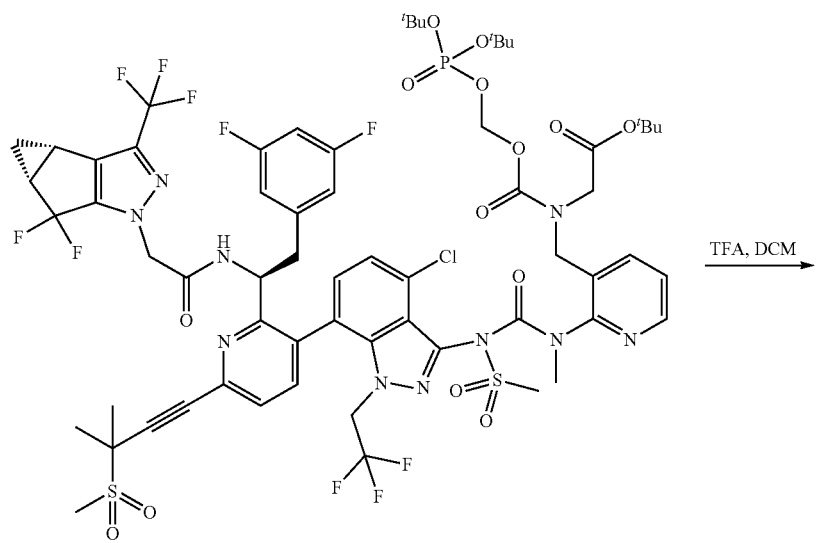
52E

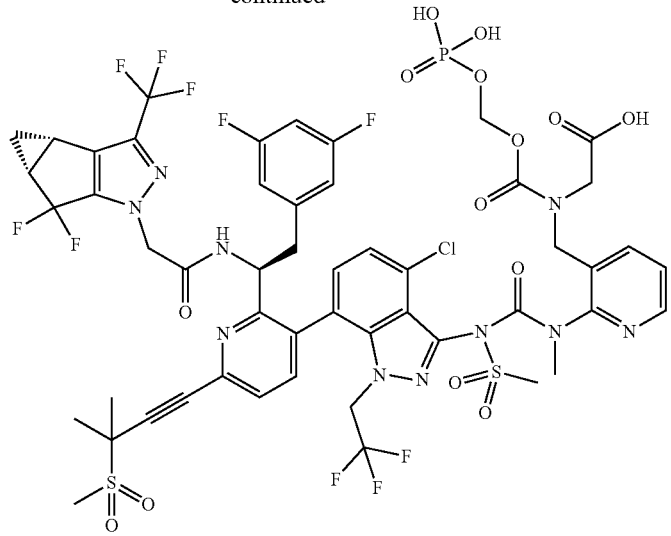

52

Synthesis of 2-(methylamino)pyridine-3-carbaldehyde (52A): To a solution of sodium hypophosphite monohydrate (360 mmol) and Raney nickel (180 mmol) in 1:1:2 v/v $H_2O$/AcOH/pyridine (450 mL) was added 2-(methylamino)pyridine-3-carbonitrile (180 mmol). The reaction was then sealed, heated to 35° C., and stirred for 2 hours. Upon completion, the reaction was cooled to room temperature, diluted sequentially with water (110 mL), NaCl (80 g), and Celite (11 g) and filtered. The cake was washed with water (225 mL) and EtOAc (225 mL). The filtrate was then transferred to a separatory funnel and the aqueous layer was extracted 2×with EtOAc (225 mL). The organic fraction was collected, dried over $Na_2SO_4$, concentrated, and purified by silica chromatography. Fractions containing the product were pooled and concentrated under reduced pressure to yield title compound 52A. $^1$H NMR (400 MHz, $CDCl_3$) δ 9.80 (s, 1H), 8.35 (dd, J=4.9, 1.9 Hz, 2H), 7.74 (dd, J=7.5, 1.9 Hz, 1H), 6.64 (dd, J=7.5, 4.9 Hz, 1H), 3.11 (d, J=4.9 Hz, 3H) ppm.

Synthesis of tert-butyl 2-[[2-(methylamino)-3-pyridyl]methylamino]acetate (52B): To a flask was added sequentially 52A (64 mmol), tert-butyl 2-aminoacetate (192 mmol), acetic acid (192 mmol), and MeOH (256 mL). The reaction was then sealed, heated to 40° C., and stirred for 30 minutes. The reaction was then cooled to 0° C. and sodium cyanoborohydride (134 mmol) was added to the reaction in one portion. The reaction was then sealed, brought to room temperature, and stirred for 90 minutes. Upon completion, the reaction mixture was concentrated and dissolved in sat. $NaHCO_3$(250 mL). The reaction was transferred to a separatory funnel and extracted 3× with DCM (125 mL). The organic fraction was collected, dried over $Na_2SO_4$, concentrated, and purified by silica chromatography. Fractions containing the product were pooled and concentrated to yield title compound 52B. $^1$H NMR (400 MHz, $CDCl_3$) δ 8.08 (dd, J=5.1, 1.8 Hz, 1H), 7.16 (dd, J=7.0, 1.8 Hz, 1H), 6.53 (s, 1H), 6.45 (dd, J=7.1, 5.1 Hz, 1H), 3.68 (s, 2H), 3.24 (s, 2H), 3.00 (s, 3H), 1.83 (s, 1H), 1.47 (s, 9H). MS (m/z): 252.20 $[M+H]^+$.

Synthesis of tert-butyl N-((chloromethoxy)carbonyl)-N-((2-(methylamino)pyridin-3-yl)methyl)glycinate (52C): To an ice-cold solution of 52B (63 mmol) in DCM (630 mL) was added chloromethyl chloroformate (63 mmol). The reaction was sealed, cooled on ice, and stirred for 15 minutes. Upon completion, the reaction mixture was transferred to a separatory funnel and washed with sat. $NaHCO_3$ (315 mL). The organic fraction was collected, dried over $Na_2SO_4$, and concentrated to yield title compound 52C, which was used without further purification.

Synthesis of tert-butyl 2-[ditert-butoxyphosphoryloxymethoxycarbonyl-[[2-(methylamino)-3-pyridyl]methyl]amino]acetate (52D): To 52C (63 mmol) was added tetrabutylammonium di-tert-butyl phosphate (95 mmol) and DME (300 mL). The reaction was then sealed, heated to 80° C., and stirred for 1 hour. Upon completion, the reaction was concentrated and dissolved in 4:1 EtOAc/Hexanes (300 mL). The solution was transferred to a separatory funnel and washed sequentially 2× with brine (150 mL), 1× with water (150 mL), and 1× with brine (150 mL). The organic fraction was collected, dried over $Na_2SO_4$, and concentrated to yield title compound 52D. $^1$H NMR (400 MHz, $CDCl_3$) δ 8.13 (d, 1H), 7.16 (d, 1H), 6.47 (t, J=6.3 Hz, 1H), 5.64 (d, 2H), 4.45 (s, 2H), 3.78 (s, 2H), 3.00 (s, 3H), 1.47 (s, 18H), 1.39 (s, 9H). MS (m/z): 518.30 $[M+H]^+$.

Synthesis of tert-butyl N-((2-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-1-methyl (methylsulfonyl)ureido)pyridin-3-yl)methyl)-N-((((di-tert-butoxyphosphoryl)oxy)methoxy)carbonyl)glycinate (52E): To an ice-cold solution of 52D (14.8 mmol), and triphosgene (4.9 mmol) in DCE (30 mL) was added triethylamine (32.6 mmol). The reaction was sealed, brought to room temperature, and stirred for 30 minutes. To the flask was added sequentially Intermediate 5 (22.3 mmol) and 4-dimethylaminopyridine (3.7 mmol). The reaction was sealed, heated to 60° C., and stirred for 6 hours. Upon completion, the reaction was brought to room temperature and diluted with DCM (240 mL). The reaction was transferred to a separatory funnel and washed 1× with saturated aqueous $NH_4Cl$ (150 mL). The organic fraction was collected, dried over $Na_2SO_4$, concentrated, and purified with silica chromatography. Fractions containing the product were pooled and concentrated to yield title compound 52E. MS (m/z): 1455.40 [M−tBu+2H]$^+$.

Synthesis of N-((2-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-1-methyl-3-(methylsulfonyl)ureido)pyridin-3-yl)methyl)-N-(((phosphonooxy)methoxy)carbonyl)glycine (52): To a flask was added 52E (3.52 mmol) and 4:6 TFA/DCM (31.5 mL). The reaction was sealed and stirred for 1 hour. Upon completion, the reaction mixture was concentrated, diluted in DMF, filtered, and purified by reverse phase HPLC. Fractions containing the product were pooled and lyophilized to yield title compound 52 as a mixture of atropisomers. $^1$H NMR (400 MHz, $CD_3CN$) δ 7.97 (s), 7.75-7.61 (m), 7.39-6.99 (m), 6.77 (s), 6.35 (s), 5.61-5.45 (m), 4.87-4.46 (m), 4.15-3.94 (m), 3.36 (s), 3.19-3.09 (m), 2.94 (s), 2.83 (d), 2.53-2.43 (m), 1.78 (s), 1.38 (q), 1.03 (h). $^{19}$F NMR (376 MHz, $CD_3CN$) δ −62.61, −71.01, −77.34, −81.72 (dd), −105.05 (d), −111.92 (d). MS (m/z): 1343.30 [M+H]$^+$.

Example 53

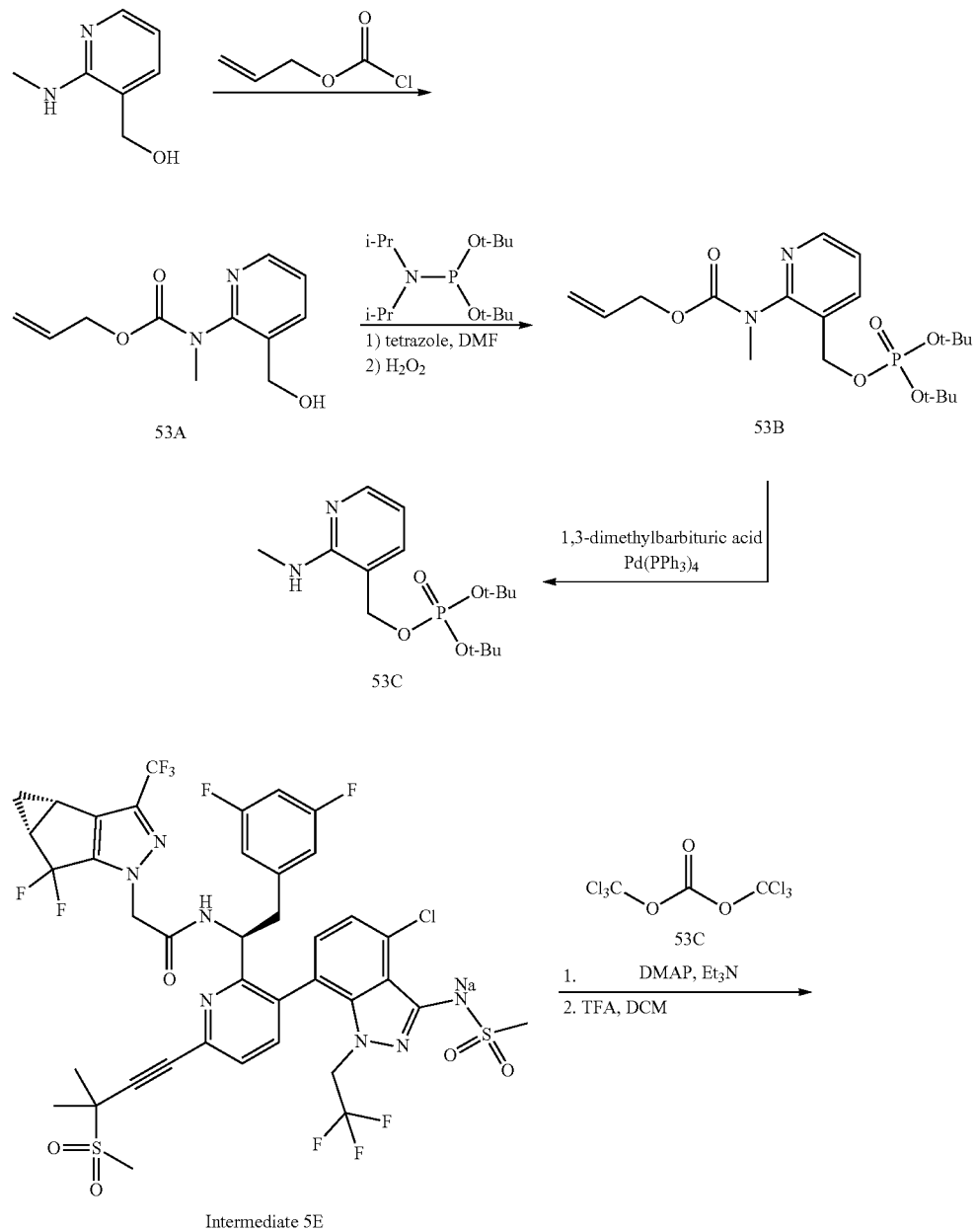

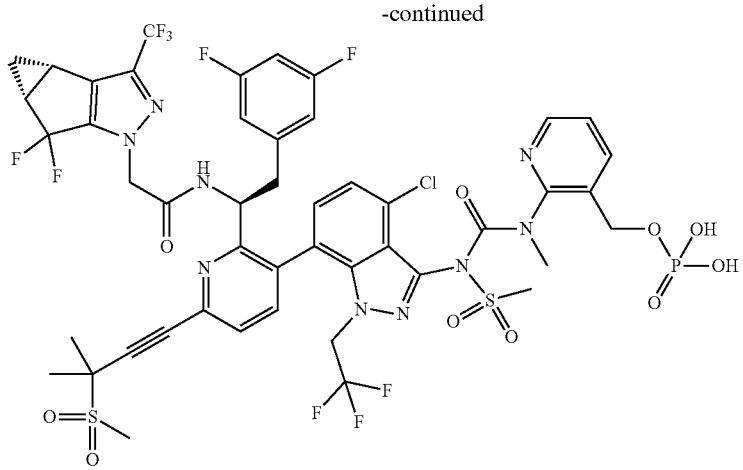

53

Synthesis of allyl (3-(hydroxymethyl)pyridin-2-yl)(methyl)carbamate (53A): To a stirred suspension of [2-(methylamino)-3-pyridyl]methanol (151 mmol) in EtOAc (100 mL) and a sat. aq. solution of NaHCO₃ (100 mL) was added allyl chloroformate (181 mmol), then the reaction mixture was stirred at room temperature for 16 h. After completion, the reaction mixture was diluted with EtOAc and washed with water. The combined organic layers were dried over anhydrous Na₂SO₄, filtered, and concentrated. The crude mixture was purified by column chromatography (0% to 100% EtOAc in hexanes) to afford title compound 53A. MS (m/z): 223.1 [M+H]⁺.

Synthesis of allyl (3-(((di-tert-butoxyphosphoryl)oxy)methyl)pyridin-2-yl)(methyl)carbamate (53B): To a solution of 53A (13.0 mmol) in DMF (100 mL) was added di-t-butyl-N,N-diisopropylphosphoramidite (39.0 mmol) and —H-tetrazole (52.0 mmol) sequentially. The reaction mixture was stirred at room temperature while monitored by TLC and LCMS. After 4 h, the reaction mixture was cooled to 0° C. and treated with aq. H₂O₂ solution (4.8 mL, 50 wt %). The reaction was gradually warmed to room temperature and stirred. After completion, the reaction mixture was diluted with ethyl ether and washed with sat. aq. sodium thiosulfate solution. The combined organic layers were dried over anhydrous Na₂SO₄, filtered, and concentrated. The crude mixture was purified by column chromatography (0% to 100% EtOAc in hexanes) to afford the title compound 53B. MS (m/z): 437.2 [M+Na]⁺.

Synthesis of di-tert-butyl ((2-(methylamino)pyridin-3-yl)methyl) phosphate (53C): To a solution of 53B (6.5 mmol) in a mixture of ethyl acetate and dichloromethane (38 mL, 1:1) was added 1,3-dimethylbarbituric acid (8.4 mmol) followed by tetrakis(triphenylphosphine)palladium(O) (0.32 mmol). The resulting reaction mixture was stirred at room temperature while monitored by LCMS. Upon completion, the reaction mixture was diluted with EtOAc and washed with water. The combined organic layers were dried over anhydrous Na₂SO₄, filtered, and concentrated. The crude mixture was purified by column chromatography (0% to 5% MeOH in CH₂Cl₂) to afford title compound 53C. MS (m/z): 331.2 [M+H]⁺.

Synthesis of (2-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-1-methyl-3-(methylsulfonyl)ureido)pyridin-3-yl)methyl dihydrogen phosphate (53): The title compound was prepared according to the method presented for the synthesis of compound 52 of Example 52 utilizing 53C in place of 52D. ¹H NMR (400 MHz, DMSO-d₆) δ 9.63-8.75 (m), 8.13-7.49 (m), 7.36-6.26 (m), 5.35-4.49 (m), 4.40-3.96 (m), 3.27 (s), 3.10 (s), 1.96-1.53 (m), 1.55-1.25 (m), 1.16-0.72 (m). ¹⁹F NMR (376 MHz, DMSO-d₆) δ −58.88--62.88 (m), −69.36, −80.10 (d), −103.77 (dd), −110.75. MS (m/z) 1213.200 [M+H]⁺.

Example 54

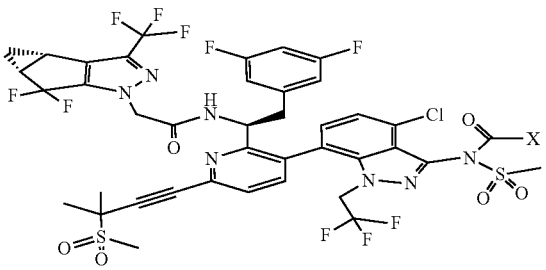

Synthesis of ditert-butyl[2-(methylamino)phenyl]phosphate (54A): To a solution of 2-(methylamino)phenol (8.12 mmol), 0.45M 1H-tetrazole in MeCN (20.3 mmol), and N,N-dimethylacetamide (16 mL) was added di-tert-butyl N,N-diisopropylphosphoramidite (16.2 mmol). The reaction was sealed, heated to 40° C., and stirred for 1 hour. Then 50% H₂O₂ (40.6 mmol) was added to the reaction. The reaction was sealed, heated to 40° C., and stirred for 1 hour. Upon completion, the reaction was diluted with water (120 mL) and quenched with sat. Na₂SO₃ (16 mL). The solution was transferred to a separatory funnel and extracted 3× with 1:1 EtOAc/Hexanes (90 mL). The organic fraction was collected, washed with 0.1M HCl (120 mL), 5% LiCl (120 mL), sat. NaCl (60 mL), dried over Na₂SO₄, concentrated, and purified with silica chromatography. Fractions containing the product were pooled and concentrated to yield title compound 54A. MS (m/z): 316.20 [M+H]⁺.

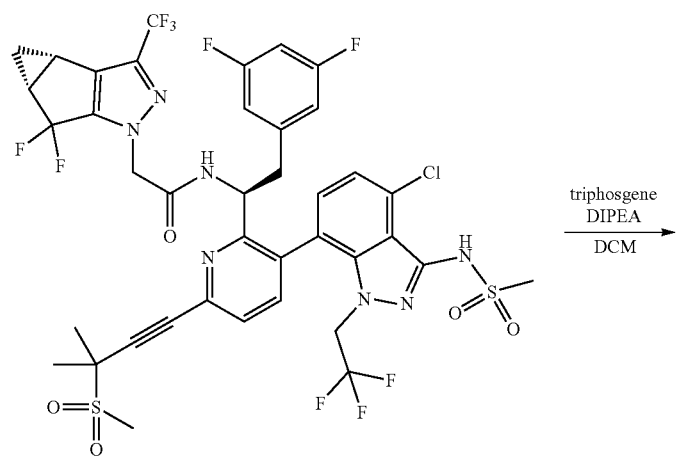
Intermediate 5
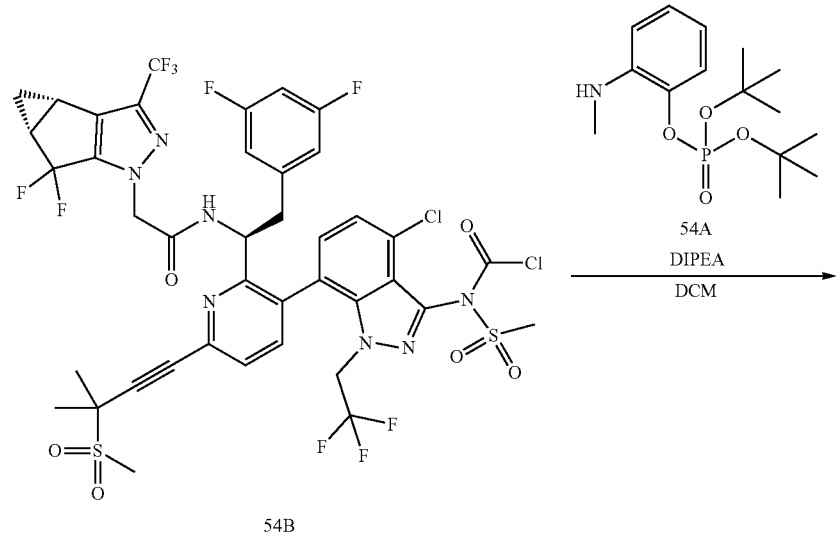
54B
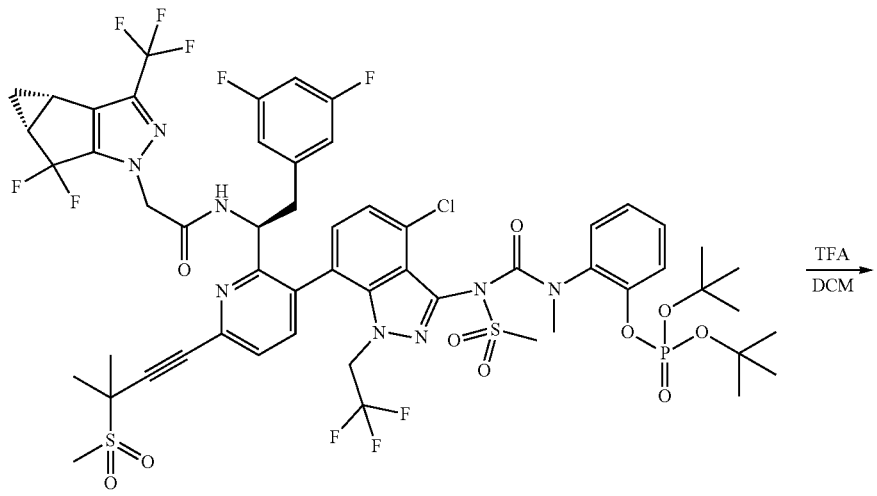
54C

-continued

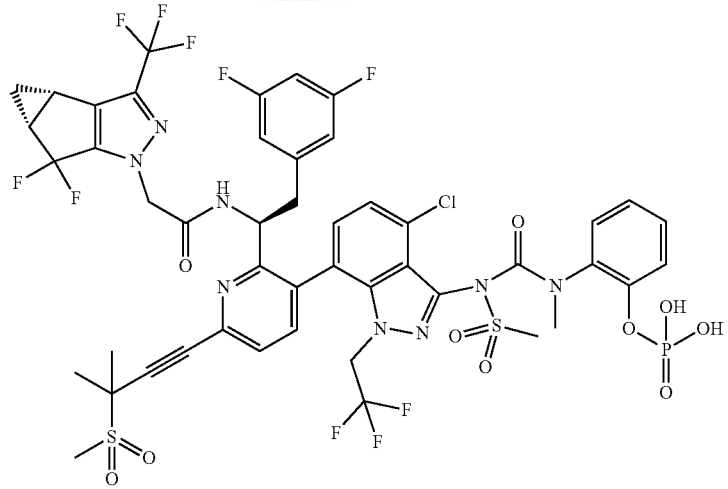

54

Synthesis of (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamic chloride 54B: To a vial containing Intermediate 5 (0.103 mmol) and triphosgene (0.309 mmol) was added DCM (2 mL) and the solution was cooled to 0° C. in an ice bath. To the mixture was then added DIPEA (0.309 mmol) and the reaction was stirred for 15 minutes. Upon completion, the reaction was concentrated under reduced pressure to yield an atropisomeric mixture of title compound 54B which was used without further purification. MS (m/z) 1030.81 [M+H]+.

Synthesis of di-tert-butyl (2-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-1-methyl (methylsulfonyl)ureido)phenyl) phosphate (54C): To a solution of 54C (0.6 mmol) in DCM (3 mL) at 0° C. were added 54A (1.80 mmol, 3 equiv) and DIPEA (0.72 mmol, 1.2 equiv). Upon completion, the reaction was partitioned between DCM and water, and the organic fraction was collected, dried over Na$_2$SO$_4$, and concentrated under reduced pressure to yield an atropisomeric mixture of title compound 54C, which was used without purification. MS (m/z) 1331.30 [M+Na]+.

Synthesis of 2-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-1-methyl-3-(methylsulfonyl)ureido)phenyl dihydrogen phosphate (54): To 54C was added a solution of TFA in DCM (5.15 mL of a 10% v/v solution). When the reaction had reached completion, the volatiles were removed under reduced pressure and the residue was purified by reverse phase HPLC. Fractions containing the product were pooled and lyophilized to yield title compound 54 as a mixture of atropisomers. $^1$H NMR (400 MHz, MeOD) δ 9.09 (d), 8.82 (s), 7.98 (s), 7.71 (s), 7.61 (s), 7.36 (d), 6.89 (q), 6.75 (s), 6.61 (s), 6.41 (d), 6.16 (s), 4.70 (s), 4.45 (q), 3.99 (q), 3.40 (s), 3.23 (s), 3.16 (s), 2.99 (s), 2.86 (s), 2.49 (s), 1.94 (s), 1.82 (s), 1.42 (q), 1.01 (s). $^{19}$F NMR (377 MHz, MeOD) δ −63.61, −71.75, −78.17, −82.42 (dd), −105.79 (d), −112.18 (d). MS (m/z): 1197.20 [M+H]+.

Example 55

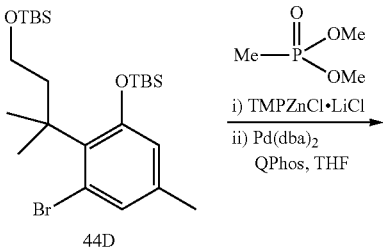

44D

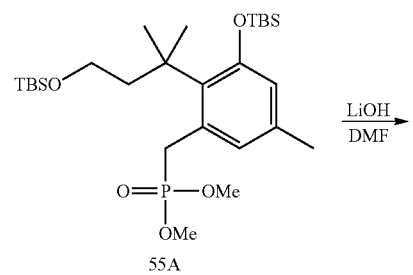

55A

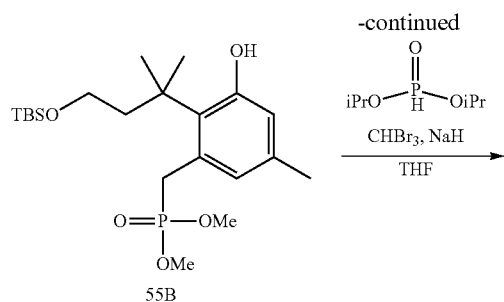
55B
-continued
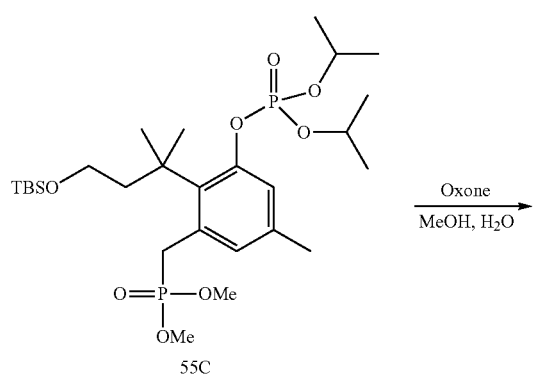
55C
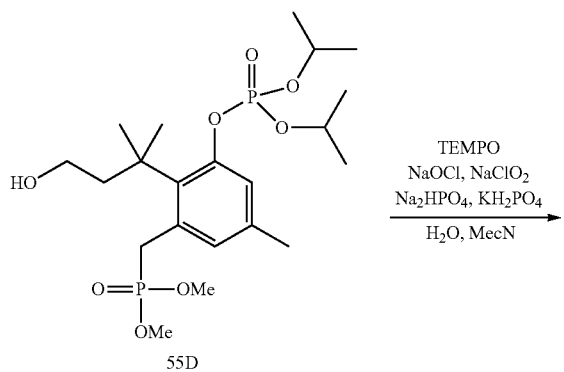
55D
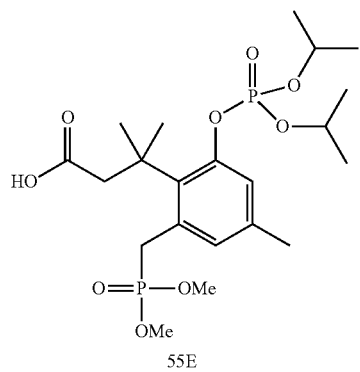
55E

-continued

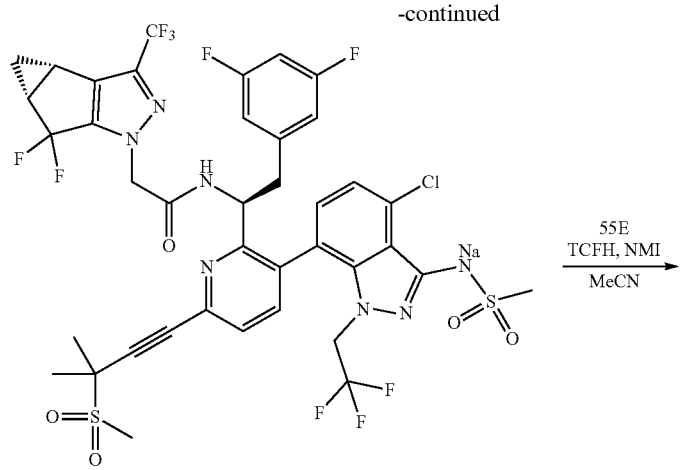

Intermediate 5E

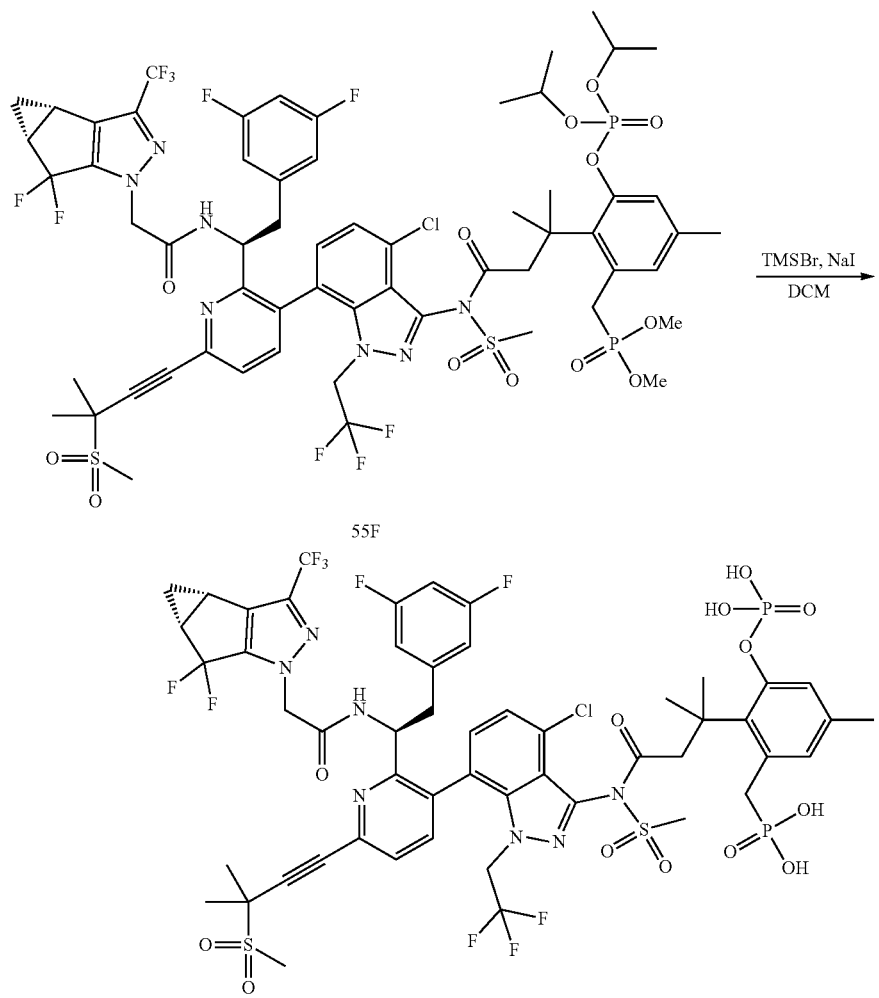

Synthesis of Dimethyl (3-((tert-butyldimethylsilyl)oxy)-2-(4-((tert-butyldimethylsilyl)oxy)-2-methylbutan-2-yl)-5-methylbenzyl)phosphonate (55A): A flask was charged with dimethyl methylphosphonate (4.78 mmol) and THF (4.8 mL) under nitrogen. TMPZnCl·LiCl (5.98 mmol, 1.0M in THF) was added and the reaction was monitored by $^{31}$P NMR. Upon completion, 1.42 mL (0.598 mmol) of the resulting organozinc reagent in solution was added under nitrogen to a flask containing 44D (0.498 mmol), Pd(dba)$_2$ (0.05 mmol), QPhos (0.05 mmol) and THF (2.5 mL). The reaction was heated at 50° C. for 3 hours, quenched with sat. NH$_4$C$_1$ (aq) and extracted with EtOAc (3×). The combined organic layers were washed with brine, dried over MgSO$_4$, filtered and concentrated under reduced pressure. The crude material was purified by silica gel chromatography to afford title compound 55A. MS (m/z) 544.93 [M+H]⁺.

Synthesis of Dimethyl (2-(4-((tert-butyldimethylsilyl)oxy)-2-methylbutan-2-yl)-3-hydroxy-5-methylbenzyl)phosphonate (55B): A flask was charged with 55A (0.158 mmol), anhydrous LiOH (0.474 mmol) and DMF (0.8 mL). The mixture was heated at 60° C. for 3 hours. The reaction was diluted with water and sat. NH$_4$C$_1$ (aq), then extracted with EtOAc (3×). The combined organic layers were washed with 5% LiCl$_{(aq)}$(2×), dried over MgSO$_4$, filtered and concentrated. The crude material was purified by silica gel chromatography to afford title compound 55B. MS (m/z) 430.99 [M+H]⁺.

Synthesis of 2-(4-((tert-butyldimethylsilyl)oxy)-2-methylbutan-2-yl)-3-((dimethoxyphosphoryl)methyl)-5-methylphenyl diisopropyl phosphate (55C): A flask charged with 55B (1.31 mmol) and THF (6.0 mL) under nitrogen was cooled to 0° C. Diisopropyl phosphite (1.52 mmol) and bromoform (1.52 mmol) were added. The solution was stirred for 5 minutes, sodium hydride (60% dispersion in mineral oil, 1.52 mmol) was added in one portion and the mixture was gradually warmed to RT. Upon completion, the reaction was quenched with water and extracted with EtOAc (3×). The combined organic layers were washed with brine, dried over MgSO$_4$, filtered and concentrated. The crude material was purified by silica gel chromatography to afford title compound 55C. MS (m/z) 594.77 [M+H]⁺.

Synthesis of 3-((Dimethoxyphosphoryl)methyl)-2-(4-hydroxy-2-methylbutan-2-yl)-5-methylphenyl diisopropyl phosphate (55D): A flask charged with 55C (0.193 mmol), MeOH (1.0 mL) and water (1.0 mL) was cooled to 0° C. Oxone® (0.387 mmol) was added, the ice bath was removed and the reaction was stirred at RT for 1 hour. The reaction was quenched with sat. sodium sulfite (aq), concentrated, diluted with water and extracted with EtOAc (3×). The combined organic layers were washed with brine, dried over MgSO$_4$, filtered and concentrated. The crude material was purified by silica gel chromatography to afford title compound 55D. MS (m/z) 480.93 [M+H]⁺.

Synthesis of 3-(2-((Diisopropoxyphosphoryl)oxy) ((dimethoxyphosphoryl)methyl)-4-methylphenyl)-3-methylbutanoic acid (55E): To a solution of 55D (2.84 mmol) in ACN/water (1:1, 30.0 mL) was added TEMPO (0.142 mmol), potassium dihydrogen phosphate (1.42 mmol) and disodium hydrogen phosphate (1.42 mmol). The solution was cooled to 0° C. Sodium chlorite (4.26 mmol) was added, followed by sodium hypochlorite (8.25% NaOCl (aq), 3.47 mmol). The ice bath was removed and the reaction was stirred for 2 hours. The reaction was diluted with water, quenched with sat. sodium sulfite$_{(aq)}$ and acidified with 1N HCl (aq) to pH 2. The aqueous layer was extracted with EtOAc (3×). The combined organic layers were washed with brine, dried over MgSO$_4$, filtered and concentrated under reduced pressure to yield title compound 55E which was used without further purification. MS (m/z) 493.39 [M–H]⁺.

Synthesis of 2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-((dimethoxyphosphoryl)methyl)-5-methylphenyl diisopropyl phosphate (55F): To a solution of crude 55E (2.84 mmol) in ACN (20.0 mL) was added N-methylimidazole (9.95 mmol), Intermediate 5E (2.84 mmol) and TCFH (2.84 mmol). The reaction was stirred at RT for 18 hours. The reaction was quenched with sat. NH$_4$C$_1$ (aq) and extracted with EtOAc (3×). The combined organic layers were washed with brine, dried over MgSO$_4$, filtered and concentrated under reduced pressure. The crude material was purified by reverse phase HPLC. Fractions containing title compound were pooled and concentrated to afford an atropisomeric mixture of title compound 55F. MS (m/z) 1443.62 [M+H]⁺.

Synthesis of (2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-5-methyl-3-(phosphonooxy)benzyl)phosphonic acid (55): A flask charged with 55F (2.35 mmol), sodium iodide (0.471 mmol) and bromotrimethylsilane (18.8 mmol) in DCM (15.0 mL) was heated under nitrogen at 45° C. for 6 hours. The reaction was diluted with water, extracted with EtOAc (3×) and the combined organic layers were concentrated. The crude product was purified by RP chromatography (50-100% ACN/water with 0.1% TFA). Fractions containing the product were pooled and lyophilized to afford an atropisomeric mixture of title compound 55. ¹H NMR (400 MHz, DMSO-d$_6$) δ 9.18 (dd), 9.01 (d), 8.94 (d), 8.00 (d), 7.94 (d), 7.88 (d), 7.83-7.71 (m), 7.43 (d), 7.39-7.23 (m), 7.11 (s), 7.08-6.96 (m), 6.96-6.88 (m), 6.77 (d), 6.59 (d), 6.50 (td), 4.95-4.58 (m), 4.30-4.13 (m), 4.08-3.95 (m), 3.70-3.33 (m), 3.26 (d), 3.24-2.91 (m), 2.81-2.45 (m), 2.16 (s), 1.74 (d), 1.64-1.26 (m), 0.99 (d). ¹⁹F NMR (376 MHz, DMSO-d$_6$) δ–60.80 (d), –60.86, –60.89, –69.34 (t), –69.51 (t), –69.58 (t), –69.77 (t), –79.80 (d), –80.07--80.30 (m), –80.48 (d), –80.75--80.96 (m), –102.01 (bs), –102.38--103.00 (m), –103.11 (d), –103.25 (d), –103.43--103.61 (m), –103.79 (d), –103.93 (d), –110.53 (t), –110.62 (t), –110.74 (t), –110.90 (t) ppm. ³¹P NMR (162 MHz, DMSO-d$_6$) δ 21.71-21.44 (m), –6.99, –7.09. MS (m/z) 1331.94 [M+H]⁺.

Example 56

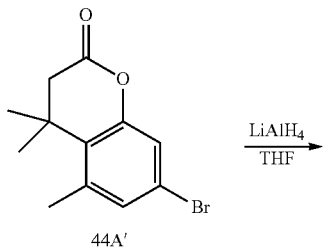

44A'

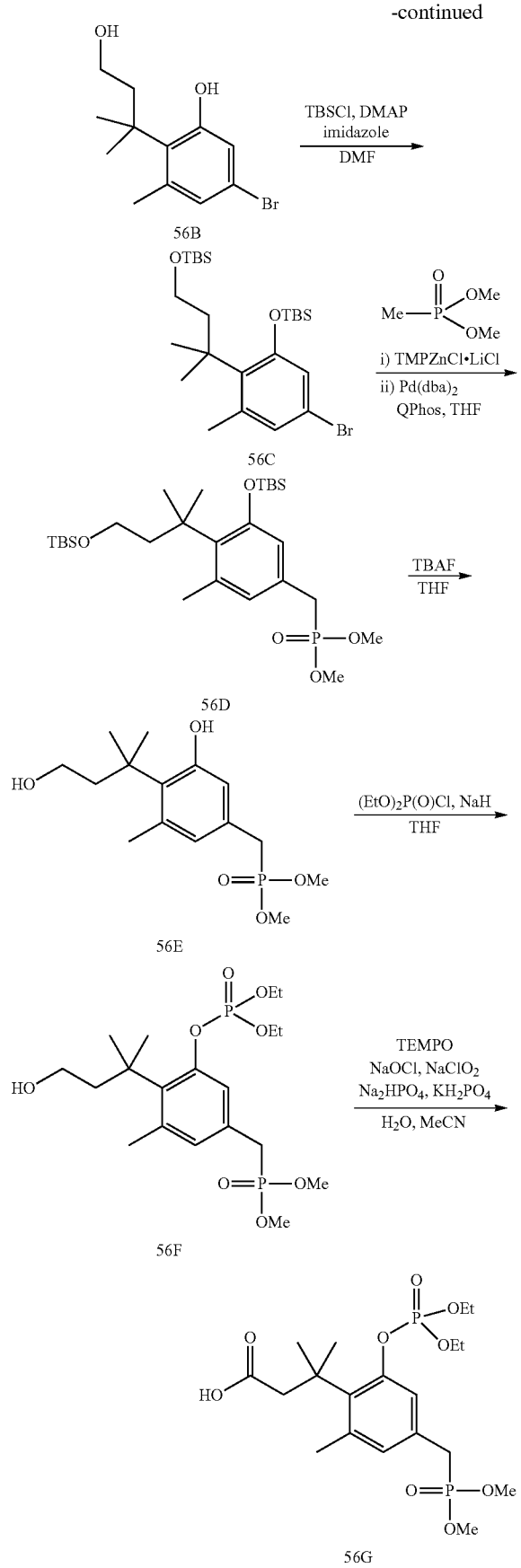

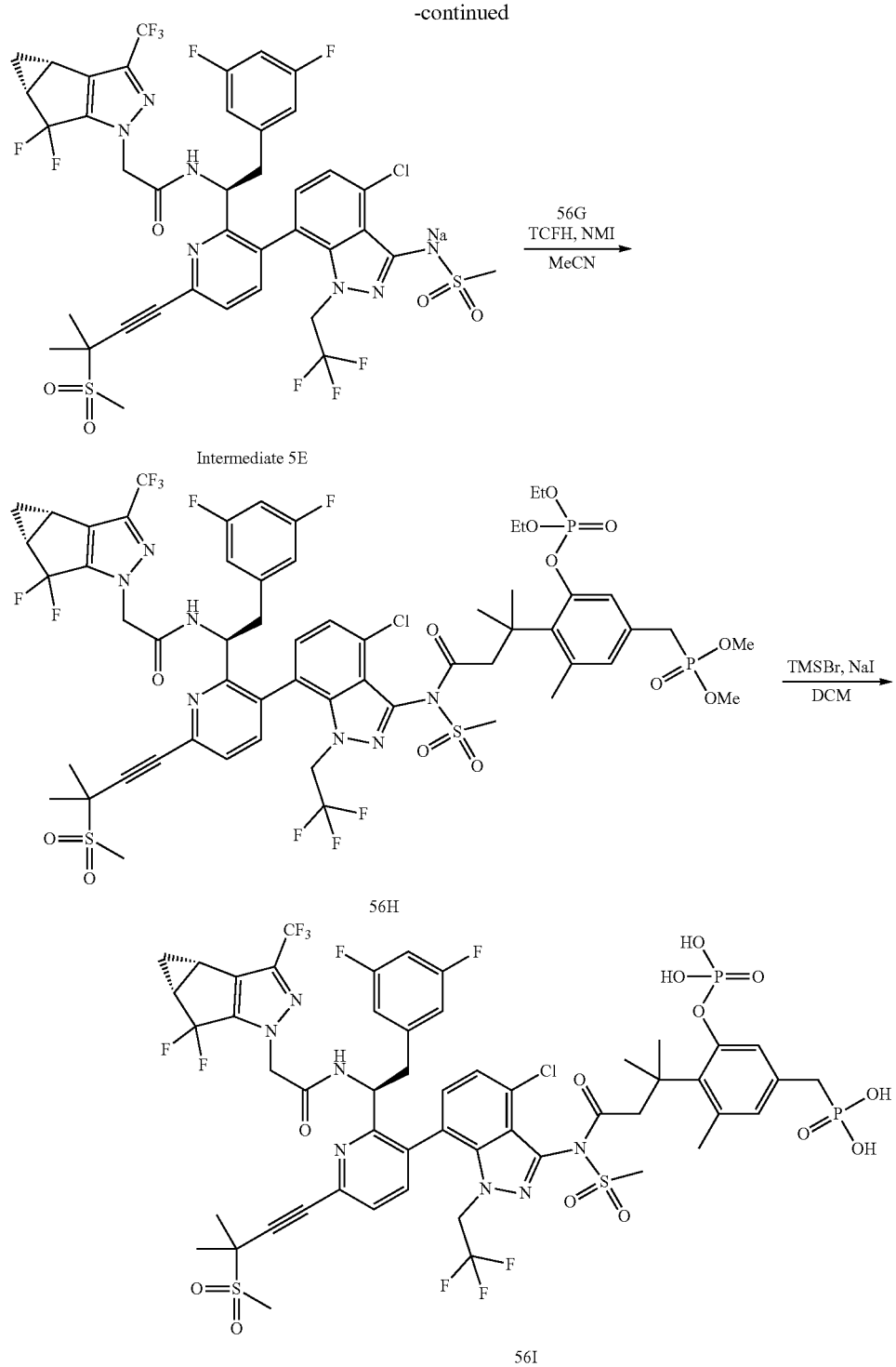

Synthesis of 5-Bromo-2-(4-hydroxy-2-methylbutan-2-yl)-3-methylphenol (56B): A flask was charged with a solution of LAH (2.0M in THF, 11.1 mmol) and THF (12 mL). The solution was cooled to 0° C. A solution of 44A' (9.29 mmol) in THF (15 mL) was added dropwise. The ice bath was removed and the reaction was stirred at RT for 6 hours. The reaction was cooled to 5° C. Water (423 µL) was added slowly, followed by 15% NaOH (aq) (423 µL), then water again (1269 µL). The mixture was warmed to RT and stirred overnight. The mixture was diluted with EtOAc, MgSO$_4$ was added and the mixture was filtered. The filter cake was rinsed with EtOAc. The crude product was purified by silica gel chromatography to afford title compound 56B. MS (m/z) 271.39/273.23 [M–H]$^+$.

Synthesis of (3-(4-Bromo-2-((tert-butyldimethylsilyl)oxy)-6-methylphenyl)-3-methylbutoxy) tert-butyl)dimethylsilane (56C): A flask was charged with 56B (9.23 mmol), DMF (25.0 mL), imidazole (46.1 mmol) and DMAP (0.923 mmol) under nitrogen. The solution was heated at 65° C. for 18 hours. The reaction was diluted with water (75 mL), extracted with 25% EtOAc/hexanes (3×), washed with 5% LiCl (aq), dried over MgSO$_4$, filtered and concentrated. The crude product was purified by silica gel chromatography to afford title compound 56C.

Synthesis of Dimethyl (3-((tert-butyldimethylsilyl)oxy)-4-(4-((tert-butyldimethylsilyl)oxy)-2-methylbutan-2-yl)-5-methylbenzyl)phosphonate (56D): A flask was charged with dimethyl methylphosphonate (13.8 mmol) and THF (15.0 mL) under nitrogen. TMPZnCl•LiCl (20.8 mmol, 1.0 M in THF) was added and the reaction was monitored by $^{31}$P NMR. Upon completion, the resulting organozinc solution was added under nitrogen to a flask containing 56C (9.22 mmol), Pd(dba)$_2$ (0.461 mmol), QPhos (0.461 mmol) and THF (9.0 mL). The reaction was heated at 45° C. for 4 hours, quenched with sat. NH$_4$Cl$_{(aq)}$ and extracted with EtOAc (3×). The combined organic layers were washed with brine, dried over MgSO$_4$, filtered and concentrated under reduced pressure. The crude material was purified by silica gel chromatography to afford title compound 56D. MS (m/z) 567.38 [M+Na]$^+$.

Synthesis of Dimethyl (3-hydroxy-4-(4-hydroxy-2-methylbutan-2-yl)-5-methylbenzyl)phosphonate (56E): A solution of 56D (2.31 mmol) in THF (10.0 mL) was cooled to 0° C. TBAF (1.0 M in THF, 5.78 mmol) was added and the reaction was stirred for 3 hours at RT. The reaction was diluted with water and extracted with EtOAc (3×). The combined organic layers were washed with brine, dried over MgSO$_4$, then filtered and concentrated under reduced pressure. The residue was purified by silica gel chromatography to yield title compound 56E. MS (m/z) 315.29 [M–H]$^+$.

Synthesis of 5-((Dimethoxyphosphoryl)methyl)-2-(4-hydroxy-2-methylbutan-2-yl)-3-methylphenyl diethyl phosphate (56F): To a solution of 56E (2.02 mmol) in THF (10.0 mL) at 0° C. was added sodium hydride (60% dispersion in mineral oil, 2.63 mmol) in one portion. The mixture was stirred for 15 minutes. Diethyl chlorophosphate (2.02 mmol) was added and the mixture was stirred vigorously at RT until consumption of starting material was observed. The reaction was diluted with sat. NaHCO$_3$(aq) and extracted with EtOAc (3×). The combined organic layers were washed with brine, dried over MgSO$_4$, filtered and concentrated. The crude material was purified by silica gel chromatography to afford title compound 56F. MS (m/z) 452.96 [M+H]$^+$.

Synthesis of 3-(2-((Diethoxyphosphoryl)oxy)-4-((dimethoxyphosphoryl)methyl)-6-methylphenyl)-3-methylbutanoic acid (56G): To a solution of 56F (1.89 mmol) in ACN/water (1:1, 10.0 mL) was added TEMPO (0.095 mmol), potassium dihydrogen phosphate (0.947 mmol) and disodium hydrogen phosphate (0.947 mmol). The solution was cooled to 0° C. Sodium chlorite (2.84 mmol) was added, followed by sodium hypochlorite (8.25% NaOCl$_{(aq)}$, 2.31 mmol). The ice bath was removed and the reaction was stirred for 3 hours. The reaction was diluted with water, quenched with sat. sodium sulfite (aq) and acidified with 1N HCl (aq) to pH 2. The aqueous layer was extracted with EtOAc (3×). The combined organic layers were washed with brine, dried over MgSO$_4$, filtered and concentrated under reduced pressure to yield title compound 56G which was used without further purification. MS (m/z) 466.84 [M+H]$^+$.

Synthesis of 2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-5-((dimethoxyphosphoryl)methyl)-3-methylphenyl diethyl phosphate (56I1): To a solution of crude 56G (0.828 mmol) in ACN (10.0 mL) was added N-methylimidazole (2.90 mmol), Intermediate 5E (0.786 mmol) and TCFH (0.828 mmol). The reaction was stirred at RT for 18 hours. The reaction was quenched with sat. NH$_4$Cl (aq) and extracted with EtOAc (3×). The combined organic layers were washed with brine, dried over MgSO$_4$, filtered and concentrated under reduced pressure. The crude material was purified by reverse phase HPLC. Fractions containing title compound were pooled and concentrated to afford an atropisomeric mixture of title compound 56I1. MS (m/z) 1416.40 [M+H]$^+$.

Synthesis of (4-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol yl)acetamido)-2-(3,5-difluorophenyl)ethyl)-6-(3-methyl-3-(methylsulfonyl)but-1-yn yl)pyridin-3-yl)-1-(2,2,2-trifluoroethyl)-1H-indazol-3-yl)methylsulfonamido)-2-methyl oxobutan-2-yl)-3-methyl-5-(phosphonooxy)benzyl) phosphonic acid (56): A flask charged with 56I1 (0.882 mmol), sodium iodide (0.088 mmol) and bromotrimethylsilane (0.011 mmol) in DCM (5.0 mL) was heated under nitrogen at 45° C. for 8 hours, then stirred at RT overnight. The reaction was diluted with water, extracted with EtOAc (3×) and the combined organic layers were concentrated. The crude product was purified by RP chromatography (50-100% ACN/water with 0.1% TFA). Fractions containing the product were pooled and lyophilized to afford an atropisomeric mixture of title compound 56. $^1$H NMR (400 MHz, DMSO-d$_6$) δ 9.17 (d), 9.01 (d), 8.79 (d), 7.98 (t), 7.94-7.84 (m), 7.84-7.78 (m), 7.75 (d), 7.49-7.40 (m), 7.40-7.32 (m), 7.29 (d), 7.15 (s), 7.06-6.80 (m), 6.77-6.65 (m), 6.65-6.54 (m), 6.48 (d), 6.39 (d), 4.99 (d), 4.91-4.54 (m), 4.53-4.30 (m), 4.29-4.11 (m), 4.11-3.93 (m), 3.52 (d), 3.47 (d), 3.27 (d), 3.17-2.30 (m), 2.23 (s), 1.75 (bs), 1.52-1.31 (m), 1.30-1.06 (m), 0.99 (bs). $^{19}$F NMR (377 MHz, DMSO-d$_6$) δ−60.76, −60.81, −60.85, −60.97, −69.45--69.62 (m), −70.07 (t), −79.80 (d), −80.13--80.36 (dd), −80.47 (d), −80.82--81.03 (dd), −81.13 (d), −101.83 (bs), −102.50 (bs), −103.13 (d), −103.24 (d), −103.80 (d), −103.91 (d), −110.54--110.77 (m), −110.80--110.95 (m). $^{31}$P NMR (162 MHz, DMSO-d$_6$) δ 20.87, 20.81, 20.75, −6.98, −7.01, −7.08. MS (m/z) 1330.90 [M−H]$^+$.

Example 57

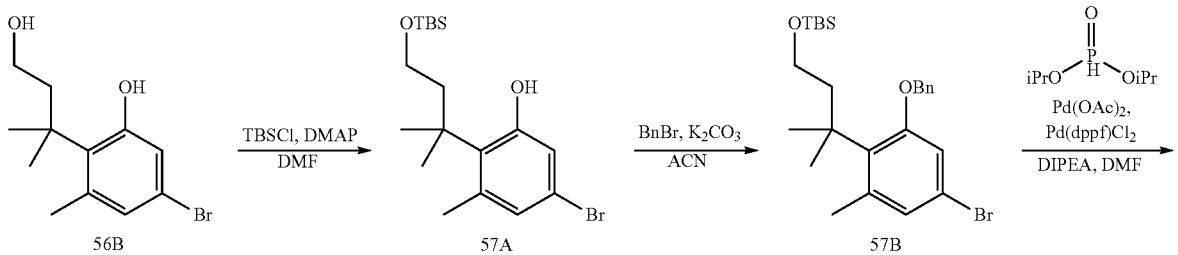

331 332
-continued
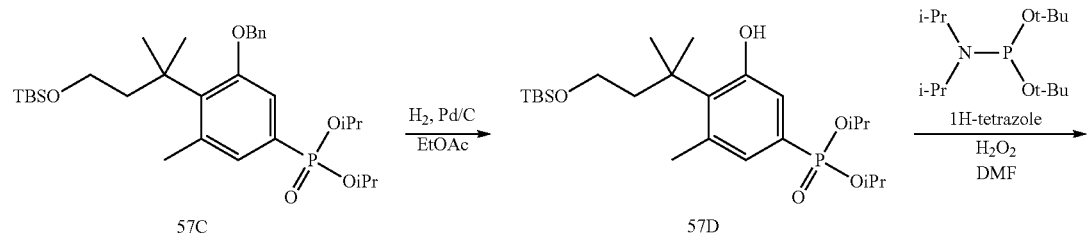
57C → 57D
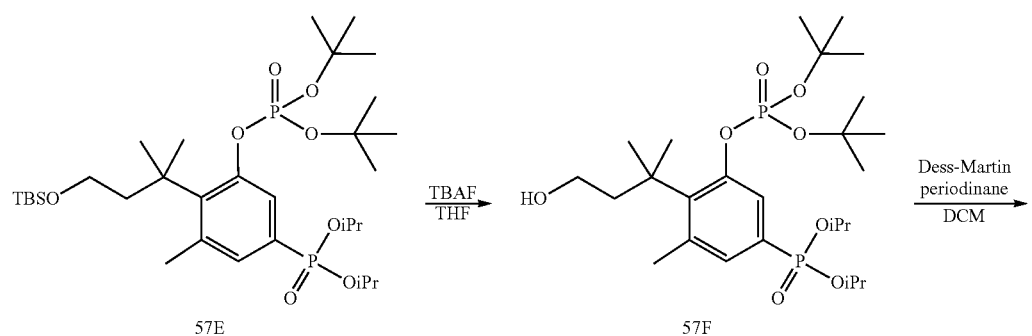
57E → 57F
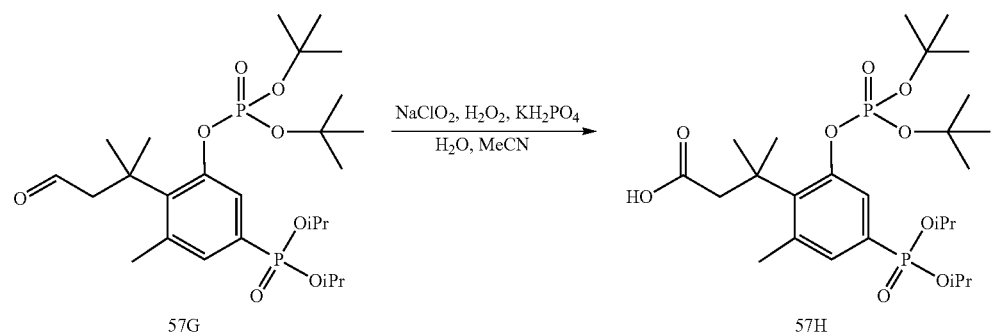
57G → 57H
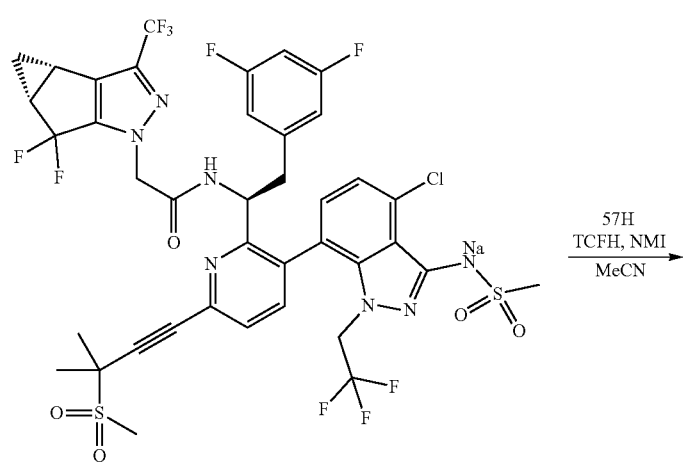
Intermediate 5E -continued

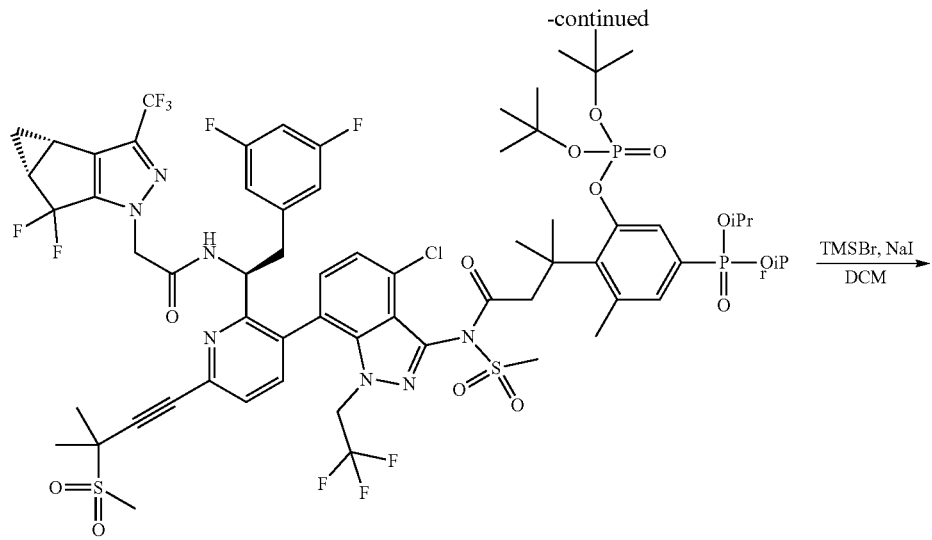

57I

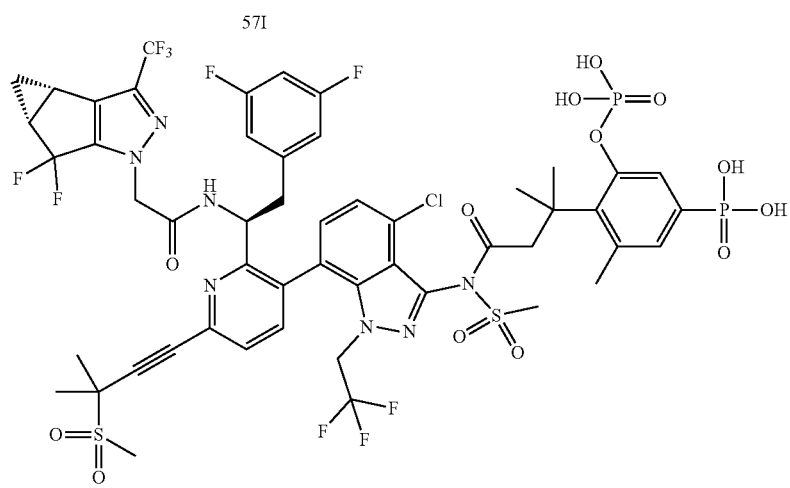

57

Synthesis of 5-bromo-2-(4-((tert-butyldimethylsilyl)oxy)-2-methylbutan yl)-3-methylphenol (57A): To a solution of 56B (36.6 mmol) in DCM (150 mL) was added DMAP (58.5 mmol) and a solution of TBSCl (43.9 mmol) in DCM (50.0 mL) at 0° C. The mixture was stirred at 0° C. for 2 hours. The reaction was concentrated under reduced pressure and the residue was purified by silica gel chromatography to yield title compound 57A. $^1$H NMR (400 MHz, Chloroform-d) δ 6.80 (d, J=2.0 Hz, 1H), 6.77 (d, J=2.0 Hz, 1H), 6.57 (s, 1H), 3.62 (t, J=6.8 Hz, 2H), 2.46 (s, 3H), 2.13 (t, J=6.8 Hz, 2H), 1.54 (s, 6H), 0.89 (s, 9H), 0.05 (s, 6H).

Synthesis of (3-(2-(benzyloxy)-4-bromo-6-methylphenyl)-3-methylbutoxy)(tert-butyl)dimethylsilane (57B): To a solution of 57A (43.8 mmol) in ACN (300 mL) was added K$_2$CO$_3$ (87.7 mmol) and benzyl bromide (46.0 mmol). The mixture was stirred at 40° C. for 2 hours. The reaction mixture was poured into water (200 mL) and extracted with ethyl acetate (200 mL×3). The combined organic phase was washed with brine (200 mL×3), dried over anhydrous Na$_2$SO$_4$, filtered and concentrated under reduced pressure to afford title compound 57B, which was used without further purification. $^1$H NMR (400 MHz, Chloroform-d) δ 7.47-7.37 (m, 5H), 6.96 (d, J=1.6 Hz, 1H), 6.89 (d, J=1.8 Hz, 1H), 5.02 (s, 2H), 3.47 (t, J=7.4 Hz, 2H), 2.51 (s, 3H), 2.12 (t, J=7.5 Hz, 2H), 1.51 (s, 6H), 0.84 (s, 9H), −0.05 (s, 6H).

Synthesis of Diisopropyl (3-(benzyloxy)-4-(4-((tert-butyldimethylsilyl)oxy)-2-methylbutan-2-yl)-5-methylphenyl)phosphonate (57C): To a vial was added 57B (12.5 mmol), Pd(dppf)Cl$_2$ (1.25 mmol) and Pd(OAc)$_2$ (1.25 mmol). The vial was backfilled with N2 3 times, followed by the addition of diisopropyl phosphite (15.0 mmol), DIPEA (16.3 mmol) and DMF (15.0 mL). The vial was heated to 110° C. for 4 hours. The reaction was filtered, concentrated and the residue was purified by RP chromatography to afford the title compound 57C. $^1$H NMR (400 MHz, Chloroform-d) δ 7.47-7.32 (m, 5H), 7.18 (dd, J=14.3, 19.3 Hz, 2H), 5.09 (s, 2H), 4.65 (qd, J=6.2, 14.1 Hz, 2H), 3.49-3.40 (m, 2H), 2.57 (s, 3H), 2.20-2.12 (m, 2H), 1.54 (s, 6H), 1.36 (d, J=6.1 Hz, 6H), 1.21 (d, J=6.1 Hz, 6H), 0.82 (s, 9H), −0.08 (s, 6H).

Synthesis of Diisopropyl (4-(4-((tert-butyldimethylsilyl)oxy)-2-methylbutan-2-yl)-3-hydroxy-5-methylphenyl)phosphonate (57D): To a solution of Pd/C (0.551 mmol, 10 wt. % loading) in EtOAc (60.0 mL) was added 57C (5.51 mmol) under N$_2$. The mixture was stirred at 25° C. for 12 hours under H$_2$ (15 psi). The reaction was filtered and concentrated under reduced pressure to afford title compound 57D. $^1$H NMR (400 MHz, Chloroform-d) δ 9.24 (s, 1H), 7.60 (br d, J=15.1 Hz, 1H), 6.86 (br d, J=13.3 Hz, 1H), 4.73-4.60 (m, 2H), 3.50 (br t, J=7.3 Hz, 2H), 2.53 (s, 3H), 2.22 (br t, J=7.3

Hz, 2H), 1.56 (s, 6H), 1.37 (d, J=6.1 Hz, 6H), 1.22 (d, J=6.1 Hz, 6H), 0.83 (s, 9H), −0.05 (s, 6H).

Synthesis of Di-tert-butyl (2-(4-((tert-butyldimethylsilyl)oxy)-2-methylbutan-2-yl)-5-(diisopropoxyphosphoryl)-3-methylphenyl) phosphate (57E): To a solution of 57D (2.75 mmol) in DMF (15.0 mL) was added di-tert-butyl diisopropylphosphoramidite (8.26 mmol) followed by 1H-tetrazole (9.63 mmol). The solution was heated at 50° C. for 2 hours. H₂O₂ (11.0 mmol, 30 wt. % in water) was added at 0° C., and the reaction was stirred for 1 hour at 0° C. The reaction was diluted with water (20 mL) and extracted with EtOAc (20 mL). The combined organic layers were washed with 10 ml 5% LiCl (aq), then 10 mL sat. sodium thiosulfate (aq), dried over MgSO₄, filtered and concentrated under reduced pressure. The residue was purified by RP chromatography to yield the title compound 57E. ¹H NMR (400 MHz, Chloroform-d) δ 7.73 (d, J=14.4 Hz, 1H), 7.36 (d, J=13.6 Hz, 1H), 4.75-4.64 (m, 2H), 3.47 (t, J=7.2 Hz, 2H), 2.59 (s, 3H), 2.14 (t, J=7.3 Hz, 2H), 1.57 (s, 6H), 1.50 (s, 18H), 1.36 (d, J=6.1 Hz, 6H), 1.27-1.25 (m, 6H), 0.83 (s, 9H), −0.06 (s, 6H).

Synthesis of Di-tert-butyl (5-(diisopropoxyphosphoryl)-2-(4-hydroxy-2-methylbutan-2-yl)-3-methylphenyl) phosphate (57F): To a solution of 57E (1.81 mmol) in THF (15.0 mL) was added TBAF (3.61 mmol, 1.0 M in THF) at 0° C. The mixture was stirred at 20° C. for 12 hours. The reaction was filtered and concentrated under reduced pressure. The residue was purified by RP chromatography to yield the title compound 57F. ¹H NMR (400 MHz, Methanol-d₄) δ 7.71 (d, J=14.3 Hz, 1H), 7.33 (d, J=13.9 Hz, 1H), 4.73-4.61 (m, 2H), 3.44-3.36 (m, 2H), 2.64 (s, 3H), 2.23-2.15 (m, 2H), 1.61 (s, 6H), 1.53 (s, 18H), 1.36 (d, J=6.2 Hz, 6H), 1.27 (d, J=6.2 Hz, 6H).

Synthesis of Di-tert-butyl (5-(diisopropoxyphosphoryl)-3-methyl-2-(2-methyl-4-oxobutan-2-yl)phenyl) phosphate (57G): To a solution of 57F (0.234 mmol) in DCM (5.0 mL) at 0° C. was added Dess-Martin periodinane (0.351 mmol). The reaction was gradually warmed to RT and was stirred for 18 hours. The reaction was quenched with sat. sodium thiosulfate (aq) and extracted with DCM (3×). The combined organic layers were washed with brine, dried over MgSO₄, filtered and concentrated under reduced pressure to yield title compound 57G which was used without further purification. MS (m/z) 570.96 [M+Na]⁺.

Synthesis of 3-(2-((Di-tert-butoxyphosphoryl)oxy) (diisopropoxyphosphoryl)-6-methylphenyl)-3-methylbutanoic acid (5711): To a solution of 57G (0.089 mmol), potassium dihydrogen phosphate (0.071 mmol) and hydrogen peroxide (0.267 mmol, 30 wt. % in water) in ACN/water (1:1, 5.0 mL) at 0° C. was added sodium chlorite (0.356 mmol). The reaction was gradually warmed up to RT and stirred for 1 hour. The reaction was quenched with sat. sodium sulfite (aq) and extracted with EtOAc (3×). The combined organic layers were washed with brine, dried over MgSO₄, filtered and concentrated under reduced pressure to yield title compound 5711 which was used without further purification. MS (m/z) 563.06 [M−H]⁻.

Synthesis of Di-tert-butyl (2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-5-(diisopropoxyphosphoryl)-3-methylphenyl) phosphate (57I): To a solution of crude 5711 (0.257 mmol) in ACN (3.0 mL) was added N-methylimidazole (0.899 mmol), Intermediate 5E (0.295 mmol) and TCFH (0.257 mmol). The reaction was stirred at RT for 18 hours. The reaction was quenched with sat. NH₄C₁ (aq) and extracted with EtOAc (3×). The combined organic layers were washed with brine, dried over MgSO₄, filtered and concentrated under reduced pressure. The crude material was purified by silica gel chromatography. Fractions containing title compound were pooled and concentrated to afford an atropisomeric mixture of title compound 571. MS (m/z) 1512.27 [M−H]⁺.

Synthesis of (4-(4-(N-(4-Chloro-7-(2-((S)-1-(2-((3bS,4aR)-5,5-difluoro-3-(trifluoromethyl)-3b,4,4a,5-tetrahydro-111-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-methyl-5-(phosphonooxy)phenyl)phosphonic acid (57): A flask charged with 57I (0.212 mmol), sodium iodide (0.021 mmol) and bromotrimethylsilane (0.170 mmol) in DCM (5.0 mL) was heated under nitrogen at 45° C. for 5 hours. The reaction was concentrated and the crude product was purified by RP chromatography (40-100% ACN/water with 0.1% TFA). Fractions containing the product were pooled and lyophilized to afford an atropisomeric mixture of title compound 57. ¹H NMR (400 MHz, DMSO-d₆) δ 9.18 (d), 9.01 (d), 8.77 (d), 8.01-7.95 (m), 7.92 (d), 7.87 (d), 7.84-7.78 (m), 7.75 (d), 7.62 (d), 7.46 (d), 7.40-6.34 (dd), 7.31-7.27 (dd), 7.14-6.95 (m), 6.89 (d), 6.62 (d), 6.51-6.44 (m), 6.42-6.35 (m), 5.00 (d), 4.90-4.56 (m), 4.27-4.16 (m), 4.08-3.94 (m), 3.52 (d), 3.47 (d), 3.27 (d), 3.17-3.07 (m), 3.07-2.71 (m), 2.70-2.40 (m), 2.30 (s), 1.74 (dd), 1.52-1.32 (m), 1.30-1.07 (m), 0.98 (bs). ¹⁹F NMR (377 MHz, DMSO-d₆) δ−60.75, −60.81, −60.86, −60.97, −69.50--69.65 (m), −70.08 (t), −79.80 (d), −80.36--80.53, −80.88 (d), −80.99 (d), −81.10 (d), −101.96 (bs), −102.64 (bs), −103.24 (d), −103.81 (d), −103.92 (d), −110.56--110.76 (m), −110.80--110.95 (m). ³¹P NMR (162 MHz, DMSO-d₆) δ 12.14, 12.06, 11.98, −7.05, −7.08, −7.14. MS (m/z) 1316.41 [M−H]⁺.

Example 58

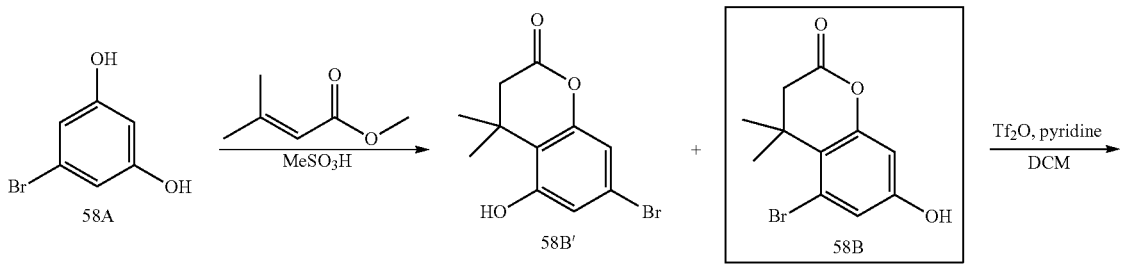

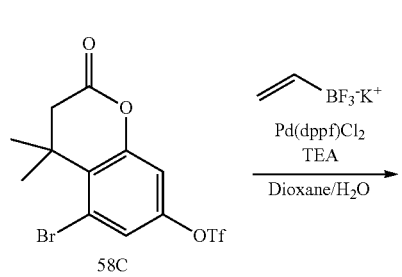
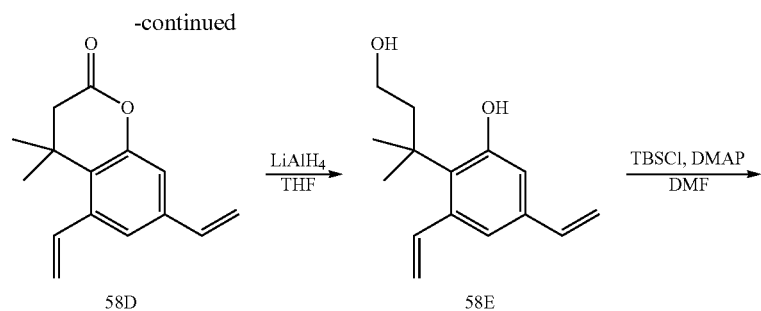
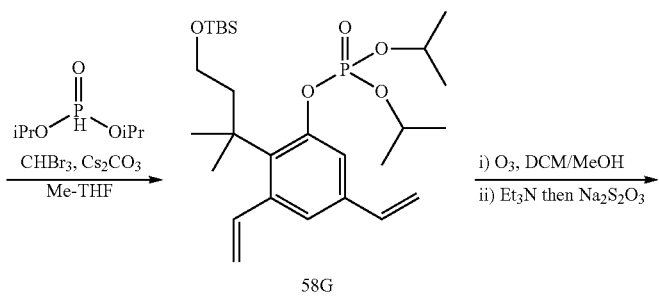
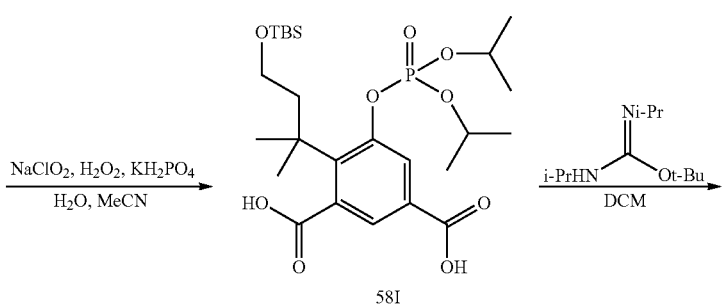
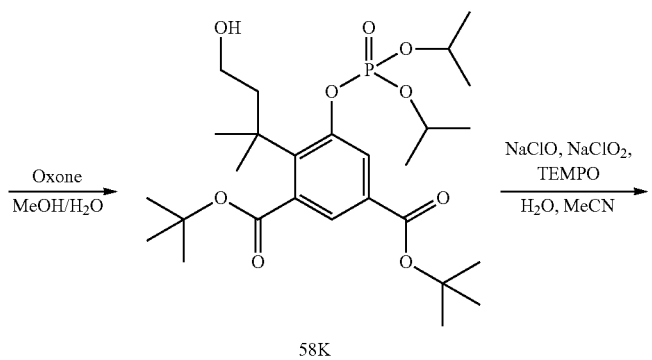

-continued

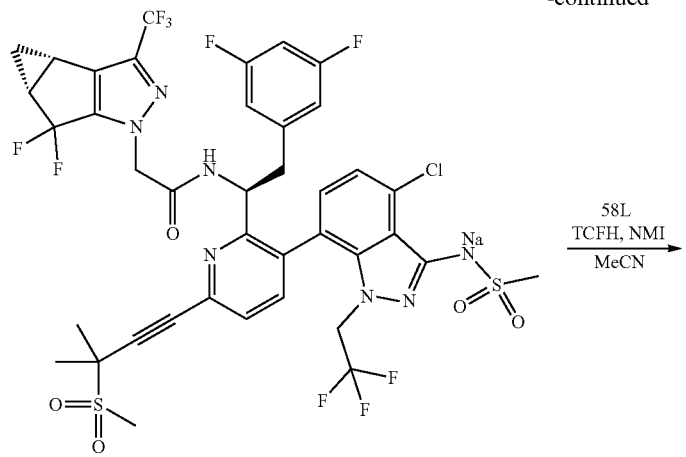

Intermediate 5E

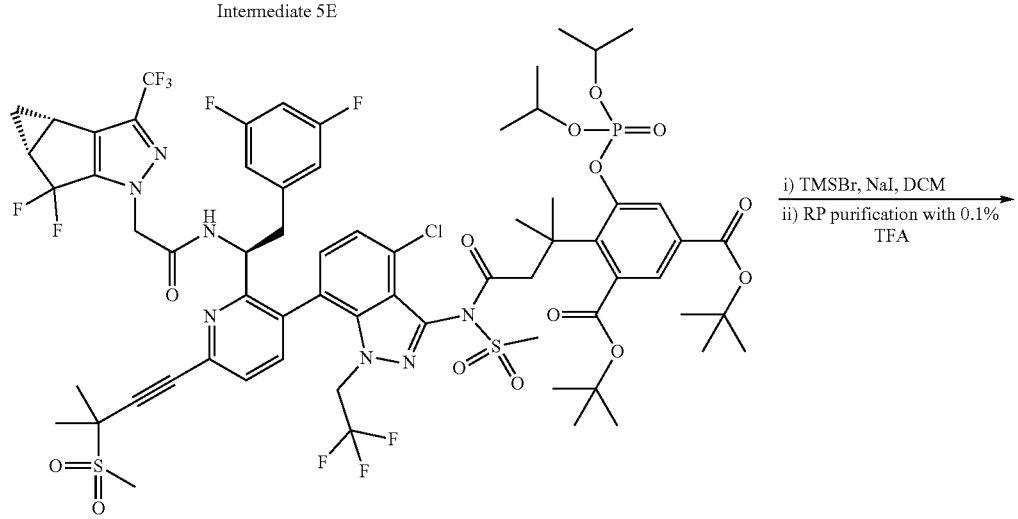

58M i) TMSBr, NaI, DCM
ii) RP purification with 0.1% TFA

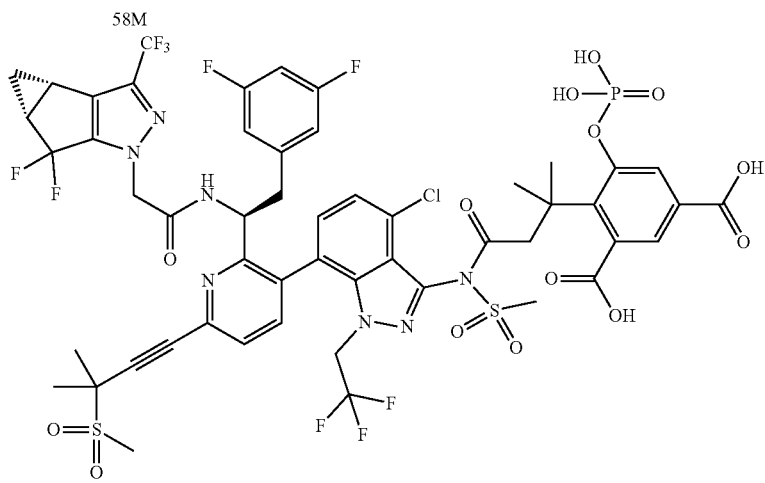

58

Synthesis of 5-Bromo-7-hydroxy-4,4-dimethylchroman-2-one (58B): A mixture of 5-bromobenzene-1,3-diol (5.29 mmol), methyl 3-methylbut-2-enoate (5.80 mmol) and MsOH (11.1 mmol) was stirred at 80° C. for 12 hours. The reaction mixture was poured into sat. NaHCO$_3$(aq) (10 mL) and extracted with EtOAc (3×). The combined organic layers were washed with brine, dried over anhydrous Na$_2$SO$_4$, filtered and concentrated under reduced pressure. The residue was purified by silica gel chromatography to yield 7-bromo-5-hydroxy-4,4-dimethyl-chroman-2-one (58B') and title compound 58B. 58B': $^1$H NMR (400 MHz, DMSO-d$_6$) δ 10.30 (s, 1H), 6.78 (d, J=2.1 Hz, 1H), 6.73 (d, J=2.0 Hz, 1H), 2.68 (s, 2H), 1.34 (s, 6H). 58B: $^1$H NMR (400 MHz, DMSO-d$_6$) δ 10.14 (s, 1H), 6.84 (d, J=2.6 Hz, 1H), 6.47 (d, J=2.4 Hz, 1H), 2.74 (s, 2H), 1.43 (s, 6H).

Synthesis of 5-Bromo-4,4-dimethyl-2-oxochroman-7-yl trifluoromethanesulfonate (58C): To a solution of 58B (2.58 mmol) in DCM (10.0 mL) was added pyridine (5.16 mmol) and Tf$_2$O (2.58 mmol) at 0° C. The mixture was stirred at RT for 12 hours. The reaction mixture was poured into water (10 mL) and extracted with DCM (3×). The combined organic layers were dried over anhydrous Na$_2$SO$_4$, filtered and concentrated under reduced pressure. The residue was purified by silica gel chromatography to yield title compound 58C. $^1$H NMR (400 MHz, Chloroform-d) δ 7.35 (d, J=2.6 Hz, 1H), 7.00 (d, J=2.6 Hz, 1H), 2.70 (s, 2H), 1.61 (s, 6H).

Synthesis of 4,4-Dimethyl-5,7-divinylchroman-2-one (58D): To a mixture of 58C (37.2 mmol), potassium trifluoro (vinyl)borate (112 mmol) and Pd(dppf)Cl$_2$ (3.72 mmol) was added 1,4-dioxane (200 mL), n-BuOH (100 mL) and TEA (112 mmol) under N$_2$. The mixture was stirred at 80° C. for 12 hours under N$_2$. The reaction was concentrated under reduced pressure, diluted with water (300 mL) and extracted with EtOAc (3×). The combined organic layers were washed with brine (300 mL×2), dried over anhydrous Na$_2$SO$_4$, filtered and concentrated under reduced pressure. The residue was purified by silica gel chromatography to yield title compound 58D. $^1$H NMR (400 MHz, Chloroform-d) δ 7.15-7.05 (m, 3H), 6.66 (dd, J=10.9, 17.6 Hz, 1H), 5.80-5.73 (m, 1H), 5.50 (dd, J=1.4, 17.2 Hz, 1H), 5.37-5.29 (m, 2H), 2.60 (s, 2H), 1.45 (s, 6H).

Synthesis of 2-(4-Hydroxy-2-methylbutan-2-yl)-3,5-divinylphenol (58E): To a solution of LAH (43.8 mmol) in THF (30.0 mL) was added a solution of 58D (21.9 mmol) in THF (20.0 mL) at 0° C. The mixture was stirred at 0° C. for 2 hours. MgSO$_4$ aqueous solution (1.7 mL) and MgSO$_4$ (3 g) were added to the mixture. The reaction mixture was filtered and the filter cake was washed with THF (50 mL×3). The filtrate was dried over Na$_2$SO$_4$ and concentrated under reduced pressure. The residue was purified by silica gel chromatography to yield title compound 58E. $^1$H NMR (400 MHz, Chloroform-d) δ=7.22 (dd, J=10.8, 17.1 Hz, 1H), 6.79 (s, 1H), 6.68 (d, J=1.4 Hz, 1H), 6.56 (dd, J=10.9, 17.6 Hz, 1H), 6.36 (bs, 1H), 5.66 (d, J=17.5 Hz, 1H), 5.30-5.14 (m, 3H), 3.61 (br t, J=7.2 Hz, 2H), 2.24 (br t, J=7.2 Hz, 2H), 1.53 (s, 6H).

Synthesis of 2-(4-((Tert-butyldimethylsilyl)oxy)-2-methylbutan-2-yl)-3,5-divinylphenol (58F): To a solution of 58E (7.75 mmol) in DCM (20.0 mL) was added DMAP (12.4 mmol) and a solution of TBSCl (9.30 mmol) in DCM (10.0 mL) at 0° C. The mixture was stirred at 0° C. for 2 hours. The reaction was concentrated under reduced pressure to give a residue. The residue was purified by silica gel chromatography to yield the title compound 58F. $^1$H NMR (400 MHz, Chloroform-d) δ 7.18 (dd, J=10.8, 17.1 Hz, 1H), 6.83 (d, J=1.6 Hz, 1H), 6.76 (d, J=1.9 Hz, 1H), 6.59 (dd, J=10.8, 17.6 Hz, 1H), 6.14 (s, 1H), 5.69 (d, J=17.5 Hz, 1H), 5.33-5.13 (m, 3H), 3.62 (t, J=6.8 Hz, 2H), 2.12 (t, J=6.8 Hz, 2H), 1.54 (s, 6H), 0.88 (s, 9H), 0.03 (s, 6H). MS (ESI): m/z=345.3 [M−H]$^+$.

Synthesis of 2-(4-((Tert-butyldimethylsilyl)oxy)-2-methylbutan-2-yl)-3,5-divinylphenyl diisopropyl phosphate (58G): A vial charged with 58F (0.271 mmol) and 2-MeTHF (1.0 mL) under nitrogen was cooled to 0° C. Diisopropyl phosphite (0.363 mmol) and bromoform (0.369 mmol) were added. The solution was stirred for 5 minutes, cesium carbonate (0.393 mmol) was added in one portion and the vial was sealed. The mixture was heated at 60° C. for 20 hours. The reaction was quenched with sat. NH$_4$C$_1$ (aq) and extracted with EtOAc (3×). The combined organic layers were washed with brine, dried over MgSO$_4$, filtered and concentrated. The crude material was purified by silica gel chromatography to afford compound 58G. MS (m/z) 510.90 [M+H]$^+$.

Synthesis of 2-(4-((Tert-butyldimethylsilyl)oxy)-2-methylbutan-2-yl)-3,5-diformylphenyl diisopropyl phosphate (58II): To a solution of 58G (0.564 mmol) in DCM/MeOH (3:1, 20.0 mL) was carefully bubbled 03 (g) at −78° C. When full conversion was observed, the reaction was sparged with 02 (g) for 5 mins, after which Et$_3$N (4.51 mmol) was carefully added. The resulting mixture was warmed to RT, then 1.0 mL of saturated Na$_2$S$_2$O$_3$ (aq) was added. The reaction was diluted with water and extracted with DCM (2×). The combined organic layers were washed with brine, dried over MgSO$_4$, filtered and concentrated under reduced pressure. The residue was purified by silica gel chromatography to yield the title compound 58II. MS (m/z) 514.97 [M+H]$^+$.

Synthesis of 4-(4-((Tert-butyldimethylsilyl)oxy)-2-methylbutan-2-yl) ((diisopropoxyphosphoryl)oxy)isophthalic acid (58I): To a solution of 58II (0.563 mmol), potassium dihydrogen phosphate (0.451 mmol) and hydrogen peroxide (1.69 mmol, 30 wt. % in water) in ACN/water (1:1, 6.0 mL) at 0° C. was added sodium chlorite (2.25 mmol). The reaction was gradually warmed up to RT and stirred for 2 hours. The reaction was quenched with sat. sodium sulfite (aq), adjusted to pH 2 with 1N HCl (aq) and extracted with DCM (2×). The combined organic layers were dried over MgSO$_4$, filtered and concentrated under reduced pressure to yield title compound 58I which was used without further purification. MS (m/z) 545.29 [M−H]$^−$.

Synthesis of Di-tert-butyl 4-(4-((tert-butyldimethylsilyl)oxy)-2-methylbutan-2-yl)-5-((diisopropoxyphosphoryl)oxy)isophthalate (58J): To a solution of 58I (0.527 mmol) in DCM (6.0 mL) was slowly added 2-tert-butyl-1,3-diisopropylurea (5.27 mmol). The resulting mixture was stirred at room temperature for 18 hours. The reaction mixture was diluted with dichloromethane and filtered over Celite®. The filtrate was concentrated and used without further purification to yield title compound 58J. MS (m/z) 602.98 [(M−tBu)+2H]$^+$.

Synthesis of Di-tert-butyl 5-((diisopropoxyphosphoryl)oxy)-4-(4-hydroxy-2-methylbutan-2-yl)isophthalate (58K): A flask charged with 58J (0.527 mmol), MeOH (2.5 mL) and water (2.5 mL) was cooled to 0° C. Oxone® (0.527 mmol) was added, the ice bath was removed and the reaction was stirred at RT for 1 hour. The reaction was quenched with sat. sodium sulfite (aq), concentrated, diluted with water and extracted with EtOAc (3×). The combined organic layers were washed with brine, dried over MgSO$_4$, filtered and concentrated. The crude material was purified by silica gel chromatography to afford title compound 58K. MS (m/z) 567.03 [M+Na]$^+$.

Synthesis of 3-(2,4-Bis(tert-butoxycarbonyl)-6-((diisopropoxyphosphoryl)oxy)phenyl)-3-methylbutanoic acid (58L): To a solution of 58K (0.465 mmol) in ACN/water (1:1, 8.0 mL) was added TEMPO (0.023 mmol), potassium dihydrogen phosphate (0.232 mmol) and disodium hydrogen phosphate (0.232 mmol). The solution was cooled to 0° C. Sodium chlorite (0.697 mmol) was added, followed by sodium hypochlorite (8.25% NaOCl (aq), 0.567 mmol). The ice bath was removed and the reaction was stirred for 1 hour. The reaction was diluted with water and quenched with sat. sodium sulfite (aq) and extracted with EtOAc (3×). The combined organic layers were washed with brine, dried over MgSO$_4$, filtered and concentrated under reduced pressure to yield title compound 58L which was used without further purification. MS (m/z) 580.92 [M+Na]$^+$.

Synthesis of di-tert-butyl 4-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methyl) (sulfonamido)

methyl-4-oxobutan-2-yl)-5-(((diisopropoxyphosphoryl)oxy) isophthalate (58M): To a solution of crude 58L (0.325 mmol) in ACN (10.0 mL) was added N-methylimidazole (1.14 mmol), Intermediate 5E (0.260 mmol) and TCFH (0.325 mmol). The reaction was stirred at RT for 18 hours. The reaction was quenched with sat. $NH_4C_1$ (aq) and extracted with EtOAc (3×). The combined organic layers were washed with brine, dried over $MgSO_4$, filtered and concentrated under reduced pressure. The crude material was purified by silica gel chromatography. Fractions containing title compound were pooled and concentrated to afford an atropisomeric mixture of title compound 58M. MS (m/z) 1506.31 $[M-H]^+$.

Synthesis of 4-(4-(N-(4-Chloro-7-(2-((S)-1-(2-((3bS, 4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-5-(phosphonooxy)isophthalic acid (58): A flask charged with 58M (0.325 mmol), sodium iodide (0.033 mmol) and bromotrimethylsilane (1.95 mmol) in DCM (20.0 mL) was heated under nitrogen at 45° C. for 8 hours. The reaction was concentrated and the crude product was purified twice by RP chromatography (40-100% ACN/water with 0.1% TFA). tBu phosphate deprotection was observed during fraction concentration under reduced pressure. After the second purification, fractions containing the desired product were pooled and lyophilized to afford an atropisomeric mixture of title compound 58. $^1$H NMR (400 MHz, DMSO-$d_6$) δ 13.05 (bs), 9.18 (t), 9.00 (d), 8.83 (d), 8.01 (d), 7.96 (d), 7.85 (d), 7.82-7.71 (m), 7.47-7.39 (m), 7.39-7.32 (m), 7.31-7.25 (m), 7.06-6.96 (m), 6.62 (d), 6.55 (d), 6.52-6.43 (m), 4.95 (d), 4.88-4.47 (m), 4.29-4.14 (m), 4.09-3.92 (m), 3.51 (d), 3.46 (d), 3.27 (d), 3.15 2.87 (m), 2.63-2.46 (m), 1.77-1.70 (m), 1.54-1.32 (m), 1.32-1.06 (m), 1.06-0.90 (m). $^{19}$F NMR (377 MHz, DMSO-$d_6$) δ −60.77, −60.81, −60.86, −60.96, −69.43 (t), −69.50 (t), −69.57 (t), −69.88 (t), −79.81 (d), −80.19 (d), −80.37 (bs), −80.49 (d), −80.87 (d), −81.07 (bs), −101.78 (bs), −102.19-−102.79 (m), −103.12 (d), −103.26 (d), −103.39 (d), −103.79 (d), −103.96 (d), −110.51 (t), −110.62 (t), −110.71 (t), −110.88 (t). $^{31}$P NMR (162 MHz, DMSO-$d_6$) δ−6.75, −6.80, −6.93. MS (m/z) 1310.83 $[M-H]^+$.

Example 59

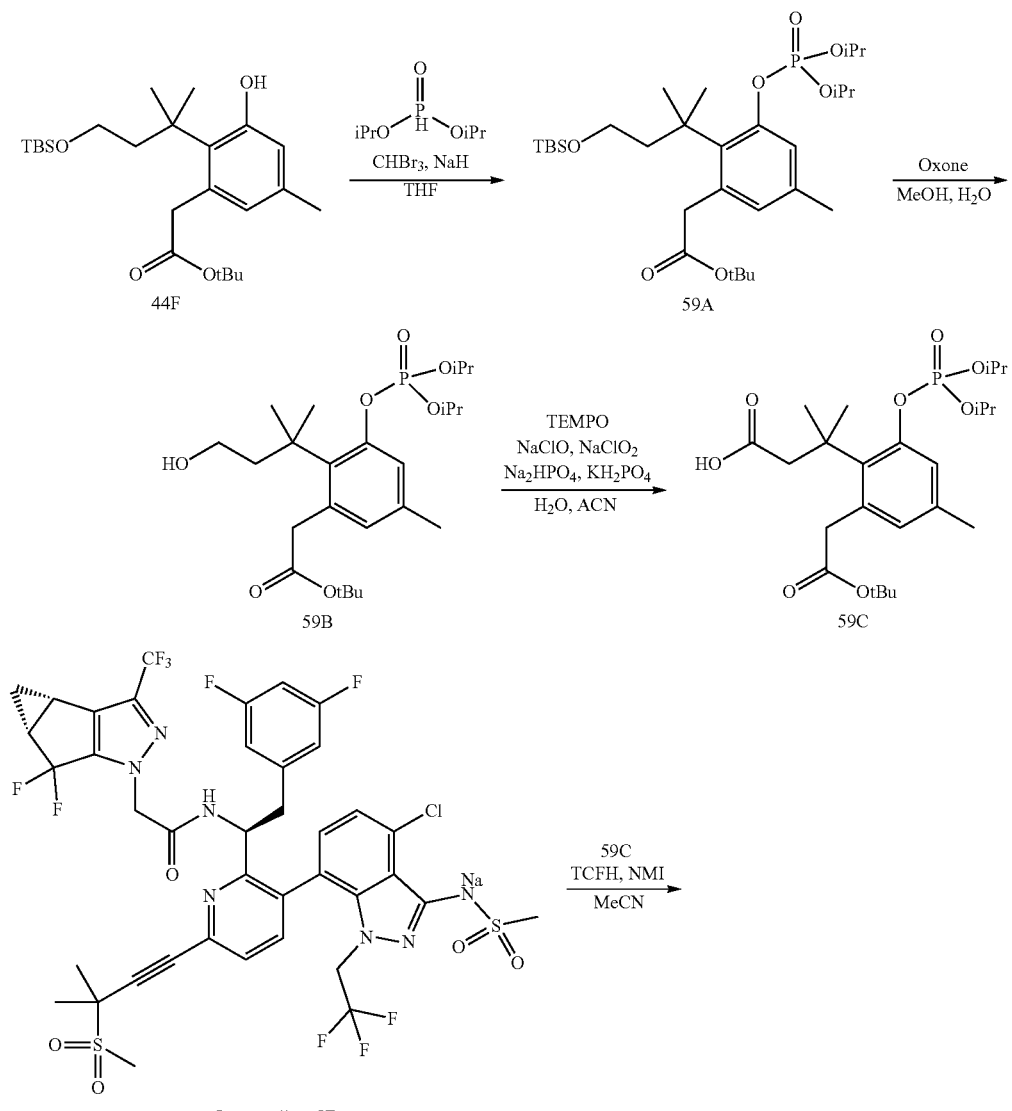

Intermediate 5E

-continued
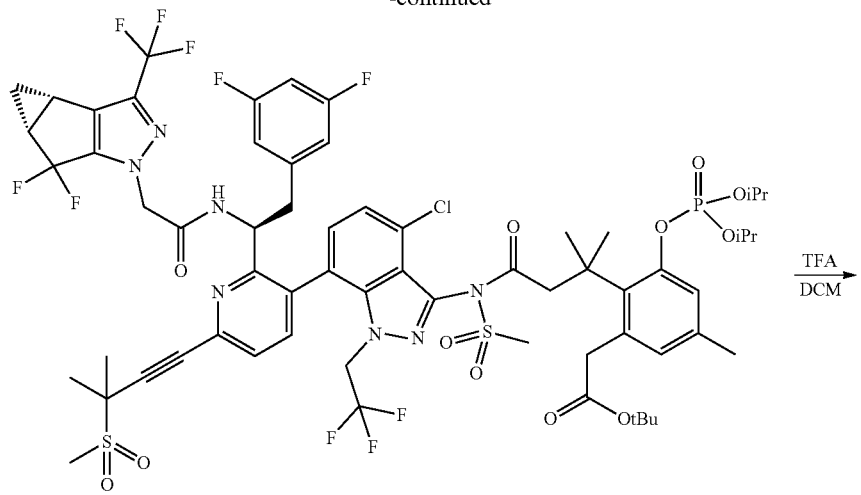
59D
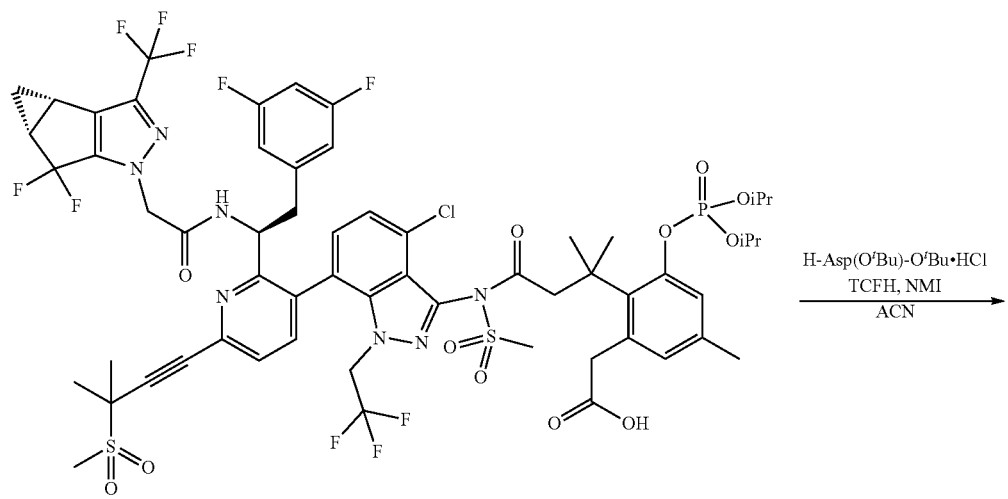
59E
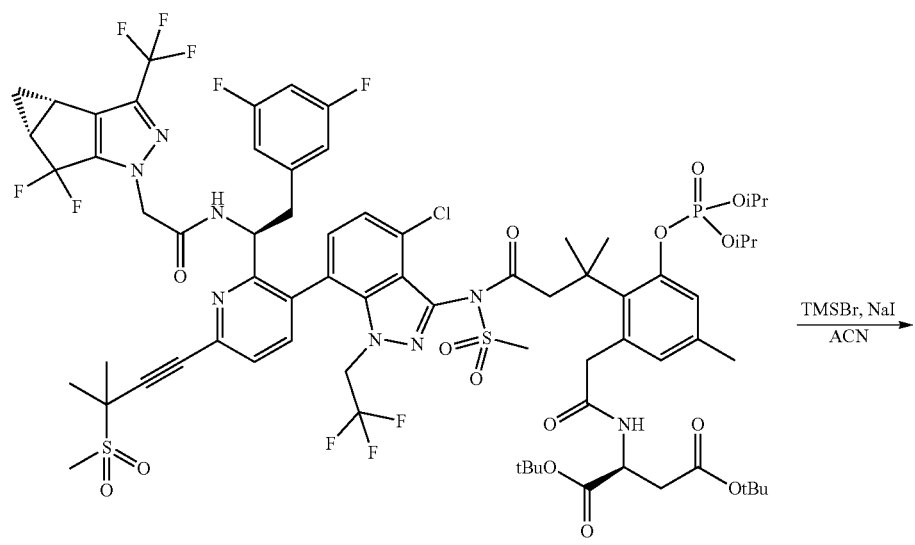
59F

-continued

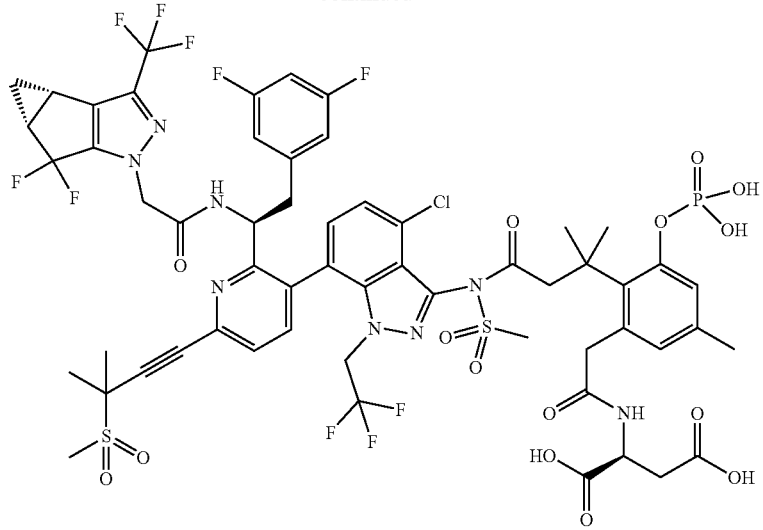

59

Synthesis of tert-butyl 2-(2-(4-((tert-butyldimethylsilyl)oxy)-2-methylbutan yl)-3-((diisopropoxyphosphoryl)oxy)-5-methylphenyl)acetate (59A): To a two-neck flask under argon and chilled on an ice bath was added 44F (1.01 mmol), THF (50.0 mL), diisopropyl phosphite (1.36 mmol) and bromoform (1.36 mmol). Sodium hydride (60% dispersion in mineral oil, 1.31 mmol) was added and the reaction was stirred at room temperature. Upon completion, the reaction mixture was diluted with DCM (150 mL), washed with water (1×50 mL), brine, dried over $Na_2SO_4$, concentrated and purified by silica gel chromatography. Fractions containing the product were pooled and concentrated to yield title compound 59A. MS (m/z) 587.40 $[M+H]^+$.

Synthesis of tert-butyl 2-(3-((diisopropoxyphosphoryl)oxy)-2-(4-hydroxy-2-methylbutan-2-yl)-5-methylphenyl)acetate (59B): To an ice-cold solution of 59A (0.256 mmol) in $MeOH/H_2O$ (1:1, 1.3 mL) was added Oxone® (0.511 mmol). The reaction was stirred at room temperature. Upon completion, the reaction mixture was quenched with sat. $Na_2SO_3$ (aq) (1 mL) and stirred for 15 minutes. The reaction was filtered and the filtrate was concentrated. The remaining aqueous solution was extracted with EtOAc (5×10 mL). The organic fraction was collected, washed with brine, dried over $Na_2SO_4$, concentrated, and purified by silica gel chromatography. Fractions containing the product were pooled and concentrated to yield title compound 59B. MS (m/z) 473.30 $[M+H]^+$.

Synthesis of 3-(2-(2-(tert-butoxy)-2-oxoethyl)-6-((diisopropoxyphosphoryl)oxy)-4-methylphenyl)-3-methylbutanoic acid (59C): To an ice-cold solution of 59B (0.635 mmol), dipotassium hydrogen phosphate (0.317 mmol), potassium dihydrogen phosphate (0.317 mmol) and TEMPO (0.032 mmol) in $MeCN/H_2O$ (1:1, 5.0 mL) was added sodium hypochlorite (8.25% $NaOCl_{(aq)}$, 0.775 mmol) and sodium chlorite (0.952 mmol). The reaction was stirred at room temperature. Upon completion, the reaction was diluted with water (10 mL), quenched with sat. $Na_2SO_3$ (aq) (1 mL), acidified to pH 2 with 1N HCl and extracted with EtOAc (3×20 mL). The organic fraction was collected, washed with brine, dried over $Na_2SO_4$, concentrated and purified by silica gel chromatography. Fractions containing the product were pooled and concentrated to yield title compound 59C which was used without further purification. MS (m/z) 509.20 $[M+Na]^+$.

Synthesis of tert-butyl 2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)methyl-4-oxobutan-2-yl)-3-((diisopropoxyphosphoryl)oxy)-5-methylphenyl)acetate (59D): To a flask was added 59C (0.674 mmol), Intermediate 5E (0.640 mmol), MeCN (7.0 mL), 1-methyl-1H-imidazole (2.36 mmol) and TCFH (0.674 mmol). The reaction was stirred at room temperature. Upon completion, the reaction was diluted with sat. $NH_4C_1$ (aq) (7 mL) and the aqueous layer was extracted with EtOAc (2×10 mL). The organic fraction was dried over $Na_2SO_4$, concentrated and purified by silica gel chromatography. Fractions containing the product were pooled and concentrated to yield title compound 59D which was used without further purification. MS (m/z) 1436.30 $[M+H]^+$.

Synthesis of 2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-((diisopropoxyphosphoryl)oxy)-5-methylphenyl)acetic acid (59E): To a flask was added 59D (0.007 mmol), DCM (0.35 mL) and TFA (6.96 mmol). The reaction was stirred at room temperature for 15 minutes. Upon completion, the reaction was concentrated under reduced pressure, reconstituted with acetonitrile, frozen in an ice bath at −78° C., and lyophilized to yield title compound 59E. MS (m/z) 1380.30 $[M+H]^+$.

Synthesis of di-tert-butyl (2-(2-(4-(N-(4-chloro-7-(2-((S)-1-(2-03bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-((diisopropoxyphosphoryl)

oxy)-5-methylphenyl)acetyl)-L-aspartate (59F): To a flask was added 59E (0.072 mmol), di-tert-butyl L-aspartate hydrochloride (0.109 mmol), MeCN (0.362 mL), NMI (0.362 mmol), and TCFH (0.087 mmol). The reaction was stirred at room temperature for 15 minutes. Upon completion, the reaction was diluted with EtOAc and washed with 0.1 N HCl. The organic fraction was washed with brine, dried over $Na_2SO_4$, concentrated and purified by silica gel chromatography. Fractions containing the product were pooled and concentrated to yield intermediate 59F. MS (m/z) 1605.45 [M–H]$^+$.

Synthesis of (2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol yl)acetamido)-2-(3,5-difluorophenyl)ethyl)-6-(3-methyl-3-(methylsulfonyl)but-1-yn yl)pyridin-3-yl)-1-(2,2,2-trifluoroethyl)-1H-indazol-3-yl)methylsulfonamido)-2-methyl oxobutan-2-yl)-5-methyl-3-(phosphonooxy)phenyl) acetyl)-L-aspartic acid (59): A flask charged with 59F (1.40 mmol), sodium iodide (2.80 mmol), MeCN (14.0 mL), and bromotrimethylsilane (14.0 mmol) was stirred at 40° C. for 2 hours. Upon completion, the reaction was brought to room temperature and quenched with a few drops of water. The solution was directly purified by reverse phase HPLC. Fractions containing the product were pooled and lyophilized to yield title compound 59 as a mixture of atropisomers. $^1$H NMR (400 MHz, DMSO-$d_6$) δ 12.29 (bs), 9.16 (d), 9.01 (d), 8.92 (d), 8.32-8.10 (m), 7.99 (d), 7.93 (d), 7.87 (d), 7.84-7.70 (m), 7.43 (d), 7.39-7.31 (m), 7.31-7.24 (m), 7.12 (s), 7.07-6.96 (m), 6.92 (t), 6.69 (d), 6.65 (s), 6.57-6.41 (m), 5.30-4.97 (m), 4.95-4.58 (m), 4.58-4.46 (m), 4.46-4.38 (m), 4.37-4.28 (m), 4.28-3.94 (m), 3.93-2.86 (m), 2.81-2.39 (m), 2.16 (s), 1.74 (s), 1.47-1.28 (m), 1.22 (s), 1.06-0.93 (m) ppm. $^{19}$F NMR (376 MHz, DMSO-$d_6$) δ–60.79, –60.80, –60.85, –60.92, –69.34 (t), –69.45--69.68 (m), –69.85 (t), –79.81 (d), –79.96--80.27 (m), –80.48 (d), –80.65--80.92 (m), –102.29 (bs), –102.75--103.18 (m), –103.27 (d), –103.79 (d), –103.94 (d), –110.53 (t), –110.61 (t), –110.75 (t), –110.88 (t) ppm. $^{31}$P NMR (162 MHz, DMSO-$d_6$) δ–6.97, –6.99, –7.06, –7.27. MS (m/z) 1411.30 [M+H]$^+$.

Exmple 60

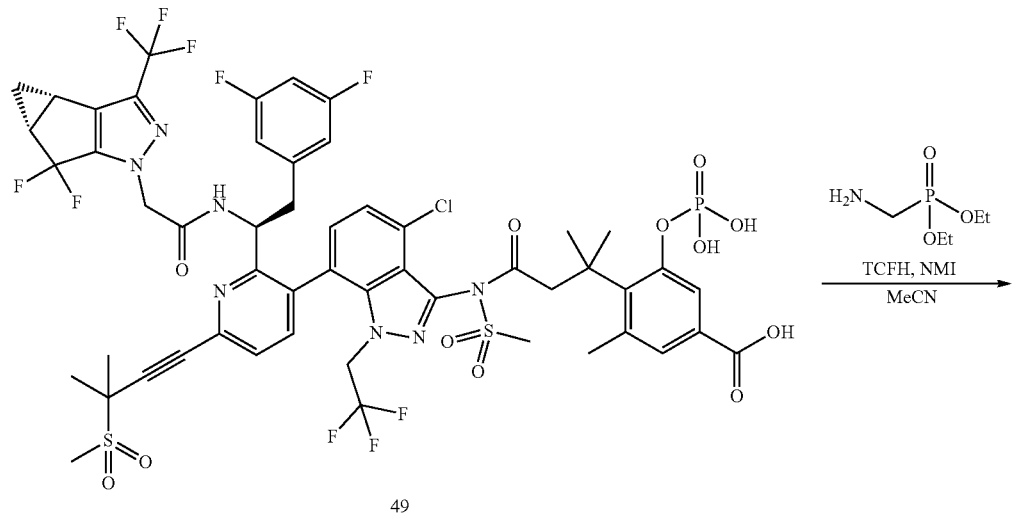

49

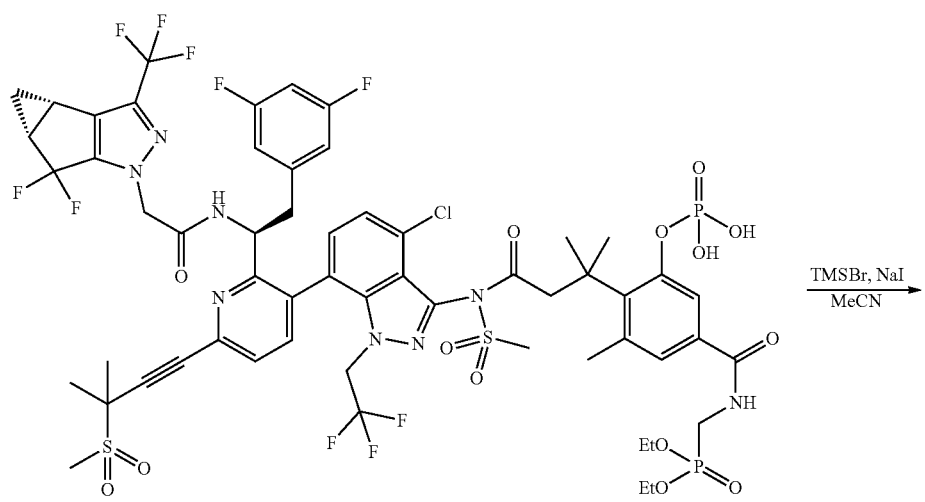

60A

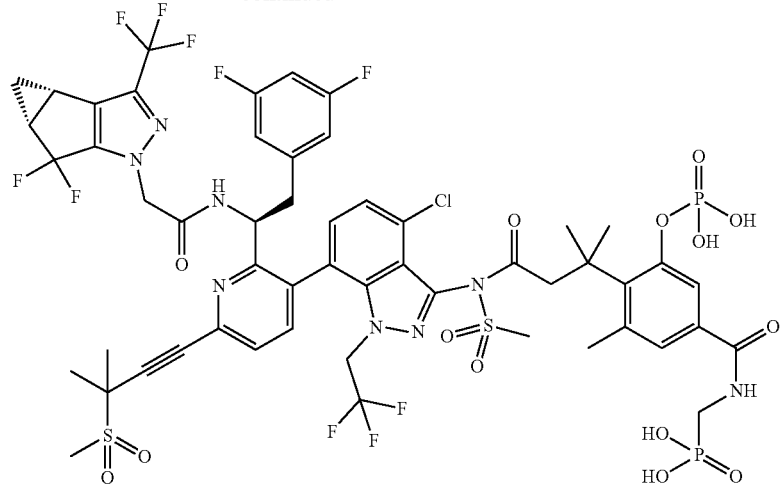

60

Synthesis of 2-(4-(N-(4-chloro-7-(2-((S)-1-(2-(((3bS, 4aR)-5,5-difluoro (trifluoromethyl)-3b,4,4a,5-tetrahydro-1H-cyclopropa[3,4]cyclopenta[1,2-c]pyrazol yl)acetamido)-2-(3,5-difluorophenyl)ethyl)-6-(3-methyl-3-(methylsulfonyl)but-1-yn yl)pyridin-3-yl)-1-(2,2,2-trifluoroethyl)-1H-indazol-3-yl)methylsulfonamido)-2-methyl oxobutan-2-yl)-5-(((diethoxyphosphoryl)methyl) carbamoyl)-3-methylphenyl dihydrogen phosphate (60A): To a vial was added 49 (0.078 mmol), diethyl (aminomethyl) phosphonate (0.156 mmol), MeCN (780 μL), NMI (0.195 mmol), and TCFH (0.094 mmol). The reaction was stirred at RT for 1 hour. Upon completion, the solution was directly purified by reverse phase HPLC. Fractions containing the product were pooled and lyophilized to yield title compound 60A as a mixture of atropisomers. MS (m/z) 1431.30 [M+H]+.

Synthesis of ((4-(4-(N-(4-chloro-7-(2-((S)-1-(2-(((3bS, 4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-methyl-5-(phosphonooxy) benzamido)methyl)phosphonic acid (60): To a vial was added 60A (0.045 mmol), sodium iodide (0.067 mmol), MeCN (450 μL) and bromotrimethylsilane (0.447 mmol). The reaction was stirred at 40° C. for 2 hours. Upon completion, the reaction was brought to room temperature and quenched with a few drops of water. The solution was directly purified by reverse phase HPLC. Fractions containing the product were pooled and lyophilized to yield title compound 60 as a mixture of atropisomers. $^1$H NMR (400 MHz, CD$_3$CN) δ 7.82 (d), 7.68 (d), 7.39-7.27 (m), 6.74 (t), 6.65 (d), 6.32 (d), 4.96-4.66 (m), 4.11-4.00 (m), 3.73 (s), 3.37 (s), 3.17 (d), 3.07 (s), 2.58 (s), 2.49 (s), 2.12-2.08 (m), 1.81-1.75 (m), 1.36 (dd), 1.09 (s), 1.04 (s). $^{19}$F NMR (376 MHz, CD$_3$CN) δ −62.51, −62.64, −71.27, −71.59 (t), −81.60, −82.28, −103.83, −104.52, −111.62, −112.06. MS (m/z) 1375.30 [M+H]+.

Example 61

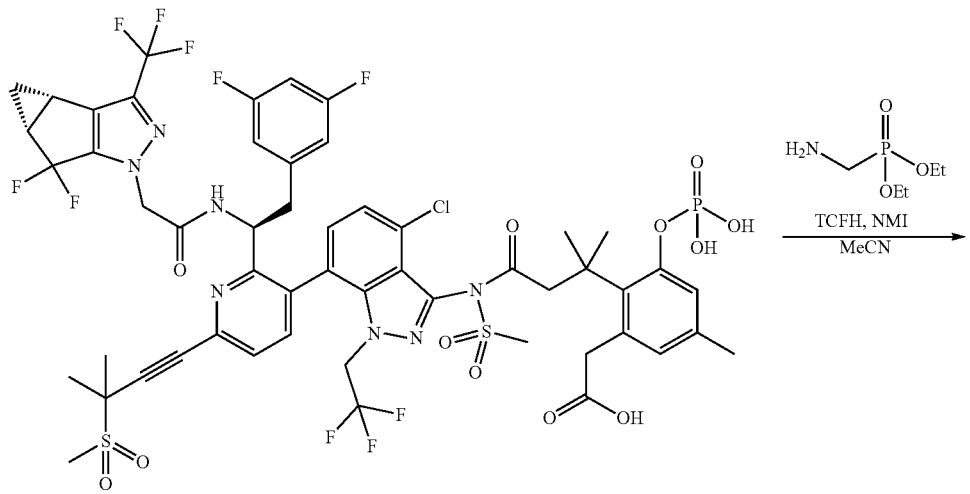

44

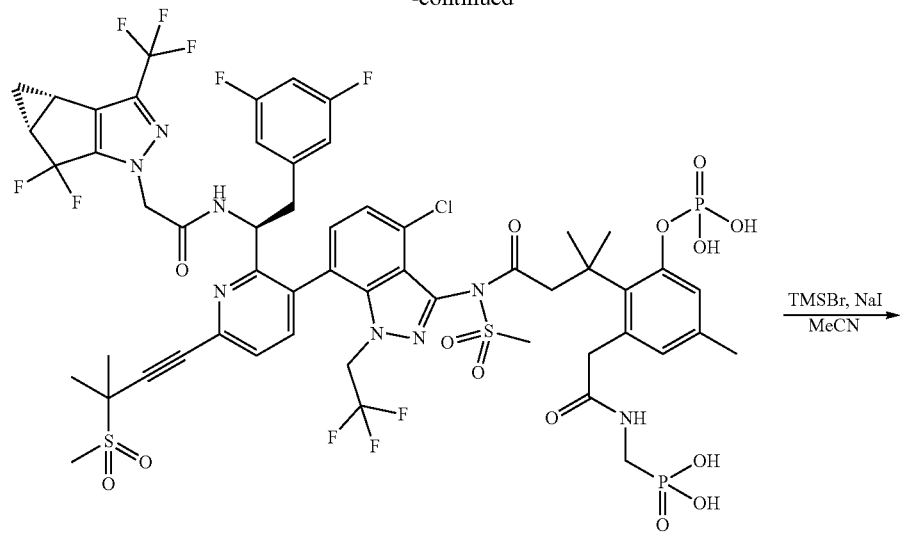

61A

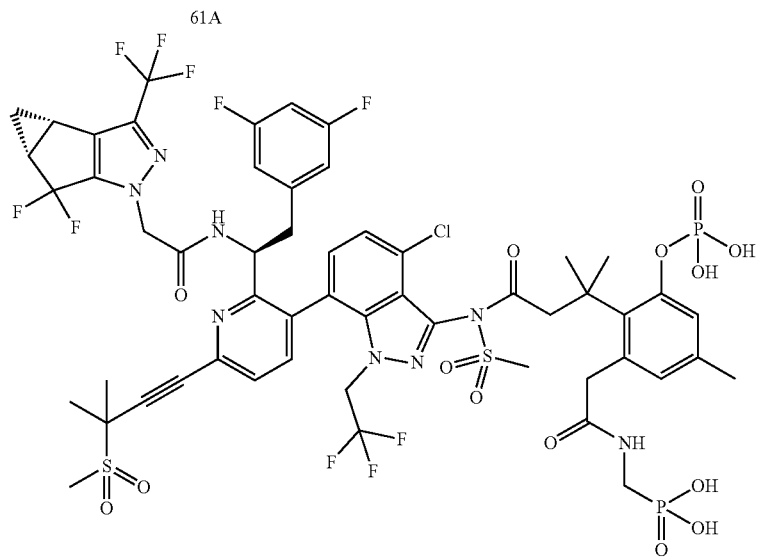

61

Synthesis of ((2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-5-methyl-3-(phosphonooxy)phenyl)acetamido)methyl)phosphonic acid (61A): To a vial was added 44 (0.066 mmol), diethyl (aminomethyl)phosphonate (0.131 mmol), MeCN (360 NMI (0.165 mmol), and TCFH (0.079 mmol). The reaction was stirred at room temperature for 1 hour. Upon completion, the solution was directly purified by reverse phase HPLC. Fractions containing the product were pooled and lyophilized to yield title compound 61A as a mixture of atropisomers. MS (m/z) 1445.30 [M+H]+.

Synthesis of ((2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-5-methyl-3-(phosphonooxy)phenyl)acetamido)methyl)phosphonic acid (61): To a vial was added 61A (0.031 mmol), sodium iodide (0.031 mmol), MeCN (500 and bromotrimethylsilane (0.311 mmol). The reaction was stirred at room temperature for 16 hours. Upon completion, the reaction was brought to room temperature and quenched with a few drops of water. The solution was directly purified by reverse phase HPLC. Fractions containing the product were pooled and lyophilized to yield title compound 61 as a mixture of atropisomers. $^1$H NMR (400 MHz, CD$_3$CN) δ 7.80 (d), 7.67 (d), 7.41-7.20 (m), 7.12 (s), 7.08 (s), 7.01 (d), 6.73 (d), 6.64-6.47 (m), 6.32 (t), 4.97-4.73 (m), 4.71 (s), 4.57 (s), 4.03 (dt), 3.76 (d), 3.63-3.28 (m), 3.19-3.13 (m), 3.03-2.89 (m), 2.73 (s), 2.50 (s), 2.14 (d), 1.88 (s), 1.78 (d), 1.47-1.26 (m), 1.11 (s), 1.04 (s). $^{19}$F NMR (376 MHz, CD$_3$CN) δ −62.38--−62.70 (m), −70.36--−72.10 (m), −81.90 (d), −103.54--−105.83 (m), −110.97--−112.50 (m). MS (m/z) 1389.30 [M+H]+.

Example 62
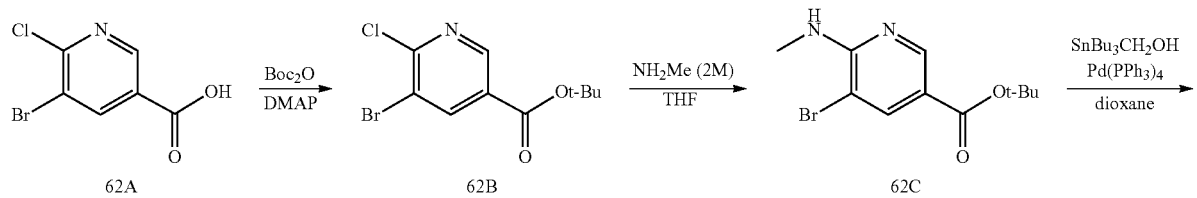
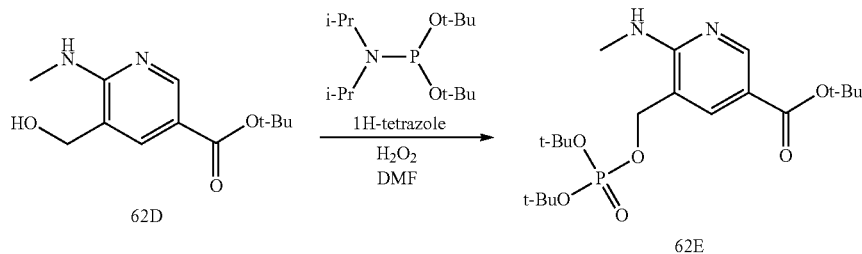
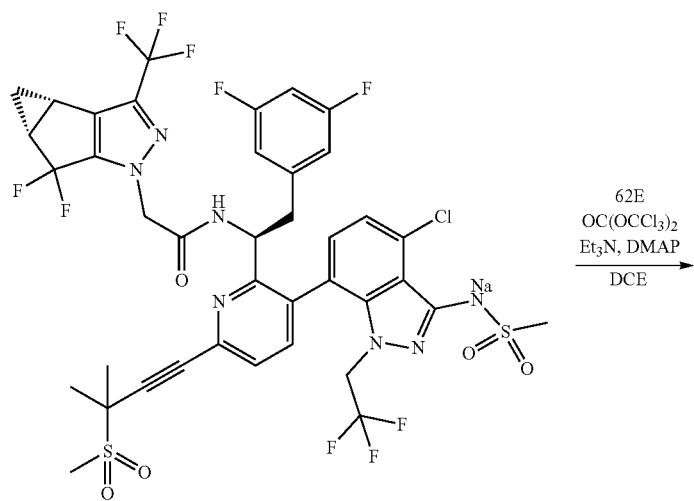
Intermediate 5E
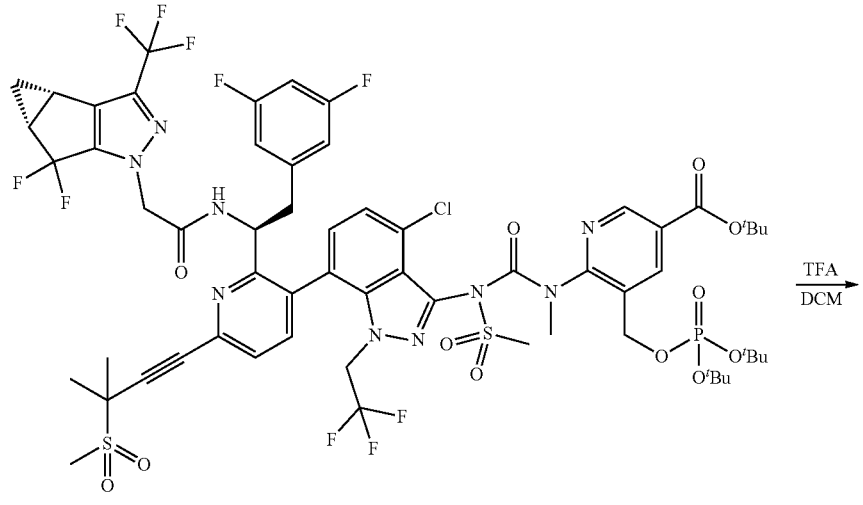
62F -continued

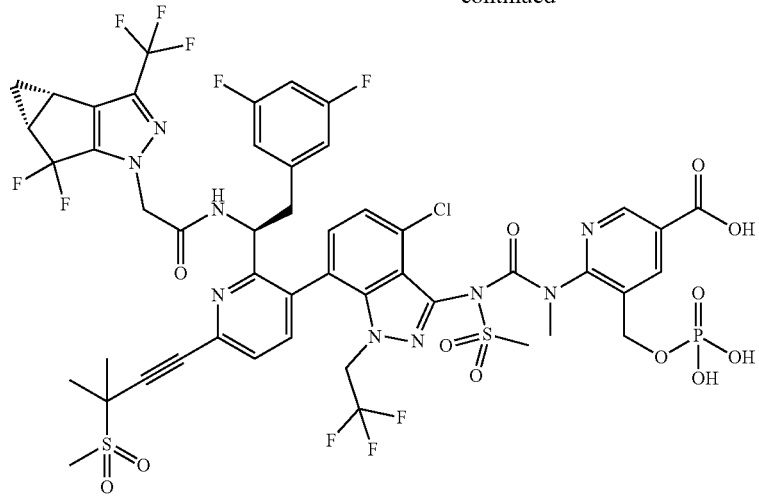

62

Synthesis of Tert-butyl 5-bromo-6-chloronicotinate (62B): To a solution of 5-bromo-6-chloronicotinic acid (84.6 mmol) in THF (300 mL) was added Boc$_2$O (254 mmol) and DMAP (8.46 mmol). The mixture was stirred at 70° C. for 12 hours. The reaction mixture was poured into water (200 mL) and extracted with ethyl acetate (3×200 mL). The combined organic phase was washed with brine (3×200 mL), dried over anhydrous Na$_2$SO$_4$, filtered and concentrated under reduced pressure. The residue was purified by silica gel chromatography to yield title compound 62B. $^1$H NMR (400 MHz, Chloroform-d) δ 8.86 (d, J=2.0 Hz, 1H), 8.44 (d, J=2.0 Hz, 1H), 1.61 (s, 9H).

Synthesis of Tert-butyl 5-bromo-6-(methylamino)nicotinate (62C): A solution of 62B (69.0 mmol) in methylamine(2 M, 393 mmol) was stirred at 30° C. for 12 hours. The reaction mixture was poured into water (100 mL) and extracted with ethyl acetate (3×100 mL). The combined organic layers were washed with brine (100 mL), dried over anhydrous Na$_2$SO$_4$, filtered and concentrated under reduced pressure. The residue was purified by silica gel chromatography to yield title compound 62C. $^1$H NMR (400 MHz, Chloroform-d) δ 8.73 (d, J=1.8 Hz, 1H), 8.15 (d, J=2.0 Hz, 1H), 3.12 (d, J=4.9 Hz, 3H), 1.60 (s, 9H).

Synthesis of Tert-butyl 5-(hydroxymethyl)-6-(methylamino)nicotinate (62D): To a solution of 62C (38.3 mmol) in dioxane (200 mL) was added tributylstannylmethanol (76.6 mmol) and Pd(PPh$_3$)$_4$ (3.83 mmol). The mixture was stirred at 100° C. for 12 hours under N$_2$. The reaction mixture was poured into water (100 mL) and extracted with ethyl acetate (3×100 mL). The combined organic phase was washed with brine (3×100 mL), dried over anhydrous Na$_2$SO$_4$, filtered and concentrated under reduced pressure. The residue was purified by silica gel chromatography to yield title compound 62D. $^1$H NMR (400 MHz, Chloroform-d) δ 8.65 (d, J=2.3 Hz, 1H), 7.60 (d, J=2.3 Hz, 1H), 5.95 (br d, J=3.9 Hz, 1H), 4.57 (s, 2H), 3.06 (d, J=4.9 Hz, 3H), 1.56 (s, 9H).

Synthesis of Tert-butyl 5-(((di-tert-butoxyphosphoryl)oxy)methyl)-6-(methylamino)nicotinate (62E): To a solution of 62D (14.6 mmol) in DMF (70.0 mL) was added di-tert-butyl N,N-diisopropylphosphoramidite (44.0 mmol) followed by 1H-tetrazole (51.4 mmol). The solution was heated at 50° C. for 2 hours. Then, 30% H$_2$O$_2$ (aq) (58.7 mmol) was added at 0° C. and the reaction was stirred for 1 hour at 20° C. The reaction mixture was poured into sat. Na$_2$SO$_3$ (aq) (100 mL) to quench excess H$_2$O$_2$ and the mixture was extracted with ethyl acetate (3×100 mL). The combined organic layers were washed with brine (3×100 mL), dried over anhydrous Na$_2$SO$_4$, filtered and concentrated under reduced pressure. The residue was purified by RP chromatography to yield title compound 62E. MS (m/z) 431.2 [M+H]$^+$.

Synthesis of tert-butyl 6-(3-(4-chloro-7-(2-((S)-1-(2-((3bS,4aR)-5,5-difluoro (trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-1-methyl-3-(methylsulfonyl)ureido)-5-(((di-tert-butoxyphosphoryl)oxy)methyl)nicotinate (62F): To an ice-cold solution of 62E (0.232 mmol) and triphosgene (0.232 mmol) in DCE (460 μL) was added TEA (0.232 mmol). The reaction was stirred at room temperature for 90 minutes. Upon completion, the reaction was concentrated to dryness. To the reaction was added Intermediate 5E (0.348 mmol), DCE (920 μL), TEA (0.488 mmol) and DMAP (0.058 mmol). The reaction was stirred at room temperature for 16 hours. Upon completion, the reaction was diluted with DCM (5 mL), washed with sat. NH$_4$C$_1$ (aq), washed with water, dried over Na$_2$SO$_4$, concentrated and purified by silica gel chromatography. Fractions containing the product were pooled and concentrated to yield title compound 62F. MS (m/z) 1446.40 [M+Na]$^+$.

Synthesis of 6-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-1-methyl-3-(methylsulfonyl)ureido)-5-((phosphonooxy)methyl)nicotinic acid (62): To a vial was added 62F (0.133 mmol), DCM (600 μL) and TFA (13.3 mmol). The reaction was stirred at room temperature for 2 hours. Upon completion, the reaction was concentrated and purified by reverse phase HPLC. Fractions containing the product were pooled and lyophilized to yield title compound 62 as a mixture of atropisomers. $^1$H NMR (400 MHz, CD$_3$CN) δ 8.71 (s), 8.31 (s), 8.23-8.18 (m), 7.74 (s), 7.71-7.65 (m), 7.16 (s), 7.00 (s), 6.75 (tt), 6.42 (s), 6.31 (s), 6.09 (s), 5.03 (d), 4.67 (s), 4.42 (s), 4.03 (s), 3.38 (s), 3.17 (s), 3.02 (dd), 2.90 (dd), 2.46 (tt), 1.78 (s), 1.37 (tdd), 1.02 (s). $^{19}$F NMR (376 MHz, CD$_3$CN) δ −62.63, −70.85, −81.80 (d), −105.04 (d), −112.03. $^{31}$P NMR (162 MHz, CD$_3$CN) δ −0.07 (t). MS (m/z) 1256.20 [M+H]$^+$.

Example 63
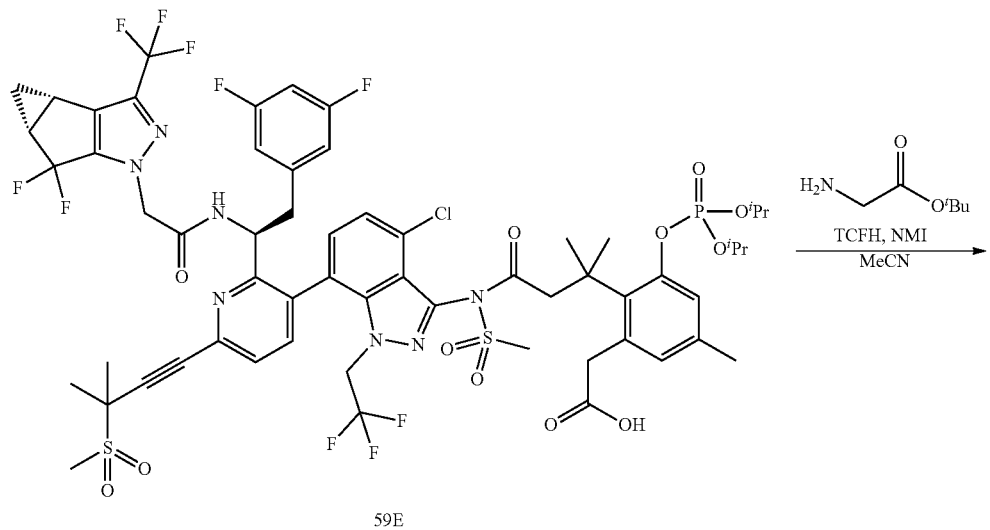
59E
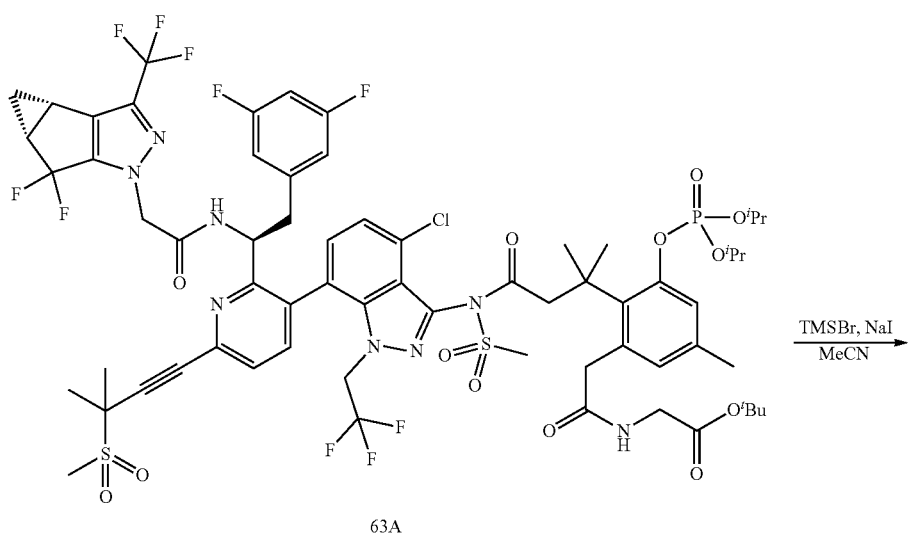
63A
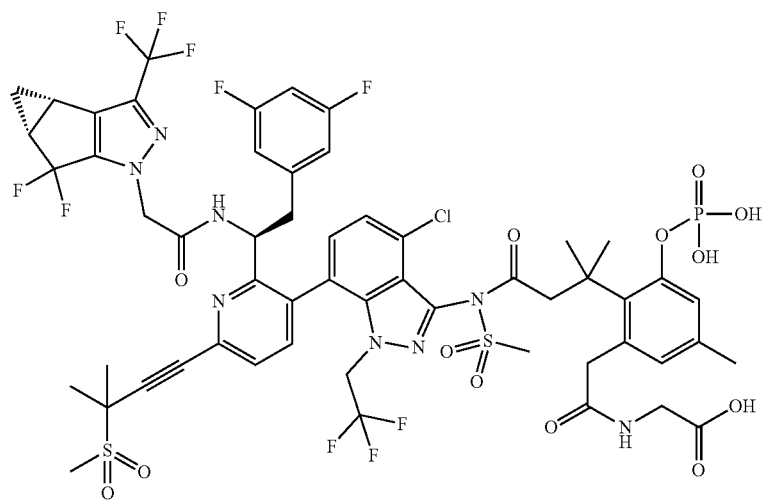
63

Synthesis of tert-butyl (2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-((diisopropoxyphosphoryl)oxy)-5-methylphenyl)acetyl)glycinate (63A): To a vial was added 59E (0.072 mmol), tert-butyl glycinate (0.145 mmol), MeCN (500 µL), NMI (0.362 mmol) and TCFH (0.087 mmol). The reaction was stirred at room temperature for 15 minutes. Upon completion, the reaction was concentrated and purified by silica gel chromatography. Fractions containing the product were pooled and concentrated to yield title compound 63A. MS (m/z) 1493.50 [M+H]$^+$.

Synthesis of (2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-5-methyl-3-(phosphonooxy)phenyl)acetyl)glycine (63): To a vial was added 63A (0.069 mmol), sodium iodide (0.069 mmol), MeCN (700 µL) and bromotrimethylsilane (0.690 mmol). The reaction was stirred at 40° C. for 2 hours. Upon completion, the reaction was brought to room temperature and quenched with a few drops of water. The solution was directly purified by reverse phase HPLC. Fractions containing the product were pooled and lyophilized to yield title compound 63B as a mixture of atropisomers. $^1$H NMR (400 MHz, CD$_3$CN) δ 7.82 (d), 7.73 (d), 7.68 (d), 7.63 (t), 7.36 (d), 7.31 (dd), 7.24 (d), 7.17 (s), 6.81-6.71 (m), 6.67 (d), 6.63 (t), 6.32 (d), 4.90 (dd), 4.82 (s), 4.78-4.65 (m), 4.60-4.39 (m), 4.31-4.16 (m), 4.05 (dt), 3.96 (s), 3.92 (s), 3.89-3.75 (m), 3.38 (s), 3.17 (s), 3.02 (s), 2.62 (d), 2.52 (ddd), 2.20 (d), 2.15 2.10 (m), 1.78 (dd), 1.45-1.37 (m), 1.29 (d). $^{19}$F NMR (376 MHz, CD$_3$CN) δ −62.52, −71.54 (t), −81.95 (dd), −104.24 (dd), −111.64 (t). $^{31}$P NMR (162 MHz, CD$_3$CN) δ −7.66. MS (m/z) 1353.30 [M+H]$^+$.

Example 64

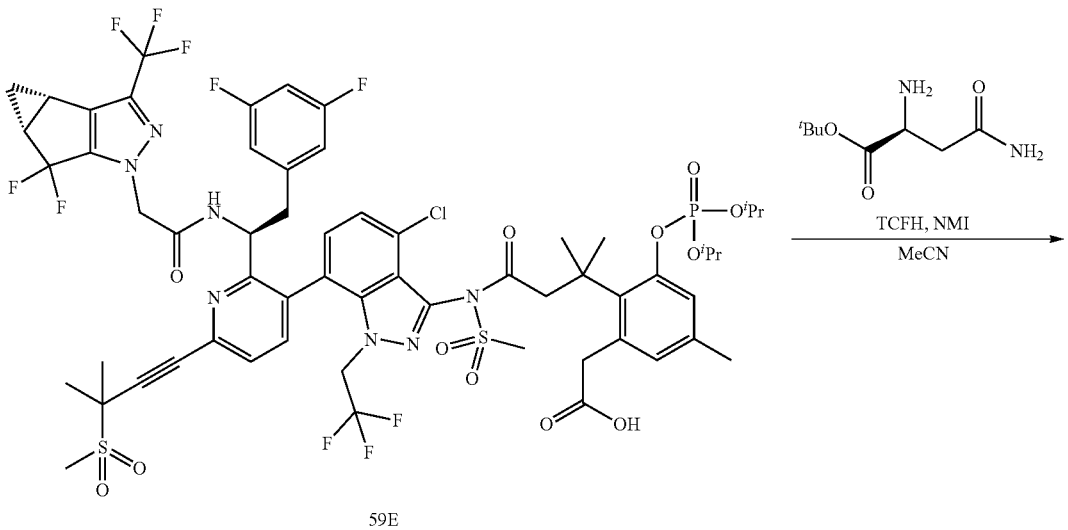

59E

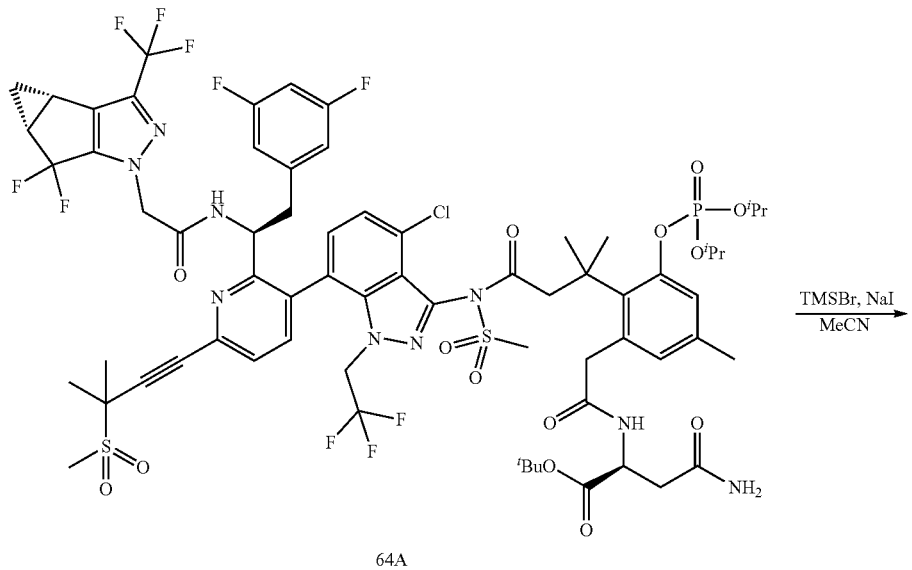

64A

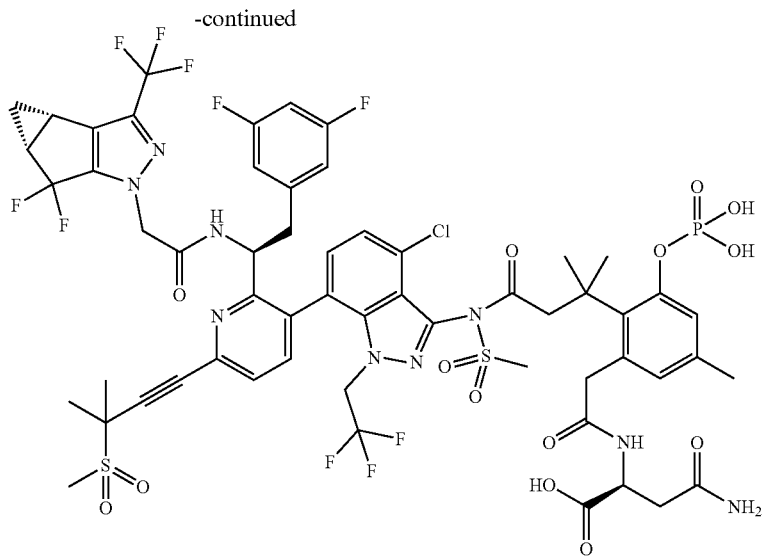

64

Synthesis of tert-butyl (2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-((diisopropoxyphosphoryl)oxy)-5-methylphenyl)acetyl)-L-asparaginate (64A): To a vial containing 59E (0.054 mmol) was added tert-butyl L-asparaginate (0.109 mmol), MeCN (500 μL), NMI (0.272 mmol) and TCFH (0.065 mmol). The reaction was stirred at room temperature for 15 minutes. Upon completion, the reaction was concentrated and purified by silica gel chromatography. Fractions containing the product were pooled and concentrated to yield title compound 64A. MS (m/z) 1494.40 [M−tBu+2H]⁺.

Synthesis of (2-(2-(4-(N-(4-chloro-7-(2-((S)-1-(2-((3bS,4aR)-5,5-difluoro (trifluoromethyl)-3b,4,4a,5-tetrahydro-1H-cyclopropa[3,4]cyclopenta[1,2-c]pyrazol yl)acetamido)-2-(3,5-difluorophenyl)ethyl)-6-(3-methyl-3-(methylsulfonyl)but-1-yn yl)pyridin-3-yl)-1-(2,2,2-trifluoroethyl)-1H-indazol-3-yl)methylsulfonamido)-2-methyl oxobutan-2-yl)-5-methyl-3-(phosphonooxy)phenyl)acetyl)-L-asparagine (64): To a vial was added 64A (0.039 mmol), sodium iodide (0.077 mmol), MeCN (700 μL) and bromotrimethylsilane (0.309 mmol). The reaction was stirred at 40° C. for 2 hours. Upon completion, the reaction was brought to room temperature and quenched with a few drops of water. The solution was directly purified by reverse phase HPLC. Fractions containing the product were pooled and lyophilized to yield title compound 64 as a mixture of atropisomers. $^1$H NMR (400 MHz, CD$_3$CN) δ 7.81 (d), 7.79-7.73 (m), 7.68 (d), 7.64 (dd), 7.43-7.22 (m), 7.15 (d), 6.83-6.70 (m), 6.63 (d), 6.57 (s), 6.36-6.25 (m), 5.00-4.84 (m), 4.81 (d), 4.79-4.69 (m), 4.65-4.48 (m), 4.29-4.19 (m), 4.04 (dt), 3.95 (d), 3.79 (d), 3.40 (d), 3.37 (s), 3.16 (d), 2.91 (s), 2.52 (ddd), 2.19 (d), 1.78 (dd), 1.43 (t), 1.31 (d), 1.14 (s), 1.04 (s). $^{19}$F NMR (376 MHz, CD$_3$CN) δ−62.51, −62.61 (d), −70.62−−71.27 (m), −71.55 (t), −81.87 (dd), −104.23 (dd), −111.66 (t), −112.10 (t). $^{31}$P NMR (162 MHz, CD$_3$CN) δ−7.27. MS (m/z) 1410.30 [M+H]⁺.

Example 65

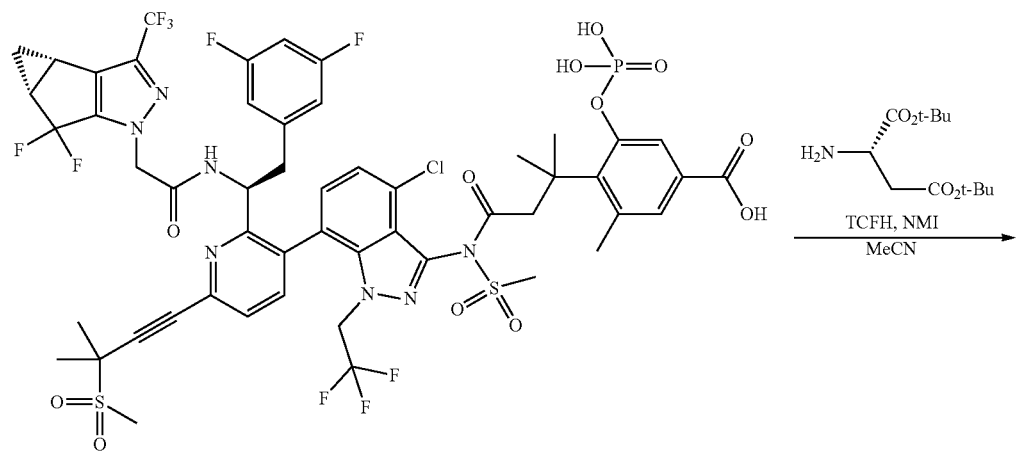

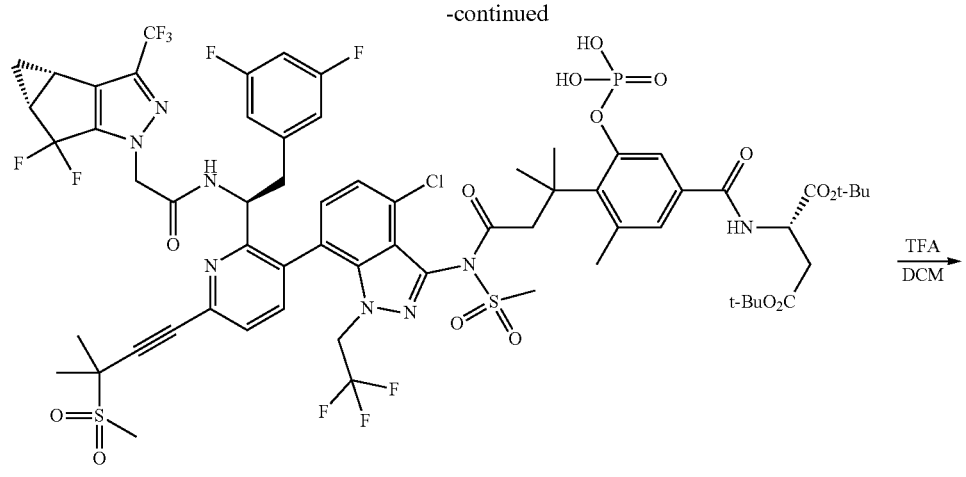

65A

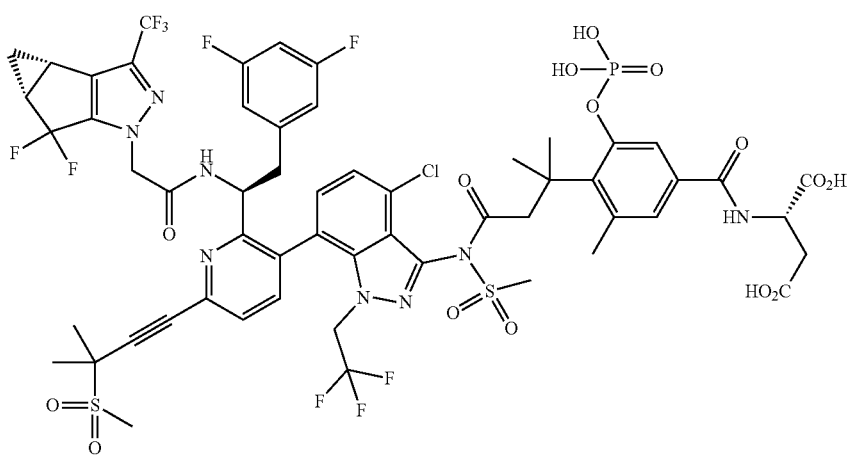

65

Synthesis of di-tert-butyl (4-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido) methyl-4-oxobutan-2-yl)-3-methyl-5-(phosphonooxy)benzoyl)-L-aspartate (65A): To a stirred solution of L-aspartic acid di-tert-butyl ester (0.192 mmol) and 1-methylimidazole (0.234 mmol) in MeCN (1 mL) were added sequentially 49 (0.094 mmol) and TCFH (0.112 mmol). When the reaction had reached completion, the volatiles were removed under reduced pressure and the residue was purified by reverse phase HPLC. Fractions containing the product were pooled and lyophilized to yield title compound 65A as a mixture of atropisomers. MS (m/z) 1453.40 [M−t−Bu+2H]⁺.

Synthesis of (4-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-methyl-5-(phosphonooxy) benzoyl)-L-aspartic acid (65): To a solution of 65A (0.940 mmol) in DCM (1.0 mL) was added trifluoroacetic acid (39.2 mmol). When the reaction had reached completion, the volatiles were removed under reduced pressure and the residue was purified by reverse phase HPLC. Fractions containing the product were pooled and lyophilized to yield title compound 65 as a mixture of atropisomers. $^1$H NMR (400 MHz, DMSO-$d_6$) δ 9.22-9.15 (m), 8.65-8.55 (m), 8.01-7.77 (m), 7.80-7.73 (m), 7.72 (s), 7.50-7.38 (m), 7.36-7.27 (m), 7.07-6.96 (m), 6.93-6.86 (m), 6.64 (s), 6.52-6.45 (m), 6.43-6.35 (m), 5.05-4.96 (m), 4.91-4.76 (m), 4.79-4.71 (m), 4.73-4.58 (m), 4.08-3.97 (m), 3.55-3.44 (m), 3.31-3.25 (m), 3.11 (s), 3.03-2.91 (m), 2.90-2.79 (m), 2.75-2.67 (m), 2.33 (s), 1.78-1.72 (m), 1.50 (s), 1.44-1.34 (m), 1.29-1.18 (m), 1.20-1.13 (m), 1.00 (s), 0.90-0.82 (m) ppm. $^{19}$F NMR (376 MHz, DMSO-$d_6$) δ −60.64--61.07 (m), −69.45--69.70 (m), −69.97--70.22 (m), −74.99, −76.34, −80.36--80.60 (m), −81.18, −102.61, −110.52--110.97 (m) ppm. MS (m/z) 1397.30 [M+H]⁺.

Example 66
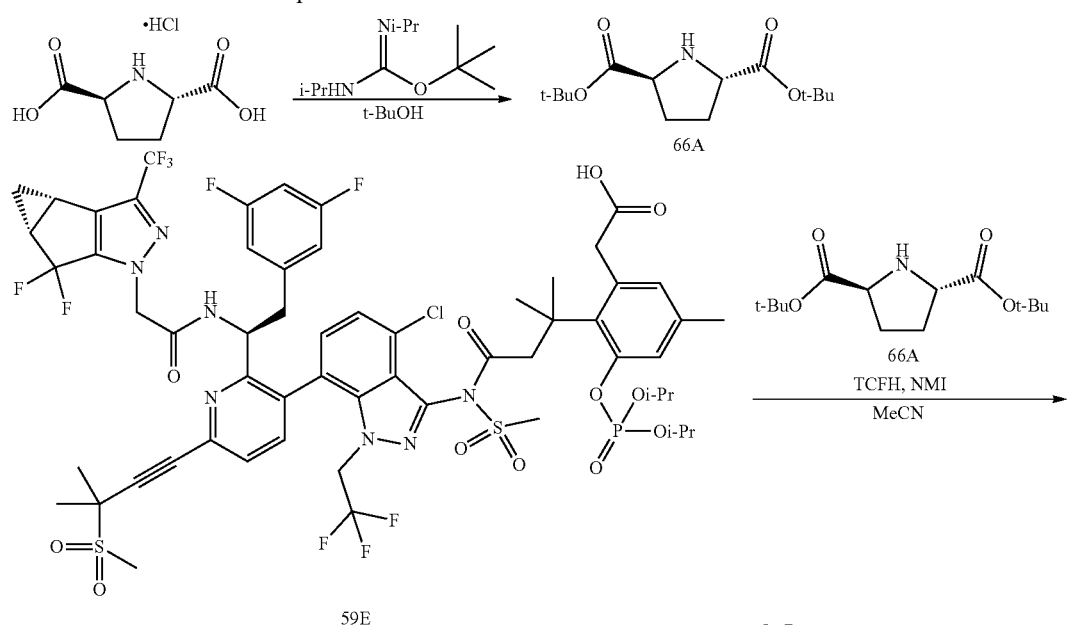
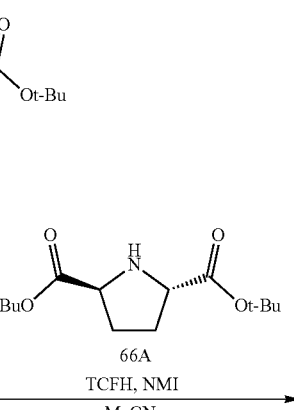
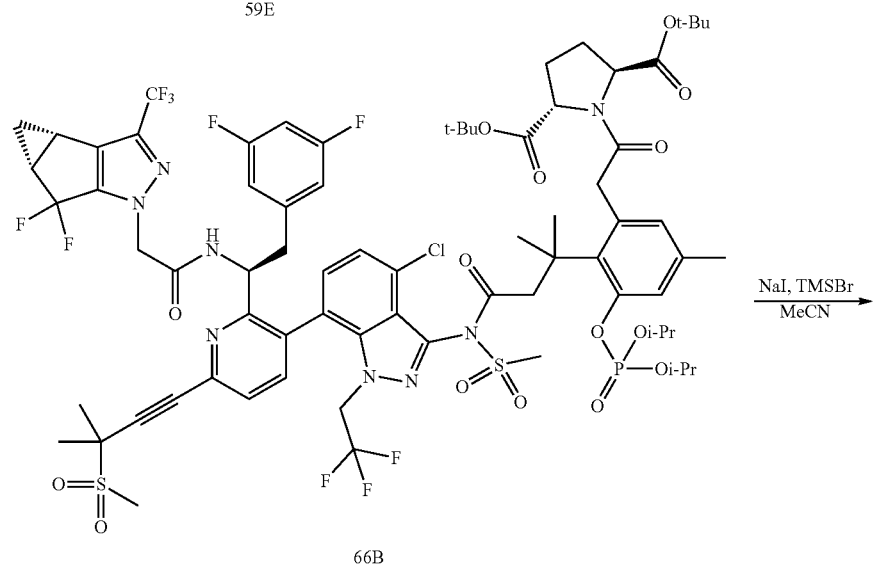
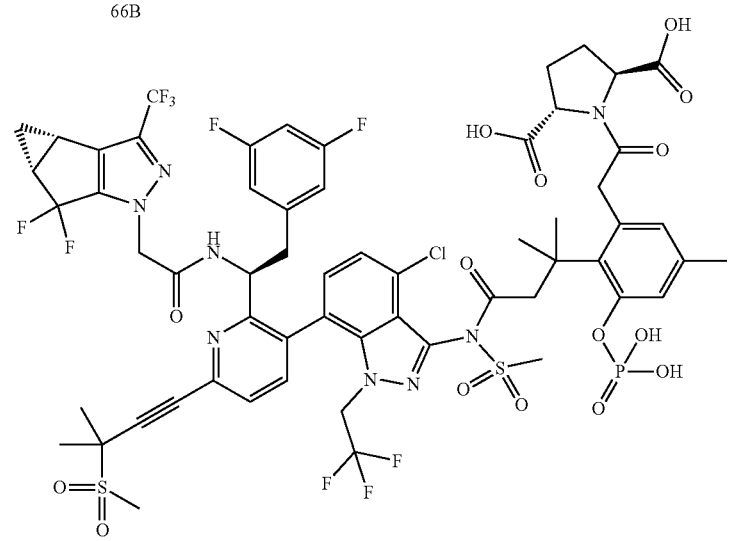

Synthesis of di-tert-butyl (2S,5S)-pyrrolidine-2,5-dicarboxylate (66A): To a stirred suspension of (2S,5S)-pyrrolidine-2,5-dicarboxylic acid hydrochloride (0.943 mmol) in tert-butanol (4.3 mL) was added O-tert-butyl-N,N'-diisopropylisourea (13.3 mmol). When the reaction had reached completion, the volatiles were removed under reduced pressure, filtered, and the filter cake washed with DCM (3×20 mL). The mother liquor was then concentrated under reduced pressure, and the residue purified by silica gel chromatography. Fractions containing the product were pooled and lyophilized to give title compound 66A. $^1$H NMR (400 MHz, CDCl$_3$) δ 3.93-3.77 (m, 2H), 2.71 (s, 1H), 2.19-2.05 (m, 2H), 1.96-1.76 (m, 2H), 1.46 (s, 18H) ppm. MS (m/z) 272.30 [M+H]$^+$.

Synthesis of di-tert-butyl (2S,5S)-1-(2-(2-(4-(N-(4-chloro-7-(2-((S)-1-(2-((3bS,4aR)-5,5-difluoro-3-(trifluoromethyl)-3b,4,4a,5-tetrahydro cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol yl)methylsulfonamido)-2-methyl-4-oxobutan-2-yl)-3-((diisopropoxyphosphoryl)oxy) methylphenyl)acetyl)pyrrolidine-2,5-dicarboxylate (66B): To a solution of compound 59E (0.087 mmol), 66A (0.130 mmol), and 1-methylimidazole (0.217 mmol) in MeCN (1.4 mL) was added TCFH (0.104 mmol). When the reaction had reached completion, the volatiles were removed under reduced pressure and the residue was purified by reverse phase HPLC. Fractions containing the product were pooled and lyophilized to yield title compound 66B as a mixture of atropisomers. MS (m/z) 1581.30 [M-t-Bu+2H]$^+$.

Synthesis of (2S,5S)-1-(2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-((diisopropoxyphosphoryl)oxy)-5-methylphenyl)acetyl)pyrrolidine-2,5-dicarboxylic acid (66): To a solution of 66B (0.031 mmol) in MeCN (1.0 mL) were added NaI (0.153 mmol) and TMSBr (0.612 mmol) in three portions over a six-hour period. When the reaction had reached completion, the excess reagents were quenched with water, and the resulting mixture filtered and purified directly by reverse phase HPLC. Fractions containing the product were pooled and lyophilized to yield title compound 66 as a mixture of atropisomers. $^1$H NMR (400 MHz, DMSO-d$_6$) δ 9.20-9.13 (m), 7.91-7.84 (m), 7.84-7.71 (m), 7.48-7.33 (m), 7.21 (s), 7.17-6.96 (m), 6.96 (s), 6.83-6.76 (m), 6.68 (s), 6.59-6.45 (m), 4.91-4.72 (m), 4.71-4.58 (m), 4.33-4.24 (m), 3.54-3.48 (m), 3.29-3.24 (m), 2.19-2.05 (m), 1.96-1.88 (m), 1.78-1.72 (m), 1.38 (s), 1.33-1.22 (m), 1.04 0.94 (m), 0.86 (s) ppm. $^{19}$F NMR (377 MHz, DMSO-d$_6$) δ −60.75-−60.91 (m), −69.49-−69.65 (m), −69.70-−69.86 (m), −75.11, −79.76-−79.90 (m), −80.52, −103.30, −103.97, −110.53-−110.69 (m) ppm. $^{31}$P NMR (162 MHz, DMSO-d$_6$) δ−6.95-−7.23 (m) ppm. MS (m/z) 1427.30 [M+H]$^+$.

Example 67

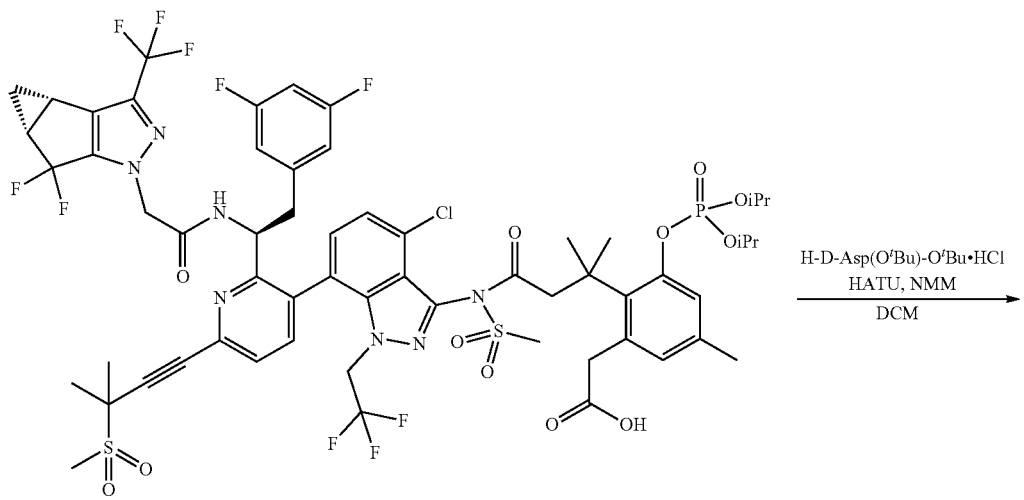

59E

H-D-Asp(O$^t$Bu)-O$^t$Bu•HCl
HATU, NMM
―――――→
DCM

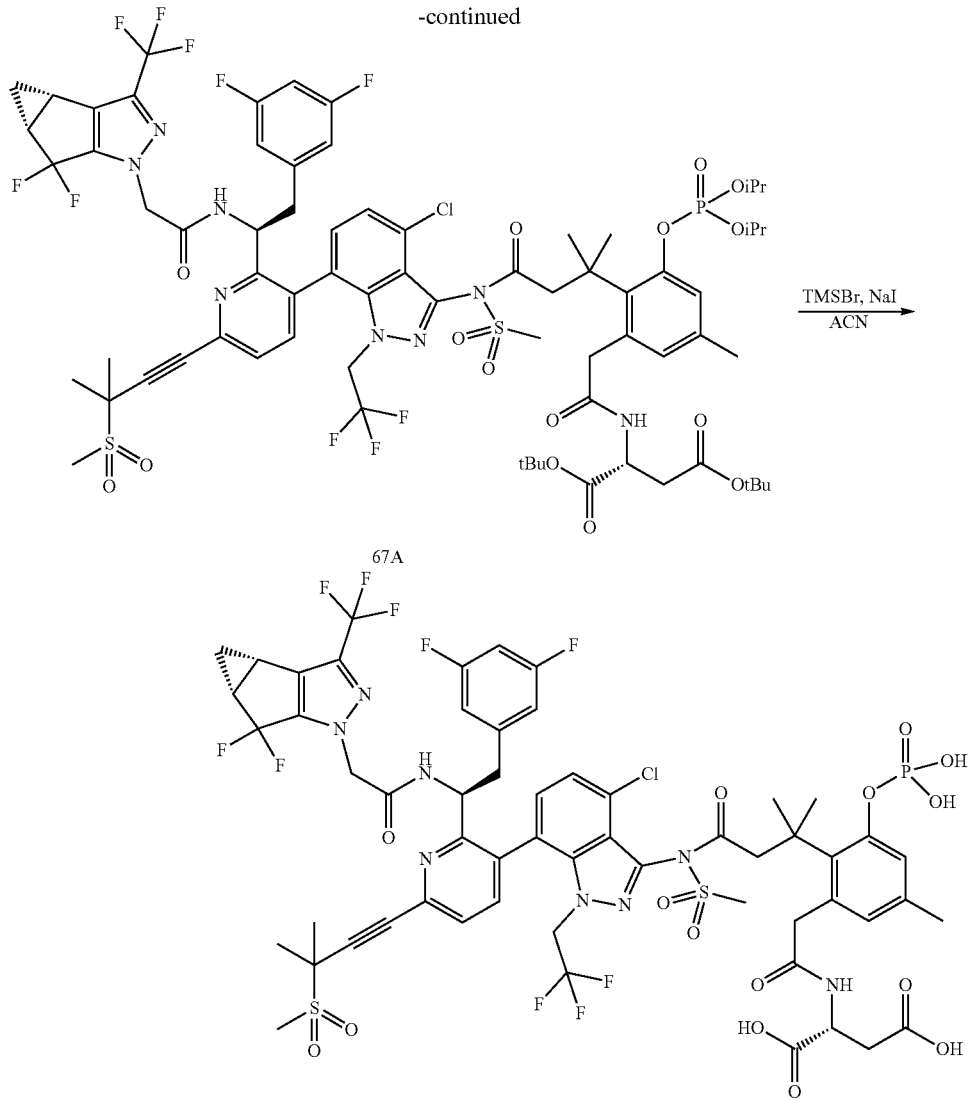

Synthesis of di-tert-butyl (2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-((diisopropoxyphosphoryl)oxy)-5-methylphenyl)acetyl)-D-aspartate (67A): To a vial was added 59E (0.0398 mmol), di-tert-butyl D-aspartate hydrochloride (0.0558 mmol), DCM (0.330 mL), and HATU (0.0598 mmol). NMM (0.240 mmol) was then added dropwise. The reaction was stirred at room temperature for 4.5 hours. Upon completion, the reaction was diluted with DCM and washed with 0.1 M HCl. The aqueous fraction was extracted twice with EtOAc. The organic fraction was washed with brine, dried over $Na_2SO_4$, concentrated and purified by silica gel chromatography. Fractions containing the product were pooled and concentrated to yield title compound 67A. MS (m/z) 1607.81 [M+H]$^+$.

Synthesis of (2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn yl)pyridin-3-yl)-1-(2,2,2-trifluoroethyl)-1H-indazol-3-yl)methylsulfonamido)-2-methyl oxobutan-2-yl)-5-methyl-3-(phosphonooxy)phenyl)acetyl)-D-aspartic acid (67): A flask charged with 67A (0.0404 mmol), sodium iodide (0.0808 mmol), MeCN (0.391 mL), and bromotrimethylsilane (0.808 mmol) was stirred at 40° C. for 18 hours. Upon completion, the reaction was brought to room temperature and quenched with water. The layers were separated, and the aqueous layer was extracted three times with EtOAc. The organic layer was concentrated to dryness with ACN three times to remove excess TMSBr. The residue was purified using reverse phase HPLC, and fractions containing the product were pooled and lyophilized to yield title compound 67 as a mixture of atropisomers. $^1$H NMR (400 MHz, DMSO-$d_6$) δ 9.16 (d), 9.01 (d), 8.15 (m), 8.01-7.68 (m), 7.44 (d), 7.40-7.24 (m), 7.13 (s), 7.07-6.88 (m), 6.73-6.62 (m), 6.49 (d), 4.96-4.60 (m), 4.54 (dq), 3.27 (d), 3.14 (d), 2.99 (m), 2.75-2.67 (m), 2.66-2.55 (m), 2.40 (s), 2.17 (d), 1.83 (d), 1.74 (d), 1.44 (d), 1.39 (d), 1.33 (s), 1.24 (s), 1.00 (d). $^{19}$F NMR (377 MHz, DMSO-$d_6$) δ −60.70−−61.02 (m), −69.24−−69.69 (m), −69.83, −74.91, −103.26, −103.94, −110.41−−111.00 (m). $^{31}$P NMR (162 MHz, DMSO-$d_6$) δ −6.98. MS (m/z) 1411.30 [M+H]$^+$.

Example 68
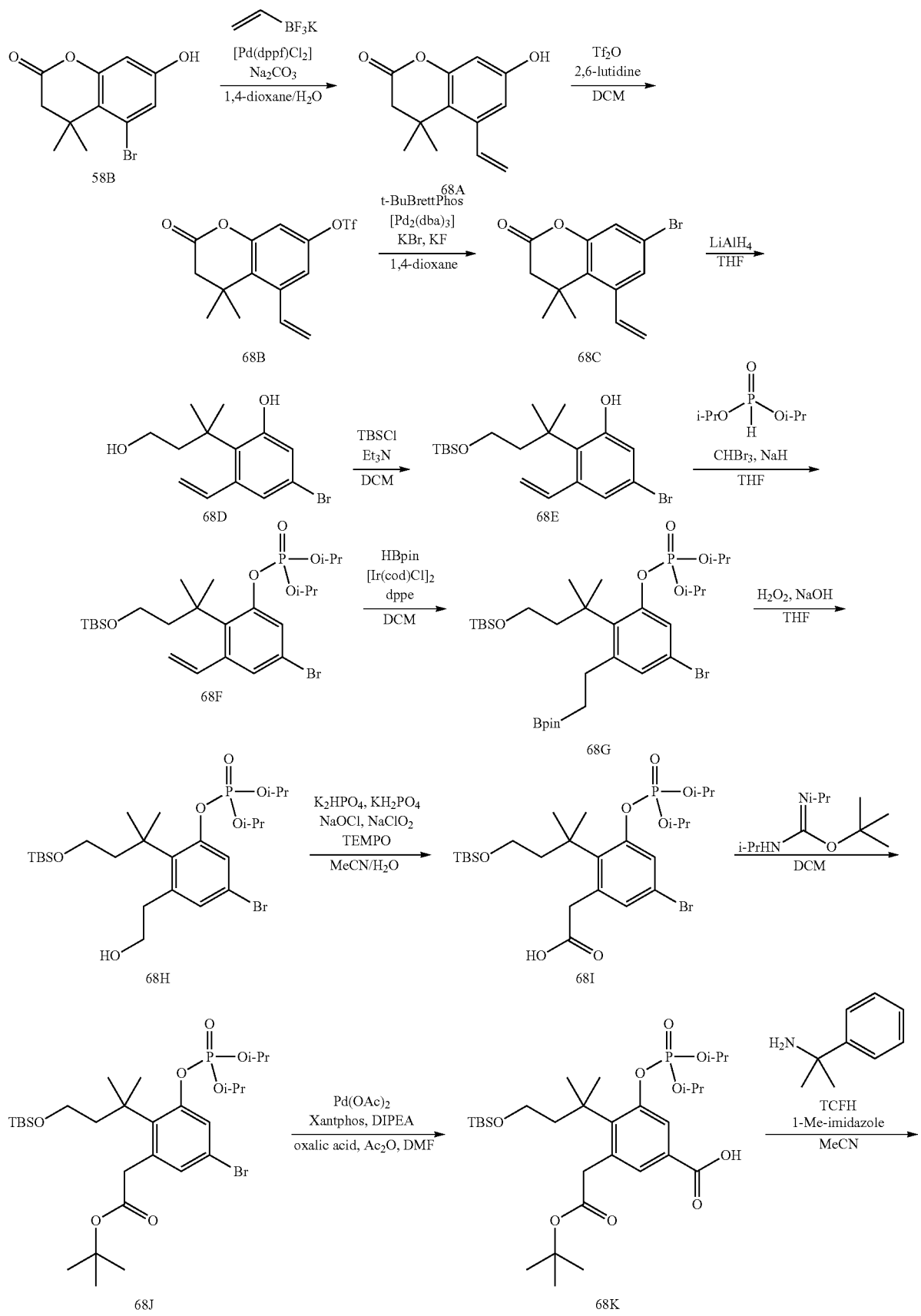

-continued
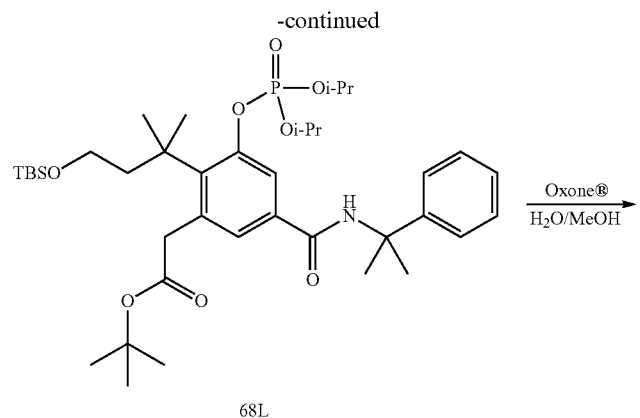
68L
Oxone®
H₂O/MeOH
→
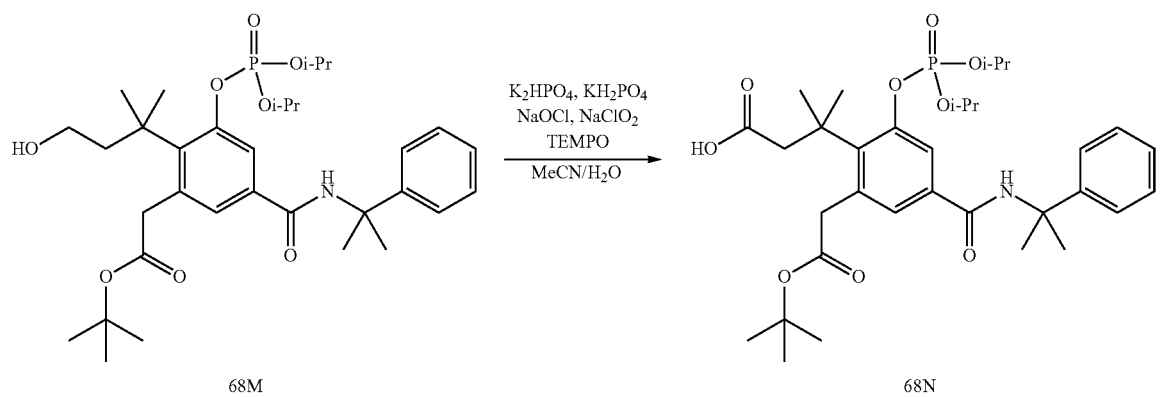
68M
K₂HPO₄, KH₂PO₄
NaOCl, NaClO₂
TEMPO
MeCN/H₂O
→
68N
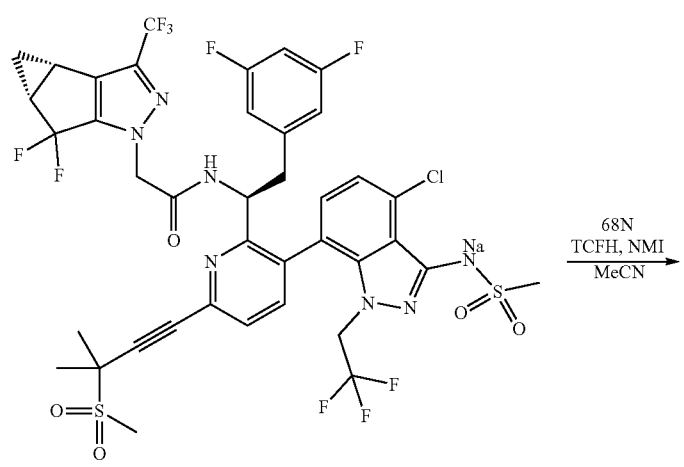
Intermediate 5E
68N
TCFH, NMI
MeCN
→

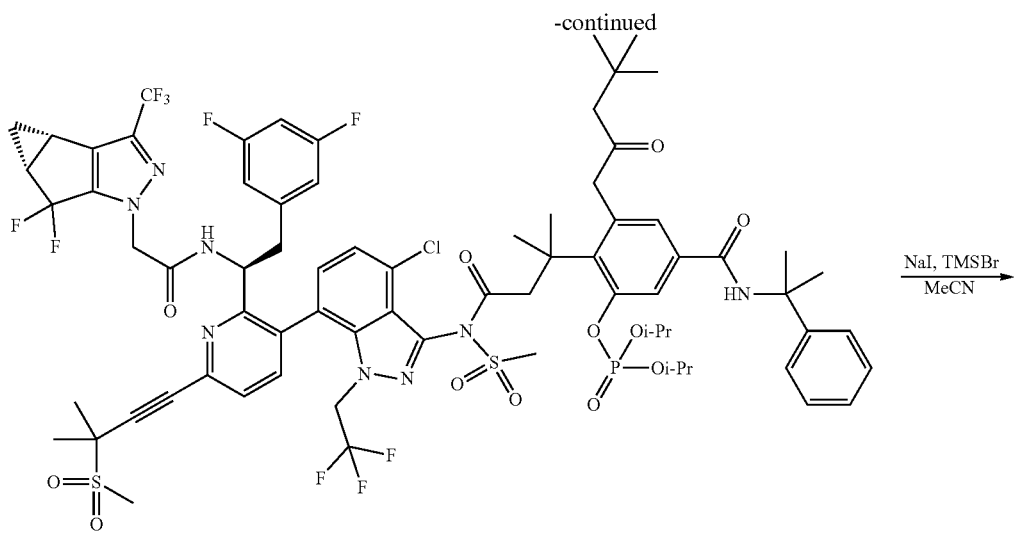

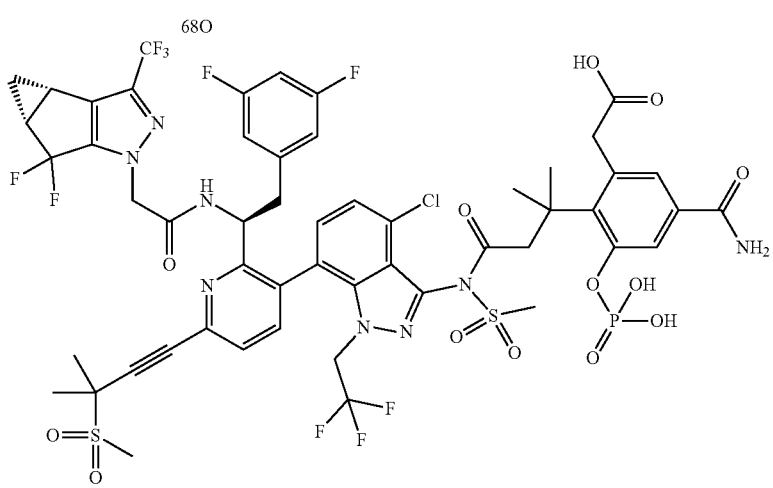

68

Synthesis of 7-hydroxy-4,4-dimethyl-5-vinylchroman-2-one (68A): To a stirred suspension of 58B (3.69 mmol), $Na_2CO_3$ (11.1 mmol), potassium vinyltrifluoroborate (4.43 mmol), and [Pd(dppf)Cl$_2$](0.37 mmol) was added 1,4-dioxane (12.5 mL) and water (2 mL). The mixture was evacuated and backfilled with Ar 3×, then heated to 75° C. When the reaction had reached completion, the mixture was diluted with EtOAc (50 mL) and washed with sat. aq. solutions of $NH_4C_1$ (20 mL) and brine (20 mL). The organic fraction was dried over anhydrous $Na_2SO_4$, filtered, concentrated under reduced pressure and purified by silica gel chromatography. Fractions containing the product were pooled and concentrated to give title compound 68A. $^1H$ NMR (400 MHz, CDCl$_3$) δ 7.08 (dd, J=17.2, 10.8 Hz, 1H), 6.63 (dd, J=19.2, 2.7 Hz, 2H), 5.56 (s, 1H), 5.47 (dd, J=17.2, 1.4 Hz, 1H), 5.32 (dd, J=10.9, 1.4 Hz, 1H), 2.60 (s, 2H), 1.44 (s, 6H) ppm. MS (m/z) 219.1 [M+H]$^+$.

Synthesis of 4,4-dimethyl-2-oxo-5-vinylchroman-7-yl trifluoromethanesulfonate (68B): 68A (0.78 mmol) was diluted with DCM (5 mL), cooled to 0° C. and trifluoromethanesulfonic anhydride (0.93 mmol) and 2,6-lutidine (1.71 mmol) were added in sequence. Upon completion, the reaction was quenched with 10 mL of water and transferred to a separatory funnel with additional DCM (20 mL) and 1M HCl (5 mL). The organic fraction was collected, dried over $Na_2SO_4$, concentrated under reduced pressure and purified by silica gel chromatography. Fractions containing the product were pooled and concentrated to give title compound 68B. MS (m/z) 351.1 [M+H]$^+$.

Synthesis of 7-bromo-4,4-dimethyl-5-vinylchroman-2-one (68C): 68B (1.43 mmol), KBr (2.85 mmol), and KF (0.71 mmol) were combined in a dry flask with 1,4-dioxane (10 mL) and carefully evacuated and backfilled with Ar 3×. In a separate dry flask, [Pd$_2$(dba)$_3$](0.09 mmol) and t-Bu-BrettPhos (0.26 mmol) were diluted with 1,4-dioxane (20 mL) then evacuated and backfilled 3× with Ar before heating to 120° C. for 10 min. The contents of the flask containing catalyst were cooled back to rt, then carefully cannulated into the second flask under positive pressure of Ar and the resulting mixture was stirred at 130° C. under Ar. Upon completion, the mixture was cooled to rt, then filtered over a pad of celite, rinsing with EtOAc and the resulting mother liquor concentrated under reduced pressure. The residue was purified by silica gel chromatography. Fractions containing the product were pooled and concentrated to give title compound 68C. MS (m/z) 281.0 [M+H]$^+$.

Synthesis of 5-bromo-2-(4-hydroxy-2-methylbutan-2-yl)-3-vinylphenol (68D): To a solution of 68C (5.7 mmol) in THF (240 mL) was added LiAlH$_4$ (3.41 mL of 2M THF solution) dropwise over 1 hour at 0° C. then warmed to room temperature. Upon completion, the reaction was diluted with 100 mL of Et$_2$O then quenched with sequential addition of 0.26 mL of H$_2$O, 0.26 mL 1M NaOH, and 0.75 mL H$_2$O. The resulting suspension was stirred for 1 hour with MgSO$_4$ and celite before being filtered. The organic filtrate was collected, concentrated under reduced pressure and purified by silica gel chromatography. Fractions containing the product were pooled and concentrated to give title compound 68D. $^1$H NMR (400 MHz, CDCl$_3$) δ 7.16 (dd, J=17.1, 10.8 Hz, 1H), 6.89 (d, J=2.2 Hz, 1H), 6.79 (d, J=2.2 Hz, 1H), 5.30-5.13 (m, 2H), 3.62 (t, J=7.4 Hz, 2H), 2.26 (t, J=7.4 Hz, 2H), 1.51 (s, 6H) ppm. MS (m/z) 285.1 [M+H]$^+$.

Synthesis of 5-bromo-2-(4-hydroxy-2-methylbutan-2-yl)-3-vinylphenol (68E): To a solution of 68D (1.5 mmol) in 1,2-DCE (7 mL) was added TBSCl (1.9 mmol) followed by Et$_3$N (3.1 mmol). Upon completion, the reaction was transferred to separatory funnel with DCM (100 mL) and 0.5M HCl (20 mL). The organic fraction was collected, dried over Na$_2$SO$_4$, filtered and concentrated under reduced pressure. The resulting residue was purified by silica gel chromatography. Fractions containing the product were pooled and concentrated to give title compound 68E. MS (m/z) 401.1 [M+H]$^+$.

Synthesis of 5-bromo-2-(4-((tert-butyldimethylsilyl)oxy)-2-methylbutan-2-yl)-3-vinylphenyl diisopropyl phosphate (68F): To a solution of 68E (0.88 mmol) in THF (5.2 mL) were added sequentially CHBr$_3$ (0.1 mL), diisopropyl phosphite (1.14 mmol) and the resulting mixture was cooled to 0° C. NaH (1.18 mmol, 60% dispersion in mineral oil) was then added as a single portion with rapid stirring. Upon completion, the reaction was quenched with water (1 mL), then transferred to a separatory funnel using EtOAc (100 mL) and water (20 mL). The organic fraction was collected, dried over Na$_2$SO$_4$, filtered and concentrated under reduced pressure. The residue was purified by silica gel chromatography. Fractions containing the product were pooled and concentrated to give title compound 68F. $^1$H NMR (400 MHz, DMSO-d$_6$) δ 7.50 (dd, J=2.3, 1.0 Hz, 1H), 7.26 (dd, J=17.1, 10.9 Hz, 1H), 7.16 (d, J=2.3 Hz, 1H), 5.39-5.18 (m, 2H), 4.70 (dh, J=7.2, 6.1 Hz, 2H), 3.42 (t, J=7.2 Hz, 2H), 2.03 (t, J=7.1 Hz, 2H), 1.46 (s, 6H), 1.28 (dd, J=18.8, 6.2 Hz, 12H), 0.79 (s, 9H), −0.08 (s, 6H) ppm. MS (m/z) 565.2 [M+H]$^+$.

Synthesis of 5-bromo-2-(4-((tert-butyldimethylsilyl)oxy)-2-methylbutan-2-yl)-3-(2-(4,4,5,5-tetramethyl-1,3,2-dioxaborolan-2-yl)ethyl)phenyl diisopropyl phosphate (68G): A solution of 68F (0.09 mmol) in THF (1 mL) was evacuated and backfilled with Ar 3×before quickly adding[Ir(cod)Cl]$_2$ (0.009 mmol) and dppe (0.018 mmol) with a second round of evacuation and backfill using Ar (3×). The resulting mixture was stirred for 3 mins, then HBpin (0.27 mmol) was added dropwise at rt under Ar. Upon completion, the reaction was quenched with 1 mL of H$_2$O, then transferred to a separatory funnel with 20 mL of EtOAc and 10 mL of water. The organic fraction was collected, dried over Na$_2$SO$_4$, filtered and concentrated under reduced pressure. The residue was purified by silica gel chromatography. Fractions containing the product were pooled and concentrated to give title compound 68G. MS (m/z) 693.4 [M+H]$^+$.

Synthesis of 5-bromo-2-(4-((tert-butyldimethylsilyl)oxy)-2-methylbutan-2-yl)-3-(2-hydroxyethyl)phenyl diisopropyl phosphate (68H): To an ice cold solution of 68G (0.035 mmol) and NaOH (0.17 mmol) in THF (1 mL) was added hydrogen peroxide (0.17 mmol, 50% aqueous solution). Upon completion, the solution was transferred to a separatory funnel with EtOAc (10 mL) and washed with saturated aq. Na$_2$S$_2$O$_3$. The organic fraction was collected, dried over Na$_2$SO$_4$, filtered and concentrated under reduced pressure to yield title compound 68H which was used without further purification. $^1$H NMR (400 MHz, CDCl$_3$) δ 7.55 (dd, J=2.3, 1.2 Hz, 1H), 7.15 (dd, J=2.3, 0.6 Hz, 1H), 4.79 (dp, J=7.1, 6.2 Hz, 2H), 3.86 (t, J=7.1 Hz, 2H), 3.53 (t, J=7.0 Hz, 2H), 3.20 (t, J=7.1 Hz, 2H), 2.13 (t, J=7.0 Hz, 2H), 1.81 (s, 2H), 1.58 (s, 6H), 1.42-1.26 (m, 14H), 0.85 (s, 9H) ppm. MS (m/z) 605.2 [M+Na]$^+$.

Synthesis of 2-(5-bromo-2-(4-((tert-butyldimethylsilyl)oxy)-2-methylbutan-2-yl)-3-((diisopropoxyphosphoryl)oxy)phenyl)acetic acid (68I): To an ice-cold mixture of 68H (0.38 mmol), KH$_2$PO$_4$ (0.19 mmol), K$_2$HPO$_4$ (0.19 mmol), and TEMPO (0.02 mmol) in water (3 mL) and MeCN (3 mL) were added sequentially NaOCl (0.47 mmol, 8.25% solution) then NaClO$_2$ (0.57 mmol) and the reaction was slowly warmed to rt. Upon completion, the mixture was partitioned between water and EtOAc (50 mL) and the pH was carefully adjusted to 1 with 1M HCl. The organic fraction was then shaken with saturated sodium thiosulfate$_{(aq)}$, which was subsequently adjusted to a pH of 1 with 1M HCl with additional agitation. The organic fraction was collected, dried over Na$_2$SO$_4$, filtered and concentrated under reduced pressure to yield title compound 68I, which was used without further purification. MS (m/z) 597.3 [M+H]$^+$.

Synthesis of tert-butyl 2-(5-bromo-2-(4-((tert-butyldimethylsilyl)oxy)-2-methylbutan-2-yl)-3-((diisopropoxyphosphoryl)oxy)phenyl)acetate (68J): To a solution of 68I (0.47 mmol) in DCM (2 mL) was added 2-tert-butyl-1,3-diisopropylisourea (4.67 mmol) at rt. Upon completion, the reaction was filtered. The filtrate was concentrated under reduced pressure and the resulting residue was purified by silica gel chromatography. Fractions containing the product were pooled and concentrated to give title compound 68J. MS (m/z) 653.3 [M+H]$^+$.

Synthesis of 3-(2-(tert-butoxy)-2-oxoethyl)-4-(4-((tert-butyldimethylsilyl)oxy)-2-methylbutan-2-yl)-5-((diisopropoxyphosphoryl)oxy)benzoic acid (68K): A suspension of 68J (0.24 mmol), DIPEA (0.27 mmol), oxalic acid dihydrate (0.29 mmol), and acetic anhydride (0.27 mmol) in DMF (2 mL) was evacuated and backfilled with Ar 3×. To this mixture was then quickly added Pd(OAc)$_2$ (0.049 mmol) and Xantphos (0.049 mmol), and the resulting mixture was evacuated then backfilled with Ar 3×before being sealing and heating to 100° C. Upon completion, the reaction was partitioned between DCM (20 mL) and 0.5M HCl (10 mL). The organic fraction was dried over Na$_2$SO$_4$, filtered, and concentrated under reduced pressure to yield the title compound 68K, which was used without further purification. MS (m/z) 653.3 [M+H]$^+$.

Synthesis of tert-butyl 2-(2-(4-((tert-butyldimethylsilyl)oxy)-2-methylbutan-2-yl)-3-((diisopropoxyphosphoryl)oxy)-5-((2-phenylpropan-2-yl)carbamoyl)phenyl)acetate (68L): To a solution of 68K (0.24 mmol), 1-methylimidazole (1.22 mmol), and cumylamine (0.292 mmol) in MeCN (1.6 mL) was added TCFH (0.29 mmol). Upon completion, the mixture was partitioned between 0.5M HCl (10 mL) and DCM (25 mL). The aqueous fraction was extracted with DCM (25 mL) and the combined organics were collected, dried over Na$_2$SO$_4$, filtered and concentrated under reduced pressure to obtain title compound 68L, which was used without further purification. MS (m/z) 734.4 [M+H]$^+$.

Synthesis of tert-butyl 2-(3-((diisopropoxyphosphoryl)oxy)-2-(4-hydroxy methylbutan-2-yl)-5-((2-phenylpropan-2-yl)carbamoyl)phenyl)acetate (68M): To an ice-cold mixture of 68L (0.12 mmol), tetrabutylammonium hydrogen sulfate (0.024 mmol) and 1:1 water/MeOH (2 mL) and MeCN (1 mL) was added solid Oxone® (0.25 mmol). Upon completion the mixture was partitioned between brine (10 mL) and DCM (10 mL). The organic fraction was washed a second time with brine (10 mL) then collected, dried over $Na_2SO_4$, filtered and concentrated under reduced pressure and the resulting residue was purified by silica gel chromatography. Fractions containing the product were pooled and concentrated to give title compound 68M. MS (m/z) 620.4 $[M+H]^+$.

Synthesis of 3-(2-(2-(tert-butoxy)-2-oxoethyl)-6-((diisopropoxyphosphoryl)oxy)-4-((2-phenylpropan-2-yl)carbamoyl)phenyl)-3-methylbutanoic acid (68N): To an ice-cold mixture of 68M (0.12 mmol), $KH_2PO_4$ (0.06 mmol), $Na_2HPO_4$ (0.06 mmol), and TEMPO (0.006 mmol) in water (0.5 mL) and MeCN (0.5 mL) were added sequentially NaOCl (0.15 mmol, 8.25% solution) then $NaClO_2$ (0.16 mmol) and the reaction was slowly warmed to rt. Upon completion, the mixture was partitioned between water and DCM (25 mL) and the pH was carefully adjusted to 1 with 1M HCl. The organic fraction was then shaken with saturated sodium thiosulfate (aq), which was subsequently adjusted to a pH of 1 with 1M HCl with additional agitation. The organic fraction was collected, dried over $Na_2SO_4$, filtered and concentrated under reduced pressure to yield title compound 68N, which was used without further purification. MS (m/z) 656.3 $[M+Na]^+$.

Synthesis of tert-butyl 2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-((diisopropoxyphosphoryl)oxy)-5-((2-phenylpropan-2-yl)carbamoyl)phenyl)acetate (68O): To a solution of 68N (0.052 mmol), Intermediate 5E (0.065 mmol) and 1-methylimidazole (0.18 mmol) in MeCN (1 mL) was added TCFH (0.062 mmol). Upon completion, the mixture was partitioned between 0.5M HCl (10 mL) and DCM (25 mL). The aqueous fraction was extracted with DCM (25 mL) and the combined organics were collected, dried over $Na_2SO_4$, filtered and concentrated under reduced pressure to obtain title compound 68O, which was used without further purification. MS (m/z) 1465.4 $[M-C_9H12+H]^+$ (primary mass detected resulted from fragmentation with loss of cumyl group).

Synthesis of 2-(5-carbamoyl-2-(4-(N-(4-chloro-7-(2-((S)-1-(2-03bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)methyl-4-oxobutan-2-yl)-3-(phosphonooxy)phenyl)acetic acid (68): To a solution of 68O (0.025 mmol) in MeCN (0.6 mL) were added sequentially NaI (0.051 mmol) and TMSBr (0.253 mmol) and the resulting mixture was heated to 45° C. Additional NaI (0.253 mmol) and TMSBr (1.012 mmol) were added in four portions. Upon completion, the reaction was concentrated under reduced pressure, diluted with DMF (3 mL), filtered, and purified by RP-HPLC. Fractions containing the product were pooled and concentrated to afford an atropisomeric mixture of title compound 68. $^1$H NMR (400 MHz, DMSO-$d_6$) δ 12.38 (s, 2H), 9.23-9.13 (m, 2H), 7.90-7.81 (m, 2H), 7.84-7.72 (m, 6H), 7.48-7.41 (m, 1H), 7.41-7.29 (m, 5H), 7.08-6.96 (m, 3H), 6.65-6.58 (m, 1H), 6.53-6.43 (m, 4H), 5.01-4.92 (m, 1H), 4.89-4.58 (m, 5H), 4.30-4.18 (m, 1H), 4.07-3.90 (m, 3H), 3.86-3.77 (m, 1H), 3.73-3.64 (m, 1H), 3.55-3.44 (m, 6H), 3.12-2.91 (m, 3H), 1.78-1.72 (m, 12H), 1.47 (s, 3H), 1.44-1.37 (m, 1H), 1.37 (s, 3H), 1.31 (s, 3H), 1.24 (s, 1H), 1.19 (s, 3H), 1.06-0.95 (m, 2H) ppm. $^{19}$F NMR (377 MHz, DMSO-$d_6$) δ−60.17--63.22 (m), −69.15--70.19 (m), −79.52--81.62 (m), −102.84--104.57 (m), −110.02--111.03 (m) ppm. $^{31}$P NMR (162 MHz, DMSO-$d_6$) δ−6.95--7.10 (m) ppm. MS (m/z) 1325.3 $[M+H]^+$.

Example 69

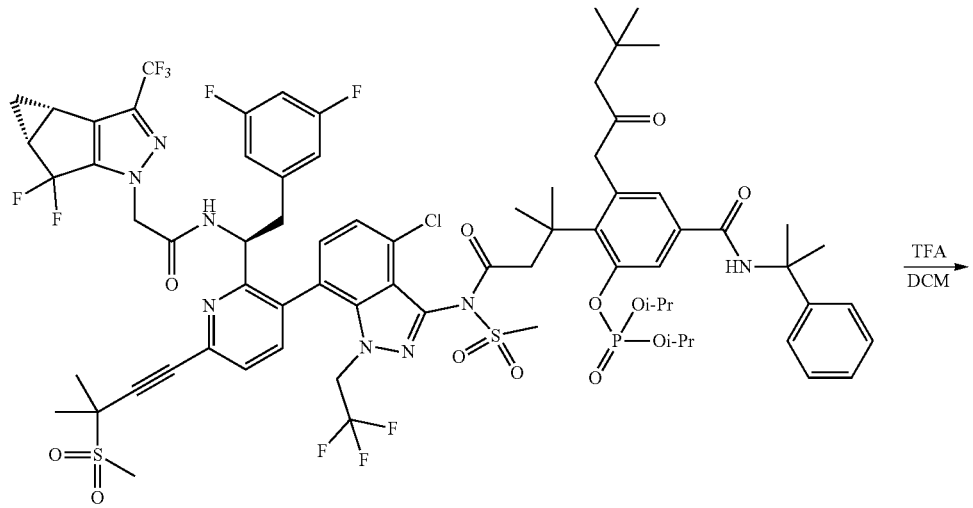

68O

383
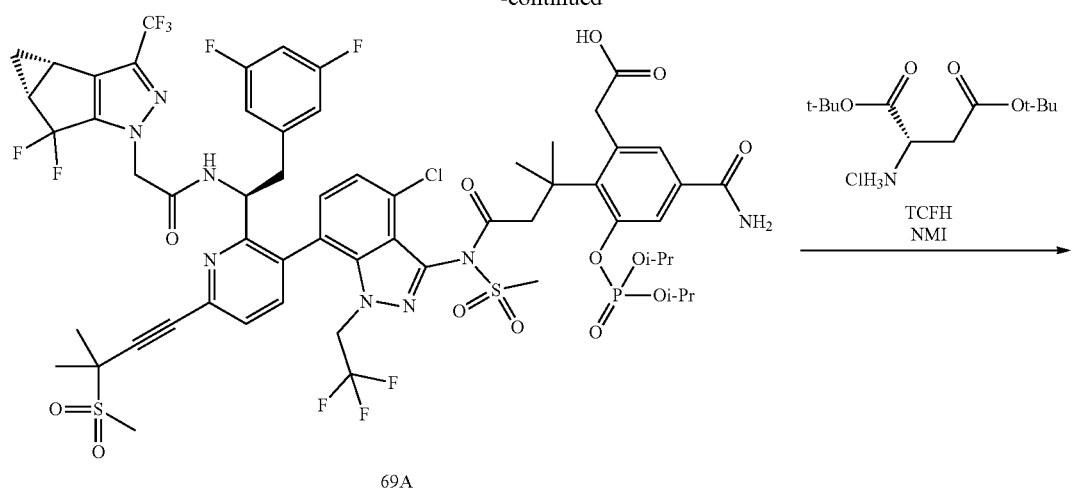
69A
384
-continued
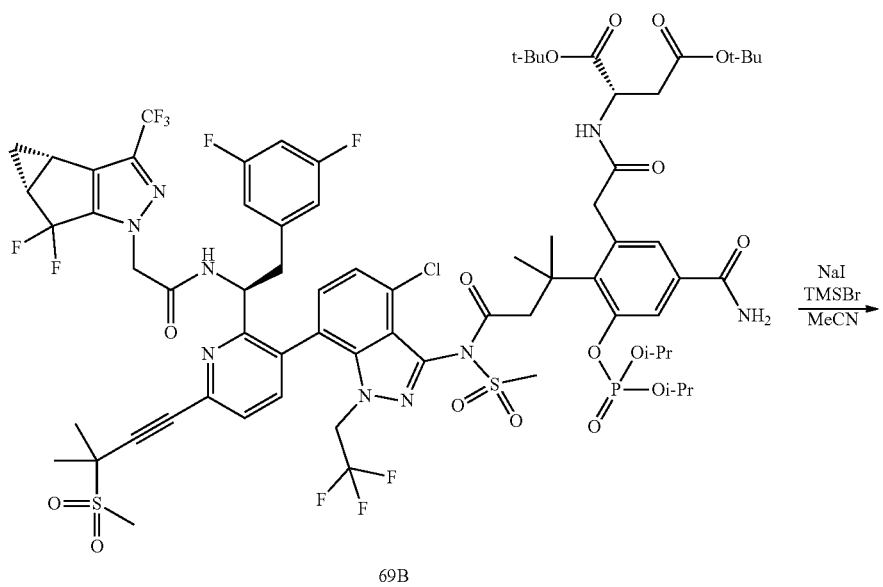
69B
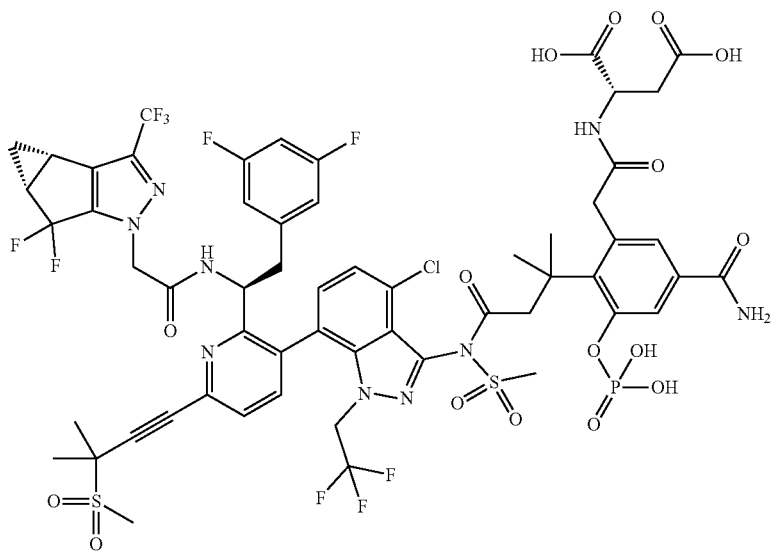
69

Synthesis of 2-(5-carbamoyl-2-(4-(N-(4-chloro-7-(2-((S)-1-(2-03bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)methyl-4-oxobutan-2-yl)-3-(((diisopropoxyphosphoryl)oxy)phenyl)acetic acid (69A): To a solution of 680 (0.025 mmol) in DCM (2 mL) was added trifluoroacetic acid (1.7 mL). Upon completion, the reaction was concentrated twice from toluene, then partitioned between 0.5M HCl (10 mL) and EtOAc (10 mL) and the organic fraction was collected, dried over $Na_2SO_4$, filtered, and concentrated under reduced pressure to afford title compound 69A, which was used without further purification. MS (m/z) 1410.4 $[M+H]^+$.

Synthesis of di-tert-butyl (2-(5-carbamoyl-2-(4-(N-(4-chloro-7-(2-((S)-1-(2-43bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-((diisopropoxyphosphoryl)oxy)phenyl)acetyl)-L-aspartate (69B): To a mixture of 69A (0.025 mmol), 1-methylimidazole (0.128 mmol), and L-aspartic acid di-tert-butyl ester hydrochloride (0.031 mmol) in MeCN (0.5 mL) was added TCFH (0.031 mmol). Upon completion the reaction was partitioned between DCM (10 mL) and 0.5M HCl (10 mL). The organic fraction was collected, dried over $Na_2SO_4$, filtered, and concentrated under reduced pressure to afford title compound 69B, which was used without further purification. MS (m/z) 1482.3 $[M-2tBu-{}^iPr+4H]^+$.

Synthesis of (2-(5-carbamoyl-2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-(phosphonooxy)phenyl)acetyl)-L-aspartic acid (69): To a solution of 69B (0.025 mmol) in MeCN (0.6 mL) were added NaI (0.051 mmol) and TMSBr (0.257 mmol) and the resulting mixture was heated to 45° C. Additional NaI (0.102 mmol) and TMSBr (0.514 mmol) were added across two portions with continued heating. Upon completion, the reaction was quenched with $H_2O$ (0.1 mL), concentrated under reduced pressure, diluted with MeCN (3 mL), filtered, and purified by RP-HPLC. Fractions containing the product were pooled and concentrated to afford an atropisomeric mixture of title compound 69. $^1H$ NMR (400 MHz, Acetonitrile-$d_3$) δ 8.09-7.57 (m, 1H), 7.62-7.02 (m, 1H), 7.04-6.58 (m, 1H), 6.50-6.22 (m, 1H), 5.17-4.48 (m, 1H), 4.35-3.79 (m, 1H), 3.40 (s, 1H), 3.20 (s, 1H), 3.06-2.80 (m, 1H), 2.19-2.08 (m, 1H), 1.87-1.74 (m, 3H), 1.49-1.25 (m, 2H) ppm. $^{19}F$ NMR (376 MHz, Acetonitrile-$d_3$) δ −62.22−−63.39 (m), −70.15−−72.25 (m), −80.91−−82.94 (m), −102.55−−105.95 (m), −110.96−−112.90 (m) ppm. MS (m/z) 1441.8 $[M+H]^+$.

Example 70

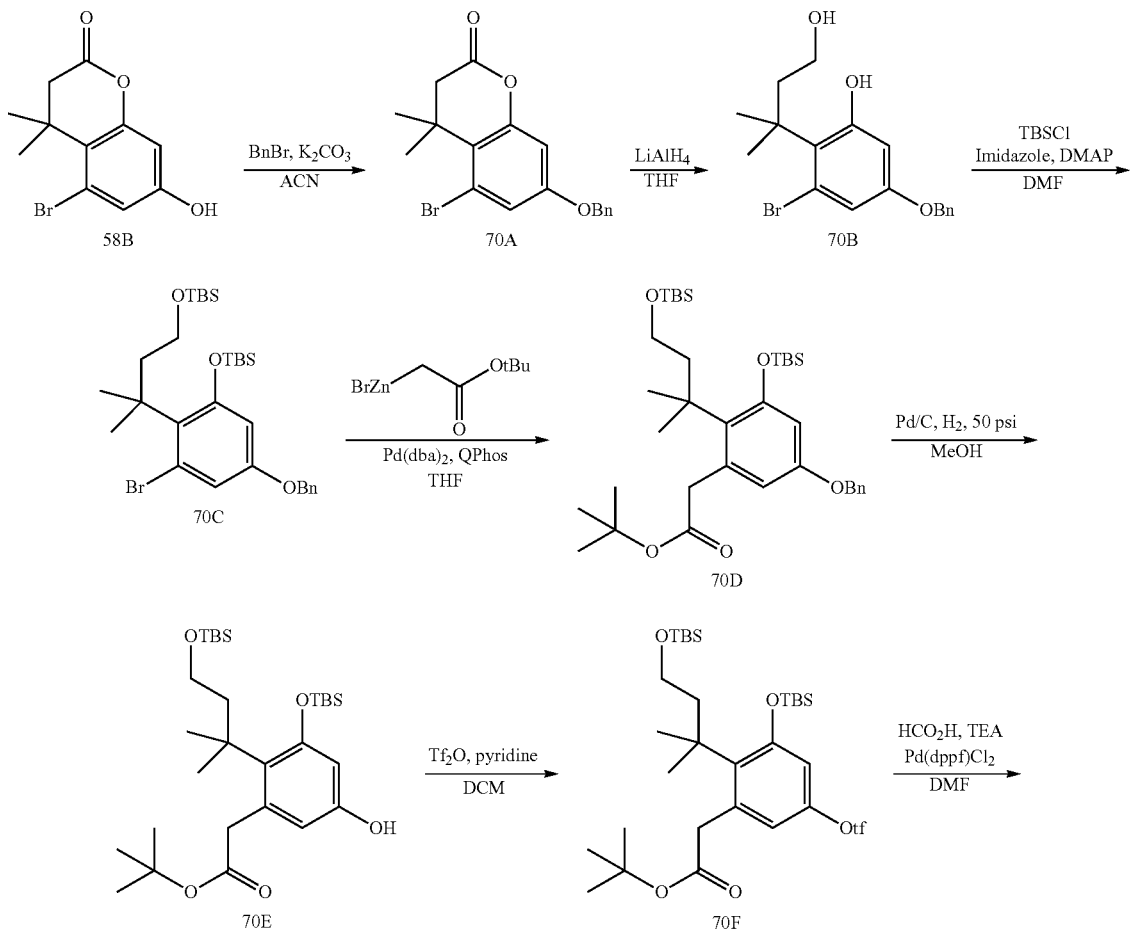

-continued
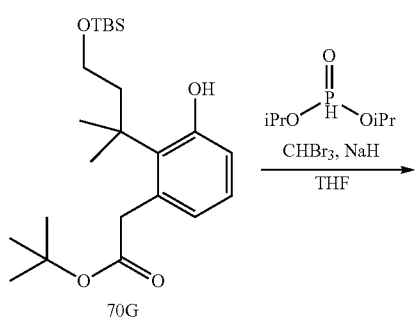
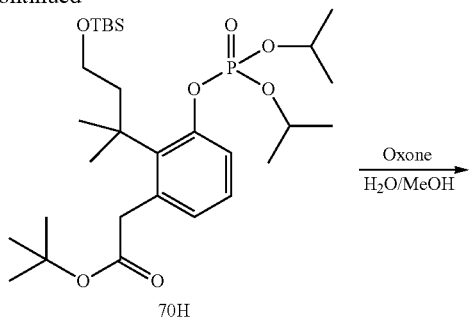
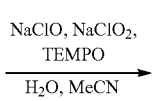
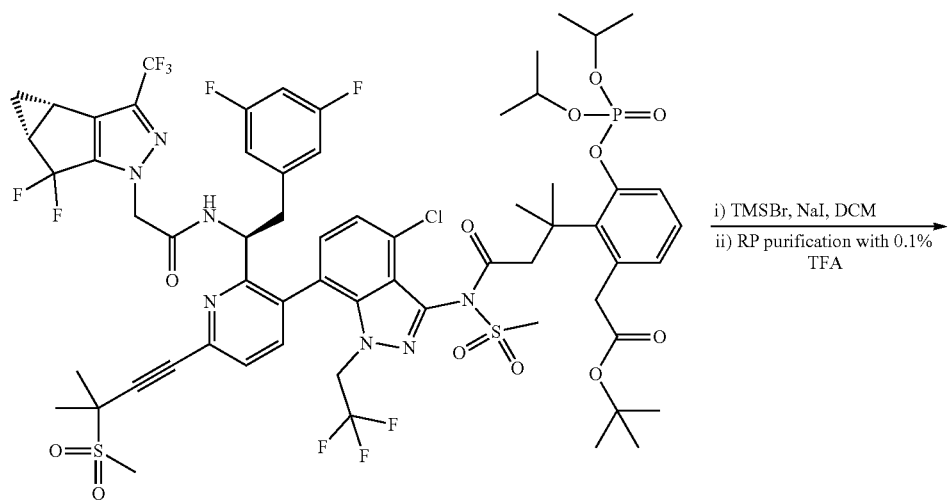

-continued

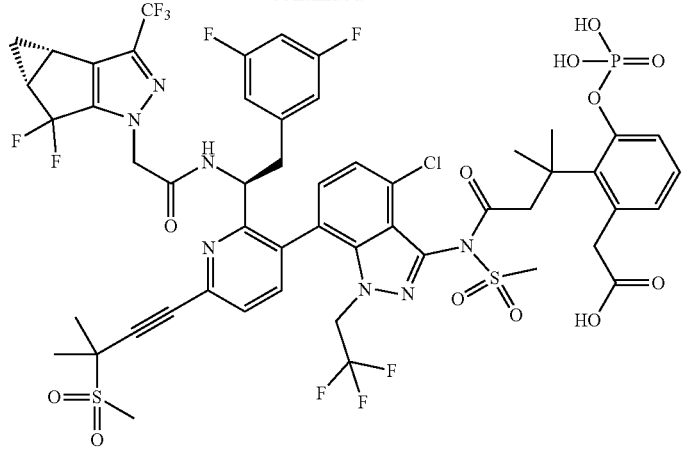

70

Synthesis of 7-(benzyloxy)-5-bromo-4,4-dimethylchroman-2-one (70A): A flask was charged with 58B (1.0 eq) and ACN (0.7 M). Potassium carbonate (2.0 eq) was added, followed by dropwise addition of benzyl bromide (1.5 eq). The reaction was heated at 80° C. for 12 hours. The reaction was concentrated, diluted with water and extracted with DCM (3×). The combined organic layers were washed with brine, dried over Na$_2$SO$_4$, filtered and concentrated under reduced pressure. The residue was purified by silica gel chromatography to yield title compound 70A. MS (m/z) 361.2 [M+H]$^+$.

Synthesis of 5-(benzyloxy)-3-bromo-2-(4-hydroxy-2-methylbutan-2-yl)phenol (70B): A flask was charged with LiAlH$_4$ (1.30 eq) and THF (0.5 M). The mixture was cooled to 0° C., 70A (1.0 eq) was added and the reaction was stirred at RT for 3 hours. The reaction was cooled to 0° C., water was added, followed by 1 M HCl. The reaction was extracted with EtOAc (3×), the combined organic layers were washed with sat. NaHCO$_{3(aq)}$ (2×) until pH=7-8. The organic layer was washed with brine, dried over Na$_2$SO$_4$, filtered and concentrated under reduced pressure to yield title compound 70B which was used without further purification. MS (m/z) 363.2/365.2 [M−H]$^-$.

Synthesis of (3-(4-(benzyloxy)-2-bromo-6-((tert-butyldimethylsilyl)oxy)phenyl)-3-methylbutoxy)(tert-butyl)dimethylsilane (70C): A flask was charged with 70B (1.0 eq) and DMF (0.5 M). Imidazole (5.0 eq), TBSCl (5.2 eq) and DMAP (0.1 eq) were added and the mixture was heated at 65° C. for 12 hours. The reaction was poured into an ice-water mixture and was extracted with EtOAc (3×). The combined organic layers were washed with brine (3×), dried over Na$_2$SO$_4$ and concentrated under reduced pressure. The residue was purified by silica gel chromatography to yield title compound 70C. $^1$H NMR (400 MHz, CDCl$_3$) δ 7.47-7.31 (m, 5H), 6.91 (d, J=2.8 Hz, 1H), 6.35 (d, J=2.8 Hz, 1H), 4.98 (s, 2H), 3.56-3.43 (m, 2H), 2.32-2.18 (m, 2H), 1.60 (s, 6H), 0.98 (s, 9H), 0.85 (s, 9H), 0.26 (s, 6H), −0.02 (s, 6H).

Synthesis of tert-butyl 2-(5-(benzyloxy)-3-((tert-butyldimethylsilyl)oxy)-2-(4-((tert-butyldimethylsilyl)oxy)-2-methylbutan-2-yl)phenyl)acetate (70D): A flask was charged with 70C (1.0 eq) in THF (0.3 M). 2-Tert-butoxy-2-oxoethylzinc bromide (3.0 eq), Pd(dba)$_2$ (0.1 eq) and XPhos (0.1 eq) were added to the mixture and the reaction was heated at 80° C. for 12 hours. The reaction was cooled to RT, quenched with a 0.5 M aqueous solution of citric acid and extracted with n-heptanes. The organic layer was washed with sat. NaHCO$_{3(aq)}$ until pH=7-8. The organic layer was washed with brine, dried over Na$_2$SO$_4$, filtered and concentrated under reduced pressure. The residue was purified by silica gel chromatography to yield title compound 70D. $^1$H NMR (400 MHz, DMSO-d$_6$) δ 7.42-7.29 (m, 5H), 6.39 (d, J=2.8 Hz, 1H), 6.25 (d, J=2.8 Hz, 1H), 5.02 (s, 2H), 3.76 (s, 2H), 3.40-3.33 (m, 2H), 2.07 (t, J=7.8 Hz, 2H), 1.44-1.35 (m, 15H), 0.95 (s, 9H), 0.79 (s, 9H), 0.22 (s, 6H), −0.09 (s, 6H).

Synthesis of tert-butyl 2-(3-((tert-butyldimethylsilyl)oxy)-2-(4-((tert-butyldimethylsilyl)oxy)-2-methylbutan-2-yl)-5-hydroxyphenyl)acetate (70E): A bottle was charged with 70D (1.0 eq), MeOH (0.2 M) and Pd/C (0.1 eq). The reaction was degassed with vacuum/hydrogen (3×). The reaction was heated under hydrogen (50 psi) at 50° C. for 2 hours. The mixture was filtered over a pad of celite and the cake was washed with MeOH (3×). The filtrate was concentrated under reduce pressure and the residue was purified by silica gel chromatography to yield title compound 70E.

Synthesis of tert-butyl 2-(3-((tert-butyldimethylsilyl)oxy)-2-(4-((tert-butyldimethylsilyl)oxy)-2-methylbutan-2-yl)-5-(((trifluoromethyl)sulfonyl)oxy)phenyl)acetate (70F): A flask charged with 70E (1.00 eq) and DCM (0.5 M) was cooled to 0° C. Pyridine (2.00 eq) was added, followed by Tf$_2$O (1.25 eq), and the reaction was stirred at RT for 12 hours. The reaction was concentrated under reduced pressure, poured into water, extracted with DCM (3×), dried over Na$_2$SO$_4$, filtered and concentrated under reduced pressure. The residue was purified by silica gel chromatography to yield title compound 70F. $^1$H NMR (400 MHz, CDCl$_3$) δ 6.68 (d, J=2.8 Hz, 1H), 6.62 (d, J=2.8 Hz, 1H), 3.82 (s, 2H), 3.43 (t, J=7.4 Hz, 2H), 2.15 (t, 2H), 1.50 (s, 6H), 1.45 (s, 9H), 1.03 (s, 9H), 0.83 (s, 9H), 0.33 (s, 6H), −0.06 (s, 6H).

Synthesis of tert-butyl 2-(2-(4-((tert-butyldimethylsilyl)oxy)-2-methylbutan-2-yl)-3-hydroxyphenyl)acetate (70G): A vial was charged with 70F (1.34 mmol), Pd(dppf)Cl$_2$ (0.02 eq), DMF (6.0 mL), triethylamine (4.02 mmol) and formic acid (2.68 mmol) under nitrogen. The mixture was heated at 60° C. for 3 hours then RT for 18 hours. The reaction was quenched with sat. NH$_4$Cl$_{(aq)}$ and extracted with EtOAc (2×). The combined organic layers were washed with a 5% aqueous solution of LiCl (2×), dried over MgSO$_4$, filtered and concentrated. The residue was purified by silica gel chromatography to yield title compound 70G. MS (m/z) 407.3 [M−H]$^+$.

Synthesis of tert-butyl 2-(2-(4-((tert-butyldimethylsilyl)oxy)-2-methylbutan-2-yl)-3-((diisopropoxyphosphoryl)oxy)phenyl)acetate (70H): To a solution of 70G (0.930 mmol) in THF (5.0 mL) at 0° C. was added diisopropyl phosphite (1.26 mmol) and bromoform (1.26 mmol). The solution was stirred for 5 minutes. Sodium hydride (60% dispersion in mineral oil, 1.26 mmol) was then added in one portion. Upon reaction completion, the reaction was quenched with water and extracted with EtOAc (3×). The combined organic layers were washed with brine, dried over MgSO$_4$, filtered and concentrated. The residue was purified by silica gel chromatography to yield title compound 70H. MS (m/z) 573.1 [M+H]$^+$.

Synthesis of tert-butyl 2-(3-((diisopropoxyphosphoryl)oxy)-2-(4-hydroxy methylbutan-2-yl)phenyl)acetate (70I): To a mixture of 70H (0.723 mmol) in H$_2$O/MeOH (1:1, 4.0 mL) at 0° C. was added Oxone® (1.08 mmol). The ice bath was removed and the reaction was stirred at RT for 2 hours. The reaction was quenched with sat. sodium sulfite$_{(aq)}$ and extracted with EtOAc (3×). The combined organic layers were washed with brine, dried over MgSO$_4$, filtered and concentrated under reduced pressure. The residue was purified by silica gel chromatography to yield title compound 70I. MS (m/z) 458.9 [M+H]$^+$.

Synthesis of 3-(2-(2-(tert-butoxy)-2-oxoethyl)-6-((diisopropoxyphosphoryl)oxy)phenyl)-3-methylbutanoic acid (70J): To a solution of 70I (0.674 mmol) in ACN/water (1:1, 6.0 mL) was added TEMPO (0.034 mmol), potassium dihydrogen phosphate (0.337 mmol) and disodium hydrogen phosphate (0.337 mmol). The solution was cooled to 0° C. Sodium chlorite (1.01 mmol) was added, followed by sodium hypochlorite (8.25% NaOCl (aq), 0.822 mmol). The ice bath was removed and the reaction was stirred for 4 hours. The reaction was diluted with water and quenched with sat. sodium sulfite (aq). The pH was adjusted to 2 with 1 M HCl (aq) and the mixture was extracted with EtOAc (3×). The combined organic layers were washed with brine, dried over MgSO$_4$, filtered and concentrated under reduced pressure to yield title compound 70J which was used without further purification. MS (m/z) 471.3 [M−H]$^−$.

Synthesis of tert-butyl 2-(2-(4-(N-(4-chloro-7-(2-((S)-1-(2-O3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-((diisopropoxyphosphoryl)oxy)phenyl)acetate (70K): To a solution of crude 70J (0.673 mmol) in ACN (5.0 mL) was added N-methylimidazole (2.36 mmol), Intermediate 5E (0.639 mmol) and TCFH (0.673 mmol). The reaction was stirred at RT for 18 hours. The reaction was quenched with sat. NH$_4$Cl$_{(aq)}$ and extracted with EtOAc (3×). The combined organic layers were washed with brine, dried over MgSO$_4$, filtered and concentrated under reduced pressure. The crude material was purified by RP chromatography. Fractions containing title compound were pooled and concentrated to afford an atropisomeric mixture of title compound 70K. MS (m/z) 1421.9. [M+H]$^+$.

Synthesis of 2-(2-(4-(N-(4-chloro-7-(2-((S)-1-(2-((3bS,4aR)-5,5-difluoro (trifluoromethyl)-3b,4,4a,5-tetrahydro-1H-cyclopropa[3,4]cyclopenta[1,2-c]pyrazol yl)acetamido)-2-(3,5-difluorophenyl)ethyl)-6-(3-methyl-3-(methylsulfonyl)but-1-yn yl)pyridin-3-yl)-1-(2,2,2-trifluoroethyl)-1H-indazol-3-yl)methylsulfonamido)-2-methyl oxobutan-2-yl)-3-(phosphonooxy)phenyl)acetic acid (70): A flask charged with 70K (0.246 mmol), sodium iodide (0.011 mmol) and bromotrimethylsilane (0.197 mmol) in DCM (3.0 mL) was heated under nitrogen at 45° C. for 8 hours. The reaction was concentrated and the crude product was purified by RP chromatography (40-100% ACN/water with 0.1% TFA). Fractions containing the product were pooled and lyophilized to afford an atropisomeric mixture of title compound 70. $^1$H NMR (400 MHz, DMSO-d$_6$) δ 9.17 (t), 7.90-7.66 (m), 7.44 (d), 7.40-7.23 (m), 7.11-6.95 (m), 6.88-6.78 (m), 6.60 (d), 6.54-6.43 (m), 4.98-4.57 (m), 4.36-4.17 (m), 4.00-3.83 (m), 3.78 (d), 3.65 (d), 3.54-3.41 (m), 3.27 (d), 3.16-2.90 (m), 2.64-2.42 (m), 1.86-1.80 (m), 1.77-1.67 (m), 1.47 (s), 1.43-1.11 (m), 1.07-0.94 (m). $^{19}$F NMR (376 MHz, DMSO-d$_6$) δ−60.86, −60.93, −69.52 (t), −69.83 (t), −79.80 (d), −80.19 (bs), −80.48 (d), −80.77--80.94 (m), −101.96 (bs), −102.66 (bs), −103.25 (d), −103.93 (d), −110.51 (t), −110.62 (t). $^{31}$P NMR (162 MHz, DMSO-d$_6$) δ−6.99 (d). MS (m/z) 1281.4 [M−H]$^+$.

Example 71

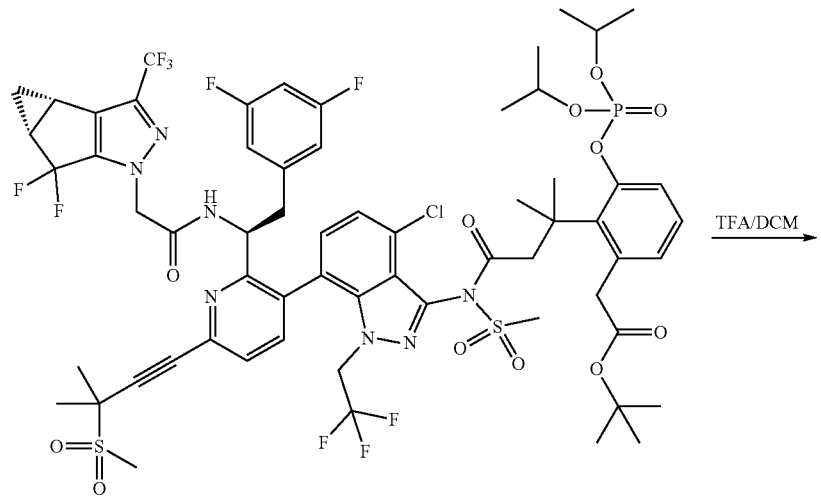

70K

TFA/DCM

-continued
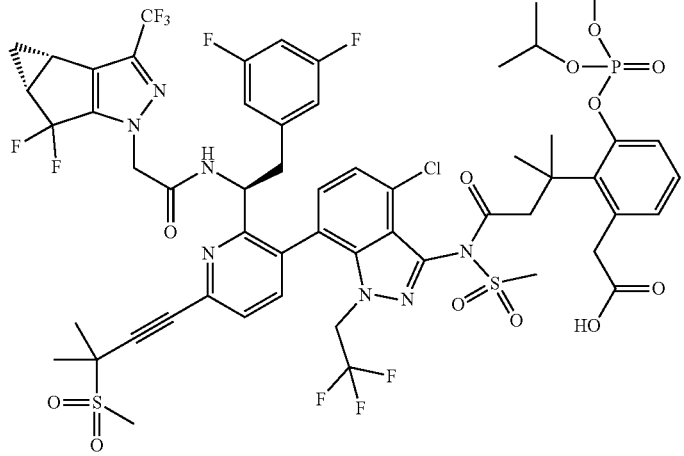
71A
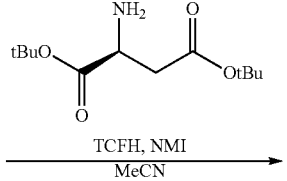
TCFH, NMI
MeCN
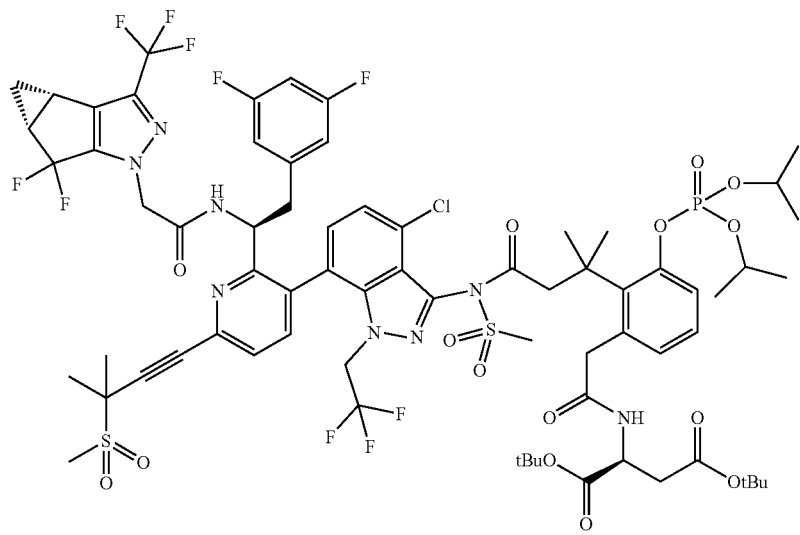
71B
i) TMSBr, NaI, DCM
ii) TFA/DCM
iii) RP purification with 0.1% TFA
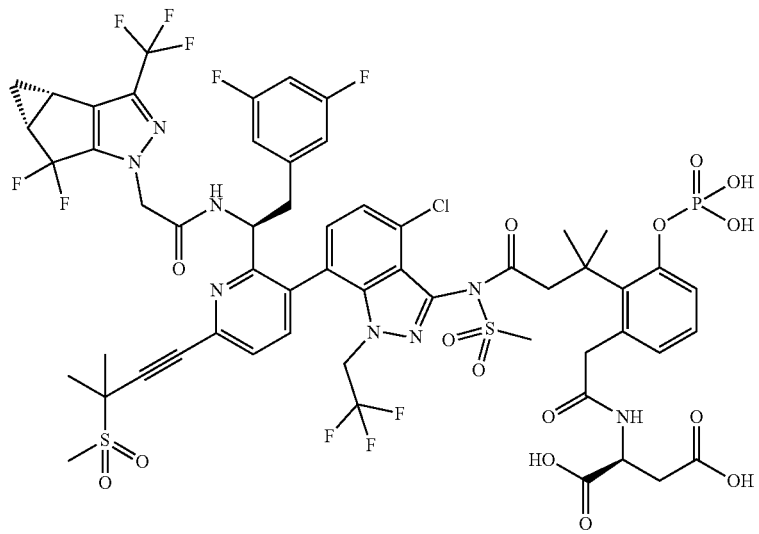
71

Synthesis of 2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-((diisopropoxyphosphoryl)oxy)phenyl)acetic acid (71A): A solution of 70K (0.434 mmol) in DCM/TFA (3:1, 6.0 mL) was stirred at RT for 1 hour. Toluene was added and the reaction was concentrated under reduced pressure to yield title compound 71A. The residue was used without further purification. MS (m/z) 1364.9 [M–H]⁻.

Synthesis of di-tert-butyl (2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)methyl-4-oxobutan-2-yl)-3-((diisopropoxyphosphoryl)oxy)phenyl)acetyl)-L-aspartate (71B): To a solution of crude 71A (0.144 mmol) in ACN (3.0 mL) was added N-methylimidazole (0.865 mmol), di-tert-butyl L-aspartate hydrochloride (0.216 mmol) and TCFH (0.173 mmol). The reaction was stirred at RT for 30 minutes. The reaction was quenched with sat. $NH_4Cl_{(aq)}$ and extracted with EtOAc (3×). The combined organic layers were washed with brine, dried over $MgSO_4$, filtered and concentrated under reduced pressure to afford title compound 71B which was used without further purification. MS (m/z) 1591.8 [M–H]⁺.

Synthesis of (2-(2-(4-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-methyl-4-oxobutan-2-yl)-3-(phosphonooxy)phenyl)acetyl)-L-aspartic acid (71): A flask charged with crude 71B (0.156 mmol), sodium iodide (0.031 mmol) and bromotrimethylsilane (0.156 mmol) in DCM (3.0 mL) was heated under nitrogen at 45° C. for 8 hours. The reaction was concentrated, reconstituted in DCM/TFA (3:1, 4 mL) and stirred at RT for 1 hour. The reaction was concentrated and was purified by RP HPLC chromatography. Fractions containing the product were pooled and lyophilized to afford an atropisomeric mixture of title compound 71. ¹H NMR (400 MHz, DMSO-$d_6$) δ 9.15 (d), 9.01 (d), 8.91 (d), 8.16 (dd), 7.99 (d), 7.93 (d), 7.87 (d), 7.84-7.71 (m), 7.43 (d), 7.39-7.25 (m), 7.08-6.96 (m), 6.85-6.77 (m), 6.67 (d), 6.56-6.45 (m), 4.96-4.47 (m), 4.29-4.18 (m), 4.10-3.98 (m), 3.94-3.58 (m), 3.54-3.50 (m), 3.48 (d), 3.26 (d), 3.11-2.90 (m), 2.74-2.52 (m), 1.76-1.70 (m), 1.51-1.30 (m), 1.25 (bs), 1.05-0.92 (m). ¹⁹F NMR (376 MHz, DMSO-$d_6$) δ–60.79, –60.81, –60.85, –60.93, –69.35 (t), –69.49-–69.68 (m), –69.85 (t), –79.81 (d), –79.99-–80.25 (m), –80.48 (d), –80.67-–80.92 (m), –102.23 (bs), –102.93 (bs), –103.12 (d), –103.27 (d), –103.79 (d), –103.94 (d), –110.53 (t), –110.63 (t), –110.74 (t), –110.89 (t). ³¹P NMR (162 MHz, DMSO-$d_6$) δ–7.00, –7.08. MS (m/z) 1396.2 [M–H]⁻.

Biological Assays

1. Solubility in Simulated Intestinal Fluids

For the solubility assay, approximately 1 to 10 mg of the compound being tested was added to 1.7 mL polypropylene centrifuge tubes. A sufficient volume of fasted state simulated intestinal fluid (FaSSIF) or fed state simulated intestinal fluid (FeSSIF) was then added to each tube to achieve a final concentration of approximately 1 to 20 mg/mL. FaSSIF and FeSSIF were prepared according to manufacturer instruction (catalog #FFF02, Biorelevant, London, UK). Samples were first vortexed for approximately 10 seconds to suspend solids in solution and immediately placed in a bench top vial mixer set to 25° C. and 1400 rpm. After predetermined incubation times, samples were removed from the vial mixer and centrifuged at 15,000 g. A sample of the supernatant was then diluted in a UPLC vial and stored at –20° C. until analysis. After sampling, tubes were vortexed for approximately 10 seconds to re-suspend any solids and returned to the vial mixer at 25° C. and 1400 rpm until the next predetermined timepoint. At completion of the study, samples were removed from the freezer, equilibrated to ambient temperature, and analyzed by reversed-phase UPLC to determine the concentration of compound in the supernatant at each timepoint. Results are presented in the second column of Table 1 below.

2. Kinetic Solubility Analysis (CLND: Total Chemiluminescent Nitrogen Determination)

Kinetic Solubility from DMSO Stocks of each compound being tested: 100-fold dilutions of a 10 μM DMSO stock solution of each compound being tested were prepared in singleton by combining 3 μL of DMSO stock with 297 μL of the appropriate media (0.1N HCL (Alfa Aesar part number 35644-K2) and 1×PBS buffer (pH 7.4)) in a Millipore solubility filter plate with 0.45 μM polycarbonate filter membrane using Hamilton Starlet liquid handling. The final DMSO Concentration is 1.0% and maximum theoretical compound concentration is 100 μM (assuming stock concentration of 10 mM). The filter plate was sealed. Following 24-hour incubation at ambient temperature (21.7-23.8° C.), the samples were vacuum filtered, and the filtrates were collected in a 96 well polypropylene plate for analysis. The collection plate was sealed for analysis.

Filtrates were injected into the nitrogen detector for quantification on Analiza's Automated Discovery Workstation. The results are reported in μM.

The equimolar nitrogen response of the detector was calibrated using standards which span the dynamic range of the instrument from 0.08 to 4500 μg/ml nitrogen. The filtrates were quantified with respect to this calibration curve. The calculated solubility values were corrected for background nitrogen present in the DMSO, and the media used to prepare the samples. The solubility results presented in the third column of Table 1 below assumed that the samples were free of nitrogen containing impurities and were stable under the assay conditions.

The 1×PBS buffer (pH 7.4) was prepared by adding 50 mL of phosphate buffered saline solution 10×, PBS (Fisher Bioreagent part number BP399-500) to approximately 450 mL HPLC grade $H_2O$. The volume of the solution was then adjusted to 500 mL for a total dilution factor of 1:10 and a final PBS concentration of 1×. The pH of the final solution was measured and found to be 7.4.

3. Oral Bioavailability PK Samples

Oral dose (suspension and solution vehicle) of the compound being tested was administered via gavage in rat (Sprague Dawley) and dog (Beagle). Serial blood samples were collected via jugular vein into pre-chilled K2EDTA with 2 mM dichlorvos (final concentration) for up to 168h. Whole blood was processed into plasma by centrifuge (3000 rpm for 10 minutes at 5C) within 30 minutes of collection.

Plasma samples were analyzed by direct protein precipitation with acetonitrile and further dilution with water before injecting onto Sciex API 5500 LC/MS/MS system for analysis. Unknown plasma samples concentration was calibrated using standard range of 5-10,000 nM for the compound being tested and 1-10,000 nM for Intermediate 5.

AUC was calculated as Area under the plasma concentration vs. time curve from 0 h to infinity.

Bioavailability (% F) was calculated by comparing plasma concentration via oral dose vs. plasma concentration via $R^a$ dose (intravenous). % F=[(PO AUCinf• $R^a$ Dose)/(IV AUCinf PO Dose)]100 and are reported in the fourth and fifth columns of Table 1 below. The plasma sample concentrations for the compounds being tested were below the limit of quantitation and are thus not reported in Table 1. The reported values in the fourth and fifth columns of Table 1 are based on observed exposure of Intermediate 5 in plasma.

The suspension vehicle was 0.5% hydroxypropyl methylcellulose, high viscosity and 99.5% water with final pH of 2.0. The solution vehicles used were 1) 5% ethanol, 20% propylene glycol, and 75% water and 2) 30% 10 mM HCl, 5% ethanol, 45% polyethylene glycol 300, and 20% propylene glycol.

TABLE 1

| Compound | FaSSIF/FeSSIF solubility[a] (µg/mL) | pH 2/pH 7 solubility (µM) | Dog F % (solution) | Dog F % (suspension) |
|---|---|---|---|---|
| Intermediate 5 | 4.0/4.2 | 0.11/0.32 | 24[b], 16[c] | 8 |
| 1 | 321/45 | 1/86 | — | — |
| 2 | 810/655 | 1/95 | 27[b] | — |
| 3 | 5597/517 | 1/65 | — | 10 |
| 4 | ND/6 | 42/1 | — | — |
| 5 | — | 45/6 | — | — |
| 6 | 21/1 | 100/9 | — | — |
| 7 | — | 1/1 | — | — |
| 8 | — | 51/1 | — | — |
| 9 | — | 1/1 | — | — |
| 10 | — | 1/1 | — | — |
| 11 | — | 100/43 | — | — |
| 12 | — | 65/8 | — | — |
| 13 | — | 1/90 | — | — |
| 14 | — | 7/1 | — | — |
| 15 | — | 1/1 | — | — |
| 16 | — | 92/20 | — | — |
| 18 | 0.5/0.4 | 60/1 | — | — |
| 19 | — | 37/6 | — | — |
| 20 | — | 69/2 | — | — |
| 21 | — | 72/2 | — | — |
| 22 | ND/0.2 | 100/27 | — | — |
| 23 | — | 14/22 | — | — |
| 24 | — | 1/14 | — | — |
| 25 | — | 1/1 | — | — |
| 26 | — | 1/1 | — | — |
| 27 | 190/450 | 1/26 | — | — |
| 28 | 555/319 | 1/86 | 51[b] | — |
| 29 | 268/130 | 2/92 | — | — |
| 30 | >1100/5826 | 1/100 | 18[c] | 18 |
| 31 | 2928/902 | 1/79 | — | 15 |
| 32 | 194/210 | 1/100 | 31[b] | — |
| 33 | 326/300 | 1/75 | 33[b] | 17 |
| 34 | >2840/454 | 3/75 | — | — |
| 35 | 883/404 | 2/48 | 29[b] | — |
| 36 | 661/486 | 3/100 | — | — |
| 37 | 674/333 | 1/79 | — | 15 |
| 38 | >1890/402 | 2/70 | — | 16 |
| 39 | 1190/3870 | 1/87 | — | — |
| 40 | — | 1/100 | — | 5 |
| 41 | 1145/440 | 1/100 | — | 4 |
| 42 | — | 1/100 | — | 9 |
| 43 | 2904/>5770 | 2/100 | — | 23 |
| 44 | 2871/460 | 1/100 | — | 27 |
| 45 | 456/129 | 1/1 | — | — |
| 46 | 700/>2150 | 1/66 | — | 10 |
| 47 | 1421/226 | 4/100 | — | 7 |
| 48 | 777/948 | 83/1 | 60[b] | 16 |
| 49 | 384/390 | 3/100 | — | 20 |
| 50 | — | 2/2 | — | — |
| 51 | 1752/1450 | 1/100 | — | — |
| 52 | 1369/>6260 | 2/100 | — | 24 |
| 53 | 391/958 | 2/78 | — | 5 |
| 54 | 1091/561 | 1/63 | — | — |
| 55 | >10000/— | 2/100 | 33[c] | — |
| 56 | >10000/— | 1/100 | — | — |
| 57 | 7300/— | 1/100 | — | — |
| 58 | — | 2/2 | — | — |
| 59 | >10000/— | 6.3/100 | 27[c] | — |
| 60 | >10000/— | 1/64 | — | — |
| 61 | >10000/— | 2/70 | — | — |
| 62 | 490/— | 1/67 | 8[c] | — |
| 63 | — | 1/85 | — | — |
| 64 | 7400/— | 2/69 | — | — |
| 65 | 1100/— | 7/68 | — | — |
| 66 | 511/— | 6/66 | — | — |
| 67 | — | <1/91 | — | — |
| 68 | — | <1/65 | — | — |
| 69 | — | 3/75 | — | — |
| 70 | — | 7/94 | — | — |
| 71 | — | 2/88 | — | — |

[a]FeSSIF = Fed-state simulated intestinal fluid; FaSSIF = Fasted-state simulated intestinal fluid.
[b]Vehicle is 30% 10 mM HCl, 5% ethanol, 45% polyethylene glycol 300, and 20% propylene glycol,
[c]Vehicle is 5% ethanol, 20% propylene glycol, and 75% water.

All references, including publications, patents, and patent documents are incorporated by reference herein, as though individually incorporated by reference. The present disclosure provides reference to various embodiments and techniques. However, it should be understood that many variations and modifications may be made while remaining within the spirit and scope of the present disclosure. The description is made with the understanding that it is to be considered an exemplification of the claimed subject matter, and is not intended to limit the appended claims to the specific embodiments illustrated.

What is claimed is:

1. A compound that is

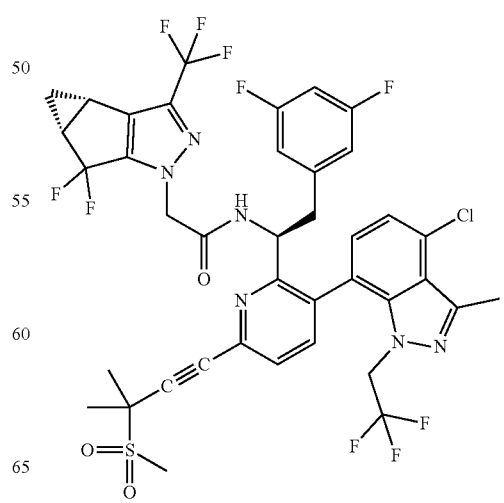

-continued
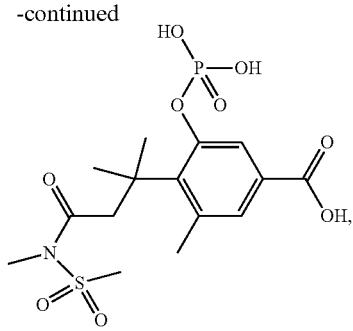
or a pharmaceutically acceptable salt thereof.
2. A compound that is
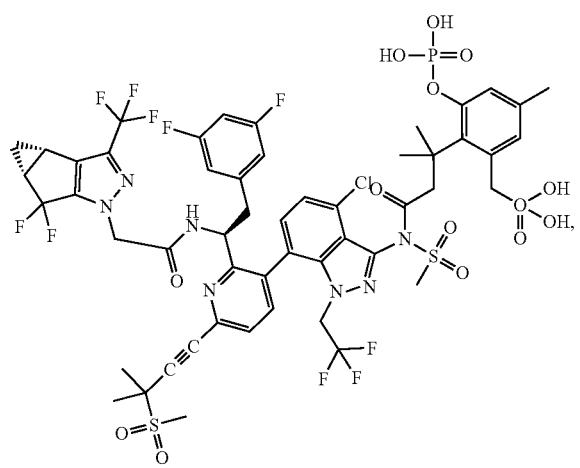
or a pharmaceutically acceptable salt thereof.
3. A compound that is
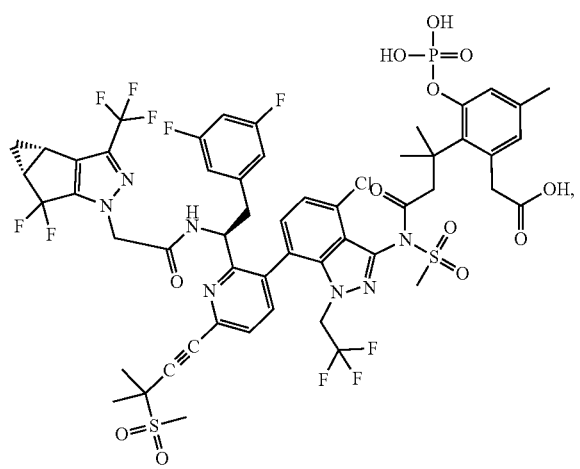 [SMILES: Cc1cc(CC(=O)O)c(C(C)(C)CC(=O)N(c2nn(CC(F)(F)F)c3c(-c4ccc(C#CC(C)(C)S(C)(=O)=O)nc4[C@H](Cc4cc(F)cc(F)c4)NC(=O)Cn4nc(C(F)(F)F)c5c4C(F)(F)[C@@H]4C[C@H]54)ccc(Cl)c23)S(C)(=O)=O)c(OP(=O)(O)O)c1]
or a pharmaceutically acceptable salt thereof.
4. A compound that is
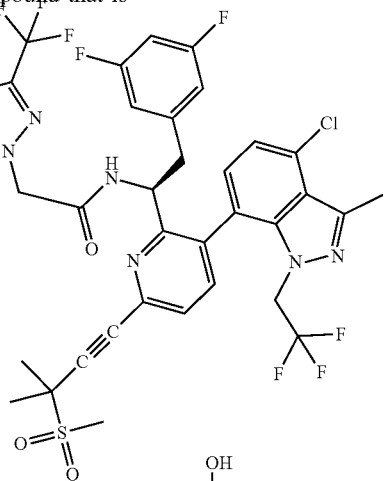
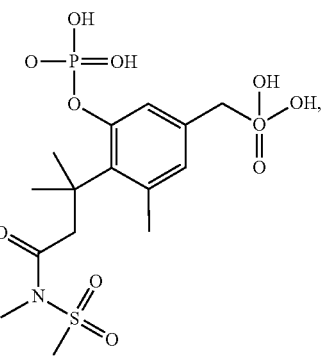
or a pharmaceutically acceptable salt thereof.
5. A compound that is
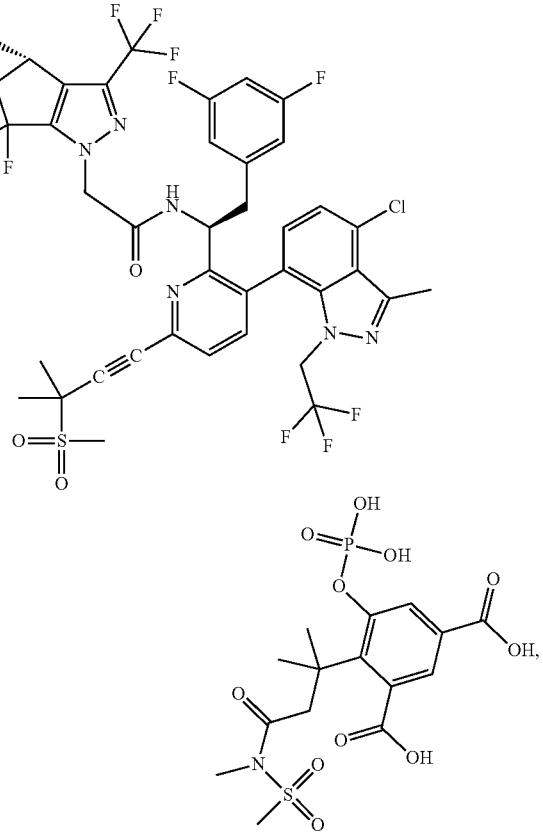
or a pharmaceutically acceptable salt thereof.

6. A pharmaceutical composition comprising a therapeutically effective amount of a compound of claim 1, or a pharmaceutically acceptable salt thereof, and a pharmaceutically acceptable excipient.

7. The pharmaceutical composition of claim 6, further comprising one, two, three, or four additional therapeutic agents.

8. A method of treating or preventing a human immunodeficiency virus (HIV) infection in a patient in need thereof comprising administering to the patient a therapeutically effective amount of the compound of claim 1, or a pharmaceutically acceptable salt thereof.

9. The method of claim 8, wherein the method further comprises administering a therapeutically effective amount of one, two, three, or four additional therapeutic agents, or a pharmaceutically acceptable salt thereof.

10. The method of claim 9, wherein the one, two, three, or four additional therapeutic agents are selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, HIV capsid inhibitors, nucleocapsid protein 7 (NCp7) inhibitors, HIV Tat or Rev inhibitors, inhibitors of Tat-TAR-P-TEFb, immunomodulators, immunotherapeutic agents, antibody-drug conjugates, gene modifiers, gene editors, latency reversing agents, immune-based therapies, phosphatidylinositol 3-kinase (PI3K) inhibitors, HIV antibodies, bispecific antibodies and antibody-like therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, Fatty acid synthase inhibitor, HIV vif gene modulators, Vif dimerization antagonists, HIV-1 viral infectivity factor inhibitors, HIV-1 Nef modulators, TNF alpha ligand inhibitors, HIV Nef inhibitors, Hck tyrosine kinase modulators, mixed lineage kinase-3 (MLK-3) inhibitors, HIV-1 splicing inhibitors, integrin antagonists, nucleoprotein inhibitors, splicing factor modulators, COMM domain containing protein 1 modulators, HIV ribonuclease H inhibitors, IFN antagonists, retrocyclin modulators, CD3 antagonists, CDK-4 inhibitors, CDK-6 inhibitors, CDK-9 inhibitors, Cytochrome P450 3 inhibitors, CXCR4 modulators, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, HPK1 (MAP4K1) inhibitors, proprotein convertase PC9 stimulators, ATP dependent RNA helicase DDX3x inhibitors, reverse transcriptase priming complex inhibitors, G6PD and NADH-oxidase inhibitors, mTOR complex 1 inhibitors, mTOR complex 2 inhibitors, P-Glycoprotein modulators, RNA polymerase modulators, TAT protein inhibitors, Prolyl endopeptidase inhibitors, Phospholipase A2 inhibitors, pharmacokinetic enhancers, HIV gene therapy, HIV vaccines, and anti-HIV peptides, or any combinations thereof.

11. The method of claim 9, wherein the one, two, three, or four additional therapeutic agents are selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, bispecific antibodies, and antibody-like therapeutic proteins, or any combinations thereof.

12. The method of claim 9, wherein the one, two, three, or four additional therapeutic agents are selected from the group consisting of dolutegravir, cabotegravir, darunavir, bictegravir, elsulfavirine, rilpivirine, abacavir sulfate, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt thereof.

13. A pharmaceutical composition comprising a therapeutically effective amount of a compound of claim 2, or a pharmaceutically acceptable salt thereof, and a pharmaceutically acceptable excipient.

14. The pharmaceutical composition of claim 13, further comprising one, two, three, or four additional therapeutic agents.

15. A method of treating or preventing a human immunodeficiency virus (HIV) infection in a patient in need thereof comprising administering to the patient a therapeutically effective amount of the compound of claim 2, or a pharmaceutically acceptable salt thereof.

16. The method of claim 15, wherein the method further comprises administering a therapeutically effective amount of one, two, three, or four additional therapeutic agents, or a pharmaceutically acceptable salt thereof.

17. The method of claim 16, wherein the one, two, three, or four additional therapeutic agents are selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, HIV capsid inhibitors, nucleocapsid protein 7 (NCp7) inhibitors, HIV Tat or Rev inhibitors, inhibitors of Tat-TAR-P-TEFb, immunomodulators, immunotherapeutic agents, antibody-drug conjugates, gene modifiers, gene editors, latency reversing agents, immune-based therapies, phosphatidylinositol 3-kinase (PI3K) inhibitors, HIV antibodies, bispecific antibodies and antibody-like therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, Fatty acid synthase inhibitor, HIV vif gene modulators, Vif dimerization antagonists, HIV-1 viral infectivity factor inhibitors, HIV-1 Nef modulators, TNF alpha ligand inhibitors, HIV Nef inhibitors, Hck tyrosine kinase modulators, mixed lineage kinase-3 (MLK-3) inhibitors, HIV-1 splicing inhibitors, integrin antagonists, nucleoprotein inhibitors, splicing factor modulators, COMM domain containing protein 1 modulators, HIV ribonuclease H inhibitors, IFN antagonists, retrocyclin modulators, CD3 antagonists, CDK-4 inhibitors, CDK-6 inhibitors, CDK-9 inhibitors, Cytochrome P450 3 inhibitors, CXCR4 modulators, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, HPK1 (MAP4K1) inhibitors, proprotein convertase PC9 stimulators, ATP dependent RNA helicase DDX3x inhibitors, reverse transcriptase priming complex inhibitors, G6PD and NADH-oxidase inhibitors, mTOR complex 1 inhibitors, mTOR complex 2 inhibitors, P-Glycoprotein modulators, RNA polymerase modulators, TAT protein inhibitors, Prolyl endopeptidase inhibitors, Phospholipase A2 inhibitors, pharmacokinetic enhancers, HIV gene therapy, HIV vaccines, and anti-HIV peptides, or any combinations thereof.

18. The method of claim 16, wherein the one, two, three, or four additional therapeutic agents are selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, bispecific antibodies, and antibody-like therapeutic proteins, or any combinations thereof.

19. The method of claim 16, wherein the one, two, three, or four additional therapeutic agents are selected from the group consisting of dolutegravir, cabotegravir, darunavir, bictegravir, elsulfavirine, rilpivirine, abacavir sulfate, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt thereof.

20. A pharmaceutical composition comprising a therapeutically effective amount of a compound of claim 3, or a pharmaceutically acceptable salt thereof, and a pharmaceutically acceptable excipient.

21. The pharmaceutical composition of claim 20, further comprising one, two, three, or four additional therapeutic agents.

22. A method of treating or preventing a human immunodeficiency virus (HIV) infection in a patient in need thereof comprising administering to the patient a therapeutically effective amount of the compound of claim 3, or a pharmaceutically acceptable salt thereof.

23. The method of claim 22, wherein the method further comprises administering a therapeutically effective amount of one, two, three, or four additional therapeutic agents, or a pharmaceutically acceptable salt thereof.

24. The method of claim 23, wherein the one, two, three, or four additional therapeutic agents are selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, HIV capsid inhibitors, nucleocapsid protein 7 (NCp7) inhibitors, HIV Tat or Rev inhibitors, inhibitors of Tat-TAR-P-TEFb, immunomodulators, immunotherapeutic agents, antibody-drug conjugates, gene modifiers, gene editors, latency reversing agents, immune-based therapies, phosphatidylinositol 3-kinase (PI3K) inhibitors, HIV antibodies, bispecific antibodies and antibody-like therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, Fatty acid synthase inhibitor, HIV vif gene modulators, Vif dimerization antagonists, HIV-1 viral infectivity factor inhibitors, HIV-1 Nef modulators, TNF alpha ligand inhibitors, HIV Nef inhibitors, Hck tyrosine kinase modulators, mixed lineage kinase-3 (MLK-3) inhibitors, HIV-1 splicing inhibitors, integrin antagonists, nucleoprotein inhibitors, splicing factor modulators, COMM domain containing protein 1 modulators, HIV ribonuclease H inhibitors, IFN antagonists, retrocyclin modulators, CD3 antagonists, CDK-4 inhibitors, CDK-6 inhibitors, CDK-9 inhibitors, Cytochrome P450 3 inhibitors, CXCR4 modulators, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, HPK1 (MAP4K1) inhibitors, proprotein convertase PC9 stimulators, ATP dependent RNA helicase DDX3×inhibitors, reverse transcriptase priming complex inhibitors, G6PD and NADH-oxidase inhibitors, mTOR complex 1 inhibitors, mTOR complex 2 inhibitors, P-Glycoprotein modulators, RNA polymerase modulators, TAT protein inhibitors, Prolyl endopeptidase inhibitors, Phospholipase A2 inhibitors, pharmacokinetic enhancers, HIV gene therapy, HIV vaccines, and anti-HIV peptides, or any combinations thereof.

25. The method of claim 23, wherein the one, two, three, or four additional therapeutic agents are selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, bispecific antibodies, and antibody-like therapeutic proteins, or any combinations thereof.

26. The method of claim 23, wherein the one, two, three, or four additional therapeutic agents are selected from the group consisting of dolutegravir, cabotegravir, darunavir, bictegravir, elsulfavirine, rilpivirine, abacavir sulfate, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt thereof.

27. A pharmaceutical composition comprising a therapeutically effective amount of a compound of claim 4, or a pharmaceutically acceptable salt thereof, and a pharmaceutically acceptable excipient.

28. The pharmaceutical composition of claim 27, further comprising one, two, three, or four additional therapeutic agents.

29. A method of treating or preventing a human immunodeficiency virus (HIV) infection in a patient in need thereof comprising administering to the patient a therapeutically effective amount of the compound of claim 4, or a pharmaceutically acceptable salt thereof.

30. The method of claim 29, wherein the method further comprises administering a therapeutically effective amount of one, two, three, or four additional therapeutic agents, or a pharmaceutically acceptable salt thereof.

31. The method of claim 30, wherein the one, two, three, or four additional therapeutic agents are selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, HIV capsid inhibitors, nucleocapsid protein 7 (NCp7) inhibitors, HIV Tat or Rev inhibitors, inhibitors of Tat-TAR-P-TEFb, immunomodulators, immunotherapeutic agents, antibody-drug conjugates, gene modifiers, gene editors, latency reversing agents, immune-based therapies, phosphatidylinositol 3-kinase (PI3K) inhibitors, HIV antibodies, bispecific antibodies and antibody-like therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, Fatty acid synthase inhibitor, HIV vif gene modulators, Vif dimerization antagonists, HIV-1 viral infectivity factor inhibitors, HIV-1 Nef modulators, TNF alpha ligand inhibitors, HIV Nef inhibitors, Hck tyrosine kinase modulators, mixed lineage kinase-3 (MLK-3) inhibitors, HIV-1 splicing inhibitors, integrin antagonists, nucleoprotein inhibitors, splicing factor modulators, COMM domain containing protein 1 modulators, HIV ribonuclease H inhibitors, IFN antagonists, retrocyclin modulators, CD3 antagonists, CDK-4 inhibitors, CDK-6 inhibitors, CDK-9 inhibitors, Cytochrome P450 3 inhibitors, CXCR4 modulators, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, HPK1 (MAP4K1) inhibitors, proprotein convertase PC9 stimulators, ATP dependent RNA helicase DDX3×inhibitors, reverse transcriptase priming complex inhibitors, G6PD and NADH-oxidase inhibitors, mTOR complex 1 inhibitors, mTOR complex 2 inhibitors, P-Glycoprotein modulators, RNA polymerase modulators, TAT protein inhibitors, Prolyl endopeptidase inhibitors, Phospholipase A2 inhibitors, pharmacokinetic enhancers, HIV gene therapy, HIV vaccines, and anti-HIV peptides, or any combinations thereof.

32. The method of claim 30, wherein the one, two, three, or four additional therapeutic agents are selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, bispecific antibodies, and antibody-like therapeutic proteins, or any combinations thereof.

33. The method of claim 30, wherein the one, two, three, or four additional therapeutic agents are selected from the group consisting of dolutegravir, cabotegravir, darunavir, bictegravir, elsulfavirine, rilpivirine, abacavir sulfate, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt thereof.

34. A pharmaceutical composition comprising a therapeutically effective amount of a compound of claim 5, or a pharmaceutically acceptable salt thereof, and a pharmaceutically acceptable excipient.

35. The pharmaceutical composition of claim 34, further comprising one, two, three, or four additional therapeutic agents.

36. A method of treating or preventing a human immunodeficiency virus (HIV) infection in a patient in need thereof comprising administering to the patient a therapeutically effective amount of the compound of claim 5, or a pharmaceutically acceptable salt thereof.

37. The method of claim 36, wherein the method further comprises administering a therapeutically effective amount of one, two, three, or four additional therapeutic agents, or a pharmaceutically acceptable salt thereof.

38. The method of claim 37, wherein the one, two, three, or four additional therapeutic agents are selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, HIV capsid inhibitors, nucleocapsid protein 7 (NCp7) inhibitors, HIV Tat or Rev inhibitors, inhibitors of Tat-TAR-P-TEFb, immunomodulators, immunotherapeutic agents, antibody-drug conjugates, gene modifiers, gene editors, latency reversing agents, immune-based therapies, phosphatidylinositol 3-kinase (PI3K) inhibitors, HIV antibodies, bispecific antibodies and antibody-like therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, Fatty acid synthase inhibitor, HIV vif gene modulators, Vif dimerization antagonists, HIV-1 viral infectivity factor inhibitors, HIV-1 Nef modulators, TNF alpha ligand inhibitors, HIV Nef inhibitors, Hck tyrosine kinase modulators, mixed lineage kinase-3 (MLK-3) inhibitors, HIV-1 splicing inhibitors, integrin antagonists, nucleoprotein inhibitors, splicing factor modulators, COMM domain containing protein 1 modulators, HIV ribonuclease H inhibitors, IFN antagonists, retrocyclin modulators, CD3 antagonists, CDK-4 inhibitors, CDK-6 inhibitors, CDK-9 inhibitors, Cytochrome P450 3 inhibitors, CXCR4 modulators, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, HPK1 (MAP4K1) inhibitors, proprotein convertase PC9 stimulators, ATP dependent RNA helicase DDX3×inhibitors, reverse transcriptase priming complex inhibitors, G6PD and NADH-oxidase inhibitors, mTOR complex 1 inhibitors, mTOR complex 2 inhibitors, P-Glycoprotein modulators, RNA polymerase modulators, TAT protein inhibitors, Prolyl endopeptidase inhibitors, Phospholipase A2 inhibitors, pharmacokinetic enhancers, HIV gene therapy, HIV vaccines, and anti-HIV peptides, or any combinations thereof.

39. The method of claim 37, wherein the one, two, three, or four additional therapeutic agents are selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, bispecific antibodies, and antibody-like therapeutic proteins, or any combinations thereof.

40. The method of claim 37, wherein the one, two, three, or four additional therapeutic agents are selected from the group consisting of dolutegravir, cabotegravir, darunavir, bictegravir, elsulfavirine, rilpivirine, abacavir sulfate, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt thereof.

* * * * *